US008039606B2

(12) United States Patent
Hallenbeck et al.

(10) Patent No.: US 8,039,606 B2
(45) Date of Patent: *Oct. 18, 2011

(54) SENECA VALLEY VIRUS BASED COMPOSITIONS AND METHODS FOR TREATING DISEASE

(75) Inventors: Paul Hallenbeck, Chester Springs, PA (US); Seshidhar Reddy Police, Chester Springs, PA (US); Laura M. Hales, Chester Springs, PA (US); Carl Hay, Damascus, MD (US); Shanthi Ganesh, San Francisco, CA (US); Ling Xu, Boyds, MD (US); Jingping Yang, Gaithersburg, MD (US); Cheng Cheng, Rockville, MD (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/576,296

(22) Filed: Oct. 9, 2009

(65) Prior Publication Data
US 2010/0129325 A1 May 27, 2010

Related U.S. Application Data

(63) Continuation of application No. 11/335,891, filed on Jan. 19, 2006, now Pat. No. 7,638,318, which is a continuation-in-part of application No. PCT/US2004/031504, filed on Sep. 23, 2004.

(60) Provisional application No. 60/506,182, filed on Sep. 26, 2003, provisional application No. 60/664,442, filed on Mar. 23, 2005, provisional application No. 60/726,313, filed on Oct. 13, 2005.

(51) Int. Cl.
*C12N 15/11* (2006.01)
*A61K 35/00* (2006.01)

(52) U.S. Cl. ............... 536/23.72; 435/235.1; 424/93.1

(58) Field of Classification Search ...................... None
See application file for complete search history.

(56) References Cited

U.S. PATENT DOCUMENTS

| 5,708,157 | A | 1/1998 | Jacobs et al. | |
| 6,531,136 | B1 | 3/2003 | Studdert et al. | |
| 7,638,318 | B2 * | 12/2009 | Hallenbeck et al. | 435/235.1 |
| 2003/0165820 | A1 | 9/2003 | Day et al. | |

FOREIGN PATENT DOCUMENTS

| WO | WO-99/08692 A1 | 2/1999 |
| WO | WO-02/103060 A2 | 12/2002 |
| WO | WO-2005/030139 | 4/2005 |

OTHER PUBLICATIONS

Adachi, M. et al., "Destruction of human retinoblastoma after treatment by the E variant of encephalomyocarditis virus," Journal of Neuro-Oncology May 2006, vol. 77, No. 3, May 2006, pp. 233-240.
Bakonyi, T., et al., "Complete genome analysis and molecular characterization of usutu virus that emerged in Austria in 2001 Comparison with South Africa Strain SAAR-1776 and other flavivirus", Virology, Oct. 2004, vol. 328, pp. 301-310.
International Search Report and Written Opinion issued for International Patent Application No. PCT/US2006/009142, 2007.
International Search Report and Wrtten Opinion issued for International Patent Application No. PCT/US2006/039523, 2007.
Supplementary European Search Report issued for European Patent Application No. EP 04 78 9044, 2007.
Cox, S.J. et al., "Protection against direct-contact challenge following emergency FMD vaccination of cattle and the effect on virus excretion from the oropharynx," Vaccine 23 (2005) 1106-1113.
Database UniProt [Online] May 1, 2000, "Polyprotein." retrieved from EBI accession No. UNIPROT: Q9QCE4, Database accession No. Q9QCE4, positions 654-664 and 1580-1610.
Database UniProt [Online] Oct. 1, 2002, "Polyprotein." retrieved from EBI accession No. UNIPROT: Q8JW41, Database accession No. Q8JW41, positions 654-664 and 1580-1610.
Gromeier, M.M., et al., Intergenic poliovirus recombinants for the treatment of malignant glioma, PNAS, Jun. 2000, vol. 97, No. 12, pp. 6803-6808.
Halet et al., J. Gene. Virol. 2008, vol. 89, pp. 1265-1275.
Hernandez, J. Virol, 2002, vol. 74(9), pp. 4220-4228.
Huang, T., et al., "Oncolysis of heepatitis Metastasis of Colorectal Cancer by Recombinant Vesicular Stomatitis Virus in Ummune-Competent Mice", Molecular Therapy, Sep. 2003, vol. 8, No. 3, pp. 424-440.
Kitamura et al., Proc. Natl. Acad. Sci. U.S.A. 1980, vol. 77, No. 6, pp. 3196-3200.
Marvil et al., J. Gene. Virol. 1999, vol. 80 (pt.3), pp. 653-662.
Mullen, T.J., et al., "Viral Oncolysis", The Oncologist, Apr. 2002, vol. 7, pp. 106-119.
NC0039 published by Marvil et al. on 1999.
Russel, S.J., "RNA Viruses as virotherapy agents", Cancer Gene Therapy, Nov. 2002, vol. 9, pp. 961-966.
Smith, M. et al., "Bovine enterovirus as an oncolytic virus: Foetal calf serum facilities its infection of human cells," International Journal of Molecular Medicine, vol. 10, No. 1, Jul. 2002, pp. 49-53.
Spryrou, V., et al., "Treansmission and pathogenecity of encephalomycardititis virus (EMCV) a moong rats", Vet. Res. Jan.-Feb. 2004, vol. 35, pp. 113-122.
Office Action dated Jun. 28, 2011 for corresponding Canadian Patent Application No. 2,540,177.

* cited by examiner

*Primary Examiner* — Bao Li
(74) *Attorney, Agent, or Firm* — Wilmer Cutler Pickering Hale and Dorr LLP

(57) ABSTRACT

The present invention relates to a novel RNA picornavirus that is called Seneca Valley virus ("SVV"). The invention provides isolated SVV nucleic acids and proteins encoded by these nucleic acids. Further, the invention provides antibodies that are raised against the SVV proteins. Because SVV has the ability to selectively kill some types of tumors, the invention provides methods of using SVV and SVV polypeptides to treat cancer. Because SVV specifically targets certain tumors, the invention provides methods of using SVV nucleic acids and proteins to detect cancer. Additionally, due to the information provided by the tumor-specific mechanisms of SVV, the invention provides methods of making new oncolytic virus derivatives and of altering viruses to have tumor-specific tropisms.

3 Claims, 129 Drawing Sheets

```
           10        20        30        40        50        60        70        80        90
    ....|....|....|....|....|....|....|....|....|....|....|....|....|....|....|....|....|....|
    NNTCTAGCCCACCATGGCAACAAGAAGAGCTTACAGGAGCTGAATGAAGAACAGTGGGTGGAAATGTCTGACGATTACCGGACCGGGAAA
     X  L  A  H  H  G  N  K  K  S  L  Q  E  L  N  E  E  Q  W  V  E  M  S  D  D  Y  R  T  G  K 100       110       120       130       140       150       160       170       180
    ....|....|....|....|....|....|....|....|....|....|....|....|....|....|....|....|....|....|
    AACATGCCTTTTCAGTCTCTTGGCACATACTATCGGCCCCCTAACTGGACTTGGGGTCCCAATTTCATCAACCCCTATCAAGTAACGGTT
     N  M  P  F  Q  S  L  G  T  Y  Y  R  P  P  N  W  T  W  G  P  N  F  I  N  P  Y  Q  V  T  V 190       200       210       220       230       240       250       260       270
    ....|....|....|....|....|....|....|....|....|....|....|....|....|....|....|....|....|....|
    TTCCCACACCAAATTCTGAACGCGAGAACCTCTACCTCGGTAGACATAAACGTCCCATACATCGGGGAGACCCCCACGCAATCCTCAGAG
     F  P  H  Q  I  L  N  A  R  T  S  T  S  V  D  I  N  V  P  Y  I  G  E  T  P  T  Q  S  S  E 280       290       300       310       320       330       340       350       360
    ....|....|....|....|....|....|....|....|....|....|....|....|....|....|....|....|....|....|
    ACACAGAACTCCTGGACCCTCCTCGTTATGGTGCTCGTTCCCCTAGACTATAAGGAAGGAGCCACAACTGACCCAGAAATTACATTTTCT
     T  Q  N  S  W  T  L  L  V  M  V  L  V  P  L  D  Y  K  E  G  A  T  T  D  P  E  I  T  F  S 370       380       390       400       410       420       430       440       450
    ....|....|....|....|....|....|....|....|....|....|....|....|....|....|....|....|....|....|
    GTAAGGCCTACAAGTCCCTACTTCAATGGGCTTCGCAACCGCTACACGGCCGGGACGGACGAAGAACAGGGGCCCATTCCTACGGCACCC
     V  R  P  T  S  P  Y  F  N  G  L  R  N  R  Y  T  A  G  T  D  E  E  Q  G  P  I  P  T  A  P 460       470       480       490       500       510       520       530       540
    ....|....|....|....|....|....|....|....|....|....|....|....|....|....|....|....|....|....|
    AGAGAAAATTCGCTTATGTTTCTCTCAACCCTCCCTGACGACACTGTCCCTGCTTACGGGAATGTGCGTACCCCTCCTGTCAATTACCTC
     R  E  N  S  L  M  F  L  S  T  L  P  D  D  T  V  P  A  Y  G  N  V  R  T  P  P  V  N  Y  L 550       560       570       580       590       600       610       620       630
    ....|....|....|....|....|....|....|....|....|....|....|....|....|....|....|....|....|....|
    CCTGGTGAAATAACCGACCTTTTGCAACTGGCCCGCATACCCACTCTCATGGCATTTGAGCGGGTGCCTGAACCCGTGCCTGCCTCAGAC
     P  G  E  I  T  D  L  L  Q  L  A  R  I  P  T  L  M  A  F  E  R  V  P  E  P  V  P  A  S  D 640       650       660       670       680       690       700       710       720
    ....|....|....|....|....|....|....|....|....|....|....|....|....|....|....|....|....|....|
    ACATATGTGCCCTACGTTGCCGTTCCCACCCAGTTCGATGACAGGCCTCTCATCTCCTTCCCGATCACCCTTTCAGATCCCGTCTATCAG
     T  Y  V  P  Y  V  A  V  P  T  Q  F  D  D  R  P  L  I  S  F  P  I  T  L  S  D  P  V  Y  Q 730       740       750       760       770       780       790       800       810
    ....|....|....|....|....|....|....|....|....|....|....|....|....|....|....|....|....|....|
    AACACCCTGGTTGGCGCCATCAGTTCAAATTTCGCCAATTACCGTGGGTGTATCCAAATCACTCTGACATTTTGTGGACCCATGATGGCG
     N  T  L  V  G  A  I  S  S  N  F  A  N  Y  R  G  C  I  Q  I  T  L  T  F  C  G  P  M  M  A 820       830       840       850       860       870       880       890       900
    ....|....|....|....|....|....|....|....|....|....|....|....|....|....|....|....|....|....|
    AGAGGGAAATTCCTGCTCTCGTATTCTCCCCCAAATGGAACGCAACCACAGACTCTTTCCGAAGCTATGCAGTGCACATACTCTATTTGG
     R  G  K  F  L  L  S  Y  S  P  P  N  G  T  Q  P  Q  T  L  S  E  A  M  Q  C  T  Y  S  I  W 910       920       930       940       950       960       970       980       990
    ....|....|....|....|....|....|....|....|....|....|....|....|....|....|....|....|....|....|
    GACATAGGCTTGAACTCTAGTTGGACCTTCGTCGTCCCCTACATCTCGCCCAGTGACTACCGTGAAACTCGAGCCATTACCAACTCGGTT
     D  I  G  L  N  S  S  W  T  F  V  V  P  Y  I  S  P  S  D  Y  R  E  T  R  A  I  T  N  S  V
```

FIG. 5A

```
            1000      1010      1020      1030      1040      1050      1060      1070      1080
     ....|....|....|....|....|....|....|....|....|....|....|....|....|....|....|....|....|....|
     TACTCCGCTGATGGTTGGTTTAGCCTGCACAAGTTGACCAAAATTACTCTACCACCTGACTGTCCGCAAAGTCCCTGCATTCTCTTTTC
      Y  S  A  D  G  W  F  S  L  H  K  L  T  K  I  T  L  P  P  D  C  P  Q  S  P  C  I  L  F  F 1090      1100      1110      1120      1130      1140      1150      1160      1170
     ....|....|....|....|....|....|....|....|....|....|....|....|....|....|....|....|....|....|
     GCTTCTGCTGGTGAGGATTACACTCTCCGTCTCCCCGTTGATTGTAATCCTTCCTATGTGTTCCACTCCACCGACAACGCCGAGACCGGG
      A  S  A  G  E  D  Y  T  L  R  L  P  V  D  C  N  P  S  Y  V  F  H  S  T  D  N  A  E  T  G 1180      1190      1200      1210      1220      1230      1240      1250      1260
     ....|....|....|....|....|....|....|....|....|....|....|....|....|....|....|....|....|....|
     GTTATTGAGGCGGGTAACACTGACACCGATTTCTCTGGTGAACTGGCGGCTCCTGGCCCTAACCACACTAATGTCAAGTTCCTGTTTGAT
      V  I  E  A  G  N  T  D  T  D  F  S  G  E  L  A  A  P  G  P  N  H  T  N  V  K  F  L  F  D 1270      1280      1290      1300      1310      1320      1330      1340      1350
     ....|....|....|....|....|....|....|....|....|....|....|....|....|....|....|....|....|....|
     CGATCTCGATTATTGAATGTAATCAAGGTACTGGAGAAGGACGCCGTTTTCCCCCGCCCTTTCCCTACACAAGAAGGTGCGCAGCAGGAT
      R  S  R  L  L  N  V  I  K  V  L  E  K  D  A  V  F  P  R  P  F  P  T  Q  E  G  A  Q  Q  D 1360      1370      1380      1390      1400      1410      1420      1430      1440
     ....|....|....|....|....|....|....|....|....|....|....|....|....|....|....|....|....|....|
     GATGGTTACTTTTGTCTTCTGACCCCCCGCCCAACAGTCCCTTCCCGACCCCCCACTCGTTTCGGCCTGTACCCCAATCCGTCCGGCACT
      D  G  Y  F  C  L  L  T  P  R  P  T  V  A  S  R  P  A  T  R  F  G  L  Y  A  N  P  S  G  S 1450      1460      1470      1480      1490      1500      1510      1520      1530
     ....|....|....|....|....|....|....|....|....|....|....|....|....|....|....|....|....|....|
     GGTGTTCTTGCTAACACTTCACTGGACTTCAATTTTTATAGCTTGGCCTGTTTCACTTACTTTAGATCGGACCTTGAGGTTACGGTGGTC
      G  V  L  A  N  T  S  L  D  F  N  F  Y  S  L  A  C  F  T  Y  F  R  S  D  L  E  V  T  V  V 1540      1550      1560      1570      1580      1590      1600      1610      1620
     ....|....|....|....|....|....|....|....|....|....|....|....|....|....|....|....|....|....|
     TCACTAGAGCCGGATCTGGAATTTGCTGTAGGGTGGTTTCCTTCTGGCAGTGAATACCAGGCTTCCAGCTTTGTCTACGACCAGCTGCAT
      S  L  E  P  D  L  E  F  A  V  G  W  F  P  S  G  S  E  Y  Q  A  S  S  F  V  Y  D  Q  L  H 1630      1640      1650      1660      1670      1680      1690      1700      1710
     ....|....|....|....|....|....|....|....|....|....|....|....|....|....|....|....|....|....|
     GTGCCCTTCCACTTTACTGGGCGCACTCCCCGCGCTTTCGCTAGCAAGGGTGGGAAGGTATCTTTCGTGCTCCCTTGGAACTCTGTCTCG
      V  P  F  H  F  T  G  R  T  P  R  A  F  A  S  K  G  G  K  V  S  F  V  L  P  W  N  S  V  S 1720      1730      1740      1750      1760      1770      1780      1790      1800
     ....|....|....|....|....|....|....|....|....|....|....|....|....|....|....|....|....|....|
     TCTGTGCTCCCCGTGCGCTGGGGGGGGGCTTCCAAGCTCTCTTCTGCTACGCGGGGTCTACCGGCGCATGCTGATTGGGGACTATTTAC
      S  V  L  P  V  R  W  G  G  A  S  K  L  S  S  A  T  R  G  L  P  A  H  A  D  W  G  T  I  Y 1810      1820      1830      1840      1850      1860      1870      1880      1890
     ....|....|....|....|....|....|....|....|....|....|....|....|....|....|....|....|....|....|
     GCCTTTGTCCCCCGTCCTAATGAGAAGAAAAGCACCGCTGTAAAACACGTGGCCGTGTACATTCGGTACAAGAACGCACGTGCCTGGTGC
      A  F  V  P  R  P  N  E  K  K  S  T  A  V  K  H  V  A  V  Y  I  R  Y  K  N  A  R  A  W  C 1900      1910      1920      1930      1940      1950      1960      1970      1980
     ....|....|....|....|....|....|....|....|....|....|....|....|....|....|....|....|....|....|
     CCCAGCATGCTTCCCTTTCGCAGCTACAAGCAGAAGATGCTGATGCAATCTGGCGATATCGAGACCAATCCTGGTCCTGCTTCTGACAAC
      P  S  M  L  P  F  R  S  Y  K  Q  K  M  L  M  Q  S  G  D  I  E  T  N  P  G  P  A  S  D  N 1990      2000      2010      2020      2030      2040      2050      2060      2070
     ....|....|....|....|....|....|....|....|....|....|....|....|....|....|....|....|....|....|
     CCAATTTTGGAGTTTCTTGAAGCAGAAAATGATCTAGTCACTCTGGCCTCTCTCTGGAAGATGGTGCACTCTGTTCAACAGACCTGGAGA
      P  I  L  E  F  L  E  A  E  N  D  L  V  T  L  A  S  L  W  K  M  V  H  S  V  Q  Q  T  W  R 2080      2090      2100      2110      2120      2130      2140      2150      2160
     ....|....|....|....|....|....|....|....|....|....|....|....|....|....|....|....|....|....|
     AAGTATGTGAAGAACGATGATTTTTGGCCCAATTTACTCAGCGAGCTAGTGGGGAAGGCTCTGTCGCCTTGGCCGCCACGCTATCCAAC
      K  Y  V  K  N  D  D  F  W  P  N  L  L  S  E  L  V  G  E  G  S  V  A  L  A  A  T  L  S  N
```

FIG. 5B

```
              2170      2180      2190      2200      2210      2220      2230      2240      2250
        ....|....|....|....|....|....|....|....|....|....|....|....|....|....|....|....|....|....|
        CAAGCTTCAGTAAAGGCTCTTTTGGGCCTGCACTTTCTCTCTCGGGGGCTCAATTACACTGACTTTTACTCTTTACTGATAGAGAAATGC
        Q  A  S  V  K  A  L  L  G  L  H  F  L  S  R  G  L  N  Y  T  D  F  Y  S  L  L  I  E  K  C 2260      2270      2280      2290      2300      2310      2320      2330      2340
        ....|....|....|....|....|....|....|....|....|....|....|....|....|....|....|....|....|....|
        TCTAGTTTCTTTACCGTAGAACCACCTCCTCCACCAGCTGAAAACCTGATGACCAAGCCCTCAGTGAAGTCGAAATTCCGAAAACTGTTT
        S  S  F  F  T  V  E  P  P  P  P  P  A  E  N  L  M  T  K  P  S  V  K  S  K  F  R  K  L  F 2350      2360      2370      2380      2390      2400      2410      2420      2430
        ....|....|....|....|....|....|....|....|....|....|....|....|....|....|....|....|....|....|
        AAGATGCAAGGACCCATGGACAAAGTCAAAGACTGGAACCAAATAGCTGCCGGCTTGAAGAATTTTCAATTTGTTCGTGACCTAGTCAAA
        K  M  Q  G  P  M  D  K  V  K  D  W  N  Q  I  A  A  G  L  K  N  F  Q  F  V  R  D  L  V  K 2440      2450      2460      2470      2480      2490      2500      2510      2520
        ....|....|....|....|....|....|....|....|....|....|....|....|....|....|....|....|....|....|
        GAGGTGGTCGATTGGCTGCAGGCCTGGATCAACAAAGAGAAAGCCAGCCCTGTCCTCCAGTACCAGTTGGAGATGAAGAAGCTCGGGCCT
        E  V  V  D  W  L  Q  A  W  I  N  K  E  K  A  S  P  V  L  Q  Y  Q  L  E  M  K  K  L  G  P 2530      2540      2550      2560      2570      2580      2590      2600      2610
        ....|....|....|....|....|....|....|....|....|....|....|....|....|....|....|....|....|....|
        GTGGCCTTGGCTCATGACGCTTTCATGGCTGGTTCCGGGCCCCCTCTTAGCGACGACCAGATTGAATACCTCCAGAACCTCAAATCTCTT
        V  A  L  A  H  D  A  F  M  A  G  S  G  P  P  L  S  D  D  Q  I  E  Y  L  Q  N  L  K  S  L 2620      2630      2640      2650      2660      2670      2680      2690      2700
        ....|....|....|....|....|....|....|....|....|....|....|....|....|....|....|....|....|....|
        GCCCTAACACTGGGGAAGACTAATTTGGCCCAAAGTCTCACCACTATGATCAATGCCAAACAAAGTTCAGCCCAACGAGTTGAACCCGTT
        A  L  T  L  G  K  T  N  L  A  Q  S  L  T  T  M  I  N  A  K  Q  S  S  A  Q  R  V  E  P  V 2710      2720      2730      2740      2750      2760      2770      2780      2790
        ....|....|....|....|....|....|....|....|....|....|....|....|....|....|....|....|....|....|
        GTGGTGGTCCTTAGAGGCAAGCCGGGATGCGGCAAGGGCTTGGCCTCTACGTTGATTGCCCAGGCTGTGTCCAAGCGCCTCTATGGCTCC
        V  V  V  L  R  G  K  P  G  C  G  K  G  L  A  S  T  L  I  A  Q  A  V  S  K  R  L  Y  G  S 2800      2810      2820      2830      2840      2850      2860      2870      2880
        ....|....|....|....|....|....|....|....|....|....|....|....|....|....|....|....|....|....|
        CAAAGTGTATATTCTCTTCCCCCAGATCCAGATTTCTTCGATGGATACAAAGGACAGTTCGTGACCTTGATGGATGATTTGGGACAAAAC
        Q  S  V  Y  S  L  P  P  D  P  D  F  F  D  G  Y  K  G  Q  F  V  T  L  M  D  D  L  G  Q  N 2890      2900      2910      2920      2930      2940      2950      2960      2970
        ....|....|....|....|....|....|....|....|....|....|....|....|....|....|....|....|....|....|
        CCGGATGGACAAGATTTCTCCACCTTTTGTCAGATGGTGTCGACCGCCCAATTTCTCCCCAACATGGCGGACCTTGCAGAGAAAGGGCGT
        P  D  G  Q  D  F  S  T  F  C  Q  M  V  S  T  A  Q  F  L  P  N  M  A  D  L  A  E  K  G  R 2980      2990      3000      3010      3020      3030      3040      3050      3060
        ....|....|....|....|....|....|....|....|....|....|....|....|....|....|....|....|....|....|
        CCCTTTACCTCCAATCTCATCATTGCAACTACAAATCTCCCCCACTTCAGTCCTGTCACCATTGCTGATCCTTCTGCAGTCTCTCGCCGT
        P  F  T  S  N  L  I  I  A  T  T  N  L  P  H  F  S  P  V  T  I  A  D  P  S  A  V  S  R  R 3070      3080      3090      3100      3110      3120      3130      3140      3150
        ....|....|....|....|....|....|....|....|....|....|....|....|....|....|....|....|....|....|
        ATCAACTACGATCTGACTCTAGAAGTATCTGAGGCCTACAAGAAACACACACGGCTGAATTTTGACTTGGCTTTCAGGCGCACAGACGCC
        I  N  Y  D  L  T  L  E  V  S  E  A  Y  K  K  H  T  R  L  N  F  D  L  A  F  R  R  T  D  A 3160      3170      3180      3190      3200      3210      3220      3230      3240
        ....|....|....|....|....|....|....|....|....|....|....|....|....|....|....|....|....|....|
        CCCCCCATTTATCCTTTTGCTGCCCATGTGCCCTTTGTGGACGTAGCTGTGCGCTTCAAAAATGGTCACCAGAATTTTAATCTCCTAGAG
        P  P  I  Y  P  F  A  A  H  V  P  F  V  D  V  A  V  R  F  K  N  G  H  Q  N  F  N  L  L  E 3250      3260      3270      3280      3290      3300      3310      3320      3330
        ....|....|....|....|....|....|....|....|....|....|....|....|....|....|....|....|....|....|
        TTGGTCGATTCCATTTGTACAGACATTCGAGCCAAGCAACAAGGTGCCCGAAACATGCAGACTCTGGTTCTACAGAGCCCAACGAGAAT
        L  V  D  S  I  C  T  D  I  R  A  K  Q  Q  G  A  R  N  M  Q  T  L  V  L  Q  S  P  N  E  N
```

FIG. 5C

```
      3340      3350      3360      3370      3380      3390      3400      3410      3420
....|....|....|....|....|....|....|....|....|....|....|....|....|....|....|....|....|....|
GATGACACCCCCGTCGACGAGGCGTTGGGTAGAGTTCTCTCCCCGCTGCCGGTCGATGAGGCGCTTGTCGACCTCACTCCAGAGGCCGAC
 D  D  T  P  V  D  E  A  L  G  R  V  L  S  P  A  A  V  D  E  A  L  V  D  L  T  P  E  A  D 3430      3440      3450      3460      3470      3480      3490      3500      3510
....|....|....|....|....|....|....|....|....|....|....|....|....|....|....|....|....|....|
CCGGTTGGCCGTTTGGCTATTCTTGCCAAGCTAGGTCTTGCCCTAGCTGCGGTCACCCCTGGTCTGATAATCTTGGCAGTGGGACTCTAC
 P  V  G  R  L  A  I  L  A  K  L  G  L  A  L  A  A  V  T  P  G  L  I  I  L  A  V  G  L  Y 3520      3530      3540      3550      3560      3570      3580      3590      3600
....|....|....|....|....|....|....|....|....|....|....|....|....|....|....|....|....|....|
AGGTACTTCTCTGGCTCTGATGCAGACCAAGAAGAAACAGAAAGTGAGGGATCTGTCAAGGCACCCAGGAGCGAAAATGCTTATGACGGC
 R  Y  F  S  C  S  D  A  D  Q  E  E  T  E  S  E  G  S  V  K  A  P  R  S  E  N  A  Y  D  C 3610      3620      3630      3640      3650      3660      3670      3680      3690
....|....|....|....|....|....|....|....|....|....|....|....|....|....|....|....|....|....|
CCGAAGAAAAACTCTAAGCCCCCTGGAGCACTCTCTCTCATGGAAATGCAACAGCCCAACGTGGACATGGGCTTTGAGGCTGCCGTCGCT
 P  K  K  N  S  K  P  P  G  A  L  S  L  M  E  M  Q  Q  P  N  V  D  M  G  F  E  A  A  V  A 3700      3710      3720      3730      3740      3750      3760      3770      3780
....|....|....|....|....|....|....|....|....|....|....|....|....|....|....|....|....|....|
AAGAAAGTGGTCGTCCCCATTACCTTCATGGTTCCCAACAGACCTTCTGGGCTTACACAGTCCGCTCTTCTGGTGACCGGCCGGACCTTC
 K  K  V  V  V  P  I  T  F  M  V  P  N  R  P  S  G  L  T  Q  S  A  L  L  V  T  G  R  T  F 3790      3800      3810      3820      3830      3840      3850      3860      3870
....|....|....|....|....|....|....|....|....|....|....|....|....|....|....|....|....|....|
CTAATCAATGAACATACATGGTCCAATCCCTCCTGGACCAGCTTCACAATCCGCGGTGAGGTACACACTCGTGATGAGCCCTTCCAAACG
 L  I  N  E  H  T  W  S  N  P  S  W  T  S  F  T  I  R  G  E  V  H  T  R  D  E  P  F  Q  T 3880      3890      3900      3910      3920      3930      3940      3950      3960
....|....|....|....|....|....|....|....|....|....|....|....|....|....|....|....|....|....|
GTTCATTTCACTCACCACGGTATTCCCACAGATCTGATGATGGTACGTCTCGGACCGGGCAATTCTTTCCCTAACAATCTAGACAAGTTT
 V  H  F  T  H  H  G  I  P  T  D  L  M  M  V  R  L  G  P  G  N  S  F  P  N  N  L  D  K  F 3970      3980      3990      4000      4010      4020      4030      4040      4050
....|....|....|....|....|....|....|....|....|....|....|....|....|....|....|....|....|....|
GGACTTGACCAGATGCCGGCACGCAACTCCCGTGTGGTTGGCGTTTCGTCCAGTTACGGAAACTTCTTCTTCTCTGGAAATTTCCTCGGA
 G  L  D  Q  M  P  A  R  N  S  R  V  V  G  V  S  S  S  Y  G  N  F  F  F  S  G  N  F  L  G 4060      4070      4080      4090      4100      4110      4120      4130      4140
....|....|....|....|....|....|....|....|....|....|....|....|....|....|....|....|....|....|
TTTGTTGATTCCGTCACCTCTGAACAAGGAACTTACGCAAGACTCTTTAGGTACAGGGTGACGACCTACAAAGGATGGTGCGGCTCGGCC
 F  V  D  S  V  T  S  E  Q  G  T  Y  A  R  L  F  R  Y  R  V  T  T  Y  K  G  W  C  G  S  A 4150      4160      4170      4180      4190      4200      4210      4220      4230
....|....|....|....|....|....|....|....|....|....|....|....|....|....|....|....|....|....|
CTGGTCTGTGAGGCCGGTGGCGTCCGACGCATCATTGGCCTGCATTCTGCTGGCGCCGCCGGTATCGGCGCCGGGACCTATATCTCAAAA
 L  V  C  E  A  G  G  V  R  R  I  I  G  L  H  S  A  G  A  A  G  I  G  A  G  T  Y  I  S  K 4240      4250      4260      4270      4280      4290      4300      4310      4320
....|....|....|....|....|....|....|....|....|....|....|....|....|....|....|....|....|....|
TTAGGACTAATCAAAGCCCTGAAACACCTCGGTGAACCTTTGGCCACAATGCAAGGACTGATGACTGAATTAGAGCCTGGAATCACCGTA
 L  G  L  I  K  A  L  K  H  L  G  E  P  L  A  T  M  Q  G  L  M  T  E  L  E  P  G  I  T  V 4330      4340      4350      4360      4370      4380      4390      4400      4410
....|....|....|....|....|....|....|....|....|....|....|....|....|....|....|....|....|....|
CATGTACCCCGGAAATCCAAATTGAGAAAGACGACCGCACACGCGGTGTACAAACCGGAGTTTGAGCCTGCTGTGTTGTCAAAATTTGAT
 H  V  P  R  K  S  K  L  R  K  T  T  A  H  A  V  Y  K  P  E  F  E  P  A  V  L  S  K  F  D 4420      4430      4440      4450      4460      4470      4480      4490      4500
....|....|....|....|....|....|....|....|....|....|....|....|....|....|....|....|....|....|
CCCAGACTGAACAAGGATGTTGACTTGGATGAAGTAATTTGGTCTAAACACACTGCCAATGTCCCTTACCAACCTCCTTTGTTCTACACA
 P  R  L  N  K  D  V  D  L  D  E  V  I  W  S  K  H  T  A  N  V  P  Y  Q  P  P  L  F  Y  T
```

FIG. 5D

```
        4510      4520      4530      4540      4550      4560      4570      4580      4590
....|....|....|....|....|....|....|....|....|....|....|....|....|....|....|....|....|....|
TACATGTCAGAGTACGCTCATCGAGTCTTCTCCTTCTTGGGGAAAGACAATGACATTCTGACCGTCAAAGAAGCAATTCTGGGCATCCCC
 Y  M  S  E  Y  A  H  R  V  F  S  F  L  G  K  D  N  D  I  L  T  V  K  E  A  I  L  G  I  P 4600      4610      4620      4630      4640      4650      4660      4670      4680
....|....|....|....|....|....|....|....|....|....|....|....|....|....|....|....|....|....|
GGACTAGACCCCATGGATCCCCACACAGCTCCGGGTCTGCCTTACGCCATCAACGGCCTTCGACGTACTGATCTCGTCGATTTTGTGAAC
 G  L  D  P  M  D  P  H  T  A  P  G  L  P  Y  A  I  N  G  L  R  R  T  D  L  V  D  F  V  N 4690      4700      4710      4720      4730      4740      4750      4760      4770
....|....|....|....|....|....|....|....|....|....|....|....|....|....|....|....|....|....|
GGTACAGTAGATGCGGCGCTGGCTGTACAAATCCAGAAATTCTTAGACGGTGACTACTCTGACCATGTCTTCCAAACTTTTCTGAAAGAT
 G  T  V  D  A  A  L  A  V  Q  I  Q  K  F  L  D  G  D  Y  S  D  H  V  F  Q  T  F  L  K  D 4780      4790      4800      4810      4820      4830      4840      4850      4860
....|....|....|....|....|....|....|....|....|....|....|....|....|....|....|....|....|....|
GAGATCAGACCCTCAGAGAAAGTCCGAGCGGGAAAAACCCGCATTGTTGATGTGCCCTCCCTGGCGCATTGCATTGTGGGCAGAATGTTG
 E  I  R  P  S  E  K  V  R  A  G  K  T  R  I  V  D  V  P  S  L  A  H  C  I  V  G  R  M  L 4870      4880      4890      4900      4910      4920      4930      4940      4950
....|....|....|....|....|....|....|....|....|....|....|....|....|....|....|....|....|....|
CTTGGGCGCTTTGCTGCCAAGTTTCAATCCCATCCTGGCTTTCTCCTCGGCTCTGCTATCGGGTCTGACCCTGATGTTTTCTGGACCGTC
 L  G  R  F  A  A  K  F  Q  S  H  P  G  F  L  L  G  S  A  I  G  S  D  P  D  V  F  W  T  V 4960      4970      4980      4990      5000      5010      5020      5030      5040
....|....|....|....|....|....|....|....|....|....|....|....|....|....|....|....|....|....|
ATAGGGGCTCAACTCGAGGGGAGAAAGAACACGTATGACGTGGACTACAGTGCCTTTGACTCTTCACACGGCACTGGCTCCTTCGAGGCT
 I  G  A  Q  L  E  G  R  K  N  T  Y  D  V  D  Y  S  A  F  D  S  S  H  G  T  G  S  F  E  A 5050      5060      5070      5080      5090      5100      5110      5120      5130
....|....|....|....|....|....|....|....|....|....|....|....|....|....|....|....|....|....|
CTCATCTCTCACTTTTTCACCGTGGACAATGGTTTTAGCCCTGCGCTGGGACCGTATCTCAGATCCCTGGCTGTCTCGGTGCACGCTTAC
 L  I  S  H  F  F  T  V  D  N  G  F  S  P  A  L  G  P  Y  L  R  S  L  A  V  S  V  H  A  Y 5140      5150      5160      5170      5180      5190      5200      5210      5220
....|....|....|....|....|....|....|....|....|....|....|....|....|....|....|....|....|....|
GGCGAGCGTCGCATCAAGATTACCGGTGGCCTCCCCTCCGGTTGTGCCGCGACCAGCCTGCTGAACACAGTGCTCAACATGTGATCATC
 G  E  R  R  I  K  I  T  G  G  L  P  S  G  C  A  A  T  S  L  L  N  T  V  L  N  N  V  I  I 5230      5240      5250      5260      5270      5280      5290      5300      5310
....|....|....|....|....|....|....|....|....|....|....|....|....|....|....|....|....|....|
AGGACTGCTCTGGCCATTGACTTACAAGGAATTTGAGTATGACACGGTTGATATCATCGCCTACGGTGACGACCTTCTGGTTGGCACGGAT
 R  T  A  L  A  L  T  Y  K  E  F  E  Y  D  T  V  D  I  I  A  Y  G  D  D  L  L  V  G  T  D 5320      5330      5340      5350      5360      5370      5380      5390      5400
....|....|....|....|....|....|....|....|....|....|....|....|....|....|....|....|....|....|
TACGATCTGGACTTCAATGAGGTGGCACGACGCGCTGCCAAGTTGGGGTATAAGATGACTCCTGCCAACAAGGGTTCTGTCTTCCCTCCG
 Y  D  L  D  F  N  E  V  A  R  R  A  A  K  L  G  Y  K  M  T  P  A  N  K  G  S  V  F  P  P 5410      5420      5430      5440      5450      5460      5470      5480      5490
....|....|....|....|....|....|....|....|....|....|....|....|....|....|....|....|....|....|
ACTTCCTCTCTTTCCGATGCTGTTTTTCTAAAGCGCAAATTCGTCCAAAACAACGACGGCTTATACAAACCAGTTATGGATTTAAAGAAT
 T  S  S  L  S  D  A  V  F  L  K  R  K  F  V  Q  N  N  D  G  L  Y  K  P  V  M  D  L  K  N 5500      5510      5520      5530      5540      5550      5560      5570      5580
....|....|....|....|....|....|....|....|....|....|....|....|....|....|....|....|....|....|
TTGGAAGCCATGCTCTCCTACTTCAAACCAGGAACACTACTCGAGAAGCTGCAATCTGTTTCTATGTTGGCTCAACATTCTGGAAAAGAA
 L  E  A  M  L  S  Y  F  K  P  G  T  L  L  E  K  L  Q  S  V  S  M  L  A  Q  H  S  G  K  E 5590      5600      5610      5620      5630      5640      5650      5660      5670
....|....|....|....|....|....|....|....|....|....|....|....|....|....|....|....|....|....|
GAATATGATAGATTGATGCACCCCTTCGCTGACTACGGTGCCGTACCGAGTCACGAGTACCTGCAGGCAAGATGGAGGGCCTTGTTCGAC
 E  Y  D  R  L  M  H  P  F  A  D  Y  G  A  V  P  S  H  E  Y  L  Q  A  R  W  R  A  L  F  D 5680      5690      5700      5710      5720      5730      5740      5750
....|....|....|....|....|....|....|....|....|....|....|....|....|....|....|....|....|.
TGACCCAGATAGCCCAAGGCGCTTCGGTGCTGCCGGCGATTCTGGGAGAACTCAGTCGGAACAGAAAAAAAAAAAAAAAAAA
 *
```

FIG. 5E

```
NNTCTAGCCC ACCATGGCAA CAAGAAGAGC TTACAGGAGC TGAATGAAGA ACAGTGGGTG  60
GAAATGTCTG ACGATTACCG GACCGGGAAA ACATGCCTT TTCAGTCTCT TGGCACATAC  120
TATCGGCCCC CTAACTGGAC TTGGGGTCCC AATTTCATCA ACCCCTATCA AGTAACGGTT  180
TTCCCACACC AAATTCTGAA CGCGAGAACC TCTACCTCGG TAGACATAAA CGTCCCATAC  240
ATCGGGGAGA CCCCCACGCA ATCCTCAGAG ACACAGAACT CCTGGACCCT CCTCGTTATG  300
GTGCTCGTTC CCTAGACTA TAAGGAAGGA GCCACAACTG ACCCAGAAAT TACATTTTCT  360
GTAAGGCCTA CAAGTCCCTA CTTCAATGGG CTTCGCAACC GCTACACGGC CGGGACGGAC  420
GAAGAACAGG GGCCCATTCC TACGGCACCC AGAGAAAATT CGCTTATGTT TCTCTCAACC  480
CTCCCTGACG ACACTGTCCC TGCTTACGGG AATGTGCGTA CCCCTCCTGT CAATTACCTC  540
CCTGGTGAAA TAACCGACCT TTTGCAACTG GCCCGCATAC CCACTCTCAT GGCATTTGAG  600
CGGGTGCCTG AACCCGTGCC TGCCTCAGAC ACATATGTGC CTACGTTGC CGTTCCCACC  660
CAGTTCGATG ACAGGCCTCT CATCTCCTTC CCGATCACCC TTTCAGATCC CGTCTATCAG  720
AACACCCTGG TTGGCGCCAT CAGTTCAAAT TCGCCAATT ACCGTGGGTG TATCCAAATC  780
ACTCTGACAT TTTGTGGACC CATGATGGCG AGAGGGAAAT TCCTGCTCTC GTATTCTCCC  840
CCAAATGGAA CGCAACCACA GACTCTTTCC GAAGCTATGC AGTGCACATA CTCTATTTGG  900
GACATAGGCT TGAACTCTAG TTGGACCTTC GTCGTCCCCT ACATCTCGCC CAGTGACTAC  960
CGTGAAACTC GAGCCATTAC CAACTCGGTT TACTCCGCTG ATGGTTGGTT TAGCCTGCAC  1020
AAGTTGACCA AAATTACTCT ACCACCTGAC TGTCCGCAAA GTCCCTGCAT TCTCTTTTTC  1080
GCTTCTGCTG GTGAGGATTA CACTCTCCGT CTCCCCGTTG ATTGTAATCC TTCCTATGTG  1140
TTCCACTCCA CCGACAACGC CGAGACCGGG GTTATTGAGG CGGGTAACAC TGACACCGAT  1200
TTCTCTGGTG AACTGGCGGC TCCTGGCCCT AACCACACTA ATGTCAAGTT CCTGTTTGAT  1260
CGATCTCGAT TATTGAATGT AATCAAGGTA CTGGAGAAGG ACGCCGTTTT CCCCCGCCCT  1320
TTCCCTACAC AAGAAGGTGC GCAGCAGGAT GATGGTTACT TTTGTCTTCT GACCCCCCGC  1380
CCAACAGTCG CTTCCCGACC CGCCACTCGT TTCGGCCTGT ACGCCAATCC GTCCGGCAGT  1440
GGTGTTCTTG CTAACACTTC ACTGGACTTC AATTTTTATA GCTTGGCCTG TTTCACTTAC  1500
```

FIG. 6A

```
TTTAGATCGG ACCTTGAGGT TACGGTGGTC TCACTAGAGC CGGATCTGGA ATTTGCTGTA 1560

GGGTGGTTTC CTTCTGGCAG TGAATACCAG GCTTCCAGCT TTGTCTACGA CCAGCTGCAT 1620

GTGCCCTTCC ACTTTACTGG GCGCACTCCC CGCGCTTTCG CTAGCAAGGG TGGGAAGGTA 1680

TCTTTCGTGC TCCCTTGGAA CTCTGTCTCG TCTGTGCTCC CCGTGCGCTG GGGGGGGGCT 1740

TCCAAGCTCT CTTCTGCTAC GCGGGGTCTA CCGGCGCATG CTGATTGGGG GACTATTTAC 1800

GCCTTTGTCC CCCGTCCTAA TGAGAAGAAA AGCACCGCTG TAAAACACGT GGCCGTGTAC 1860

ATTCGGTACA AGAACGCACG TGCCTGGTGC CCCAGCATGC TTCCCTTTCG CAGCTACAAG 1920

CAGAAGATGC TGATGCAATC TGGCGATATC GAGACCAATC CTGGTCCTGC TTCTGACAAC 1980

CCAATTTTGG AGTTTCTTGA AGCAGAAAAT GATCTAGTCA CTCTGGCCTC TCTCTGGAAG 2040

ATGGTGCACT CTGTTCAACA GACCTGGAGA AAGTATGTGA AGAACGATGA TTTTTGGCCC 2100

AATTTACTCA GCGAGCTAGT GGGGGAAGGC TCTGTCGCCT TGGCCGCCAC GCTATCCAAC 2160

CAAGCTTCAG TAAAGGCTCT TTTGGGCCTG CACTTTCTCT CTCGGGGGCT CAATTACACT 2220

GACTTTTACT CTTTACTGAT AGAGAAATGC TCTAGTTTCT TTACCGTAGA ACCACCTCCT 2280

CCACCAGCTG AAAACCTGAT GACCAAGCCC TCAGTGAAGT CGAAATTCCG AAAACTGTTT 2340

AAGATGCAAG GACCCATGGA CAAAGTCAAA GACTGGAACC AAATAGCTGC CGGCTTGAAG 2400

AATTTTCAAT TTGTTCGTGA CCTAGTCAAA GAGGTGGTCG ATTGGCTGCA GGCCTGGATC 2460

AACAAAGAGA AAGCCAGCCC TGTCCTCCAG TACCAGTTGG AGATGAAGAA GCTCGGGCCT 2520

GTGGCCTTGG CTCATGACGC TTTCATGGCT GGTTCCGGGC CCCCTCTTAG CGACGACCAG 2580

ATTGAATACC TCCAGAACCT CAAATCTCTT GCCCTAACAC TGGGGAAGAC TAATTTGGCC 2640

CAAAGTCTCA CCACTATGAT CAATGCCAAA CAAAGTTCAG CCCAACGAGT TGAACCCGTT 2700

GTGGTGGTCC TTAGAGGCAA GCCGGGATGC GGCAAGGGCT TGGCCTCTAC GTTGATTGCC 2760

CAGGCTGTGT CCAAGCGCCT CTATGGCTCC AAAGTGTAT ATTCTCTTCC CCCAGATCCA 2820

GATTTCTTCG ATGGATACAA AGGACAGTTC GTGACCTTGA TGGATGATTT GGGACAAAAC 2880

CCGGATGGAC AAGATTTCCC CACCTTTTGT CAGATGGTGT CGACCGCCCA ATTTCTCCCC 2940

AACATGGCGG ACCTTGCAGA GAAGGGCGT CCCTTTACCT CCAATCTCAT CATTGCAACT 3000
```

FIG. 6B

```
ACAAATCTCC CCCACTTCAG TCCTGTCACC ATTGCTGATC CTTCTGCAGT CTCTCGCCGT 3060
ATCAACTACG ATCTGACTCT AGAAGTATCT GAGGCCTACA AGAAACACAC ACGGCTGAAT 3120
TTTGACTTGG CTTTCAGGCG CACAGACGCC CCCCCATTT ATCCTTTTGC TGCCCATGTG 3180
CCCTTTGTGG ACGTAGCTGT GCGCTTCAAA AATGGTCACC AGAATTTTAA TCTCCTAGAG 3240
TTGGTCGATT CCATTTGTAC AGACATTCGA GCCAAGCAAC AAGGTGCCCG AAACATGCAG 3300
ACTCTGGTTC TACAGAGCCC CAACGAGAAT GATGACACCC CCGTCGACGA GGCGTTGGGT 3360
AGAGTTCTCT CCCCCGCTGC GGTCGATGAG GCGCTTGTCG ACCTCACTCC AGAGGCCGAC 3420
CCGGTTGGCC GTTTGGCTAT TCTTGCCAAG CTAGGTCTTG CCCTAGCTGC GGTCACCCCT 3480
GGTCTGATAA TCTTGGCAGT GGGACTCTAC AGGTACTTCT CTGGCTCTGA TGCAGACCAA 3540
GAAGAAACAG AAAGTGAGGG ATCTGTCAAG GCACCCAGGA GCGAAAATGC TTATGACGGC 3600
CCGAAGAAAA ACTCTAAGCC CCCTGGAGCA CTCTCTCTCA TGGAAATGCA ACAGCCCAAC 3660
GTGGACATGG GCTTTGAGGC TGCGGTCGCT AAGAAAGTGG TCGTCCCCAT TACCTTCATG 3720
GTTCCCAACA GACCTTCTGG GCTTACACAG TCCGCTCTTC TGGTGACCGG CCGGACCTTC 3780
CTAATCAATG AACATACATG GTCCAATCCC TCCTGGACCA GCTTCACAAT CCGCGGTGAG 3840
GTACACACTC GTGATGAGCC CTTCCAAACG GTTCATTTCA CTCACCACGG TATTCCCACA 3900
GATCTGATGA TGGTACGTCT CGGACCGGGC AATTCTTTCC CTAACAATCT AGACAAGTTT 3960
GGACTTGACC AGATGCCGGC ACGCAACTCC CGTGTGGTTG GCGTTTCGTC CAGTTACGGA 4020
AACTTCTTCT TCTCTGGAAA TTTCCTCGGA TTTGTTGATT CCGTCACCTC TGAACAAGGA 4080
ACTTACGCAA GACTCTTTAG GTACAGGGTG ACGACCTACA AGGATGGTC CGGCTCGGCC 4140
CTGGTCTGTG AGGCCGGTGG CGTCCGACGC ATCATTGGCC TGCATTCTGC TGGCGCCGCC 4200
GGTATCGGCG CCGGGACCTA TATCTCAAAA TTAGGACTAA TCAAAGCCCT GAAACACCTC 4260
GGTGAACCTT TGGCCACAAT GCAAGGACTG ATGACTGAAT TAGAGCCTGG AATCACCGTA 4320
CATGTACCCC GGAAATCCAA ATTGAGAAAG ACGACCGCAC ACGCGGTGTA CAAACCGGAG 4380
TTTGAGCCTG CTGTGTTGTC AAAATTTGAT CCCAGACTGA ACAAGGATGT TGACTTGGAT 4440
GAAGTAATTT GGTCTAAACA CACTGCCAAT GTCCCTTACC AACCTCCTTT GTTCTACACA 4500
```

FIG. 6C

```
TACATGTCAG AGTACGCTCA TCGAGTCTTC TCCTTCTTGG GGAAAGACAA TGACATTCTG 4560
ACCGTCAAAG AAGCAATTCT GGGCATCCCC GGACTAGACC CCATGGATCC CCACACAGCT 4620
CCGGGTCTGC CTTACGCCAT CAACGGCCTT CGACGTACTG ATCTCGTCGA TTTTGTGAAC 4680
GGTACAGTAG ATGCGGCGCT GGCTGTACAA ATCCAGAAAT CTTAGACGG TGACTACTCT 4740
GACCATGTCT TCCAAACTTT TCTGAAAGAT GAGATCAGAC CCTCAGAGAA AGTCCGAGCG 4800
GGAAAAACCC GCATTGTTGA TGTGCCCTCC CTGGCGCATT GCATTGTGGG CAGAATGTTG 4860
CTTGGGCGCT TGCTGCCAA GTTTCAATCC CATCCTGGCT TTCTCCTCGG CTCTGCTATC 4920
GGGTCTGACC CTGATGTTTT CTGGACCGTC ATAGGGGCTC AACTCGAGGG GAGAAAGAAC 4980
ACGTATGACG TGGACTACAG TGCCTTTGAC TCTTCACACG GCACTGGCTC CTTCGAGGCT 5040
CTCATCTCTC ACTTTTTCAC CGTGGACAAT GGTTTTAGCC CTGCGCTGGG ACCGTATCTC 5100
AGATCCCTGG CTGTCTCGGT GCACGCTTAC GGCGAGCGTC GCATCAAGAT TACCGGTGGC 5160
CTCCCCTCCG GTTGTGCCGC GACCAGCCTG CTGAACACAG TGCTCAACAA TGTGATCATC 5220
AGGACTGCTC TGGCATTGAC TTACAAGGAA TTTGAGTATG ACACGGTTGA TATCATCGCC 5280
TACGGTGACG ACCTTCTGGT TGGCACGGAT TACGATCTGG ACTTCAATGA GGTGGCACGA 5340
CGCGCTGCCA AGTTGGGGTA TAAGATGACT CCTGCCAACA AGGGTTCTGT CTTCCCTCCG 5400
ACTTCCTCTC TTTCCGATGC TGTTTTTCTA AAGCGCAAAT TCGTCCAAAA CAACGACGGC 5460
TTATACAAAC CAGTTATGGA TTTAAAGAAT TTGGAAGCCA TGCTCTCCTA CTTCAAACCA 5520
GGAACACTAC TCGAGAAGCT GCAATCTGTT TCTATGTTGG CTCAACATTC TGGAAAAGAA 5580
GAATATGATA GATTGATGCA CCCCTTCGCT GACTACGGTG CCGTACCGAG TCACGAGTAC 5640
CTGCAGGCAA GATGGAGGGC CTTGTTCGAC TGACCCAGAT AGCCCAAGGC GCTTCGGTGC 5700
TGCCGGCGAT TCTGGGAGAA CTCAGTCGGA ACAGAAAAAA AAAAAAAAA AA        5752

(SEQ ID NO:1)
```

FIG. 6D

```
XLAHHGNKKS  LQELNEEQWV  EMSDDYRTGK  NMPFQSLGTY  YRPPNWTWGP  NFINPYQVTV    60

FPHQILNART  STSVDINVPY  IGETPTQSSE  TQNSWTLLVM  VLVPLDYKEG  ATTDPEITFS   120

VRPTSPYFNG  LRNRYTAGTD  EEQGPIPTAP  RENSLMFLST  LPDDTVPAYG  NVRTPPVNYL   180

PGEITDLLQL  ARIPTLMAFE  RVPEPVPASD  TYVPYVAVPT  QFDDRPLISF  PITLSDPVYQ   240

NTLVGAISSN  FANYRGCIQI  TLTFCGPMMA  RGKFLLSYSP  PNGTQPQTLS  EAMQCTYSIW   300

DIGLNSSWTF  VVPYISPSDY  RETRAITNSV  YSADGWFSLH  KLTKITLPPD  CPQSPCILFF   360

ASAGEDYTLR  LPVDCNPSYV  FHSTDNAETG  VIEAGNTDTD  FSGELAAPGP  NHTNVKFLFD   420

RSRLLNVIKV  LEKDAVFPRP  FPTQEGAQQD  DGYFCLLTPR  PTVASRPATR  FGLYANPSGS   480

GVLANTSLDF  NFYSLACFTY  FRSDLEVTVV  SLEPDLEFAV  GWFPSGSEYQ  ASSFVYDQLH   540

VPFHFTGRTP  RAFASKGGKV  SFVLPWNSVS  SVLPVRWGGA  SKLSSATRGL  PAHADWGTIY   600

AFVPRPNEKK  STAVKHVAVY  IRYKNARAWC  PSMLPFRSYK  QKMLQSGDI   ETNPGPASDN   660

PILEFLEAEN  DLVTLASLWK  MVHSVQQTWR  KYVKNDDFWP  NLLSELVGEG  SVALAATLSN   720

QASVKALLGL  HFLSRGLNYT  DFYSLLIEKC  SSFFTVEPPP  PPAENLMTKP  SVKSKFRKLF   780

KMQGPMDKVK  DWNQIAAGLK  NFQFVRDLVK  EVVDWLQAWI  NKEKASPVLQ  YQLEMKKLGP   840

VALAHDAFMA  GSGPPLSDDQ  IEYLQNLKSL  ALTLGKTNLA  QSLTTMINAK  QSSAQRVEPV   900

VVVLRGKPGC  GKGLASTLIA  QAVSKRLYGS  QSVYSLPPDP  DFFDGYKGQF  VTLMDDLGQN   960

PDGQDFSTFC  QMVSTAQFLP  NMADLAEKGR  PFTSNLIIAT  TNLPHFSPVT  IADPSAVSRR  1020

INYDLTLEVS  EAYKKHTRLN  FDLAFRRTDA  PPIYPFAAHV  PFVDVAVRFK  NGHQNFNLLE  1080

LVDSICTDIR  AKQQGARNMQ  TLVLQSPNEN  DDTPVDEALG  RVLSPAAVDE  ALVDLTPEAD  1140

PVGRLAILAK  LGLALAAVTP  GLIILAVGLY  RYFSGSDADQ  EETESEGSVK  APRSENAYDG  1200
```

FIG. 7A

```
PKKNSKPPGA LSLMEMQQPN VDMGFEAAVA KKVVVPITFM VPNRPSGLTQ SALLVTGRTF 1260
LINEHTWSNP SWTSFTIRGE VHTRDEPFQT VHFTHHGIPT DLMMVRLGPG NSFPNNLDKF 1320
GLDQMPARNS RVVGVSSSYG NFFFSGNFLG FVDSVTSEQG TYARLFRYRV TTYKGWCGSA 1380
LVCEAGGVRR IIGLHSAGAA GIGAGTYISK LGLIKALKHL GEPLATMQGL MTELEPGITV 1440
HVPRKSLRK  TTAHAVYKPE FEPAVLSKFD PRLNKDVDLD EVIWSKHTAN VPYQPPLFYT 1500
YMSEYAHRVF SFLGKDNDIL TVKEAILGIP GLDPMDPHTA PGLPYAINGL RRTDLVDFVN 1560
GTVDAALAVQ IQKFLDGDYS DHVFQTFLKD EIRPSEKVRA GKTRIVDVPS LAHCIVGRML 1620
LGRFAAKFQS HPGFLLGSAI GSDPDVFWTV IGAQLEGRKN TYDVDYSAFD SSHGTGSFEA 1680
LISHFFTVDN GFSPALGPYL RSLAVSVHAY GERRIKITGG LPSGCAATSL LNTVLNNVII 1740
RTALALTYKE FEYDTVDIIA YGDDLLVGTD YDLDFNEVAR RAAKLGYKMT PANKGSVFPP 1800
TSSLSDAVFL KRKFVQNNDG LYKPVMDLKN LEAMLSYFKP GTLLEKLQSV SMLAQHSGKE 1860
EYDRLMHPFA DYGAVPSHEY LQARWRALFD * (SEQ ID NO:2)                 1890
```

FIG. 7B

CTAGCCCACC ATGGCAACAA GAAGAGCTTA CAGGAGCTGA ATGAAGAACA GTGGGTGGAA 60

ATGTCTGACG ATTACCGGAC CGGGAAAAAC ATGCCTTTTC AGTCTCTTGG CACATACTAT 120

CGGCCCCCTA ACTGGACTTG GGGTCCCAAT TCATCAACC CCTATCAAGT AACGGTTTTC 180

CCACACCAAA TTCTGAACGC GAGAACCTCT ACCTCGGTAG ACATAAACGT CCCATACATC 240

GGGGAGACCC CCACGCAATC CTCAGAGACA CAGAACTCCT GGACCCTCCT CGTTATGGTG 300

CTCGTTCCCC TAGACTATAA GGAAGGAGCC ACAACTGACC CAGAAATTAC ATTTTCTGTA 360

AGGCCTACAA GTCCCTACTT CAATGGGCTT CGCAACCGCT ACACGGCCGG GACGGACGAA 420

GAACAG (SEQ ID NO:3)                                              426

FIG. 8

LAHHGNKKSL QELNEEQWVE MSDDYRTGKN MPFQSLGTYY RPPNWTWGPN FINPYQVTVF 60

PHQILNARTS TSVDINVPYI GETPTQSSET QNSWTLLVMV LVPLDYKEGA TTDPEITFSV 120

RPTSPYFNGL RNRYTAGTDE EQ (SEQ ID NO:4)                            142

FIG. 9

```
GGGCCCATTC CTACGGCACC CAGAGAAAAT TCGCTTATGT TTCTCTCAAC CCTCCCTGAC   60
GACACTGTCC CTGCTTACGG GAATGTGCGT ACCCTCCTG TCAATTACCT CCCTGGTGAA   120
ATAACCGACC TTTTGCAACT GGCCCGCATA CCCACTCTCA TGGCATTTGA GCGGGTGCCT   180
GAACCCGTGC CTGCCTCAGA CACATATGTG CCCTACGTTG CCGTTCCCAC CCAGTTCGAT   240
GACAGGCCTC TCATCTCCTT CCCGATCACC CTTTCAGATC CGTCTATCA GAACACCCTG   300
GTTGGCGCCA TCAGTTCAAA TTTCGCCAAT TACCGTGGGT GTATCCAAAT CACTCTGACA   360
TTTTGTGGAC CCATGATGGC GAGAGGGAAA TTCCTGCTCT CGTATTCTCC CCCAAATGGA   420
ACGCAACCAC AGACTCTTTC CGAAGCTATG CAGTGCACAT ACTCTATTTG GACATAGGC   480
TTGAACTCTA GTTGGACCTT CGTCGTCCCC TACATCTCGC CAGTGACTA CCGTGAAACT   540
CGAGCCATTA CCAACTCGGT TTACTCCGCT GATGGTTGGT TTAGCCTGCA CAAGTTGACC   600
AAAATTACTC TACCACCTGA CTGTCCGCAA AGTCCCTGCA TTCTCTTTTT CGCTTCTGCT   660
GGTGAGGATT ACACTCTCCG TCTCCCCGTT GATTGTAATC CTTCCTATGT GTTCCAC     717
(SEQ ID NO:5)
```

FIG. 10

```
GPIPTAPREN SLMFLSTLPD DTVPAYGNVR TPPVNYLPGE ITDLLQLARI PTLMAFERVP   60
EPVPASDTYV PYVAVPTQFD DRPLISFPIT LSDPVYQNTL VGAISSNFAN YRGCIQITLT  120
FCGPMMARGK FLLSYSPPNG TQPQTLSEAM QCTYSIWDIG LNSSWTFVVP YISPSDYRET  180
RAITNSVYSA DGWFSLHKLT KITLPPDCPQ SPCILFFASA GEDYTLRLPV DCNPSYVFH   239
(SEQ ID NO:6)
```

FIG. 11

```
TCCACCGACA ACGCCGAGAC CGGGGTTATT GAGGCGGGTA ACACTGACAC CGATTTCTCT  60
GGTGAACTGG CGGCTCCTGG CCCTAACCAC ACTAATGTCA AGTTCCTGTT TGATCGATCT 120
CGATTATTGA ATGTAATCAA GGTACTGGAG AAGGACGCCG TTTTCCCCCG CCCTTTCCCT 180
ACACAAGAAG GTGCGCAGCA GGATGATGGT TACTTTGTC TTCTGACCCC CCGCCCAACA 240
GTCGCTTCCC GACCCGCCAC TCGTTTCGGC CTGTACGCCA ATCCGTCCGG CAGTGGTGTT 300
CTTGCTAACA CTTCACTGGA CTTCAATTTT TATAGCTTGG CCTGTTTCAC TTACTTTAGA 360
TCGGACCTTG AGGTTACGGT GGTCTCACTA GAGCCGGATC TGGAATTTGC TGTAGGGTGG 420
TTTCCTTCTG GCAGTGAATA CCAGGCTTCC AGCTTTGTCT ACGACCAGCT GCATGTGCCC 480
TTCCACTTTA CTGGGCGCAC TCCCCGCGCT TCGCTAGCA AGGGTGGGAA GGTATCTTTC 540
GTGCTCCCTT GGAACTCTGT CTCGTCTGTG CTCCCCGTGC GCTGGGGGGG GGCTTCCAAG 600
CTCTCTTCTG CTACGCGGGG TCTACCGGCG CATGCTGATT GGGGGACTAT TTACGCCTTT 660
GTCCCCCGTC CTAATGAGAA GAAAAGCACC GCTGTAAAAC ACGTGGCCGT GTACATTCGG 720
TACAAGAACG CACGTGCCTG GTGCCCCAGC ATGCTTCCCT TTCGCAGCTA CAAGCAG    777
(SEQ ID NO:7)
```

FIG. 12

```
STDNAETGVI EAGNTDTDFS GELAAPGPNH TNVKFLFDRS RLLNVIKVLE KDAVFPRPFP  60
TQEGAQQDDG YFCLLTPRPT VASRPATRFG LYANPSGSGV LANTSLDFNF YSLACFTYFR 120
SDLEVTVVSL EPDLEFAVGW FPSGSEYQAS SFVYDQLHVP FHFTGRTPRA FASKGGKVSF 180
VLPWNSVSSV LPVRWGGASK LSSATRGLPA HADWGTIYAF VPRPNEKKST AVKHVAVYIR 240
YKNARAWCPS MLPFRSYKQ (SEQ ID NO:8)                                259
```

FIG. 13

AAGATGCTGA TGCAATCTGG CGATATCGAG ACCAATCCTG GT (SEQ ID NO:9)    42

FIG. 14

KMLMQSGDIE TNPG (SEQ ID NO:10)    14

FIG. 15

CCTGCTTCTG ACAACCCAAT TTTGGAGTTT CTTGAAGCAG AAAATGATCT AGTCACTCTG 60
GCCTCTCTCT GGAAGATGGT GCACTCTGTT CAACAGACCT GGAGAAAGTA TGTGAAGAAC 120
GATGATTTTT GGCCCAATTT ACTCAGCGAG CTAGTGGGGG AAGGCTCTGT CGCCTTGGCC 180
GCCACGCTAT CCAACCAAGC TTCAGTAAAG GCTCTTTTGG GCCTGCACTT TCTCTCTCGG 240
GGGCTCAATT ACACTGACTT TTACTCTTTA CTGATAGAGA AATGCTCTAG TTTCTTTACC 300
GTAGAACCAC CTCCTCCACC AGCTGAAAAC CTGATGACCA AGCCCTCAGT GAAGTCGAAA 360
TTCCGAAAAC TGTTTAAGAT GCAA (SEQ ID NO:11)    384

FIG. 16

PASDNPILEF LEAENDLVTL ASLWKMVHSV QQTWRKYVKN DDFWPNLLSE LVGEGSVALA 60
ATLSNQASVK ALLGLHFLSR GLNYTDFYSL LIEKCSSFFT VEPPPPPAEN LMTKPSVKSK 120
FRKLFKMQ (SEQ ID NO:12)    128

FIG. 17

```
GGACCCATGG ACAAAGTCAA AGACTGGAAC CAAATAGCTG CCGGCTTGAA GAATTTTCAA   60
TTTGTTCGTG ACCTAGTCAA AGAGGTGGTC GATTGGCTGC AGGCCTGGAT CAACAAAGAG  120
AAAGCCAGCC CTGTCCTCCA GTACCAGTTG GAGATGAAGA AGCTCGGGCC TGTGGCCTTG  180
GCTCATGACG CTTTCATGGC TGGTTCCGGG CCCCCTCTTA GCGACGACCA GATTGAATAC  240
CTCCAGAACC TCAAATCTCT TGCCCTAACA CTGGGGAAGA CTAATTTGGC CCAAAGTCTC  300
ACCACTATGA TCAATGCCAA ACAAGTTCA GCCCAACGAG TTGAACCCGT TGTGGTGGTC  360
CTTAGAGGCA AGCCGGGATG CGGCAAGGGC TTGGCCTCTA CGTTGATTGC CCAGGCTGTG  420
TCCAAGCGCC TCTATGGCTC CCAAAGTGTA TATTCTCTTC CCCCAGATCC AGATTTCTTC  480
GATGGATACA AGGACAGTT CGTGACCTTG ATGGATGATT TGGGACAAAA CCCGGATGGA  540
CAAGATTTCC CCACCTTTTG TCAGATGGTG TCGACCGCCC AATTTCTCCC CAACATGGCG  600
GACCTTGCAG AGAAAGGGCG TCCCTTTACC TCCAATCTCA TCATTGCAAC TACAAATCTC  660
CCCCACTTCA GTCCTGTCAC CATTGCTGAT CCTTCTGCAG TCTCTCGCCG TATCAACTAC  720
GATCTGACTC TAGAAGTATC TGAGGCCTAC AAGAAACACA CACGGCTGAA TTTTGACTTG  780
GCTTTCAGGC GCACAGACGC CCCCCCCATT TATCCTTTTG CTGCCCATGT GCCCTTTGTG  840
GACGTAGCTG TGCGCTTCAA AAATGGTCAC CAGAATTTTA ATCTCCTAGA GTTGGTCGAT  900
TCCATTTGTA CAGACATTCG AGCCAAGCAA CAAGGTGCCC GAAACATGCA GACTCTGGTT  960
CTACAG (SEQ ID NO:13)                                              966
```

FIG. 18

```
GPMDKVKDWN QIAAGLKNFQ FVRDLVKEVV DWLQAWINKE KASPVLQYQL EMKKLGPVAL   60
AHDAFMAGSG PPLSDDQIEY LQNLKSLALT LGKTNLAQSL TTMINAKQSS AQRVEPVVVV  120
LRGKPGCGKG LASTLIAQAV SKRLYGSQSV YSLPPDPDFF DGYKGQFVTL MDDLGQNPDG  180
QDFSTFCQMV STAQFLPNMA DLAEKGRPFT SNLIIATTNL PHFSPVTIAD PSAVSRRINY  240
DLTLEVSEAY KKHTRLNFDL AFRRTDAPPI YPFAAHVPFV DVAVRFKNGH QNFNLLELVD  300
SICTDIRAKQ QGARNMQTLV LQ (SEQ ID NO:14)                            322
```

FIG. 19

```
AGCCCCAACG AGAATGATGA CACCCCCGTC GACGAGGCGT TGGGTAGAGT TCTCTCCCCC  60
GCTGCGGTCG ATGAGGCGCT TGTCGACCTC ACTCCAGAGG CCGACCCGGT TGGCCGTTTG 120
GCTATTCTTG CCAAGCTAGG TCTTGCCCTA GCTGCGGTCA CCCTGGTCT GATAATCTTG 180
GCAGTGGGAC TCTACAGGTA CTTCTCTGGC TCTGATGCAG ACCAAGAAGA AACAGAAAGT 240
GAGGGATCTG TCAAGGCACC CAGGAGCGAA (SEQ ID NO:15)                  270
```

FIG. 20

```
SPNENDDTPV DEALGRVLSP AAVDEALVDL TPEADPVGRL AILAKLGLAL AAVTPGLIIL  60
AVGLYRYFSG SDADQEETES EGSVKAPRSE (SEQ ID NO:16)                   90
```

FIG. 21

```
AATGCTTATG ACGGCCCGAA GAAAAACTCT AAGCCCCCTG GAGCACTCTC TCTCATGGAA  60
ATGCAA (SEQ ID NO:17)                                              66
```

FIG. 22

```
NAYDGPKKNS KPPGALSLME MQ (SEQ ID NO:18)                            22
```

FIG. 23

```
CAGCCCAACG TGGACATGGG CTTTGAGGCT GCGGTCGCTA AGAAAGTGGT CGTCCCCATT  60
ACCTTCATGG TTCCCAACAG ACCTTCTGGG CTTACACAGT CCGCTCTTCT GGTGACCGGC 120
CGGACCTTCC TAATCAATGA ACATACATGG TCCAATCCCT CCTGGACCAG CTTCACAATC 180
CGCGGTGAGG TACACACTCG TGATGAGCCC TTCCAAACGG TTCATTTCAC TCACCACGGT 240
ATTCCCACAG ATCTGATGAT GGTACGTCTC GGACCGGGCA ATTCTTTCCC TAACAATCTA 300
GACAAGTTTG GACTTGACCA GATGCCGGCA CGCAACTCCC GTGTGGTTGG CGTTTCGTCC 360
AGTTACGGAA ACTTCTTCTT CTCTGGAAAT TTCCTCGGAT TGTTGATTC CGTCACCTCT 420
GAACAAGGAA CTTACGCAAG ACTCTTTAGG TACAGGGTGA CGACCTACAA AGGATGGTGC 480
GGCTCGGCCC TGGTCTGTGA GGCCGGTGGC GTCCGACGCA TCATTGGCCT GCATTCTGCT 540
GGCGCCGCCG GTATCGGCGC CGGGACCTAT ATCTCAAAAT TAGGACTAAT CAAAGCCCTG 600
AAACACCTCG GTGAACCTTT GGCCACAATG CAA (SEQ ID NO:19)              633
```

FIG. 24

```
QPNVDMGFEA AVAKKVVVPI TFMVPNRPSG LTQSALLVTG RTFLINEHTW SNPSWTSFTI  60
RGEVHTRDEP FQTVHFTHHG IPTDLMMVRL GPGNSFPNNL DKFGLDQMPA RNSRVVGVSS 120
SYGNFFFSGN FLGFVDSVTS EQGTYARLFR YRVTTYKGWC GSALVCEAGG VRRIIGLHSA 180
GAAGIGAGTY ISKLGLIKAL KHLGEPLATM Q (SEQ ID NO:20)                211
```

FIG. 25

```
GGACTGATGA CTGAATTAGA GCCTGGAATC ACCGTACATG TACCCCGGAA ATCCAAATTG    60
AGAAAGACGA CCGCACACGC GGTGTACAAA CCGGAGTTTG AGCCTGCTGT GTTGTCAAAA   120
TTTGATCCCA GACTGAACAA GGATGTTGAC TTGGATGAAG TAATTTGGTC TAAACACACT   180
GCCAATGTCC CTTACCAACC TCCTTTGTTC TACACATACA TGTCAGAGTA CGCTCATCGA   240
GTCTTCTCCT TCTTGGGGAA AGACAATGAC ATTCTGACCG TCAAAGAAGC AATTCTGGGC   300
ATCCCCGGAC TAGACCCCAT GGATCCCCAC ACAGCTCCGG GTCTGCCTTA CGCCATCAAC   360
GGCCTTCGAC GTACTGATCT CGTCGATTTT GTGAACGGTA CAGTAGATGC GGCGCTGGCT   420
GTACAAATCC AGAAATTCTT AGACGGTGAC TACTCTGACC ATGTCTTCCA AACTTTTCTG   480
AAAGATGAGA TCAGACCCTC AGAGAAAGTC CGAGCGGGAA AAACCCGCAT TGTTGATGTG   540
CCCTCCCTGG CGCATTGCAT TGTGGGCAGA ATGTTGCTTG GGCGCTTTGC TGCCAAGTTT   600
CAATCCCATC CTGGCTTTCT CCTCGGCTCT GCTATCGGGT CTGACCCTGA TGTTTTCTGG   660
ACCGTCATAG GGCTCAACT CGAGGGGAGA AGAACACGT ATGACGTGGA CTACAGTGCC    720
TTTGACTCTT CACACGGCAC TGGCTCCTTC GAGGCTCTCA TCTCTCACTT TTTCACCGTG   780
GACAATGGTT TTAGCCCTGC GCTGGGACCG TATCTCAGAT CCCTGGCTGT CTCGGTGCAC   840
GCTTACGGCG AGCGTCGCAT CAAGATTACC GGTGGCCTCC CCTCCGGTTG TGCCGCGACC   900
AGCCTGCTGA ACACAGTGCT CAACAATGTG ATCATCAGGA CTGCTCTGGC ATTGACTTAC   960
AAGGAATTTG AGTATGACAC GGTTGATATC ATCGCCTACG GTGACGACCT TCTGGTTGGC  1020
ACGGATTACG ATCTGGACTT CAATGAGGTG GCACGACGCG CTGCCAAGTT GGGGTATAAG  1080
ATGACTCCTG CCAACAAGGG TTCTGTCTTC CCTCCGACTT CCTCTCTTTC CGATGCTGTT  1140
TTTCTAAAGC GCAAATTCGT CCAAAACAAC GACGGCTTAT ACAAACCAGT TATGGATTTA  1200
AAGAATTTGG AAGCCATGCT CTCCTACTTC AAACCAGGAA CACTACTCGA GAAGCTGCAA  1260
TCTGTTTCTA TGTTGGCTCA ACATTCTGGA AAAGAAGAAT ATGATAGATT GATGCACCCC  1320
TTCGCTGACT ACGGTGCCGT ACCGAGTCAC GAGTACCTGC AGGCAAGATG GAGGGCCTTG  1380
TTCGACTGA (SEQ ID NO:21)                                          1389
```

FIG. 26

```
GLMTELEPGI  TVHVPRKSKL  RKTTAHAVYK  PEFEPAVLSK  FDPRLNKDVD  LDEVIWSKHT   60
ANVPYQPPLF  YTYMSEYAHR  VFSFLGKDND  ILTVKEAILG  IPGLDPMDPH  TAPGLPYAIN  120
GLRRTDLVDF  VNGTVDAALA  VQIQKFLDGD  YSDHVFQTFL  KDEIRPSEKV  RAGKTRIVDV  180
PSLAHCIVGR  MLLGRFAAKF  QSHPGFLLGS  AIGSDPDVFW  TVIGAQLEGR  KNTYDVDYSA  240
FDSSHGTGSF  EALISHFFTV  DNGFSPALGP  YLRSLAVSVH  AYGERRIKIT  GGLPSGCAAT  300
SLLNTVLNNV  IIRTALALTY  KEFEYDTVDI  IAYGDDLLVG  TDYDLDFNEV  ARRAAKLGYK  360
MTPANKGSVF  PPTSSLSDAV  FLKRKFVQNN  DGLYKPVMDL  KNLEAMLSYF  KPGTLLEKLQ  420
SVSMLAQHSG  KEEYDRLMHP  FADYGAVPSH  EYLQARWRAL  FD *  (SEQ ID NO:22)   462
```

| Polypeptide | aa | Predicted sequence |
|---|---|---|
| L Leader | ? | No data |
| VP4 (1A) | ? | No data |
| VP2 (1B) | >142 | LAHHGNKKSLQELNEEQWVEMSDDYRTGKNMPFQSLGTYYRPPNWTWGPN FINPYQVTVFPHQILNARTSTSVDINVPYIGETPTQSSETQNSWTLLVMV LVPLDYKEGATTDPEITFSVRPTSPYFNGLRNRYTAGTDEEQ |
| VP3 (1C) | 239 | GPIPTAPRENSLMFLSTLPDDTVPAYGNVRTPPVNYLPGEITDLLQLARI PTLMAFERVPEPVPASDTYVPYVAVPTQFDDRPLISFPITLSDPVYQNTL VGAISSNFANYRGCIQITLTFCGPMMARGKFLLSYSPPNGTQPQTLSEAM QCTYSIWDIGLNSSWTFVVPYISPSDYRETRAITNSVYSADGWFSLHKLT KITLPPDCPQSPCILFFASAGEDYTLRLPVDCNPSYVFH |
| VP1 (1D) | 259 | STDNAETGVIEAGNTDTDFSGELAAPGPNHTNVKFLFDRSRLLNVIKVLE KDAVFPRPFPTQEGAQQDDGYFCLLTPRPTVASRPATRFGLYANPSGSGV LANTSLDFNFYSLACFTYFRSDLEVTVVSLEPDLEFAVGWFPSGSEYQAS SFVYDQLHVPFHFTGRTPRAFASKGGKVSFVLPWNSVSSVLPVRWGGASK LSSATRGLPAHADWGTIYAFVPRPNEKKSTAVKHVAVYIRYKNARAWCPS MLPFRSYKQ |
| 2A | 14 | KMLMQSGDIETNPG |
| 2B | 128 | PASDNPILEFLEAENDLVTLASLWKMVHSVQQTWRKYVKNDDFWPNLLSE LVGEGSVALAATLSNQASVKALLGLHFLSRGLNYTDFYSLLIEKCSSFFT VEPPPPPAENLMTKPSVKSKFRKLFKMQ |
| 2C | 322 | GPMDKVKDWNQIAAGLKNFQFVRDLVKEVVDWLQAWINKEKASPVLQYQL EMKKLGPVALAHDAFMAGSGPPLSDDQIEYLQNLKSLALTLGKTNLAQSL TTMINAKQSSAQRVEPVVVVLRGKPGCGKGLASTLIAQAVSKRLYGSQSV YSLPPDPDFFDGYKGQFVTLMDDLGQNPDGQDFSTFCQMVSTAQFLPNMA DLAEKGRPFTSNLIIATTNLPHFSPVTIADPSAVSRRINYDLTLEVSEAY KKHTRLNFDLAFRRTDAPPIYPFAAHVPFVDVAVRFKNGHQNFNLLELVD SICTDIRAKQQGARNMQTLVLQ |
| 3A | 90 | SPNENDDTPVDEALGRVLSPAAVDEALVDLTPEADPVGRLAILAKLGLAL AAVTPGLIILAVGLYRYFSGSDADQEETESEGSVKAPRSE |
| 3B (VPg) | 22 | NAYDGPKKNSKPPGALSLMEMQ |
| 3C (pro) | 211 | QPNVDMGFEAAVAKKVVVPITFMVPNRPSGLTQSALLVTGRTFLINEHTW SNPSWTSFTIRGEVHTRDEPFQTVHFTHHGIPTDLMMVRLGPGNSFPNNL DKFGLDQMPARNSRVVGVSSSYGNFFFSGNFLGFVDSVTSEQGTYARLFR YRVTTYKGWCGSALVCEAGGVRRIIGLHSAGAAGIGAGTYISKLGLIKAL KHLGEPLATMQ |
| 3D (pol) | 462 | GLMTELEPGITVHVPRKSKLRKTTAHAVYKPEFEPAVLSKFDPRLNKDVD LDEVIWSKHTANVPYQPPLFYTYMSEYAHRVFSFLGKDNDILTVKEAILG IPGLDPMDPHTAPGLPYAINGLRRTDLVDFVNGTVDAALAVQIQKFLDGD YSDHVFQTFLKDEIRPSEKVRAGKTRIVDVPSLAHCIVGRMLLGRFAAKF QSHPGFLLGSAIGSDPDVFWTVIGAQLEGRKNTYDVDYSAFDSSHGTGSF EALISHFFTVDNGFSPALGPYLRSLAVSVHAYGERRIKITGGLPSGCAAT SLLNTVLNNVIIRTALALTYKEFEYDTVDIIAYGDDLLVGTDYDLDFNEV ARRAAKLGYKMTPANKGSVFPPTSSLSDAVFLKRKFVQNNDGLYKPVMDL KNLEAMLSYFKPGTLLEKLQSVSMLAQHSGKEEYDRLMHPFADYGAVPSH EYLQARWRALFD |

Fig. 29

| Genus | Species | Abbrev. | Serotype |
|---|---|---|---|
| *Enterovirus* | *Poliovirus* | PV-1 | = Poliovirus 1 |
| | *Human enterovirus A* | CV-A16 | = Coxsackievirus A16 |
| | *Human enterovirus B* | CV-B5 | = Coxsackievirus B5 |
| | *Human enterovirus C* | CV-A21 | = Coxsackievirus A21 |
| | *Human enterovirus D* | EV-70 | = Enterovirus 70 |
| | *Simian enterovirus A* | SEV-A | = Simian enterovirus A1 |
| | *Bovine enterovirus* | BEV-1 | = Bovine enterovirus 1 |
| | *Porcine enterovirus B* | PEV-9 | = Porcine enterovirus 9 |
| *Rhinovirus* | *Human rhinovirus A* | HRV-2 | = Human rhinovirus 2 |
| | *Human rhinovirus B* | HRV-14 | = Human rhinovirus 14 |
| New genus? | Not yet designated | SV2 | = Simian virus 2 |
| | *Porcine enterovirus A* | PEV-8 | = Porcine enterovirus 8 |
| *Cardiovirus* | *Encephalomyocarditis virus* | EMCV | = Encephalomyocarditis virus |
| | *Theilovirus* | TMEV | = Theiler's murine encephalomyelitis |
| | ? | virus | |
| *Aphthovirus* | *Foot-and-mouth disease virus* | SVV | = Seneca Valley virus |
| | *Equine rhinitis A virus* | FMDV-O | = Foot-and-mouth disease virus O |
| *Hepatovirus* | *Hepatitis A virus* | ERAV | = Equine rhinitis A virus |
| | Avian encephalomyelitis-like | HAV | = Hepatitis A virus |
| | viruses | AEV | = Avian encephalomyelitis virus |
| *Parechovirus* | *Human parechovirus* | HPeV-1 | = Human parechovirus 1 |
| | *Ljungan virus* | LV | = Ljungan virus |
| *Kobuvirus* | *Aichi virus* | AiV | = Aichi virus |
| | *Bovine kobuvirus* | BKV | = Bovine kobuvirus |
| *Erbovirus* | *Equine rhinitis B virus* | ERBV-1 | = Equine rhinitis B virus 1 |
| *Teschovirus* | *Porcine teschovirus* | PTV-1 | = Porcine teschovirus 1 |

| | Cardiovirus | | | Aphthovirus | | Erbo | Teschо | Enterovirus | | | | | | | | Rhinovirus | | Entero? | | Kobu | | Hepato | | Parecho | |
|---|---|---|---|---|---|---|---|---|---|---|---|---|---|---|---|---|---|---|---|---|---|---|---|---|---|
| | SVV | EMCV | TMEV | FMDV-O | ERAV | ERBV | PTV-1 | PV-1 | CV-A21 | CV-A16 | CV-B5 | EV-70 | SEV-A | BEV-1 | PEV-9 | HRV-14 | HRV-2 | SV2 | PEV-8 | AiV | BKV | HAV | AEV | HPeV-1 | LV |
| SVV | 100 | 33 | 35 | 24 | 26 | 30 | 24 | 24 | 24 | 29 | 29 | 30 | 35 | 25 | 27 | 26 | 25 | 31 | 31 | 27 | 21 | 20 | 19 | 18 | 18 |
| EMCV | 33 | 100 | 70 | 32 | 35 | 47 | 29 | 32 | 30 | 31 | 34 | 30 | 34 | 34 | 31 | 34 | 33 | 40 | 37 | 20 | 21 | 25 | 25 | 22 | 21 |
| TMEV | 35 | 70 | 100 | 33 | 34 | 45 | 31 | 35 | 34 | 30 | 32 | 31 | 34 | 33 | 31 | 31 | 28 | 36 | 37 | 21 | 21 | 25 | 25 | 23 | 21 |
| FMDV-O | 24 | 32 | 33 | 100 | 31 | 35 | 31 | 27 | 26 | 30 | 27 | 25 | 28 | 28 | 25 | 31 | 25 | 32 | 29 | 15 | 17 | 24 | 24 | 19 | 17 |
| ERAV | 26 | 35 | 34 | 31 | 100 | 35 | 36 | 32 | 31 | 28 | 35 | 30 | 31 | 28 | 27 | 29 | 30 | 39 | 34 | 22 | 22 | 20 | 24 | 18 | 22 |
| ERBV | 30 | 47 | 45 | 35 | 35 | 100 | 29 | 26 | 28 | 34 | 31 | 31 | 33 | 30 | 31 | 33 | 32 | 36 | 35 | 21 | 21 | 26 | 28 | 20 | 21 |
| PTV-1 | 24 | 29 | 31 | 31 | 36 | 29 | 100 | 30 | 31 | 27 | 29 | 26 | 30 | 30 | 30 | 30 | 26 | 28 | 30 | 18 | 22 | 25 | 22 | 19 | 22 |
| PV-1 | 24 | 32 | 35 | 27 | 32 | 26 | 30 | 100 | 71 | 52 | 52 | 51 | 55 | 54 | 48 | 53 | 51 | 42 | 44 | 21 | 23 | 19 | 21 | 18 | 20 |
| CV-A21 | 24 | 30 | 34 | 26 | 31 | 28 | 31 | 71 | 100 | 51 | 53 | 52 | 52 | 53 | 47 | 54 | 55 | 43 | 46 | 19 | 23 | 23 | 22 | 20 | 19 |
| CV-A16 | 29 | 31 | 30 | 30 | 28 | 34 | 27 | 52 | 51 | 100 | 52 | 53 | 53 | 54 | 52 | 52 | 48 | 49 | 48 | 18 | 19 | 22 | 22 | 19 | 17 |
| CV-B5 | 29 | 34 | 32 | 27 | 35 | 31 | 29 | 52 | 53 | 52 | 100 | 55 | 54 | 53 | 49 | 56 | 51 | 51 | 48 | 20 | 17 | 23 | 22 | 20 | 18 |
| EV-70 | 30 | 30 | 31 | 25 | 30 | 31 | 26 | 51 | 52 | 53 | 55 | 100 | 57 | 63 | 62 | 52 | 53 | 46 | 49 | 20 | 20 | 25 | 23 | 18 | 17 |
| SEV-A | 35 | 34 | 34 | 28 | 31 | 33 | 30 | 55 | 52 | 53 | 54 | 57 | 100 | 55 | 54 | 47 | 50 | 43 | 45 | 21 | 20 | 21 | 22 | 22 | 19 |
| BEV-1 | 25 | 34 | 33 | 28 | 28 | 30 | 30 | 54 | 53 | 54 | 53 | 63 | 55 | 100 | 67 | 54 | 52 | 45 | 46 | 20 | 23 | 21 | 21 | 16 | 16 |
| PEV-9 | 27 | 31 | 31 | 25 | 27 | 31 | 30 | 48 | 47 | 52 | 49 | 62 | 54 | 67 | 100 | 53 | 49 | 45 | 45 | 21 | 23 | 24 | 25 | 20 | 18 |
| HRV-14 | 26 | 34 | 31 | 31 | 29 | 33 | 30 | 53 | 54 | 52 | 56 | 52 | 47 | 54 | 53 | 100 | 61 | 46 | 49 | 23 | 21 | 22 | 21 | 19 | 21 |
| HRV-2 | 25 | 33 | 28 | 25 | 30 | 32 | 26 | 51 | 55 | 48 | 51 | 53 | 50 | 52 | 49 | 61 | 100 | 46 | 46 | 22 | 21 | 22 | 24 | 20 | 22 |
| SV2 | 31 | 40 | 36 | 32 | 39 | 36 | 28 | 42 | 43 | 49 | 51 | 46 | 43 | 45 | 45 | 46 | 46 | 100 | 74 | 23 | 22 | 25 | 27 | 20 | 19 |
| PEV-8 | 31 | 37 | 37 | 29 | 34 | 35 | 30 | 44 | 46 | 48 | 48 | 49 | 45 | 46 | 45 | 49 | 46 | 74 | 100 | 24 | 22 | 25 | 26 | 18 | 21 |
| AiV | 27 | 20 | 21 | 15 | 22 | 21 | 18 | 21 | 19 | 18 | 20 | 20 | 21 | 20 | 21 | 23 | 22 | 23 | 24 | 100 | 56 | 19 | 18 | 16 | 16 |
| BKV | 21 | 21 | 21 | 17 | 22 | 21 | 22 | 23 | 23 | 19 | 17 | 20 | 20 | 23 | 23 | 21 | 21 | 22 | 22 | 56 | 100 | 16 | 18 | 16 | 16 |
| HAV | 20 | 25 | 25 | 24 | 20 | 26 | 25 | 19 | 23 | 22 | 23 | 25 | 21 | 21 | 24 | 22 | 22 | 25 | 25 | 19 | 16 | 100 | 57 | 18 | 23 |
| AEV | 19 | 25 | 25 | 24 | 24 | 28 | 22 | 21 | 22 | 22 | 22 | 23 | 22 | 21 | 25 | 21 | 24 | 27 | 26 | 18 | 18 | 57 | 100 | 18 | 23 |
| HPeV-1 | 18 | 22 | 23 | 19 | 18 | 20 | 19 | 18 | 20 | 19 | 20 | 18 | 22 | 16 | 20 | 19 | 20 | 20 | 18 | 16 | 16 | 18 | 18 | 100 | 53 |
| LV | 18 | 21 | 21 | 17 | 22 | 21 | 22 | 20 | 19 | 17 | 18 | 17 | 19 | 16 | 18 | 21 | 22 | 19 | 21 | 16 | 16 | 23 | 23 | 53 | 100 |

Fig. 38

| | Cardiovirus | | | Aphthovirus | | Erbo | Tescho | Enterovirus | | | | | | | | Rhinovirus | | Entero? | | Kobu | | Hepato | | Parecho | |
|---|---|---|---|---|---|---|---|---|---|---|---|---|---|---|---|---|---|---|---|---|---|---|---|---|---|
| | SVV | EMCV | TMEV | FMDV-O | ERAV | ERBV | PTV-1 | PV-1 | CV-A21 | CV-A16 | CV-B5 | EV-70 | SEV-A | BEV-1 | PEV-9 | HRV-14 | HRV-2 | SV2 | PEV-8 | AiV | BKV | HAV | AEV | HPeV-1 | LV |
| SVV | 100 | 42 | 39 | 32 | 34 | 43 | 31 | 32 | 30 | 25 | 29 | 26 | 30 | 25 | 29 | 28 | 28 | 35 | 30 | 26 | 28 | 19 | 17 | 17 | 19 |
| EMCV | 42 | 100 | 67 | 29 | 38 | 39 | 35 | 28 | 31 | 29 | 31 | 31 | 29 | 31 | 30 | 26 | 31 | 31 | 35 | 27 | 26 | 19 | 18 | 17 | 18 |
| TMEV | 39 | 67 | 100 | 31 | 37 | 35 | 33 | 29 | 29 | 31 | 29 | 27 | 27 | 27 | 28 | 26 | 30 | 31 | 35 | 27 | 28 | 18 | 17 | 17 | 20 |
| FMDV-O | 32 | 29 | 31 | 100 | 39 | 31 | 23 | 26 | 23 | 26 | 27 | 25 | 26 | 25 | 24 | 26 | 23 | 30 | 32 | 20 | 25 | 14 | 15 | 14 | 17 |
| ERAV | 34 | 38 | 37 | 39 | 100 | 38 | 25 | 25 | 24 | 20 | 27 | 23 | 23 | 23 | 25 | 24 | 27 | 31 | 32 | 25 | 24 | 20 | 15 | 15 | 19 |
| ERBV | 43 | 39 | 35 | 31 | 38 | 100 | 30 | 27 | 29 | 27 | 28 | 27 | 30 | 29 | 28 | 28 | 28 | 34 | 34 | 27 | 29 | 21 | 19 | 18 | 17 |
| PTV-1 | 31 | 35 | 33 | 23 | 25 | 30 | 100 | 23 | 22 | 24 | 24 | 23 | 27 | 25 | 28 | 22 | 27 | 28 | 27 | 24 | 23 | 16 | 16 | 19 | 18 |
| PV-1 | 32 | 28 | 29 | 26 | 25 | 27 | 23 | 100 | 75 | 42 | 55 | 42 | 46 | 41 | 43 | 43 | 50 | 36 | 36 | 24 | 29 | 17 | 17 | 15 | 15 |
| CV-A21 | 30 | 31 | 29 | 23 | 24 | 29 | 22 | 75 | 100 | 43 | 61 | 42 | 46 | 42 | 45 | 48 | 53 | 36 | 35 | 24 | 26 | 16 | 20 | 13 | 13 |
| CV-A16 | 25 | 29 | 31 | 26 | 20 | 27 | 24 | 42 | 43 | 100 | 48 | 51 | 50 | 55 | 54 | 40 | 41 | 40 | 38 | 24 | 26 | 13 | 14 | 13 | 14 |
| CV-B5 | 29 | 31 | 29 | 27 | 27 | 28 | 24 | 55 | 61 | 48 | 100 | 47 | 48 | 49 | 49 | 51 | 52 | 40 | 36 | 24 | 27 | 16 | 17 | 14 | 15 |
| EV-70 | 26 | 31 | 27 | 25 | 23 | 27 | 23 | 42 | 42 | 51 | 47 | 100 | 49 | 49 | 53 | 45 | 44 | 32 | 38 | 25 | 27 | 16 | 15 | 15 | 15 |
| SEV-A | 30 | 29 | 27 | 26 | 23 | 30 | 27 | 46 | 46 | 50 | 48 | 49 | 100 | 48 | 53 | 41 | 43 | 37 | 37 | 28 | 28 | 13 | 14 | 14 | 15 |
| BEV-1 | 25 | 31 | 27 | 25 | 23 | 29 | 25 | 41 | 42 | 55 | 49 | 49 | 48 | 100 | 63 | 45 | 45 | 40 | 40 | 23 | 25 | 11 | 12 | 13 | 17 |
| PEV-9 | 29 | 30 | 28 | 24 | 25 | 28 | 28 | 43 | 45 | 54 | 49 | 53 | 53 | 63 | 100 | 43 | 48 | 39 | 39 | 22 | 27 | 15 | 12 | 14 | 13 |
| HRV-14 | 28 | 26 | 26 | 26 | 24 | 28 | 22 | 43 | 48 | 40 | 51 | 45 | 41 | 45 | 43 | 100 | 52 | 33 | 33 | 26 | 27 | 16 | 17 | 14 | 19 |
| HRV-2 | 28 | 31 | 30 | 23 | 27 | 28 | 27 | 50 | 53 | 41 | 52 | 44 | 43 | 45 | 48 | 52 | 100 | 35 | 38 | 25 | 28 | 19 | 16 | 14 | 17 |
| SV2 | 35 | 31 | 31 | 30 | 31 | 34 | 28 | 36 | 36 | 40 | 40 | 32 | 37 | 40 | 39 | 33 | 35 | 100 | 63 | 25 | 29 | 18 | 16 | 16 | 21 |
| PEV-8 | 30 | 35 | 35 | 32 | 32 | 34 | 27 | 36 | 35 | 38 | 36 | 38 | 37 | 40 | 39 | 33 | 38 | 63 | 100 | 24 | 30 | 18 | 17 | 18 | 18 |
| AiV | 26 | 27 | 27 | 20 | 25 | 27 | 24 | 24 | 24 | 24 | 24 | 25 | 28 | 23 | 22 | 26 | 25 | 25 | 24 | 100 | 58 | 16 | 18 | 17 | 19 |
| BKV | 28 | 26 | 28 | 25 | 24 | 29 | 23 | 29 | 26 | 26 | 27 | 27 | 28 | 25 | 27 | 27 | 28 | 29 | 30 | 58 | 100 | 17 | 20 | 16 | 19 |
| HAV | 19 | 19 | 18 | 14 | 20 | 21 | 16 | 17 | 16 | 13 | 16 | 16 | 13 | 11 | 15 | 16 | 19 | 18 | 18 | 16 | 17 | 100 | 53 | 18 | 19 |
| AEV | 17 | 18 | 17 | 15 | 15 | 19 | 16 | 17 | 20 | 14 | 17 | 15 | 14 | 12 | 12 | 17 | 16 | 16 | 17 | 18 | 20 | 53 | 100 | 20 | 20 |
| HPeV-1 | 17 | 17 | 17 | 14 | 15 | 18 | 19 | 15 | 13 | 13 | 14 | 15 | 14 | 13 | 14 | 14 | 14 | 16 | 18 | 17 | 16 | 18 | 20 | 100 | 55 |
| LV | 19 | 18 | 20 | 17 | 19 | 17 | 18 | 15 | 13 | 14 | 15 | 15 | 15 | 17 | 13 | 19 | 17 | 21 | 18 | 19 | 19 | 19 | 20 | 55 | 100 |

Fig. 39

| | Cardiovirus | | | Aphthovirus | | Erbo | Tescho | Enterovirus | | | | | | | | Rhinovirus | | Entero? | | Kobu | | Hepato | | Parecho | |
|---|---|---|---|---|---|---|---|---|---|---|---|---|---|---|---|---|---|---|---|---|---|---|---|---|---|
| | SVV | EMCV | TMEV | FMDV-O | ERAV | ERBV | PTV-1 | PV-1 | CV-A21 | CV-A16 | CV-B5 | EV-70 | SEV-A | BEV-1 | PEV-9 | HRV-14 | HRV-2 | SV2 | PEV-8 | AiV | BKV | HAV | AEV | HPeV-1 | LV |
| SVV | 100 | 20 | 21 | 12 | 13 | 13 | 11 | 17 | 16 | 16 | 16 | 14 | 17 | 13 | 13 | 18 | 16 | 14 | 13 | 13 | 13 | 9 | 10 | 11 | 8 |
| EMCV | 20 | 100 | 48 | 11 | 15 | 16 | 15 | 16 | 16 | 14 | 14 | 15 | 18 | 17 | 17 | 17 | 15 | 16 | 16 | 14 | 13 | 12 | 12 | 11 | 11 |
| TMEV | 21 | 48 | 100 | 12 | 15 | 15 | 14 | 15 | 16 | 16 | 13 | 13 | 17 | 14 | 15 | 16 | 15 | 16 | 15 | 17 | 14 | 15 | 13 | 9 | 11 |
| FMDV-O | 12 | 11 | 12 | 100 | 23 | 13 | 9 | 11 | 13 | 12 | 11 | 11 | 11 | 10 | 11 | 10 | 13 | 9 | 12 | 12 | 8 | 11 | 10 | 11 | 10 |
| ERAV | 13 | 15 | 15 | 23 | 100 | 18 | 12 | 13 | 14 | 16 | 14 | 11 | 14 | 14 | 12 | 14 | 14 | 10 | 14 | 11 | 9 | 9 | 9 | 9 | 11 |
| ERBV | 13 | 16 | 15 | 13 | 18 | 100 | 13 | 13 | 13 | 14 | 15 | 15 | 13 | 12 | 11 | 12 | 12 | 12 | 13 | 17 | 12 | 10 | 12 | 13 | 11 |
| PTV-1 | 11 | 15 | 14 | 9 | 12 | 13 | 100 | 19 | 18 | 21 | 19 | 19 | 18 | 17 | 17 | 18 | 17 | 17 | 17 | 16 | 12 | 12 | 9 | 13 | 12 |
| PV-1 | 17 | 16 | 15 | 11 | 13 | 13 | 19 | 100 | 57 | 34 | 46 | 34 | 41 | 35 | 32 | 46 | 36 | 23 | 21 | 16 | 16 | 10 | 10 | 14 | 10 |
| CV-A21 | 16 | 16 | 16 | 13 | 14 | 13 | 18 | 57 | 100 | 36 | 43 | 37 | 39 | 33 | 35 | 42 | 40 | 24 | 24 | 15 | 13 | 10 | 14 | 14 | 11 |
| CV-A16 | 16 | 14 | 16 | 12 | 16 | 14 | 21 | 34 | 36 | 100 | 37 | 38 | 42 | 43 | 40 | 35 | 37 | 27 | 24 | 15 | 15 | 12 | 13 | 13 | 8 |
| CV-B5 | 16 | 14 | 13 | 11 | 14 | 15 | 19 | 46 | 43 | 37 | 100 | 42 | 40 | 38 | 32 | 38 | 42 | 27 | 25 | 14 | 16 | 13 | 12 | 13 | 9 |
| EV-70 | 14 | 15 | 13 | 11 | 11 | 15 | 19 | 34 | 37 | 38 | 42 | 100 | 37 | 39 | 33 | 38 | 37 | 24 | 23 | 13 | 13 | 16 | 12 | 13 | 12 |
| SEV-A | 17 | 18 | 17 | 11 | 14 | 13 | 18 | 41 | 39 | 42 | 40 | 37 | 100 | 39 | 40 | 39 | 40 | 25 | 25 | 13 | 13 | 13 | 13 | 14 | 12 |
| BEV-1 | 13 | 17 | 14 | 10 | 14 | 12 | 17 | 35 | 33 | 43 | 38 | 39 | 39 | 100 | 46 | 37 | 35 | 25 | 25 | 15 | 14 | 15 | 11 | 12 | 10 |
| PEV-9 | 13 | 17 | 15 | 11 | 12 | 11 | 17 | 32 | 35 | 40 | 32 | 33 | 40 | 46 | 100 | 36 | 34 | 23 | 22 | 13 | 13 | 12 | 11 | 12 | 9 |
| HRV-14 | 18 | 17 | 16 | 10 | 14 | 12 | 18 | 46 | 42 | 35 | 38 | 38 | 39 | 37 | 36 | 100 | 42 | 23 | 22 | 15 | 16 | 11 | 13 | 14 | 10 |
| HRV-2 | 16 | 15 | 15 | 13 | 14 | 12 | 17 | 36 | 40 | 37 | 42 | 37 | 40 | 35 | 34 | 42 | 100 | 24 | 21 | 16 | 14 | 13 | 14 | 14 | 9 |
| SV2 | 14 | 16 | 16 | 9 | 10 | 12 | 17 | 23 | 24 | 27 | 27 | 24 | 25 | 25 | 23 | 23 | 24 | 100 | 46 | 15 | 12 | 11 | 12 | 12 | 11 |
| PEV-8 | 13 | 16 | 15 | 12 | 14 | 13 | 17 | 21 | 24 | 24 | 25 | 23 | 25 | 25 | 22 | 22 | 21 | 46 | 100 | 14 | 12 | 13 | 12 | 13 | 8 |
| AiV | 13 | 14 | 17 | 12 | 11 | 17 | 16 | 16 | 15 | 15 | 14 | 13 | 13 | 15 | 13 | 15 | 16 | 15 | 14 | 100 | 28 | 11 | 13 | 11 | 10 |
| BKV | 13 | 13 | 14 | 8 | 9 | 12 | 12 | 16 | 13 | 15 | 16 | 13 | 13 | 14 | 13 | 16 | 14 | 12 | 12 | 28 | 100 | 11 | 11 | 13 | 10 |
| HAV | 9 | 12 | 15 | 11 | 9 | 10 | 12 | 10 | 10 | 12 | 13 | 16 | 13 | 15 | 12 | 11 | 13 | 11 | 13 | 11 | 11 | 100 | 43 | 15 | 14 |
| AEV | 10 | 12 | 13 | 10 | 9 | 12 | 9 | 10 | 14 | 13 | 12 | 12 | 13 | 11 | 11 | 13 | 14 | 12 | 12 | 13 | 11 | 43 | 100 | 18 | 14 |
| HPeV-1 | 11 | 11 | 9 | 11 | 9 | 13 | 13 | 14 | 14 | 13 | 13 | 13 | 14 | 12 | 12 | 14 | 14 | 12 | 13 | 11 | 13 | 15 | 18 | 100 | 43 |
| LV | 8 | 11 | 11 | 10 | 11 | 11 | 12 | 10 | 11 | 8 | 9 | 12 | 12 | 10 | 9 | 10 | 9 | 11 | 8 | 10 | 10 | 14 | 14 | 43 | 100 |

Fig. 40

|  | Cardiovirus | | | Aphthovirus | | Erbo | Tescho | Enterovirus | | | | | | | | | | Rhinovirus | | Entero? | | Kobu | | Hepato | | Parecho | |
|---|---|---|---|---|---|---|---|---|---|---|---|---|---|---|---|---|---|---|---|---|---|---|---|---|---|---|---|
|  | SVV | EMCV | TMEV | FMDV-O | ERAV | ERBV | PTV-1 | PV-1 | CV-A21 | CV-A16 | CV-B5 | EV-70 | SEV-A | BEV-1 | PEV-9 | HRV-14 | HRV-2 | SV2 | PEV-8 | AiV | BKV | H

Fig. 42

| | Cardiovirus | | | Aphthovirus | | Erbo | Tescho | Enterovirus | | | | | | | | Rhinovirus | | Entero? | | Kobu | | Hepato | | Parecho | |
|---|---|---|---|---|---|---|---|---|---|---|---|---|---|---|---|---|---|---|---|---|---|---|---|---|---|
| | SVV | EMCV | TMEV | FMDV-O | ERAV | ERBV | PTV-1 | PV-1 | CV-A21 | CV-A16 | CV-B5 | EV-70 | SEV-A | BEV-1 | PEV-9 | HRV-14 | HRV-2 | SV2 | PEV-8 | AiV | BKV | HAV | AEV | HPeV-1 | LV |
| SVV | 100 | 38 | 37 | 24 | 21 | 19 | 27 | 19 | 18 | 14 | 16 | 17 | 14 | 18 | 19 | 18 | 15 | 17 | 16 | 16 | 14 | 17 | 16 | 13 | 14 |
| EMCV | 38 | 100 | 48 | 27 | 27 | 18 | 24 | 18 | 18 | 18 | 20 | 20 | 19 | 17 | 20 | 19 | 20 | 19 | 19 | 15 | 16 | 22 | 18 | 17 | 19 |
| TMEV | 37 | 48 | 100 | 20 | 28 | 20 | 25 | 19 | 20 | 20 | 18 | 20 | 16 | 19 | 18 | 15 | 18 | 17 | 17 | 16 | 17 | 17 | 16 | 16 | 19 |
| FMDV-O | 24 | 27 | 20 | 100 | 40 | 23 | 20 | 19 | 19 | 22 | 17 | 19 | 17 | 22 | 23 | 18 | 20 | 20 | 20 | 16 | 13 | 20 | 20 | 13 | 15 |
| ERAV | 21 | 27 | 28 | 40 | 100 | 25 | 22 | 21 | 20 | 20 | 20 | 21 | 22 | 20 | 18 | 19 | 20 | 21 | 22 | 19 | 20 | 22 | 22 | 15 | 17 |
| ERBV | 19 | 18 | 20 | 23 | 25 | 100 | 18 | 19 | 20 | 16 | 17 | 17 | 17 | 20 | 16 | 18 | 14 | 20 | 17 | 18 | 20 | 15 | 20 | 14 | 16 |
| PTV-1 | 27 | 24 | 25 | 20 | 22 | 18 | 100 | 20 | 19 | 20 | 19 | 20 | 19 | 20 | 20 | 22 | 21 | 18 | 21 | 16 | 17 | 20 | 15 | 13 | 14 |
| PV-1 | 19 | 18 | 19 | 19 | 21 | 19 | 20 | 100 | 95 | 55 | 60 | 60 | 56 | 57 | 60 | 46 | 44 | 43 | 47 | 21 | 17 | 18 | 18 | 18 | 18 |
| CV-A21 | 18 | 18 | 20 | 19 | 20 | 20 | 19 | 95 | 100 | 56 | 59 | 57 | 57 | 57 | 60 | 46 | 44 | 42 | 46 | 22 | 17 | 18 | 18 | 19 | 18 |
| CV-A16 | 14 | 18 | 20 | 22 | 20 | 16 | 20 | 55 | 56 | 100 | 56 | 54 | 57 | 57 | 60 | 51 | 45 | 46 | 50 | 17 | 18 | 19 | 18 | 20 | 22 |
| CV-B5 | 16 | 20 | 18 | 17 | 20 | 17 | 19 | 60 | 59 | 56 | 100 | 64 | 55 | 58 | 56 | 52 | 49 | 46 | 52 | 20 | 19 | 19 | 19 | 19 | 20 |
| EV-70 | 17 | 20 | 20 | 19 | 21 | 17 | 20 | 60 | 57 | 54 | 64 | 100 | 57 | 54 | 55 | 51 | 48 | 43 | 51 | 20 | 20 | 21 | 18 | 14 | 17 |
| SEV-A | 14 | 19 | 16 | 17 | 22 | 17 | 19 | 56 | 57 | 57 | 55 | 57 | 100 | 54 | 55 | 53 | 46 | 40 | 49 | 20 | 17 | 19 | 18 | 17 | 19 |
| BEV-1 | 18 | 17 | 19 | 22 | 20 | 20 | 20 | 57 | 57 | 57 | 58 | 54 | 54 | 100 | 63 | 47 | 47 | 41 | 44 | 16 | 16 | 20 | 20 | 19 | 16 |
| PEV-9 | 19 | 20 | 18 | 23 | 18 | 16 | 20 | 60 | 60 | 60 | 56 | 55 | 55 | 63 | 100 | 50 | 45 | 45 | 50 | 18 | 14 | 19 | 18 | 18 | 21 |
| HRV-14 | 18 | 19 | 15 | 18 | 19 | 18 | 22 | 46 | 46 | 51 | 52 | 51 | 53 | 47 | 50 | 100 | 50 | 42 | 49 | 20 | 20 | 20 | 20 | 16 | 18 |
| HRV-2 | 15 | 20 | 18 | 20 | 20 | 14 | 21 | 44 | 44 | 45 | 49 | 48 | 46 | 47 | 45 | 50 | 100 | 43 | 43 | 20 | 23 | 18 | 19 | 17 | 18 |
| SV2 | 17 | 19 | 17 | 20 | 21 | 20 | 18 | 43 | 42 | 46 | 46 | 43 | 40 | 41 | 45 | 42 | 43 | 100 | 60 | 16 | 18 | 18 | 19 | 22 | 24 |
| PEV-8 | 16 | 19 | 17 | 20 | 22 | 17 | 21 | 47 | 46 | 50 | 52 | 51 | 49 | 44 | 50 | 49 | 43 | 60 | 100 | 16 | 17 | 19 | 20 | 20 | 19 |
| AiV | 16 | 15 | 16 | 16 | 19 | 18 | 16 | 21 | 22 | 17 | 20 | 20 | 20 | 16 | 18 | 20 | 20 | 16 | 16 | 100 | 48 | 19 | 17 | 13 | 15 |
| BKV | 14 | 16 | 17 | 13 | 20 | 20 | 17 | 17 | 17 | 18 | 19 | 20 | 17 | 16 | 14 | 20 | 23 | 18 | 17 | 48 | 100 | 18 | 18 | 13 | 14 |
| HAV | 17 | 22 | 17 | 20 | 22 | 15 | 20 | 18 | 18 | 19 | 19 | 21 | 19 | 20 | 19 | 20 | 18 | 18 | 19 | 19 | 18 | 100 | 40 | 16 | 15 |
| AEV | 16 | 18 | 16 | 20 | 22 | 20 | 15 | 18 | 18 | 18 | 19 | 18 | 18 | 20 | 18 | 20 | 19 | 19 | 20 | 17 | 18 | 40 | 100 | 14 | 16 |
| HPeV-1 | 13 | 17 | 16 | 13 | 15 | 14 | 13 | 18 | 19 | 20 | 19 | 14 | 17 | 19 | 18 | 16 | 17 | 22 | 20 | 13 | 13 | 16 | 14 | 100 | 48 |
| LV | 14 | 19 | 19 | 15 | 17 | 16 | 14 | 18 | 18 | 22 | 20 | 17 | 19 | 16 | 21 | 18 | 18 | 24 | 19 | 15 | 14 | 15 | 16 | 48 | 100 |

Fig. 44

Polypeptide lengths of Seneca Valley virus compared to other picornaviruses

| Polyprotein | SVV | EMCV | TMEV | ERBV-1 | FMDV-O | ERAV | PTV-1 | PV-1 | HRV-1B | SV2 | PEV-8 | DPV | HAV | AEV | AiV | BKV | HPeV-1 | LV |
|---|---|---|---|---|---|---|---|---|---|---|---|---|---|---|---|---|---|---|
| P1 | ? | 2292 | | 2590 | 2332 | 2249 | | 2209 | 2157 | | | | 2227 | 2134 | 2432 | 2463 | 2180 | 2253 |
| P2 | 465 | 834 | | 880 | 736 | 784 | | 881 | 857 | | | | 791 | 757 | 846 | 857 | 776 | 820 |
| P3 | 785 | 618 | | 616 | 488 | 467 | | 575 | 559 | | | | 631 | 590 | 636 | 634 | 598 | 606 |
| Leader | ? | 773 | | 875 | 907 | 789 | | 753 | 741 | | | | 805 | 787 | 780 | 785 | 806 | 827 |
| VP0 | ? | 67 | | 219 | 201 | 209 | | - | - | | | | - | - | 170 | 187 | - | - |
| VP4 | ? | 326 | | 327 | 303 | 310 | | 341 | 332 | | | | 245 | 242 | 370 | 367 | 289 | 259 |
| VP2 | ? | 70 | | 71 | 85 | 80 | | 69 | 69 | | | | 23 | 19 | - | - | - | - |
| VP3 | 239 | 256 | | 256 | 218 | 230 | | 272 | 263 | | | | 222 | 223 | - | - | - | - |
| VP1 | 259 | 231 | | 229 | 220 | 226 | | 238 | 238 | | | | 246 | 245 | 223 | 223 | 253 | 244 |
| 2A | 14 | 277 | | 324 | 211 | 248 | | 302 | 287 | | | | 300 | 270 | 253 | 267 | 234 | 317 |
| 2B | 128 | 143 | | 16 | 18 | 16 | | 149 | 142 | | | | 45 | 13 | 136 | 134 | 147 | 135 |
| 2C | 323 | 150 | | 283 | 154 | 136 | | 97 | 95 | | | | 251 | 251 | 165 | 165 | 122 | 138 |
| 3A | 90 | 325 | | 317 | 318 | 315 | | 329 | 322 | | | | 335 | 326 | 335 | 335 | 329 | 333 |
| 3B | 22 | 88 | | 133 | 153 | 95 | | 87 | 77 | | | | 74 | 65 | 95 | 94 | 117 | 130 |
| 3C | 211 | 20 | | 21 | 23-24† | 24 | | 22 | 21 | | | | 23 | 21 | 27 | 30 | 20 | 29 |
| 3D | 462 | 205 | | 252 | 213 | 205 | | 183 | 183 | | | | 219 | 215 | 190 | 192 | 200 | 198 |
|  | 460 | | | 469 | 470 | 465 | | 461 | 460 | | | | 489 | 486 | 468 | 469 | 469 | 470 |

*, assuming that the 20 aa peptide ending in NPG is the C-terminus of VP1.
†, FMDV has three copies of VPg in tandem.
na, these individual polypeptides do not exist in these viruses.

```
   1 MATTMEQETC AHSLTFEECP KCSALQYRNG FYLLKYDEEW YPEELLTDGE DDVFDPELDM
  61 EVVFELQGNS TSSDKNNSSS EGNEGVIINN FYSNQYQNSI DLSANAAGSD PPRTYGQFSN
 121 LFSGAVNAFS NMLPLLADQN TEEMENLSDR VSQDTAGNTV TNTQSTVGRL VGYGTVHDGE
 181 HPASCADTAS EKILAVERYY TFKVNDWTST QKPFEYIRIP LPHVLSGEDG GVFGAALRRH
 241 YLVKTGWRVQ VQCNASQFHA GSLLVFMAPE YPTLDAFAMD NRWSKDNLPN GTRTQTNKKG
 301 PFAMDHQNFW QWTLYPHQFL NLRTNTTVDL EVPYVNIAPT SSWTQHASWT LVIAVVAPLT
 361 YSTGASTSLD ITASIQPVRP VFNGLRHETL SRQSPIPVTI REHAGTWYST LPDSTVPIYG
 421 KTPVAPSNYM VGEYKDFLEI AQIPTFIGNK IPNAVPYIEA SNTAVKTQPL ATYQVTLSCS
 481 CLANTFLAAL SRNFAQYRGS LVYTFVFTGT AMMKGKFLIA YTPPGAGKPT SRDQAMQATY
 541 AIWDLGLNSS YSFTVPFISP THFRMVGTDQ VNITNADGWV TVWQLTPLTY PPGCPTSAKI
 601 LTMVSAGKDF SLKMPISPAP WSPQGVENAE KGVTENTNAT ADFVAQPVYL PENQTKVAFF
 661 YNRSSPIGAF TVKSGSLESG FAPFSNGTCP NSVILTPGPQ FDPAYDQLRP QRLTEIWGNG
 721 NEETSKVFPL KSKQDYSFCL FSPFVYYKCD LEVTLSPHTS GNHGLLVRWC PTGTPTKPTT
 781 QVLHEVSSLS EGRTPQVYSA GPGISNQISF VVPYNSPLSV LSAVWYNGHK RFDNTGSLGI
 841 APNSDFGTLF FAGTKPDIKF TVYLRYKNKR VFCPRPTVFF PWPTSGDKID MTPRAGVLML
 901 ESPNALDISR TYPTLHVLIQ FNHRGLEVRL FRHGHFWAET RADVILRSKT KQVSFLSNGN
 961 YPSMDSRAPW NPWKNTYQAV LRAEPCRVTM DIYYKRVRPF RLPLVQKEWP VREENVFGLY
1021 RIFNAHYAGY FADLLIHDIE TNPGPFMFRP RKQVFQTQGA AVSSMAQTLL PNDLASKAMG
1081 SAFTALLDAN EDAQKAMKII KTLSSLSDAW ENVKETLNNP EFWKQLLSRC VQLIAGMTIA
1141 VMHPDPLTLL CLGTLTAAEI TSQTSLCEEI AAKFTIFIT PPPRFPTISL FQQQSPLKQV
1201 NDIFSLAKNL DWAVKTVEKV VDWFGTWIVQ EEKEQTLDQL LQRFPEHAKR ISDLRNGMAA
1261 YVECKESFDF FEKLYNQAVK EKRTGIAAVC EKFRQKHDHA TARCEPVVIV LRGDAGQGKS
1321 LSSQVIAQAV SKTIFGRQSV YSLPPDSDFF DGYENQFAAI MDDLGQNPDG SDFTTFCQMV
1381 STTNFLPNMA SLERKGTPFT SQLVVATTNL PEFRPVTIAH YPAVERRITF DYSVSAGPVC
```

Fig. 71A

```
1441 SKTEAGYKVL DVERAFRPTG EAPLPCFQNN CLFLEKAGLQ FRDNRTKEII SLVDVIERAV

1501 ARIERKKKVL TTVQTLVAQG PVDEVSFHSV VQQLKARQQA TDEQLEELQE AFAKVQERNS

1561 VFSDWLKISA MLCAATLALS QVVKMAKAVK QMVKPDLVRV QLDEQEQGPY NETARVKPKT

1621 LQLLDIQGPN PVMDFEKYVA KHVTAPIGFV YPTGVSTQTC LLVRGRTLVV NRHMAESDWT

1681 SIVVRGVTHA RSTVKILAIA KAGKETDVSF IRLSSGPLFR DNTSKFVKAG DVLPTGAAPV

1741 TGIMNTDIPM MYTGTFLKAG VSVPVETGQT FNHCIHYKAN TRKGWCGSAL LADLGGSKKI

1801 LGIHSAGSMG IAAASIVSQE MIRAVVNAFE PQGALERLPD GPRIHVPRKT ALRPTVARQV

1861 FQPAYAPAVL SKFDPRTEAD VDEVAFSKHT SNQESLPPVF RMVAKEYANR VFTLLGKDNG

1921 RLTVKQALEG LEGMDPMDRN TSPGLPYTAL GMRRTDVVDW ESATLIPFAA ERLRKMNEGD

1981 FSEVVYQTFL KDELRPIEKV QAAKTRIVDV PPFEHCILGR QLLGKFASKF QTQPGLELGS

2041 AIGCDPDVHW TAFGVAMQGF ERVYDVDYSN FDSTHSVAMF RLLAEEFFTP ENGFDPLTRE

2101 YLESLAISTH AFEEKRFLIT GGLPSGCAAT SMLNTIMNNI IIRAGLYLTY KNFEFDDVKV

2161 LSYGDDLLVA TNYQLDFDKV RASLAKTGYK ITPANKTSTF PLNSTLEDVV FLKRKFKKEG

2221 PLYRPVMNRE ALEAMLSYYR PGTLSEKLTS ITMLAVHSGK QEYDRLFAPF REVGVVVPSF

2281 ESVEYRWRSL FW (SEQ ID NO:23)
```

Fig. 71B

```
   1 MATTMEQETC AHSLTFEECP KCSALQYRNG FYLLKYDEEW YPEELLTDGE DDVFDPELDM
  61 EVVFELQGNS TSSDKNNSSS EGNEGVIINN FYSNQYQNSI DLSANAAGSD PPRTYGQFSN
 121 LFSGAVNAFS NMLPLLADQN TEEMENLSDR VSQDTAGNTV TNTQSTVGRL VGYGTVHDGE
 181 HPASCADTAS EKILAVERYY TFKVNDWTST QKPFEYIRIP LPHVLSGEDG GVFGAALRRH
 241 YLVKTGWRVQ VQCNASQFHA GSLLVFMAPE YPTLDTFVMD NRWSKDNLPN GARTQTNKKG
 301 PFAMDHQNFW QWTLYPHQFL NLRTNTTVDL EVPYVNIAPT SSWTQHASWT LVIAVVAPLT
 361 YSTGASTSLD ITASIQPVRP VFNGLRHETL SRQSPIPVTI REHAGTWYST LPDSTVPIYG
 421 KTPVAPSNYM VGEYKDFLEI AQIPTFIGNK IPNAVPYIEA SNTAVKTQPL ATYQVTLSCS
 481 CLANTFLAAL SRNFAQYRGS LVYTFVFTGT AMMKGKFLIA YTPPGAGKPT SRDQAMQATY
 541 AIWDLGLNSS YSFTVPFISP THFRMVGTDQ VNITNADGWV TVWQLTPLTY PPGCPTSAKI
 601 LTMVSAGKDF SLKMPISPAP WSPQGVENAE KGVTENADAT ADFVAQPVYL PENQTKVAFF
 661 YDRSSPIGAF TVQSGSLESG FAPFSNKTCP NSVILTPGPQ FDPAYDQLRP QRLTEIWGNG
 721 NEETSKVFPL KSKQDYSFCL FSPFVYYKCD LEVTLSPHTS GNHGLLVRWC PTGTPTKPTT
 781 QVLHEVSSLS EGRTPQVYSA GPGISNQISF VVPYNSPLSV LPAVWYNGHK RFDNTGSLGI
 841 APNSDFGTLF FAGTKPDIKF TVYLRYKNMR VFCPRPTVFF PWPTSGDKID MTPRAGVLML
 901 ESPNALDISR TYPTLHVLIQ FNHRGLEVRL FRHGQFWAET RADVILRSKT KQVSFLSNGN
 961 YPSMDSRAPW NPWKNTYQAV LRAEPCRVTM DIYYKRVRPF RLPLVQKEWR VREENVFGLY
1021 RIFNAHYAGY FADLLIHDIE TNPGPFMFRP RKQVFQTQGA AVSSMAQTLL PNDLASKAMG
1081 SAFTALLDAN EDARKAMKII KTLSSLSDAW ENVKETLNNP EFWKQLLSRC VQLIAGMTIA
1141 VMHPDPLTLL CLGTLTAAEI TSQTSLCEEI AAKFKTIFIT PPPRFPTISL FQQQSPLKQV
1201 NDFFSLAKNL DWAVKTVEKV VDWFGTWIVQ EEKEQTLDQL LQRFPEHAKR ISDLRNGMAA
1261 YVECKESFDF FEKLYNQAVK EKRTGIAAVC EKFRQKHDHA TARCEPVVIV LRGDAGQGKS
1321 LSSQVIAQAV SKTIFGRQSV YSLPPDSDFF DGYENQFAAI MDDLGQNPDG SDFTTFCQMV
```

Fig. 72A

```
1381 STTNFLPNMA SLERKGTPFT SQLVVATTNL PEFRPVTIAH YPAVERRITF DYSVSAGPVC
1441 SKTEAGYKVL DVERAFRPTG EAPLPCFQNN CLFLEKAGLQ FRDNRTKEII SLVDVIERAV
1501 ARIERKKKVL TTVQTLVAQA PVDEVSFHSV VQQLKARQEA TDEQLEELQE AFAKVQERNS
1561 VFSDWLKISA MLCAATLALS QVVKMAKAVK QMVKPDLVRV QLDEQEQGPY NETARAKPKT
1621 LQLLDIQGPN PVMDFEKYVA KHVTAPIDFV YPTGVSTQTC LLVRGRTLAV NRHMAESDWT
1681 SIVVRGVTHA RSTVKILAIA KAGKETDVSF IRLSSGPLFR DNTSKFVKAG DVLPTGAAPV
1741 TGIMNTDIPM MYTGTFLKAG VSVPVETGQT FNHCIHYKAN TRKGWCGSAL LADLGGSKKI
1801 LGIHSAGSMG IAAASIVSQE MIRAVVNAFE PQGALERLPD GPRIHVPRKT ALRPTVARQV
1861 FQPAYAPAVL SKFDPRTEAD VDEVAFSKHT SNQESLPPVF RMVAKEYANR VFTLLGKDNG
1921 RLTVKQALEG LEGMDPMDRN TSPGLPYTAL GMRRTDVVDW ESATLIPFAA ERLRKMNEGD
1981 FSEVVYQTFL KDELRPIEKV QAAKTRIVDV PPFEHCILGR QLLGKFASKF QTQPGLELGS
2041 AIGCDPDVHW TAFGVAMQGF ERVYDVDYSN FDSTHSVAMF RLLAEEFFTP ENGFDPLTRE
2101 YLESLAISTH AFEEKRFLIT GGLPSGCAAT SMLNTIMNNI IIRAGLYLTY KNFEFDDVKV
2161 LSYGDDLLVA TNYQLDFDKV RASLAKTGYK ITPANKTSTF PLNSTLEDVV FLKRKFKKEG
2221 PLYRPVMNRE ALEAMLSYYR PGTLSEKLTS ITMLAVHSGK QEYDRLFAPF REVGVVVPSF
2281 ESVEYRWRSL FW (SEQ ID NO:24)
```

Fig. 72B

```
   1 MATTMEQEIC AHSLTLKGCP KCSALQYRNG FYLLKYDEEW YPEELLTDGE DDVFDPELDM
  61 EVVFELQGNS TSSDKNNSSS DGNEGVIINN FYSNQYQNSI DLSANATGSD PPRTYGQFSN
 121 LLSGAVNAFS NMIPLLADQN TEEMENLSDR VLQDTAGNTV TNTQSTVGRL VGYGAVHDGE
 181 HPASCADTAS EKILAVERYY TFKVNDWTST QKPFEYIRIP LPHVLSGEDG GVFGAALRRH
 241 YLVKTGWRVQ VQCNASQFHA GSLLVFMAPE YPTLDAFAMD NRWSKDNLPN GTKTQTNRKG
 301 PFAMDHQNFW QWTLYPHQFL NLRTNTTVDL EVPYVNIAPT SSWTQHASWT LVIAVVAPLT
 361 YSTGASTSLD ITASIQPVRP VFNGLRHETL SRQSPIPVTI REHAGTWYST LPDSTVPIYG
 421 KTPVAPANYM VGEYKDFLEI AQIPTFIGNK IPNAVPYIEA SNTAVKTQPL ATYQVTLSCS
 481 CLANTFLAAL SRNFAQYRGS LVYTFVFTGT AMMKGKFLIA YTPPGAGKPT SRDQAMQATY
 541 AIWDLGLNSS YSFTVPFISP THFRMVGTDQ VNITNVDGWV TVWQLTPLTY PPGCPTSAKI
 601 LTMVSAGKDF SLKMPISPAP WSPQGVENAE RGVTEDTDAT ADFVAQPVYL PENQTKVAFF
 661 YDRSSPIGAF TVKSGSLESG FTPFSNQTCP NSVILTPGPQ FDPAYDQLRP QRLTEIWGNG
 721 NEETSKVFPL KSKQDYSFCL FSPFVYYKCD LEVTLSPHTS GNHGLLVRWC PTGTPTKPTT
 781 QVLHEVSSLS EGRTPQVYSA GPGITNQISF VVPYNSPLSV LPAVWYNGHK RFDNTGSLGI
 841 APNSDFGTLF FAGTKPDIKF TVYLRYKNMR VFCPRPTVFF PWPSSGDKID MTPRAGVLML
 901 ESPNALDISR TYPTLHILIQ FNHGGLEIRL FRHGMFWAEA HADVILRSRT KQISFLNNGS
 961 FPSMDARAPW NPWKNTYHAV LRAEPYRVTM DVYHKRIRPF RLPLVQKEWN VREENVFGLY
1021 GIFNAHYAGY FADLLIHDIE TNPGPFMAKP KKQVFQTQGA AVSSMAQTLL PNDLASKVMG
1081 SAFTALLDAN EDAQKAMRII KTLSSLSDAW ENVKETLNNP EFWKQLLSRC VQLIAGMTIA
1141 VMHPDPLTLL CLGTLTAAEI TSQTSLCEEI VAKFKKIFTT PPPRFPTISL FQQQSPLKQV
1201 NDVFSLAKNL DWAVKTVEKV VDWFGTWVVQ EEKEQTLDQL LQRFPEHAKR ISDLRNGMSA
1261 YVECKESFDF FEKLYNQAVK EKRTGIAAVC EKFRQKHDHA TARCEPVVIV LRGDAGQGKS
1321 LSSQVIAQAV SKTIFGRQSV YSLPPDSDFF DGYENQFAAI MDDLGQNPDG SDFTTFCQMV
```

Fig. 73A

```
1381 STTNFLPNMA SLERNGTPFT SQIVVATTNL PEFRPVTIAH YPAVERRITF DYSVSAGPVC
1441 SKTEAGYKVL DVERAFRPTG DAPLPCFQNN CLFLEKAGLQ FRDNRTKEIL SLVDVIERAV
1501 ARIERKKKVL TTVQTLVAQA PVDEVSFHSV VQQLKARQEA TDEQLEELQE AFAKTQERSS
1561 VFSDWMKISA MLCAATLALS QVVKMAKTVK QMVRPDLVRV QLDEQEQGPY NEAVRAKPKT
1621 LQLLDIQGPN PVMDFEKYVA KFVTAPIDFV YPTGVSTQTC LLVKGRTLAV NRHMAESDWS
1681 SIVVRGVTHA RSTVRILAIA KAGKETDVSF IRLSSGPLFR DNTSKFVKAD DVLPATSAPV
1741 IGIMNTDIPM MFTGTFLKAG VSVPVETGQT FNHCIHYKAN TRKGWCGSAL LADLGGKKKI
1801 LGMHSAGSMG RTAASIVSQE MICAVVSAFE PQGALERLPD GPRIHVPRKT ALRPTVARRV
1861 FQPAYAPAVL SKFDPRTEAD VDEVAFSKHT SNQESLPPVF RMVAKEYANR VFTLLGRDNG
1921 RLTVKQALEG LEGMDPMDKN TSPGLPYTAL GMRRTDVVDW ESATLIPYAA DRLKKMNEGD
1981 FSDIVYQTFL KDELRPVEKV QAAKTRIVDV PPFEHCILGR QLLGRFASKF QTQPGLELGS
2041 AIGCDPDVHW TAFGVAMQGF ERVYDVDYSN FDSTHSVAMF RLLAEEFFTP ENGFDPLVKE
2101 YLESLAISTH AFEEKRYLIT GGLPSGCAAT SMLNTIMNNI IIRAGLYLTY KNFEFDDVKV
2161 LSYGDDLLVA TNYQLNFDKV RASLAKTGYK ITPANKTSTF PLDSTLEDVV FLKRKFKKEG
2221 PLYRPVMNRE ALEAMLSYYR PGTLSEKLTS ITMLAVHSGK PEYDRLFAPF REVGVVVPSF
2281 ESVEYRWRSL FW (SEQ ID NO:25)
```

Fig. 73B

```
   1 MATTMEQEIC AHSLTFKGCP KCSALQYRNG FYLLKYDEEW YPEELLTDGE DDVFDPELDM
  61 EVVFELQGNS TSSDKNNSSS DGNEGVIINN FYSNQYQNSI DLSANATGSD PPRTYGQFSN
 121 LLSGAVNAFS NMIPLLADQN TEEMENLSDR VLQDTAGNTV TNTQSTVGRL VGYGAVHDGE
 181 HPASCADTAS EKILAVERYY TFKVNDWTST QKPFEYIRIP LPHVLSGEDG GVFGAALRRH
 241 YLVKTGWRVQ VQCNASQFHA GSLLVFMAPE YPTLDAFAMD NRWSKDNLPN GTKTQTNRKG
 301 PFAMDHQNFW QWTLYPHQFL NLRTNTTVDL EVPYVNIAPT SSWTQHASWT LVIAVVAPLT
 361 YSTGASTSLD ITASIQPVRP VFNGLRHETL SRQSPIPVTI REHAGTWYST LPDSTVPIYG
 421 KTPVAPANYM VGEYKDFLEI AQIPTFIGNK IPNAVPYIEA SNTAVKTQPL ATYQVTLSCS
 481 CLANTFLAAL SRNFAQYRGS LVYTFVFTGT AMMKGKFLIA YTPPGAGKPT SRDQAMQATY
 541 AIWDLGLNSS YSFTVPFISP THFRMVGTDQ VNITNVDGWV TVWQLTPLTY PPGCPTSAKI
 601 LTMVSAGKDF SLKMPISPAP WSPQGVENAE RGVTEDTDAT ADFVAQPVYL PENQTKVAFF
 661 YDRSSPIGAF AVKSGSLESG FAPFSNETCP NSVILTPGPQ FDPAYDQLRP QRLTEIWGNG
 721 NEETSKVFPL KSKQDYSFCL FSPFVYYKCD LEVTLSPHTS GNHGLLVRWC PTGTPAKPTT
 781 QVLHEVSSLS EGRTPQVYSA GPGISNQISF VVPYNSPLSV LPAVWYNGHK RFDNTGSLGI
 841 APNSDFGTLF FAGTKPDIKF TVYLRYKNMR VFCPRPTVFF PWPSSGDKID MTPRAGVLML
 901 ESPNALDISR TYPTLHILIQ FNHGGLEIRL FRHGMFWAEA HADVILRSRT KQISFLNNGS
 961 FPSMDARAPW NPWKNTYHAV LRAEPYRVTM DVYHKRIRPF RLPLVQKEWN VREENVFGLY
1021 GIFNAHYAGY FADLLIHDIE TNPGPFMAKP KKQVFQTQGA AVSSMAQTLL PNDLASKVMG
1081 SAFTALLDAN EDAQKAMRII KTLSSLSDAW ENVKETLNNP EFWKQLLSRC VQLIAGMTIA
1141 VMHPDPLTLL CLGTLTAAEI TSQTSLCEEI VAKFKKIFTT PPPRFPTISL FQQQSPLKQV
1201 NDVFSLAKNL DWAVKTVEKV VDWFGTWVVQ EEKEQTLDQL LQRFPEHAKR ISDLRNGMSA
1261 YVECKESFDF FEKLYNQAVK EKRTGIAAVC EKFRQKHDHA TARCEPVVIV LRGDAGQGKS
1321 LSSQVIAQAV SKTIFGRQSV YSLPPDSDFF DGYENQFAAI MDDLGQNPDG SDFTTFCQMV
```

Fig. 74A

```
1381 STTNFLPNMA SLERNGTPFT SQIVVATTNL PEFRPVTIAH YPAVERRITF DYSVSAGPVC
1441 SKTEAGYKVL DVERAFRPTG DAPLPCFQNN CLFLEKAGLQ FRDNRTKEIL SLVDVIERAV
1501 ARIERKKKVL TTVQTLVAQA PVAEVSFHSV VQQLKARQEA TDEQLEELQE AFAKTQERSS
1561 VFSDWMKISA MLCAATLALS QVVKMAKTVK QMVRPDLVRV QLDEQEQGPY NEAVRAKPKT
1621 LQLLDIQGPN PVMDFEKYVA KFVTAPIDFV YPTGVSTQTC LLVKGRTLAV NRHMAESDWS
1681 SIVVRGVTHA RSTVRILAIA KAGKETDVSF IRLSSGPLFR DNTSKFVKAD DVLPATSAPV
1741 IGIMNTDIPM MFTGTFLKAG VSVPVETGQT FNHCIHYKAN TRKGWCGSAL LADLGGKKKI
1801 LGMHSAGSMG RTAASIVSQE MICAVVSAFE PQGALERLPD GPRIHVPRKT ALRPTVARRV
1861 FQPAYAPAVL SKFDPRTEAD VDEVAFSKHT SNQESLPPVF RMVAKEYANR VFTLLGRDNG
1921 RLTVKQALEG LEGMDPMDKN TSPGLPYTAL GMRRTDVVDW ESATLIPYAA DRLKKMNEGD
1981 FSDIVYQTFL KDELRPVEKV QAAKTRIVDV PPFEHCILGR QLLGRFASKF QTQPGLELGS
2041 AIGCDPDVHW TAFGVAMQGF ERVYDVDYSN FDSTHSVAMF RLLAEEFFTP ENGFDPLVKE
2101 YLESLAISTH AFEEKRYLIT GGLPSGCAAT SMLNTIMNNI IIRAGLYLTY KNFEFDDVKV
2161 LSYGDDLLVA TNYQLNFDKV RASLAKTGYK ITPANKTSTF PLDSTLEDVV FLKRKFKKEG
2221 PLYRPVMNRE ALEAMLSYYR PGTLSEKLTS ITMLAVHSGK PEYDRLFAPF REVGVVVPSF
2281 ESVEYRWRSL FW (SEQ ID NO:26)
```

Fig. 74B

```
   1 MATTMEQEIC AHSLTFKGCP KCSALQYRNG FYLLKYDEEW YPEELLTDGE DDVFDPELDM
  61 EVVFELQGNS TSSDKNNSSS DGNEGVIINN FYSNQYQNSI DLSANATGSD PPRTYGQFSN
 121 LLSGAVNAFS NMIPLLADQN TEEMENLSDR VLQDTAGNTV TNTQSTVGRL VGYGAVHDGE
 181 HPASCADTAS EKILAVERYY TFKVNDWTST QKPFEYIRIP LPHVLSGEDG GVFGAALRRH
 241 YLVKTGWPVQ VQCNASQFHA GSLLVFMAPE YPTLDAFAMD NRWSKDNLPN GTKTQTNRKG
 301 PFAMDHQNFW QWTLYPHQFL NLRTNTTVDL EVPYVNIAPT SSWTQHASWT LVIAVVAPLT
 361 YSTGASTSLD ITASIQPVRP VFNGLRHETL SRQSPIPVTI REHAGTWYST LPDSTVPIYG
 421 KTPVAPANYM VGEYKDFLEI AQIPTFIGNK IPNAVPYIEA SNTAVKTQPL ATYQVTLSCS
 481 CLANTFLAAL SRNFAQYRGS LVYTFVFTGT AMMKGKFLIA YTPPGAGKPT SRDQAMQATY
 541 AIWDLGLNSS YSFTVPFISP THFRMVGTDQ VNITNVDGWV TVWQLTPLTY PPGCPTSAKI
 601 LTMVSAGKDF SLKMPISPAP WSPQGVENAE RGVTEDTDAT ADFVAQPVYL PENQTKVAFF
 661 YDRSSPIGAF TVKSGSLESG FAPFSNETCP NSVILTPGPQ FDPAYDQLRP QRLTEIWGNG
 721 NEETSKVFPL KSKQDYSFCL FSPFVYYKCD LEVTLSPHTS GNHGLLVRWC PTGTPAKPTT
 781 QVLHEVSSLS EGRTPQVYSA GPGVSNQISF VVPYNSPLSV LPAVWYNGHK RFDNTGSLGI
 841 APNSDFGTLF FAGTKPDIKF TVYLRYKNMR VFCPRPTVFF PWPSSGDKID MTPRAGVLML
 901 ESPNALDISR TYPTLHILIQ FNHGGLEIRL FRHVQFWAEA HADVILRSRT KQISFLNNGS
 961 FPSMDARAPW NPWKNTYHAV LRAEPYRVTM DVYHKRIRPF RLPLVQKEWN VREENVFGLY
1021 GIFNAHYAGY FADLLIHDIE TNPGPFMAKP KKQVFQTQGA AVSSMAQTLL PNDLASKVMG
1081 SAFTALLDAN EDAQKAMRII KTLSSLSDAW ENVKETLNNP EFWKQLLSRC VQLIAGMTIA
1141 VMHPDPLTLL CLGTLTAAEI TSQTSLCEEI VAKFKKIFTT PPPRFPTISL FQQQSPLKQV
1201 NDVFSLAKNL DWAVKTVEKV VDWFGTWVVQ EEKEQTLDQL LQRFPEHAKR ISDLRNGMSA
1261 YVECKESFDF FEKLYNQAVK EKRTGIAAVC EKFRQKHDHA TARCEPVVIV LRGDAGQGKS
```

Fig. 75A

```
1321 LSSQVIAQAV SKTIFGRQSV YSLPPDSDFF DGYENQFAAI MDDLGQNPDG SDFTTFCQMV

1381 STTNFLPNMA SLERNGTPFT SQLVVATTNL PEFRPVTIAH YPAVERRITF DYSVSAGPVC

1441 SKTEAGYKVL DVERAFRPTG DAPLPCFQNN CLFLEKAGLQ FRDNRTKEIL SLVDVIERAV

1501 ARIERKKKVL TTVQTLVAQA PVAEVSFHSV VQQLKARQEA TDEQLEELQE AFAKTQERSS

1561 VFSDWMKISA MLCAATLALT QVVKMAKTVK QMVRPDLVRV QLDEQEQGPY NEAVRAKPKT

1621 LQLLDIQGPN PVMDFEKYVA KFVTAPIDFV YPTGVSTQTC LLVKGRTLAV NRHMAESDWS

1681 SIVVRGVTHA RSTVRILAIA KAGKETDVSF IRLSSGPLFR DNTSKFVKAD DVLPATSAPV

1741 IGIMNTDIPM MFTGTFLKAG VSVPVETGQT FNHCIHYKAN TRKGWCGSAL LADLGGKKKI

1801 LGMHSAGSMG VAAASIVSQE MICAVVSAFE PQGALERLPD GPRIHVPRKT ALRPTVARQV

1861 FQPAYAPAVL SKFDPRTEAD VDEVAFSKHT SNQESLPPVF RMVAKEYANR VFTLLGRDNG

1921 RLTVKQALEG LEGMDPMDKN TSPGLPYTAL GMRRTDVVDW ESATLIPYAA DRLKKMNEGD

1981 FSDIVYQTFL KDELRPVEKV QAAKTRIVDV PPFEHCILGR QLLGRFASKF QTQPGLELGS

2041 AIGCDPDVHW TAFGVAMQGF ERVYDVDYSN FDSTHSVAMF RLLAEEFFTP ENGFDPLVKE

2101 YLESLAISTH AFEEKRYLIT GGLPSGCAAT SMLNTIMNNI IIRAGLYLTY KNFEFDDVKV

2161 LSYGDDLLVA TNYQLNFDKV RASLAKTGYK ITPANKTSTF PLDSTLEDVV FLKRKFKKEG

2221 PLYRPVMNRE ALEAMLSYYR PGTLSEKLTS ITMLAVHSGK PEYDRLFAPF REVGVVVPSF

2281 ESVEYRWRSL FW (SEQ ID NO:27)
```

Fig. 75B

```
   1 MATTMEQEIC AHSLTFKGCP KCSALQYRNG FYLLKYDEEW YPEELLTDGE DDVFDPELDM
  61 EVVFELQGNS TSSDKNNSSS DGNEGVIINN FYSNQYQNSI DLSANATGSD PPRTYGQFSN
 121 LLSGAVNAFS NMIPLLADQN TEEMENLSDR VLQDTAGNTV TNTQSTVGRL VGYGAVHDGE
 181 HPASCADTAS EKILAVERYY TFKVNDWTST QKPFEYIRIP LPHVLSGEDG GVFGAALRRH
 241 YLVKTGWRVQ VQCNASQFHA GSLLVFMAPE YPTLDAFAMD NRWSKDNLPN GTKTQTNRKG
 301 PFAMDHQNFW QWTLYPHQFL NLRTNTTVDL EVPYVNIAPT SSWTQHASWT LVIAVVAPLT
 361 YSTGASTSLD ITASIQPVRP VFNGLRHETL SRQSPIPVTI REHAGTWYST LPDSTVPIYG
 421 KTPVAPANYM VGEYKDFLEI AQIPTFIGNK IPNAVPYIEA SNTAVKTQPL ATYQVTLSCS
 481 CLANTFLAAL SRNFAQYRGS LVYTFVFTGT AMMKGKFLIA YTPPGAGKPT SRDQAMQATY
 541 AIWDLGLNSS YSFTVPFISP THFRMVGTDQ VNITNVDGWV TVWQLTPLTY PPGCPTSAKI
 601 LTMVSAGKDF SLKMPISPAP WSPQGVENAE RGVTEDTDAT ADFVAQPVYL PENQTKVAFF
 661 YDRSSPIGAF TVKSGSLESG FAPFSNKTCP NSVILTPGPQ FDPAYDQLRP QRLTEIWGNR
 721 NEETSKVFPL KSKQDYSFCL FSPFVYYKCD LEVTLSPHTS GNHGLLVRWC PTGTPAKPTT
 781 QVLHEVSSLS EGRTPQVYSA GPGISNQISF VVPYNSPLSV LPAVWYNGHK RFDNTGSLGI
 841 APNSDFGTLF FAGTKPDIKF TVYLRYKNMR VFCPRPTVFF PWPSSGDKID MTPRAGVLML
 901 ESPNALDISR TYPTLHILIQ FNHGGLEIRL FRHGQFWAEA HADVILRSRT KQISFLNNGS
 961 FPSMDARAPW NPWKNTYHAV LRAEPYRVTM DVYHKRIRPF RLPLVQKEWN VREENVFGLY
1021 SIFNAHYAGY FADLLIHDIE TNPGPFMAKP KKQVFQTQGA AVSSMAQTLL PNDLASKVMG
1081 SAFTALLDAN EDAQKAMRII KTLSSLSDAW ENVKETLNNP EFWKQLLSRC VQLIAGMTIA
1141 VMHPDPLTLL CLGTLTAAEI TSQTSLCEEI VAKFKKIFTT PPPRFPTISL FQQQSPLKQV
1201 NDVFSLAKNL DWAVKTVEKV VDWFGTWVVQ EEKEQTLDQL LQRFPEHAKR ISDLRNGMSA
1261 YVECKESFDF FEKLYNQAVK EKRTGIAAVC EKFRQKHDHA TARCEPVVIV LRGDAGQGKS
1321 LSSQVIAQAV SKTIFGRQSV YSLPPDSDFF DGYENQFAAI MDDLGQNPDG SDFTTFCQMV
```

Fig. 76A

```
1381 STTNFLPNMA SLERKGTPFT SQLVVATTNL PEFRPVTIAH YPAVERRITF DYSVSAGPVC
1441 SKTEAGYKVL DVERAFRPTG DAPLPCFQNN CLFLEKAGLQ FRDNRTKEIL SLVDVIERAV
1501 ARIERKKKVL TTVQTLVAQA PVDEVSFHSV VQQLKARQEA TDEQLEELQE AFAKTQERSS
1561 VFSDWMKISA MLCAATLALT QVVKMAKTVK QMVRPDLVRV QLDEQEQGPY NEAVRAKPKT
1621 LQLLDIQGPN PVMDFEKYVA KFVTAPIDFV YPTGVSTQTC LLVKGRTLAV NRHMAESDWS
1681 SIVVRGVTHA RSTVRILAIA KAGKETDVSF IRLSSGPLFR DNTSKFVKAD DVLPATSAPV
1741 IGIMNTDIPM MFTGTFLKAG VSVPVETGQT FNHCIHYKAN TRKGWCGSAL LADLGGKKKI
1801 LGMHSAGSMG RTAASIVSQE MICAVVSAFE PQGALERLPD GPRIHVPRKT ALRPTVARQV
1861 FQPAYAPAVL SKFDPRTEAD VDEVAFSKHT SNQESLPPVF RMVAKEYANR VFTLLGRDNG
1921 RLTVKQALEG LEGMDPMDKN TSPGLPYTAL GMRRTDVVDW ESATLIPYAA DRLKKMNEGD
1981 FSDIVYQTFL KDELRPVEKV QAAKTRIVDV PPFEHCILGR QLLGRFASKF QTQPGLELGS
2041 AIGCDPDVHW TAFGVAMQGF ERVYDVDYSN FDSTHSVAMF RLLAEEFFTP ENGFDPLVKE
2101 YLESLAISTH AFEEKRYLIT GGLPSGCAAT SMLNTIMNNI IIRAGLYLTY KNFEFDDVKV
2161 LSYGDDLLVA TNYQLNFDKV RASLAKTGYK ITPANKTSTF PLDSTLEDVV FLKRKFKKEG
2221 PLYRPVMNRE ALEAMLSYYR PGTLSEKLTS ITMLAVHSGK PEYDRLFAPF REVGVVVPSF
2281 ESVEYRWRSL FW (SEQ ID NO:28)
```

Fig. 76B

```
   1 MATTMEQEIC AHSMTFEECP KCSALQYRNG FYLLKYDEEW YPEESLTDGE DDVFDPDLDM
  61 EVVFETQGNS TSSDKNNSSS EGNEGVIINN FYSNQYQNSI DLSANATGSD PPKTYGQFSN
 121 LLSGAVNAFS NMLPLLADQN TEEMENLSDR VSQDTAGNTV TNTQSTVGRL VGYGTVHDGE
 181 HPASCADTAS EKILAVERYY TFKVNDWTST QKPFEYIRIP LPHVLSGEDG GVFGATLRRH
 241 YLVKTGWRVQ VQCNASQFHA GSLLVFMAPE YPTLDVFAMD NRWSKDNLPN GTRTQTNRKG
 301 PFAMDHQNFW QWTLYPHQFL NLRTNTTVDL EVPYVNIAPT SSWTQHASWT LVIAVVAPLT
 361 YSTGASTSLD ITASIQPVRP VFNGLRHEVL SRQSPIPVTI REHAGTWYST LPDSTVPIYG
 421 KTPVAPANYM VGEYKDFLEI AQIPTFIGNK VPNAVPYIEA SNTAVKTQPL AVYQVTLSCS
 481 CLANTFLAAL SRNFAQYRGS LVYTFVFTGT AMMKGKFLIA YTPPGAGKPT SRDQAMQATY
 541 AIWDLGLNSS YSFTVPFISP THFRMVGTDQ ANITNVDGWV TVWQLTPLTY PPGCPTSAKI
 601 LTMVSAGKDF SLKMPISPAP WSPQGVENAE KGVTENTDAT ADFVAQPVYL PENQTKVAFF
 661 YDRSSPIGAF AVKSGSLESG FAPFSNKACP NSVILTPGPQ FDPAYDQLRP QRLTEIWGNG
 721 NEETSEVFPL KTKQDYSFCL FSPFVYYKCD LEVTLSPHTS GAHGLLVRWC PTGTPTKPTT
 781 QVLHEVSSLS EGRTPQVYSA GPGTSNQISF VVPYNSPLSV LPAVWYNGHK RFDNTGDLGI
 841 APNSDFGTLF FAGTKPDIKF TVYLRYKNMR VFCPRPTVFF PWPTSGDKID MTPRAGVLML
 901 ESPNPLDVSK TYPTLHILLQ FNHRGLEARI FRHGQLWAET HAEVVLRSKT KQISFLSNGS
 961 YPSMDATTPL NPWKSTYQAV LRAEPHRVTM DVYHKRIRPF RLPLVQKEWR TCEENVFGLY
1021 HVFETHYAGY FSDLLIHDVE TNPGPFTFKP RQRPVFQTQG AAVSSMAQTL LPNDLASKAM
1081 GSAFTALLDA NEDAQKAMKI IKTLSSLSDA WENVKGTLNN PEFWKQLLSR CVQLIAGMTI
1141 AVMHPDPLTL LCLGVLTAAE ITSQTSLCEE IAAKFKTIFT TPPPRFPVIS LFQQQSPLKQ
1201 VNDVFSLAKN LDWAVKTVEK VVDWFGTWVA QEEREQTLDQ LLQRFPEHAK RISDLRNGMA
1261 AYVECKESFD FFEKLYNQAV KEKRTGIAAV CEKFRQKHDH ATARCEPVVI VLRGDAGQGK
```

Fig. 77A

```
1321 SLSSQIIAQA VSKTIFGRQS VYSLPPDSDF FDGYENQFAA IMDDLGQNPD GSDFTTFCQM
1381 VSTTNLLPNM ASLERKGTPF TSQLVVATTN LPEFRPVTIA HYPAVERRIT FDYSVSAGPV
1441 CSKTEAGCKV LDVERAFRPT GDAPLPCFQN NCLFLEKAGL QFRDNRSKEI LSLVDVIERA
1501 VTRIERKKKV LTAVQTLVAQ GPVDEVSFYS VVQQLKARQE ATDEQLEELQ EAFARVQERS
1561 SVFSDWMKIS AMLCAATLAL TQVVKMAKAV KQMVRPDLVR VQLDEQEQGP YNETTRIKPK
1621 TLQLLDVQGP NPTMDFEKFV AKFVTAPIGF VYPTGVSTQT CLLVKGRTLA VNRHMAESDW
1681 TSIVVRGVSH TRSSVKIIAI AKAGKETDVS FIRLSSGPLF RDNTSKFVKA SDVLPHSSSP
1741 LIGIMNVDIP MMYTGTFLKA GVSVPVETGQ TFNHCIHYKA NTRKGWCGSA ILADLGGSKK
1801 ILGFHSAGSM GVAAASIISQ EMIDAVQAF EPQGALERLP DGPRIHVPRK TALRPTVARQ
1861 VFQPAFAPAV LSKFDPRTDA DVDEVAFSKH TSNQETLPPV FRMVAREYAN RVFALLGRDN
1921 GRLSVKQALD GLEGMDPMDK NTSPGLPYTT LGMRRTDVVD WETATLIPFA AERLEKMNNK
1981 DFSDIVYQTF LKDELRPIEK VQAAKTRIVD VPPFEHCILG RQLLGKFASK FQTQPGLELG
2041 SAIGCDPDVH WTAFGVAMQG FERVYDVDYS NFDSTHSVAI FRLLAEEFFS EENGFDPLVK
2101 DYLESLAISK HAYEEKRYLI TGGLPSGCAA TSMLNTIMNN IIIRAGLYLT YKNFEFDDVK
2161 VLSYGDDLLV ATNYQLNFDR VRTSLAKTGY KITPANKTST FPLESTLEDV VFLKRKFKKE
2221 GPLYRPVMNR EALEAMLSYY RPGTLSEKLT SITMLAVHSG KQEYDRLFAP FREVGIVPT
2281 FESVEYRWRS LFW (SEQ ID NO:29)
```

Fig. 77B

```
   1 MACKHGYPDV CPICTAVDVT PGFEYLLLAD GEWFPTDLLC VDLDDDVFWP SNSSNQSETM
  61 EWTDLPLVRD IVMEPQGNAS SSDKSNSQSS GNEGVIINNF YSNQYQNSID LSASGGNAGD
 121 APQNNGQLSN ILGGAANAFA TMAPLLLDQN TEEMENLSDR VASDKAGNSA TNTQSTVGRL
 181 CGYGEAHHGE HPASCADTAT DKVLAAERYY TIDLASWTTT QEAFSHIRIP LPHVLAGEDG
 241 GVFGATLRRH YLCKTGWRVQ VQCNASQFHA GSLLVFMAPE FYTGKGTKTG DMEPTDPFTM
 301 DTTWRAPQGA PTGYRYDSRT GFFAMNHQNQ WQWTVYPHQI LNLRTNTTVD LEVPYVNIAP
 361 TSSWTQHANW TLVVAVFSPL QYASGSSSDV QITASIQPVN PVFNGLRHET VIAQSPIAVT
 421 VREHKGCFYS TNPDTTVPIY GKTISTPNDY MCGEFSDLLE LCKLPTFLGN PNSNNKRYPY
 481 FSATNSVPTT SLVDYQVALS CSCMCNSMLA AVARNFNQYR GSLNFLFVFT GAAMVKGKFL
 541 IAYTPPGAGK PTTRDQAMQA TYAIWDLGLN SSFVFTAPFI SPTHYRQTSY TSATIASVDG
 601 WVTVWQLTPL TYPSGAPVNS DILTLVSAGD DFTLRMPISP TKWAPQGSDN AEKGKVSNDD
 661 ASVDFVAEPV KLPENQTRVA FFYDRAVPIG MLRPGQNIES TFVYQENDLR LNCLLLTPLP
 721 SFCPDSTSGP VKTKAPVQWR WVRSGGTTNF PLMTKQDYAF LCFSPFTYYK CDLEVTVSAL
 781 GTDTVASVLR WAPTGAPADV TDQLIGYTPS LGETRNPHMW LVGAGNTQIS FVVPYNSPLS
 841 VLPAAWFNGW SDFGNTKDFG VAPNADFGRL WIQGNTSASV RIRYKKMKVF CPRPTLFFPW
 901 PVSTRSKINA DNPVPILELE NPAAFYRIDL FITFIDEFIT FDYKVHGRPV LTFRIPGFGL
 961 TPAGRMLVCM GEKPAHGPFT SSRSLYHVIF TATCSSFSFS IYKGRYRSWK KPIHDELVDR
1021 GYTTFGEFFR AVRAYHADYY KQRLIHDVEM NPGPVQSVFQ PQGAVLTKSL APQAGIQNLL
1081 LRLLGIDGDC SEVSKAITVV TDLFAAWERA KTTLVSPEFW SKLILKTTKF IAASVLYLHN
1141 PDFTTTVCLS LMTGVDLLTN DSVFDWLKNK LSSFFRTPPP VCPNVLQPQG PLREANEGFT
1201 FAKNIEWAMK TIQSIVNWLT SWFKQEEDHP QSKLDKFLME FPDHCRNIMD MRNGRKAYCE
1261 CTASFKYFDE LYNLAVTCKR IPLASLCEKF KNRHDHSVTR PEPVVVVLRG AAGQGKSVTS
1321 QIIAQSVSKM AFGRQSVYSM PPDSEYFDGY ENQFSVIMDD LGQNPDGEDF TVFCQMVSST
```

Fig. 78A

```
1381 NFLPNMAHLE RKGTPFTSSF IVATTNLPKF RPVTVAHYPA VDRRITFDFT VTAGPHCTTS
1441 NGMLDIEKAF DEIPGSKPQL ACFSADCPLL HKRGVMFTCN RTKAVYNLQQ VVKMVNDTIT
1501 RKTENVKKMN SLVAQSPPDW EHFENILTCL RQNNAALQDQ LDELQEAFAQ ARERSDFLSD
1561 WLKVSAIIFA GIASLSAVIK LASKFKESIW PSPVRVELSE GEQAAYAGRA RAQKQALQVL
1621 DIQGGGKVLA QAGNPVMDFE LFCAKNMVAP ITFYYPDKAE VTQSCLLLRA HLFVVNRHVA
1681 ETEWTAFKLK DVRHERDTVV TRSVNRSGAE TDLTFIKVTK GPLFKDNVNK FCSNKDDFPA
1741 RNDAVTGIMN TGLAFVYSGN FLIGNQPVNT TTGACFNHCL HYRAQTRRGW CGSAVICNVN
1801 GKKAVYGMHS AGGGGLAAAT IITRELIEAA EKSMLALEPQ GAIVDISTGS VVHVPRKTKL
1861 RRTVAHDVFQ PKFEPAVLSR YDPRTDKDVD VVAFSKHTTN MESLPPVFDI VCDEYANRVF
1921 TILGKDNGLL TVEQAVLGLP GMDPMEKDTS PGLPYTQQGL RRTDLLNFNT AKMTPQLDYA
1981 HSKLVLGVYD DVVYQSFLKD EIRPLEKIHE AKTRIVDVPP FAHCIWGRQL LGRFASKFQT
2041 KPGLELGSAI GTDPDVDWTP YAAELSGFNY VYDVDYSNFD ASHSTAMFEC LIKNFFTEQN
2101 GFDRRIAEYL RSLAVSRHAY EDRRVLIRGG LLSGCAATSM LNTIMNNVII RAALYLTYSN
2161 FEFDDIKVLS YGDDLLIGTN YQIDFNLVKE RLAPFGYKIT PANKTTTFPL TSHLQDVTFL
2221 KRRFVRFNSY LFRPQMDAVN LKAMVSYCKP GTLKEKLMSI ALLAVHSGPD IYDEIFLPFR
2281 NVGIVVPTYS SMLYRWLSLF R (SEQ ID NO:30)
```

Fig. 78B

```
   1 MACKHGYPDV CPICTAVDAT PDFEYLLMAD GEWFPTDLLC VDLDDDVFWP SDTSTQPQTM
  61 EWTDVPLVCD TVMEPQGNAS SSDKSNSQSS GNEGVIINNF YSNQYQNSID LSASGGNAGD
 121 APQNNGQLSS ILGGAANAFA TMAPLLMDQN TEEMENLSDR VASDKAGNSA TNTQSTVGRL
 181 CGYGKSHHGE HPTSCADAAT DKVLAAERYY TIDLASWTTS QEAFSHIRIP LPHVLAGEDG
 241 GVFGATLRRH YLCKTGWRVQ VQCNASQFHA GSLLVFMAPE FYTGKGTKSG TMEPSDPFTM
 301 DTTWRSPQSA PTGYRYDRQA GFFAMNHQNQ WQWTVYPHQI LNLRTNTTVD LEVPYVNVAP
 361 SSSWTQHANW TLVVAVLSPL QYATGSSPDV QITASLQPVN PVFNGLRHET VLAQSPIPVT
 421 VREHQGCFYS TNPDTTVPIY GKTISTPSDY MCGEFSDLLE LCKLPTFLGN PSTDNKRYPY
 481 FSATNSVPAT SLVDYQVALS CSCTANSMLA AVARNFNQYR GSLNFLFVFT GAAMVKGKFR
 541 IAYTPPGAGK PTTRDQAMQA TYAIWDLGLN SSFNFTAPFI SPTHYRQTSY TSPTITSVDG
 601 WVTVWQLTPL TYPSGTPTHS DILTLVSAGD DFTLRMPISP TKWVPQGIDN AEKGKVSNDD
 661 ASVDFVAEPV KLPENQTRVA FFYDRAVPIG MLRPGQNMET TFSYQENDFR LNCLLLTPLP
 721 SYCPDSSSGP VRTKAPVQWR WVRSGGANGA NFPLMTKQDY AFLCFSPFTY YKCDLEVTVS
 781 AMGAGTVSSV LRWAPTGAPA DVTDQLIGYT PSLGETRNPH MWIVGSGNSQ ISFVVPYNSP
 841 LSVLPAAWFN GWSDFGNTKD FGVAPTSDFG RIWIQGNSSA SVRIRYKKMK VFCPRPTLFF
 901 PWPTPTTTKI NADNPVPILE LENPASLYRI DLFITFTDEL ITFDYKVHGR PVLTFRIPGF
 961 GLTPAGRMLV CMGAKPAHSP FTSSKSLYHV IFTSTCNSFS FTIYKGRYRS WKKPIHDELV
1021 DRGYTTFREF FKAVRGYHAD YYKQRLIHDV EMNPGPVQSV FQPQGAVLTK SLAPQAGIQN
1081 ILLRLLGIEG DCSEVSKAIT VVTDLVAAWE KAKTTLVSPE FWSELILKTT KFIAASVLYL
1141 HNPDFTTTVC LSLMTGVDLL TNDSVFDWLK SKLSSFFRTP PPACPNVMQP QGPLREANEG
1201 FTFAKNIEWA TKTIQSIVNW LTSWFKQEED HPQSKLDKLL MEFPDHCRNI MDMRNGRKAY
1261 CECTASFKYF DDLYNLAVTC KRIPLASLCE KFKNRHDHSV TRPEPVVAVL RGAAGQGKSV
1321 TSQIIAQSVS KMAFGRQSVY SMPPDSEYFD GYENQFSVIM DDLGQNPDGE DFTVFCQMVS
1381 STNFLPNMAH LERKGTPFTS SFIVATTNLP KFRPVTAHY PAVDRRITFD FTVTAGPHCK
```

Fig. 79A

```
1441 TPAGMLDIEK AFDEIPGSKP QLACFSADCP LLHKRGVMFT CNRTKTVYNL QQVVKMVNDT
1501 ITRKTENVKK MNSLVAQSPP DWQHFENILT CLRQNNAALQ DQVDELQEAF TQARERSDFL
1561 SDWLKVSAII FAGIVSLSAV IKLASKFKES IWPTPVRVEL SEGEQAAYAG RARAQKQALQ
1621 VLDIQGGGKV LAQAGNPVMD FELFCAKNMV SPITFYYPDK AEVTQSCLLL RAHLFVVNRH
1681 VAETEWTAFK LRDVRHERDT VVMRSVNRSG AETDLTFVKV TKGPLFKDNV NKFCSNKDDF
1741 PARNDTVTGI MNTGLAFVYS GNFLIGNQPV NTTTGACFNH CLHYRAQTRR GWCGSAIICN
1801 VNGKKAVYGM HSAGGGGLAA ATIITRELIE AAEKSMLALE PQGAIVDIST GSVVHVPRKT
1861 KLRRTVAHDV FQPKFEPAVL SRYDPRTDKD VDVVAFSKHT TNMESLPPIF DIVCGEYANR
1921 VFTILGKDNG LLTVEQAVLG LSGMDPMEKD TSPGLPYTQQ GLRRTDLLDF NTAKMTPQLD
1981 YAHSKLVLGV YDDVVYQSFL KDEIRPLEKI HEAKTRIVDV PPFAHCIWGR QLLGRFASKF
2041 QTKPGFELGS AIGTDPDVDW TRYAAELSGF NYVYDVDYSN FDASHSTAMF ECLINNFFTE
2101 QNGFDRRIAE YLRSLAVSRH AYEDRRVLIR GGLPSGCAAT SMLNTIMNNV IIRAALYLTY
2161 SNFEFDDIKV LSYGDDLLIG TNYQIDFNLV KERLAPFGYK ITPANKTTTF PLTSHLQDVT
2221 FLKRRFVRFN SYLFRPQMDA VNLKAMVSYC KPGTLKEKLM SIALLAVHSG PDIYDEIFLP
2281 FRNVGIVVPT YDSMLYRWLS LFR (SEQ ID NO:31)
```

Fig. 79B

```
   1 MACKHGYPDV CPICTAVDAT PGFEYLLMAD GEWYPTDLLC VDLDDDVFWP SDTSNQSQTM
  61 DWTDVPLIRD IVMEPQGNSS SSDKSNSQSS GNEGVIINNF YSNQYQNSID LSASGGNAGD
 121 APQTNGQLSN ILGGAANAFA TMAPLLLDQN TEEMENLSDR VASDKAGNSA TNTQSTVGRL
 181 CGYGKSHHGE HPASCADTAT DKVLAAERYY TIDLASWTTS QEAFSHIRIP LPHVLAGEDG
 241 GVFGATLRRH YLCKTGWRVQ VQCNASQFHA GSLLVFMAPE FYTGKGTKTG TMEPSDPFTM
 301 DTEWRSPQGA PTGYRYDSRT GFFATNHQNQ WQWTVYPHQI LNLRTNTTVD LEVPYVNVAP
 361 SSSWTQHANW TLVVAVLSPL QYATGSSPDV QITASLQPVN PVFNGLRHET VIAQSPIPVT
 421 VREHKGCFYS TNPDTTVPIY GKTISTPSDY MCGEFSDLLE LCKLPTFLGN PNTNNKRYPY
 481 FSATNSVPAT SMVDYQVALS CSCMANSMLA AVARNFNQYR GSLNFLFVFT GAAMVKGKFL
 541 IAYTPPGAGK PTTRDQAMQS TYAIWDLGLN SSFNFTAPFI SPTHYRQTSY TSPTITSVDG
 601 WVTVWKLTPL TYPSGTPTNS DILTLVSAGD DFTLRMPISP TKWVPQGVDN AEKGKVSNDD
 661 ASVDFVAEPV KLPENQTRVA FFYDRAVPIG MLRPGQNMET TFNYQENDYR LNCLLLTPLP
 721 SFCPDSSSGP QKTKAPVQWR WVRSGGVNGA NFPLMTKQDY AFLCFSPFTF YKCDLEVTVS
 781 ALGMTRVASV LRWAPTGAPA DVTDQLIGYT PSLGETRNPH MWLVGAGNSQ VSFVVPYNSP
 841 LSVLPAAWFN GWSDFGNTKD FGVAPNADFG RLWIQGNTSA SVRIRYKKMK VFCPRPTLFF
 901 PWPTPTTTKI NADNPVPILE LENPAALYRI DLFITFTDEF ITFDYKVHGR PVLTFRIPGF
 961 GLTPAGRMLV CMGEQPAHGP FTSSRSLYHV IFTATCSSFS FSIYKGRYRS WKKPIHDELV
1021 DRGYTTFGEF FKAVRGYHAD YYRQRLIHDV ETNPGPVQSV FQPQGAVLTK SLAPQAGIQN
1081 LLLRLLGIDG DCSEVSKAIT VVTDLVAAWE KAKTTLVSPE FWSKLILKTT KFIAASVLYL
1141 HNPDFTTTVC LSLMTGVDLL TNDSVFDWLK QKLSSFFRTP PPACPNVMQP QGPLREANEG
1201 FTFAKNIEWA MKTIQSVVNW LTSWFKQEED HPQSKLDKLL MEFPDHCRNI MDMRNGRKAY
1261 CECTASFKYF DELYNLAVTC KRIPLASLCE KFKNRHDHSV TRPEPVVVVL RGAAGQGKSV
1321 TSQIIAQSVS KMAFGRQSVY SMPPDSEYFD GYENQFSVIM DDLGQNPDGE DFTVFCQMVS
1381 STNFLPNMAH LERKGTPFTS SFIVATTNLP KFRPVTVAHY PAVDRRITFD FTVTAGPHCK
```

Fig. 80A

```
1441 TPAGMLDVEK AFDEIPGSKP QLACFSADCP LLHKRGVMFT CNRTQTVYNL QQVVKMVNDT

1501 ITRKTENVKK MNSLVAQSPP DWEHFENILT CLRQNNAALQ DQLDELQEAF AQARERSDFL

1561 SDWLKVSAII FAGIASLSAV IKLASKFKES IWPTPVRVEL SEGEQAAYAG RARAQKQALQ

1621 VLDIQGGGKV LAQAGNPVMD FELFCAKNIV APITFYYPDK AEVTQSCLLL RAHLFVVNRH

1681 VAETDWTAFK LKDVRHERHT VALRSVNRSG AKTDLTFIKV TKGPLFKDNV NKFCSNKDDF

1741 PARNDTVTGI MNTGLAFVYS GNFLIGNQPV NTTTGACFNH CLHYRAQTRR GWCGSAIICN

1801 VNGKKAVYGM HSAGGGGLAA ATIITKELIE AAEKSMLALE PQGAIVDIAT GSVVHVPRKT

1861 KLRRTVAHDV FQPKFEPAVL SRYDPRTDKD VDVVAFSKHT TNMESLPPIF DVVCGEYANR

1921 VFTILGKENG LLTVEQAVLG LPGMDPMEKD TSPGLPYTQQ GLRRTDLLNF ITAKMTPQLD

1981 YAHSKLVIGV YDDVVYQSFL KDEIRPIEKI HEAKTRIVDV PPFAHCIWGR QLLGRFASKF

2041 QTKPGLELGS AIGTDPDVDW TRYAVELSGF NYVYDVDYSN FDASHSTAMF ECLINNFFTE

2101 QNGFDRRIAE YLRSLAVSRH AYEDRRVLIR GGLPSGCAAT SMLNTIMNNV IIRAALYLTY

2161 SNFDFDDIKV LSYGDDLLIG TNYQIDFNLV KERLAPFGYK ITPANKTTTF PLTSHLQDVT

2221 FLKRRFVRFN SYLFRPQMDA VNLKAMVSYC KPGTLKEKLM SIALLAVHSG PDIYDEIFLP

2281 FRNVGIVVPT YSSMLYRWLS LFR (SEQ ID NO:32)
```

Fig. 80B

```
   1 MMACIHGYPS VCPICTAIDK SSDGMYLLLA DNEWFPADLL TMDLDDDVFW PNDESDVSET
  61 MDWTDLPFIL DTIMEPQGNS TSSDKSNSQS SGNEGVIINN FYSNQYQNSI DLSANGGNAG
 121 GAPKTEGQLG NILGNAANAF STMAPLLLDQ NTEEMENLSD RVDSDKAGNS AVNTQSSVGR
 181 LCGYGMHHKG KHPASCADTA TDKVLSAERY YTIDLATWTT TLGTFSHIRI PLPHVLAGED
 241 GGVFGSTLRR HYLCKCGWRI QVQCNASQFH AGSLLVFMAP EFYTGHTPVT GTTEPATPFT
 301 MDSSWQTPQQ NPVGFRYDGR TGYFALNHQN YWQWMVYPHQ ILNLRTNTSV DLEVPFTNIA
 361 PTSSWTQHAN WTLVVAVLTP LQYAAGSATD VQITASIQPV KPVFNGLRHE AVVPQSPIPV
 421 TVREHQGTFY STNPDTTVPI YGKTIATPSD YMCGEFSDLV ELCKLPTFLG NPANTSPAGG
 481 RYPYFSATNS VPATALASYQ VALSCSCMSN SMLAAVARNF NQYRGSLNFL FVFTGTAMTK
 541 GKFLIAYTPP GAGKPTTREQ AMQATYAIWD LGLNSSYNFT VPFISPTHYR QTSYTSTSIT
 601 SVDGWLTVWQ LTPLTYPANT PPNADILTLV SAGDDFTLRM PISPTKWIPQ GVDNAEKGKV
 661 SNDDATVDFV AEPVKFPDNQ TKVSFFYDRS VPLGLLRPAQ GMEQDFAYAA NDSRANSILL
 721 TPLPSYAPDS TTGPTETQAP IQWRWLRGTS DGSTTFPLMT KQDYAFLLFS PFTYYKADLE
 781 VTLSAISNSN NVTVVRWAPT GAPADISRQL SGYTPSIGDT RDPHLWFVGA GNSQTSFVVP
 841 YNSPLSVLPA AWFNGWSDFG NTKDFGVAPN ADFGRLWIQG NISVAVRVRY KKMKVFCPRP
 901 TLFLPWPSTT TTRIHADNPV SVMELQNPFS FYRVDLFITF TDELITFDYK VHGRPVLQYQ
 961 VPGLGLTCAG RMLVCMGQMP NHAPFSTVRH LYHVVFTGSR NSFGVVIYYK RHRPWKKPLH
1021 EELHDYGFEC FSDFFKHVRE YHAAYYKQRL MHDVETNPGP PVQSVFRPQG GVLTKSQAPM
1081 SGIQNLFLRA LGIDADHGEF TRAVTMITDL CNTWEKAKNT LVSPEFWTVL IMKTVKFIAA
1141 SVLYLHNPDL TATICLSLMT GVDVLTNESI FNWLSNKLSK LFHTPPPPTS PLLQAQSPLR
1201 EANDGFNLAK NIEWAIKTVQ KIVDWLMSWF KQEEAHPQAK LDKMLADFPE HCASILAMRN
1261 GRKAYTDCAG AFKYFEDLYN LAVQCKRIPL ATLCEKFKNK HDHAVARPEP VVVVLRGNAG
1321 QGKSVTSQII AQAVSKLAFG RQSVYSIPPD SDYLDGYENQ FSVIMDDLGQ NPDGEDFKVF
1381 CQMVSSTNFL PNMAHLEKKG TPFTSNFIVA TTNLPKFRPV TVAHYPAVDR RITFDLTVEA
```

Fig. 81A

```
1441 GPACKTPTGM LDVEKAFQEI PGEPQLDCFS SDCALLHKRG VQFICNRTKK IYNLQQIVKM
1501 VKDTIDNKVA NLKKMNTLVA QSPNNGNDME HIITCLRQNN AALQDQIDEL QEAFAQAQER
1561 QNFLSDWMKV SAIIFAGIAS LSAVCKLVGR LKNLIWPSPV HVELSEGEQA AYAGAKRGAK
1621 QALQVLDLQG GGRIIAQAGN PVMDYEVCVA KNMVAPITFY YADKAQVTQS CLLVKGRLFV
1681 VNRHVAETDW VSFELRDVRH ERDTVTMRSV NRSGMEVDLT FIKVTKGPLF KDNTKKFCSN
1741 KDDFPQKNET VTGIMNTGLP FVFNGKFIIG NHPVNTTTGA TFNHCLHYRA NTRRGWCGSA
1801 VICQVNGKKA VYGMHSAGGG GLAAATIITQ ELVEAAEQNM DRLVPQGAIM EIGTGSVVHV
1861 PRKTKLRRTV AHEIFLPKFE PAVLSRYDPR TEKDVDQVAF SKHTTNMEEL PAVFSMVAKE
1921 YANRVFTKLG KENQLLTTQQ AILGLPGMDP MEKDTSPGLP YTQQGLRRTD LVNFETGKMD
1981 HNLDYAHSKL MLGHYEDVVY QSFLKDEIRP IEKIHEAKTR IVDVPPFHHC IWGRQLLGRF
2041 ASRFQTNPGL DLGSAIGTDP DVDWTVFAHQ LAEFKYIYDV DYSNFDASHS TAIFEILIQE
2101 FFTPQNGFDP RIGEYLRSLA VSRHAYEDRR VLIRGGLPSG CAATSMINTI INNIVIRAAL
2161 YMTYANFEFD DIKVLSYGDD LLIATNYEIN FNLVKERLAP FNYKITPANK TSTFPQTSHL
2221 QDVVFLKRRF VQFNSFLFRP QMETENLKAM VSYCRPGVLK EKLMSIALLA VHSGPDVYDE
2281 IFMPFRRIGV VVPEYSTMLY RWLNLFR (SEQ ID NO:33)
```

Fig. 81B

```
  1 MACKHGYPDV CPICTAIDVT PGFEYLLLAD GEWFPTDLLC VDLDDDVFWP SDSSNQSQTM
 61 EWTDIPLICD TVMEPQGNST SSDKSNSQSS GNEGVIINNF YSNQYQNSID LSANGGNAGD
121 GPKTEGQLSN ILGGAANAFA TMAPLLLDEN TEEMENLSDR VDSDKAGNSA TNTQSSVGRL
181 HGYGATHRGD HPASCADTAT DKVLAAERYY TIDLATWTTA QTTFSHIRVP LPHALAGEHG
241 GVFGATLRRH YLAKCGWRVQ VQCNASQFHA GSLLVFLAPE FYTGTGVATS GQEPNKVFLM
301 DTTWQEPQAA PTGFRYDGKN GFFTLNHQNY WQWTVYPHQI LNLRTNTSVD LEVPYVNVAP
361 TSSWTQHANW ALVVAVLTPL QYSTGAATDV AITVSLQPVN PVFNGLRHEA QVPQSPVAVT
421 VREHQGSFYS TNPDTTVPIY GKTIVTPSDY MCGEFTDLLE LCKLPTFLGN LSNDTRVPFF
481 TATNSVPTES LVEYQVTLSC SCMSNSMLAS VARNFNQYRG SLNFLFVFTG SAMTKGKFLI
541 AYTPPGAGKP TTRDQAXQST YAIWDLGLNS SYNFTVPFIS PSHYRQTSYT SPSIAAVDGW
601 LTVWQLTPLT FPANVPPSSD ILTLVSAGND FTLRMPISPT KWIPQGVDNA EKGKVSDDNA
661 SVDFVAEPIK LPENQTRVNF FYDRSSPIGL LRPNQAIESN FSYSADSNGA TNCALLTPLP
721 SYSPDRPGQS PDTSKAPIQW RWISAVTESG TVSNTFPTRT RQDYAFLLFS PFTYYKCDLE
781 VTLSSVGNGV VASLVRWAPT GAPADITTQL TTSTPSIGDT RDPHMWLVGA GNSQTSFVIP
841 YNSPLSVLPA AWFNGWSNFS NTYDFGIAPC SDFGRLWIQG NAPLAIRVRY KKMRVFCPRP
901 TLFFPWPTPT TTKVNADNPV PILDLENPAA (SEQ ID NO:34)
```

Fig. 82

```
          10        20        30        40        50        60        70        80        90
....|....|....|....|....|....|....|....|....|....|....|....|....|....|....|....|....|....|
TTTCAAATGCGCGCCTGCGCCCCTGATGCCCAGTCCTTCCTTTCCCCTTCCGCGCGGGTTAACCGGCTCTGTTTCCTAGACGCACACAGCGG
< 5' UTR
         100       110       120       130       140       150       160       170       180
....|....|....|....|....|....|....|....|....|....|....|....|....|....|....|....|....|....|
CAACATCCAACCTGCTTTTGCGGGGAACGGTGCGGCTCCGATTCCTGCGTCGCCAAAGGTGTTAGCGCACCCAAACGGCGCACCTACCAA 190       200       210       220       230       240       250       260       270
....|....|....|....|....|....|....|....|....|....|....|....|....|....|....|....|....|....|
TGTTATTGGTGTGGTCTGCGAGTTCTAGCCTACTCGTTTCTCCCCCGACCATTCACTCACCCACGAAAAGTGTGTTGTAACCATAAGATT 280       290       300       310       320       330       340       350       360
....|....|....|....|....|....|....|....|....|....|....|....|....|....|....|....|....|....|
TAACCCCCGCACGGGATGTGCGATAACCGTAAGACTGGCTCAAGCGCGGAAAGCGCTGTAACCACATGCTGTTAGTCCCTTTATGGCTGC 370       380       390       400       410       420       430       440       450
....|....|....|....|....|....|....|....|....|....|....|....|....|....|....|....|....|....|
AAGATGGCTACCCACCTCGGATCACTGAACTGGAGCTCGACCCTCCTTAGTAAGGGAACCGAGAGGCCTTCGTGCAACAAGCTCCGACAC 460       470       480       490       500       510       520       530       540
....|....|....|....|....|....|....|....|....|....|....|....|....|....|....|....|....|....|
AGAGTCCACGTGACTGCTACCACCATGAGTACATGGTTCTCCCCTCTCGACCCAGGACTTCTTTTTTGAATATCCACGGCTCGATCCAGAG 550       560       570       580       590       600       610       620       630
....|....|....|....|....|....|....|....|....|....|....|....|....|....|....|....|....|....|
GGTGGGGCATGACCCCTAGCATAGCGAGCTACAGCGGGAACTGTAGCTAGGCCTTAGCGTGCCTTGGATACTGCCTGATAGGGCGACGGC 640       650       660       670       680       690       700       710       720
....|....|....|....|....|....|....|....|....|....|....|....|....|....|....|....|....|....|
CTAGTCGTGTCGGTTCTATAGGTAGCACATACAAATATGCAGAACTCTCATTTTTCTTTCGATACAGCCTCTGGCACCTTTGAAGATGTA
                                      M Q  N  S  H  F  S  F  D  T  A  S  G  T  F  E  D  V
                             5' UTR >< Leader 730       740       750       760       770       780       790       800       810
....|....|....|....|....|....|....|....|....|....|....|....|....|....|....|....|....|....|
ACCGGAACAAAAGTCAAGATCGTTGAATACCCCAGATCGGTGAACATGGTGTTTACGATTCGTCTACTCATTTGGAGATACTGAACCTA
 T  G  T  K  V  K  I  V  E  Y  P  R  S  V  N  N  G  V  Y  D  S  S  T  H  L  E  I  L  N  L 820       830       840       850       860       870       880       890       900
....|....|....|....|....|....|....|....|....|....|....|....|....|....|....|....|....|....|
CAGGGTGAAATTGAAATTTTAAGGTCTTTCAATGAATACCAAATTCGCGCCGCCAAACAACAACTCGGACTGGACATCGTGTACGAACTA
 Q  G  E  I  E  I  L  R  S  F  N  E  Y  Q  I  R  A  A  K  Q  Q  L  G  L  D  I  V  Y  E  L 910       920       930       940       950       960       970       980       990
....|....|....|....|....|....|....|....|....|....|....|....|....|....|....|....|....|....|
CAGGGTAATGTTCAGACAACGTCAAAGAATGATTTTGATTCCCGTGGCAATAATGGTAACATGACCTTCAATTACTACGCAAACACTTAT
 Q  G N  V  Q  T  T  S  K  N  D  F  D  S  R  G  N  N  G  N  M  T  F  N  Y  Y  A  N  T  Y
 L >< VP4

1000      1010      1020      1030      1040      1050      1060      1070      1080
....|....|....|....|....|....|....|....|....|....|....|....|....|....|....|....|....|....|
CAGAATTCAGTAGACTTCTCGACCTCCTCGTCGGCGTCAGGCGCCGGACCCGGGAACTCCCGGGGCGGATTAGCGGGTCTCCTCACAAAT
 Q  N  S  V  D  F  S  T  S  S  S  A  S  G  A  G  P  G  N  S  R  G  G  L  A  G  L  L  T  N
```

FIG. 83A

```
       1090      1100      1110      1120      1130      1140      1150      1160      1170
....|....|....|....|....|....|....|....|....|....|....|....|....|....|....|....|....|....|
TTCAGTGGAATCTTGAACCCTCTTGGCTACCTCAAAGATCACAACACCGAAGAAATGGAAAACTCTGCTGATCGAGTCACAACGCAAACG
 F  S  G  I  L  N  P  L  G  Y  L  K  D  H  N  T  E  E  M  E  N  S  A  D  R  V  T  T  Q  T
                                  VP4 >< VP2

1180      1190      1200      1210      1220      1230      1240      1250      1260
....|....|....|....|....|....|....|....|....|....|....|....|....|....|....|....|....|....|
GCGGGCAACACTGCCATAAACACGCAATCATCATTGGGTGTGTTGTGTGCCTACGTTGAAGACCCCGACCAAATCTGATCCTCCGTCCAGC
 A  G  N  T  A  I  N  T  Q  S  S  L  G  V  L  C  A  Y  V  E  D  P  T  K  S  D  P  P  S  S 1270      1280      1290      1300      1310      1320      1330      1340      1350
....|....|....|....|....|....|....|....|....|....|....|....|....|....|....|....|....|....|
AGCACAGATCAACCCACCACCACTTTCACTGCCATCGACAGGTGGTACACTGGACGTCTCAATTCTTGGACAAAAGCTGTAAAAACCTTC
 S  T  D  Q  P  T  T  T  F  T  A  I  D  R  W  Y  T  G  R  L  N  S  W  T  K  A  V  K  T  F 1360      1370      1380      1390      1400      1410      1420      1430      1440
....|....|....|....|....|....|....|....|....|....|....|....|....|....|....|....|....|....|
TCTTTTCAGGCCGTCCCGCTTCCCGGGGCCTTTCTGTCTAGGCAGGGAGGCCTCAACGGAGGGCCTTCACAGCTACCCTACATAGACAC
 S  F  Q  A  V  P  L  P  G  A  F  L  S  R  Q  G  G  L  N  G  G  A  F  T  A  T  L  H  R  H 1450      1460      1470      1480      1490      1500      1510      1520      1530
....|....|....|....|....|....|....|....|....|....|....|....|....|....|....|....|....|....|
TTTTTGATGAAGTGCGGGTGGCAGGTGCAGGTCCAATGTAATTTGACACAATTCCACCAAGCGGCTCTTCTTGTTGCCATGGTTCCTGAA
 F  L  M  K  C  G  W  Q  V  Q  V  Q  C  N  L  T  Q  F  H  Q  G  A  L  L  V  A  M  V  P  E 1540      1550      1560      1570      1580      1590      1600      1610      1620
....|....|....|....|....|....|....|....|....|....|....|....|....|....|....|....|....|....|
ACCACCCTTGATGTCAAGCCCGACGGTAAGGCAAAGAGCTTACAGGAGCTGAATGAAGAACAGTGGGTGGAAATGTCTGACGATTACCGG
 T  T  L  D  V  K  P  D  G  K  A  K  S  L  Q  E  L  N  E  E  Q  W  V  E  M  S  D  D  Y  R 1630      1640      1650      1660      1670      1680      1690      1700      1710
....|....|....|....|....|....|....|....|....|....|....|....|....|....|....|....|....|....|
ACCGGGAAAAACATGCCTTTTCAGTCTCTTGGCACATACTATCGGCCCCCTAACTGGACTTGGGGTCCCAATTTCATCAACCCCTATCAA
 T  G  K  N  M  P  F  Q  S  L  G  T  Y  Y  R  P  P  N  W  T  W  G  P  N  F  I  N  P  Y  Q 1720      1730      1740      1750      1760      1770      1780      1790      1800
....|....|....|....|....|....|....|....|....|....|....|....|....|....|....|....|....|....|
GTAACGGTTTTCCCACACCAAATTCTGAACGCGAGAACCTCTACCTCGGTAGACATAAACGTCCCATACATCGGGGAGACCCCCACGCAA
 V  T  V  F  P  H  Q  I  L  N  A  R  T  S  T  S  V  D  I  N  V  P  Y  I  G  E  T  P  T  Q 1810      1820      1830      1840      1850      1860      1870      1880      1890
....|....|....|....|....|....|....|....|....|....|....|....|....|....|....|....|....|....|
TCCTCAGAGACACAGAACTCCTGGACCCTCCTCGTTATGGTGCTCGTTCCCCTAGACTATAAGGAAGGAGCCACAACTCACCCAGAAATT
 S  S  E  T  Q  N  S  W  T  L  L  V  M  V  L  V  P  L  D  Y  K  E  G  A  T  T  D  P  E  I 1900      1910      1920      1930      1940      1950      1960      1970      1980
....|....|....|....|....|....|....|....|....|....|....|....|....|....|....|....|....|....|
ACATTTTCTGTAAGGCCTACAAGTCCCTACTTCAATGGGCTTCGCAACCGCTACACGGCCGGGACGGACGAAGAACAGGGGCCCATTCCT
 T  F  S  V  R  P  T  S  P  Y  F  N  G  L  R  N  R  Y  T  A  G  T  D  E  E  Q  G  P  I  P
                                                                        VP2 >< VP3

1990      2000      2010      2020      2030      2040      2050      2060      2070
....|....|....|....|....|....|....|....|....|....|....|....|....|....|....|....|....|....|
ACGGCACCCAGAGAAAATTCGCTTATGTTTCTCTCAACCCTCCCTGACGACACTGTCCCTGCTTACGGGAATGTGCGTACCCCTCCTGTC
 T  A  P  R  E  N  S  L  M  F  L  S  T  L  P  D  D  T  V  P  A  Y  G  N  V  R  T  P  P  V
```

FIG. 83B

```
        2080       2090       2100       2110       2120       2130       2140       2150       2160
   ....|....|....|....|....|....|....|....|....|....|....|....|....|....|....|....|....|....|
   AATTACCTCCCTGGTGAAATAACCGACCTTTTGCAACTGGCCCGCATACCCACTCTCATGGCATTTGAGCGGGTGCCTGAACCCGTGCCT
    N  Y  L  P  G  E  I  T  D  L  L  Q  L  A  R  I  P  T  L  M  A  F  E  R  V  P  E  P  V  P 2170       2180       2190       2200       2210       2220       2230       2240       2250
   ....|....|....|....|....|....|....|....|....|....|....|....|....|....|....|....|....|....|
   GCCTCAGACACATATGTGCCCTACGTTGCCGTTCCCACCCAGTTCGATGACAGGCCTCTCATCTCCTTCCCGATCACCCTTTCAGATCCC
    A  S  D  T  Y  V  P  Y  V  A  V  P  T  Q  F  D  D  R  P  L  I  S  F  P  I  T  L  S  D  P 2260       2270       2280       2290       2300       2310       2320       2330       2340
   ....|....|....|....|....|....|....|....|....|....|....|....|....|....|....|....|....|....|
   GTCTATCAGAACACCCTGGTTGGCGCCATCAGTTCAAATTTCGCCAATTACCGTGGGTGTATCCAAATCACTCTGACATTTTGTGGACCC
    V  Y  Q  N  T  L  V  G  A  I  S  S  N  F  A  N  Y  R  G  C  I  Q  I  T  L  T  F  C  G  P 2350       2360       2370       2380       2390       2400       2410       2420       2430
   ....|....|....|....|....|....|....|....|....|....|....|....|....|....|....|....|....|....|
   ATGATGGCGAGAGGGAAATTCCTGCTCTCGTATTCTCCCCCAAATGGAACGCAACCACAGACTCTTTTCCGAAGCTATGCAGTGCACATAC
    M  M  A  R  G  K  F  L  L  S  Y  S  P  P  N  G  T  Q  P  Q  T  L  S  E  A  M  Q  C  T  Y 2440       2450       2460       2470       2480       2490       2500       2510       2520
   ....|....|....|....|....|....|....|....|....|....|....|....|....|....|....|....|....|....|
   TCTATTTGGGACATAGGCTTGAACTCTAGTTGGACCTTCGTCGTCCCCTACATCTCGCCCAGTGACTACCGTGAAACTCGAGCCATTACC
    S  I  W  D  I  G  L  N  S  S  W  T  F  V  V  P  Y  I  S  P  S  D  Y  R  E  T  R  A  I  T 2530       2540       2550       2560       2570       2580       2590       2600       2610
   ....|....|....|....|....|....|....|....|....|....|....|....|....|....|....|....|....|....|
   AACTCGGTTTACTCCGCTGATGGTTGGTTTAGCCTGCACAAGTTGACCAAAATTACTCTACCACCTGACTGTCCGCAAAGTCCCTGCATT
    N  S  V  Y  S  A  D  G  W  F  S  L  E  K  L  T  K  I  T  L  P  P  D  C  P  Q  S  P  C  I 2620       2630       2640       2650       2660       2670       2680       2690       2700
   ....|....|....|....|....|....|....|....|....|....|....|....|....|....|....|....|....|....|
   CTCTTTTTTCGCTTCTGCTGGTGAGGATTACACTCTCCGTCTCCCCGTTGATTGTAATCCTTCCTATGTGTTCCACTCCACCGACAACGCC
    L  F  F  A  S  A  G  E  D  Y  T  L  R  L  P  V  D  C  N  P  S  Y  V  F  H  S  T  D  N  A
                                                                          VP3 >< VP1

2710       2720       2730       2740       2750       2760       2770       2780       2790
   ....|....|....|....|....|....|....|....|....|....|....|....|....|....|....|....|....|....|
   GAGACCGGGGTTATTGAGGCGGGTAACACTGACACCGATTTCTCTGGTGAACTGGCGGCTCCTGGCTCTAACCACACTAATGTCAAGTTC
    E  T  G  V  I  E  A  G  N  T  D  T  D  F  S  G  E  L  A  A  P  G  S  N  H  T  N  V  K  F 2800       2810       2820       2830       2840       2850       2860       2870       2880
   ....|....|....|....|....|....|....|....|....|....|....|....|....|....|....|....|....|....|
   CTGTTTGATCGATCTCCATTATTGAATCTAATCAACGTACTGGAGAAGCACGCCGTTTTCCCCCCCCCTTTCCCTACACAAGAAGCTGCG
    L  F  D  R  S  R  L  L  N  V  I  K  V  L  E  K  D  A  V  F  P  R  P  F  P  T  Q  E  A 2890       2900       2910       2920       2930       2940       2950       2960       2970
   ....|....|....|....|....|....|....|....|....|....|....|....|....|....|....|....|....|....|
   CAGCAGGATGATGGTTACTTTTGTCTTCTGACCCCCCGCCCAACAGTCGCTTCCCGACCCGCCACTCGTTTCGGCCTGTACGCCAATCCG
    Q  Q  D  D  G  Y  F  C  L  L  T  P  R  P  T  V  A  S  R  P  A  T  R  F  G  L  Y  A  N  P 2980       2990       3000       3010       3020       3030       3040       3050       3060
   ....|....|....|....|....|....|....|....|....|....|....|....|....|....|....|....|....|....|
   TCCGGCAGTGGTGTTCTTGCTAACACTTCACTGGACTTCAATTTTTATAGCTTGGCCTGTTTCACTTACTTTAGATCGGACCTTGAGGTT
    S  G  S  G  V  L  A  N  T  S  L  D  F  N  F  Y  S  L  A  C  F  T  Y  F  R  S  D  L  E  V
```

FIG. 83C

```
           3070      3080      3090      3100      3110      3120      3130      3140      3150
    ....|....|....|....|....|....|....|....|....|....|....|....|....|....|....|....|....|....|
    ACGGTGGTCTCACTAGAGCCGGATCTGGAATTTGCTGTAGGGTGGTTTCCTTCTGGCAGTGAATACCAGGCTTCCAGCTTTGTCTACGAC
     T  V  V  S  L  E  P  D  L  E  F  A  V  G  W  F  P  S  G  S  E  Y  Q  A  S  S  F  V  Y  D 3160      3170      3180      3190      3200      3210      3220      3230      3240
    ....|....|....|....|....|....|....|....|....|....|....|....|....|....|....|....|....|....|
    CAGCTGCATGTGCCCTTCCACTTTACTGGGCGCACTCCCCGCGCTTTCGCTAGCAAGGGTGGGAAGGTATCTTTCGTGCTCCCTTGGAAC
     Q  L  H  V  P  F  H  F  T  G  R  T  P  R  A  F  A  S  K  G  G  K  V  S  F  V  L  P  W  N 3250      3260      3270      3280      3290      3300      3310      3320      3330
    ....|....|....|....|....|....|....|....|....|....|....|....|....|....|....|....|....|....|
    TCTGTCTCGTCTGTGCTCCCCGTGCGCTGGGGGGGGCTTCCAAGCTCTCTTCTGCTACGCGGGGTCTACCGGCGCATGCTGATTGGGGG
     S  V  S  S  V  L  P  V  R  W  G  G  A  S  K  L  S  S  A  T  R  G  L  P  A  H  A  D  W  G 3340      3350      3360      3370      3380      3390      3400      3410      3420
    ....|....|....|....|....|....|....|....|....|....|....|....|....|....|....|....|....|....|
    ACTATTTACGCCTTTGTCCCCCGTCCTAATGAGAAGAAAAGCACCGCTGTAAAACACGTGGCCGTGTACATTCGGTACAAGAACGCACGT
     T  I  Y  A  F  V  P  R  P  N  E  K  K  S  T  A  V  K  H  V  A  V  Y  I  R  Y  K  N  A  R 3430      3440      3450      3460      3470      3480      3490      3500      3510
    ....|....|....|....|....|....|....|....|....|....|....|....|....|....|....|....|....|....|
    GCCTGGTGCCCCAGCATGCTTCCCTTTCGCAGCTACAAGCAGAAGATGCTGATGCAATCTGGCGATATCGAGACCAATCCTGGTCCTGCT
     A  W  C  P  S  M  L  P  F  R  S  Y  K  Q  K  M  L  M  Q  S  G  D  I  E  T  N  P  G  P  A
                                             VP1ᵃˡᵗ ><  2Aᵃˡᵗ       VP1 ><  2A                 2A ><  2B 3520      3530      3540      3550      3560      3570      3580      3590      3600
    ....|....|....|....|....|....|....|....|....|....|....|....|....|....|....|....|....|....|
    TCTGACAACCCAATTTTGGAGTTTCTTGAAGCAGAAAATGATCTAGTCACTCTGGCCTCTCTCTGGAAGATGGTGCACTCTGTTCAACAG
     S  D  N  P  I  L  E  F  L  E  A  E  N  D  L  V  T  L  A  S  L  W  K  M  V  H  S  V  Q  Q 3610      3620      3630      3640      3650      3660      3670      3680      3690
    ....|....|....|....|....|....|....|....|....|....|....|....|....|....|....|....|....|....|
    ACCTGGAGAAAGTATGTGAAGAACGATGATTTTTGGCCCAATTTACTCAGCGAGCTAGTGGGGGAAGGCTCTGTCGCCTTGGCCGCCACG
     T  W  R  K  Y  V  K  N  D  D  F  W  P  N  L  L  S  E  L  V  G  E  G  S  V  A  L  A  A  T 3700      3710      3720      3730      3740      3750      3760      3770      3780
    ....|....|....|....|....|....|....|....|....|....|....|....|....|....|....|....|....|....|
    CTATCCAACCAAGCTTCAGTAAAGGCTCTTTTGGGCCTGCACTTTCTCTCGGGGGCTCAATTACACTGACTTTTACTCTTTACTGATA
     L  S  N  Q  A  S  V  K  A  L  L  G  L  H  F  L  S  R  G  L  N  Y  T  D  F  Y  S  L  L  I 3790      3800      3810      3820      3830      3840      3850      3860      3870
    ....|....|....|....|....|....|....|....|....|....|....|....|....|....|....|....|....|....|
    GAGAAATGCTCTAGTTTCTTTACCGTAGAACCACCTCCTCCACCAGCTGAAAACCTGATGACCAAGCCCTCAGTGAAGTCGAAATTCCGA
     E  K  C  S  S  F  F  T  V  E  P  P  P  P  P  A  E  N  L  M  T  K  P  S  V  K  S  K  F  R 3880      3890      3900      3910      3920      3930      3940      3950      3960
    ....|....|....|....|....|....|....|....|....|....|....|....|....|....|....|....|....|....|
    AAACTGTTTAAGATGCAAGGACCCATGGACAAAGTCAAAGACTGGAACCAAATAGCTGCCGGCTTGAAGAATTTTCAATTTGTTCGTGAC
     K  L  F  K  M  Q  G  P  M  D  K  V  K  D  W  N  Q  I  A  A  G  L  K  N  F  Q  F  V  R  D
                    2B ><  2C 3970      3980      3990      4000      4010      4020      4030      4040      4050
    ....|....|....|....|....|....|....|....|....|....|....|....|....|....|....|....|....|....|
    CTAGTCAAAGAGGTGGTCGATTGGCTGCAGGCCTGGATCAACAAAGAGAAAGCCAGCCCTGTCCTCCAGTACCAGTTGGAGATGAAGAAG
     L  V  K  E  V  V  D  W  L  Q  A  W  I  N  K  E  K  A  S  P  V  L  Q  Y  Q  L  E  M  K  K
```

FIG. 83D

```
         4060      4070      4080      4090      4100      4110      4120      4130      4140
    ....|....|....|....|....|....|....|....|....|....|....|....|....|....|....|....|....|....|
    CTCGGGCCTGTGGCCTTGGCTCATGACGCTTTCATGGCTGGTTCCGGGCCCCCTCTTAGCGACGACCAGATTGAATACCTCCAGAACCTC
     L  G  P  V  A  L  A  H  D  A  F  M  A  G  S  G  P  P  L  S  D  D  Q  I  E  Y  L  Q  N  L 4150      4160      4170      4180      4190      4200      4210      4220      4230
    ....|....|....|....|....|....|....|....|....|....|....|....|....|....|....|....|....|....|
    AAATCTCTTGCCCTAACACTGGGGAAGACTAATTTGGCCCAAAGTCTCACCACTATGATCAATGCCAAACAAAGTTCAGCCCAACGAGTT
     K  S  L  A  L  T  L  G  K  T  N  L  A  Q  S  L  T  T  M  I  N  A  K  Q  S  S  A  Q  R  V 4240      4250      4260      4270      4280      4290      4300      4310      4320
    ....|....|....|....|....|....|....|....|....|....|....|....|....|....|....|....|....|....|
    GAACCCGTTGTGGTGGTCCTTAGAGGCAAGCCGGGATGCGGCAAGAGCTTGGCCTCTACGTTGATTGCCCAGGCTGTGTCCAAGCGCCTC
     E  P  V  V  V  V  L  R  G  K  P  G  C  G  K  S  L  A  S  T  L  I  A  Q  A  V  S  K  R  L 4330      4340      4350      4360      4370      4380      4390      4400      4410
    ....|....|....|....|....|....|....|....|....|....|....|....|....|....|....|....|....|....|
    TATGGCTCCCAAAGTGTATATTCTCTTCCCCCAGATCCAGATTTCTTCGATGGATACAAAGGACAGTTCGTGACCTTGATGGATGATTTG
     Y  G  S  Q  S  V  Y  S  L  P  P  D  P  D  F  F  D  G  Y  K  G  Q  F  V  T  L  M  D  D  L 4420      4430      4440      4450      4460      4470      4480      4490      4500
    ....|....|....|....|....|....|....|....|....|....|....|....|....|....|....|....|....|....|
    GGACAAAACCCCGATGCACAACATTTCTCCACCTTTTGTCAGATGGTGTCCACCCCCCAATTTCTCCCCAACATGGCCGACCTTGCCGAG
     G  Q  N  P  D  G  Q  D  F  S  T  F  C  Q  M  V  S  T  Q  F  I  P  N  M  A  D  L  A  E 4510      4520      4530      4540      4550      4560      4570      4580      4590
    ....|....|....|....|....|....|....|....|....|....|....|....|....|....|....|....|....|....|
    AAAGGGCGTCCCTTTACCTCCAATCTCATCATTGCAACTACAAATCTCCCCCACTTCAGTCCTGTCACCATTGCTGATCCTTCTGCAGTC
     K  G  R  P  F  T  S  N  L  I  I  A  T  T  N  L  P  H  F  S  P  V  T  I  A  D  P  S  A  V 4600      4610      4620      4630      4640      4650      4660      4670      4680
    ....|....|....|....|....|....|....|....|....|....|....|....|....|....|....|....|....|....|
    TCTCGCCGTATCAACTACGATCTGACTCTAGAAGTATCTGAGGCCTACAAGAAACACACACGGCTGAATTTTGACTTGGCTTTCAGGCGC
     S  R  R  I  N  Y  D  L  T  L  E  V  S  E  A  Y  K  K  H  T  R  L  N  F  D  L  A  F  R  R 4690      4700      4710      4720      4730      4740      4750      4760      4770
    ....|....|....|....|....|....|....|....|....|....|....|....|....|....|....|....|....|....|
    ACAGACGCCCCCCCCATTTATCCTTTTGCTGCCCATGTGCCCTTTGTGGACGTAGCTGTGCGCTTCAAAAATGGTCACCAGAATTTTAAT
     T  D  A  P  P  I  Y  P  F  A  A  H  V  P  F  V  D  V  A  V  R  F  K  N  G  H  Q  N  F  N 4780      4790      4800      4810      4820      4830      4840      4850      4860
    ....|....|....|....|....|....|....|....|....|....|....|....|....|....|....|....|....|....|
    CTCCTAGAGTTGGTCGATTCCATTTGTACAGACATTCGAGCCAAGCAACAAGGTGCCCGAAACATGCAGACTCTGGTTCTACAGAGCCCC
     L  L  E  L  V  D  S  I  C  T  D  I  R  A  K  Q  Q  G  A  R  N  M  Q  T  L  V  L  Q  S  P
                                                                                   2C >< 3A 4870      4880      4890      4900      4910      4920      4930      4940      4950
    ....|....|....|....|....|....|....|....|....|....|....|....|....|....|....|....|....|....|
    AACGAGAATGATGACACCCCCGTCGACGAGCCCGTTGGGTAGAGTTCTCTCCCCCCTGCCGTCGATGAGCCCCTTGTCCACCTCACTCCA
     N  E  N  D  D  T  P  V  D  E  A  L  G  R  V  L  S  P  A  A  V  D  E  A  L  V  D  L  T  P 4960      4970      4980      4990      5000      5010      5020      5030      5040
    ....|....|....|....|....|....|....|....|....|....|....|....|....|....|....|....|....|....|
    GAGGCCGACCCGGTTGGCCGTTTGGCTATTCTTGCCAAGCTAGGTCTTGCCCTAGCTGCGGTCACCCCTGGTCTGATAATCTTGGCAGTG
     E  A  D  P  V  G  R  L  A  I  L  A  K  L  G  L  A  L  A  A  V  T  P  G  L  I  I  L  A  V
```

FIG. 83E

```
              5050      5060      5070      5080      5090      5100      5110      5120      5130
       ....|....|....|....|....|....|....|....|....|....|....|....|....|....|....|....|....|....|
       GGACTCTACAGGTACTTCTCTGGCTCTGATGCAGACCAAGAAGAAACAGAAAGTGAGGGATCTGTCAAGGCACCCAGGAGCGAAAATGCT
        G  L  Y  R  Y  F  S  G  S  D  A  D  Q  E  E  T  E  S  E  G  S  V  K  A  P  R  S  E  N  A
                                                                                    3A ><  3B^VPg 5140      5150      5160      5170      5180      5190      5200      5210      5220
       ....|....|....|....|....|....|....|....|....|....|....|....|....|....|....|....|....|....|
       TATGACGGCCCGAAGAAAAACTCTAAGCCCCCTGGAGCACTCTCTCTCATGGAAATGCAACAGCCCAACGTGGACATGGGCTTTGAGGCT
        Y  D  G  P  K  K  N  S  K  P  P  G  A  L  S  L  M  E  M  Q  Q  P  N  V  D  M  G  F  E  A
                                                                 3B^VPg ><  3C^pro 5230      5240      5250      5260      5270      5280      5290      5300      5310
       ....|....|....|....|....|....|....|....|....|....|....|....|....|....|....|....|....|....|
       GCGGTCGCTAAGAAAGTGGTCGTCCCCATTACCTTCATGGTTCCCAACAGACCTTCTGGGCTTACACAGTCCGCTCTTCTGGTGACCGGC
        A  V  A  K  K  V  V  V  P  I  T  F  M  V  P  N  R  P  S  G  L  T  Q  S  A  L  L  V  T  G 5320      5330      5340      5350      5360      5370      5380      5390      5400
       ....|....|....|....|....|....|....|....|....|....|....|....|....|....|....|....|....|....|
       CGGACCTTCCTAATCAATGAACATACATGGTCCAATCCCTCCTGGACCAGCTTCACAATCCGCGGTGAGGTACACACTCGTGATGAGCCC
        R  T  F  L  I  N  E  H  T  W  S  N  P  S  W  T  S  F  T  I  R  G  E  V  H  T  R  D  E  P 5410      5420      5430      5440      5450      5460      5470      5480      5490
       ....|....|....|....|....|....|....|....|....|....|....|....|....|....|....|....|....|....|
       TTCCAAACGGTTCATTTCACTCACCACGGTATTCCCACAGATCTGATGATGGTACGTCTCGGACCGGGCAATTCTTTCCCTAACAATCTA
        F  Q  T  V  H  F  T  H  H  G  I  P  T  D  L  M  M  V  R  L  G  P  G  N  S  F  P  N  N  L 5500      5510      5520      5530      5540      5550      5560      5570      5580
       ....|....|....|....|....|....|....|....|....|....|....|....|....|....|....|....|....|....|
       GACAAGTTTCGACTTCACCACATGCCCGCACGCAACTCCCGTGTCGTTGCCCTTTCGTCCAGTTACGCAAACTTCTTCTTCTCTCGAAAT
        D  K  F  G  L  D  Q  M  P  A  R  N  S  R  V  V  G  V  S  S  S  Y  G  N  F  F  F  S  G  N 5590      5600      5610      5620      5630      5640      5650      5660      5670
       ....|....|....|....|....|....|....|....|....|....|....|....|....|....|....|....|....|....|
       TTCCTCGGATTTGTTGATTCCATCACCTCTGAACAAGGAACTTACGCAAGACTCTTTAGGTACAGGGTGACGACCTACAAAGGATGGTGC
        F  L  G  F  V  D  S  I  T  S  E  Q  G  T  Y  A  R  L  F  R  Y  R  V  T  T  Y  K  G  W  C 5680      5690      5700      5710      5720      5730      5740      5750      5760
       ....|....|....|....|....|....|....|....|....|....|....|....|....|....|....|....|....|....|
       GGCTCGGCCCTGGTCTGTGAGGCCGGTGGCGTCCGACGCATCATTGGCCTGCATTCTGCTGGCGCCGCCGGTATCGGCGCCGGGACCTAT
        G  S  A  L  V  C  E  A  G  G  V  R  R  I  I  G  L  H  S  A  G  A  A  G  I  G  A  G  T  Y 5770      5780      5790      5800      5810      5820      5830      5840      5850
       ....|....|....|....|....|....|....|....|....|....|....|....|....|....|....|....|....|....|
       ATCTCAAAATTAGGACTAATCAAAGCCCTGAAACACCTCGGTGAACCTTTGGCCACAATGCAAGGACTGATGACTGAATTAGAGCCTGGA
        I  S  K  L  G  L  I  K  A  L  K  H  L  G  E  P  L  A  T  M  Q  G  L  M  T  E  L  E  P  G
                                                                  3C^pro ><  3D^pol 5860      5870      5880      5890      5900      5910      5920      5930      5940
       ....|....|....|....|....|....|....|....|....|....|....|....|....|....|....|....|....|....|
       ATCACCGTACATGTACCCCGGAAATCCAAATTGAGAAAGACGACCGCACACGCGGTGTACAAACCGGAGTTTGAGCCTGCTGTGTTGTCA
        I  T  V  H  V  P  R  K  S  K  L  R  K  T  T  A  H  A  V  Y  K  P  E  F  E  P  A  V  L  S 5950      5960      5970      5980      5990      6000      6010      6020      6030
       ....|....|....|....|....|....|....|....|....|....|....|....|....|....|....|....|....|....|
       AAATTTGATCCCAGACTGAACAAGGATGTTGACTTGGATGAAGTAATTTGGTCTAAACACACTGCCAATGTCCCTTACCAACCTCCTTTG
        K  F  D  P  R  L  N  K  D  V  D  L  D  E  V  I  W  S  K  H  T  A  N  V  P  Y  Q  P  P  L
```

FIG. 83F

```
        6040      6050      6060      6070      6080      6090      6100      6110      6120
   ....|....|....|....|....|....|....|....|....|....|....|....|....|....|....|....|....|....|
   TTCTACACATACATGTCAGAGTACGCTCATCGAGTCTTCTCCTTCTTGGGGAAAGACAATGACATTCTGACCGTCAAAGAAGCAATTCTG
    F  Y  T  Y  M  S  E  Y  A  H  R  V  F  S  F  L  G  K  D  N  D  I  L  T  V  K  E  A  I  L 6130      6140      6150      6160      6170      6180      6190      6200      6210
   ....|....|....|....|....|....|....|....|....|....|....|....|....|....|....|....|....|....|
   GGCATCCCCGGACTAGACCCCATGGATCCCCACACAGCTCCGGGTCTGCCTTACGCCATCAACGGCCTTCGACGTACTGATCTCGTCGAT
    G  I  P  G  L  D  P  M  D  P  H  T  A  P  G  L  P  Y  A  I  N  G  L  R  R  T  D  L  V  D 6220      6230      6240      6250      6260      6270      6280      6290      6300
   ....|....|....|....|....|....|....|....|....|....|....|....|....|....|....|....|....|....|
   TTTGTGAACGGTACAGTAGATGCGGCGCTGGCTGTACAAATCCAGAAATTCTTAGACGGTGACTACTCTGACCATGTCTTCCAAACTTTT
    F  V  N  G  T  V  D  A  A  L  A  V  Q  I  Q  K  F  L  D  G  D  Y  S  D  H  V  F  Q  T  F 6310      6320      6330      6340      6350      6360      6370      6380      6390
   ....|....|....|....|....|....|....|....|....|....|....|....|....|....|....|....|....|....|
   CTGAAAGATGAGATCAGACCCTCAGAGAAAGTCCGAGCGGGAAAAACCCGCATTGTTGATGTGCCCTCCCTGGCGCATTGCATTGTGGGC
    L  K  D  E  I  R  P  S  E  K  V  R  A  G  K  T  R  I  V  D  V  P  S  L  A  H  C  I  V  G 6400      6410      6420      6430      6440      6450      6460      6470      6480
   ....|....|....|....|....|....|....|....|....|....|....|....|....|....|....|....|....|....|
   AGAATGTTGCTTGGGCGCTTTGCTGCCAAGTTTCAATCCCATCCTGGCTTTCTCCTCGGCTCTGCTATCGGTCTGACCCTGATGTTTTC
    R  M  L  L  G  R  F  A  A  K  F  Q  S  H  P  G  F  L  L  G  S  A  I  G  S  D  P  D  V  F 6490      6500      6510      6520      6530      6540      6550      6560      6570
   ....|....|....|....|....|....|....|....|....|....|....|....|....|....|....|....|....|....|
   TGGACCGTCATAGGGGCTCAACTCGAGGGGAGAAAGAACACGTATGACGTGGACTACAGTGCCTTTGACTCTTCACACGGCACTGGCTCC
    W  T  V  I  G  A  Q  L  E  G  R  K  N  T  Y  D  V  D  Y  S  A  F  D  S  S  H  G  T  G  S 6580      6590      6600      6610      6620      6630      6640      6650      6660
   ....|....|....|....|....|....|....|....|....|....|....|....|....|....|....|....|....|....|
   TTCGAGGCTCTCATCTCTCACTTTTTCACCGTGGACAATGGTTTTAGCCCTGCGCTGGGACCGTATCTCAGATCCCTGGCTGTCTCGGTG
    F  E  A  L  I  S  H  F  F  T  V  D  N  G  F  S  P  A  L  G  P  Y  L  R  S  L  A  V  S  V 6670      6680      6690      6700      6710      6720      6730      6740      6750
   ....|....|....|....|....|....|....|....|....|....|....|....|....|....|....|....|....|....|
   CACGCTTACGGCGAGCGTCGCATCAAGATTACCGGTGGCCTCCCCTCCGGTTGTGCCGCGACCAGCCTGCTGAACACAGTGCTCAACAAT
    H  A  Y  G  E  R  R  I  K  I  T  G  G  L  P  S  G  C  A  A  T  S  L  L  N  T  V  L  N  N 6760      6770      6780      6790      6800      6810      6820      6830      6840
   ....|....|....|....|....|....|....|....|....|....|....|....|....|....|....|....|....|....|
   GTGATCATCAGGACTGCTCTGGCATTGACTTACAAGGAATTTGAATATGACATGGTTGATATCATCGCCTACGGTGACGACCTTCTGGTT
    V  I  I  R  T  A  L  A  L  T  Y  K  E  F  E  Y  D  M  V  D  I  I  A  Y  G  D  D  L  L  V 6850      6860      6870      6880      6890      6900      6910      6920      6930
   ....|....|....|....|....|....|....|....|....|....|....|....|....|....|....|....|....|....|
   GGCACGGATTACGATCTGGACTTCAATGAGGTGGCACGACGCGCTGCCAAGTTGGGGTATAAGATGACTCCTGCCAACAAGGGTTCTGTC
    G  T  D  Y  D  L  D  F  N  E  V  A  R  R  A  A  K  L  G  Y  K  M  T  P  A  N  K  G  S  V 6940      6950      6960      6970      6980      6990      7000      7010      7020
   ....|....|....|....|....|....|....|....|....|....|....|....|....|....|....|....|....|....|
   TTCCCTCCGACTTCCTCTCTTTCCGATGCTGTTTTTCTAAAGCGCAAATTCGTCCAAAACAACGACGGCTTATACAAACCAGTTATGGAT
    F  P  P  T  S  S  L  S  D  A  V  F  L  K  R  K  F  V  Q  N  N  D  G  L  Y  K  P  V  M  D
```

FIG. 83G

```
         7030      7040      7050      7060      7070      7080      7090      7100      7110
    ....|....|....|....|....|....|....|....|....|....|....|....|....|....|....|....|....|....|
    TTAAAGAATTTGGAAGCCATGCTCTCCTACTTCAAACCAGGAACACTACTCGAGAAGCTGCAATCTGTTTCTATGTTGGCTCAACATTCT
     L  K  N  L  E  A  M  L  S  Y  F  K  P  G  T  L  L  E  K  L  Q  S  V  S  M  L  A  Q  H  S 7120      7130      7140      7150      7160      7170      7180      7190      7200
    ....|....|....|....|....|....|....|....|....|....|....|....|....|....|....|....|....|....|
    GGAAAAGAAGAATATGATAGATTGATGCACCCCTTCGCTGACTACGGTGCCGTACCGAGTCACGAGTACCTGCAGGCAAGATGGAGGGCC
     G  K  E  E  Y  D  R  L  M  H  P  F  A  D  Y  G  A  V  P  S  H  E  Y  L  Q  A  R  W  R  A 7210      7220      7230      7240      7250      7260      7270      7280      7290
    ....|....|....|....|....|....|....|....|....|....|....|....|....|....|....|....|....|....|
    TTGTTCGACTGACCCAGATAGCCCAAGGCGCTTCGGTGCTGCCGGCGATTCTGGGAGAACTCAGTCGGAACAGAAAAGGGAAAAAAAAAA
     L  F  D  *
      3D^pol >< 3' UTR                                                              3' UTR >< poly(A)

7300      7310
    ....|....|....|....|
    AAAAAAAAAAAAAAAAAAAA
```

FIG. 83H

```
   1  TTTGAAATGG GGGGCTGGGC CCTGATGCCC AGTCCTTCCT TTCCCCTTCC GGGGGGTTAA
  61  CCGGCTGTGT TTGCTAGAGG CACAGAGGGG CAACATCCAA CCTGCTTTTG CGGGGAACGG
 121  TGCGGCTCCG ATTCCTGCGT CGCCAAAGGT GTTAGCGCAC CCAAACGGCG CACCTACCAA
 181  TGTTATTGGT GTGGTCTGCG AGTTCTAGCC TACTCGTTTC TCCCCCGACC ATTCACTCAC
 241  CCACGAAAAG TGTGTTGTAA CCATAAGATT TAACCCCCGC ACGGGATGTG CGATAACCGT
 301  AAGACTGGCT CAAGCGCGGA AAGCGCTGTA ACCACATGCT GTTAGTCCCT TTATGGCTGC
 361  AAGATGGCTA CCCACCTCGG ATCACTGAAC TGGAGCTCGA CCCTCCTTAG TAAGGGAACC
 421  GAGAGGCCTT CGTGCAACAA GCTCCGACAC AGAGTCCACG TGACTGCTAC CACCATGAGT
 481  ACATGGTTCT CCCCTCTCGA CCCAGGACTT CTTTTTGAAT ATCCACGGCT CGATCCAGAG
 541  GGTGGGGCAT GACCCCTAGC ATAGCGAGCT ACAGCGGGAA CTGTAGCTAG GCCTTAGCGT
 601  GCCTTGGATA CTGCCTGATA GGGCGACGGC CTAGTCGTGT CGGTTCTATA GGTAGCACAT
 661  ACAAATATGC AGAACTCTCA TTTTTCTTTC GATACAGCCT CTGGCACCTT TGAAGATGTA
 721  ACCGGAACAA AAGTCAAGAT CGTTGAATAC CCCAGATCGG TGAACAATGG TGTTTACGAT
 781  TCGTCTACTC ATTTGGAGAT ACTGAACCTA CAGGGTGAAA TTGAAATTTT AAGGTCTTTC
 841  AATGAATACC AAATTCGCGC CGCCAAACAA CAACTCGGAC TGGACATCGT GTACGAACTA
 901  CAGGGTAATG TTCAGACAAC GTCAAAGAAT GATTTTGATT CCCGTGGCAA TAATGGTAAC
 961  ATGACCTTCA ATTACTACGC AAACACTTAT CAGAATTCAG TAGACTTCTC GACCTCCTCG
1021  TCGGCGTCAG GCGCCGGACC CGGGAACTCC CGGGGCGGAT TAGCGGGTCT CCTCACAAAT
1081  TTCAGTGGAA TCTTGAACCC TCTTGGCTAC CTCAAAGATC ACAACACCGA AGAAATGGAA
1141  AACTCTGCTG ATCGAGTCAC AACGCAAACG GCGGGCAACA CTGCCATAAA CACGCAATCA
1201  TCATTGGGTG TGTTGTGTGC CTACGTTGAA GACCCGACCA AATCTGATCC TCCGTCCAGC
1261  AGCACAGATC AACCCACCAC CACTTTCACT GCCATCGACA GGTGGTACAC TGGACGTCTC
1321  AATTCTTGGA CAAAAGCTGT AAAAACCTTC TCTTTTCAGG CCGTCCCGCT TCCCGGGGCC
1381  TTTCTGTCTA GGCAGGGAGG CCTCAACGGA GGGGCCTTCA CAGCTACCCT ACATAGACAC
1441  TTTTTGATGA AGTGCGGGTG GCAGGTGCAG GTCCAATGTA ATTTGACACA ATTCCACCAA
1501  GGCGCTCTTC TTGTTGCCAT GGTTCCTGAA ACCACCCTTG ATGTCAAGCC CGACGGTAAG
1561  GCAAAGAGCT TACAGGAGCT GAATGAAGAA CAGTGGGTGG AAATGTCTGA CGATTACCGG
1621  ACCGGGAAAA ACATGCCTTT TCAGTCTCTT GGCACATACT ATCGGCCCCC TAACTGGACT
1681  TGGGGTCCCA ATTTCATCAA CCCCTATCAA GTAACGGTTT CCCACACCA AATTCTGAAC
1741  GCGAGAACCT CTACCTCGGT AGACATAAAC GTCCCATACA TCGGGGAGAC CCCCACGCAA
1801  TCCTCAGAGA CACAGAACTC CTGGACCCTC CTCGTTATGG TGCTCGTTCC CCTAGACTAT
1861  AAGGAAGGAG CCACAACTGA CCCAGAAATT ACATTTCTG TAAGGCCTAC AAGTCCCTAC
1921  TTCAATGGGC TTCGCAACCG CTACACGGCC GGGACGGACG AAGAACAGGG GCCCATTCCT
1981  ACGGCACCCA GAGAAAATTC GCTTATGTTT CTCTCAACCC TCCCTGACGA CACTGTCCCT
2041  GCTTACGGGA ATGTGCGTAC CCCTCCTGTC AATTACCTCC CTGGTGAAAT AACCGACCTT
```

FIG. 84A

```
2101  TTGCAACTGG CCCGCATACC CACTCTCATG GCATTTGAGC GGGTGCCTGA ACCCGTGCCT
2161  GCCTCAGACA CATATGTGCC CTACGTTGCC GTTCCCACCC AGTTCGATGA CAGGCCTCTC
2221  ATCTCCTTCC CGATCACCCT TTCAGATCCC GTCTATCAGA ACACCCTGGT TGGCGCCATC
2281  AGTTCAAATT CGCCAATTA CCGTGGGTGT ATCCAAATCA CTCTGACATT TTGTGGACCC
2341  ATGATGGCGA GAGGGAAATT CCTGCTCTCG TATTCTCCCC CAAATGGAAC GCAACCACAG
2401  ACTCTTTCCG AAGCTATGCA GTGCACATAC TCTATTTGGG ACATAGGCTT GAACTCTAGT
2461  TGGACCTTCG TCGTCCCCTA CATCTCGCCC AGTGACTACC GTGAAACTCG AGCCATTACC
2521  AACTCGGTTT ACTCCGCTGA TGGTTGGTTT AGCCTGCACA AGTTGACCAA AATTACTCTA
2581  CCACCTGACT GTCCGCAAAG TCCCTGCATT CTCTTTTTCG CTTCTGCTGG TGAGGATTAC
2641  ACTCTCCGTC TCCCCGTTGA TTGTAATCCT TCCTATGTGT TCCACTCCAC CGACAACGCC
2701  GAGACCGGGG TTATTGAGGC GGGTAACACT GACACCGATT TCTCTGGTGA ACTGGCGGCT
2761  CCTGGCTCTA ACCACACTAA TGTCAAGTTC CTGTTTGATC GATCTCGATT ATTGAATGTA
2821  ATCAAGGTAC TGGAGAAGGA CGCCGTTTTC CCCCGCCCTT TCCCTACACA AGAAGGTGCG
2881  CAGCAGGATG ATGGTTACTT TTGTCTTCTG ACCCCCCGCC AACAGTCGC TTCCCGACCC
2941  GCCACTCGTT TCGGCCTGTA CGCCAATCCG TCCGGCAGTG GTGTTCTTGC TAACACTTCA
3001  CTGGACTTCA ATTTTTATAG CTTGGCCTGT TTCACTTACT TTAGATCGGA CCTTGAGGTT
3061  ACGGTGGTCT CACTAGAGCC GGATCTGGAA TTTGCTGTAG GGTGGTTTCC TTCTGGCAGT
3121  GAATACCAGG CTTCCAGCTT TGTCTACGAC CAGCTGCATG TGCCCTTCCA CTTTACTGGG
3181  CGCACTCCCC GCGCTTTCGC TAGCAAGGGT GGGAAGGTAT CTTTCGTGCT CCCTTGGAAC
3241  TCTGTCTCGT CTGTGCTCCC CGTGCGCTGG GGGGGGGCTT CCAAGCTCTC TTCTGCTACG
3301  CGGGGTCTAC CGGCGCATGC TGATTGGGGG ACTATTTACG CCTTTGTCCC CCGTCCTAAT
3361  GAGAAGAAAA GCACCGCTGT AAAACACGTG GCCGTGTACA TTCGGTACAA GAACGCACGT
3421  GCCTGGTGCC CCAGCATGCT TCCCTTTCGC AGCTACAAGC AGAAGATGCT GATGCAATCT
3481  GGCGATATCG AGACCAATCC TGGTCCTGCT TCTGACAACC CAATTTTGGA GTTTCTTGAA
3541  GCAGAAAATG ATCTAGTCAC TCTGGCCTCT CTCTGGAAGA TGGTGCACTC TGTTCAACAG
3601  ACCTGGAGAA AGTATGTGAA GAACGATGAT TTTTGGCCCA ATTTACTCAG CGAGCTAGTG
3661  GGGGAAGGCT CTGTCGCCTT GGCCGCCACG CTATCCAACC AAGCTTCAGT AAAGGCTCTT
3721  TTGGGCCTGC ACTTTCTCTC TCGGGGGCTC AATTACACTG ACTTTTACTC TTTACTGATA
3781  GAGAAATGCT CTAGTTTCTT TACCGTAGAA CCACCTCCTC CACCAGCTGA AAACCTGATG
3841  ACCAAGCCCT CAGTGAAGTC GAAATTCCGA AAACTGTTTA AGATGCAAGG ACCCATGGAC
3901  AAAGTCAAAG ACTGGAACCA AATAGCTGCC GGCTTGAAGA ATTTTCAATT TGTTCGTGAC
3961  CTAGTCAAAG AGGTGGTCGA TTGGCTGCAG GCCTGGATCA ACAAAGAGAA AGCCAGCCCT
4021  GTCCTCCAGT ACCAGTTGGA GATGAAGAAG CTCGGGCCTG TGGCCTTGGC TCATGACGCT
```

FIG. 84B

```
4081  TTCATGGCTG GTTCCGGGCC CCCTCTTAGC GACGACCAGA TTGAATACCT CCAGAACCTC
4141  AAATCTCTTG CCCTAACACT GGGGAAGACT AATTTGGCCC AAAGTCTCAC CACTATGATC
4201  AATGCCAAAC AAAGTTCAGC CAACGAGTT  GAACCCGTTG TGGTGGTCCT TAGAGGCAAG
4261  CCGGGATGCG GCAAGAGCTT GGCCTCTACG TTGATTGCCC AGGCTGTGTC CAAGCGCCTC
4321  TATGGCTCCC AAAGTGTATA TTCTCTTCCC CCAGATCCAG ATTTCTTCGA TGGATACAAA
4381  GGACAGTTCG TGACCTTGAT GGATGATTTG GACAAAACC  CGGATGGACA AGATTTCTCC
4441  ACCTTTTGTC AGATGGTGTC GACCGCCCAA TTTCTCCCCA ACATGGCGGA CCTTGCAGAG
4501  AAAGGGCGTC CCTTTACCTC CAATCTCATC ATTGCAACTA CAAATCTCCC CCACTTCAGT
4561  CCTGTCACCA TTGCTGATCC TTCTGCAGTC TCTCGCCGTA TCAACTACGA TCTGACTCTA
4621  GAAGTATCTG AGGCCTACAA GAAACACACA CGGCTGAATT TTGACTTGGC TTTCAGGCGC
4681  ACAGACGCCC CCCCCATTTA TCCTTTTGCT GCCCATGTGC CCTTTGTGGA CGTAGCTGTG
4741  CGCTTCAAAA ATGGTCACCA GAATTTTAAT CTCCTAGAGT TGGTCGATTC CATTTGTACA
4801  GACATTCGAG CCAAGCAACA AGGTGCCCGA ACATGCAGA  CTCTGGTTCT ACAGAGCCCC
4861  AACGAGAATG ATGACACCCC CGTCGACGAG GCGTTGGGTA GAGTTCTCTC CCCCGCTGCG
4921  GTCGATGAGG CGCTTGTCGA CCTCACTCCA GAGGCCGACC CGGTTGGCCG TTTGGCTATT
4981  CTTGCCAAGC TAGGTCTTGC CCTAGCTGCG GTCACCCCTG GTCTGATAAT CTTGCCAGTG
5041  GGACTCTACA GGTACTTCTC TGGCTCTGAT GCAGACCAAG AAGAAACAGA AAGTGAGGGA
5101  TCTGTCAAGG CACCCAGGAG CGAAAATGCT TATGACGGCC CGAAGAAAAA CTCTAAGCCC
5161  CCTGGAGCAC TCTCTCTCAT GGAAATGCAA CAGCCCAACG TGGACATGGG CTTTGAGGCT
5221  GCGGTCGCTA AGAAAGTGGT CGTCCCCATT ACCTTCATGG TTCCCAACAG ACCTTCTGGG
5281  CTTACACAGT CCGCTCTTCT GGTGACCGGC CGGACCTTCC TAATCAATGA ACATACATGG
5341  TCCAATCCCT CCTGGACCAG CTTCACAATC CGCGGTGAGG TACACACTCG TGATGAGCCC
5401  TTCCAAACGG TTCATTTCAC TCACCACGGT ATTCCCACAG ATCTGATGAT GGTACGTCTC
5461  GGACCGGGCA ATTCTTTCCC TAACAATCTA GACAAGTTTG GACTTGACCA GATGCCGGCA
5521  CGCAACTCCC GTGTGGTTGG CGTTTCGTCC AGTTACGGAA ACTTCTTCTT CTCTGGAAAT
5581  TTCCTCGGAT TTGTTGATTC CATCACCTCT GAACAAGGAA CTTACGCAAG ACTCTTTAGG
5641  TACAGGGTGA CGACCTACAA AGGATGGTGC GGCTCGGCCC TGGTCTGTGA GGCCGGTGGC
5701  GTCCGACGCA TCATTGGCCT GCATTCTGCT GGCGCCGCCG TATCGGCGC  CGGGACCTAT
5761  ATCTCAAAAT TAGGACTAAT CAAAGCCCTG AAACACCTCG GTGAACCTTT GGCCACAATG
5821  CAAGGACTGA TGACTGAATT AGAGCCTGGA ATCACCGTAC ATGTACCCCG GAAATCCAAA
5881  TTGAGAAAGA CGACCGCACA CGCGGTGTAC AAACCGGAGT TGAGCCTGC  TGTGTTGTCA
5941  AAATTTGATC CCAGACTGAA CAAGGATGTT GACTTGGATG AAGTAATTTG GTCTAAACAC
6001  ACTGCCAATG TCCCTTACCA ACCTCCTTTG TTCTACACAT ACATGTCAGA GTACGCTCAT
```

FIG. 84C

```
6061  CGAGTCTTCT CCTTCTTGGG GAAAGACAAT GACATTCTGA CCGTCAAAGA AGCAATTCTG
6121  GGCATCCCCG GACTAGACCC CATGGATCCC CACACAGCTC CGGGTCTGCC TTACGCCATC
6181  AACGGCCTTC GACGTACTGA TCTCGTCGAT TTTGTGAACG GTACAGTAGA TGCGGCGCTG
6241  GCTGTACAAA TCCAGAAATT CTTAGACGGT GACTACTCTG ACCATGTCTT CCAAACTTTT
6301  CTGAAAGATG AGATCAGACC CTCAGAGAAA GTCCGAGCGG GAAAAACCCG CATTGTTGAT
6361  GTGCCCTCCC TGGCGCATTG CATTGTGGGC AGAATGTTGC TTGGGCGCTT TGCTGCCAAG
6421  TTTCAATCCC ATCCTGGCTT TCTCCTCGGC TCTGCTATCG GGTCTGACCC TGATGTTTTC
6481  TGGACCGTCA TAGGGGCTCA ACTCGAGGGG AGAAAGAACA CGTATGACGT GGACTACAGT
6541  GCCTTTGACT CTTCACACGG CACTGGCTCC TTCGAGGCTC TCATCTCTCA CTTTTTCACC
6601  GTGGACAATG GTTTTAGCCC TGCGCTGGGA CCGTATCTCA GATCCCTGGC TGTCTCGGTG
6661  CACGCTTACG GCGAGCGTCG CATCAAGATT ACCGGTGGCC TCCCCTCCGG TTGTGCCGCG
6721  ACCAGCCTGC TGAACACAGT GCTCAACAAT GTGATCATCA GGACTGCTCT GGCATTGACT
6781  TACAAGGAAT TTGAATATGA CATGGTTGAT ATCATCGCCT ACGGTGACGA CCTTCTGGTT
6841  GGCACGGATT ACGATCTGGA CTTCAATGAG GTGGCACGAC GCGCTGCCAA GTTGGGGTAT
6901  AAGATGACTC CTGCCAACAA GGGTTCTGTC TTCCCTCCGA CTTCCTCTCT TTCCGATGCT
6961  GTTTTTCTAA AGCGCAAATT CGTCCAAAAC AACGACGGCT TATACAAACC AGTTATGGAT
7021  TTAAAGAATT TGGAAGCCAT GCTCTCCTAC TTCAAACCAG GAACACTACT CGAGAAGCTG
7081  CAATCTGTTT CTATGTTGGC TCAACATTCT GGAAAAGAAG AATATGATAG ATTGATGCAC
7141  CCCTTCGCTG ACTACGGTGC CGTACCGAGT CACGAGTACC TGCAGGCAAG ATGGAGGGCC
7201  TTGTTCGACT GACCCAGATA GCCCAAGGCG CTTCGGTGCT GCCGGCGATT CTGGGAGAAC
7261  TCAGTCGGAA CAGAAAAGGG AAAAAAAAAA AAAAAAAAAA AAAAAAAAA (SEQ ID NO:168)
```

FIG. 84D

```
   1  MQNSHFSFDT ASGTFEDVTG TKVKIVEYPR SVNNGVYDSS THLEILNLQG EIEILRSFNE
  61  YQIRAAKQQL GLDIVYELQG NVQTTSKNDF DSRGNNGNMT FNYYANTYQN SVDFSTSSSA
 121  SGAGPGNSRG GLAGLLTNFS GILNPLGYLK DHNTEEMENS ADRVTTQTAG NTAINTQSSL
 181  GVLCAYVEDP TKSDPPSSST DQPTTTFTAI DRWYTGRLNS WTKAVKTFSF QAVPLPGAFL
 241  SRQGGLNGGA FTATLHRHFL MKCGWQVQVQ CNLTQFHQGA LLVAMVPETT LDVKPDGKAK
 301  SLQELNEEQW VEMSDDYRTG KNMPFQSLGT YYRPPNWTWG PNFINPYQVT VFPHQILNAR
 361  TSTSVDINVP YIGETPTQSS ETQNSWTLLV MVLVPLDYKE GATTDPEITF SVRPTSPYFN
 421  GLRNRYTAGT DEEQGPIPTA PRENSLMFLS TLPDDTVPAY GNVRTPPVNY LPGEITDLLQ
 481  LARIPTLMAF ERVPEPVPAS DTYVPYVAVP TQFDDRPLIS FPITLSDPVY QNTLVGAISS
 541  NFANYRGCIQ ITLTFCGPMM ARGKFLLSYS PPNGTQPQTL SEAMQCTYSI WDIGLNSSWT
 601  FVVPYISPSD YRETRAITNS VYSADGWFSL HKLTKITLPP DCPQSPCILF FASAGEDYTL
 661  RLPVDCNPSY VFHSTDNAET GVIEAGNTDT DFSGELAAPG SNHTNVKFLF DRSRLLNVIK
 721  VLEKDAVFPR PFPTQEGAQQ DDGYFCLLTP RPTVASRPAT RFGLYANPSG SGVLANTSLD
 781  FNFYSLACFT YFRSDLEVTV VSLEPDLEFA VGWFPSGSEY QASSFVYDQL HVPFHFTGRT
 841  PRAFASKGGK VSFVLPWNSV SSVLPVRWGG ASKLSSATRG LPAHADWGTI YAFVPRPNEK
 901  KSTAVKHVAV YIRYKNARAW CPSMLPFRSY KQKMLMQSGD IETNPGPASD NPILEFLEAE
 961  NDLVTLASLW KMVHSVQQTW RKYVKNDDFW PNLLSELVGE GSVALAATLS NQASVKALLG
1021  LHFLSRGLNY TDFYSLLIEK CSSFFTVEPP PPPAENLMTK PSVKSKFRKL FKMQGPMDKV
1081  KDWNQIAAGL KNFQFVRDLV KEVVDWLQAW INKEKASPVL QYQLEMKKLG PVALAHDAFM
1141  AGSGPPLSDD QIEYLQNLKS LALTLGKTNL AQSLTTMINA KQSSAQRVEP VVVVLRGKPG
1201  CGKSLASTLI AQAVSKRLYG SQSVYSLPPD PDFFDGYKGQ FVTLMDDLGQ NPDGQDFSTF
1261  CQMVSTAQFL PNMADLAEKG RPFTSNLIIA TTNLPHFSPV TIADPSAVSR RINYDLTLEV
1321  SEAYKKHTRL NFDLAFRRTD APPIYPFAAH VPFVDVAVRF KNGHQNFNLL ELVDSICTDI
1381  RAKQQGARNM QTLVLQSPNE NDDTPVDEAL GRVLSPAAVD EALVDLTPEA DPVGRLAILA
1441  KLGLALAAVT PGLIILAVGL YRYFSGSDAD QEETESEGSV KAPRSENAYD GPKKNSKPPG
1501  ALSLMEMQQP NVDMGFEAAV AKKVVVPITF MVPNRPSGLT QSALLVTGRT FLINEHTWSN
1561  PSWTSFTIRG EVHTRDEPFQ TVHFTHHGIP TDLMMVRLGP GNSFPNNLDK FGLDQMPARN
```

FIG. 85A

```
1621  SRVVGVSSSY GNFFFSGNFL GFVDSITSEQ GTYARLFRYR VTTYKGWCGS ALVCEAGGVR
1681  RIIGLHSAGA AGIGAGTYIS KLGLIKALKH LGEPLATMQG LMTELEPGIT VHVPRKSKLR
1741  KTTAHAVYKP EFEPAVLSKF DPRLNKDVDL DEVIWSKHTA NVPYQPPLFY TYMSEYAHRV
1801  FSFLGKDNDI LTVKEAILGI PGLDPMDPHT APGLPYAING LRRTDLVDFV NGTVDAALAV
1861  QIQKFLDGDY SDHVFQTFLK DEIRPSEKVR AGKTRIVDVP SLAHCIVGRM LLGRFAAKFQ
1921  SHPGFLLGSA IGSDPDVFWT VIGAQLEGRK NTYDVDYSAF DSSHGTGSFE ALISHFFTVD
1981  NGFSPALGPY LRSLAVSVHA YGERRIKITG GLPSGCAATS LLNTVLNNVI IRTALALTYK
2041  EFEYDMVDII AYGDDLLVGT DYDLDFNEVA RRAAKLGYKM TPANKGSVFP PTSSLSDAVF
2101  LKRKFVQNND GLYKPVMDLK NLEAMLSYFK PGTLLEKLQS VSMLAQHSGK EEYDRLMHPF
2161  ADYGAVPSHE YLQARWRALF D* (SEQ ID NO:169)
```

FIG. 85B

```
VP2(partial)-VP3-VP1-2A(partial)

VP2 >< VP3
                    10        20        30        40        50        60        70        80
                 ....|....|....|....|....|....|....|....|....|....|....|....|....|....|....|....|
SVV-001          AATGGGCTTCGCAACCGCTACACGGCCGGGACGGACGAAGAACAGGGGCCCATTCCTACGGCACCCAGAGAAAATTCGCT
89-47752         AATGGGCNTCCCAACCGCTACATGGCCGGGACGGACGAAGAACAGGGGCCNATTCCCACGGCACCCAGAGAGAATTCGCT
131395           AATGGGCTTCGCAACCGCTACGACGGGACGGACGAAGAACAGGGGCCCATTCCCACGGCACCCAGAGAACATTCGCT
Consensus        AATGGGC  CGCAACCGCTACA G CCGGGACGGACGA GAACAGGGGCC ATTCC ACGGCACCCAGAGA  ATTCGCT 90       100       110       120       130       140       150       160
                 ....|....|....|....|....|....|....|....|....|....|....|....|....|....|....|....|
SVV-001          TATGTTTCTCTCAACCCTCCCTGACGACACTGTCCCTGCTTACGGGAATGTGCGTACCCCTCCTGTCAATTACCTCCCTG
89-47752         TATGTTTCTTTTCAACTCTGCCTGACGACACAGTTCCTGCTTACGGGAATGTGCGCACCCCTCCTGTCAATTACCTCCCTG
131395           TATGTTTCTCTCAACCCTCCCTGACGACACTGTCCCTGCTTACGGGAATGTGCGTACCCCTCCTGTCAATTACCTCCCTG
Consensus        TATGTTTCT TCAAC CT CCTGACGACAC GT CCTGCTTACGGGAATGTGCG ACCCCTCCTGTCAATTACCTCCCTG 170       180       190       200       210       220       230       240
                 ....|....|....|....|....|....|....|....|....|....|....|....|....|....|....|....|
SVV-001          GTGAAATAACCGACCTTTTGCAACTGGCCCGCATACCCACTCTCATGGCATTTGAGCGGGTGCCTGAACCCGTGCCTGCC
89-47752         GTGAAATAACCGACCTCTTGCAACTGGCCCGCATACCCACTCTCATGGCATTTGAGCGGGTGCCCGAACCCGTGCCTGCC
131395           GTGAAATAACCGACCTTTTGCAACTGGCCCGCATACCCACTCTCATGGCGTTTGAGCGGGTGCCTGAACCCGTGCCTGCC
Consensus        GTGAAATAACCGACCT TTGCAACTGGCCCGCATACCCACTCTCATGGC  TTTGAGCGGGTGCC GAACCCGT CCTGCC 250       260       270       280       290       300       310       320
                 ....|....|....|....|....|....|....|....|....|....|....|....|....|....|....|....|
SVV-001          TCAGACACATATGTGCCCTACGTTGCCGTTCCCACCCAGTTCGATGACAGGCCTCTCATCTCCTTCCCGATCACCCTTTC
89-47752         TCAGATACGTATGTGCCCTACGTTGCCGTTCCCACCCAATTCGCTGACAGGCCTCTCATCTCCTTCCCGATCACCCTTTC
131395           TCAGACACATATGTGCCCTACGTTGCCGTTCCCACCCAGTTTGATGACAAGCCTCTCATCTCCTTCCCGATCACCCTTTC
Consensus        TCAGA AC TATGTGCCCTACGTTGCCGTTCCCACCCA TT G TGACA GCCTCTCATCTCCTTCCCGATCACCCTTTC 330       340       350       360       370       380       390       400
                 ....|....|....|....|....|....|....|....|....|....|....|....|....|....|....|....|
SVV-001          AGATCCGTCTATCAGAACACCCTGGTTGGCGCCATCAGTTCAAATTTCGCCAATTACCGTGGGTGTATCCAAATCACTC
89-47752         AGACCCTGTCTATCAAAACACCCTGGTTGGCGCCATCAGTTCTTACTTTGCCAATTACCGTGGGTGTATCCAGATCACTC
131395           AGATCCTGTCTATCAGAACACCCTGGTAGGCGCCATCAGTTCAAATTTCGCCAACTACCGTGGGTGTATCCAAATCACTC
Consensus        AGA CC G CTATCA AACACCCTGGT GGCGCCATCAGTTC  A TT GCCAA TACCGTGGGTGTATCCA ATCACTC 410       420       430       440       450       460       470       480
                 ....|....|....|....|....|....|....|....|....|....|....|....|....|....|....|....|
SVV-001          TGACATTTTGTGGACCCATGATGGCGAGAGGGAAATTCCTGCTCTCGTATTCTCCCCCAAATGGAACGCAACCACAGACT
89-47752         TGACGTTTTGTGGACCCATGATGGCGAGAGGGAAATTCCTACTGTTATATTCTCCCCCAAATGGAACGCAACCACAGACT
131395           TGACATTTTGTGGACCCATGATGGCAAGAGGGAAATTCCTACTCTCGTATTCTCCCCCAAATGGAACGCAACCACAGACT
Consensus        TGAC TTTTGTGGACCCATGATGGC AGAGGGAAATTCCT CT T  TATTCTCCCCCAAATGGAACGCAACCACAGACT 490       500       510       520       530       540       550       560
                 ....|....|....|....|....|....|....|....|....|....|....|....|....|....|....|....|
SVV-001          CTTTCCGAAGCTATGCAGTGCACATACTCTATTTGGGACATAGGCTTGAACTCTAGTTGGACCTTCGTCGTCCCCTACAT
89-47752         CTTTCCGAAGCTATGCAGTGCACATACTCTATTTGGGACATAGGCTTGAACTCGAGTTGGACCTTCGTCGTCCCCTACAT
131395           CTTTCCGAAGCTATGCAGTGCACATACTCTATTTGGGACATAGGCTTGAACTCTAGTTGGACCTTCGTCGTCCCCTACAT
Consensus        CTTTCCGAAGCTATCCAGTGCACATACTCTATTTGCCGACATAGGCTTGAACTC AGTTGGACCTTCGTCGTCCCCTACAT
```

FIG. 87A

```
              570       580       590       600       610       620       630       640
          ....|....|....|....|....|....|....|....|....|....|....|....|....|....|....|
SVV-001   CTCGCCCAGTGACTACCGTGAAACTCGAGCCATTACCAACTCGGTTTACTCCGCTGATGGTTGGTTTAGCCTGCACAAGT
88-23626  ----------------------------------------------------------------TTTAGCCTGCACAAGT
88-36695  ----------------------------------------------------------------TTTAGCCTGCACAAGT
89-47752  CTCGCCCAGTGACTACCGTGAAACCCGGGCCATTACCAACTCGGTTTACTCCGCTGATGGTTGGTTTAGCCTGCACAAGT
90-10324  ----------------------------------------------------------------TTTAGCCTGCACAAGT
92-48963  ----------------------------------------------------------------TTTAGCCTGCACAAGT
97-1278   ----------------------------------------------------------------TTTAGCCTGCACAAGT
131395    CTCGCCCAGTGACTACCGTGAAACTCGGGCCATTACCAACTCGGTTTACTCCGCTGATGGTTGGTTTAGTCTGCACAAGT
Consensus CTCGCCCAGTGACTACCGTGAAAC CG GCCATTACCAACTCGGTTTACTCCGCTGATGGTTGGTTTAG CTGCACAAGT 650       660       670       680       690       700       710       720
          ....|....|....|....|....|....|....|....|....|....|....|....|....|....|....|
SVV-001   TGACCAAAATTACTCTACCACCTGACTGTCCGCAAAGTCCCTGCATTCTCTTTTTCGCTTCTGCTGGTGAGGATTACACT
88-23626  TGACCAAAATTACTCTACCACCTGACTGCCCGCAAAATCCCTGCATTCTCTTTTTCGCTTCTGCTGGTGAGGATTACACT
88-36695  TGACCAAAATTACTCTACCACCTGACTGCCCGCAAAATCCCTGCATTCTCTTTTTCGCTTCTGCTGGTGAGGATTACACT
89-47752  TGACCAAAATTACTCTCCCACCTGACTGTCCGCAAAGTCCCTGCATTCTCTTTTTCGCTTCTGCTGGTGAGGATTACACT
90-10324  TGACCAAAATTACTYTACCACCTGACTGTCCGCAAAGTCCCTGCATTCTCTTTTTCGCTTCTGCTGGTGAGGATTACACT
92-48963  TGACAAAAATTACTCTACCACCTGACTGTCCGCAAAGTCCCTGCATTCTCTTTTTCGCTTCTGCTGGTGAGGATTACACT
97-1278   TGACCAAAATTACTCTACCACCTGACTGTCCGCAAAGTCCCTGCATTCTCTTTTTCGCTTCTGCTGGTGAGGATTACACT
131395    TGACCAAAATTACTCT ACCACCTGACTGCCCGCAAAGTCCCTGTATTCTCTTTTTCGCTTCTGCTGGTGACCATTACACC
Consensus TGAC AAAAT ACT T CCACCTGACTG CCGCAAA TCCCTG  TTCTCTTTTTCGCTTCTGCTGGTGAGGATTACAC VP3 >< VP1
              730       740       750       760       770       780       790       800
          ....|....|....|....|....|....|....|....|....|....|....|....|....|....|....|
SVV-001   CTCCGTCTCCCCGTTGATTGTAATCCTTCCTATGTGTTCCACTCCACCGACAACGCCGAGACCGGGGTATTGAGGCGGG
88-23626  CTCCGTCTCCCCATTGATTGCAATCCTTCCTACCTGTTCCACTCCACCGACAACGCCGAAACTCGGGTTGTCGACGCGG
88-36695  CTCCGTCTCCCCATTGATTGCAATCCTTCCTACGTGTTCCACTCCACCGACAACGCCGAAACTGGGGTTGTCGAGGCGGG
89-47752  CTCCGTCTCCCCATTGATTGTAATCCTTCCTACGTGTTCCACTCCACCGACAACGCCGAAACTGGGGTTGTTGAGGCGGG
90-10324  CTCCGTCTCCCCATTGATTGTAATCCTTCCTACGTGTTCCACTCCACCGACAACGCCGAAACTGGGGTTGTTGAGGCGGG
92-48963  CTCCGTCTCCCCGTTGATTGTAATCCTTCTTACGTGTTCCACTCCACCGACAACGCCGAAACTGGGGTTGTTGAGGCGGG
97-1278   CTCCGTCTCCCCGTTGATTGTAATCCTTCCTATGTGTTCCACTCCACCGACAACGCCGAGACTGGGGTATTGAGGCGGG
131395    CTCCGTCTCCCCGTTGATTGTAATCCTTCCTATGTGTTCCACTCCACCGACAACGCCGAGACTGGGGTATTGAGGCGGG
Consensus CTCCGTCTCCCC TTGATTG AATCCTTC TA GTGTTCCACTCCACCGACAACGCCGA AC GGGGTT T GAGGCGGG 810       820       830       840       850       860       870       880
          ....|....|....|....|....|....|....|....|....|....|....|....|....|....|....|
SVV-001   TAACACTGACACCGATTTCTCTGGTGAACTGGCGGCTCCTGGCTCTAACCACACTAATGTCAAGTTCCTGTTTGATCGAT
88-23626  TAACACTGACACCGATTTCTCTGGTGAACTAGCGGCTCCTGGCTCCAACCACACTAATGTCAAGTTCCTGTTTGATCGAT
88-36695  TAACACTGACACCGATTTCTCTGGTGAACTAGCGGCTCCTGGCTCCAACCACACTAATGTCAAGTTCCTGTTTGATCGAT
89-47752  TAACACTGACACCGATTTCTCTGGTGAACTAGCGGCTCCTGGCTCCAACCACACTAATGTCAAGTTCCTGTTTGATCGAT
90-10324  TAACACTGACACCGATTTCTCTGGTGAACTAGCGGCTCCTGGCTCCAACCACACTAATGTCAAGTTCCTGTTTGATCGAT
92-48963  TAACACTGACACCGATTTCTCTGGTGAACTAGCGGCTCCTGGTTCCAACCACACTAACGTCAAGTTCCTGTTTGATCGAT
97-1278   TAACACTGACACCGATTTCTCTGGTGAACTGGCGGCTCCTGGCTCTAACCACACTAATGTCAAGTTCCTGTTTGATCGAT
131395    TAACACTGACACCGATTTCTCTGGTGAACTGGCGGCTCCTGGCTCTAACCACACTAATGTCAAGTTCCTGTTTGATCGAT
Consensus TAACACTGACACCGATTTCTCTGGTGAACT GCGGCTCCTGG TC AACCACACTAA GTCAAGTTCCTGTTTGATCGAT
```

FIG. 87B

```
            890       900       910       920       930       940       950       960
           ....|....|....|....|....|....|....|....|....|....|....|....|....|....|....|
SVV-001    CTCGATTATTGAATGTAATCAAGGTACTGGAGAAGGACGCCGTTTTCCCCCGCCCTTTCCCTACACAAGAAGGTGCGCAG
88-23626   CTCGGTTATTGAATGTAATTAAGGTACTGGAGAAAGACGCTGTTTTCCCTCACCCTTTCCCTACGCTAGAAGGTGTGCAA
88-36695   CTCGGTTATTGAATGTAATTAAGGTACTGGAGAAAGACGCTGTTTTCCCTCACCCTTTCCCTACGCTAGAAGGTGTGCAA
89-47752   CTCGATTATTGAATGTAATTAAGGTACTGGAGAAAGACCCGTTTTCCCCCACCCTTTCCCTACGCTAGAAGGTCCCCAA
90-10324   CTCGATTATTGAATGTAATTAAGGTACTGGAGAAAGACGCCGTTTTCCCCCACCCTTTCCCTACGCTAGAAGGTGCGCAA
92-48963   CTCGATTATTGAATGTAATTAAGGTACTGGAGAAAGACGCCGTTTTCCCTCACCCTTTCCCTACGCTAGAAGGTGCGCAA
97-1278    CTCGATTATTGAATGTAATTAAGGTACTGGAGAAGGACGCCGTTTTCCCCCGCCCTTTCCCTACACAAGAAGGTGCGCAG
131395     CTCGATTACTGAATGTAATTAAGGTACTGGAGAAGGACGCCGTTTTCCCCCGTCCTTTCCCTACAAAAGAAGGTGCGCAG
Consensus  CTCG TTA TGAATGTAAT AAGGTACTGGAGAA GACGC GTTTTCCC C  CCTTTCCCTAC   AGAAGGTG GCA 970       980       990       1000      1010      1020      1030      1040
           ....|....|....|....|....|....|....|....|....|....|....|....|....|....|....|
SVV-001    CAGGATGATGGTTACTTTTGTCTTCTGACCCCCCGCCCAACAGTCGCTTCCCGACCCGCCACTCGTTTCGGCCTGTACGC
88-23626   CAGGATGATGGCTACTTTTTCTCTTCTCACCCCCCGCCCAACAGTCGCTTCCCGACCCGCCACTCGTTTCGCCCTGTACGC
88-36695   CAGGATGATGGCTACTTTTGTCTTCTGACCCCCCGCCCAACAGTCGCTTCCCGGCCTGCCACTCGTTTCGGCCTGTACGC
89-47752   CAGGATGATGGTTACTTTTGTCTTCTGACCCCCCGCCCAACAGTCGCTTCCCGACCCGCCACTCGTTTCGGCCTGTACGC
90-10324   CAGGATGATGGTTACTTTTGTCTTCTGACCCCCCGCCCAACAGTCGCTTCCCGACCCGCCACTCGTTTCGGCCTGTACGC
92-48963   CAGGATGATGGTTACTTTTTCTCTTCTGACCCCCCGCCCAACAGTCGCTTCCCGACCCGCCACTCGTTTCGCCCTGTACGC
97-1278    CAGGACGATGGTTACTTTTGTCTTCTGACCCCCCGCCCAACAGTCGCTTCCCGACCCGCCACTCGTTTCGGCCTGTACGC
131395     CAGGACGATGGTTACTTTTGTCTTCTCACACCCCGCCCAACAGTCGCCTCCCGACCCGCCACTCGTTTCGGCCTGTACGT
Consensus  CAGGA GATGG TACTTTTGTCTTCTGAC CCCCGCCCAACAGTCGC TCCCG CC GCCACTCGTTTCGGCCTGTACG 1050      1060      1070      1080      1090      1100      1110      1120
           ....|....|....|....|....|....|....|....|....|....|....|....|....|....|....|
SVV-001    CAATCCGTCCGGCAGTGGTGTTCTTGCTAACACTTCACTGGACTTCAATTTTTATAGCTTGGCCTGTTTCACTTACTTTA
88-23626   CAATCCGTCCGGCAGCGGTGTCTTCTTCCTAATACTTCATTCGACTTTAACTTTTATAGCTTGGCCCTGTTTCACTTACTTTA
88-36695   CAATCCGTCCGGCAGCGGTGTTCTTGCTAATACTTCATTGGACTTTAACTTTTATAGCTTGGCCTGTTTCACTTACTTTA
89-47752   CAATCCGTCCGGCAGCGGTGTTCTTGCTAATACTTCATTGGACTTTAACTTTTATAGCTTGGCCTGTTTCACTTACTTTA
90-10324   CAATCCGTCCGGCAGCGGTGTTCTTGCTAATACTTCATTGGACTTTAACTTTTATAGCTTGGCCTGCTTCACTTACTTTA
92-48963   CAATCCGTCCGGCAGTGGTGTCTTCTTCCTAATACTTCATTCGACTTTAACTTTTATAGCTTGGCCTGTTTCACTTACTTTA
97-1278    CAATCCGTCCGGCAGTGGTGTTCTCGCCAACACTTCACTGGACTTCAATTTTTATAGCTTGGCCTGTTTCACTTACTTTA
131395     CAATCCGTCCGGCAGTGGTGTTCTCGCCAACACTTCACTGGACTTCAATTTTTATAGCTTGGCCTGTTTCACTTACTTTA
Consensus  CAATCCGTCCGGCAG GGTGTTCT GC AA ACTTCA TGGACTT AA TTTTATAGCTTGGCCTG TTCACTTACTTTA 1130      1140      1150      1160      1170      1180      1190      1200
           ....|....|....|....|....|....|....|....|....|....|....|....|....|....|....|
SVV-001    GATCGGACCTTGAGGTTACGGTGGTCTCACTAGAGCCGGATCTGGAATTTGCTGTAGGGTGGTTTCCTTCTGGCAGTGAA
88-23626   GATCGCACCTCGAGGTTACCGTGGTCTCACTACAGCCCGATCTGGAATTTGCTCTCGGTCCTTTCCTTCCCGCAGTGAA
88-36695   GATCGGACCTCGAGGTTACGGTGGTCTCACTAGAGCCGGATCTGGAATTTGCTGTGGGGTGGTTTCCTTCCGGCAGTGAA
89-47752   GATCGGACCTCGAGGTTACGGTGGTCTCACTGGAGCCAGATCTGGAATTTGCTGTAGGGTGGTTTCCTTCCGGCAGTGAA
90-10324   GATCGGACCTCGAGGTTACGGTGGTCTCACTGGAGCCAGATCTGGAATTTGCTGTAGGGTGGTTTCCTTCCGGCAGTGAA
92-48963   GATCGCACCTCGAGGTTACCGTGGTCTCACTGCAGCCAGATCTGGAATTTGCTCTACGATCGTTTCCTTCCCGCAGTGAA
97-1278    GATCGGACCTTGAGGTTACGGTGGTCTCACTGGAGCCAAATCTGGAATTTGCTGTAGGGTGGTTTCCTTCCGGTAGTGAA
131395     GATCGGACCTTGAAGTTACGGTGGTCTCACTGGAGCCAGATCTGGAATTTGCTGTAGGGTGGTTTCCTTCTGGCAGTGAA
Consensus  GATCGGACCT GA GTTACGGTGGTCTCACT GAGCC  ATCT GAATTTGCTGT GG TGGTTTCCTTC GG AGTGAA
```

FIG. 87C

```
                 1210      1220      1230      1240      1250      1260      1270      1280
              ....|....|....|....|....|....|....|....|....|....|....|....|....|....|....|....|
SVV-001       TACCAGGCTTCCAGCTTTGTCTACGACCAGCTGCATGTGCCCTTCCACTTTACTGGGCGCACTCCCCGCGCTTTCGCTAG
88-23626      TATCAGGCTTCCAGCTTTGTCTACGACCAGCTGCACGTGCCCTTCCACTTCACTGGACGCACCCCCCGCGCTTTTGCTAG
88-36695      TATCAGGCTTCCAGCTTTGTCTACGACCAGCTGCACGTGCCCTTCCACTTCACTGGACGCACCCCCCGCGCTTTTGCTAG
89-47752      TATCAGGCTTCCAGCTTTGTCTACGACCAGCTGCACGTGCCCTTCCACTTCACTGGACGCACCCCCCGCGCTTTTGCTAG
90-10324      TATCAGGCTTCCAGCTTTGTCTACGACCAGCTGCACGTGCCCTTCCACTTCACTGGACGCACCCCCCGCGCTTTTGCTAG
92-48963      TACCAGGCTTCCAGCTTTGTCTACGACCAGCTGCACGTGCCCTTTCCACTTCACTGGGCGCACTCCCCGCGCTTTTGCTAG
97-1278       TACCAGGCTTCCAGTTTTGTCTACGACCAGCTCCACCTCCCCTTCCACTTCACTCGCCCACTCCCCGCGCTTTCGCTAG
131395        TACCAGGCTTCCAGCTTTGTCTACGGCCAGCTGCATGTACCCTTCCACTTTACTGGGCGCACTCCCCGCGCTTTCGCCAG
Consensus     TA CAGGCTTCCAG TTTGTCTACG CCAGCTGCA GT CC TTCCACTT ACTGG CGCAC CCCCGCGCTTT GC AG 1290      1300      1310      1320      1330      1340      1350      1360
              ....|....|....|....|....|....|....|....|....|....|....|....|....|....|....|....|
SVV-001       CAAGGGTGGGAAGGTATCTTTCGTGCTCCCTTGGAACTCTGTCTCGTCTGTGCTCCCCGTGCGCTGGGGGGGGGCTTCCA
88-23626      CAAGGGTGGGAAGGTATCCTTTGTGCTCCCTTGGAACTCTGTCTCGTCTGTGCTCCCCGTGCGCTGGGGGGGGAGCTTCCA
88-36695      CAAGGGTGGGAAGGTATCCTTTGTGCTCCCTTGGAACTCTGTCTCATCTGTGCTCCCCGTGCGCTGGGGGGGGAGCTTCCA
89-47752      CAAGGGTGGGAAGGTATCCTTTGTGCTCCCTTGGAACTCTGTCTCATCTGTGCTCCCCGTGCGCTGGGGGGGGGCTTCCA
90-10324      CAAGGGTGGGAAGGTATCTTTCGTGCTCCCTTGGAACTCTGTCTCATCTGTGCTCCCCGTGCGCTGGGGGGGGGCTTCCA
92-48963      CAAGGGTGGGAAGGTATCCTTCGTGCTCCCTTGGAACTCTGTTTCGTCTGTGCTCCCCGTGCGCTGGGGGGGGGCTTCCA
97-1278       CAAGGGTGGGAAGGTGTCCTTCGTGCTCCCTTGGAACTCTGTCTCGTCTGTGCTCCCCGTGCGCTGGGGGGGGGCTTCCA
131395        CAAGGGTGGGAAGGTATCTTTCGTGCTCCCTTGGAACTCTGTCTCATCTGTGCTCCCCGTGCGCTGGGGGGGCGCTTCCA
Consensus     CAAGGGTGGGAAGGT TC TT GTGCTCCCTTGGAACTCTGT TC TCTGTGCTCCCCGTGCGCTGGGGGGG GCTTCCA 1370      1380      1390      1400      1410      1420      1430      1440
              ....|....|....|....|....|....|....|....|....|....|....|....|....|....|....|....|
SVV-001       AGCTCTCTTCTGCTACGCGGGGTCTACCGGCGCATGCTCATTGGGGACTATTTACGCCTTTGTCCCCCGTCCTAATGAG
88-23626      AGCTCTCTTCTGCCACGCGGGGTCTACCGGTGCACGCTGACTGGGGGACTATCTACGCCTTTGTCCCCCGTCCCAATGAA
88-36695      AGCTCTCTTCTGCCACGCGGGGTCTACCGGTGCACGCTGACTGGGGGACTATCTACGCCTTTGTCCCCCGTCCCAATGAA
89-47752      AGCTCTCTTCTGCCACGCGGGGTCTACCGGCCCATCCTCACTCCCCCACTATCTACGCCTTTGTCCCCCGTCCCAATGAA
90-10324      AGCTCTCTTCTGCCACGCGGGGTCTACCGGCGCATGCTGACTGGGGACTATCTACGCCTTTGTCCCCCGTCCCAATGAA
92-48963      AGCTCTCTTCTGCCACGCGGGGTCTACCGGCGCATGCTGACTGGGGGACTATCTACGCCTTTGTCCCCCGTCCCAATGAA
97-1278       AGCTCTCTTCTGCCACACGGGGTCTACCAGTGCATGCTGACTGGGGGACTATTTACGCCTTTGTCCCCCGTCCCAATGAA
131395        AGCTCTCTTCTGCCACGCGGGGTCTACCGGCGCATGCTGACTGGGGGACTATTTACGCCTTTGTCCCCCGTCCTAATGAG
Consensus     AGCTCTCTTCTGC AC CGGGGTCTACC G GCA GCTGA TGGGGACTAT TACGCCTTTGTCCCCCGTCC AATGA 1450      1460      1470      1480      1490      1500      1510      1520
              ....|....|....|....|....|....|....|....|....|....|....|....|....|....|....|....|
SVV-001       AAGAAAGCACCGCTGTAAAACACGTGGCCGTCTACATTCGGTACAAGAACGCACGTGCCTGGTGCCCCAGCATGCTTCC
88-23626      AAGAAAAGCACCGCTGCAAAACATGTGGCCGTCTACATTCGGTACAAGAACGCACGCGCCTGGTGTCCCAACATGCTCCC
88-36695      AAGAAAAGCACCGCTGCAAAACATGTGGCCGTCTACATTCGGTACAAGAACGCACGCGCCTGGTGTCCCAACATGCTCCC
89-47752      AAGAAAAGCACCGCTGCAAAACACGTGGCCGTCTACATTCGGTACAAGAACGCACGCGCCTGGTGCCCCAGCATGCTTCC
90-10324      AAGAAAAGCACCGCTGCAAAACACGTGGCCGTCTACATTCCCTACAAGAACGCACCCCCTGGTGCCCCCAGCATGCTTCC
92-48963      AAGAAAAGCACCGCTGCAAAACACGTGGCCGTCTACATTCGGTACAAGAACGCACGCGCCTGGTGCCCCAGCATGCTTCC
97-1278       AAGAAAAGCACTGCTGTAAAACACGTGGCCGTCTACATTCGGTACAAGAACGCACGCGCCTGGTGCCCCAGCATGCTTCC
131395        AAGAAAAGCACCGCTGTAAAGCACGTGGCCGTCTACGTTCGGTACAAGAACGCACGTGCCTGGTGCCCCAGCATGCTTCC
Consensus     AAGAAAAGCAC GCTG AAA CA GTGGCCGTCTAC TTCCCTACAAGAACGCACG GCCTGGTG CCCA CATGCT CC VP1 >< 2A (partial)
                 1530      1540      1550      1560
              ....|....|....|....|....|....|....|....|
SVV-001       CTTTCGCAGCTACAAGCAGAAGATGCTGATGCAATCTGGC
88-23626      CTTTCGCAGCTATAAGCAGAAGATGCTGATGCAATCTGGC
88-36695      CTTTCGCAGCTATAAGCAGAAGATGCTGATGCAATCTGGC
89-47752      CTTTCGCAGCTATAAGCAGAAGATGCTGATGCAATCTGGC
90-10324      CTTTCGCAGCTATAAGCAGAAGATGCTGATGCAATCTGCC
92-48963      CTTTCGCAGCTATAAGCAGAAGATGCTGATGCAATCTGGC
97-1278       TTTTCGCAGCTACAAGCAGAAGATGCTGATGCAATCTGGC
131395        TTTTCGCAGCTACAAGCAGAAGATGCTGATGCAATCTGGC
Consensus      TTTCGCAGCTA AAGCAGAAGATGCTGATGCAATCTC CC
```

FIG. 87D

Partial 2C

```
                    10         20         30         40         50         60         70         80
              ....|....|....|....|....|....|....|....|....|....|....|....|....|....|....|....|
SVV-001       AAACTGTTTAAGATGCAAGCACCCATGGACAAAGTCAAAGACTGGAACCAAATAGCTGCCCGCTTGAAGAATTTTCAATT
89-47752      AAACTGTTTAAGATGCAAGTACCCATGGACAAAGTCAAAGACTGGAACCAAATAGCCGCCGGCTTGAAGAACTTTCAATT
131395        AAACTGTTTAAGATGCAAGTACCCATGGACAAAGTCAAAGACTGGAACCAAATAGCCGCCGGCTTGAAGAATTTTCAATT
Consensus     AAACTGTTTAAGATGCAAG ACCCATGCACAAAGTCAAAGACTGGAACCAAATAGC GCCCGCTTGAAGAA TTTCAATT 90        100        110        120        130        140        150        160
              ....|....|....|....|....|....|....|....|....|....|....|....|....|....|....|....|
SVV-001       TGTTCGTGACCTAGTCAAAGAGGTGGTCGATTGGCTGCAGGCCTGGATCAACAAAGAGAAAGCCAGCCCTGTCCTCCAGT
89-47752      TGTTCGTGACCTAGTCAAAGAGGTGGTCGACTGGCTGCAGGCCTGGATCAACAAGGAGAAAGCCAGCCCTGTCCTCCAAT
131395        TGTTCGTGACCTAGTCAAAGAGGTGGTCGACTGGCTGCAGGCCTGGATCAACAAAGAGAAAGCCAGCCCTGTCCTCCAGT
Consensus     TGTTCGTGACCTAGTCAAAGAGGTGGTCGA TGGCTGCAGGCCTGGATCAACAA GAGAAAGCCAGCCCTGTCCTCCA T 170        180        190        200        210        220        230        240
              ....|....|....|....|....|....|....|....|....|....|....|....|....|....|....|....|
SVV-001       ACCAGTTGGAGATGAAGAAGCTCGGGCCTGTGGCCTTGGCTCATGACGCTTTCATGGCTGGTTCCGGGCCCCCTCTTAGC
89-47752      ACCAGTTGGAGATGAAGAAGCTCGGGCCTGTGGCTTTGGCTCATGACGCTTTTATGGCTGGTTCCGGGCCCCCTCTTAGC
131395        ACCAGTTGGAGATGAAGAAGCTCGGGCCCGTGGCTTTGGCTCATGACGCTTTCATGGCTGGTTCCGGGCCCCCTCTTAGC
Consensus     ACCAGTTGGAGATGAAGAAGCTCGGGCC GTGGC TTGGCTCATGACGCTTT ATGGCTGGTTCCGGGCCCCCTCTTAGC 250        260        270        280        290        300        310        320
              ....|....|....|....|....|....|....|....|....|....|....|....|....|....|....|....|
SVV-001       GACGACCAGATTGAATACCTCCAGAACCTCAAATCTCTTGCCCTAACACTAGGGAACACTAATTTGGCCCAAAGTCTCAC
89-47752      GACCACCAGATTGAGTATCTCCACAACCTCAAATCTCTTGCCCTAACACTAGGGAACACTAATTTGGCCCAAAGTCTCAC
131395        GACGACCAGATTGAATACCTCCAGAACCTCAAATCTCTTGCCCTAACACTGGGGAAGACTAATTTGGCCCAAAGTCTCAC
Consensus     GACGACCAGATTGA TA CTCCAGAACCTCAAATCTCTTGCCCTAACACT GGGAAGACTAATTTGGCCCAAAGTCTCAC 330        340        350        360        370        380        390        400
              ....|....|....|....|....|....|....|....|....|....|....|....|....|....|....|....|
SVV-001       CACTATGATCAATGCCAAACAAAGTTCAGCCCAACGAGTTGAACCCGTTGTGGTGGTCCTTAGAGGCAAGCCGGGATGCG
89-47752      CACTATGATCAATGCCAAACAAAGTTCCGCCCAACGAGTTGAACCCGTTGTGGTGGTCCTTAGAGGTAAGCCTGGATGTG
131395        CACTATGATCAATGCCAAACAAAGTTCCGCCCAACGAGTTGAACCCGTTGTGGTGGTCCTTAGAGGCAAGCCGGGATGCG
Consensus     CACTATGATCAATGCCAAACAAAGTTC GCCCAACGAGTTGAACCCGTTGTGGTGGTCCTTAGAGG AAGCC GGATG G 410        420        430        440        450        460        470        480
              ....|....|....|....|....|....|....|....|....|....|....|....|....|....|....|....|
SVV-001       GCAAGAGCTTGGCCTCTACCTTGATTGCCCAGGCTGTGTCCAAGCGCCTCTATGGCTCCCAAAGTGTATATTCTCTTCCC
89-47752      GCAAGAGCTTGGCCTCTACGCTGATTGCTCAGGCTGTGTCCAAGCGCCTCTATGGCTCCCAAAGTGTATATTCCCTCCCC
131395        GCAAGAGCTTGGCCTCCACGTTGATTGCCCAGGCTGTGTCCAAGCGTCTCTATGGCTCCCAAAGTGTGTATTCTCTTCCC
Consensus     GCAAGAGCTTGGCCTC ACG TGATTGC CAGGCTGTGTCCAAGCG CTCTATGGCTCCCAAAGTGT TATTC CT CCC 490        500        510        520        530        540        550
              ....|....|....|....|....|....|....|....|....|....|....|....|....|....|....|.
SVV-001       CCAGATCCAGATTTCTTCGATGGATACAAAGGACAGTTCGTGACCTTGATGGATGATTTGGGACAAAACCC
89-47752      CCAGACCCAGATTTCTTTGATGGATACAAAGGACAATTCGTGACCTTGATGGATGATTTGGGACAAAACCC
131395        CCGGATCCAGATTTCTTCGATGGATACAAAGGACAGTTTGTGACCTTGATGGATGATTTGGGACAAAACCC
Consensus     CC GA CCAGATTTCTT GATGGATACAAAGGACA TT GTGACCTTGATGGATGATTTGGGACAAAACCC
```

FIG. 88

Partial 3Dpol and 3' UTR

```
                      10        20        30        40        50        60        70        80
               ....|....|....|....|....|....|....|....|....|....|....|....|....|....|....|....|
SVV-001        CTTCTGGTTGGCACGGATTACGATCTGGACTTCAATGAGGTGGCACGACGCGCTGCCAAGTTGGGGTATAAGATGACTCC
NC-88-23626    CTTCTGGTTGGCACGGATNACNATCTGGACTTCAATGAGGTGGCGCGGCGCGCTGCCAAATTGGGGTATAAGATGACGCC
MN-88-36695    CTTCTGGTTGGCACGGATTACGATCTGGACTTCAATGAGNTGGCGCGGCGCGCTGCCAAATTGGGGTATAAGATGACGCC
IA-89-47752    CTTCTGGTTGGCACGGATGACGATCTGGACTTCAATGAGGTGGCGCGGCGCGCTGCCAAATTGGGGTATAAGATGACGCC
NJ-90-10324    CTTCNGGTTGGCACGGATGACGATCTGGACTTCAATGAGGTGGCGCGGCGCGCTGCCAAATTGGGGTATAAGATGACGCC
IL-92-48963    CTTCTGGTTCNCACGGATNACCATCTGNACTTCAATGAGGTGCCGCGCGCGCCTGCCAAATTCGGGTATAAGATGACGCC
LA-97-1278     CTTCTGGTTGGCACGGATTACGATCTGGACTTCAATGAGGTGGCGCGACGCGCTGCCAAATTGGGGTATAAGATGACTCC
CA-131395      CTTCTGGTTGGTACGGATTACGATCTGGACTTCAATGAGGTGGCGCGACGCGCTGCCAAGCTGGGGTATAAGATGACTCC
Consensus      CTTC GGTTG  ACGGAT AC ATCTG ACTTCAATGAG TGGC CG CGCGCTGCCAA  TGGGGTATAAGATGAC CC 90       100       110       120       130       140       150       160
               ....|....|....|....|....|....|....|....|....|....|....|....|....|....|....|....|
SVV-001        TGCCAACAAGGGTTCTGTCTTCCCTCCGACTTCCTCTCTTTCCGATGCTGTTTTTCTAAAGCGCAAATTCGTCCAAAACA
NC-88-23626    TGCCAACAAGGGTTCCGTCTTCCCTCCGACTTCCTCTCTTTCCAATGCTGTTTTTCTAAAACGTAAATTCGTCCAAAACA
MN-88-36695    TGCCAACAAGGGTTCCGTCTTCCCTCCGACTTCCTCTCTTTCCAATGCTGTTTTTTCTAAAACGTAAATTCGTCCAAAACA
IA-89-47752    TGCCAACAAGGGTTCCGTCTTCCCTCCGACTTCCTCTCTTTCCGATGCTGTTTTTCTAAAACGCAAATTCGTCCAAAACA
NJ-90-10324    TGCCAACAAGGGTTCCGTCTTCCCTCCGACTTCCTCTCTTTCCGATGCTGTTTTTCTAAAACGCAAATTCGTCCAAAACA
IL-92-48963    TGCCAACAAGGGTTCCGTCTTCCCTCCGACTTCCTCTCTTTCCGATGCTGTTTTTCTAAAACGCAAATTCGTCCAAAACA
LA-97-1278     TGCCAACAAGGGTTCCGTCTTCCCTTCGACTTCCTCTCTTTCCGACGCTGTTTTTTCTAAAACGCAAATTCGTCCAAAACA
CA-131395      TGCCAACAAGGGTTCCGTCTTCCCTCCGACTTCCTCTCTCTCCGATGCTGTTTTCCTAAAACGCAAATTCGTCCAAAACA
Consensus      TGCCAACAAGGGTTC GTCTTCCCT CGACTTCCTCTCT TCC A GCTGTTTT CTAAA CG AAATTCGTCCAAAACA 170       180       190       200       210       220       230       240
               ....|....|....|....|....|....|....|....|....|....|....|....|....|....|....|....|
SVV-001        ACGACGGCTTATACAAACCAGTTATGGATTTAAAGAATTTGGAAGCCATGCTCTCCTACTTCAAACCAGGAACACTACTC
NC-88-23626    ATGACGGCTTGTACAAGCCAGTTATGGATTCAAAGAATTTGGAAGCCATGCTCTCCTACTTCAAACCAGGAACACTACTC
MN-88-36695    ATGACGGCTTGTACAAGCCAGTTATGGATTCAAAGAATTTGGAAGCCATGCTCTCCTACTTCAAACCAGGAACACTACTC
IA-89-47752    ACGACGGCTTGTACAAACCAGTTATGGATTCAAAGAATTTGGAAGCCATGCTCTCCTACTTCAAACCAGGAACACTACTC
NJ-90-10324    ACGACGGCTTGTACAAACCAGTTATGGATTCAAAGAATTTGGAAGCCATGCTCTCCTACTTCAAACCAGGAACACTACTC
IL-92-48963    ACGACGGCTTGTACAAACCAGTTATGGATTCAAAGAATTTGGAAGCCATGCTCTCCTACTTCAAACCAGGAACACTACTC
LA-97-1278     ACGACGGCTTATACAAACCAGTTATGGATTTAAAGAATTTGGAAGCCATGCTCTCCTACTTCAAACCAGGAACACTACTC
CA-131395      ACGACGGCTTATACAAACCAGTTATGGATTTAAAGAATTTGGAAGCCATGCTCTCCTACTTCAAACCAGGAACACTACTC
Consensus      A GACGGCTT TACAA CCAGTTATGGATT AAAGAATTTGGAAGCCATGCTCTCCTACTTCAAACCAGGAACACTACTC 250       260       270       280       290       300       310       320
               ....|....|....|....|....|....|....|....|....|....|....|....|....|....|....|....|
SVV-001        GAGAAGCTGCAATCTGTTTCTATGTTGGCTCAACATTCTGGAAAAGAAGAATATGATAGATTCATGCACCCCTTCGCTGA
NC-88-23626    GAGAAGCTGCAATCTGTTTCTATGTTGGCTCAACATTCTGGAAAAGAAGAATACGATAGATTGATGCATCCCTTCGCTGA
MN-88-36695    GAGAAGCTGCAATCTGTTTCTATGTTGGCTCAACATTCTGGAAAAGAAGAATACGATAGATTGATGCATCCCTTCGCTGA
IA-89-47752    GAGAAGCTGCAATCTGTTTCTATGTTGGCTCAACATTCTGGAAAAGAAGAATATGATAGATTGATGCATCCCTTCGCTGA
NJ-90-10324    GAGAAGCTGCAATCTGTCTCTATGTTGGCTCAACATTCTGGAAAAGAAGAATATGATAGATTGATGCATCCCTTCGCTGA
IL-92-48963    GAGAAGCTGCAATCTGTTTCTATGTTGGCTCAACATTCTGGAAAAGAAGAATATGATAGACTGATGCACCCCTTCGCTGA
LA-97-1278     GAGAAGCTGCAATCTGTTTCTATGTTGGCTCAACATTCTGGAAAAGAAGAATATGATAGATTGATGCACCCCTTCGCTGA
CA-131395      GAGAAGCTGCAATCTGTTTCTATGTTGCCTCAACATTCTGGAAAAGAAGAATATGATACATTCATGCACCCCTTCGCTGA
Consensus      GAGAAGCTGCAATCTGT TCTATGTTGGCTCAACATTCTGGAAAAGAAGAATA GATAGA TGATGCA CCCTTCGCTGA
```

FIG. 89A

```
              330       340       350       360       370       380       390       400
          ....|....|....|....|....|....|....|....|....|....|....|....|....|....|....|....|
SVV-001   CTACGGTGCCGTACCGAGTCACGAGTACCTGCAGGCAAGATGGAGGGCCTTGTTCGACTGACCCAGATAGCCCAAGGCGC
NC-88-23626   CTACGGTGCCGTACCGAGTCACGAGTACCTGCAGGCAAGATGGAGGGCCTTGTTCGATTGACCCAGATAGCCCAAGGCGC
MN-88-36695   CTACGGTGCCGTACCGAGTCACGAGTACCTGCAGGCAAGATGGAGGGCCTTGTTCGATTGACCCAGANAGCCCAAGGCGC
IA-89-47752   CTACGGTGCCGTACCGAGTCACGAGTACCTGCAGGCAAGATGGAGGGCCTTGTTCGACTGACCCAGATAGCCCAAGGCGC
NJ-90-10324   CTACGGTGCCGTACCGAGTCACGAGTACCTGCAGGCAAGATGGAGGGCCTTGTTCGACTGACCCAGATAGCCCAAGGCGC
IL-92-48963   CTACGGTGCCGTACCGAGTCACGAGTACCTGCAGGCAAGATGGAGGGCCTTGTTCGACTGACCCAGATAGCCCAAGGCGC
LA-97-1278    CTACGGTGCCGTACCGAGTCACGAGTACCTGCAGGCAAGATGGAGGGCCTTGTTCGACTGACCCAGATAGCCCAAGGCGC
CA-131395     CTACGGTGCCGTACCGAGTCACGAGTACCTGCAGGCAAGATGGAGGGCCTTGTTCGACTGACCCAGATAGCCCAAGGCGC
Consensus     CTACGGTGCCGTACCGAGTCACGAGTACCTGCAGGCAAGATGGAGGGCCTTGTTCGA TCACCCAGA AGCCCAAGGCGC 410       420       430       440       450       460
          ....|....|....|....|....|....|....|....|....|....|....|....|
SVV-001   TTCGGTGCTGCCGGCGATTCTGGGAGAACTCAGTCGGAACAGAAAAGGGGAAAAAAAAAA
NC-88-23626   TTCGGTGCTGACGGTGATTCTGGGAGAACTCAGTCGGAACAAAAAGGGGAAAAAAAAAA
MN-88-36695   TTNGGTGCTGACGGTGATTCTGGGAGAACTCAGTCGGAACAAAAAGGGGAAAAAAAAAA
IA-89-47752   TTCGGTGCTGACGGTGATTCTGGGAGAACTCAGTCGGAACAGAAAAGGGGAAAAAAAAAA
NJ-90-10324   TTCGGTGCTGACGGTGATTCTGGGAGAACTCAGTCGGAACAGAAAAGGGGAAAAAAAAAA
IL-92-48963   CTCGGTGCTGCCGGTGATTNTGGGAGAACTCAGTCGGAACAGAAAAGGGGAGAAAAAAAA
LA-97-1278    TTCGGTGCTGCCGGCGATTCTGGGAGAACTCAGTCGGAACAGAAAAGGGGAAAAAAAAAA
CA-131395     TTCGGTGCTGCCGGCGATTCTGGGAGAACTCAGTCGGAACAGAAAAGGGGAAAAAAAAAA
Consensus      T GGTGCTG CGG GATT T GGAGAACTCAGTCGGAACA AAA GGG  AAAAAAAA
```

FIG. 95B atten# SENECA VALLEY VIRUS BASED COMPOSITIONS AND METHODS FOR TREATING DISEASE This application is a continuation of U.S. Ser. No. 11/335,891, which was filed on Jan. 19, 2006, which is a continuation-in-part of International Application No. PCT/US2004/031504 (International Publication No. WO 2005/030139), which was filed on Sep. 23, 2004, which claims priority to U.S. Ser. No. 60/506,182, which was filed on Sep. 26, 2003. This application also claims priority to U.S. Ser. No. 60/664,442, which was filed on Mar. 23, 2005 and U.S. Ser. No. 60/726,313, which was filed on Oct. 13, 2005. These applications are hereby incorporated by reference in their entirety.

This disclosure contains material that is subject to copyright protection. The copyright owner has no objection to the facsimile reproduction by anyone of the patent document or the patent disclosure, as it appears in the U.S. Patent and Trademark Office patent file or records, but otherwise reserves any and all copyright rights.

All patent applications, published patent applications, issued and granted patents, texts, and literature references cited in this specification are hereby incorporated herein by reference in their entirety to more fully describe the state of the art to which the present invention pertains.

BACKGROUND OF THE INVENTION

Virotherapy holds great promise for treating cancer. Oncolytic viruses, which aim to specifically infect and kill cancer cells, whether native and/or engineered, may be more efficacious and less toxic than alternative treatments, such as chemotherapy and radiation. In addition, oncolytic virus therapy that uses replication competent viruses is the only therapy known that can amplify the therapeutic at the pharmacologically desired site.

A key aspect of cancer therapy is to achieve a high rate of killing of cancer cells versus normal cells. Accomplishing this goal has been difficult for many reasons, including the wide array of cell types involved, the systemic dissemination of cancer cells due to metastases, and the narrow biological differences between normal and cancer cells. While progress has been made, much still needs to be done to improve upon current cancer therapies.

In the past, surgeons have tried to remove tumors surgically without substantially harming the patient. Even complete removal of a primary tumor does not ensure survival since earlier metastases to unknown sites in the body are left undetected. There is also some research suggesting that surgical intervention may enhance the growth of distant metastases due to removal of tumor cells producing angiogenesis inhibitors. Finally, in many cases, the tumor grows back at the original site after surgical removal. Radiation aims to selectively destroy the most rapidly proliferating cells at the expense of the others. However, tumor cells can escape radiation therapy either by becoming resistant or by being in a non-dividing state during treatment. In addition, radiation is not always selective in that many normal cells are actively dividing and killed by the treatment (cells in bone marrow, gastrointestinal cells, hair follicles, etc.).

Like radiation, chemotherapy is not completely selective and thus destroys many normal cells, and does not kill all tumor cells due to drug resistance and/or division state of the cell. Thus, chemotherapy and radiation therapies exploit a small differential sensitivity that exists between normal and cancer cells, giving them a narrow therapeutic index. A small therapeutic index is clearly an undesirable property of any modality to treat cancer. Therefore, novel cancer therapeutic approaches overcoming these limitations are desired.

One such novel approach is oncolytic virus therapy. Initially, replication-defective viruses carrying cytotoxic transgenes were utilized in attempts to treat cancer. However, they were found to be inefficient in transduction of tumors, inadequate spread within the tumor mass and not adequately selective toward cancers. To overcome this limitation, viruses were either modified to replicate selectively in tumor cells or viruses were discovered to have natural tumor-selective properties. These oncolytic viruses thus had the properties to replicate, spread, and kill tumor cells selectively through a tumor mass by locally injecting the virus or by systemically delivering the virus (FIG. 1).

Despite the early promise of this newly defined class of anti-cancer therapeutics, several limitations remain that may limit their use as a cancer therapeutic. Therefore, there is an ongoing need for novel oncolytic viruses that can be utilized for cancer therapy.

SUMMARY OF THE INVENTION

A novel RNA picornavirus has been discovered (hereafter referred to as Seneca Valley virus ("SVV")) whose native properties include the ability to selectively kill some types of tumors. As demonstrated below in the examples, SVV selectively kills tumor lines with neurotropic properties, in most cases with a greater than 10,000 fold difference in the amount of virus necessary to kill 50% of tumor cells versus normal cells (i.e., the $EC_{50}$ value). This result also translates in vivo, where tumor explants in mice are selectively eliminated. Further, in vivo results indicate that SVV is not toxic to normal cells, in that up to $1\times10^{14}$ vp/kg (vector or virus particles per kilogram) systemically administered causes no mortality and no visible clinical symptoms in immune deficient or immune competent mice.

SVV elicits efficacy at doses as low as $1\times10^{8}$ vp/kg; therefore, a very high therapeutic index of >100,000 is achieved. Efficacy is very robust in that 100% of large pre-established tumors in mice can be completely eradicated (see Example 11). This efficacy may be mediated with a single systemic injection of SVV without any adjunct therapy. Furthermore, SVV injected mice show neither clinical symptoms nor recurrence of tumors for at least 200 days following injection. SVV can also be purified to high titer and can be produced at >200,000 virus particles per cell in permissive cell lines. SVV-based viral therapy therefore shows considerable promise as a safe, effective and new line of treatment for selected types of cancers. Further, SVV has a small and easily manipulatable genome, simple and fast lifecycle, and a well-understood biology of replication, and thus is amenable to modification. These properties, at least in part, allow for methods that generate modified SVVs that have new cell or tissue specific tropisms, such that SVV-based therapy can be directed to new tumor types resistant to infection by the original SVV isolate.

Accordingly, the present invention provides an isolated nucleic acid comprising a nucleic acid sequence having at least 65%, 70%, 75%, 80%, 85%, 90%, 95% or 99% sequence identity to SEQ ID NOS: 1, 3, 5, 7, 9, 11, 13, 15, 17, 19, 21, 168, or a contiguous portion of any one of these sequences that is at least 50 nucleotides in length, or 95% identical to a contiguous portion of any one of these sequences that is at least 10, 15 or 20 nucleotides in length. The isolated nucleic acids of the invention can be RNA or DNA.

For all aspects of the invention, an isolated nucleic acid can comprise a nucleic acid sequence having at least about 65%, 70%, 75%, 80%, 85%, 90%, 95%, 96%, 97%, 98%, or 99% sequence identity to a contiguous portion of any one of the SVV nucleic acid SEQ ID NO sequences herein, wherein the contiguous portion is at least about 20, 25, 50, 75, 100, 150, 200, 250, 300, 350, 400, 450, 500, 750, 1000, 1250, 1500, 2000 or 2500 nucleotides in length, for example. The SVV nucleic acid SEQ ID NO sequences include, for example, SEQ ID NOS: 1, 3, 5, 7, 9, 11, 13, 15, 17, 19, 21 and 168.

For all aspects of the invention, an isolated protein or peptide can comprise an amino acid sequence having at least about 50%, 55%, 65%, 70%, 75%, 80%, 85%, 90%, 95%, 96%, 97%, 98%, or 99% sequence identity to a contiguous portion of any one of the SVV amino acid SEQ ID NO sequences herein, wherein the contiguous portion is at least at least about 5, 6, 7, 8, 9, 10, 15, 20, 30, 40, 50, 60, 70, 80, 90, 100, 125, 150, 175, 200, 225, 250, 275, 300, or 350 amino acids in length, for example. The SVV amino acid SEQ ID NO sequences include, for example, SEQ ID NOS: 2, 4, 6, 8, 10, 12, 14, 16, 18, 20, 22 and 169.

In another aspect, the invention provides an isolated nucleic acid comprising a nucleic acid sequence having at least 95%, 96%, 97%, 98%, or 99% sequence identity to SEQ ID NO:168, or to a contiguous portion of SEQ ID NO:168 that is at least 20, 50, 100, or 200 nucleotides in length. The isolated nucleic acids can comprise specific portions of SEQ ID NO:168, including but not limited to: the 5' untranslated region (UTR) of SVV spanning nucleotides 1-666 of SEQ ID NO:168; the coding sequence for the SVV polyprotein spanning nucleotides 667-7209 of SEQ ID NO:168; the coding sequence for the leader peptide of SVV spanning nucleotides 667-903 of SEQ ID NO:168; the coding sequence for the SVV VP4 protein spanning nucleotides 904-1116 of SEQ ID NO:168; the coding sequence for the SVV VP2 protein spanning nucleotides 1117-1968 of SEQ ID NO:168; the coding sequence for the SVV VP3 protein spanning nucleotides 1969-2685 of SEQ ID NO:168; the coding sequence for the SVV VP1 protein spanning nucleotides 2686-3477 of SEQ ID NO:168; the coding sequence for the SVV 2A protein spanning nucleotides 3478-3504 of SEQ ID NO:168; the coding sequence for the SVV 2B protein spanning nucleotides 3505-3888 of SEQ ID NO:168; the coding sequence for the SVV 2C protein spanning nucleotides 3889-4854 of SEQ ID NO:168; the coding sequence for the SVV 3A protein spanning nucleotides 4855-5124 of SEQ ID NO:168; the coding sequence for the SVV 3B protein spanning nucleotides 5125-5190 of SEQ ID NO:168; the coding sequence for the SVV 3C protein spanning nucleotides 5191-5823 of SEQ ID NO:168; the coding sequence for the SVV 3D protein spanning nucleotides 5824-7209 of SEQ ID NO:168; and the 3'UTR of SVV spanning nucleotides 7210-7280 of SEQ ID NO:168.

In one aspect, the invention provides methods for using the SVV 2A, SVV leader peptide, or other SVV proteins or peptide portions thereof, to shut off host cell protein translation. In one aspect, such SVV proteins can be used to shut off host cell protein translation by interfering or inhibiting with the cap binding protein complex in the host cell.

In another aspect, the invention provides methods for using SVV 2A or other SVV proteins or peptide portions thereof in order to cleave a peptide or protein.

In other aspects, the invention provides an isolated nucleic acid that hybridizes under conditions of high, moderate stringency or low stringency to SEQ ID NO: 1, 3, 5, 7, 9, 11, 13, 15, 17, 19, 21, 168, or to a contiguous portion of any one of these sequences that is at least 50 nucleotides in length.

In another aspect, the invention provides a vector comprising a nucleic acid sequence having at least 65%, 70%, 75%, 80%, 85%, 90%, 95% or 99% sequence identity to SEQ ID NOS 1, 3, 5, 7, 9, 11, 13, 15, 17, 19, 21, 168, or to a contiguous portion of any one of these sequences that is at least 50 nucleotides in length. Vector compositions can also comprise the nucleic acid regions of SEQ ID NO:168 that code for SVV proteins.

The present invention also provides an isolated polypeptide encoded by a nucleic acid having at least 65%, 70%, 75%, 80%, 85%, 90%, 95% or 99% sequence identity to a nucleic acid sequence comprising SEQ ID NOS: 1, 3, 5, 7, 9, 11, 13, 15, 17, 19, 21, or to a contiguous portion of any one of these sequences that is at least 50 nucleotides in length. The invention also provides an isolated polypeptide encoded by a nucleic acid having at least 95%, 96%, 97%, 98%, or 99% sequence identity to a nucleic acid region of SEQ ID NO:168 that encodes a SVV protein.

In one aspect, the invention provides an isolated polypeptide comprising an amino acid sequence having at least 65%, 70%, 75%, 80%, 85%, 90%, 95% or 99% sequence identity to SEQ ID NOS: 2, 4, 6, 8, 10, 12, 14, 16, 18, 20, 22, 169, or to a contiguous portion of any one of these sequences that is at least 10 amino acids in length.

In another aspect, the invention provides an isolated polypeptide comprising an amino acid sequence having at least 95%, 96%, 97%, 98%, or 99% sequence identity to a contiguous portion of SEQ ID NO:169 that is at least 9, 10, 15, 20 or 50 amino acids in length. Exemplary contiguous portions of SEQ ID NO:169, include but are not limited to, regions that comprise a SVV protein, such as: the leader peptide spanning residues 1-79; VP4 spanning residues 80-150; VP2 spanning residues 151-434; VP3 spanning residues 435-673; VP1 spanning residues 674-937; 2A spanning residues 938-946; 2B spanning residues 947-1074; 2C spanning residues 1075-1396; 3A spanning residues 1397-1486; 3B spanning residues 1487-1508; 3C spanning residues 1509-1719; and 3D spanning residues 1720-2181.

In another aspect, the invention provides an isolated antibody which specifically binds a polypeptide comprising an amino acid sequence having at least 65%, 70%, 75%, 80%, 85%, 90%, 95% or 99% sequence identity to SEQ ID NOS: 2, 4, 6, 8, 10, 12, 14, 16, 18, 20, 22, 169, or to a contiguous portion of any one of these sequences that is at least 9, 10, 15, or 20 amino acids in length. The isolated antibody can be generated such that it binds to any protein epitope or antigen of SEQ ID NOS:2 or 169. Further, the antibody can be a polyclonal antibody, a monoclonal antibody or a chimeric antibody.

In one aspect, the invention provides an isolated SVV or derivative or relative thereof, having a genomic sequence comprising a sequence that is at least 65%, 70%, 75%, 80%, 85%, 90%, 95% or 99% identical to SEQ ID NO:1 or SEQ ID NO:168.

In another aspect, the invention provides an isolated virus having all the identifying characteristics and nucleic acid sequence of American Type Culture Collection (ATCC) Patent Deposit number PTA-5343. Some of the viruses of the present invention are directed to the PTA-5343 isolate, variants, homologues, relatives, derivatives and mutants of the PTA-5343 isolate, and variants, homologues, derivatives and mutants of other viruses that are modified in respect to sequences of SVV (both wild-type and mutant) that are determined to be responsible for its oncolytic properties.

The present invention further provides an isolated SVV comprising the following characteristics: a single stranded RNA genome (positive (+) sense strand) of ~7.5 or of ~7.3 kilobases (kb); a diameter of ~27 nanometers (nm); a capsid comprising at least 3 proteins that have approximate molecular weights of about 31 kDa, 36 kDa and 27 kDa; a buoyant density of approximately 1.34 g/mL on cesium chloride (CsCl) gradients; and replication competence in tumor cells. In this aspect, the 31 kDa capsid protein (VP1) can comprise an amino acid sequence that is at least 65%, 70%, 75%, 80%, 85%, 90%, 95% or 99% identical to SEQ ID NO:8 or residues 674-937 of SEQ ID NO:169; the 36 kDa capsid protein (VP2) can comprise an amino acid sequence that is at least 65%, 70%, 75%, 80%, 85%, 90%, 95% or 99% identical to SEQ ID NO:4 or residues 151-434 of SEQ ID NO:169; and the 27 kDa capsid protein (VP3) can comprise an amino acid sequence that is at least 65%, 70%, 75%, 80%, 85%, 90%, 95% or 99% identical to SEQ ID NO:6 or residues 435-673 of SEQ ID NO:169.

In another aspect, the invention provides an isolated SVV derivative or relative comprising the following characteristics: replication competence in tumor cells, tumor-cell tropism, and lack of cytolysis in normal cells. An SVV relative includes SVV-like picornaviruses, including viruses from the following USDA isolates: MN 88-36695, NC 88-23626, IA 89-47552, NJ 90-10324, IL 92-48963, CA 131395; LA 1278; IL 66289; IL 94-9356; MN/GA 99-29256; MN 99197; and SC 363649. If an SVV-like picornavirus does not naturally have the characteristics of replication competence in tumor cells, tumor-cell tropism, and lack of cytolysis in non-tumor cells, then the SVV-like picornavirus can be mutated such that these characteristics are obtained. Such mutations can be designed by comparing the sequence of the SVV-like picornavirus to SVV, and making mutations into the SVV-like picornavirus such that its amino acid sequence is identical or substantially identical (in a particular region) to SVV. In another aspect, the virus is replication competent in tumor cell types having neuroendocrine properties.

In other aspects, the present invention provides: a pharmaceutical composition comprising an effective amount of a virus of the invention and a pharmaceutically acceptable carrier; a cell comprising a virus of the invention; a viral lysate containing antigens of a virus of the invention; and an isolated and purified viral antigen obtained from a virus of the invention.

In yet another aspect, the invention provides a method of purifying a virus of the invention, comprising: infecting a cell with the virus; harvesting cell lysate; subjecting cell lysate to at least one round of gradient centrifugation; and isolating the virus from the gradient.

In another aspect, the invention provides a method for treating cancer comprising administering an effective amount of a virus or derivative thereof, so as to treat the cancer, wherein the virus has a genomic sequence that comprises a sequence that is at least 65%, 70%, 75%, 80%, 85%, 90%, 95% or 99% identical to SEQ ID NOS: 1, 3, 5, 7, 9, 11, 13, 15, 17, 19, 21, 168, or to a portion of SEQ ID NO:1 or SEQ ID NO:168. In one aspect, the invention provides a method for treating cancer a method for treating cancer comprising administering an effective amount of a virus or derivative thereof, so as to treat the cancer, wherein the virus has a genomic sequence that is at least 95%, 96%, 97%, 98%, or 99% identical to SEQ ID NO:1. The virus that has a genomic sequence that is at least 95%, 96%, 97%, 98%, or 99% identical to SEQ ID NO:1 can be, for example, a SVV mutant, a SVV-like picornavirus, or a cardiovirus. The SVV-like picornavirus can be, for example, a virus from one of the following isolates MN 88-36695, NC 88-23626, IA 89-47552, NJ 90-10324, IL 92-48963, CA 131395; LA 1278; IL 66289; IL 94-9356; MN/GA 99-29256; MN 99197; and SC 363649. The SVV-like picornaviruses can be wild-type or mutant.

In another aspect, the invention provides a method for treating cancer comprising administering an effective amount of a virus comprising a capsid encoding region that comprises a sequence that is at least 65%, 70%, 75%, 80%, 85%, 90%, 95%, 96%, 97%, 98%, or 99% identical to SEQ ID NOS:3, 5, 7, nucleotides 904-3477 of SEQ ID NO:169, or to a contiguous portion thereof that is at least 75, 100, 200, or 500 nucleotides in length. The invention also provides a method for treating cancer comprising administering an effective amount of a virus comprising a capsid that comprises an amino acid sequence that is at least 65%, 70%, 75%, 80%, 85%, 90%, 95%, 96%, 97%, 98%, or 99% identical to SEQ ID NO:4, 6, 8, residues 80-937 of SEQ ID NO:169, or a contiguous portion thereof that is at least 25, 50, or 100 amino acids in length.

In one aspect, the present invention provides a method for inhibiting cancer progression comprising contacting a cancer cell with a virus or derivative thereof, wherein the virus or derivative thereof specifically binds to the cancerous cell, wherein the virus has a genomic sequence that comprises a sequence that is at least 65%, 70%, 75%, 80%, 85%, 90%, 95% or 99% identical to SEQ ID NO: 1, 3, 5, 7, 9, 11, 13, 15, 17, 19, 21, or 168.

In another aspect, the invention provides a method for inhibiting cancer progression comprising contacting a cancer cell with a virus or derivative thereof, wherein the virus or derivative thereof specifically infects the cancerous cell, wherein the virus has a genomic sequence that comprises a sequence that is at least 95%, 96%, 97%, 98%, or 99% identical to SEQ ID NO: 168, or to a contiguous portion of SEQ ID NO:168 that is at least 50, 100, 200, or 500 nucleotides in length.

In another aspect, the present invention provides a method for killing cancer cells comprising contacting a cancer cell with an effective amount of a virus or derivative thereof, wherein the virus has a genomic sequence that comprises a sequence that is at least 65%, 70%, 75%, 80%, 85%, 90%, 95% or 99% identical to SEQ ID NO: 1, 3, 5, 7, 9, 11, 13, 15, 17, 19, 21, or 168.

In another aspect, the present invention provides a method for killing cancer cells comprising contacting a cancer cell with an effective amount of a virus or derivative thereof, wherein the virus has a genomic sequence that comprises a sequence that is at least 95%, 96%, 97%, 98%, or 99% identical to SEQ ID NO:168, or to a contiguous portion of SEQ ID NO:168 that is at least 50, 100, 200 or 500 nucleotides in length.

In these methods directed to cancer, the virus can be a picornavirus. The picornavirus can be a cardiovirus, erbovirus, aphthovirus, kobuvirus, hepatovirus, parechovirus, teschovirus, enterovirus, rhinovirus, SVV, or an SVV-like picornavirus. The cardiovirus can be selected from the group consisting of: vilyuisk human encephalomyelitis virus, Theiler's murine encephalomyelitis virus, and encephalomyocarditis virus. The SVV can be a virus having the ATCC deposit number PTA-5343 or a virus comprising a nucleic acid sequence that is at least 65%, 70%, 75%, 80%, 85%, 90%, 95%, 96%, 97%, 98%, or 99% identical to SEQ ID NO:1 or SEQ ID NO:168, or to a contiguous portion thereof that is at least 50, 100, 200, or 500 nucleotides in length. The SVV-like picornavirus can be a virus comprising a nucleic acid sequence that is at least 95%, 96%, 97%, 98%, or 99% identical to SEQ ID NO:168, or to a contiguous portion thereof that is at least 50, 100, 200, or 500 nucleotides in length. The SVV-like picornavirus can be, for example, a virus from one of the following isolates MN 88-36695, NC 88-23626, IA 89-47552, NJ 90-10324, IL 92-48963, CA 131395; LA 1278; IL 66289; IL 94-9356; MN/GA 99-29256; MN 99197; and SC 363649. The SVV-like picornaviruses can be wild-type or mutant.

The present invention also provides a method of killing an abnormally proliferative cell comprising contacting the cell with a virus of the invention. In one aspect, the abnormally proliferative cell is a tumor cell. In various aspects of this method, the tumor cell is selected from the group consisting of: human small cell lung cancer, human retinoblastoma, human neuroblastoma, human medulloblastoma, mouse neuroblastoma, Wilms' tumor, and human non-small cell lung cancer.

The present invention also provides a method of treating a neoplastic condition in a subject comprising administering to the subject an effective amount of a virus of the invention to the mammal. In one aspect, the neoplastic condition is a neuroendocrine cancer. In another aspect, the subject is a mammal. In another aspect, the mammal is a human.

The present invention also provides a method of producing a virus of the invention, comprising: culturing cells infected with the virus under conditions that allow for replication of the virus and recovering the virus from the cells or the supernatant. In one aspect of this method, the cells are PER.C6 cells. In another aspect of this method, the cells are H446 cells. In the various aspects of this method, the cells may produce over 200,000 virus particles per cell.

In another aspect, the present invention provides a method for detecting a virus of the invention, comprising: isolating RNA from test material suspected to contain the virus of the invention; labeling RNA corresponding to at least 15 contiguous nucleotides of SEQ ID NO:1 or SEQ ID NO:168; probing the test material with the labeled RNA; and detecting the binding of the labeled RNA with the RNA isolated from the test material, wherein binding indicates the presence of the virus. In another aspect, the present invention provides a nucleic acid probe comprising a nucleotide sequence corresponding to at least 15 contiguous nucleotides of SEQ ID NO:1 or SEQ ID NO:168, or its complement.

The present invention also provides a method for making an oncolytic virus, the method comprising: (a) comparing a SVV genomic sequence with a test virus genomic sequence; (b) identifying at least a first amino acid difference between a polypeptide encoded by the SVV genomic sequence and a polypeptide encoded by the test virus genomic sequence; (c) mutating the test virus genomic sequence such that the polypeptide encoded by the test virus genomic sequence has at least one less amino acid difference to the polypeptide encoded by the SVV genomic sequence; (d) transfecting the mutated test virus genomic sequence into a tumor cell; and (e) determining whether the tumor cell is lytically infected by the mutated test virus genomic sequence. In one aspect, the amino acid(s) mutated in the test virus are amino acids in a structural region, such as in the capsid encoding region. In another aspect, the amino acids mutated in the test virus are amino acids in a non-structural region.

In one aspect of the method for making an oncolytic virus, the SVV genomic sequence is obtained from the isolated SVV having the ATCC deposit number PTA-5343 or from a virus comprising a sequence that is at least 65%, 70%, 75%, 80%, 85%, 90%, 95% or 99% identical to SEQ ID NOS: 1, 3, 5, 7, 9, 11, 13, 15, 17, 19, 21, 168, or a contiguous portion thereof. In one aspect, the SVV genomic sequence is obtained from the isolated SVV having the ATCC deposit number PTA-5343 or from a virus comprising a sequence that is at least 95%, 96%, 97%, 98%, or 99% identical to SEQ ID NO: 168, or a contiguous portion thereof that is at least 50, 100, 200, or 500 nucleotides in length. In another aspect of this method, the step of mutating the test virus genomic sequence comprises mutating a cDNA having the test virus genomic sequence. In another aspect of this method, the step of transfecting the mutated test virus genomic sequence comprises transfecting RNA, wherein the RNA is generated from the cDNA having the mutated test virus genomic sequence.

In another aspect of the method for making an oncolytic virus, the test virus is a picornavirus. The test picornavirus can be a teschovirus, enterovirus, rhinovirus, cardiovirus, erbovirus, apthovirus, kobuvirus, hepatovirus, parechovirus or teschovirus. In another aspect, the test virus is a cardiovirus. In another aspect, the test virus is a SVV-like picornavirus. The SVV-like picornavirus can be, for example, a virus from one of the following isolates: MN 88-36695, NC 88-23626, IA 89-47552, NJ 90-10324, IL 92-48963, CA 131395; LA 1278; IL 66289; IL 94-9356; MN/GA 99-29256; MN 99197; and SC 363649. In another aspect, the amino acid differences identified in the methods for making an oncolytic virus are between a SVV capsid protein and a test virus capsid protein sequence. In another aspect for making an oncolytic virus, the test virus genomic sequence is selected from the group consisting of: Vilyuisk human encephalomyelitis virus, Theiler's murine encephalomyelitis virus, and encephalomyocarditis virus. In another aspect, the test virus genomic sequence is selected from an encephalomyocarditis virus. In yet another aspect, the encephalomyocarditis virus, the SVV-like picornavirus, or any other test virus can be selected from an isolate having a nucleic acid sequence comprising at least 65%, 70%, 75%, 80%, 85%, 90%, 95% or 99% sequence identity to SVV of ATCC deposit number PTA-5343 or SEQ ID NO:1, 3, 5, 7, 9, 11, 13, 15, 17, 19, 21, 168, or a contiguous portion thereof that is at least 50, 100, 200, or 500 nucleotides in length.

In another aspect of the method for making an oncolytic cardiovirus, the amino acid difference between the test virus and SVV is in a capsid protein region of SVV, wherein the amino acid difference is aligned within SVV SEQ ID NO:4, 6, 8, residues 80-937 of SEQ ID NO:169, residues 80-150 of SEQ ID NO:169, residues 151-434 of SEQ ID NO:169, residues 435-673 of SEQ ID NO:169, or residues 674-937 of SEQ ID NO:169.

The present invention also provides a method for making a mutant virus having an altered cell-type tropism, the method comprising: (a) creating a library of viral mutants comprising a plurality of nucleic acid sequences; (b) transfecting the library of viral mutants into a permissive cell, such that a plurality of mutant viruses is produced; (c) isolating the plurality of mutant viruses; (d) incubating a non-permissive cell with the isolated plurality of mutant viruses; and (e) recovering a mutant virus that was produced in the non-permissive cell, thereby making a mutant virus having an altered tropism. In one aspect, this method further comprises the steps of (f) incubating the recovered mutant virus in the non-permissive cell; and (g) recovering a mutant virus that that was produced in the non-permissive cell. In another aspect, the method further comprises iteratively repeating steps (f) and (g). In another aspect, the library of viral mutants is created from a parental sequence comprising SEQ ID NO: 1, 3, 5, 7, 9, 11, 13, 15, 17, 19, 21, 168, or a contiguous portion thereof.

In one aspect of the method for making a mutant virus having an altered cell-type tropism, the incubating is conducted in a multi-well high-throughput platform wherein the platform comprises a different non-permissive cell-type in each well. In this aspect, the method can further comprise screening the platform to identify which wells contain a mutant virus that kills the cells. In another aspect, the screening is conducted by analyzing light absorbance in each well.

In another aspect of the method for making a mutant virus having an altered cell-type tropism, the non-permissive cell is a tumor cell.

In another aspect of the method for making a mutant virus having an altered cell-type tropism, the step of creating the library of viral mutants comprises: (i) providing a polynucleotide having a sequence identical to a portion of a genomic sequence of a virus; (ii) mutating the polynucleotide in order to generate a plurality of different mutant polynucleotide sequences; and (iii) ligating the plurality of mutated polynucleotides into a vector having the genomic sequence of the virus except for the portion of the genomic sequence of the virus that the polynucleotide in step (i) contains, thereby creating the library of viral mutants. In one aspect, the genomic sequence of a virus is from a picornavirus. In another aspect, the genomic sequence of a virus comprises a sequence that is at least 65%, 70%, 75%, 80%, 85%, 90%, 95% or 99% identical to SEQ ID NO: 1, 3, 5, 7, 9, 11, 13, 15, 17, 19, 21, 168, or a contiguous portion thereof. In another aspect, the genomic sequence of a virus comprises a sequence that is at least 95%, 96%, 97%, 98%, or 99% identical to SEQ ID NO: 168, or a contiguous portion thereof that is at least 50, 100, 200, or 500 nucleotides in length. In one aspect, the virus that comprises a sequence that is at least 95%, 96%, 97%, 98%, or 99% identical to a contiguous portion of SEQ ID NO:168 that is at least 50, 100, 200, or 500 nucleotides in length is a SVV-like picornavirus. In another aspect, in the step of creating the library of viral mutants, the mutating of step (ii) is conducted by random insertion of nucleotides into the polynucleotide. In one aspect, the random insertion of nucleotides is conducted by trinucleotide-mutagenesis (TRIM). In another aspect, at least a portion of the nucleotides inserted into the polynucleotide encodes an epitope tag. In another aspect, in the step of creating the library of viral mutants, the mutating of step (ii) is conducted in a capsid encoding region of the polynucleotide.

The present invention also provides a method for making a mutant virus having an altered cell-type tropism, the method comprising: (a) creating a library of mutant polynucleotide sequences of a virus, wherein the creating comprises: providing a polynucleotide encoding a capsid region of the virus; mutating the polynucleotide in order to generate a plurality of different mutant capsid-encoding polynucleotide sequences; and ligating the plurality of mutated capsid-encoding polynucleotides into a vector having the genomic sequence of the virus except for the capsid-encoding region, thereby creating the library of mutant polynucleotide sequences of the virus; (b) transfecting the library of mutant polynucleotide sequences into a permissive cell, such that a plurality of mutant viruses is produced; (c) isolating the plurality of mutant viruses; (d) incubating a non-permissive cell with the isolated plurality of mutant viruses; and (e) recovering a mutant virus that that was produced in the non-permissive cell, thereby making a mutant virus having an altered tropism. In one aspect, the method further comprises the steps of: (f) incubating the recovered mutant virus in the non-permissive cell; and (g) recovering a mutant virus that that was produced in the non-permissive cell. In another aspect, the method further comprises iteratively repeating steps (f) and (g). In another aspect, the mutating is conducted by random insertion of nucleotides into the capsid-encoding polynucleotide. In another aspect, at least a portion of the nucleotides randomly inserted into the capsid-encoding polynucleotide encodes an epitope tag. In another aspect, the random insertion of nucleotides is conducted by TRIM. In another aspect, the plurality of different mutant capsid-encoding polynucleotide sequences comprises greater than $10^8$ or $10^9$ different capsid-encoding polynucleotide sequences. The library of mutant polynucleotide sequences can be from, for example, a cardiovirus or an SVV-like picornavirus.

In one aspect, a method for making a mutant SVV having an altered cell-type tropism comprises: (a) creating a cDNA library of SVV mutants; (b) generating SVV RNA from the cDNA library of SVV mutants; (c) transfecting the SVV RNA into a permissive cell, such that a plurality of mutant SVV is produced; (d) isolating the plurality of mutant SVV; (e) incubating a non-permissive tumor cell with the isolated plurality of mutant SVV; and (f) recovering a mutant SVV that lytically infects the non-permissive tumor cell, thereby making a mutant SVV having an altered tropism. In another aspect, the method further comprises the steps of: (g) incubating the recovered mutant SVV in the non-permissive cell; and (h) recovering a mutant SVV that lytically infects the non-permissive tumor cell. In another aspect, the method further comprises iteratively repeating steps (g) and (h). In one aspect, the incubating is conducted in a multi-well high-throughput platform wherein the platform comprises a different non-permissive tumor cell-type in each well. In another aspect, the method further comprises screening the platform to identify which wells contain a mutant SVV that lytically infects the cells. In another aspect, the screening is conducted by analyzing light absorbance in each well. In one aspect, the cDNA library of SVV mutants comprises a plurality of mutant SVV capsid polynucleotide sequences. In another aspect, the plurality of mutant SVV capsid polynucleotide sequences is generated by random insertion of nucleotides. In another aspect, at least a portion of the sequence of the nucleotides randomly inserted encodes an epitope tag. In another aspect, the random insertion of nucleotides is conducted by TRIM. In another aspect, the cDNA library of SVV mutants is generated from a SVV of ATCC deposit number PTA-5343. In another aspect, the cDNA library of SVV mutants is generated from a SVV comprising a sequence having at least 99%, 95%, 90%, 85%, 80%, 75%, 70%, or 65% sequence identity to SEQ ID NO:1, 3, 5, 7, 9, 11, 13, 15, 17, 19, 21, 168, or to a contiguous portion thereof that is at least 50, 100, 200, or 500 nucleotides in length. In one aspect, the cDNA library of SVV mutants is generated from an SVV comprising a sequence having at least 95%, 96%, 97%, 98%, or 99% sequence identity to SEQ ID NO:168, or to a contiguous portion thereof that is at least 50, 100, 200, or 500 nucleotides in length. In another aspect, the non-permissive tumor cell is a tumor cell-line or a tumor cell-type isolated from a patient.

The present invention also provides a method for making a mutant virus having a tumor cell-type tropism in vivo, the method comprising: (a) creating a library of viral mutants comprising a plurality of nucleic acid sequences; (b) transfecting the library of viral mutants into a permissive cell, such that a plurality of mutant viruses is produced; (c) isolating the plurality of mutant viruses; (d) administering the isolated plurality of mutant viruses to a mammal with a tumor, wherein the mammal is not a natural host of the unmutated form of the mutant virus; and (e) recovering a virus that replicated in the tumor, thereby making a mutant virus having a tumor cell-type tropism in vivo. In one aspect, the step of creating a library of viral mutants comprises: providing a polynucleotide encoding a capsid region of a virus; mutating the polynucleotide in order to generate a plurality of different mutant capsid-encoding polynucleotide sequences; and ligating the plurality of mutated capsid-encoding polynucleotides into a vector having the genomic sequence of the virus except for the capsid-encoding region, thereby creating the library of viral mutants. In another aspect, the virus recovered in step (e) lytically infects cells of the tumor. In another aspect for a method for making a mutant virus having a tumor cell-type tropism in vivo, the tumor is a xenograft, a syngeneic tumor, an orthotopic tumor or a transgenic tumor. In another aspect, the mammal is a mouse.

For all the methods of the present invention, the virus can be a picornavirus. The picornavirus can be a cardiovirus, erbovirus, aphthovirus, kobuvirus, hepatovirus, parechovirus, teschovirus, entrovirus, rhinovirus, or a virus belonging to the genus to which SVV belongs. The virus can be a cardiovirus. The virus can be an SVV-like picornavirus. The virus can be SVV. The SVV can be a SVV having the ATCC Patent Deposit No. PTA-5343 or a SVV comprising a sequence that is at least 65%, 70%, 75%, 80%, 85%, 90%, 95% or 99% identical to SEQ ID NO:1, 3, 6, 7, 9, 11, 13, 15, 17, 19, 21, 168, or a contiguous portion thereof. Further, the cardiovirus can be selected from the group consisting of: vilyuisk human encephalomyelitis virus, Theiler's murine encephalomyelitis virus, and encephalomyocarditis virus. In one aspect, the SVV-like picornavirus is selected from the group of isolates consisting of: MN 88-36695, NC 88-23626, IA 89-47552, NJ 90-10324, IL 92-48963, CA 131395; LA 1278; IL 66289; IL 94-9356; MN/GA 99-29256; MN 99197; and SC 363649. In another aspect, the present invention encompasses any virus that is selected from an isolate having at least 99%, 95%, 90%, 85%, 80%, 75%, 70%, or 65% sequence identity to SVV of ATCC deposit number PTA-5343 or SEQ ID NO:1, 3, 5, 7, 9, 11, 13, 15, 17, 19, 21, 168, or a contiguous portion thereof or is otherwise considered related to SVV to by sequence homology.

In another aspect, the present invention encompasses any virus having at least 65%, 70%, 75%, 80%, 85%, 90%, 95%, 96%, 97%, 98%, or 99% nucleic acid sequence identity to SVV of ATCC deposit number PTA-5343, to SEQ ID NO:168, or to a contiguous portion of SEQ ID NOS: 1 or 168 that is at least 100, 200, 300, 400, 500, 750, 1000, 1500, or 2000 nucleotides in length.

The present invention also provides an oncolytic virus made by any of the methods for making a mutant virus disclosed herein. In one aspect, the present invention provides a method for treating a patient with an oncolytic virus, the method comprising: (a) inactivating an oncolytic virus made by any of the methods for making a mutant virus disclosed herein, such that the oncolytic virus is non-infectious and the tropism of the oncolytic virus is unaffected; and (b) administering the irradiated oncolytic virus to a patient afflicted with a tumor. In another aspect, the method for treating a patient further comprises attaching a toxin to the inactivated oncolytic virus.

In another aspect, the present invention provides a method for treating a patient with a tumor with SVV, the method comprising: (a) inactivating a SVV such that the virus is non-infectious and the tropism is unaffected; and (b) administering the inactivated SVV in a patient afflicted with a tumor. In another aspect, the method for treating a patient with a tumor with SVV further comprises attaching a toxin to the inactivated SVV.

In another aspect, the present invention provides a SVV composition comprising an inactivated SVV or attenuated SVV. In another aspect, the present invention provides a SVV comprising an epitope tag incorporated in the capsid region.

The present invention also provides a method for treating a patient with a tumor with SVV, the method comprising: (a) creating a mutant SVV comprising an epitope tag encoded in the capsid; (b) attaching a toxin to the epitope tag; and (c) administering the mutant SVV with the attached toxin to a patient afflicted with a tumor. In one aspect, the creating comprises: inserting an oligonucleotide encoding an epitope tag into a capsid-encoding region polynucleotide of SVV. In one aspect, the mutant SVV does not have an altered cell-type tropism. In another aspect, the method further comprises inactivating the mutant SVV such that the mutant SVV is not infectious or cannot replicate.

The present invention also provides a method for detecting a tumor cell in a sample comprising: (a) isolating a tumor sample from a patient; (b) incubating the tumor sample with an epitope-tagged SVV; and (c) screening the tumor sample for bound SVV by detecting the epitope tag.

In one aspect, the invention provides a method for detecting a tumor cell in vivo comprising: (a) administering to a patient an inactivated epitope-tagged SVV, wherein a label is conjugated to the epitope-tag; and (b) detecting the label in the patient. In the methods for detecting a tumor cell of the present invention, the SVV can be a mutant SVV generated by the methods disclosed herein.

In one aspect, the invention provides a method for detecting a tumor cell in a sample comprising: (a) isolating a cell sample from a subject; (b) incubating the cell sample with SVV (or an SVV-like picornavirus); (c) incubating the cell sample from step (b) with an antibody specific to SVV (or an antibody specific to an SVV-like picornavirus); and (d) screening the cell sample for bound antibody, wherein bound antibody indicates that the sample contains a tumor cell.

In one aspect, the invention provides a method for determining whether a subject is candidate for SVV therapy, the method comprising: (a) isolating a cell from the subject; (b) incubating the cell with SVV; (c) incubating the sample from step (b) with an anti-SVV antibody; and (d) detecting for the presence of the anti-SVV antibody on or in the cell, wherein a positive detection indicates that the subject is a candidate for SVV therapy.

Screening a cell sample for bound antibody or detecting for the presence of an anti-SVV antibody can be conducted by adding a secondary antibody that can bind to the constant regions or non-epitope binding regions of the anti-SVV antibody, wherein the secondary antibody is conjugated or labeled with a detectable marker. The detectable marker can be, for example, a fluorophore such as fluorescein. When a secondary antibody is labeled with a detectable marker, the detectable marker can be detected, for example, by fluorescent microscopy. The cell from the subject can be from a tissue biopsy from the subject. The tissue biopsy can be from a tumor in the subject or from a region in the subject that is suspected to contain tumor cells. SVV directly labeled with fluorophore can also be used in identification of tumor cells.

Further, the methods for treating neoplastic conditions, for detecting neoplastic conditions and for producing SVV, apply to wild-type SVV, mutant (including modified or variant) SVV, relatives of SVV, SVV-like picornaviruses, and other tumor-specific viruses of the invention.

The viruses of the present invention, and the compositions thereof, can be used in the manufacture of a medicament for treating the diseases mentioned herein. Further, the viruses and composition thereof of the invention can be used for the treatment of the diseases mentioned herein. Thus, in one aspect of the present invention, the present invention provides the use of SVV (or mutants, derivatives, relatives, and compositions thereof) for the treatment of cancer or in the manufacture of a medicament for treating cancer.

SVV and SVV-like viruses for gene therapy: Replication defective SVV expressing gene(s) of interest can be used to deliver genes to correct genetic disorders. SVV and SVV-like viruses can also be used as delivery vehicle for siRNA to prevent any specific gene expression. Replication defective viruses can be grown in complementing cell lines and/or in the presence of a helper virus to provide for missing functions in the recombinant virus.

IRES of picornaviruses known to play a role in expression of genes in a tissue specific manner. IRES of SVV and SVV-like viruses can be used to replace IRES of other picornaviruses. This strategy can be used to generate viruses with altered tissue tropism. In one aspect, the invention provides an IRES of SVV or an IRES from an SVV-related virus for the purpose of expressing two genes from a single promoter in a tissue specific manner.

Self-cleavage properties of 2A protease of SVV can be used to express more than one gene in equal amounts using single promoter and transcription termination signal sequences. In one aspect, the invention provides a self-cleaving 2A peptide of SVV or of an SVV-related virus for the purpose of expressing of two or more proteins in equal amounts under the control of single promoter and a single poly(A) signal. In another aspect, the invention provides the use of an SVV or an SVV-related virus 3C protease to cleave polypeptides for production of proteins from a eukaryotic cell. In another aspect, the invention provides for the use of an SVV or an SVV-like virus leader peptide to cause shut off of cell protein synthesis in tumor cells or another cell type of interest.

Virus like particles of SVV can be generated and used as vaccines and identify a particular cell type in a mixed population of cells.

Deposit Information

The following material has been deposited with the American Type Culture Collection (ATCC), 10801 University Blvd., Manassas, Va., 20110-2209, U.S.A., under the terms of the Budapest Treaty on the International Recognition of the Deposit of Microorganisms for the Purposes of Patent Procedure. All restrictions on the availability of the deposited material will be irrevocably removed upon the granting of a patent. Material: Seneca Valley Virus (SVV). ATCC Patent Deposit Number: PTA-5343. Date of Deposit: Jul. 25, 2003.

BRIEF DESCRIPTION OF THE DRAWINGS

FIGS. 5A-5E presents the nucleotide sequence of SVV (SEQ ID NO:1) and the encoded amino acid sequence (SEQ ID NO:2). The stop codon is depicted by a "s" at positions 5671-3. As a general note, in sequence disclosures that include positions where the exact nucleotide is being confirmed, these positions are represented by an "n". Therefore, in codons that possess an "n", the relevant amino acid is depicted by a "x".

FIGS. 6A-6D presents the nucleotide sequence (SEQ ID NO:1) of the majority of the full-length genome of SVV. The nucleotide sequence was derived from the SVV isolate having the ATCC Patent Deposit Number: PTA-5343. Date of Deposit: Jul. 25, 2003.

FIGS. 7A-7B presents the amino acid sequence (SEQ ID NO:2) encoded by SEQ ID NO:1.

FIG. 8 presents the nucleotide sequence (SEQ ID NO:3) of the partial 1B or VP2 encoding region of SVV. This sequence is identical to nucleotides 4-429 of SEQ ID NO:1.

FIG. 9 presents the amino acid sequence (SEQ ID NO:4) of the partial SVV VP2 protein that is encoded by SEQ ID NO:3. The sequence listed in SEQ ID NO:4 is identical to amino acids 2-143 of SEQ ID NO:2.

FIG. 10 presents the nucleotide sequence (SEQ ID NO:5) of the 1C or VP3 encoding region of SVV. This sequence is identical to nucleotides 430-1146 of SEQ ID NO:1.

FIG. 11 presents the amino acid sequence (SEQ ID NO:6) of the SVV VP3 protein that is encoded by SEQ ID NO:5. The sequence listed in SEQ ID NO:6 is identical to amino acids 144-382 of SEQ ID NO:2.

FIG. 12 presents the nucleotide sequence (SEQ ID NO:7) of the 1D or VP1 encoding region of SVV. This sequence is identical to nucleotides 1147-1923 of SEQ ID NO:1.

FIG. 13 presents the amino acid sequence (SEQ ID NO:8) of the SVV VP1 protein that is encoded by SEQ ID NO:7. The sequence listed in SEQ ID NO:8 is identical to amino acids 383-641 of SEQ ID NO:2.

FIG. 14 presents the nucleotide sequence (SEQ ID NO:9) of the 2A encoding region of SVV. This sequence is identical to nucleotides 1924-1965 of SEQ ID NO:1.

FIG. 15 presents the amino acid sequence (SEQ ID NO:10) of the SVV 2A protein that is encoded by SEQ ID NO:9. The sequence listed in SEQ ID NO:10 is identical to amino acids 642-655 of SEQ ID NO:2.

FIG. 16 presents the nucleotide sequence (SEQ ID NO:11) of the 2B encoding region of SVV. This sequence is identical to nucleotides 1966-2349 of SEQ ID NO:1.

FIG. 17 presents the amino acid sequence (SEQ ID NO:12) of the SVV 2B protein that is encoded by SEQ ID NO:11. The sequence listed in SEQ ID NO:12 is identical to amino acids 656-783 of SEQ ID NO:2.

FIG. 18 presents the nucleotide sequence (SEQ ID NO:13) of the 2C encoding region of SVV. This sequence is identical to nucleotides 2350-3315 of SEQ ID NO:1.

FIG. 19 presents the amino acid sequence (SEQ ID NO:14) of the SVV 2C protein that is encoded by SEQ ID NO:13. The sequence listed in SEQ ID NO:14 is identical to amino acids 784-1105 of SEQ ID NO:2.

FIG. 20 presents the nucleotide sequence (SEQ ID NO:15) of the 3A encoding region of SVV. This sequence is identical to nucleotides 3316-3585 of SEQ ID NO:1.

FIG. 21 presents the amino acid sequence (SEQ ID NO:16) of the SVV 3A protein that is encoded by SEQ ID NO:15. The sequence listed in SEQ ID NO:16 is identical to amino acids 1106-1195 of SEQ ID NO:2.

FIG. 22 presents the nucleotide sequence (SEQ ID NO:17) of the 3B encoding region of SVV. This sequence is identical to nucleotides 3586-3651 of SEQ ID NO:1.

FIG. 23 presents the amino acid sequence (SEQ ID NO:18) of the SVV 3B protein that is encoded by SEQ ID NO:17. The sequence listed in SEQ ID NO:18 is identical to amino acids 1196-1217 of SEQ ID NO:2.

FIG. 24 presents the nucleotide sequence (SEQ ID NO:19) of the 3C encoding region of SVV. This sequence is identical to nucleotides 3652-4284 of SEQ ID NO:1.

FIG. 25 presents the amino acid sequence (SEQ ID NO:20) of the SVV 3C protein that is encoded by SEQ ID NO:19. The sequence listed in SEQ ID NO:20 is identical to amino acids 1218-1428 of SEQ ID NO:2.

FIG. 26 presents the nucleotide sequence (SEQ ID NO:21) of the 3D encoding region of SVV. This sequence is identical to nucleotides 4285-5673 of SEQ ID NO:1.

FIG. 27 presents the amino acid sequence (SEQ ID NO:22) of the SVV 3D protein that is encoded by SEQ ID NO:21. The sequence listed in SEQ ID NO:22 is identical to amino acids 1429-1890 of SEQ ID NO:2.

Figure 28A:
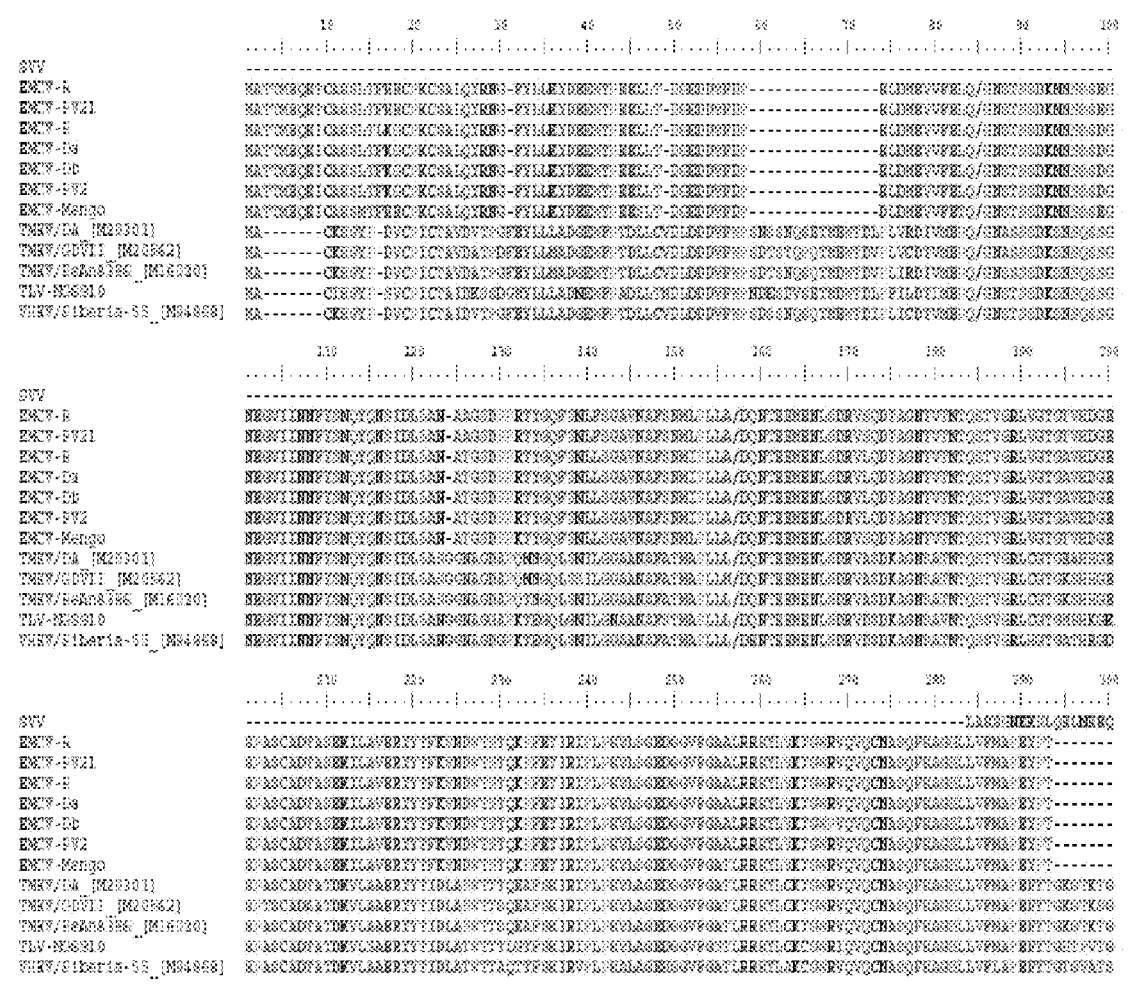
Figure 28B:
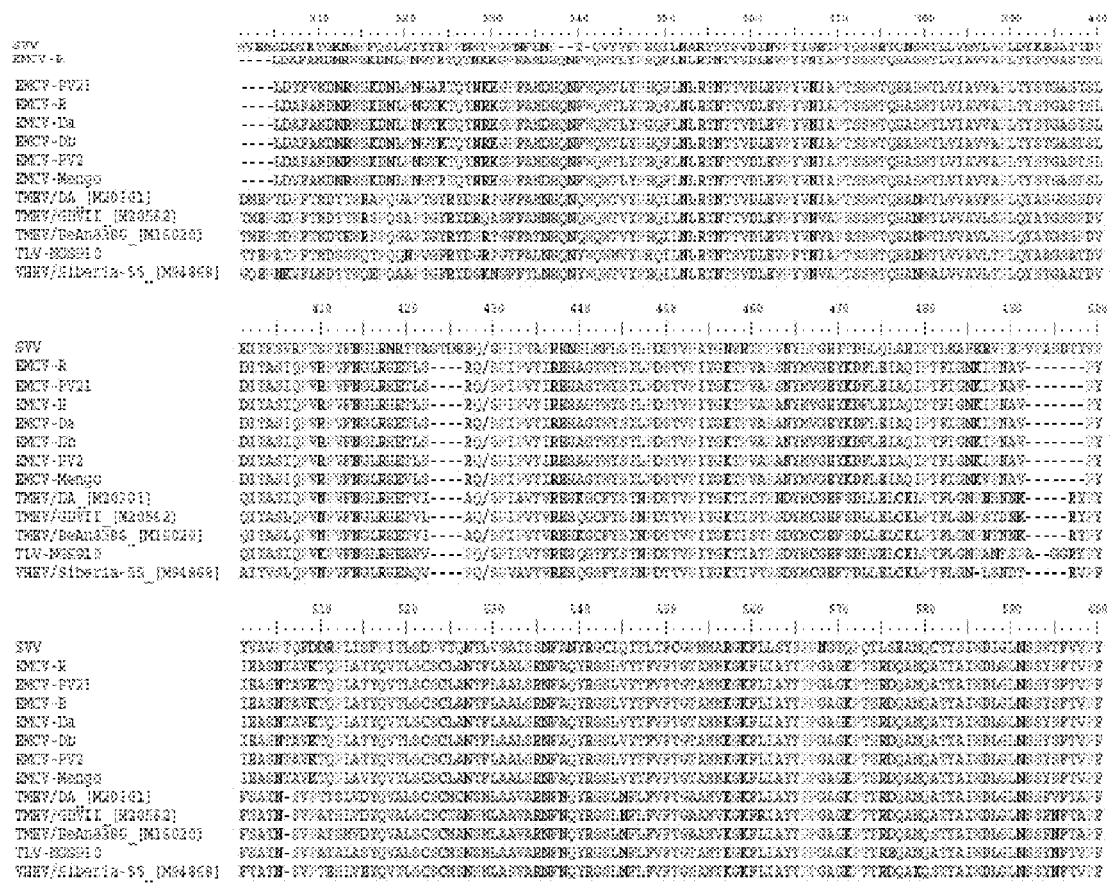
Figure 28C:
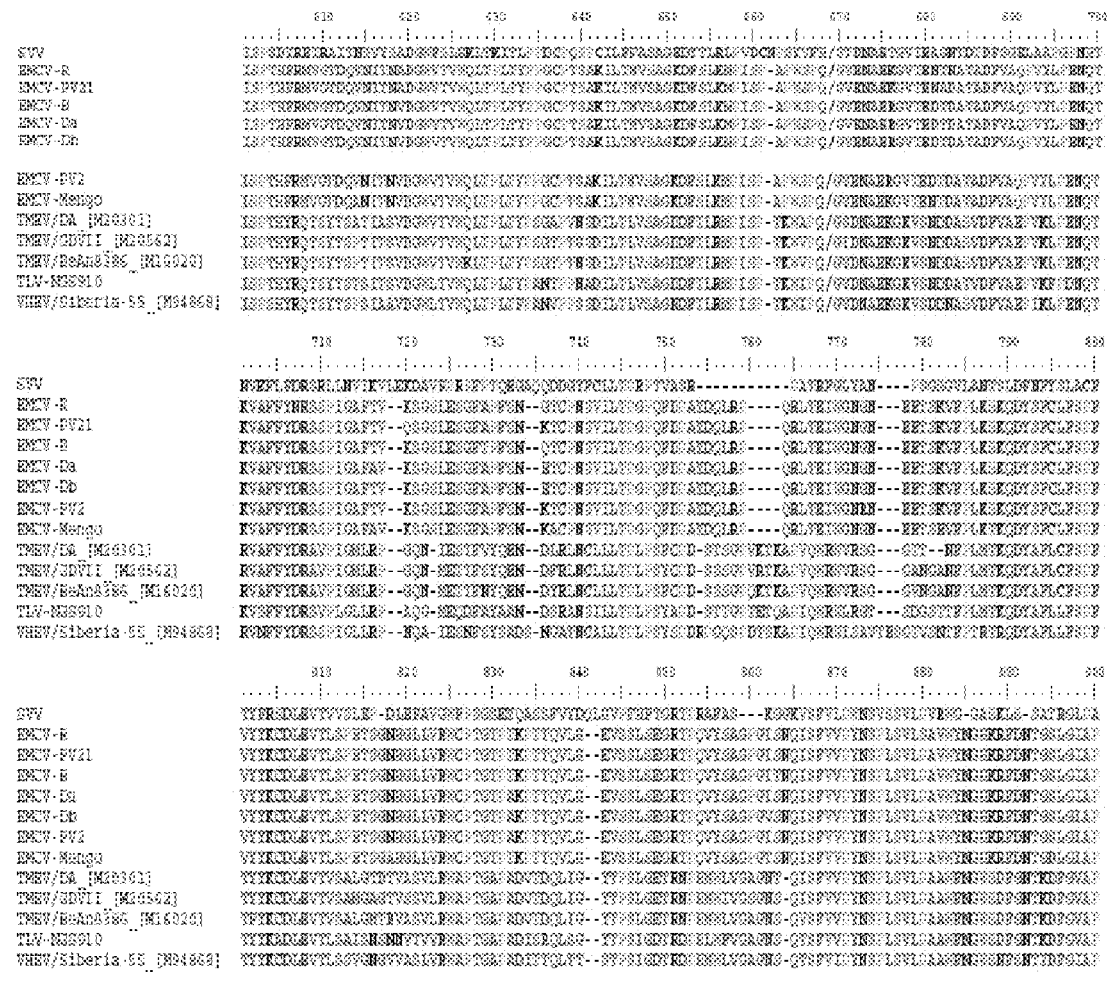
Figure 28D:
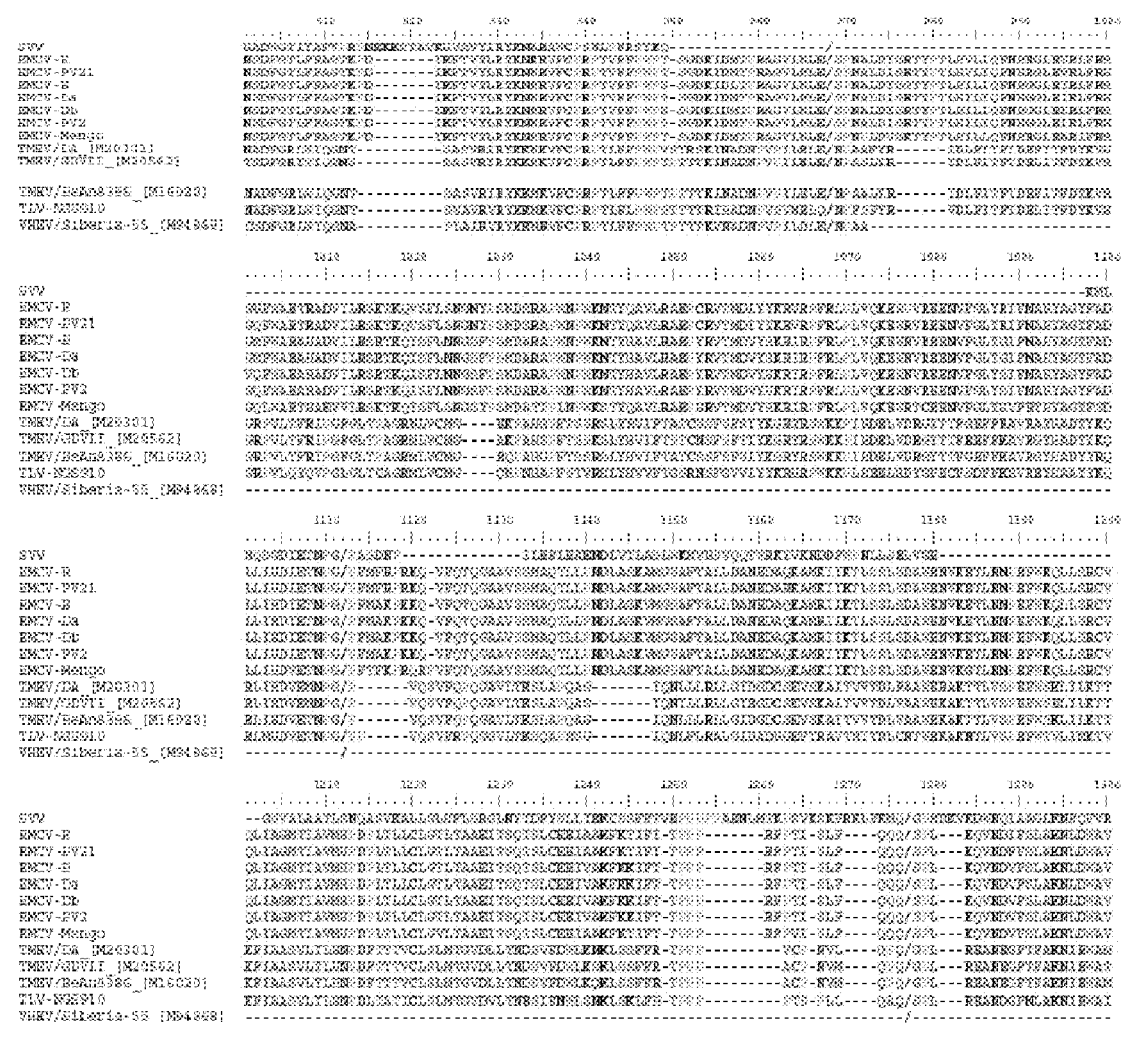
Figure 28E:
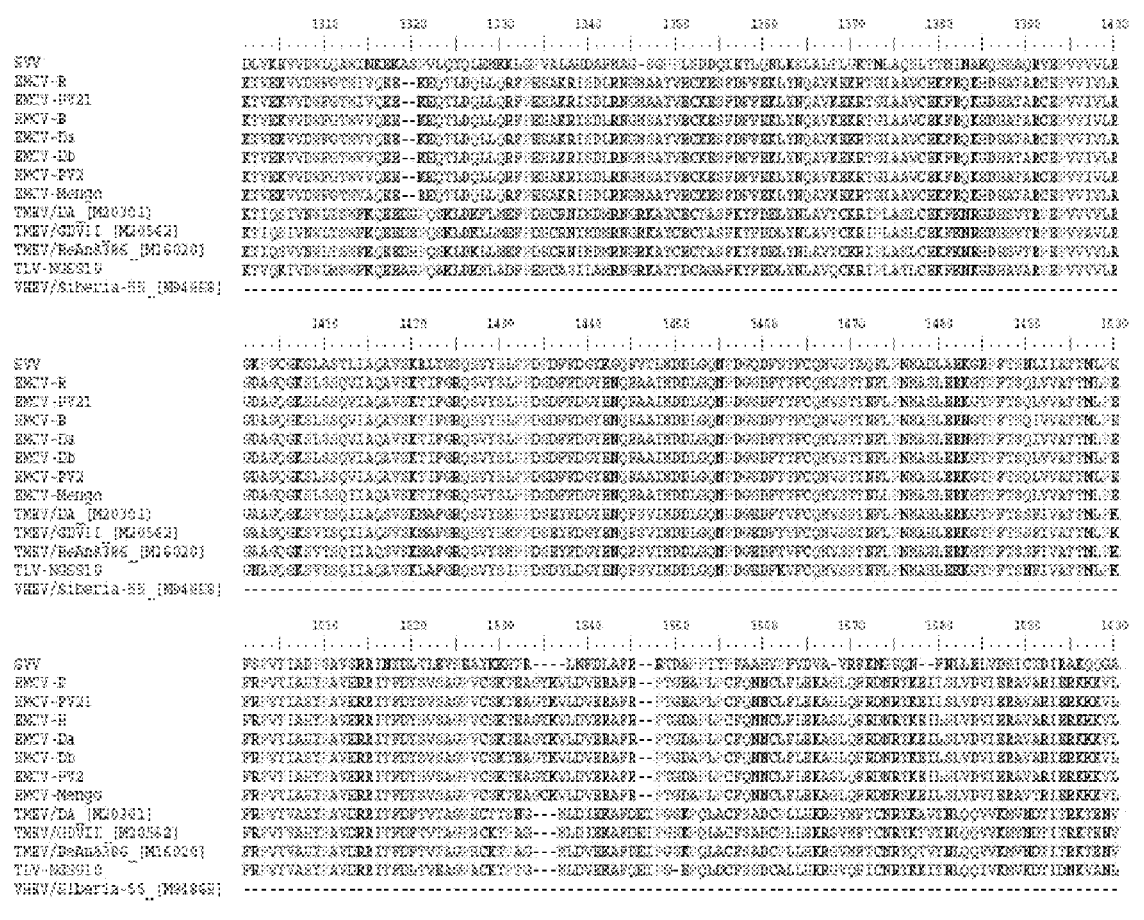
Figure 28F:
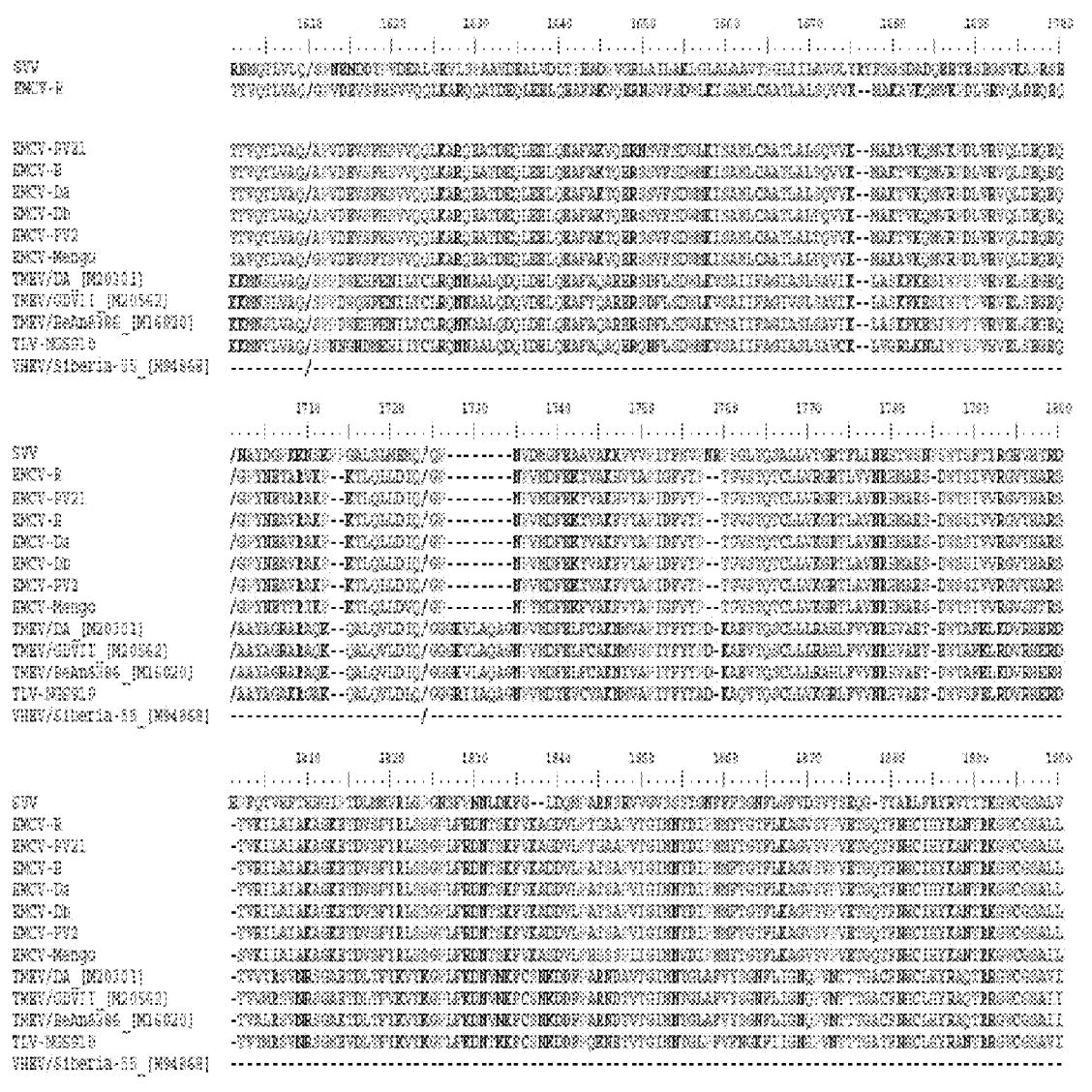
Figure 28G:
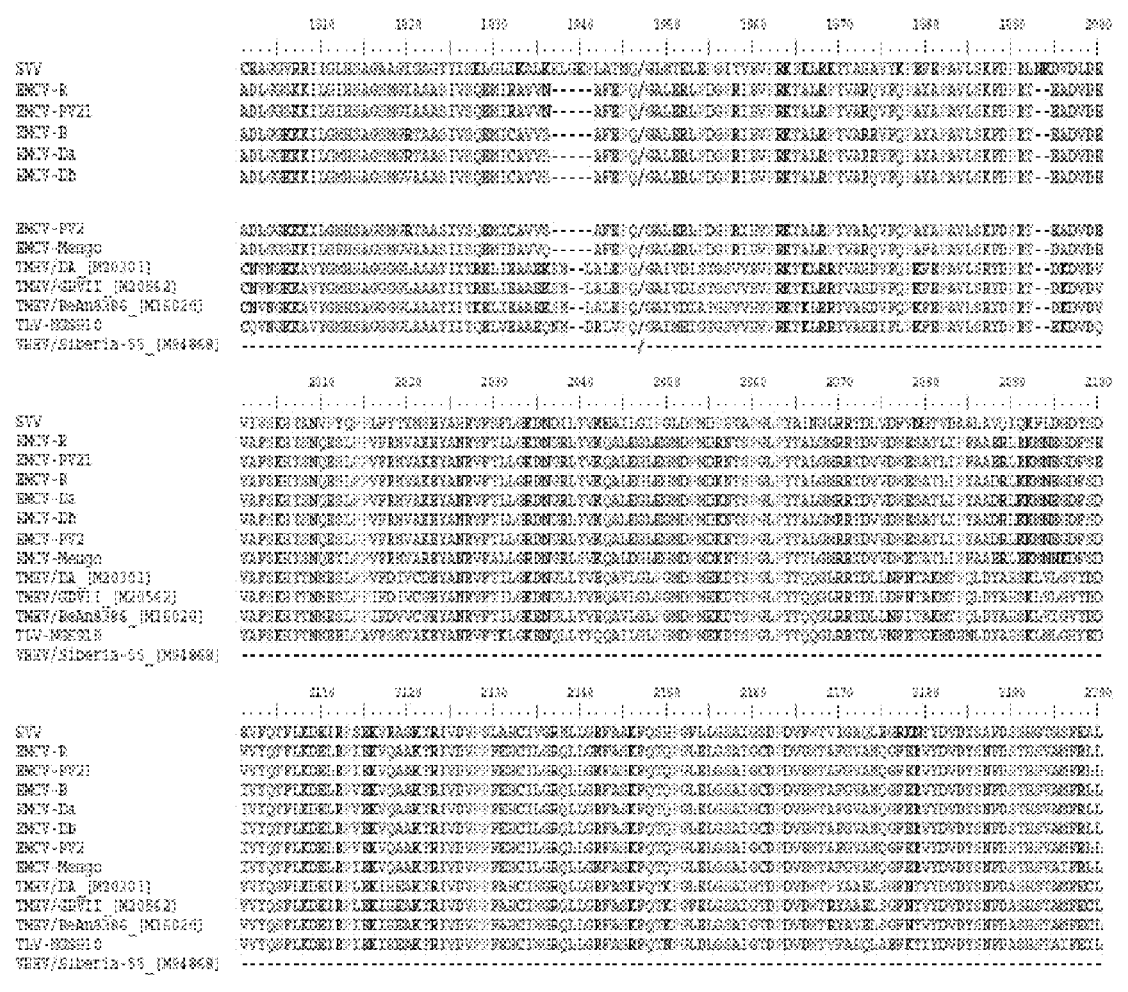
Figure 28H:
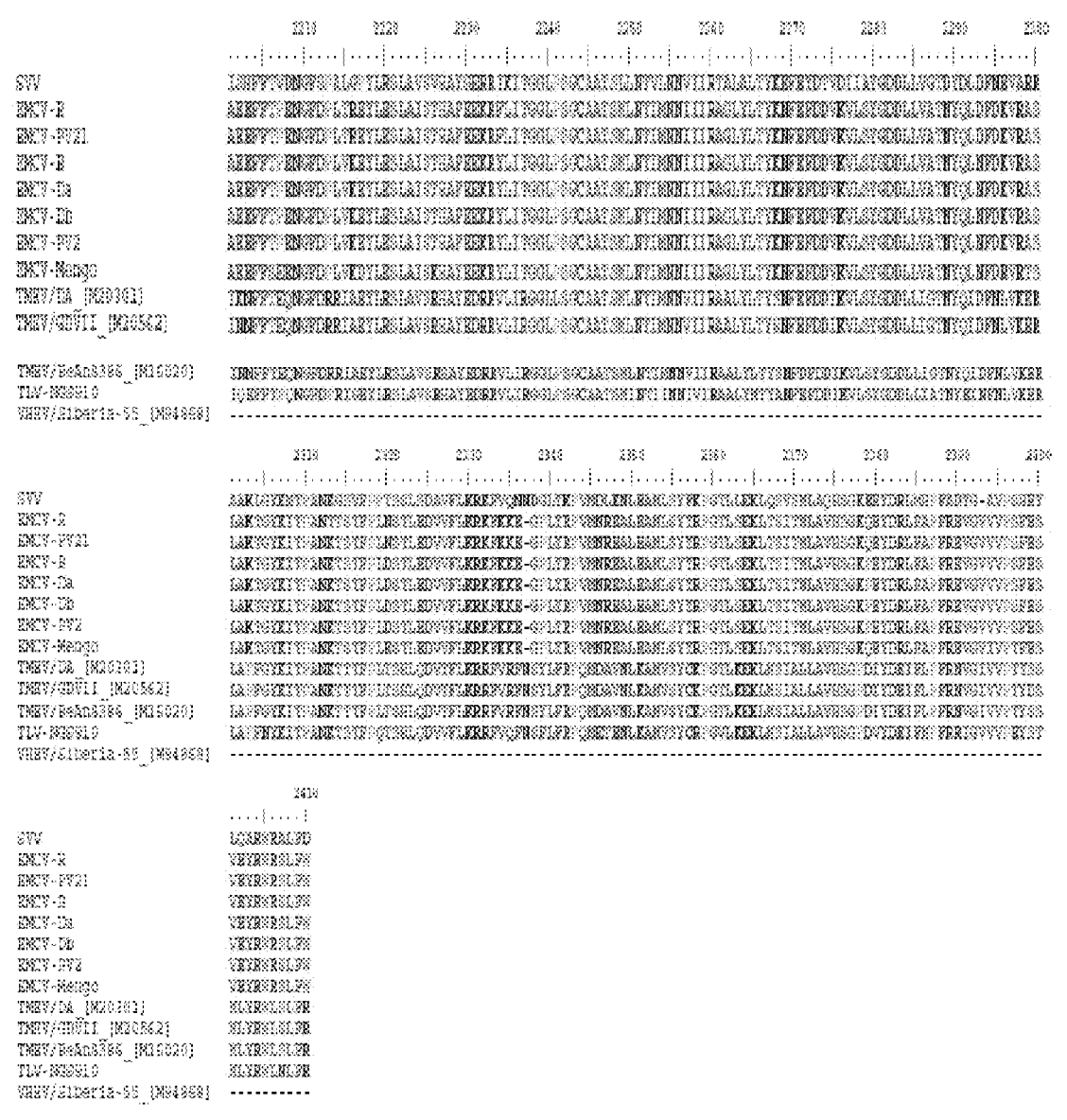

FIGS. 28A-28H present an amino acid sequence alignment between SVV SEQ ID NO:2 and various members of the Cardiovirus genus, such as Encephalomyocarditis virus (EMCV; species Encephalomyocarditis virus), Theiler's murine encephalomyocarditis virus (TMEV; species Theilovirus), a rat TMEV-like agent (TLV; species Theilovirus), and Vilyuisk human encephalomyelitis virus (VHEV; species Theilovirus). The specific sequences of the various Cardioviruses are presented in: SEQ ID NOS: 23 (EMCV-R), 24 (EMCV-PV21), 25 (EMCV-B), 26 (EMCV-Da), 27 (EMCV-Db), 28 (EMCV-PV2), 29 (EMCV-Mengo), 30 (TMEV/DA), 31 (TMEV/GDVII), 32 (TMEV/BeAn8386), 33 (TLV-NGS910) and 34 (VHEV/Siberia-55).

Number positions in FIG. 28 do not correspond to the numbering of the sequence listings. The "/" symbol indicates cleavage sites where the polyprotein is cleaved into its final functional products. For example, the alignment between positions 1 and 157 is in the 1A (VP4) region. The alignment between positions: 159 and 428 is in the 1B (VP2) region; 430 and 668 is in the 1C (VP3) region; 670 and 967 is in the 1D (VP1) region; 969 and 1111 is in the 2A region; 1112 and 1276 is in the 2B region; 1278 and 1609 is in the 2C region; 1611 and 1700 is in the 3A region; 1702 and 1723 is in the 3B region; 1725 and 1946 is in the 3C region; 1948 and 2410 is in the 3D region. The alignment also shows regions of potential conservation or similarity between the viral sequences as can be determined by standard sequence analysis programs. The alignments were generated using BioEdit 5.0.9 and Clustal W 1.81.

FIG. 29 lists the final polypeptide products of SVV with respect to SEQ ID NO:2. Some conserved motifs are bolded and underlined: 2A/2B "cleavage" (NPGP (SEQ ID NO:111)); 2C ATP-binding (GxxGxGKS/T (SEQ ID NO:112) and hyhyhyxxD); 3B (VPg)/RNA attachment residue (Y); 3C (pro) active site residues (H, C, H); 3D (pol) motifs (KDEL/IR (SEQ ID NO:113), PSG, YGDD (SEQ ID NO:114), FLKR (SEQ ID NO:115)).

FIG. 30 lists the picornavirus species that were used in sequence analyses with SEQ ID NOS:1 and 2 to determine the phylogenetic relationship between SVV and these picornaviruses (see Example 4, Part I).

Figure 31:
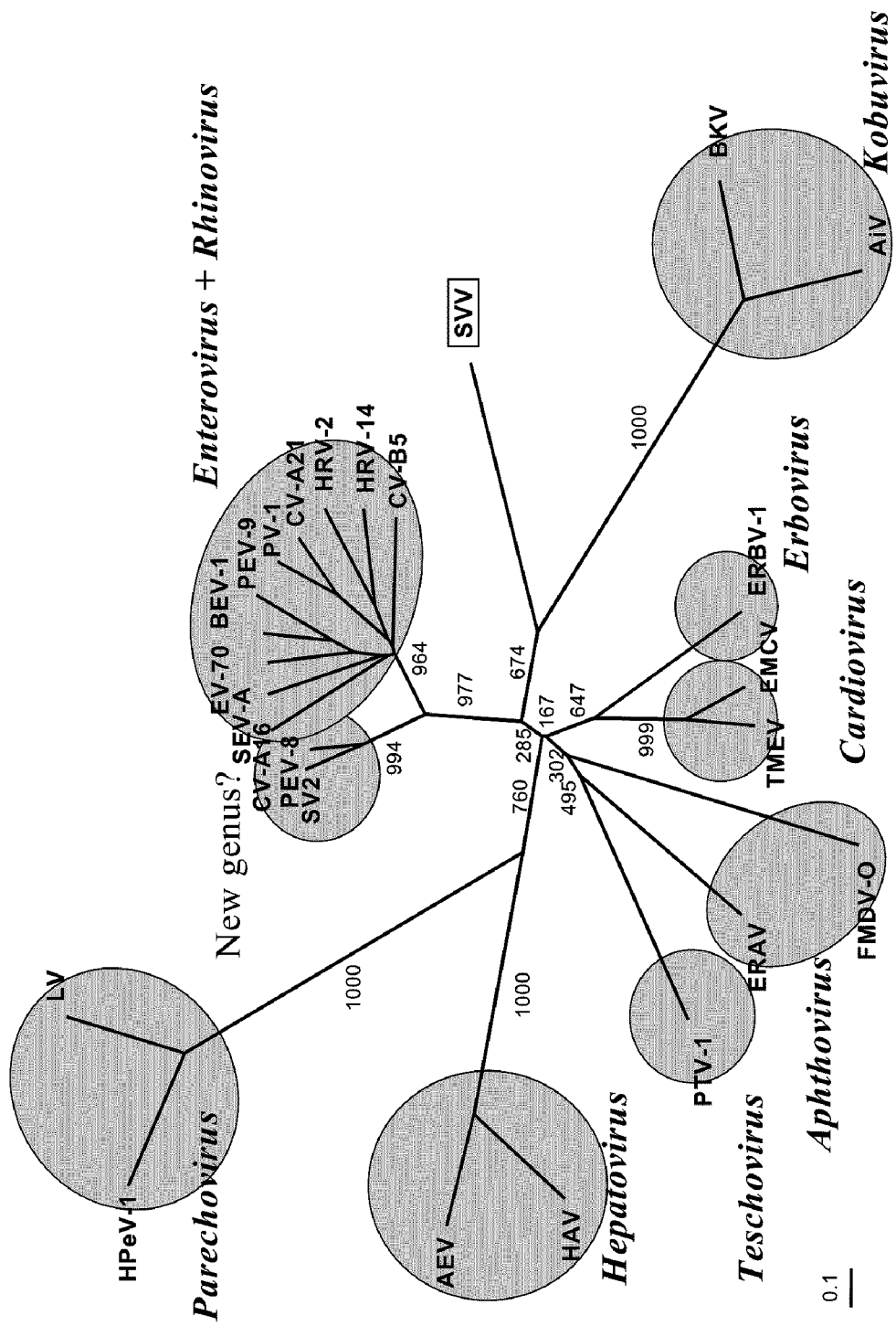

FIG. 31 shows the phylogenetic relationship between SVV (SEQ ID NO:4) and other picornaviruses in view of VP2 sequence analyses. The figure shows a bootstrapped neighbor-joining tree (see Example 4, Part I).

Figure 32:
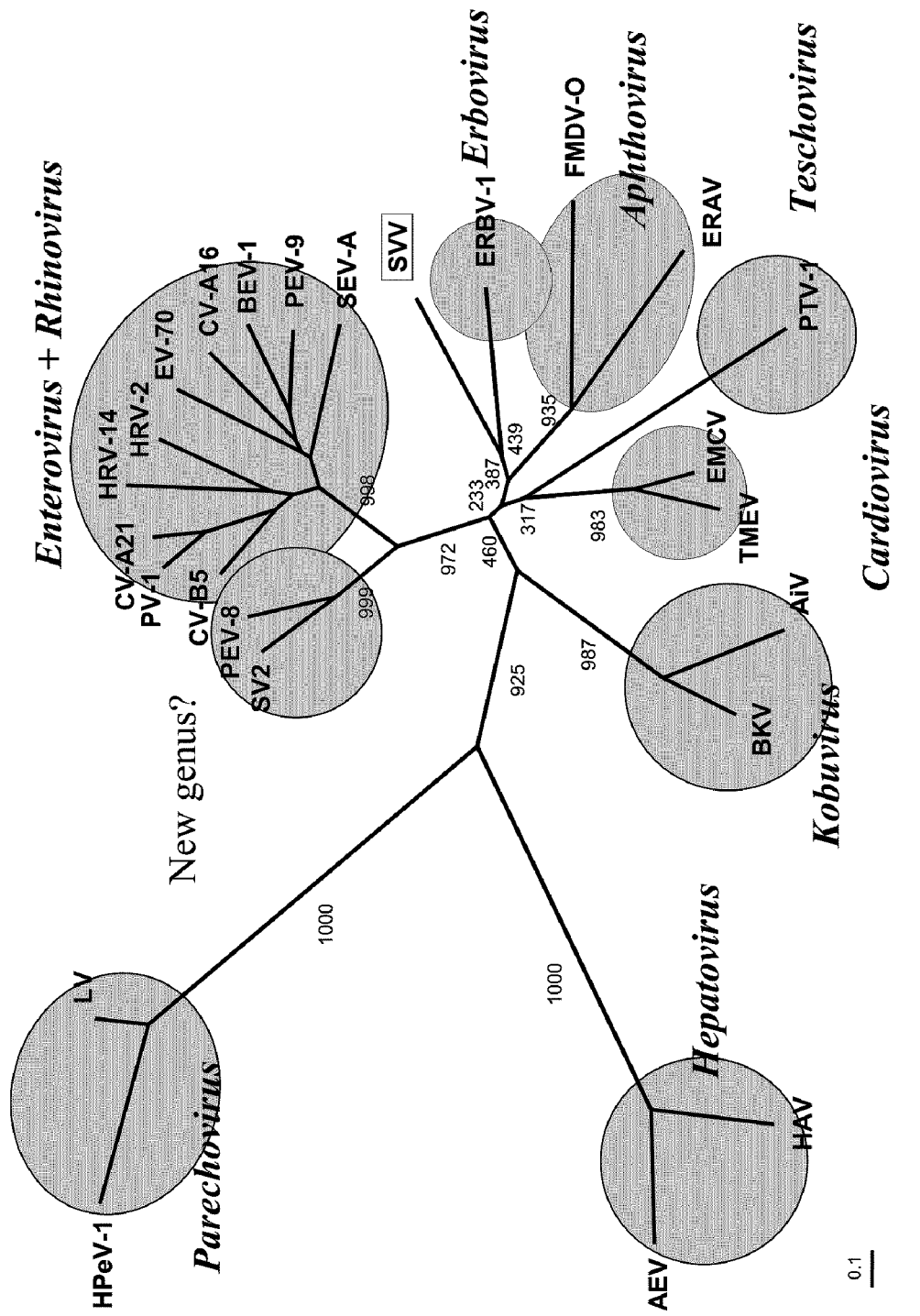

FIG. 32 shows a bootstrapped neighbor-joining tree for VP3 between SVV (SEQ ID NO:6) and other picornaviruses (see Example 4, Part I).

Figure 33:
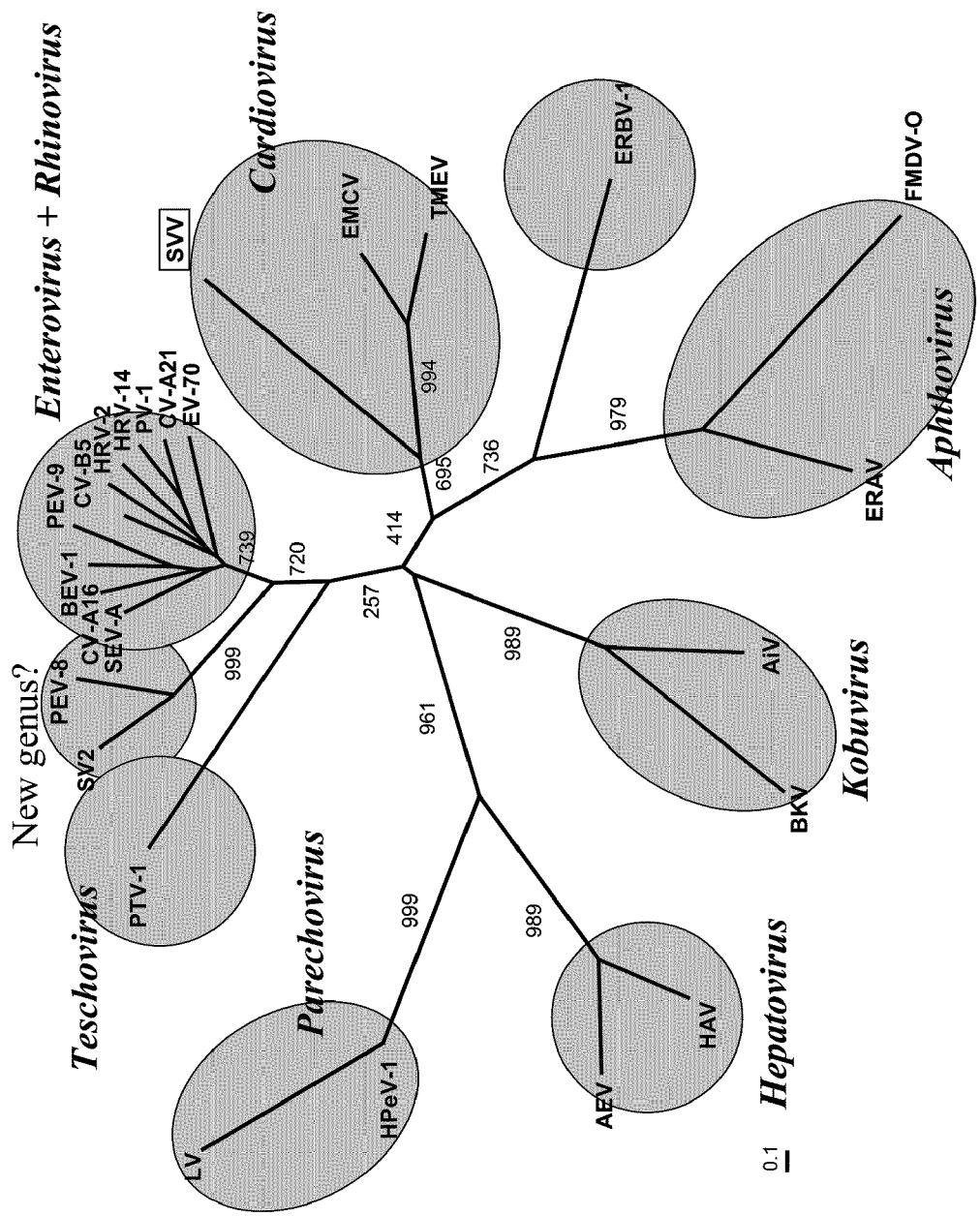

FIG. 33 shows a bootstrapped neighbor-joining tree for VP1 between SVV (SEQ ID NO:8) and other picornaviruses (see Example 4, Part I).

Figure 34:
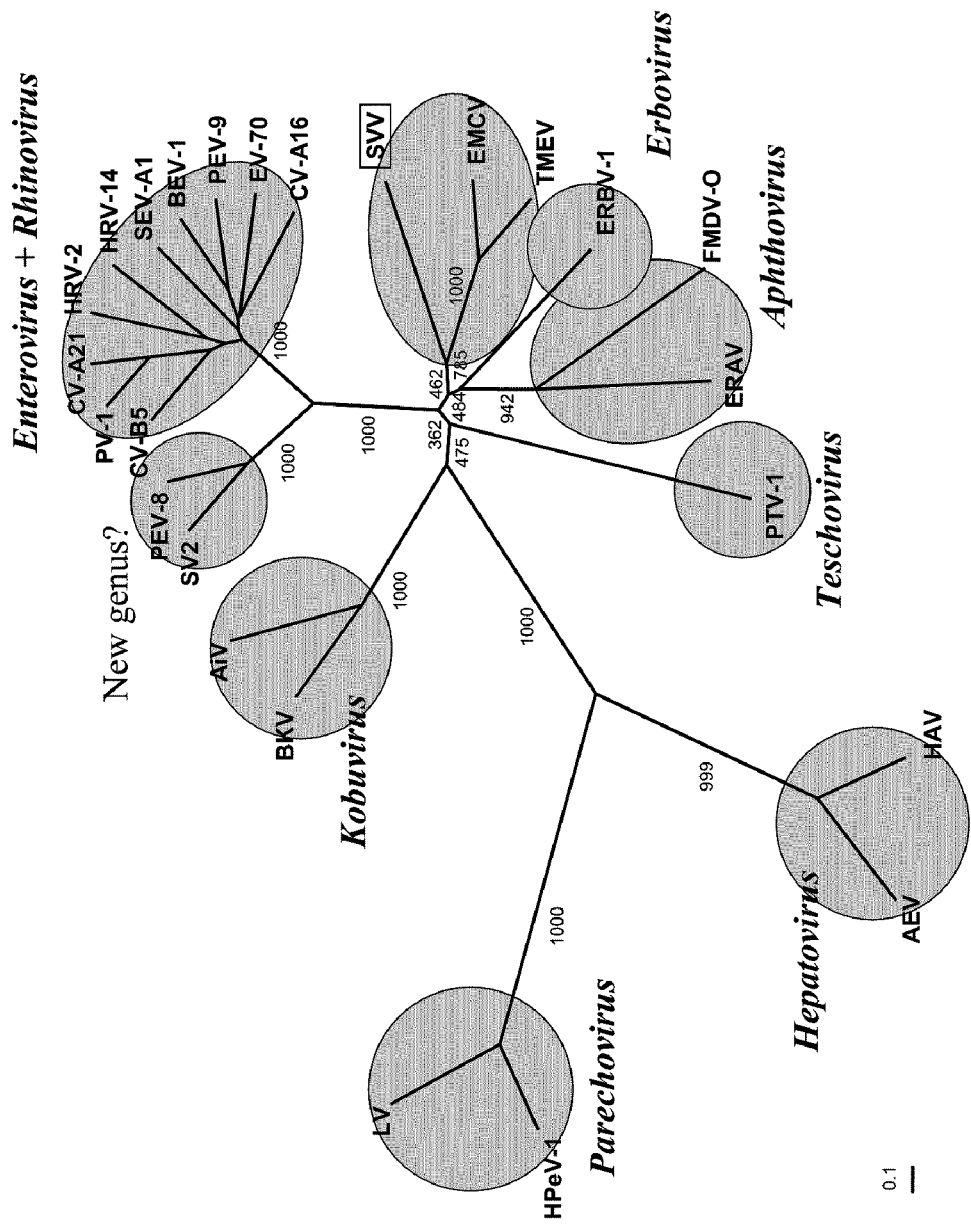

FIG. 34 shows a bootstrapped neighbor-joining tree for P1 (i.e., 1A, 1B, 1C and 1D) between SVV (i.e., partial P1-amino acids 2-641 of SEQ ID NO:2) and other picornaviruses (see Example 4, Part I).

Figure 35:
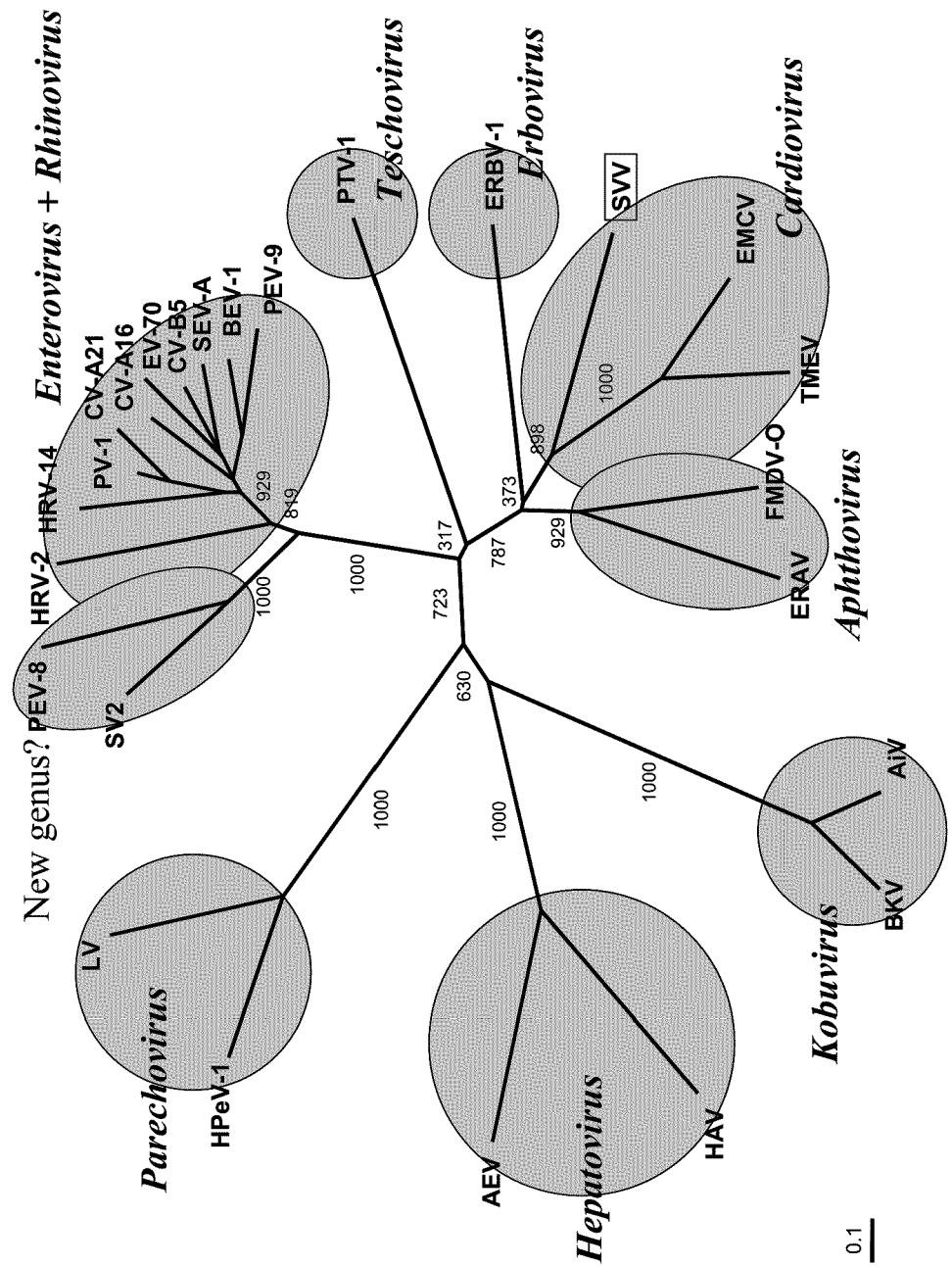

FIG. 35 shows a bootstrapped neighbor-joining tree for 2C between SVV (SEQ ID NO:14) and other picornaviruses (see Example 4, Part I).

Figure 36:
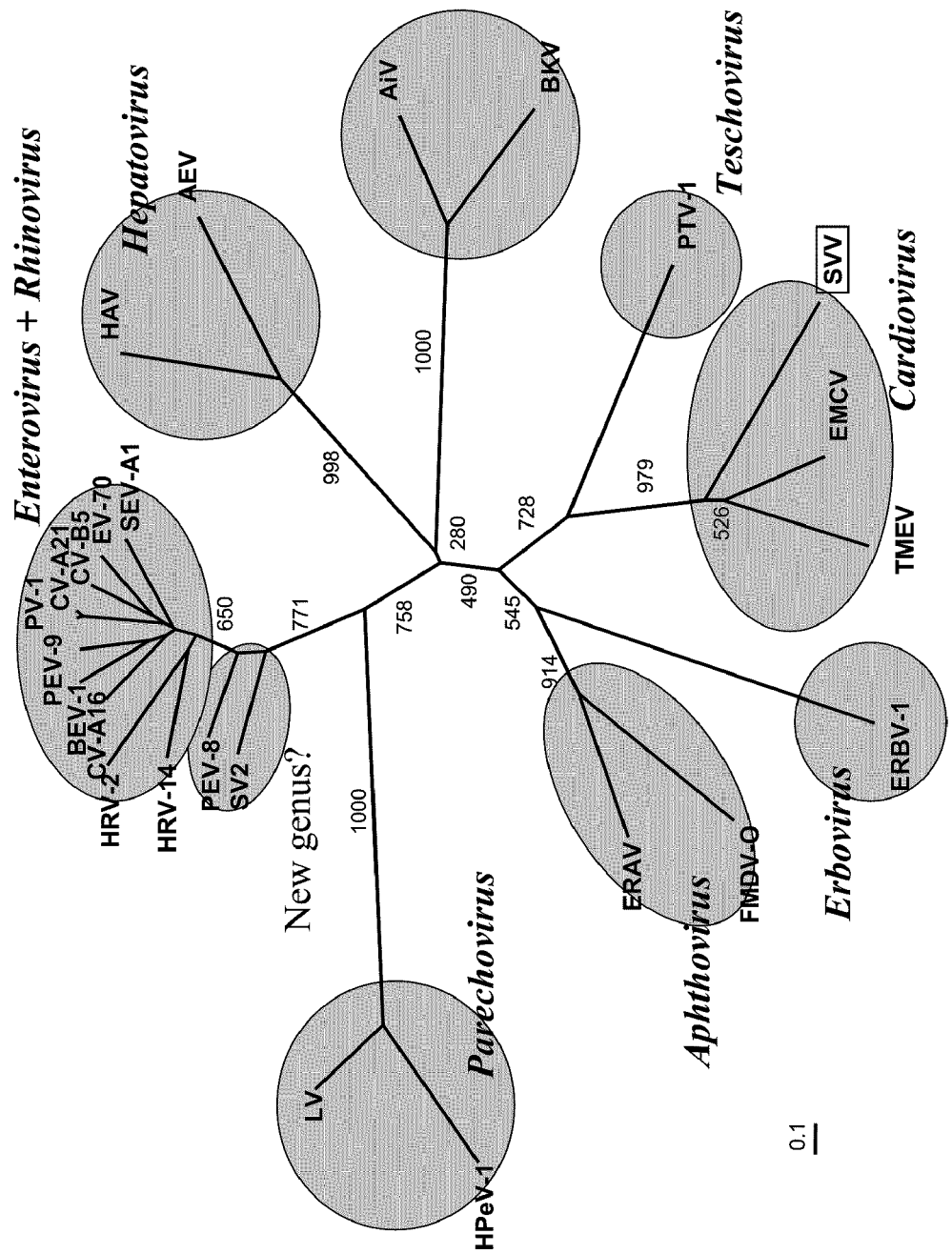

FIG. 36 shows a bootstrapped neighbor-joining tree for 3C (pro) between SVV (SEQ ID NO:20) and other picornaviruses (see Example 4, Part I).

Figure 37:
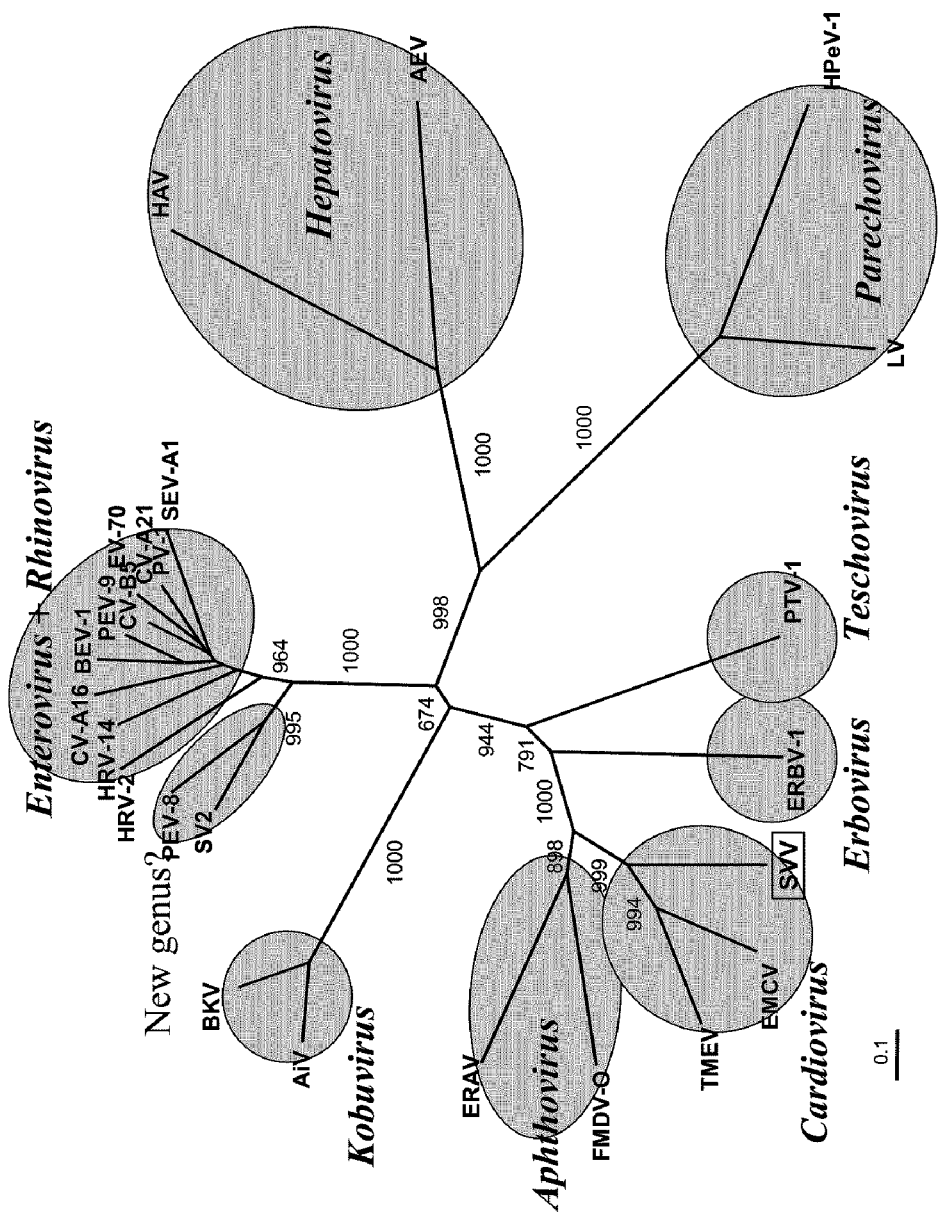

FIG. 37 shows a bootstrapped neighbor-joining tree for 3D (pol) between SVV (SEQ ID NO:22) and other picornaviruses (see Example 4, Part I).

FIG. 38 presents the actual amino acid percent identities of VP2 between SVV (SEQ ID NO:4) and other picornaviruses (see Example 4, Part I).

FIG. 39 presents the actual amino acid percent identities of VP3 between SVV (SEQ ID NO:6) and other picornaviruses (see Example 4, Part I).

FIG. 40 presents the actual amino acid percent identities of VP1 between SVV (SEQ ID NO:8) and other picornaviruses (see Example 4, Part I).

FIG. 41 presents the actual amino acid percent identities of P1 between SVV (partial capsid or P1-amino acids 2-641 of SEQ ID NO:2) and other picornaviruses (see Example 4, Part I).

Figure 42:
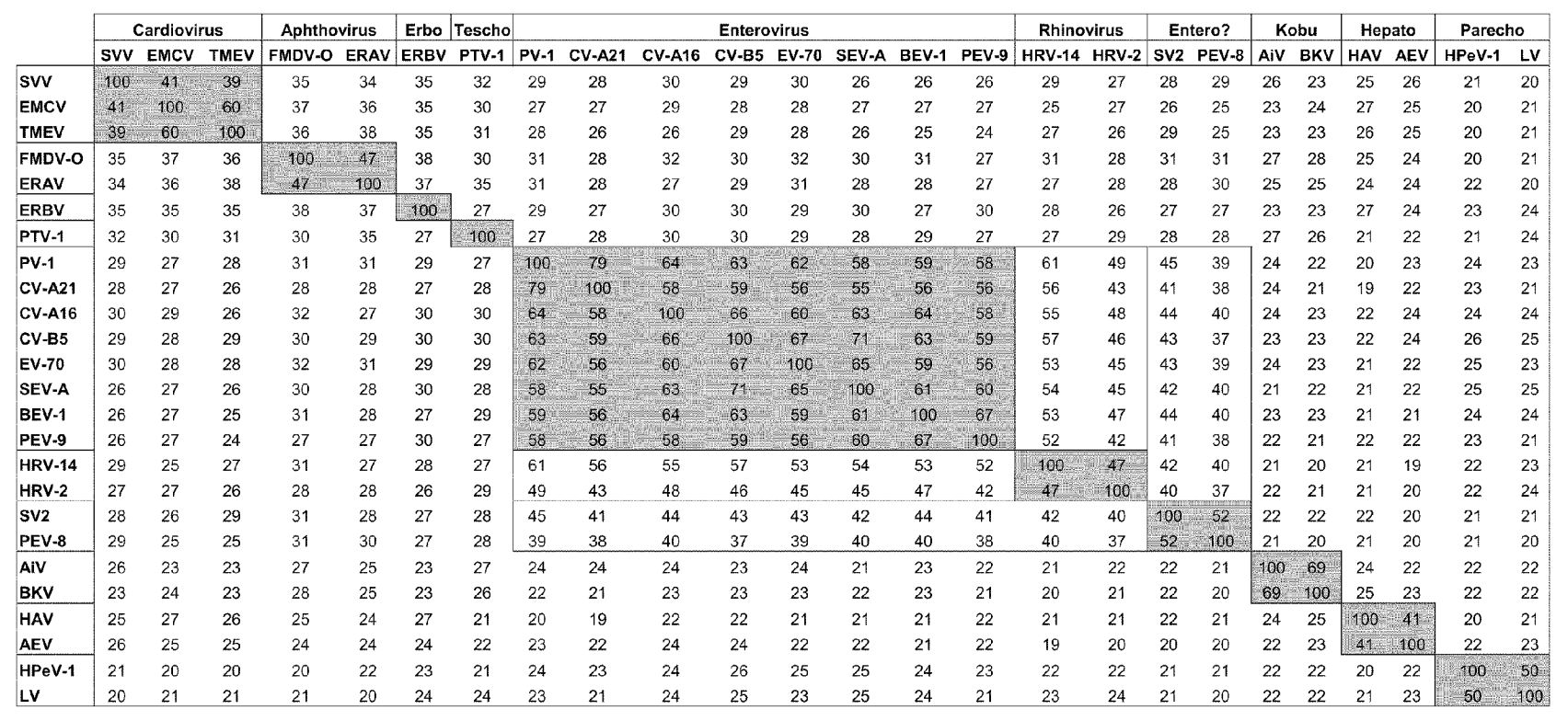

FIG. 42 presents the actual amino acid percent identities of 2C between SVV (SEQ ID NO:14) and other picornaviruses (see Example 4, Part I).

FIG. 43 presents the actual amino acid percent identities of 3C (pro) between SVV (SEQ ID NO:20) and other picornaviruses (see Example 4, Part I).

Figure 44:
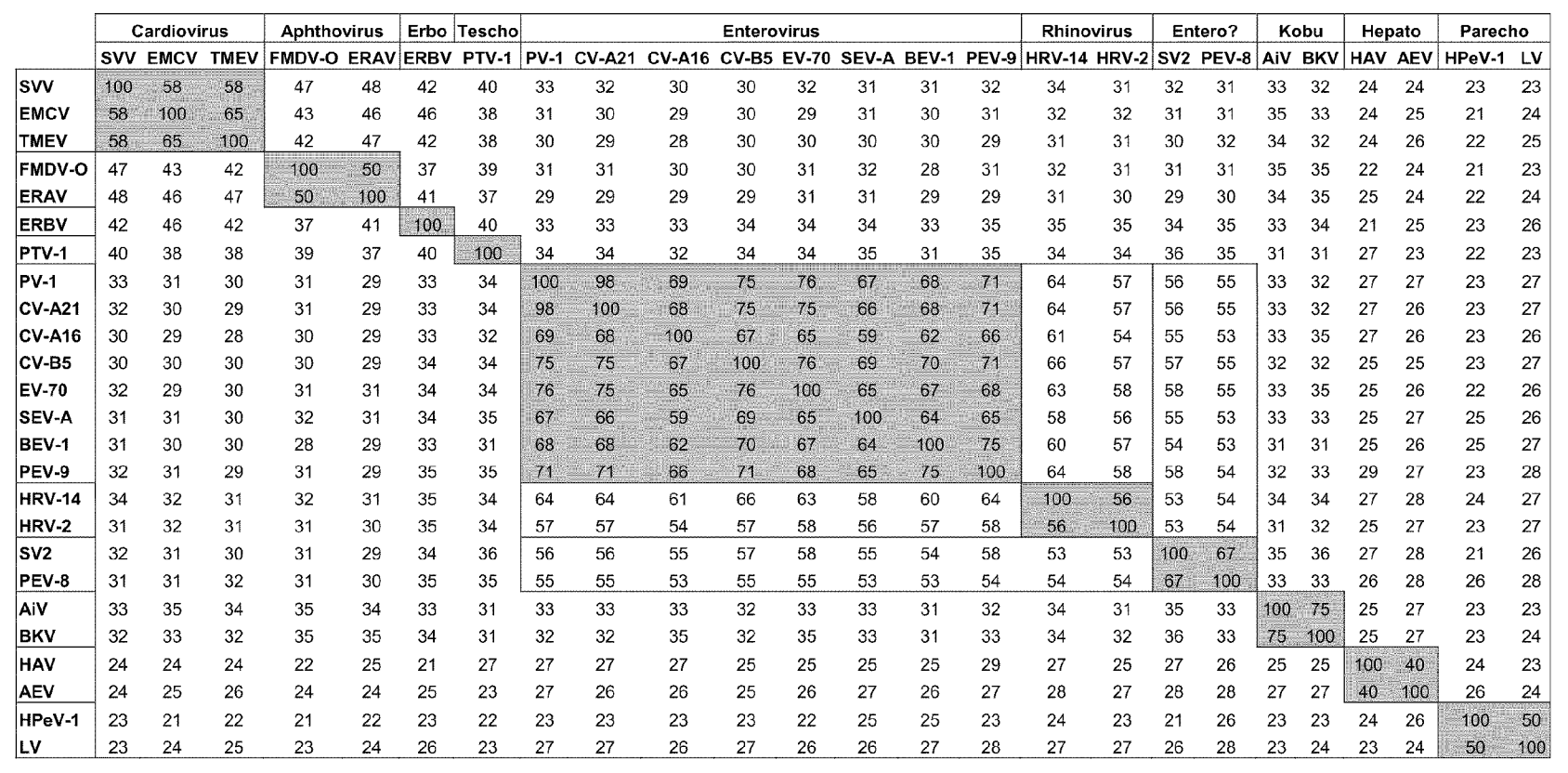

FIG. 44 presents the actual amino acid percent identities of 3D (pol) between SVV (SEQ ID NO:22) and other picornaviruses (see Example 4, Part I).

Figure 45:
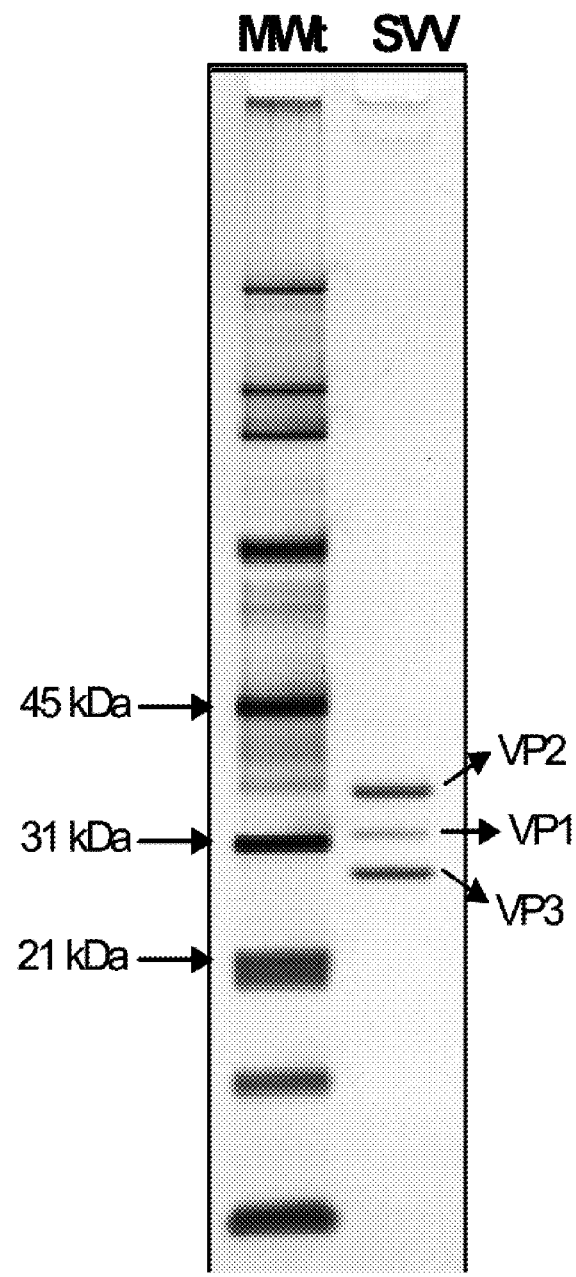

FIG. 45 shows the VP2 (~36 kDa), VP1 (~31 kDa) and VP3 (~27 kDa) proteins of SVV as analyzed by SDS-PAGE. Purified SVV was subjected to SDS-PAGE and proteins were visualized by silver stain. Lane "MWt" is molecular weight markers; lane "SVV" contains structural proteins of SVV. The sizes of three molecular weight markers and the names of viral proteins are also given.

Figure 46A:
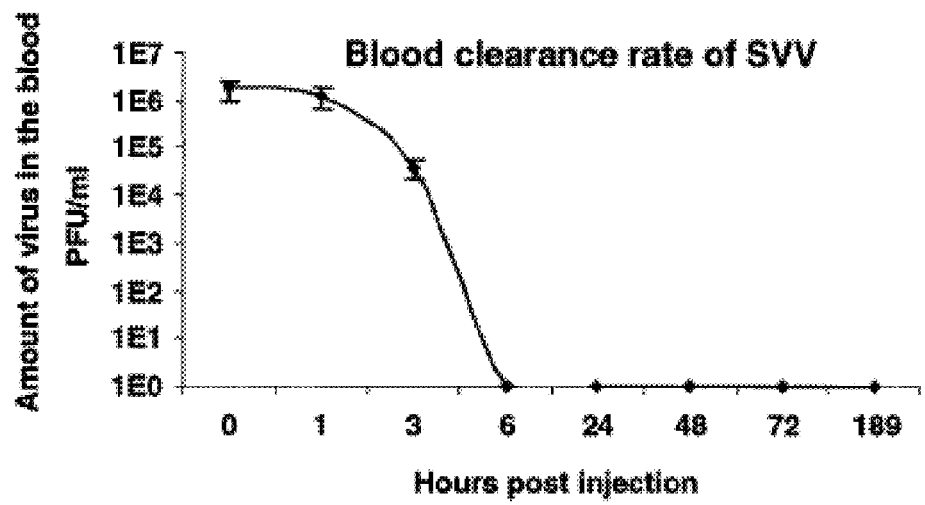
Figure 46B:
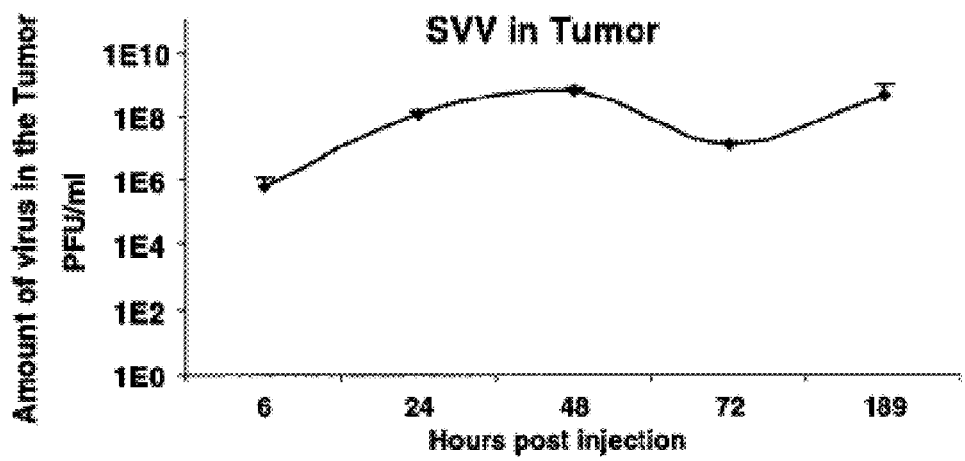

FIGS. 46A-46B show the amounts of SVV in blood and tumor following systemic administration (Example 7). H446 tumor bearing nude mice were treated with SVV at a dose of $1 \times 10^{12}$ vp/kg by tail vein injection. The mice were bled at 0, 1, 3, 6, 24, 48, 72 hours and at 7 days post-injection, and the plasma was separated from the blood immediately after collection, diluted in infection medium, and used to infect PER.C6 cells. The tumors were harvested at 6, 24, 48, 72 hours and at 7 days post-injection. The tumors were cut into small sections and suspended in one mL of medium and CVL was made.

Figure 46C:
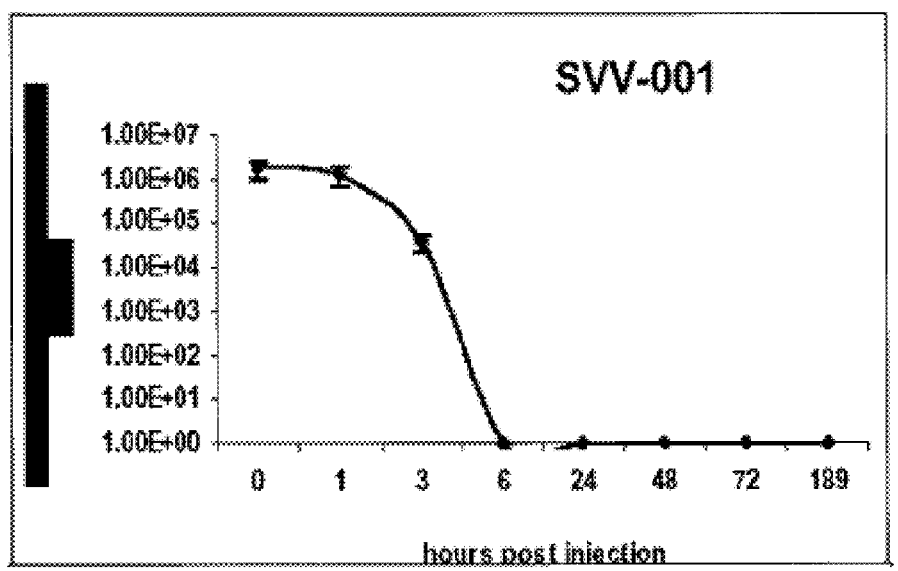
Figure 46D:
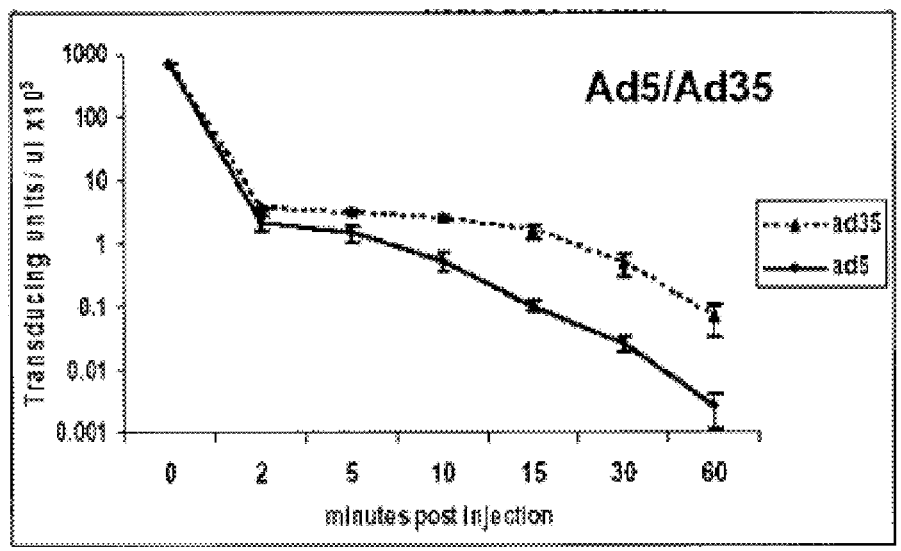

FIGS. 46C-46D presents data relating to SVV clearance in vivo. The figures show that SVV exhibits a substantially longer resident time in the blood compared to similar doses of i.v. adenovirus (Example 7), and therefore SVV has a slower clearance rate than adenovirus in vivo. Following a single intravenous (i.v.) dose, SVV remains present in the blood for up to 6 hours (FIG. 46C; FIG. 46C is a duplication of FIG. 46A for comparison purposes to FIG. 46D), whereas adenovirus is cleared or depleted from the blood in about an hour (FIG. 46D).

Figure 47:
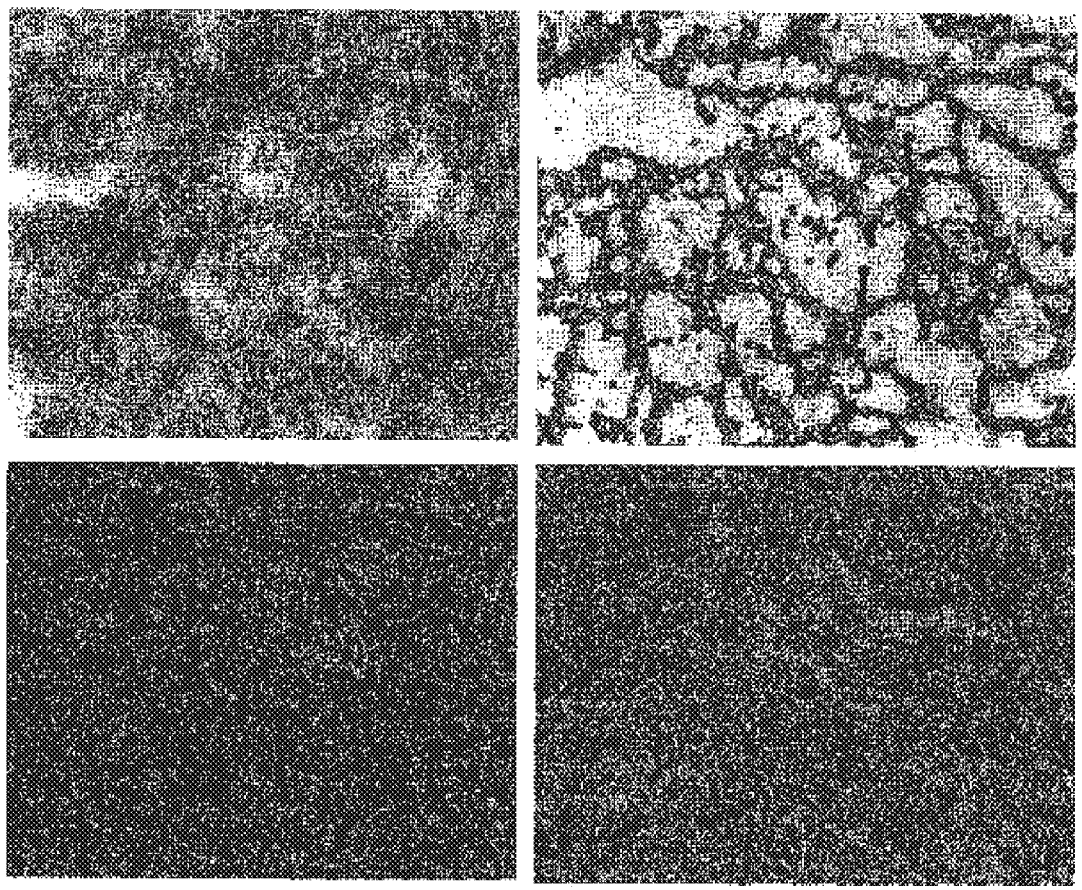

FIG. 47 shows immunohistochemistry and hematoxylin and eosin (H&E) staining of H446 xenograft sections (Example 7). H446 tumor bearing nude mice were treated with Hank's balanced salt solution (HBSS) or SVV at a dose of $1\times10^{12}$ vp/kg by tail vein injection. The mice were sacrificed at 3 days post-injection and the tumors were collected. The virus proteins in the tumor cells are visualized by immunohistochemistry using SVV-specific mouse antibodies (upper panels). The general morphology of H446 tumor cells collected from HBSS or SVV treated mice were stained by H&E stain (lower panels).

Figure 48:
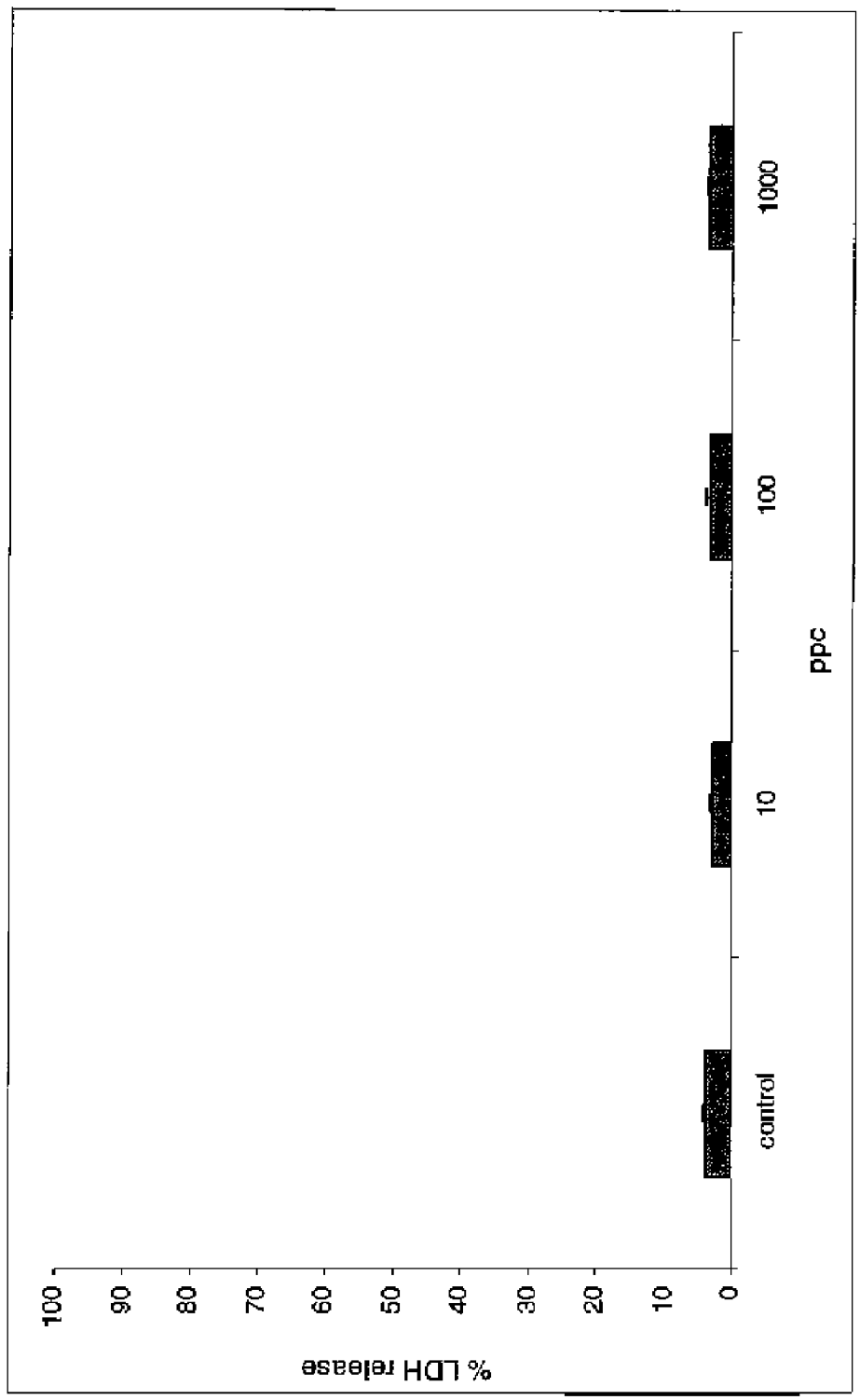

FIG. 48 shows SVV mediated cytotoxicity in primary human hepatocytes (Example 9). Primary human hepatocytes plated in collagen coated 12-well plates were infected with SVV at 1, 10 and 100 and 1000 particles per cell (ppc). Three days after infection, the cell associated lactate dehydrogenase (LDH) and LDH in the culture supernatant were measured separately. Percent cytotoxicity was determined as a ration of LDH units in supernatant over maximal cellular LDH plus supernatant LDH.

Figure 49:
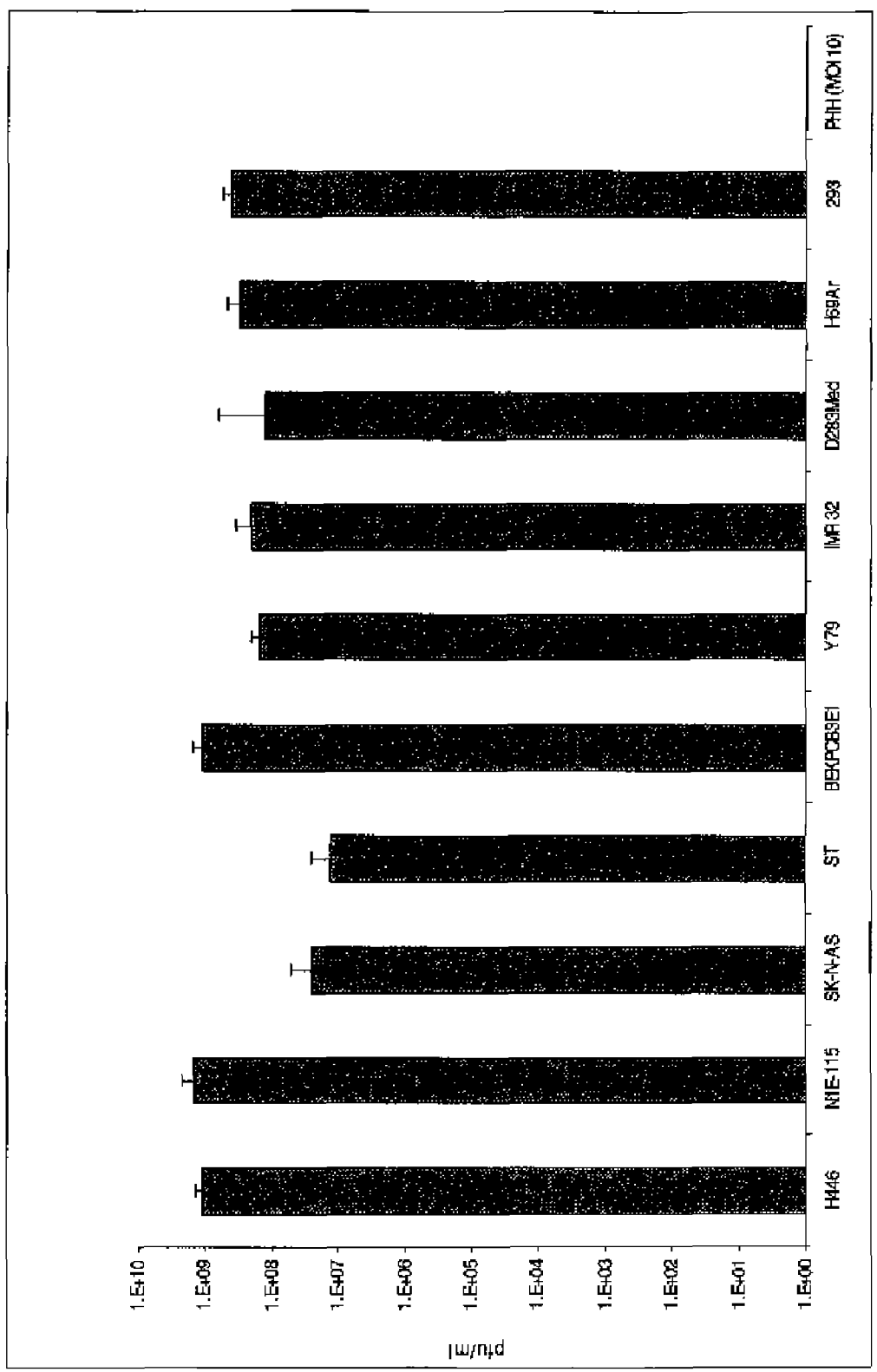

FIG. 49 shows virus production by SVV in selected cell lines. To assess the replicative abilities of SVV, selected normal cells and tumor cells were infected with SVV at one virus particle per cell (ppc) (Example 9). After 72 hours, cells were harvested and CVL was assayed for titer on PER.C6 cells. For each cell line, the efficiency of SVV replication was expressed as plaque forming units per milliliter (pfu/ml).

Figure 50:
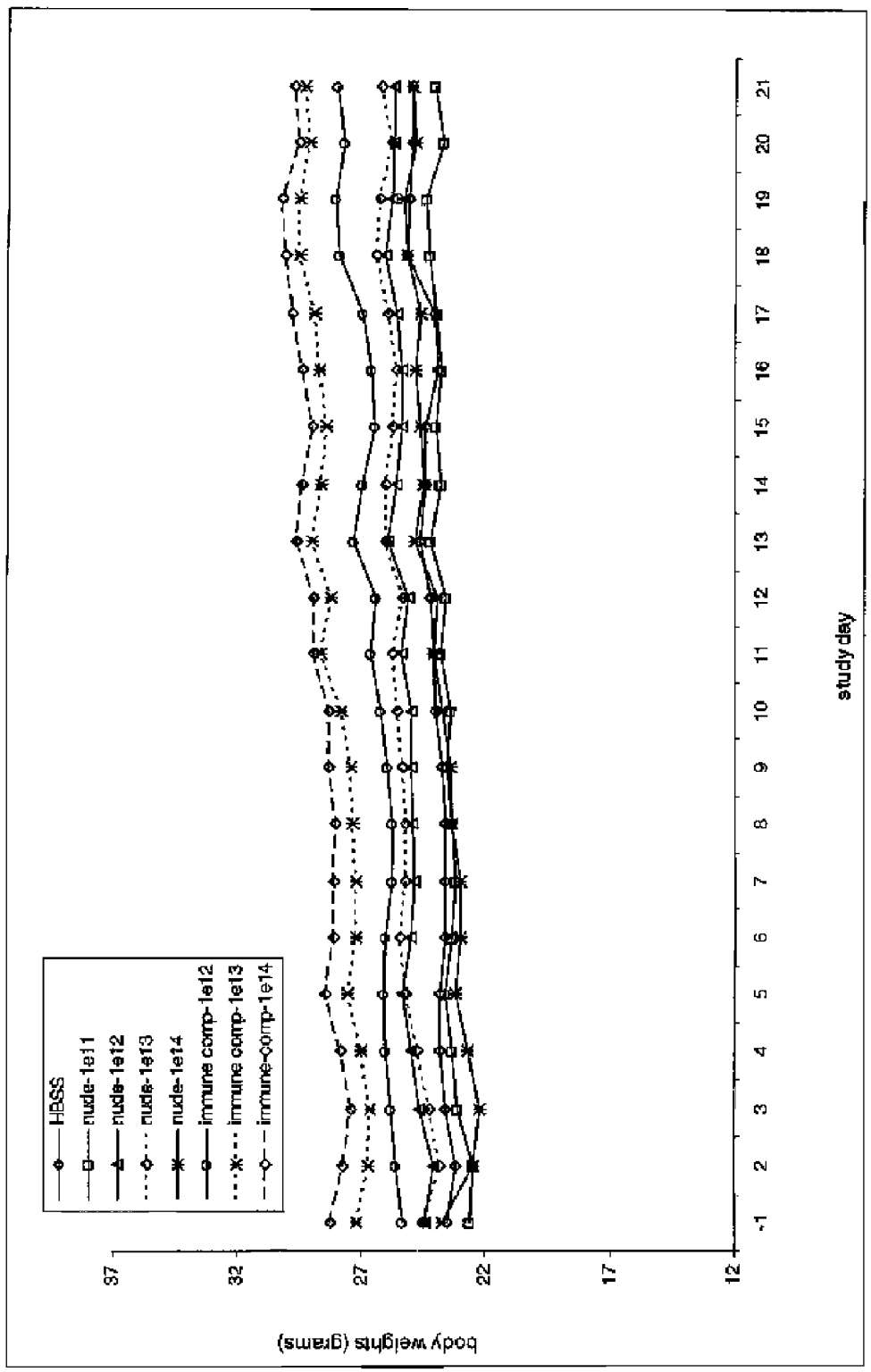

FIG. 50 shows toxicity in nude and CD1 mice according to body weights (Example 10). The mean body weight of mice in each treatment group were measured different days post virus administration. Mice were injected with a single dose of SVV or PBS by tail vein on day 1.

Figure 51:
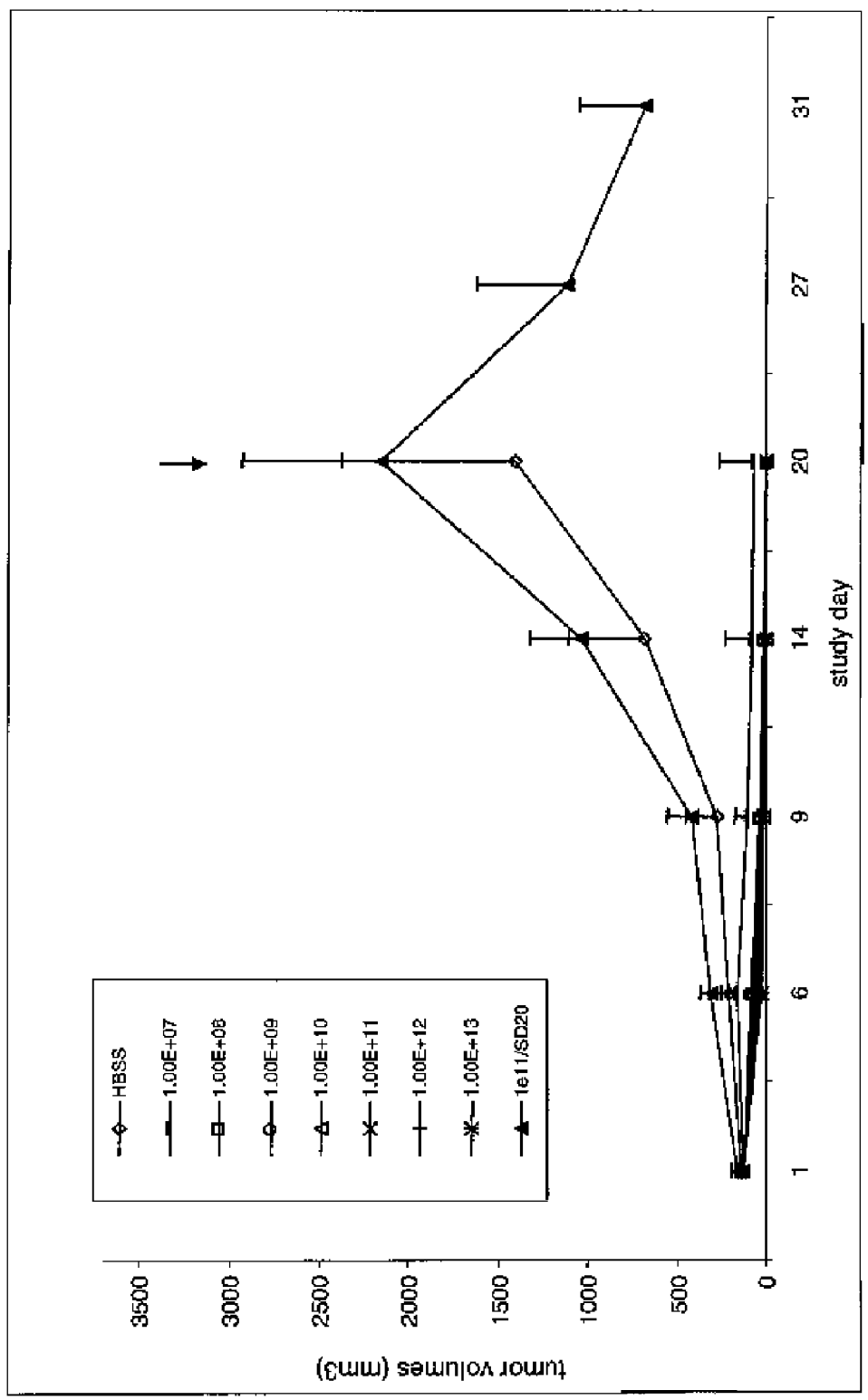

FIG. 51 shows efficacy in a H446 xenograft model. H446 tumors are established in nude mice and the mice are sorted into groups (n=10) and treated via tail vein injection with either HBSS or six different doses of SVV (Example 11). On study day 20, five mice from the HBSS group that bear large tumors (mean tumor volume=2000 mm$^3$) were injected with $1\times10^{11}$ vp/kg (indicated by an arrow). Data is expressed as mean tumor volume+standard deviation (SD).

Figure 52:
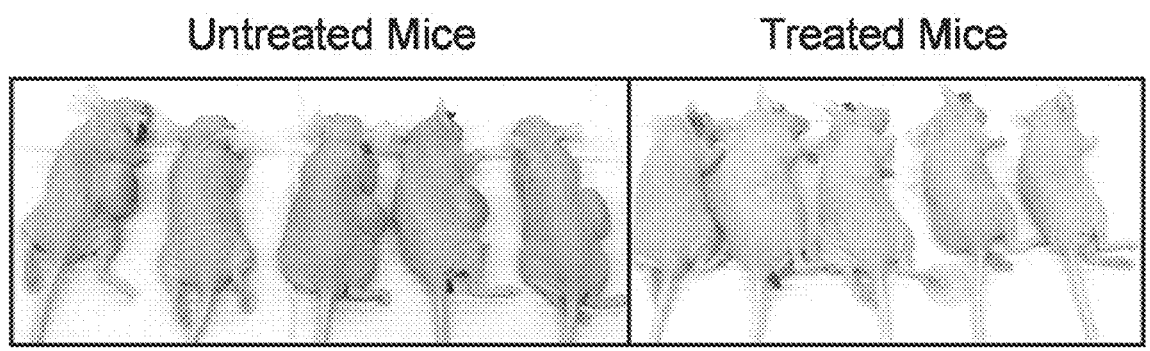

FIG. 52 shows a picture of H446 xenograft nude mice that have been untreated or treated with SVV (Example 11). The efficacy of SVV is very robust in that 100% of large pre-established tumors were completely eradicated. SVV-treated mice show neither clinical symptoms nor recurrence of tumors for at least 200 days following injection.

Figure 53:
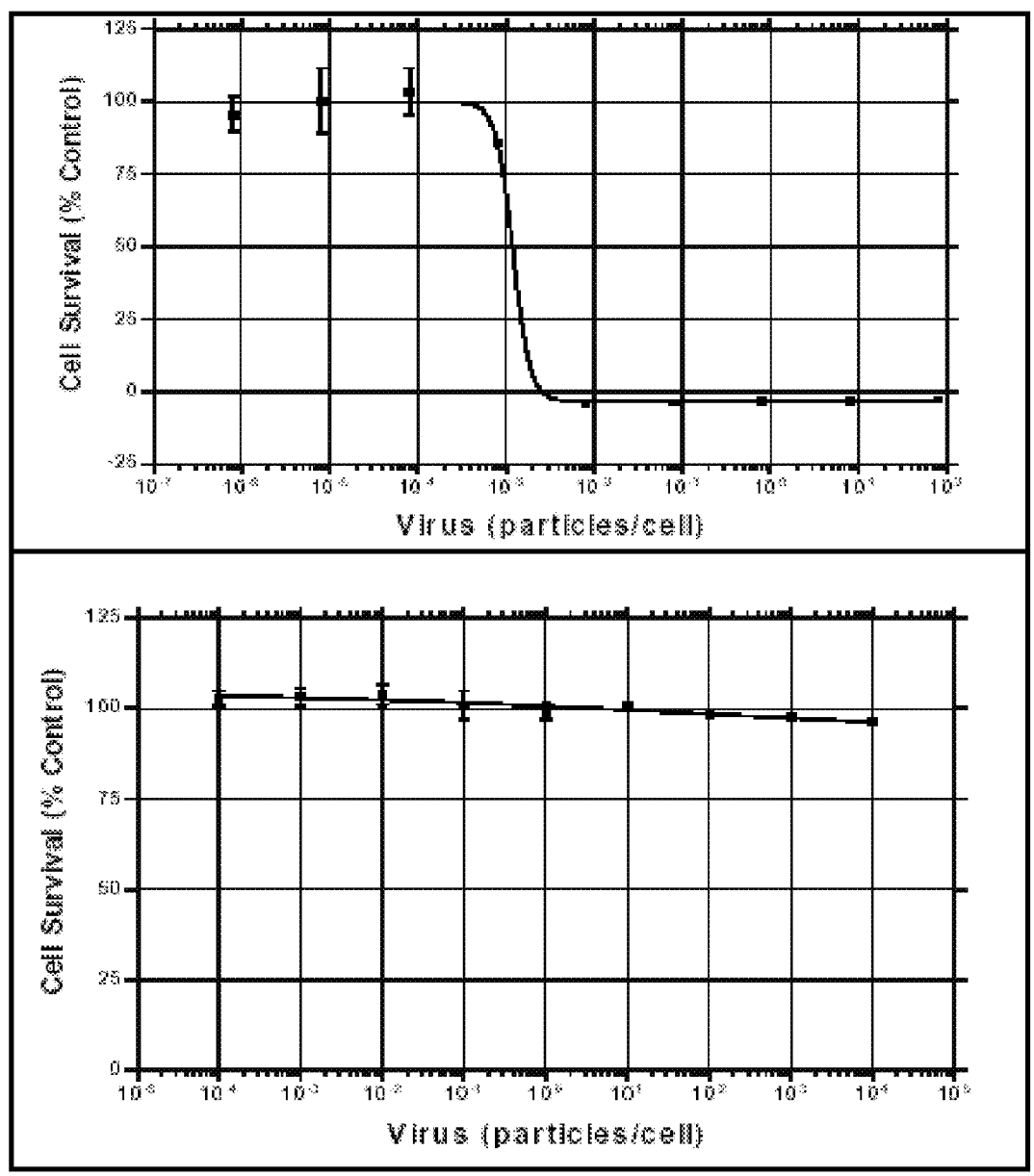

FIG. 53 presents data relating to SVV tumor specificity and efficacy in vitro (Example 11). The graphs show cell survival following incubation of either H446 human small cell lung carcinoma (SCLC) tumor cells (top graph) or normal human H460 cells (bottom graph). SVV specifically killed the tumor cells with an EC$_{50}$ of approximately 10$^{-3}$ particles per cell. In contrast, normal human cells were not killed at any concentration of SVV.

Figure 54:
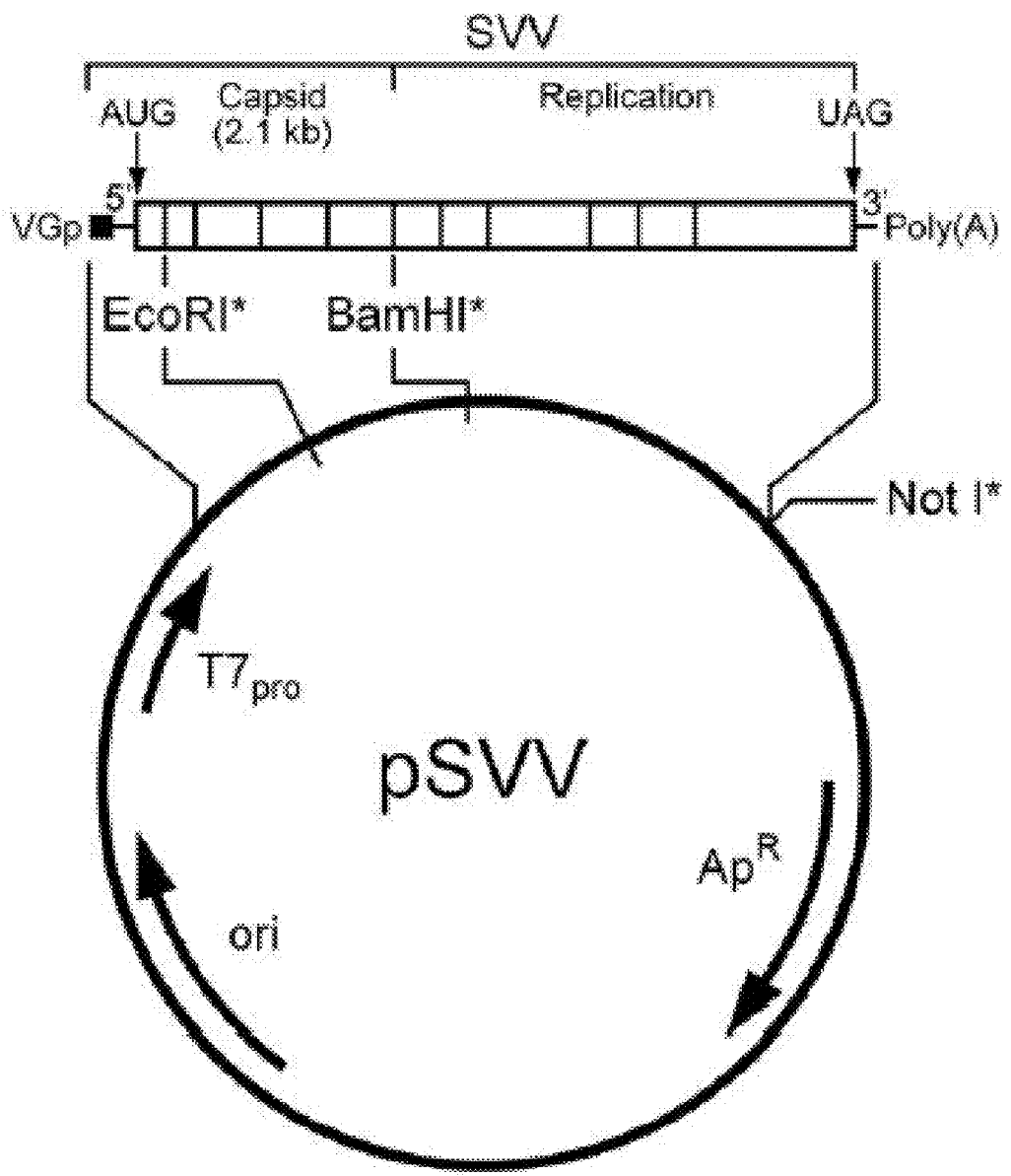

FIG. 54 depicts a representative plasmid containing the complete genome of SVV (Example 15). The presence of the T7 promoter on the vector upstream of the SVV sequence allows for the in vitro transcription of the SVV sequence such that SVV RNA molecules can be generated.

Figure 55:
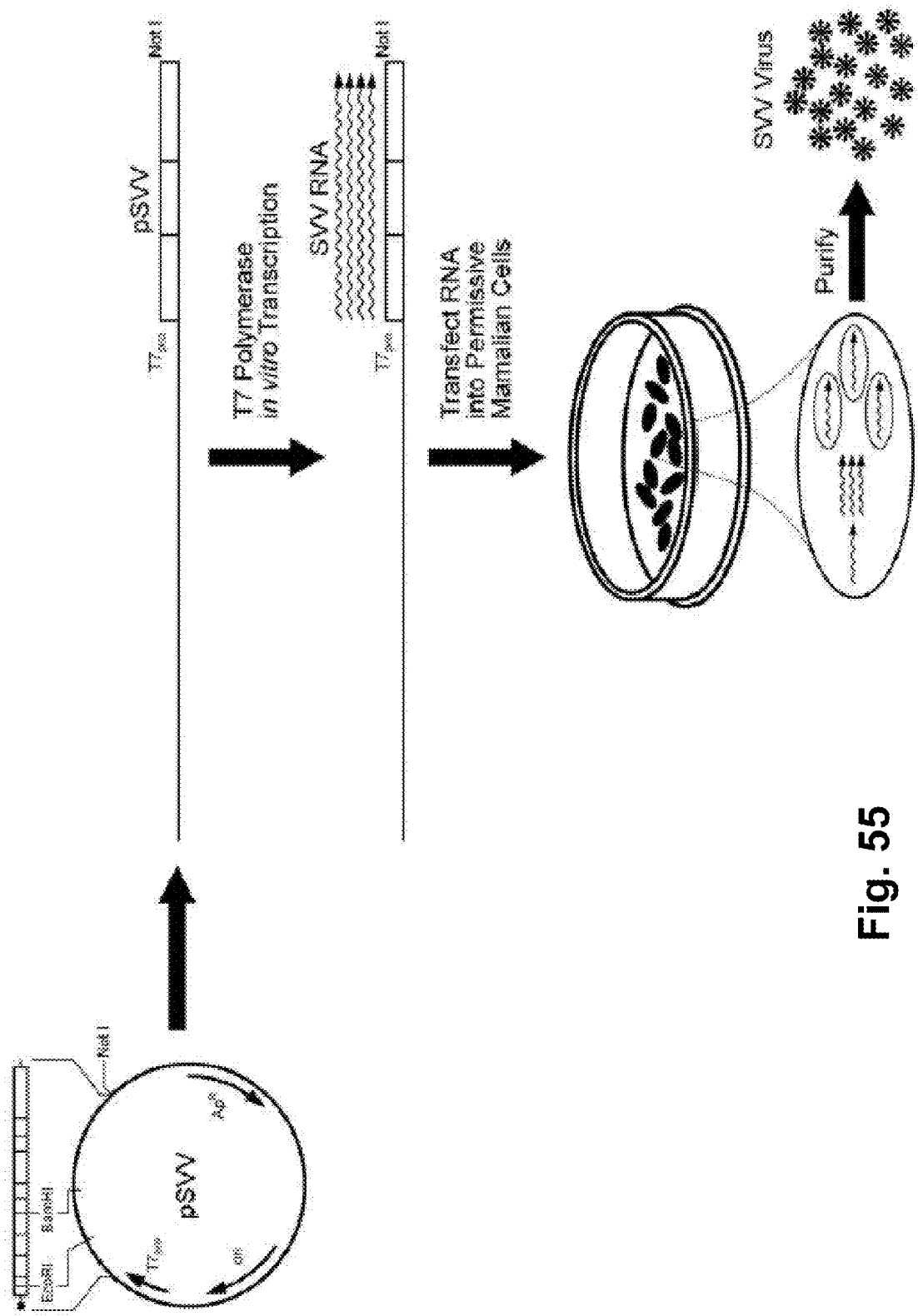

FIG. 55 depicts a schematic for the construction of a full-length and functional genomic SVV plasmid and subsequent SVV virus production (Example 16). To obtain a functional genomic SVV clone, the complete genome of a SVV can be cloned into a vector with a T7 promoter. This can be accomplished by making cDNA clones of the virus, sequencing them and cloning contiguous pieces into one plasmid, resulting in the plasmid depicted "pSVV". The plasmid with the full genome of SVV can then be reverse-transcribed to generate SVV RNA. The SVV RNA is then transfected into permissive mammalian cells and SVV virus particles can then be recovered and purified.

Figure 56:
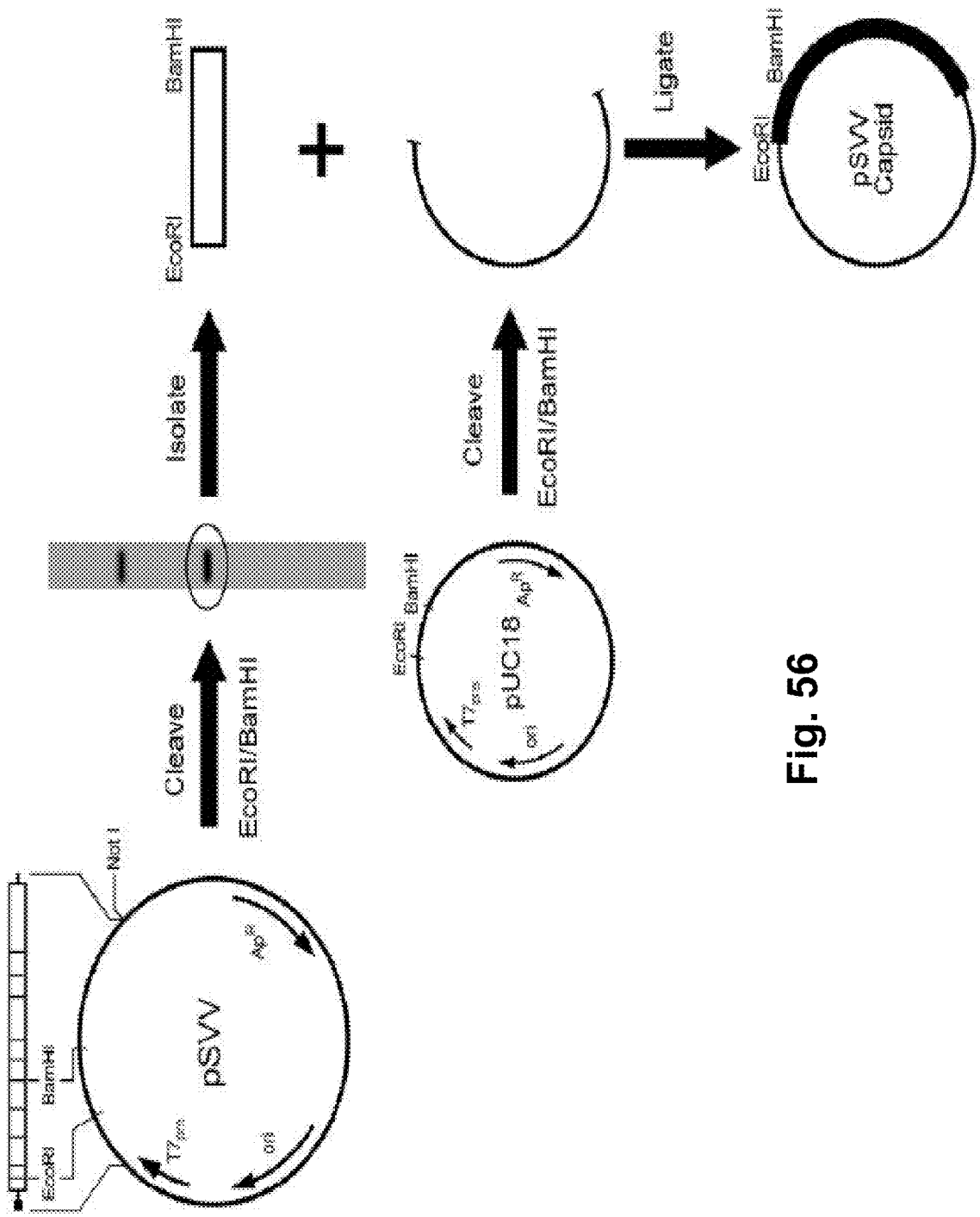

FIG. 56 depicts a schematic for the construction of a vector ("pSVV capsid") containing the coding sequence (i.e., coding regions for 1A-1D) for the SVV capsid (Example 16). The pSVV capsid can then be used to generate a library of SVV capsid mutants.

Figure 57:
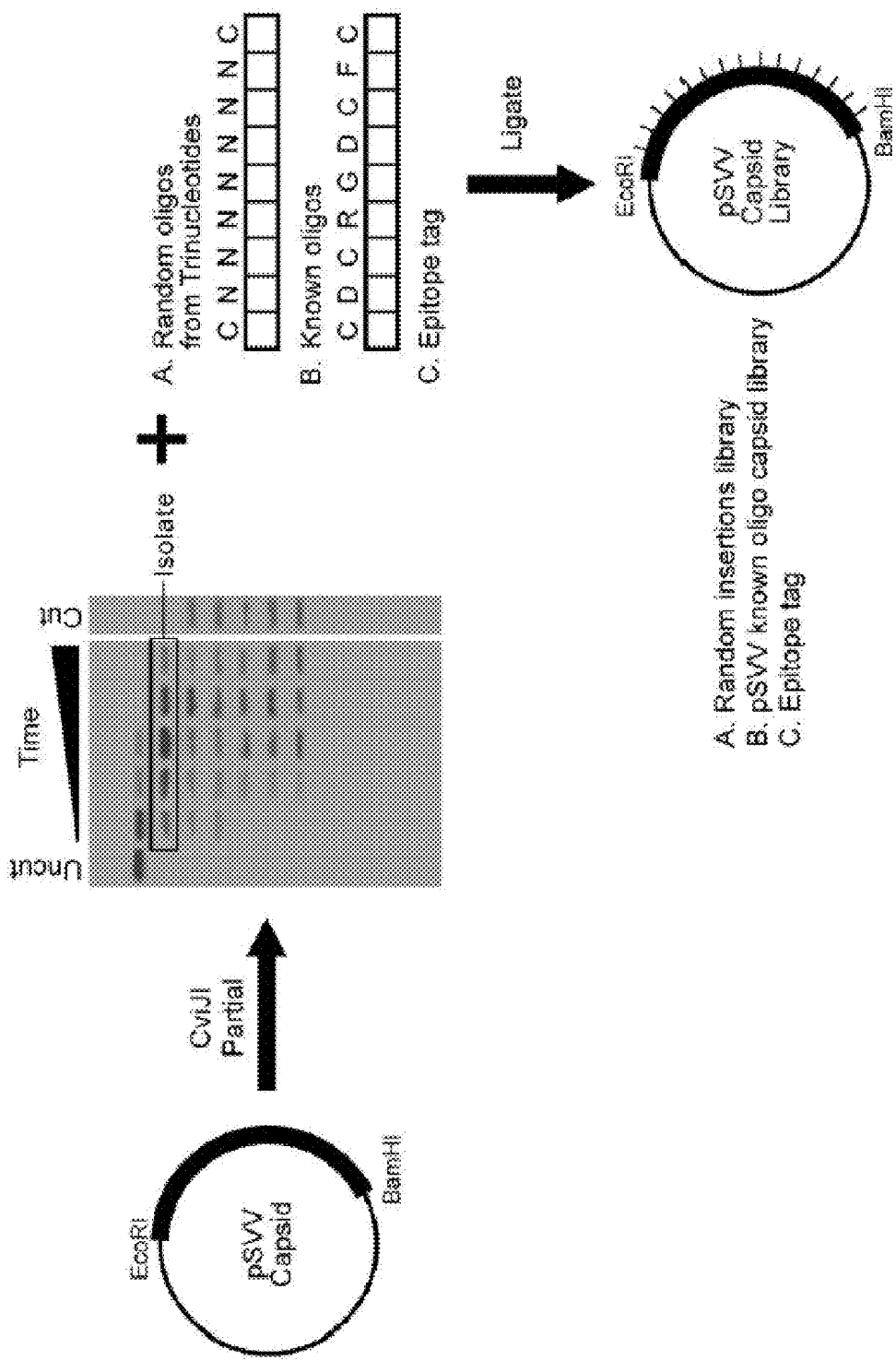

FIG. 57 shows one method of mutating the SVV capsid for the generation of a library of SVV capsid mutants (Example 16). The figure illustrates the insertion of an oligonucleotide sequence at random sites of the plasmid. The oligonucleotides can be random oligonucleotides, oligonucleotides with known sequences, or an oligonucleotide encoding an epitope tag. In the figure, the restriction enzyme CviJI randomly cleaves the pSVV capsid DNA. Linearized pSVV capsid DNA that has been cut at a single site is isolated and purified from a gel, and ligated with oligonucleotides.

Figure 58:
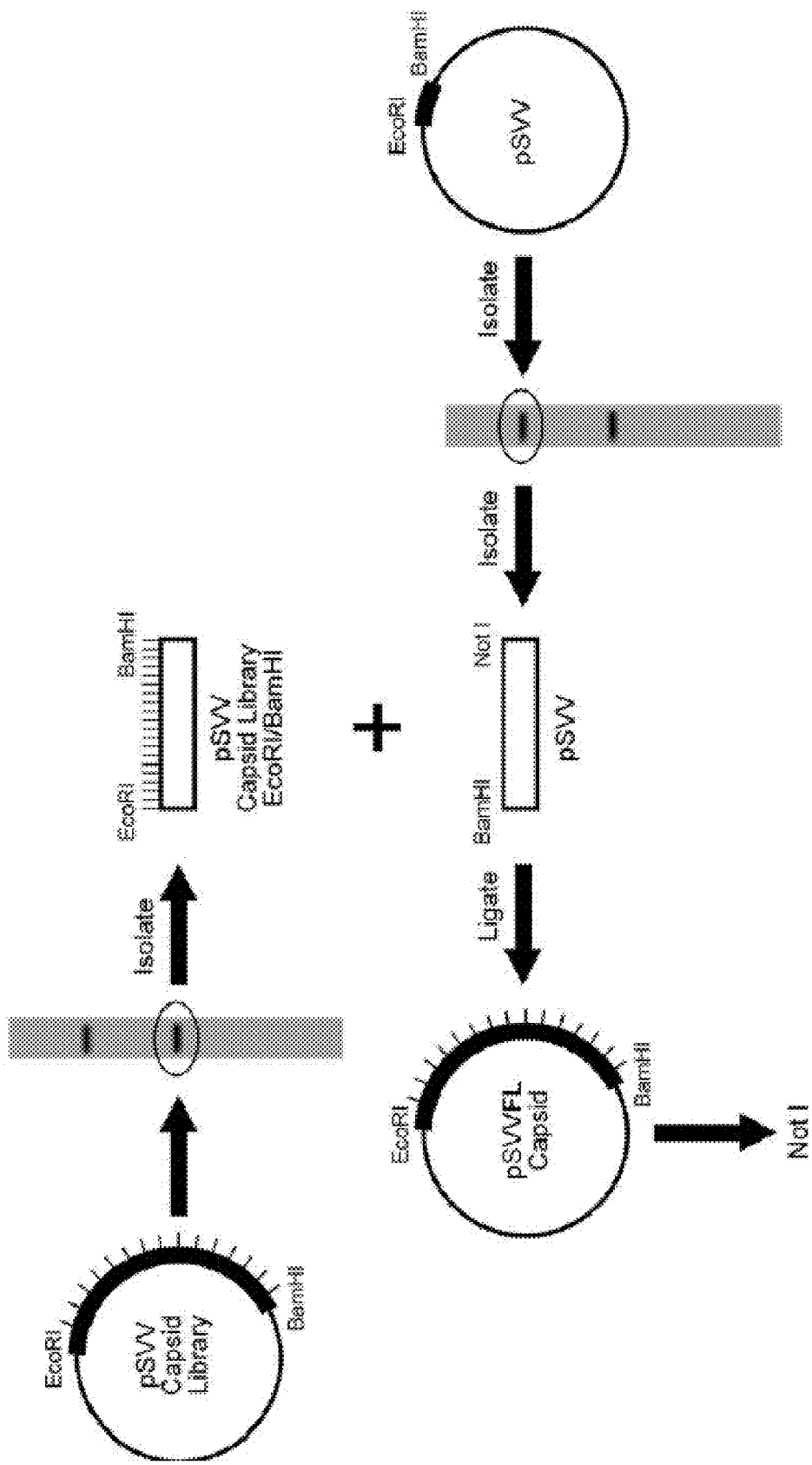

FIG. 58 presents a scheme to generate a library of full-length SVV mutants comprising sequence mutations in the capsid encoding region (Example 16). For example, the capsid encoding region from a pSVV capsid mutant library (generated according to the scheme depicted in FIG. 57, for example) is isolated by restriction digestion and gel purification. The vector containing the full-length SVV sequence is also digested such that the capsid encoding region is cut out. The capsid encoding region from the pSVV capsid mutant library is then ligated to the pSVV vector that is missing its wild-type capsid sequence, thereby generating a library of full-length SVV mutants (the "pSVVFL" vector) having a plurality of mutations in the capsid encoding region.

Figure 59:
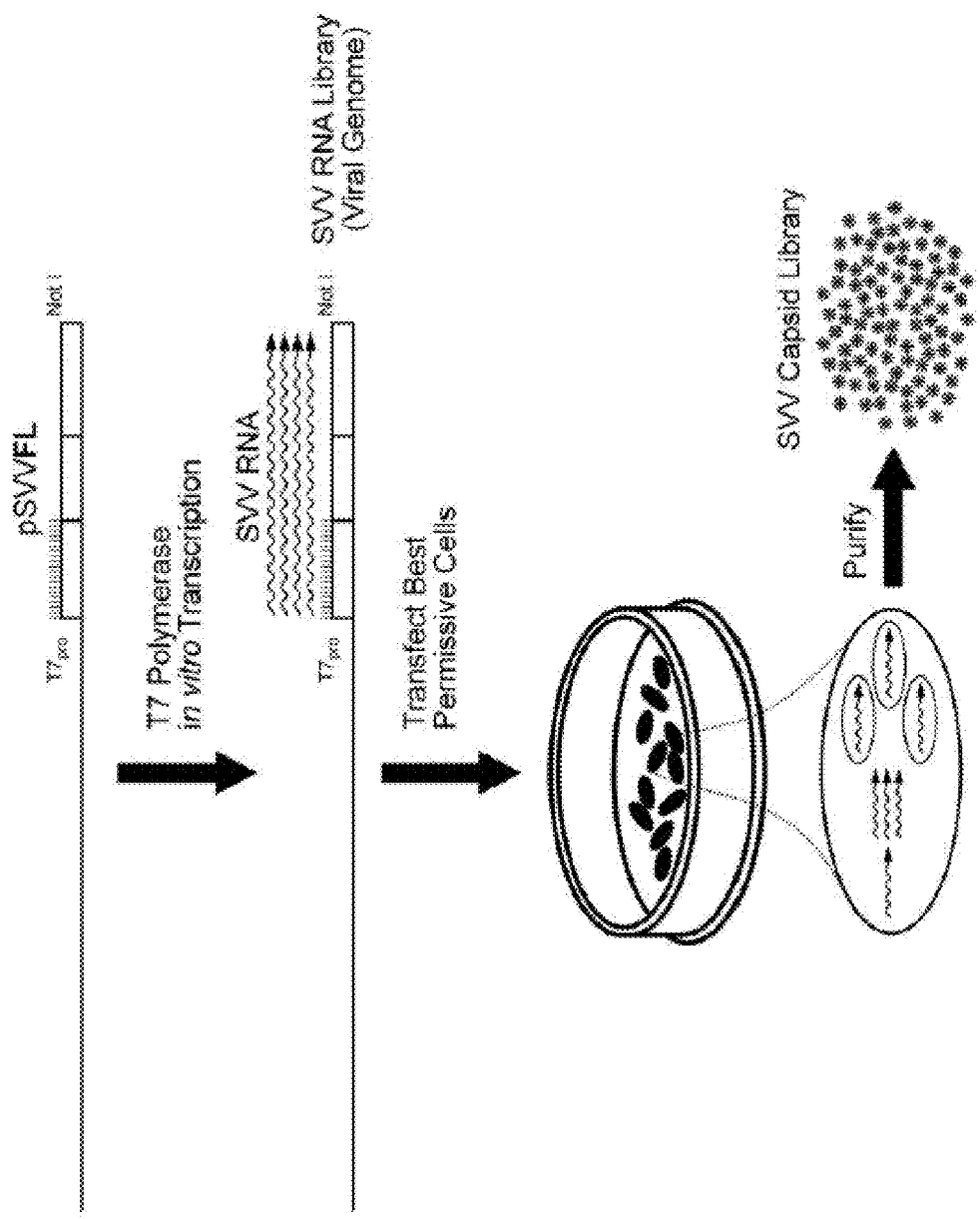

FIG. 59 presents a general method for producing the SVV virus particles comprising a library of capsid mutations (Example 16). The pSVVFL vector is reverse-transcribed to generate SVV RNA. The SVV RNA is transfected into permissive cells, wherein SVV mutant virus particles are produced. The virus particles lyse the cells and a population of SVV virus particles comprising a plurality of capsid variants, "SVV capsid library," are isolated.

Figure 60:
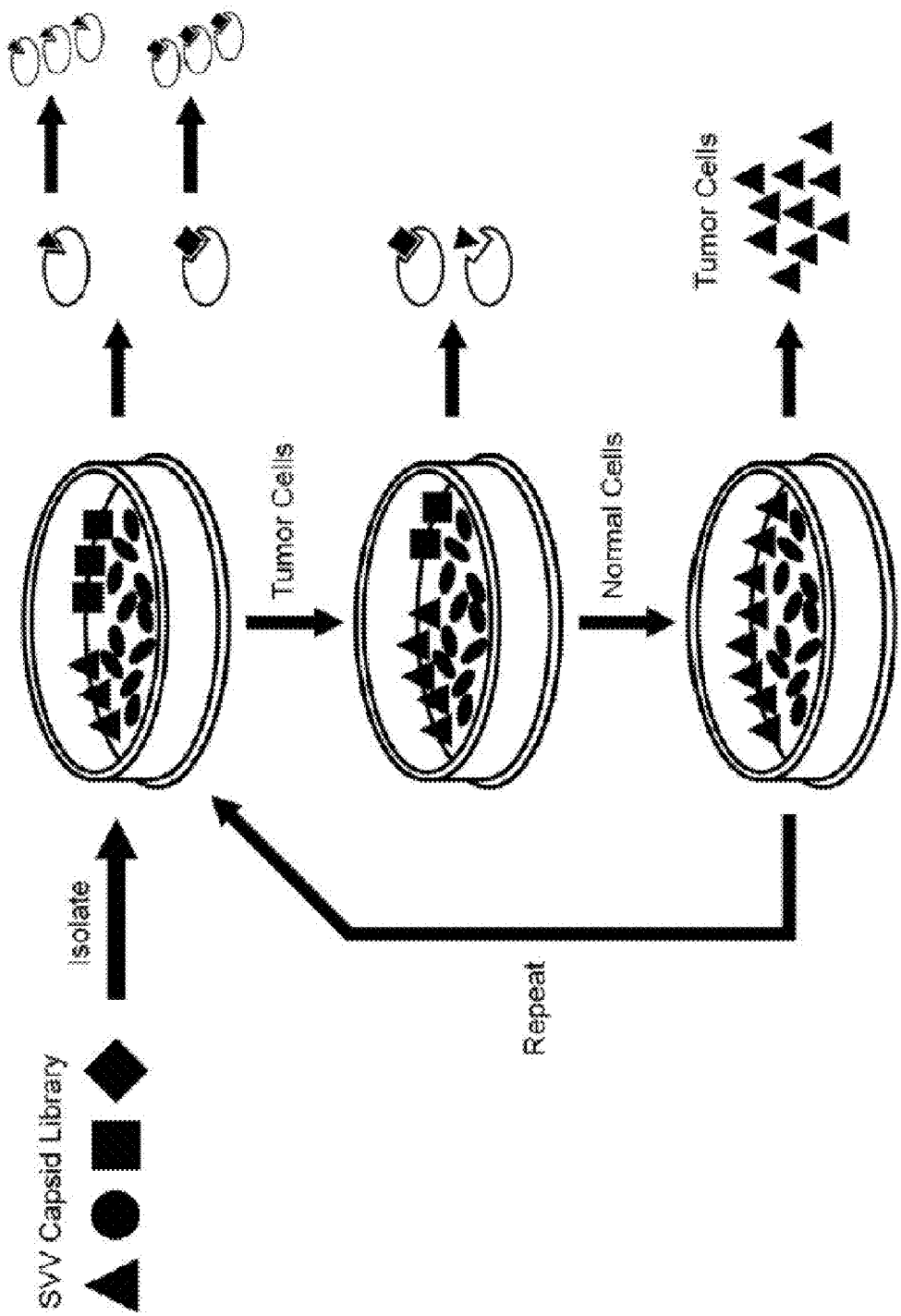

FIG. 60 shows a general method for screening SVV capsid mutants that can specifically infect tumor cells while being unable to infect non-tumor cells. The SVV capsid library is incubated with a tumor cell line or tissue of interest. After an initial incubation period, the cells are washed such that SVV virus particles that were unable to gain entry into the cells are eliminated. The cells are then maintained in culture until viral lysis is observed. Culture supernatant is then collected to isolate SVV capsid mutants that were able to lytically infect the tumor cell. These viruses can then be grown-up by infecting a known permissive cell-line prior to a counter-screen. A counter-screen is performed by incubating the SVV capsid mutant viruses that were able to infect the tumor cell with normal cells. Only those viruses that remain unbound in the supernatant are collected, thereby isolating mutant SVV viruses that have tumor-specificity. This process can be repeated to further refine the isolation of SVV tumor-specific viruses.

Figure 61:
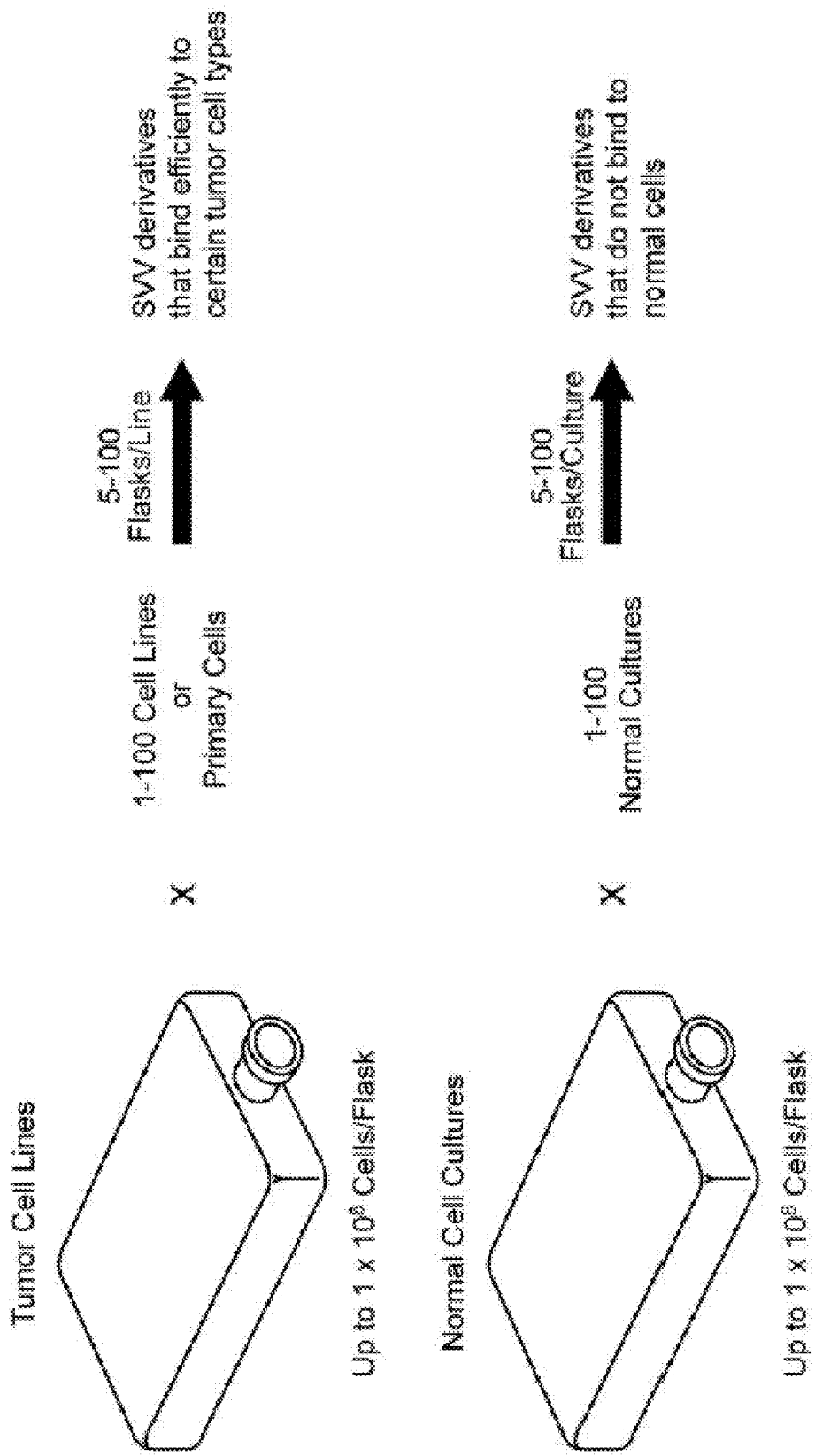

FIG. 61 shows a traditional method for testing whether virus mutants can bind and/or infect cell lines. Traditional methods require what are often inefficient methods for growing cell-lines, i.e. flasks, such that a mass-screen of a library of virus mutants in relation to a number of different cell-lines becomes burdensome.

Figure 62:
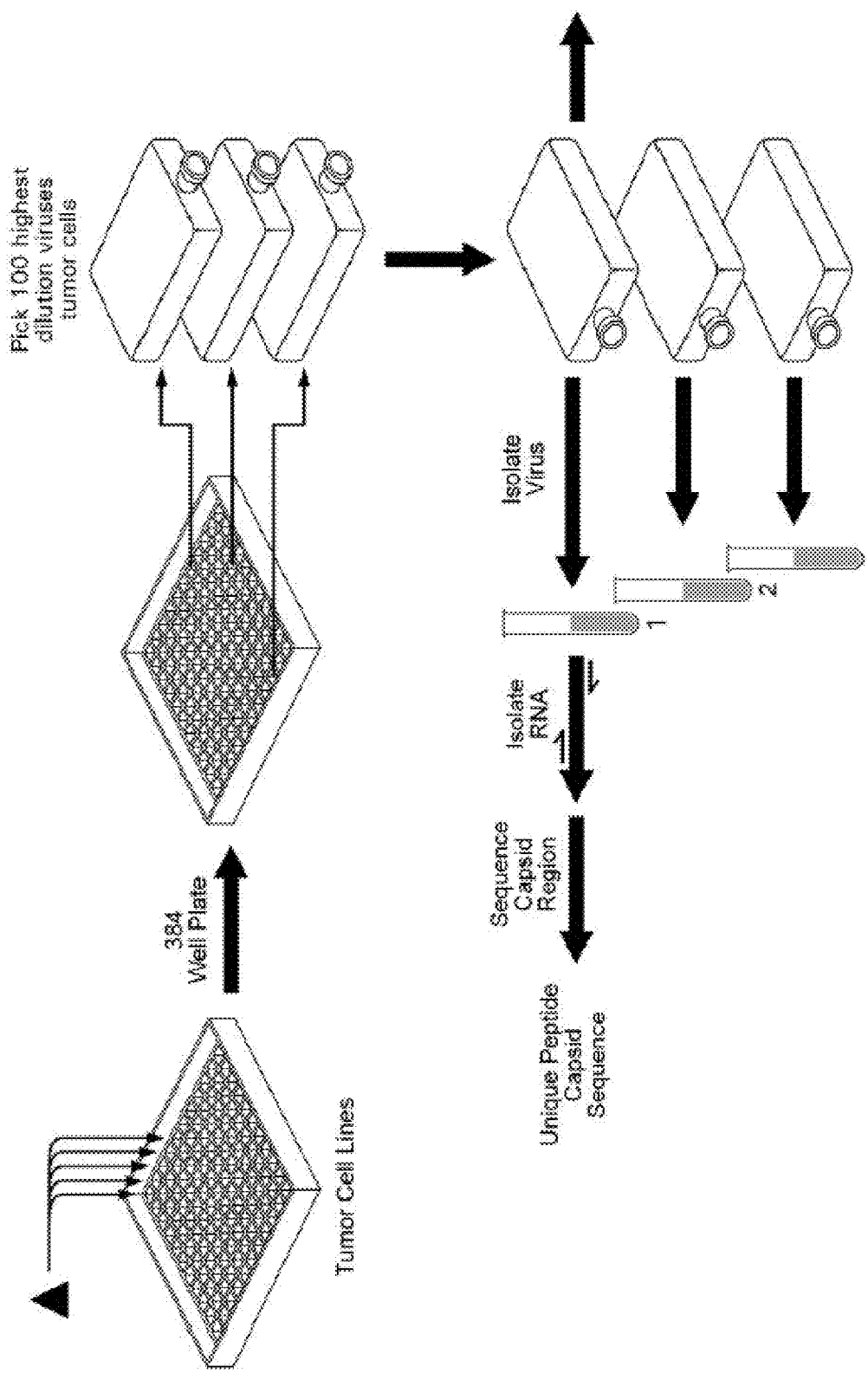

FIG. 62 shows a high-throughput method of the invention for screening virus mutants that have the ability to specifically infect different cell-lines (Example 16). In this figure, a number of different tumor cell-lines are grown in a 384 well-plate. To each well, a sample of a virus is added (for example, a sample of a SVV capsid library). From those wells which show cytopathic effects, the media is collected such that any viruses in the media can be amplified by infecting permissive cell lines (for example, for SVV, H446 or PER.C6) in flasks or large tissue culture plates. The viruses are grown such that the RNA can be isolated and the sequence analyzed to determine the encoded peptide sequence inserted by the oligonucleotide-insertion mutagenesis of the capsid. The peptide itself can then be tested to determine whether it can bind to a tumor cell-type specifically.

FIG. 63 shows another high-throughput screening schematic (Example 16). Tumor and normal cell lines are grown in multi-well plates. Viruses are added to each well to test whether the cells are killed by virus-mediated lysis. Cytopathic effects can be quickly assayed by reading the light-absorbance in each well. Viruses from the wells showing cytopathic effects are grown up and tested in further in vitro (re-testing of tumor and normal cell lines) and in vivo models (testing whether the virus can kill explanted tumors in mice).

FIG. 64 shows that SVV capsid mutants (SEQ ID NOS: 45-48, respectively, in order of appearance) having new tumor-specific tropisms can be analyzed to generate tumor-selective peptides. Those SVV capsid mutants that enable the specific infection of a tumor cell line are sequenced to determine the peptide encoded by the oligonucleotide insertion. An amino acid consensus sequence can thereby be determined from the successful capsid mutants. Peptides having the consensus sequence can then be tested to determine whether they can bind specifically to the tumor cell-type in question. Tumor-selective peptides can then be attached to toxins or drugs in order to serve as tumor-specific targeting vehicles.

FIG. 65 illustrates that an SVV capsid library can be first tested in vivo. Mice (including normal, athymic, nude, CD-1 transgenics, etc.) can be explanted with a specific tumor. These mice are then injected with a SVV derivative library, such as a SVV capsid library. At certain time points, tumor cells are recovered from the mice, such that in those mice that display the elimination of a tumor, viruses will be isolated from initial tumor samples and grown-up in permissive cell lines.

FIG. 66 shows a clinical testing program for the SVV derivatives of the present invention.

FIG. 67 illustrates that SVV derivatives (with new tumor tropisms) encoding epitope tags in their capsid can be used for a variety of purposes. They can be used as a screening reagent to detect whether a specific tumor cell is present in tissue samples by assaying for the presence of the epitope. Alternatively, toxins or other therapeutics can be attached to the epitope tag, and the virus then administered to patients. Further, wild-type or derivative SVV can be irradiated or inactivated such that the virus particle itself is used as a therapeutic device. Either the virus particle induces cellular apoptosis due to the presence of apoptosis-inducing peptides, or the particle can have a toxin or some other therapeutic attached such that the virus is used a specific-targeting delivery device.

FIG. 68 shows the basic life-cycle of the picornavirus.

FIG. 69 shows a comparison of the polypeptide lengths of SVV compared to other picornaviruses.

FIG. 70 lists an amino acid comparison of the picornavirus 2A-like NPG/P proteins (SEQ ID NOS: 49-110, respectively, in order of appearance). The sequence for SVV is listed at residues 635-656 of SEQ ID NO:2.

FIG. 71 lists the amino acid sequence (SEQ ID NO:23) for EMCV-R.

FIG. 72 lists the amino acid sequence (SEQ ID NO:24) for EMCV-PV21 (Accession CAA52361).

FIG. 73 lists the amino acid sequence (SEQ ID NO:25) for EMCV-B (Accession P17593).

FIG. 74 lists the amino acid sequence (SEQ ID NO:26) for EMCV-Da (Accession P17594).

FIG. 75 lists the amino acid sequence (SEQ ID NO:27) for EMCV-Db.

FIG. 76 lists the amino acid sequence (SEQ ID NO:28) for EMCV-PV2 (Accession CAA60776).

FIG. 77 lists the amino acid sequence (SEQ ID NO:29) for EMCV-mengo (Accession AAA46547).

FIG. 78 lists the amino acid sequence (SEQ ID NO:30) for TMEV/DA (Accession AAA47928).

FIG. 79 lists the amino acid sequence (SEQ ID NO:31) for TMEV/GDVII (Accession AAA47929).

FIG. 80 lists the amino acid sequence (SEQ ID NO:32) for TMEV/BeAn8386 (Accession AAA47930).

FIG. 81 lists the amino acid sequence (SEQ ID NO:33) for TLV-NGS910 (Accession BAC58035).

FIG. 82 lists the amino acid sequence (SEQ ID NO:34) for VHEV/Siberia-55 (Accession AAA47931).

FIGS. 83A-83H present the full-length genomic sequence of SVV (SEQ ID NO:168) and the encoded polyprotein amino acid sequence (SEQ ID NO:169), where this full-length genomic sequence was obtained from SVV viruses grown from the SVV isolate having ATCC Patent Deposit Number PTA-5343. Specific features of the SVV genomic sequence, such as the specific coding regions for proteins cleaved from the polyprotein sequence are described herein.

FIGS. 84A-84D present the full-length genomic sequence of SVV (SEQ ID NO:168). The sequence was obtained from SVV grown from the SVV isolate having ATCC Patent Deposit Number PTA-5343.

FIGS. 85A-85B present the amino acid sequence of the full-length polyprotein of SVV (SEQ ID NO:169) encoded by the nucleotides 667-7209 of SEQ ID NO:168.

FIG. 86 provides a phylogenetic analysis or epidemiology of SVV with respect to the full-length genome and polyprotein sequence of SVV from SEQ ID NOS:168 and 169. SVV is a unique virus, phylogenetically similar to cardioviruses, but in a separate tree. The SVV-like picornaviruses are most likely in the same tree or genus as SVV due to the high level of sequence identity between SVV and the SVV-like picornaviruses (see FIGS. 87-89) and due to the ability of antibodies raised against SVV-like picornaviruses to bind SVV (and vice versa) (see Example 4, Part III, Serum Studies).

FIGS. 87A-87D show a nucleic acid sequence comparison between SVV and some SVV-like picornaviruses in the areas of the P1 structural region and 2A. In particular, the comparison is in the VP2(partial)-VP3-VP1-2A(partial) regions. The listed SVV sequence is SEQ ID NO:170; the listed sequence for isolate IA 89-47752 is SEQ ID NO:171; the listed sequence for isolate CA 131395 is SEQ ID NO:172; the listed sequence for isolate NC 88-23626 is SEQ ID NO:173; the listed sequence for isolate MN 88-36695 is SEQ ID NO:174; the listed sequence for isolate NJ 90-10324 is SEQ ID NO:175; the listed sequence for isolate IL 92-48963 is SEQ ID NO:176; the listed sequence for isolate LA 1278 (97-1278) is SEQ ID NO:177; and the listed consensus sequence is SEQ ID NO:178.

FIG. 88 shows a nucleic acid sequence comparison between SVV and isolates IA 89-47752 and CA 131395 in the 2C coding region (partial). The listed SVV sequence is SEQ ID NO:179; the listed sequence for isolate IA 89-47752 is SEQ ID NO:180; the listed sequence for isolate CA 131395 is SEQ ID NO:181; and the listed consensus sequence is SEQ ID NO:182.

FIGS. 89A-89B show a nucleic acid sequence comparison between SVV and isolates NC 88-23626, MN 88-36695, IA 89-47752, NJ 90-10324, IL 92-48963, LA 97-1278, and CA 131395 in the 3D polymerase coding region (partial) and 3' UTR region. The listed sequences are SVV (SEQ ID NO:183), NC 88-23626 (SEQ ID NO:184), MN 88-36695 (SEQ ID NO:185), IA 89-47752 (SEQ ID NO:186), NJ 90-10324 (SEQ ID NO:187), IL 92-48963 (SEQ ID NO:188), LA 97-1278 (SEQ ID NO:189), CA 131395 (SEQ ID NO:190), and consensus sequence (SEQ ID NO:191).

Figure 90A:
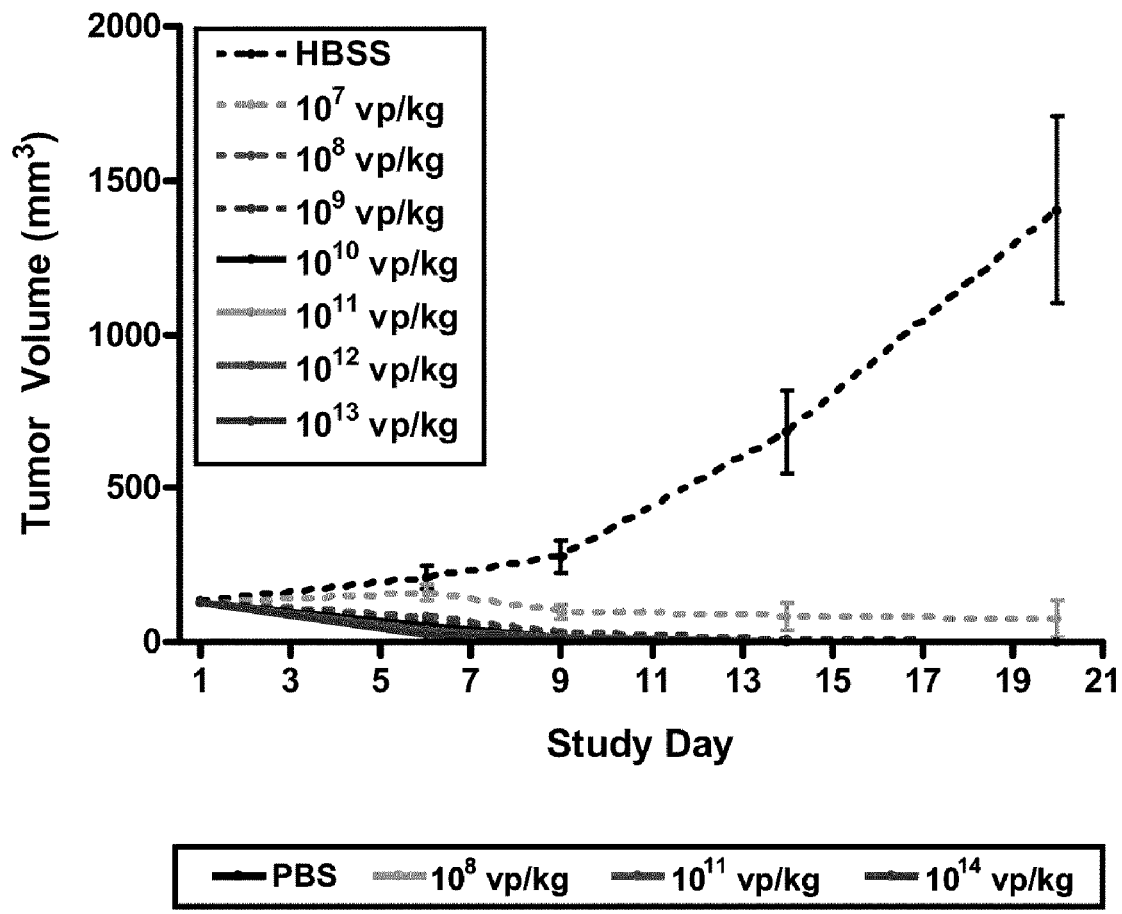
Figure 90B:
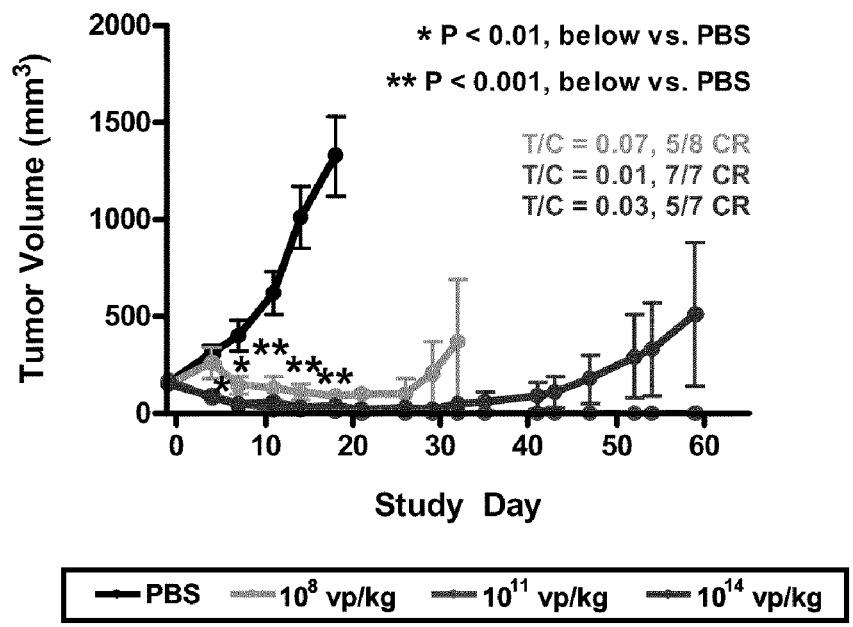
Figure 90C:
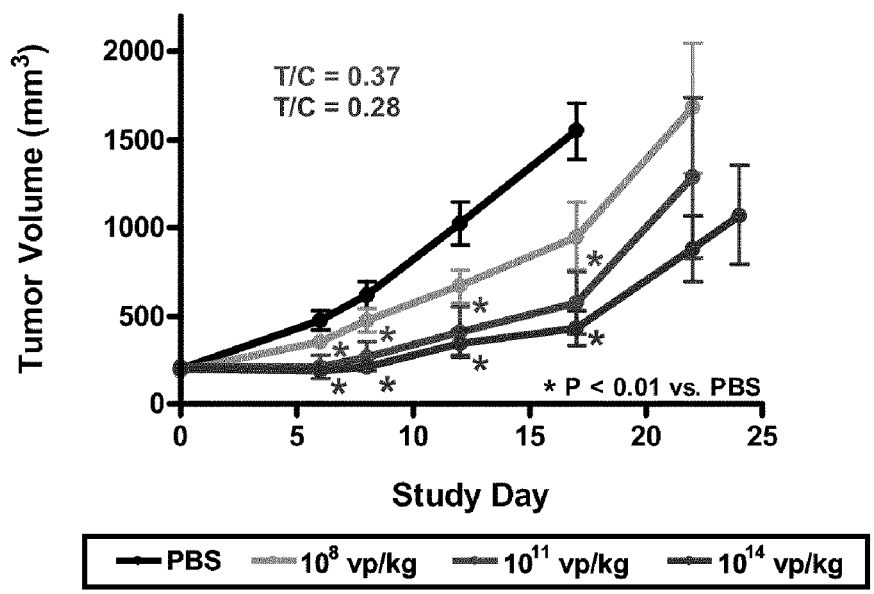
Figure 90D:
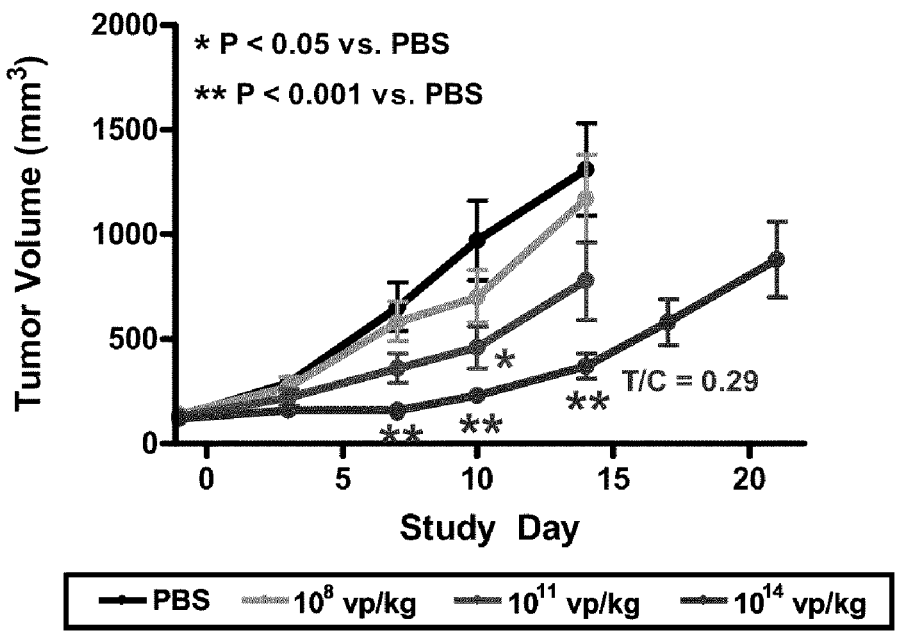
Figure 90E:
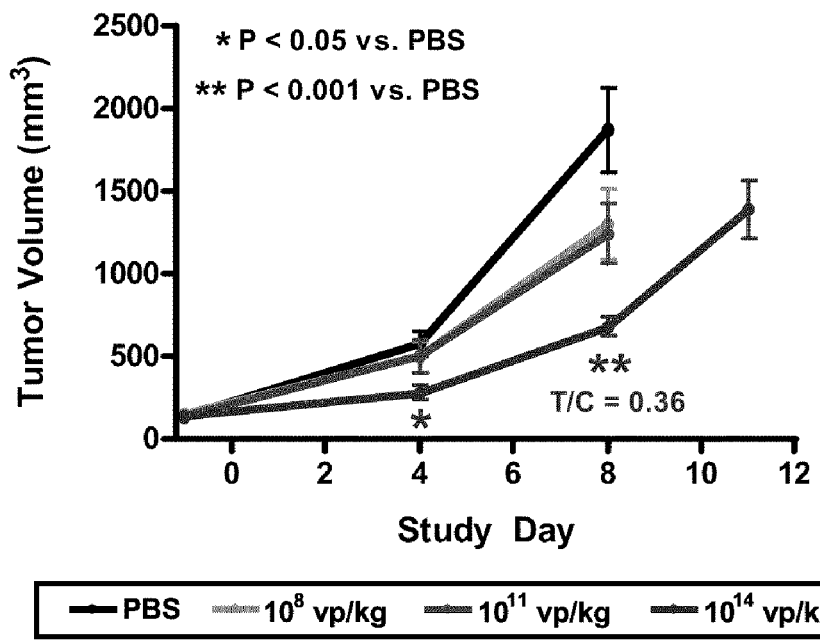

FIGS. 90A-90E show that a single dose of SVV is efficacious in reducing the size and preventing the growth of explanted tumors in mice. FIG. 90A shows that SVV can reduce the size and prevent the growth of explanted H446 human SCLC tumors ($ED_{50}$=0.0007). FIG. 90B shows that SVV can reduce the size and prevent the growth of explanted Y79 human retinoblastoma tumors ($ED_{50}$=0.0007). FIG. 90C shows that SVV can reduce the size and prevent the growth of explanted H69AR human SCLC-MDR (multi drug resistant) tumors ($ED_{50}$=0.05). FIG. 90D shows that SVV can reduce the size and prevent the growth of explanted H1299 human HSCLC tumors ($ED_{50}$=4.8). FIG. 90E shows that SVV can reduce the size and prevent the growth of explanted N1E-115 murine neuroblastoma tumors in A/J mice (normal immunocompetent mice) ($ED_{50}$=0.001).

Figure 91:
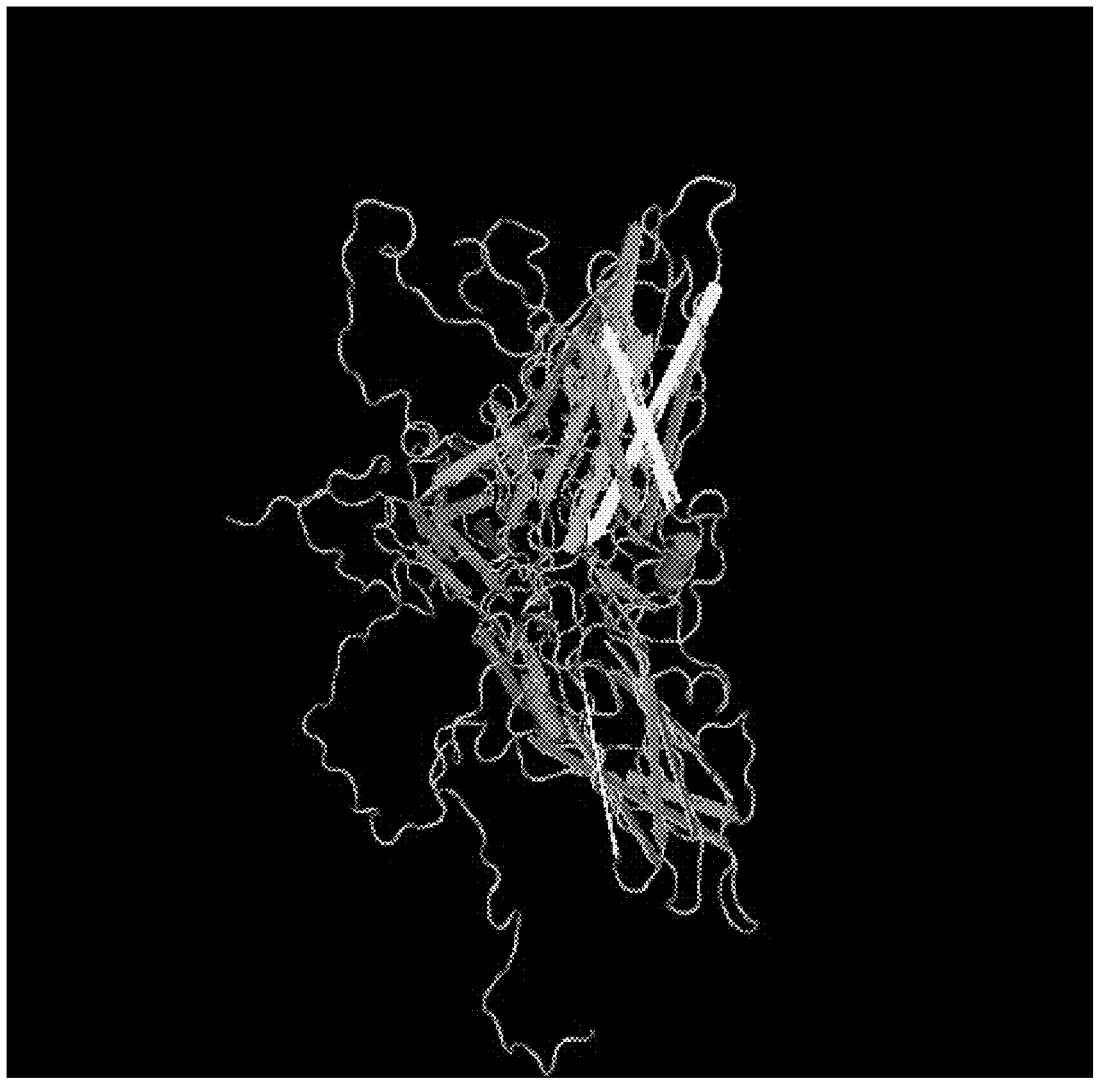

FIG. 91 show a molecular model of the EMCV and TMEV capsid structures in comparison with the sequence of SVV. A molecular model in conjunction with the use of algorithms for antigenic prediction allows for peptide sequences to be chosen for polyclonal antibody generation. β-sheets are shown in brown, α-helices are shown in green, and a 12-mer peptide sequence chosen for polyclonal generation is shown in yellow. The particular sequence (in the VP2 region) was chosen because it presents good surface exposure according to the model.

Figure 92A:
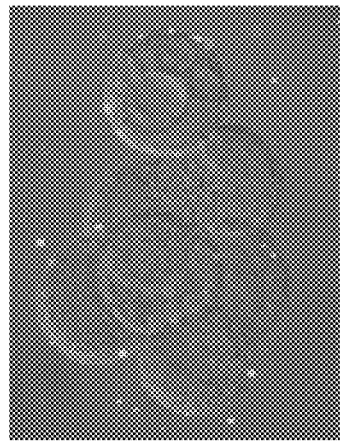
Figure 92B:
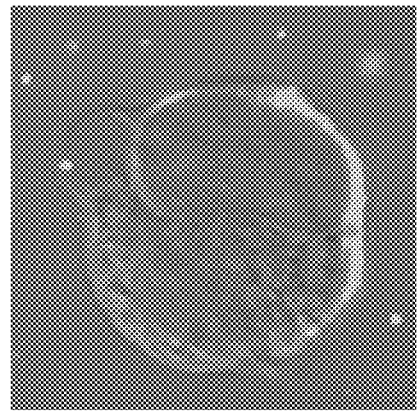
Figure 92C:
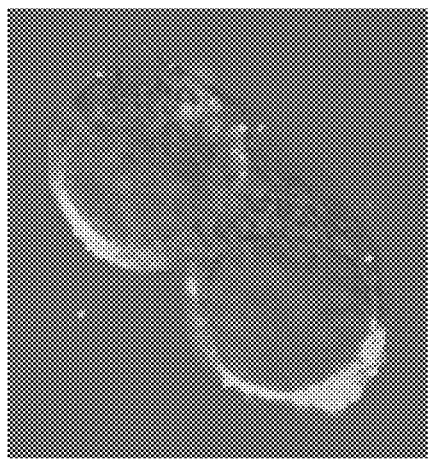
Figure 92D:
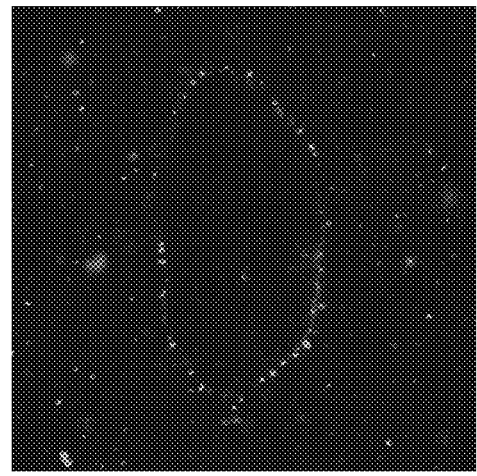

FIGS. 92A-92D show the specificity of polyclonal antibodies against SVV. FIG. 92A is a negative control, and presents an immunofluorescence image of cells infected with SVV that are stained with non-specific anti-mouse sera and secondary antibody. FIGS. 92B and 92C show immunofluorescence images of cells infected with SVV that are stained with mouse anti-SVV sera diluted 1:50 and secondary antibody (anti-mouse Ig conjugated to fluorescein). FIG. 92D shows that polyclonal anti-SVV antibodies can be used in viral binding assays; the image shows an immunofluorescence image of SVV concentrated in an outline around a cell because the cell was put on ice to prevent SVV internalization.

Figure 93:
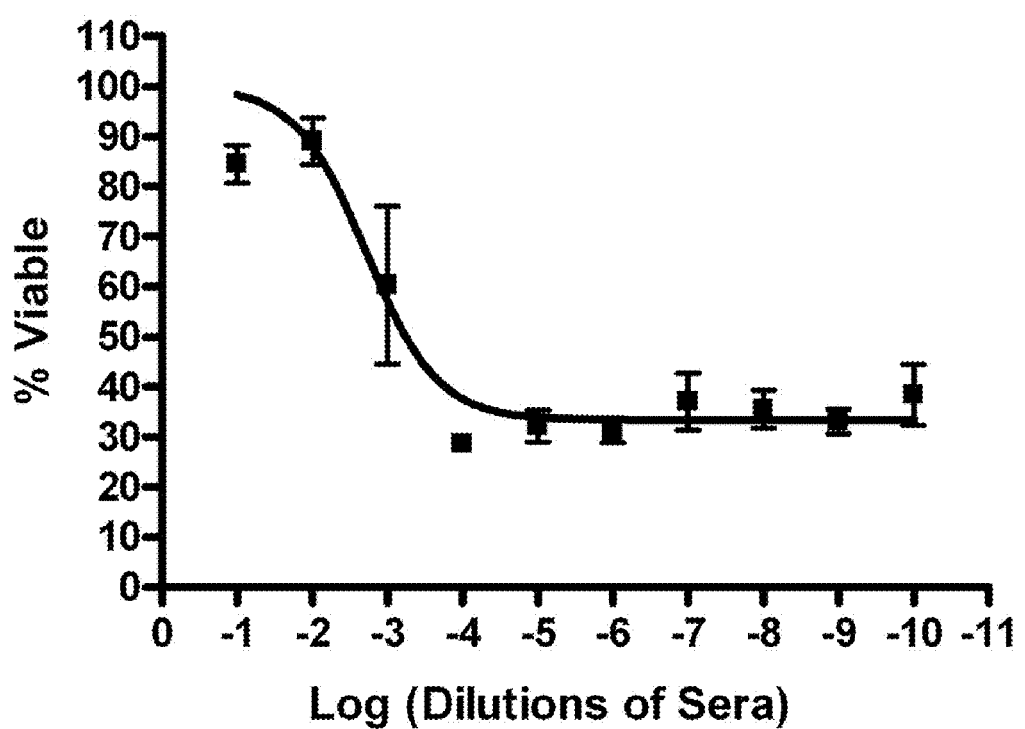

FIG. 93 shows the results of a neutralization assay of GP102 sera on SVV (see Example 18). The neutralization titer (calculated as the highest dilution that neutralizes the virus is 100%) is 1:100.

Figure 94:
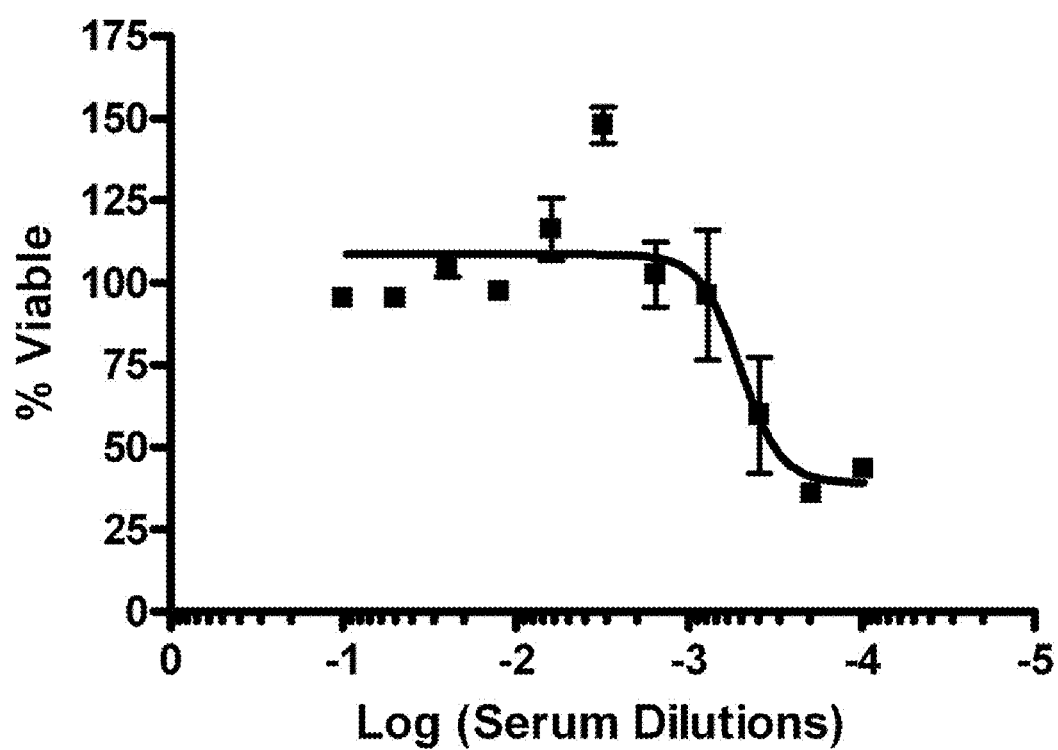

FIG. 94 shows the results of a neutralization assay of anti-SVV antisera on MN 88-36695 (see Example 18). The neutralization titer is 1:560.

Figures 95A, 95B:
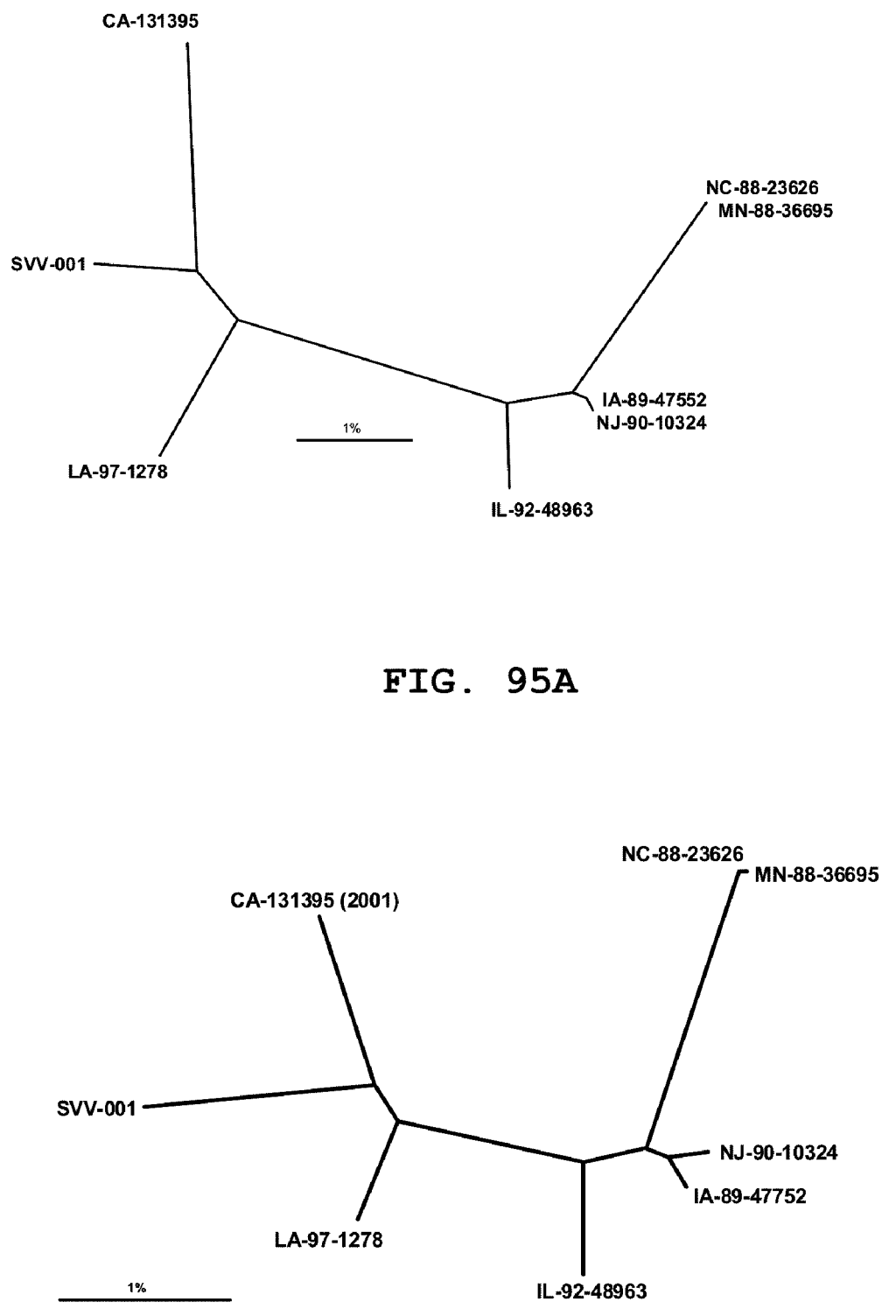

FIG. 95A and FIG. 95B depict neighbor-joining trees. These trees were constructed using PHYLIP (Phylogeny Inference Package Computer Programs for Inferring Phylogenies) and show the relationship between SVV and seven SVV-like picornaviruses when comparing sequences from regions in P1 and partial 2A (FIG. 95A) and in the 3' end of the genome (FIG. 95B).

DETAILED DESCRIPTION OF THE INVENTION

The terms "virus," "viral particle," "virus particle," and "virion" are used interchangeably.

The terms "vector particle" and "viral vector particle" are interchangeable and are to be understood broadly—for example—as meaning infectious viral particles that are formed when, e.g., a viral vector of the invention is transduced or transfected into an appropriate cell or cell line for the generation of infectious particles.

The terms "derivative," "mutant," "variant" and "modified" are used interchangeably to generally indicate that a derivative, mutant, variant or modified virus can have a nucleic acid or amino acid sequence difference in respect to a template viral nucleic acid or amino acid sequence. For example, a SVV derivative, mutant, variant or modified SVV may refer to a SVV that has a nucleic acid or amino acid sequence difference with respect to the wild-type SVV nucleic acid or amino acid sequence of ATCC Patent Deposit Number PTA-5343.

An "SVV-like picornavirus" as used herein can have at least about 65%, 70%, 75%, 80%, 85%, 90%, 95%, 96%, 97%, 98%, or 99% identity to SVV at the nucleotide level (see SEQ ID NO:168, FIG. 84, and FIG. 83 for the SVV full-length genomic sequence), where the sequence comparison is not limited to a whole-genome analysis, but can be focused on a particular region of the genome, such as the 5'UTR, structural encoding regions, non-structural encoding regions, 3'UTR, and portions thereof. The particular length of the genome for sequence comparison that is adequate to determine relatedness/likeness to SVV is known to one skilled in the art, and the adequate length can very with respect to the percentage of identity that is present. The length for sequence comparison can be, for example, at least 20, 50, 100, 200, 300, 400, 500, 750, 1000, 1500, 2000, or 2500 nucleotides. Where the length is shorter, one skilled in the art understands, for example, that the identity between sequences can be higher in order to consider the two sequences to be related. However, such guidance is qualified at least with respect to considerations of sequence conservation, in that certain regions of the genome are more conserved than others between related species. Additionally, if an antiserum generated from a virus can neutralize SVV infection of an SVV permissive cell line, then the virus is considered to be an SVV-like picornavirus. Additionally, if an antiserum generated from a virus can neutralize SVV infection of an SVV permissive cell line, and that antiserum can also bind to other viruses (for example, if the antiserum can be used in indirect immunofluorescence assays to detect virus), then the other viruses that can be bound by the antiserum are considered to be SVV-like picornaviruses. For purposes of the invention, SVV-like picornaviruses can include cardioviruses. Exemplary SVV permissive cells or cell lines include, but are not limited to, Y79, NCI-H446, N1E-115, NCI-H1770, NCI-H82, PER.C6®, NCI-H69AR, SK-NEP-1, IMR-32, NCI-H187, NCI-H209, HCC33, NCI-H1184, D283 Med, SK-N-AS, BEK PCB3E1, ST, NCI-H1299, DMS 153, NCI-H378, NCI-H295R, BEK, PPASMC, PCASMC, PAoSMC, NCI-H526, OVCAR-3, NCI-H207, ESK-4, SVV-13, 293, Hs 578T, HS1.Tes, and LOX IMVI.

As used herein, the terms "cancer," "cancer cells," "neoplastic cells," "neoplasia," "tumor," and "tumor cells," are used interchangeably, and refer to cells that exhibit relatively autonomous growth, so that they exhibit an aberrant growth phenotype characterized by a significant loss of control of cell proliferation. Neoplastic cells can be malignant or benign. According to the present invention, one type of preferred tumor cells are those with neurotropic properties.

The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using a sequence comparison algorithm such as Protein-Protein BLAST (Protein-Protein BLAST of GenBank databases (Altschul, S. F., Gish, W., Miller, W., Myers, E. W. & Lipman, D. J. (1990) "Basic local alignment search tool." *J. Mol. Biol.* 215:403-410)) or by visual inspection. The BLAST algorithm is described in Altschul et al., *J. Mol. Biol.*, 215:403-410 (1990), and publicly available BLAST software is provided through the National Center for Biotechnology Information (NCBI).

For example, as used herein, the term "at least 90% identical to" refers to percent identities from 90 to 100 relative to the reference polypeptides (or polynucleotides). Identity at a level of 90% or more is indicative of the fact that, assuming for exemplification purposes a test and reference polypeptide length of 100 amino acids are compared, no more than 10% (i.e., 10 out of 100) amino acids in the test polypeptide differs from that of the reference polypeptide. Similar comparisons can be made between a test and reference polynucleotide. Such differences can be represented as point mutations randomly distributed over the entire length of an amino acid sequence or they can be clustered in one or more locations of varying length up to the maximum allowable, e.g., 10 out of 100 amino acid differences (90% identity). Differences are defined as nucleic acid or amino acid substitutions, insertions or deletions. At the level of identities above about 85-90%, the result should be independent of the program and gap parameters set; such high levels of identity can be assessed readily, often without relying on software.

The concepts of "high stringency," "intermediate stringency" or "low stringency" refer to nucleic acid hybridization conditions. High stringency conditions refers to conditions that require a greater identity between a target's nucleic acid sequence and a probe's nucleic acid sequence in order for annealing or hybridization to occur between the target and the probe. Low stringency conditions refer to conditions that require a lower identity between a target's nucleic acid sequence and a probe's nucleic acid sequence in order for annealing or hybridization to occur between the target and the probe. Stringency conditions can be controlled by the salt concentration of the buffer or by the temperature at which the hybridization is carried out, where higher salt concentrations result in less stringent conditions and where higher temperatures result in more stringent conditions. Although stringency conditions will vary based on the length and nucleic acid content of the sequences undergoing hybridization, representative conditions of high, intermediate and low stringency are described in the following exemplary conditions. A commonly used hybridization buffer is SSC (sodium chloride sodium citrate) with a 20× stock concentration corresponding to 0.3 M trisodium citrate and 3 M NaCl. For high stringency conditions, the working concentration of SSC can be 0.1×-0.5× (1.5-7.5 mM trisodium citrate, 15-75 mM NaCl) with the hybridization temperature set at 65° C. Intermediate conditions typically utilize a 0.5-2×SSC concentration (7.5-30 mM trisodium citrate, 75-300 mM NaCl) at a temperature of 55-62° C. Hybridizations conducted under low stringency conditions can use a 2×-5×SSC concentration (30-75 mM trisodium citrate, 300-750 mM NaCl) at a temperature of 50-55° C. Note that these conditions are merely exemplary and are not to be considered limitations.

Figure 86:
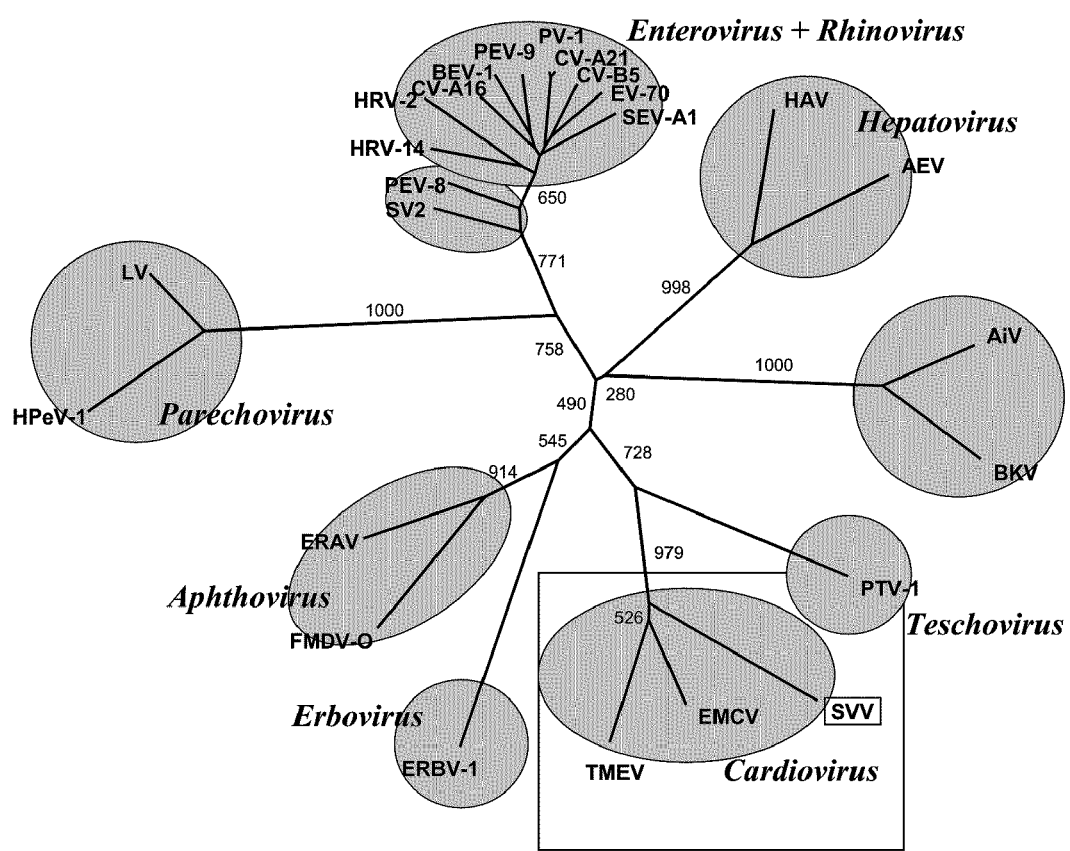

Seneca Valley Virus (SVV):

SVV is a novel, heretofore undiscovered RNA virus, and with respect to previously characterized picornaviruses, SVV is most closely related to members from the genus Cardiovirus in the family Picornaviridae (see International Application No. PCT/US2004/031594). The results of sequence analyses between SVV and other cardioviruses are discussed in PCT/US2004/031594, which is hereby incorporated by reference in its entirety. Since the time of the sequence analysis of SVV described in PCT/US2004/031594, the Picornavirus Study Group has initiated discussion as to whether SVV will be a member of a new genus. FIG. 86 presents a genetic relationship tree between members of the family Picornaviridae.

From initial sequence comparisons to known picornaviruses (see International Application No. PCT/US2004/031504), there were two phylogenetic classification options: (1) to include SVV as a new species in the genus Cardiovirus; or (2) assign SVV to a new genus. At that time and for the International application, SVV was designated to be a novel member of the genus Cardiovirus. After further analyses however, it has been found that several characteristics of SVV differ with that of cardioviruses. For example, some cardiovirus genomes contain an extended internal poly(C) tract in their 5' UTRs. SVV does not contain a poly(C) tract. From the additional 5' sequence information, the Internal Ribosome Entry Sequence (IRES) of SVV has been mapped and compared to other picornaviruses, and it has been determined that the SVV IRES is Type IV, whereas cardiovirus IRES's are Type II. The cardioviruses have a long (150 amino acid (aa)) 2A protease while SVV has a short (9 aa) 2A protease. The size of this protein as well as others (Leader peptide, 3A) differs significantly between SVV and cardioviruses. From the study of other picornaviruses, it is know that these proteins are likely involved in host cell interactions including tropism and virulence. Lastly, it is now thought that the overall sequences differ too much in a number of genome regions and SVV should therefore be considered to form a new genus. Additionally, multiple unique picornaviruses have been discovered at the USDA that are more similar to SVV than SVV is to other cardioviruses. Therefore, it has been decided by the Executive Committee of the International Committee for the Taxonomy of Viruses (ICVT) based on recommendations made by the Picornavirus Study Group that SVV will make up a new species of picornavirus, named Seneca Valley virus. However, currently, SVV and these unique USDA picornaviruses (herein referred to as being members of the group of SVV-like picornaviruses) are currently unassigned to any genus.

Several of the SVV-like picornaviruses discovered at the USDA are about 95-98% identical to SVV at the nucleotide level (for example, see FIGS. 87-89). Antisera against one virus (MN 88-36695) neutralizes SVV, and this virus is reactive to other antisera that can neutralize SVV. The SVV-like picornaviruses were isolated from pigs, and thus, pigs are likely a permissive host for SVV and other SVV-like viruses. Examples of SVV-like picornaviruses isolated from pigs include, but are not limited to, the following USDA isolates MN 88-36695, NC 88-23626, IA 89-47552, NJ 90-10324, IL 92-48963, CA 131395; LA 1278; IL 66289; IL 94-9356; MN/GA 99-29256; MN 99197; and SC 363649. SVV-like picornaviruses may also include cardioviruses closely related to SVV (as determined by sequence analysis or by cross-reactivity to antibodies raised against SVV antigens). Thus, for purposes of the present invention, SVV can be considered: (1) to be closely related to (or to be a member of) the genus Cardiovirus of the family Picornaviridae, and (2) to be a member of a new genus of the family Picornaviridae, where members of the new genus can include SVV and SVV-like picornaviruses not classified to be members of other genuses.

SVV, like cardioviruses, can be distinguished from other picornaviruses by special features of their genome organization, common pathological properties, and the dissociability of their virions at pHs between 5 and 7 in 0.1M NaCl (Scraba, D. et al., "Cardioviruses (Picornaviridae)," in *Encyclopedia of Virology*, 2nd Edition, R. G. Webseter and A. Granoff, Editors, 1999). The genome of SVV consists of one single-stranded positive (+) sense strand RNA molecule having a size of 7,310 nucleotides including a poly(A) tail of 30 nucleotides in length (see FIGS. 83A-83H; FIGS. 84A-84D; SEQ ID NO:168). As SVV is a picornavirus, it has a number of features that are conserved in all picornaviruses: (i) genomic RNA is infectious, and thus can be transfected into cells to bypass the virus-receptor binding and entry steps in the viral life cycle; (ii) a long (about 600-1200 bp) untranslated region (UTR) at the 5' end of the genome (for SVV, nucleotides 1-666 of SEQ ID NO:168), and a shorter 3' untranslated region (about 50-100 bp; for SVV, nucleotides 7210-7280 of SEQ ID NO:168; (iii) the 5' UTR contains a clover-leaf secondary structure known as the internal ribosome entry site (IRES) (which can be, for example, from about nucleotide 300 to about nucleotide 366 of SEQ ID NO:168); cardioviruses have a Type II IRES and SVV has a Type IV IRES; (iv) the rest of the genome encodes a single polyprotein (for SVV, nucleotides 667-7209 of SEQ ID NO:168 encode the polyprotein (SEQ ID NO:169)) and (v) both ends of the genome are modified, the 5' end by a covalently attached small, basic protein, "Vpg," and the 3' end by polyadenylation (for SVV, nucleotides 7281-7310 of SEQ ID NO:168).

The invention provides the isolated SVV virus (ATCC Patent Deposit number PTA-5343) and the complete genomic content of SVV therefrom. At first, the largest SVV genomic fragment that was sequenced is an isolated SVV nucleic acid, derived from the PTA-5343 isolate, that comprises the majority of the SVV genomic sequence, and is listed in FIGS. 5A-5E and FIGS. 6A-6D, and has the designation of SEQ ID NO:1 herein. Translation of this nucleotide sequence shows that the majority of the single polyprotein of SVV is encoded by SEQ ID NO:1. The amino acid sequence encoded by nucleotides 1 to 5673 of SEQ ID NO:1 is listed in FIGS. 5A-E and FIGS. 7A-7B has the designation of SEQ ID NO:2 herein. The full-length genome or what appears to be the full-length genome has since been obtained, and is listed in FIGS. 83A-83H and SEQ ID NO:168. Nucleotides 667-7209 encode the full-length polyprotein of SVV, and the amino acid sequence of the polyprotein is listed in FIGS. 83A-83H and SEQ ID NO:169.

The invention provides isolated (or purified) portions of SEQ ID NO:1, including SEQ ID NOS:3, 5, 7, 9, 11, 13, 15, 17, 19 and 21, and isolated portions of SEQ ID NO:168, including the 5'UTR region (1-666), coding region for the leader peptide (667-903), coding region for the VP4 protein (904-1116), coding region for the VP2 protein (1117-1968), coding region for the VP3 protein (1969-2685), coding region for the VP1 protein (2686-3474), coding region for the coding region for the 2A protein (3478-3504), coding region for the 2B protein (3505-3888), coding region for the 2C protein (3889-4854), coding region for the 3A protein (4855-5124), coding region for the 3B protein (5125-5190), coding region for the 3C protein (5191-5823), coding region for the 3D protein (5824-7209), and the 3'UTR region including the poly(A) tail (7210-7310). The invention also provides isolated nucleic acids that are portions of the specified portions listed above. The invention also provides mutants or derivatives of such isolated portions. The isolated portions of SEQ ID NOS:1 and 168 can be subcloned into expression vectors such that polypeptides encoded by these portions can be isolated. Further encompassed by the invention are isolated nucleic acids that can hybridize to SEQ ID NO:1 or SEQ ID NO:168, or any portion thereof, under high, moderate or low stringency conditions. The following table lists the nucleotides of SEQ ID NO:168 that encode the SVV proteins. The invention provides isolated (or purified) SVV proteins or portions thereof. The table also lists the amino acid sequences of the SVV proteins with respect to the polyprotein sequence listed in SEQ ID NO:169.

TABLE A

SVV Genome and Protein Features

| SVV feature | Location in SEQ ID NO: 168 | Location in SEQ ID NO: 169 |
|---|---|---|
| 5'UTR | 1-666 | N/A (not allowed) |
| Leader | 667-903 (coding sequence for Leader peptide) | 1-79 |
| VP4 | 904-1116 (coding sequence for VP4) | 80-150 |
| VP2 | 1117-1968 (coding sequence for VP2) | 151-434 |
| VP3 | 1969-2685 (coding sequence for VP3) | 435-673 |
| VP1 | 2686-3474 or 3477 (coding sequence for VP1) | 674-936 or 937 |
| 2A | 3478-3504 (coding sequence for 2A) | 938-946 |
| 2B | 3505-3888 (coding sequence for 2B) | 947-1074 |
| 2C | 3889-4854 (coding sequence for 2C) | 1075-1396 |
| 3A | 4855-5124 (coding sequence for 3A) | 1397-1486 |
| 3B | 5125-5190 (coding sequence for 3B) | 1487-1508 |
| 3C | 5191-5823 (coding sequence for 3C) | 1509-1719 |
| 3D | 5824-7209 (coding sequence for 3D) | 1720-2181 |
| 3'UTR | 7210-7310 | N/A |

The invention provides an isolated SVV leader sequence peptide with the amino acid sequence of residues 1-79 of SEQ ID NO:169, which is encoded by nucleotides 667-903 of SEQ ID NO:168.

The invention provides an isolated SVV VP4 (1A) protein with the amino acid sequence of residues 80-150 of SEQ ID NO:169, which is encoded by nucleotides 904-1116 of SEQ ID NO:168.

The invention provides an isolated SVV VP2 (1B) protein with the amino acid sequence of residues 151-434 of SEQ ID NO:169, which is encoded by nucleotides 1117-1968 of SEQ ID NO:168. The invention also provides an isolated partial SVV VP2 (1B) protein with the amino acid sequence of SEQ ID NO:4, as listed in FIG. 9 (which corresponds to amino acids 2-143 of SEQ ID NO:2). The amino acid sequence of the partial SVV VP2 protein is encoded by the nucleic acid sequence of SEQ ID NO:3, as listed in FIG. 8 (which corresponds to nucleotides 4-429 of SEQ ID NO:1).

The invention provides an isolated SVV VP3 (1C) protein with the amino acid sequence of residues 435-673 of SEQ ID NO:169, which is encoded by nucleotides 1969-2685 of SEQ ID NO:168. The invention also provides an isolated SVV VP3 (1C) protein with the amino acid sequence of SEQ ID NO:6, as listed in FIG. 11 (which corresponds to amino acids 144-382 of SEQ ID NO:2). The amino acid sequence of the SVV VP3 protein is encoded by the nucleic acid sequence of SEQ ID NO:5, as listed in FIG. 10 (which corresponds to nucleotides 430-1146 of SEQ ID NO:1).

The invention provides an isolated SVV VP1 (1D) protein with the amino acid sequence of residues 674-937 of SEQ ID NO:169, which is encoded by nucleotides 2686-3477 of SEQ ID NO:168. The invention also provides an isolated SVV VP1 (1D) protein with the amino acid sequence of SEQ ID NO:8, as listed in FIG. 13 (which corresponds to amino acids 383-641 of SEQ ID NO:2). The amino acid sequence of the SVV VP1 protein is encoded by the nucleic acid sequence of SEQ ID NO:7, as listed in FIG. 12 (which corresponds to nucleotides 1147-1923 of SEQ ID NO:1).

The invention provides an isolated SVV 2A protein with the amino acid sequence of residues 938-946 of SEQ ID NO:169, which is encoded by nucleotides 3478-3504 of SEQ ID NO:168. The invention also provides an isolated SVV 2A protein with the amino acid sequence of SEQ ID NO:10, as listed in FIG. 15 (which corresponds to amino acids 642-655 of SEQ ID NO:2). The amino acid sequence of the SVV 2A protein is encoded by the nucleic acid sequence of SEQ ID NO:9, as listed in FIG. 14 (which corresponds to nucleotides 1924-1965 of SEQ ID NO:1).

The invention provides an isolated SVV 2B protein with the amino acid sequence of residues 947-1074 of SEQ ID NO:169, which is encoded by nucleotides 3505-3888 of SEQ ID NO:168. The present invention also provides an isolated SVV 2B protein with the amino acid sequence of SEQ ID NO:12, as listed in FIG. 17 (which corresponds to amino acids 656-783 of SEQ ID NO:2). The amino acid sequence of the SVV 2B protein is encoded by the nucleic acid sequence of SEQ ID NO:11, as listed in FIG. 16 (which corresponds to nucleotides 1966-2349 of SEQ ID NO:1).

The invention provides an isolated SVV 2C protein with the amino acid sequence of residues 1075-1396 of SEQ ID NO:169, which is encoded by nucleotides 3889-4854 of SEQ ID NO:168. The invention also provides an isolated SVV 2C protein with the amino acid sequence of SEQ ID NO:14, as listed in FIG. 19 (which corresponds to amino acids 784-1105 of SEQ ID NO:2). The amino acid sequence of the SVV 2B protein is encoded by the nucleic acid sequence of SEQ ID NO:13, as listed in FIG. 18 (which corresponds to nucleotides 2350-3315 of SEQ ID NO:1).

The invention provides an isolated SVV 3A protein with the amino acid sequence of residues 1397-1486 of SEQ ID NO:169, which is encoded by nucleotides 4855-5124 of SEQ ID NO:168. The invention also provides an isolated SVV 3A protein with the amino acid sequence of SEQ ID NO:16, as listed in FIG. 21 (which corresponds to amino acids 1106-1195 of SEQ ID NO:2). The amino acid sequence of the SVV 3A protein is encoded by the nucleic acid sequence of SEQ ID NO:15, as listed in FIG. 20 (which corresponds to nucleotides 3316-3585 of SEQ ID NO:1).

The invention provides an isolated SVV 3B (VPg) protein with the amino acid sequence of residues 1487-1508 of SEQ ID NO:169, which is encoded by nucleotides 5125-5190 of SEQ ID NO:168. The invention also provides an isolated SVV 3B protein with the amino acid sequence of SEQ ID NO:18, as listed in FIG. 23 (which corresponds to amino acids 1196-1217 of SEQ ID NO:2). The amino acid sequence of the SVV 3B protein is encoded by the nucleic acid sequence of SEQ ID NO:17, as listed in FIG. 22 (which corresponds to nucleotides 3586-3651 of SEQ ID NO:1).

The invention provides an isolated SVV 3C ("pro" or "protease") protein with the amino acid sequence of residues 1509-1719 of SEQ ID NO:169, which is encoded by nucleotides 5191-5823 of SEQ ID NO:168. The invention also provides an isolated SVV 3C protein with the amino acid sequence of SEQ ID NO:20, as listed in FIG. 25 (which corresponds to amino acids 1218-1428 of SEQ ID NO:2). The amino acid sequence of the SVV 3C protein is encoded by the nucleic acid sequence of SEQ ID NO:19, as listed in FIG. 24 (which corresponds to nucleotides 3652-4284 of SEQ ID NO:1).

The invention provides an isolated SVV 3D ("pol" or "polymerase") protein with the amino acid sequence of residues 1720-2181 of SEQ ID NO:169, which is encoded by nucleotides 5824-7209 of SEQ ID NO:168. The invention also provides an isolated SVV 3D protein with the amino acid sequence of SEQ ID NO:22, as listed in FIG. 27 (which corresponds to amino acids 1429-1890 of SEQ ID NO:2). The amino acid sequence of the SVV 3C protein is encoded by the nucleic acid sequence of SEQ ID NO:19, as listed in FIG. 24 (which corresponds to nucleotides 4285-5673 of SEQ ID NO:1; nucleotides 5671-5673, "tga," code for a stop-codon, which is depicted in the amino acid sequence listings as an asterisk "*").

The nucleic acids of the present invention include both RNA and DNA forms, and implicitly, the complementary sequences of the provided listings.

Thus, the isolated SVV nucleic acid depicted by SEQ ID NO:168 has a length of 7,310 nucleotides that encodes a polyprotein with the amino acid sequence depicted by SEQ ID NO:169. The isolated SVV nucleic acid depicted by SEQ ID NO:1 has a length of 5,752 nucleotides that encodes a polypeptide with the amino acid sequence depicted by SEQ ID NO:2. The SVV genomic sequence is translated as a single polyprotein that is cleaved into various downstream "translation products." The present invention encompasses all nucleic acid fragments of SEQ ID NO: 168 and SEQ ID NO:1, and all polypeptides encoded by such fragments.

The full-length SVV polyprotein amino acid sequence is depicted by SEQ ID NO:169 and is encoded by nucleotides 667-7209 of SEQ ID NO:168. The majority of the full-length SVV polyprotein amino acid sequence is encoded by nucleotides 1-5673 of SEQ ID NO:1. The polyprotein is cleaved into three precursor proteins, P1, P2 and P3 (see FIG. 4B). P1, P2 and P3 are further cleaved into smaller products. The cleavage products of the structural region P1 (1ABCD; or the capsid region) are 1ABC, VP0, VP4, VP2, VP3 and VP1. The cleavage products of the non-structural protein P2 (2ABC) are 2A, 2BC, 2B and 2C. The cleavage products of the non-structural region P3 polyprotein (3ABCD) are 3AB, 3CD, 3A, 3C, 3D, 3C', and 3D'.

In certain embodiments, the invention provides isolated nucleic acids that comprise: (i) the coding sequence of 1ABCD or the capsid region (nucleotides 904-3477 of SEQ ID NO:168); (ii) the coding sequence of 1ABC (nucleotides 904-2685 of SEQ ID NO:168); (iii) the coding sequence of VP0 (nucleotides 904-1968 of SEQ ID NO:168); (iv) the coding sequence of 2ABC (nucleotides 3478-4854 of SEQ ID NO:168; nucleotides 1924-3315 of SEQ ID NO:1); (v) the coding sequence of 2BC (nucleotides 3505-4854 of SEQ ID NO:168; nucleotides 1966-3315 of SEQ ID NO:1); (iii) the coding sequence of 3ABCD (nucleotides 4855-7209 of SEQ ID NO:168; nucleotides 3316-5673 of SEQ ID NO:1); (iv) the coding sequence of 3AB (nucleotides 4855-5190 of SEQ ID NO:168; nucleotides 3316-3651 of SEQ ID NO:1); and (v) the coding sequence of 3CD (nucleotides 5191-7209 of SEQ ID NO:168; nucleotides 3652-5673 of SEQ ID NO:1). The invention also provides isolated proteins or peptides encoded by the coding sequences described above, including fragments thereof.

The basic capsid structure of picornaviruses consists of a densely packed icosahedral arrangement of 60 protomers, each consisting of 4 polypeptides, VP1, VP2, VP3 and VP4, all of which are derived from the cleavage of the original protomer, VP0. The SVV virus particle is about 27 nm in diameter (see FIG. 2), which is consistent with the size of other picornavirus particles, which are about 27-30 nm in diameter.

Figure 68:
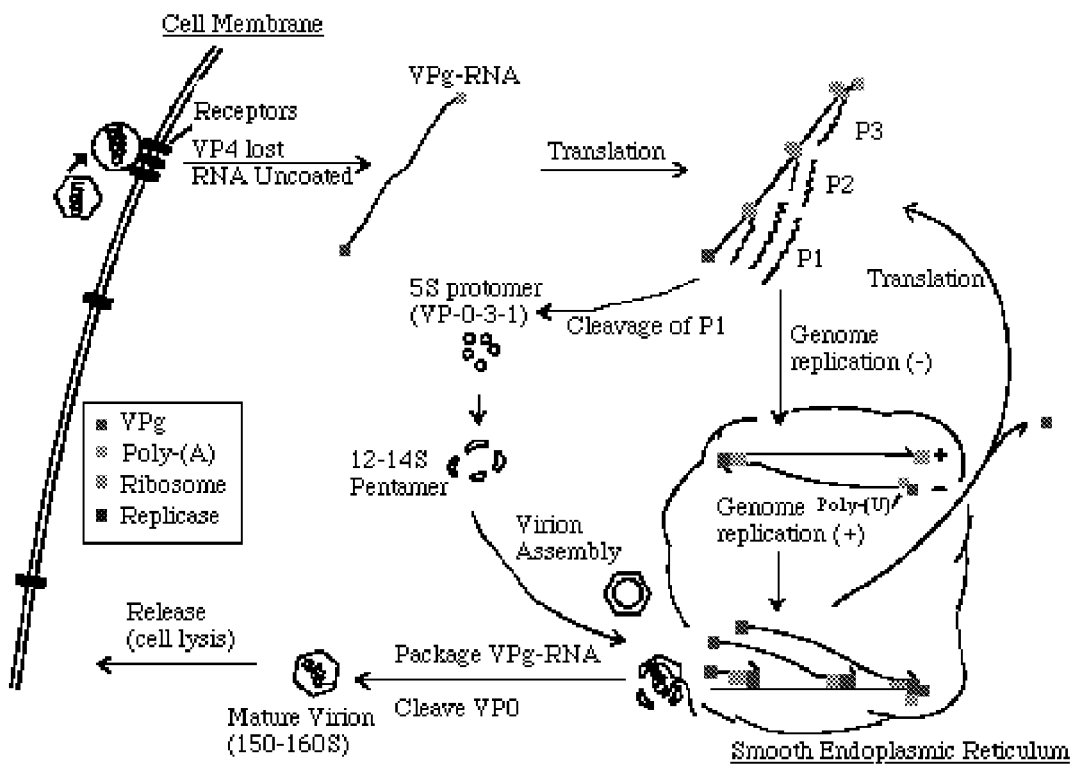

The kinetics of picornavirus replication is rapid, the cycle being completed in about 5-10 hours (typically by about 8 hours) (see FIG. 68 for a schematic of the picornavirus replication cycle). Upon receptor binding, the genomic RNA is released from the particle into the cytoplasm. Genomic RNA is then translated directly by polysomes, but in about 30 minutes after infection, cellular protein synthesis declines sharply, almost to zero. This phenomenon is called "shutoff,"

and is a primary cause of cytopathic effects (cpe). Shutoff appears to be due to cleavage of the host cell's 220 kDa cap-binding complex (CBC) that is involved in binding the m7G cap structure at the 5' end of all eukaryotic mRNA during initiation of translation. The cleavage of the CBC appears to be caused by the 2A protease.

The 5' UTR contains the IRES. Normally, eukaryotic translation is initiated when ribosomes bind to the 5' methylated cap and then scans along the mRNA to find the first AUG initiation codon. The IRES overcomes this process and allows Picornavirus RNA's to continue to be translated after degradation of CBC. In one embodiment, the invention provides for an isolated nucleic acid comprising the SVV IRES, wherein the IRES is contained within the 5'UTR. In one embodiment, the SVV IRES can be from nucleotides 300-366 of SEQ ID NO:168. The 5'UTR of SVV is present at nucleotides 1-666 of SEQ ID NO:168.

The virus polyprotein is initially cleaved by the 2A protease into polyproteins P1, P2 and P3 (see FIG. 4B). Further cleavage events are then carried out by 3C, the main picornavirus protease. One of the cleavage products made by 3C is the virus RNA-dependent RNA polymerase (3D), which copies the genomic RNA to produce a negative (−) sense strand. The (−) sense strand forms the template for the (+) strand (genomic) RNA synthesis. Some of the (+) strands are translated to produce additional viral proteins are some (+) strands are packaged into capsids to form new virus particles.

The (+) strand RNA genome is believed to be packaged into preformed capsids, although the molecular interactions between the genome and the capsid are not clear. Empty capsids are common in all picornavirus infections. The capsid is assembled by cleavage of the P1 polyprotein precursor into a protomer consisting of VP0, VP3, and VP1, which join together enclosing the genome. Maturation and infectivity of the virus particle relies on an internal autocatalytic cleavage of VP0 into VP2 and VP4. Release of newly formed virus particles occurs when the cell lyses.

The present invention also provides an isolated virus having all the identifying characteristics and nucleic acid sequence of ATCC Patent Deposit number PTA-5343. Viruses of the present invention can be directed to the PTA-5343 isolate, variants, homologues, derivatives and mutants of the PTA-5343 isolate, and variants, homologues, derivatives and mutants of other picornaviruses that are modified in respect to sequences of SVV (both wild-type as disclosed herein and mutant) that are determined to be responsible for its oncolytic properties.

The present invention further provides antibodies that are specific against: the isolated SVV having the ATTC Patent Deposit number PTA-5343, and epitopes from the isolated SVV proteins having the amino acid sequences SEQ ID NOS: 2, 4, 6, 8, 10, 12, 14, 16, 18, 20, 22, and 169 (including entire polyprotein, VP4, VP2, VP3, VP1, 2A, 2B, 2C, 3A, 3B, 3C, 3D, and portions thereof; see Table A supra for amino acids in SEQ ID NO:169 that make up these proteins). The invention also includes antibodies that are specific against epitopes from the proteins that are encoded by fragments or portions of SEQ ID NO:1 or SEQ ID NO:168.

Comparative analyses of the RNA sequences from a variety of cardiovirus isolates have shown >45% nucleotide identity between genomes. Cardioviruses can be subclassified into the EMC-like viruses ("EMCV"—such as, Mengo, B, R; and also MM, ME, Columbia-SK), the Theiler's-like viruses ("TMEV"—such as, BeAn, DA and GD VII strains), and the Vilyuisk viruses.

In analyzing the SVV sequence to other viruses, it appears that SVV is a cardiovirus (see Example 4 and Figures referenced therein). If EMCV and TMEV are taken as the standard cardioviruses, SVV is clearly not a typical cardiovirus. However, even these two viruses have their differences, notably in the 5' UTR (Pevear et al., 1987, *J. Virol.*, 61: 1507-1516). Phylogenetically SVV clusters with EMCV and TMEV in much of its polyprotein (P1, 2C, $3C^{pro}$ and $3D^{pol}$ regions; see FIGS. 31-37), indicating that SVV is most likely a cardiovirus.

SVV is phylogenetically similar to cardioviruses, but it has now been determined to be in a separate tree (see FIG. 86). SVV can be in a separate genus because: (1) SVV IRES is Type IV (cardiovirus IRES are Type II); (2) multiple unique viruses ("SVV-like picornaviruses") are more similar to SVV than SVV is to other cardioviruses (see Example 18 and FIGS. 87-89); and antibodies that can neutralize SVV infection of permissive cell lines or were raised against SVV are able to bind to the SVV-like picornaviruses. Thus, an SVV-like picornavirus can be used in any of the present methods, including the methods to treat cancer, where it is determined that the SVV-like picornavirus is naturally oncolytic or is made to be oncolytic (for example, by designing mutations in the SVV-like picornavirus genome based on the SVV sequence). In one embodiment, MN 88-36696 is used in the present methods to treat cancer.

Methods for Treating Cancer:

The present invention provides methods for cancer therapy using viruses modified in view of the oncolytic properties of SVV, including picornaviruses (including SVV-like picornaviruses), derivatives, variants, mutants or homologues thereof. The present invention shows that wild-type SVV (i.e., ATTC Patent Deposit number PTA-5343) has the ability to selectively kill some types of tumors. For example, SVV can selectively kill tumor cells that have neurotropic or neuroendocrine properties, including small cell lung cancer (SCLC) and neuroblastomas. Other examples of neuroendocrine tumors that are contemplated to be treated by the viruses of the present invention include, but are not limited to: adrenal pheochromocytomas, gastrinomas (causing Zollinger-Ellison syndrome), glucagonomas, insulinomas, medullary carcinomas (including medullary thyroid carcinoma), multiple endocrine neoplasia syndromes, pancreatic endocrine tumors, paragangliomas, VIPomas (vasoactive intestinal polypeptide tumor), islet cell tumors, and pheochromocytoma.

In one embodiment, the invention provides methods for treating or reducing neuroendocrine tumors by administering to a subject SVV or an SVV-like picornavirus, where the neuroendocrine tumor expresses (or overexpresses) one or more neuroendocrine tumor markers, including but not limited to, NTR (Neurotensin receptor), ATOH (, GL11, Myc, GRP receptors, GRP, Neuronal enolase (neuron specific enolase (NSE)), carcinoembryonic antigen (CEA), chromoganin A, NCAM, IgF2, BCL-2, sonic hedgehog pathway, and a chemokine receptor.

Also encompassed in the present invention are the four types of neuroendocrine lung tumors. The most serious type, small cell lung cancer (SCLC), is among the most rapidly growing and spreading of all cancers. Large cell neuroendocrine carcinoma is a rare cancer that, with the exception of the size of the cells forming the cancer, is very similar to SCLC in its prognosis and in how patients are treated. Carcinoid tumors, also known as carcinoids, comprise the other 2 types of lung neuroendocrine cancer. These two types are typical carcinoid and atypical carcinoid.

Not being bound by theory, the ability of SVV to specifically kill tumor cells may include, but is not limited to: selective replication, cell protein synthesis shut-off, apoptosis, lysis via tumor-selective cell entry, tumor-selective translation, tumor-selective proteolysis, tumor-selective RNA replication, and combinations thereof.

SVV has many advantageous characteristics over other oncolytic viruses, including modified adenoviruses, for example: (i) SVV has a very high selectivity for cancers with neural properties, including SCLC, Wilms' tumor, retinoblastoma, and neuroblastoma—for example, SVV shows a greater than 10,000-fold selectivity toward neuroendocrine tumor cells; (ii) SVV has been shown to have a 1,000 fold better cell-killing specificity than chemotherapy treatments; (iii) SVV exhibits no overt toxicity in mice following systemic administration with as high as $10^{14}$ viral particles per kilogram; (iv) the efficacy of SVV is very robust in that 100% of large pre-established tumors can be eradicated in mice, with no recurrence of tumor growth; (v) SVV can be purified to high titer and can be produced at more than 200,000 particles per cell in permissive cell lines; (vi) SVV has a small size (the SVV virus particle is less than 30 nm in diameter) enabling better penetration and spread in tumors than other oncolytic viruses, (vii) SVV replicates quickly (less than 12 hours) and (viii) no modification of SVV is necessary for its use as a specific anti-tumor agent.

Further, initial studies (see Example 6) indicate some additional factors that make SVV an advantageous tool for oncolytic viral therapy: (i) human serum samples do not contain neutralizing antibodies directed against SVV; (ii) SVV is not inhibited by complement; and (iii) SVV does not produce hemagglutination of human erythrocytes. All of these factors contribute to the fact that SVV exhibits a longer circulation time in vivo than other oncolytic viruses (for example, see Example 7).

The present invention provides methods for selectively killing a neoplastic cell in a cell population that comprises contacting an effective amount of SVV with said cell population under conditions where the virus can transduce the neoplastic cells in the cell population, replicate and kill the neoplastic cells. Besides methods where SVV kills tumor cells in vivo, the present methods encompass embodiments where the tumors can be: (1) cultured in vitro when infected by SVV; (2) cultured in the presence of non-tumor cells; and (3) the cells are mammalian (both tumor and non-tumor cells), including where the cells are human cells. The in vitro culturing of cells and infection by SVV can have various applications. For example, in vitro infection be used as a method to produce large amounts of SVV, as method for determining or detecting whether neoplastic cells are present in a cell population, or as a method for screening whether a mutant SVV can specifically target and kill various tumor cell or tissue types.

The present invention further provides an ex vivo method of treating cancer wherein cells are isolated from a human cancer patient, cultured in vitro, infected with a SVV which selectively kills the cancer cells, and the non-tumor cells are introduced back to the patient. Alternatively, cells isolated form a patient can be infected with SVV and immediately introduced back to the patient as a method for administering SVV to a patient. In one embodiment, the cancer cells are of a hematopoietic origin. Optionally, the patient may receive treatment (e.g., chemotherapy or radiation) to destroy the patient's tumor cell in vivo before the cultured cells are introduced back to the patient. In one embodiment, the treatment may be used to destroy the patient's bone marrow cells.

Polymer coated SVV can be used to target the SVV to any specific cell type. This coating strategy can also be used to overcome antibodies to SVV.

SVV possesses potent antitumor activity against tumor cell-types with neural characteristics. SVV does not exhibit cytolytic activity against tested normal human. Further SVV is not cytotoxic to primary human hepatocytes. Table 1 below summarizes initial studies that have been conducted to determine the in vitro cytolytic potency of SVV against selected tumor cell types.

TABLE 1

SVV Cytolytic Potency Against Selected Tumor Cell-Types

| Cell Line | Cell Type | $EC_{50}$ (VP/cell) |
|---|---|---|
| H446 | Human SCLC | 0.0012 |
| PER.C6 | Human Embryonic Retinoblast | 0.02 |
| H69AR | SCLC-Multidrug Resistant | 0.035 |
| 293 | AD5 DNA Transformed Human Kidney | 0.036 |
| Y79 | Human Retinoblastoma | 0.00035 |
| IMR32 | Human Brain Neuroblastsoma | 0.035 |
| D283 | Med Human Brain Cerebellar Medulloblastoma | 0.25 |
| SK-N-AS | Human Brain Neuroblastoma | 0.474 |
| N1E-115 | Mouse Neuroblastoma | 0.0028 |
| BEKPCB3E1 | Bovine embryonic Kidney cells transformed with Ad5E1 | 0.99 |
| H1299 | Human non-SCLC | 7.66 |
| ST | Porcine Testis | 5.9 |
| DMS153 | Human SCLC | 9.2 |
| BEK | Bovine Embryonic Kidney | 17.55 |
| M059K | Human Brain Malignant Glioblastoma | 1,061 |
| PK15 | Porcine Kidney | 1,144 |
| FBRC | Fetal Bovine Retina | 10,170 |
| HCN-1A | Human Brain | 23,708 |
| H460 | Human LCLC | >30,000 (inactive) |
| Neuro 2A | Mouse Neuroblastoma | >30,000 (inactive) |
| DMS79 | Human SCLC | >30,000 (inactive) |
| H69 | Human SCLC | >30,000 (inactive) |
| C8D30 | Mouse Brain | >30,000 (inactive) |
| MRC-5 | Human Fetal Lung Fibroblast | >30,000 (inactive) |
| HMVEC | Neonatal vascular endothelial cells | >30,000 (inactive) |
| HMVEC | Adult vascular endothelial cells | >30,000 (inactive) |
| A375-S2 | Human Melanoma | >30,000 (inactive) |
| SK-MEL-28 | Melanoma | >30,000 (inactive) |
| PC3 | Human prostate cancer | >30,000 (inactive) |
| PC3M2AC6 | Human prostate cancer | >30,000 (inactive) |
| LnCap | Human Prostate cancer | >30,000 (inactive) |
| DU145 | Human prostate cancer | >30,000 (inactive) |

Table 1-A below provides a list of cell lines that are permissive are non-permissive to SVV infection. The Table shows the cytolytic potency and selectivity of SVV.

TABLE 1-A

In Vitro Cytolytic Potency and Selectivity of SVV

| Cell Line | Species | Stage | State | Organ | Type | Metastatic Site | EC50* |
|---|---|---|---|---|---|---|---|
| PERMISSIVE | | | | | | | |
| Y79 | Human | Adult | Cancer | Eye, Retina | Retinoblastoma | | 0.00035, 0.0007 |
| NCI-H446 | Human | Adult | Metastatic Cancer | Lung | Variant Small Cell Lung Carcinoma (SCLC) | Pleural effusion | 0.0012, 0.002, 0.0007 |

TABLE 1-A-continued

In Vitro Cytolytic Potency and Selectivity of SVV

| Cell Line | Species | Stage | State | Organ | Type | Metastatic Site | EC50* |
|---|---|---|---|---|---|---|---|
| N1E-115 | Murine | Adult | Cancer | Brain | Neuroblastoma | | 0.0028, 0.001 |
| NCI-H1770 | Human | Adult | Metastatic Cancer | Lung | Non-Small Cell Lung Carcinoma (NSCLC) | Lymph Node | 0.00724 |
| NCI-H82 | Human | Adult | Metastatic Cancer | Lung | Variant Small Cell Lung Carcinoma (SCLC) | Pleural effusion | 0.015 |
| PER.C6 ® | Human | Fetal | Cancer | Eye, Retina | Retinoblast | | 0.02, 0.0049 |
| NCI-H69AR | Human | Adult | Cancer | Lung | Small Cell Lung Carcinoma, multi-drug resistant (SCLC) | | 0.035, 0.05 |
| SK-NEP-1 | Human | Adult | Metastatic Cancer | Kidney | Wilms' Tumor | Pleural effusion | 0.03 |
| IMR-32 | Human | Adult | Cancer | Brain | Neuroblastoma | | 0.035, 0.0059, 0.05 |
| NCI-H187 | Human | Adult | Metastatic Cancer | Lung | Classic Small Cell Lung Carcinoma (SCLC) | Pleural effusion | 0.00343 |
| NCI-H209 | Human | Adult | Metastatic Cancer | Lung | Small Cell Lung Carcinoma (SCLC) | Bone Marrow | 0.04 |
| NCI-H1184 | Human | Adult | Metastatic Cancer | Lung | Small Cell Lung Carcinoma (SCLC) | Lymph Node | 0.155 |
| D283 Med | Human | Adult | Metastatic Cancer | Brain, Cerebellum | Medulloblastoma | Peritoneum | 0.25 |
| SK-N-AS | Human | Adult | Metastatic Cancer | Brain | Neuroblastoma | Bone Marrow | 0.474 |
| BEK PCB3E1 | Bovine | Fetal | Normal, Ad5 transformed | Kidney | Ad5E1 transformed | | 0.99 |
| ST | Porcine | Fetal | Normal, immortalized | Testis | | | 5.9 |
| NCI-H1299 | Human | Adult | Metastatic Cancer | Lung | Large Cell Lung Carcinoma | Lymph Node | 7.66, 4.8 |
| DMS 153 | Human | Adult | Metastatic Cancer | Lung | Small Cell Lung Carcinoma (SCLC) | Liver | 9.2 |
| NCI-H295R | Human | Adult | Cancer | Adrenal Gland, Cortex | Adrenocortical Carcinoma | | 16.5 |
| BEK | Bovine | Fetal | Normal, immortalized | Kidney | | | 17.55 |
| PPASMC | Porcine | Adult | Normal, Primary | Lung, Pulmonary Artery | Smooth Muscle Cells | | 18.4 |
| PCASMC | Porcine | Adult | Normal, Primary | Heart, Coronary Artery | Smooth Muscle Cells | | 11.9 |
| PAoSMC | Porcine | Adult | Normal, Primary | Heart, Aorta | Smooth Muscle Cells | | 88 |
| NCI-H526 | Human | Adult | Metastatic Cancer | Lung | Variant Small Cell Lung Carcinoma (SCLC) | Bone Marrow | 46.4 |
| OVCAR-3 | Human | Adult | Cancer | Ovary | Adenocarcinoma | | 39 |
| ESK-4 | Porcine | Fetal | Normal, immortalized | Kidney | Fibroblast | | 60 |
| SW-13 | Human | Adult | Cancer | Adrenal Gland, Cortex | Small Cell Adenocarcinoma | | <100 |
| 293 | Human | Fetal | Normal, Ad5 transformed | Kidney | Ad5 transformed | | 0.036, 184.8 |
| Hs 578T | Human | Adult | Cancer | Breast | Carcinoma | | 273 |
| Hs 1.Tes | Human | Fetal | Normal, Immortalized | Testis | | | 416 |
| LOX IMVI | Human | Adult | Cancer | Skin | Melanoma | | 569 |
| PK(15) | Porcine | Adult | Normal, Immortalized | Kidney | | | 1144, 129 |
| NON PERMISSIVE | | | | | | | |
| WI-38 | Human | Fetal | Normal, Immortalized | Lung | Fibroblast | | >10,000 |
| IMR-90 | Human | Fetal | Normal, Immortalized | Lung | Fibroblast | | >10,000 |
| MRC-5 | Human | Fetal | Normal, Immortalized | Lung | Fibroblast | | >10,000 |
| HCN-1A | Human | Adult | Normal, Immortalized | Brain, Cortical Neuron | | | >10,000 |
| HMVEC | Human | Adult (neonatal) | Normal, Primary | Skin | Microvascular Endothelial Cells | | >10,000 |
| HMVEC | Human | Adult | Normal, Primary | Skin | Microvascular Endothelial Cells | | >10,000 |

TABLE 1-A-continued

In Vitro Cytolytic Potency and Selectivity of SVV

| Cell Line | Species | Stage | State | Organ | Type | Metastatic Site | EC50* |
|---|---|---|---|---|---|---|---|
| HUVEC | Human | Adult | Normal, Primary | Umbilical Vein | Endothelial Cells | | >10,000 |
| HRE | Human | Adult | Normal, Primary | Kidney | Epithelial Cells | | >10,000 |
| HRCE | Human | Adult | Normal, Primary | Kidney | Cortical Epithelial Cells | | >10,000 |
| PHH | Human | Adult | Normal, Primary | Liver | Hepatocyte | | >10,000 |
| HCASMC-c | Human | Adult | Normal, Primary | Heart, Coronary Artery | Smooth Muscle Cells | | >10,000 |
| HCAEC | Human | Adult | Normal, Primary | Heart, Coronary Artery | Endothelial Cells | | >10,000 |
| HAEC | Human | Adult | Normal, Primary | Heart, Aorta | Endothelial Cells | | >10,000 |
| HAoSMC-c | Human | Adult | Normal, Primary | Heart, Aorta | Smooth Muscle Cells | | >10,000 |
| NHA | Human | Adult | Normal, Primary | Brain | Astrocytes | | 1713 |
| HPASMC | Human | Adult | Normal, Primary | Lung | Smooth Muscle Cells | | >10,000 |
| PBMC | Human | Adult | Normal, Primary | Peripheral Blood | Mononuclear Cells | | >10,000 |
| SF-295 | Human | Adult | Cancer | Brain | Glioblastoma | | >10,000 |
| U251 | Human | Adult | Cancer | Brain | Glioblastoma | | >10,000 |
| SF-539 | Human | Adult | Cancer | Brain | Glioblastoma | | >10,000 |
| SNB-19 | Human | Adult | Cancer | Brain | Glioblastoma | | >10,000 |
| SF-268 | Human | Adult | Cancer | Brain | Glioblastoma | | 3103 |
| U-118MG | Human | Adult | Cancer | Brain | Glioblastoma, Astrocytoma | | >10,000 |
| SNB-75 | Human | Adult | Cancer | Brain | Astrocytoma | | >10,000 |
| M059K | Human | Adult | Cancer | Brain, Glial Cell | Malignant Glioblastoma | | 1061 |
| KK | Human | Adult | Cancer | Brain, Glial Cell | Glioblastoma | | >10,000 |
| HCC-2998 | Human | Adult | Cancer | Colon | Carcinoma | | >10,000 |
| KM12 | Human | Adult | Cancer | Colon | Carcinoma | | >10,000 |
| HT-29 | Human | Adult | Cancer | Colon | Adenocarcinoma | | >10,000 |
| HCT 116 | Human | Adult | Cancer | Colon | Carcinoma | | >10,000 |
| HCT-15 | Human | Adult | Cancer | Colon | Carcinoma | | >10,000 |
| COLO 205 | Human | Adult | Metastatic Cancer | Colon | Adenocarcinoma | Ascites | >10,000 |
| SW620 | Human | Adult | Metastatic Cancer | Colon | Colorectal Carcinoma | Lymph Node | 6503, >10,000 |
| PC3M-2AC6 | Human | Adult | Cancer | Prostate | | | >10,000 |
| PC3M-2AC6 + 2-AP | Human | Adult | Cancer | Prostate | | | ND |
| PC-3 | Human | Adult | Metastatic Cancer | Prostate | Adenocarcinoma | Bone | >10,000 |
| LNCaP.FGC | Human | Adult | Metastatic Cancer | Prostate | Adenocarcinoma | Lymph Node | >10,000 |
| DU 145 | Human | Adult | Metastatic Cancer | Prostate | Adenocarcinoma | Brain | >10,000 |
| Hep3B | Human | Adult | Cancer | Liver | Hepatocellular Carcinoma | | >10,000 |
| Hep G2 | Human | Adult | Cancer | Liver | Hepatocellular Carcinoma | | >10,000 |
| 786-O | Human | Adult | Cancer | Kidney | Clear Cell Adenocarcinoma | | >10,000 |
| TK-10 | Human | Adult | Cancer | Kidney | Carcinoma | | >10,000 |
| RXF 393 | Human | Adult | Cancer | Kidney | Carcinoma | | >10,000 |
| UO-31 | Human | Adult | Cancer | Kidney | Carcinoma | | >10,000 |
| SN12C | Human | Adult | Cancer | Kidney | Carcinoma | | >10,000 |
| A-498 | Human | Adult | Cancer | Kidney | Carcinoma | | >10,000 |
| ACHN | Human | Adult | Cancer | Kidney | Carcinoma | | >10,000 |
| SW839 | Human | Adult | Cancer | Kidney | Renal Clear Cell Adenocarcinoma | | >10,000 |
| Caki-1 | Human | Adult | Metastatic Cancer | Kidney | Clear Cell Adenocarcinoma | Skin | >10,000 |
| 5637 | Human | Adult | Cancer | Bladder | Carcinoma | | >10,000 |
| NCI-H1339 | Human | Adult | Cancer | Lung | | | >10,000 |
| NCI-H1514 | Human | Adult | Cancer | Lung | | | >10,000 |
| A549 | Human | Adult | Cancer | Lung | Carcinoma | | >10,000 |
| S8 | Human | Adult | Cancer | Lung | Carcinoma | | >10,000 |
| NCI-H727 | Human | Adult | Cancer | Lung | Carcinoid | | >10,000 |
| NCI-H835 | Human | Adult | Cancer | Lung | Carcinoid | | >10,000 |
| UMC-11 | Human | Adult | Cancer | Lung | Carcinoid | | >10,000 |

TABLE 1-A-continued

In Vitro Cytolytic Potency and Selectivity of SVV

| Cell Line | Species | Stage | State | Organ | Type | Metastatic Site | EC50* |
|---|---|---|---|---|---|---|---|
| DMS 114 | Human | Adult | Cancer | Lung | Small Cell Lung Carcinoma (SCLC) | | >10,000 |
| DMS 53 | Human | Adult | Cancer | Lung | Small Cell Lung Carcinoma (SCLC) | | >10,000 |
| NCI-H69 | Human | Adult | Cancer | Lung | Small Cell Lung Carcinoma (SCLC) | | >10,000 |
| NCI-H2195 | Human | Adult | Metastatic Cancer | Lung | Small Cell Lung Carcinoma (SCLC) | Bone Marrow | >10,000 |
| DMS 79 | Human | Adult | Metastatic Cancer | Lung | Small Cell Lung Carcinoma (SCLC) | Pleural effusion | >10,000 |
| NCI-H146 | Human | Adult | Metastatic Cancer | Lung | Classic Small Cell Lung Carcinoma (SCLC) | Bone Marrow | >10,000 |
| NCI-H1618 | Human | Adult | Metastatic Cancer | Lung | Classic Small Cell Lung Carcinoma (SCLC) | Bone Marrow | >10,000 |
| NCI-H345 | Human | Adult | Metastatic Cancer | Lung | Classic Small Cell Lung Carcinoma (SCLC) | Bone Marrow | >10,000 |
| HOP-62 | Human | Adult | Cancer | Lung | Non-Small Cell Lung Carcinoma (NSCLC) | | >10,000 |
| EKVX | Human | Adult | Cancer | Lung | Non-Small Cell Lung Carcinoma (NSCLC) | | >10,000 |
| HOP-92 | Human | Adult | Cancer | Lung | Non-Small Cell Lung Carcinoma (NSCLC) | | >10,000 |
| NCI-H522 | Human | Adult | Cancer | Lung | Non-Small Cell Lung Carcinoma (NSCLC) | | >10,000 |
| NCI-H23 | Human | Adult | Cancer | Lung | Non-Small Cell Lung Carcinoma (NSCLC) | | >10,000 |
| NCI-H322M | Human | Adult | Cancer | Lung | Non-Small Cell Lung Carcinoma (NSCLC) | | >10,000 |
| NCI-H226 | Human | Adult | Metastatic Cancer | Lung | Squamous Cell Carcinoma, Mesothelioma (NSCLC) | Pleural effusion | >10,000 |
| NCI-H460 | Human | Adult | Metastatic Cancer | Lung | Large Cell Lung Carcinoma | Pleural effusion | >10,000 |
| HeLa, HeLa S3 | Human | Adult | Cancer | Cervix | Adenocarcinoma | | >10,000 |
| CCRF-CEM | Human | Adult | Cancer | Peripheral Blood, T lymphoblast | Acute Lymphoblastic Leukemia (ALL) | | >10,000 |
| MOLT-4 | Human | Adult | Cancer | Peripheral Blood, T lymphoblast | Acute Lymphoblastic Leukemia (ALL) | | >10,000 |
| RPMI 8226 | Human | Adult | Cancer | Peripheral Blood, B lymphocyte | Plasmacytoma, Myeloma | | >10,000 |
| SR | Human | Adult | Metastatic Cancer | Lymphoblast | Large Cell Lymphoblastic Lymphoma | Pleural effusion | >10,000 |
| HL-60(TB) | Human | Adult | Cancer | Peripheral Blood, Promyeloblast | Acute Promyelocytic Leukemia (APL) | | >10,000 |
| K-562 | Human | Adult | Metastatic Cancer | Bone Marrow | Chronic Myelogenous Leukemia (CML) | Pleural effusion | >10,000 |
| UACC-257 | Human | Adult | Cancer | Skin | Melanoma | | >10,000 |
| M14 | Human | Adult | Cancer | Skin | Melanoma | | >10,000 |
| UACC-62 | Human | Adult | Cancer | Skin | Melanoma | | 6614 |
| SK-MEL-2 | Human | Adult | Cancer | Skin | Malignant Melanoma | | >10,000 |
| SK-MEL-28 | Human | Adult | Cancer | Skin | Malignant Melanoma | | >10,000 |
| A375.S2 | Human | Adult | Cancer | Skin | Malignant Melanoma | | >10,000 |
| SK-MEL-28 | Human | Adult | Cancer | Skin | Malignant Melanoma | | >10,000 |
| SK-MEL-5 | Human | Adult | Metastatic Cancer | Skin | Malignant Melanoma | Lymph Node | >10,000 |
| MALME-3M | Human | Adult | Metastatic Cancer | Skin | Malignant Melanoma | Lung | >10,000 |
| BT-549 | Human | Adult | Cancer | Breast | Ductal Carcinoma | | >10,000 |
| NCI/ADR-RES | Human | Adult | Cancer | Breast | Carcinoma | | >10,000 |
| MCF7 | Human | Adult | Metastatic Cancer | Breast | Adenocarcinoma | Pleural effusion | >10,000 |
| MDA-MB-231 | Human | Adult | Metastatic Cancer | Breast | Adenocarcinoma | Pleural effusion | >10,000 |
| T-47D | Human | Adult | Metastatic Cancer | Breast | Ductal Carcinoma | Pleural effusion | >10,000 |

TABLE 1-A-continued

In Vitro Cytolytic Potency and Selectivity of SVV

| Cell Line | Species | Stage | State | Organ | Type | Metastatic Site | EC50* |
|---|---|---|---|---|---|---|---|
| MDA-MB-435 | Human | Adult | Metastatic Cancer | Breast | Ductal Adenocarcinoma | Pleural effusion | >10,000 |
| IGR-OV1 | Human | Adult | Cancer | Ovary | Carcinoma | | >10,000 |
| OVCAR-4 | Human | Adult | Cancer | Ovary | Adenocarcinoma | | >10,000 |
| OVCAR-5 | Human | Adult | Cancer | Ovary | Adenocarcinoma | | >10,000 |
| OVCAR-8 | Human | Adult | Cancer | Ovary | Adenocarcinoma | | >10,000 |
| SK-OV-3 | Human | Adult | Metastatic Cancer | Ovary | Adenocarcinoma | Ascites | >10,000 |
| BxPC-3 | Human | Adult | Cancer | Pancreas | Adenocarcinoma | | >10,000 |
| AsPC-1 | Human | Adult | Metastatic Cancer | Pancreas | Adenocarcinoma | Ascites | >1000 |
| NCI-H295 | Human | Adult | Cancer | Adrenal Gland, Cortex | Adrenocortical Carcinoma | | >10,000 |
| TT | Human | Adult | Cancer | Thyroid | Medullary Carcinoma | | >10,000 |
| C8-D30 | Murine | Adult | Normal | Brain, Cerebellum | | | >10,000 |
| LLC1 | Murine | Adult | Cancer | Lung | Lewis Lung Carcinoma | | >10,000 |
| RM-1 | Murine | Adult | Cancer | Prostate | | | >10,000 |
| MLTC-1 | Murine | Adult | Cancer | Testis | Leydig Cell Tumor | | >10,000 |
| KLN 205 | Murine | Adult | Cancer | Lung | Squamous Cell Carcinoma | | >10,000 |
| CMT-64 | Murine | Adult | Cancer | Lung | Small Cell Lung Carcinoma (SCLC) | | >10,000 |
| CMT-93 | Murine | Adult | Cancer | Rectum | Polyploid Carcinoma | | >10,000 |
| B16-F0 | Murine | Adult | Cancer | Skin | Melanoma | | >10,000 |
| RM-2 | Murine | Adult | Cancer | Prostate | | | >10,000 |
| RM-9 | Murine | Adult | Cancer | Prostate | | | >10,000 |
| Neuro-2A | Murine | Adult | Cancer | Brain | Neuroblastoma | | >10,000 |
| FBRC | Bovine | Fetal | | Eye, Retina | | | >10,000 |
| MDBK | Bovine | Adult | Normal, Immortalized | Kidney | | | >10,000 |
| CSL 503 | Ovine | Adult | Normal, Immortalized | Lung | Ad5E1 transformed | | >10,000 |
| OFRC | Ovine | Adult | Normal, Immortalized | Eye, Retina | Ad5E1 transformed | | >10,000 |
| PC-12 | Rat | Adult | Cancer | Adrenal Gland | Pheochromocytoma | | >10,000 |
| Vero | Monkey | Adult | Normal, Immortalized | Kidney | | | >10,000 |
| PAOEC | Porcine | Adult | Normal, Primary | Heart, Aorta | Endothelial Cells | | >10,000 |
| PCAEC | Porcine | Adult | Normal, Primary | Heart, Coronary Artery | Endothelial Cells | | >10,000 |
| PPAEC | Porcine | Adult | Normal, Primary | Lung, Pulmonary Artery | Endothelial Cells | | >10,000 |
| TBD | | | | | | | |
| NCI-H289 | Human | Adult | Cancer | Lung | | | TBD |
| NCI-H1963 | Human | Adult | Cancer | Lung | Small Cell Lung Carcinoma (SCLC) | | TBD |
| NCI-H2227 | Human | Adult | Cancer | Lung | Small Cell Lung Carcinoma (SCLC) | | TBD |
| NCI-H378 | Human | Adult | Metastatic Cancer | Lung | Classic Small Cell Lung Carcinoma (SCLC) | Pleural effusion | TBD |
| NCI-H2107 | Human | Adult | Metastatic Cancer | Lung | Small Cell Lung Carcinoma (SCLC) | Bone Marrow | TBD |
| HCC970 | Human | Adult | Metastatic Cancer | Lung | Small Cell Lung Carcinoma (SCLC) | Bone Marrow | TBD |
| HCC33 | Human | Adult | Metastatic Cancer | Lung | Small Cell Lung Carcinoma (SCLC) | Pleural effusion | <1000/TBD |
| BON | Human | Adult | Cancer | Pancreas | Carcinoid | | TBD |
| H1T-T15 | Hamster | Adult | Normal, Immortalized | Pancreas | Islets of Langerhans, b-cell | | TBD |

*EC50 determined after 3 days except where noted

Table 1-A lists the results of SVV permissivity experiments on 165 primary cells and cell lines, representing 22 tissues from 8 different species. The results indicate that virtually all adult normal are nonpermissive for SVV. Thirteen primary adult human cell cultures tested were nonpermissive. Of the twelve bovine, ovine, porcine and primate normal cell cultures tested, only three cell cultures were permissive, which were porcine smooth muscle cells. This result is consistent with the hypothesis that the natural host for SVV may be pigs. Besides the porcine smooth muscle cells, only neuroendocrine cancer cell lines or most fetal lines were permissive.

Murine studies (see Examples) show that SVV can specifically kill tumors with great efficacy and specificity in vivo.

These in vivo studies show that SVV has a number of advantages over other oncolytic viruses. For example, one important factor affecting the ability of an oncolytic tumor virus to eradicate established tumors is viral penetration. In studies with adenoviral vectors, Ad5 based vectors had no effect on SCLC tumor development in athymic mice. Based on immunohistochemical results, adenovirus did not appear to penetrate the established tumors. In contrast, SVV was able to eliminate H446 SCLC tumors in athymic nude mice following a single systemic administration. SVV has a small size (<30 nm in diameter) enabling better penetration and spread in tumor tissue than other viruses, and thus, the small size of SVV may contribute to its ability to successfully penetrate and eradicate established tumors.

Additional in vivo tests demonstrate the efficacy of a single intravenous dose of SVV in murine tumor models using athymic nude mice and immunocompetent mice. The tumor models tested were: (1) H446 (human SCLC); (2) Y79 (human retinoblastoma); (3) H69AR (human multi-drug resistant SCLC); (4) H1299 (human NSCLC); and (5) N1E-115 (murine neuroblastoma). The results of these tests are shown in FIGS. 90A-E and Example 11. The tests demonstrate efficacy of a single intravenous dose of SVV in all models and show an agreement between relative ranks of in vitro $ED_{50}$ and in vivo efficacy in human xenograft models. The results in the N1E-115 immunocompetent murine neuroblastoma model shows that SVV can be efficacious against tumors in subjects with normal immune systems.

Chemoresistance is a major issue facing any patient that receives chemotherapy as a facet of cancer therapy. Patients that become chemoresistant often, if not always, have a much poorer prognosis and may be left with no alternative therapy. It is well known that one of the major causes of chemoresistance is the expression, over expression, or increased activity of a family of proteins called Multiple Drug Resistant proteins (MRPs). Applicants have found that a sensitivity of certain tumor cells for SVV is also correlated with the chemoresistant state of cancer cells and MRP expression. H69 is a chemosensitive (adriamycin) cell line that is resistant to SVV in vitro, whereas H69AR is a chemoresistant cell line that overexpresses MRPs and is sensitive to SVV (see Table 1). Evidence indicates that overexpression of MRPs, including MDR, correlates with sensitivity of cells to SVV killing. Thus, in one embodiment, the present invention provides a method for treating cancer wherein SVV kills cells overexpressing an MRP.

The invention also provides methods for treating diseases that are a result of abnormal cells, such as abnormally proliferative cells. The method comprises contacting said abnormal cells with SVV in a manner that results in the destruction of a portion or all of the abnormal cells. SVV can be used to treat a variety of diseases that are a result of abnormal cells. Examples of these diseases include, but are not limited to, cancers wherein the tumor cells display neuroendocrine features and neurofibromatosis.

Neuroendocrine tumors can be identified by a variety of methods. For example, neuroendocrine tumors produce and secrete a multitude of peptide hormones and amines. Some of these substances cause a specific clinical syndrome: carcinoid, Zollinger-Ellison, hyperglycemic, glucagonoma and WDHA syndrome. Specific markers for these syndromes are basal and/or stimulated levels of urinary 5-HIAA, serum or plasma gastrin, insulin, glucagon and vasoactive intestinal polypeptide, respectively. Some carcinoid tumors and about one third of endocrine pancreatic tumors do not present any clinical symptoms and are called 'nonfunctioning' tumors. Therefore, general tumor markers such as chromogranin A, pancreatic polypeptide, serum neuron-specific enolase and subunits of glycoprotein hormones have been used for screening purposes in patients without distinct clinical hormone-related symptoms. Among these general tumor markers chromogranin A, although its precise function is not yet established, has been shown to be a very sensitive and specific serum marker for various types of neuroendocrine tumors. This is because it may also be elevated in many cases of less well-differentiated tumors of neuroendocrine origin that do not secrete known hormones. At the moment, chromogranin A is considered the best general neuroendocrine serum or plasma marker available both for diagnosis and therapeutic evaluation and is increased in 50-100% of patients with various neuroendocrine tumors. Chromogranin A serum or plasma levels reflect tumor load, and it may be an independent marker of prognosis in patients with midgut carcinoids.

The invention also provides a pharmaceutical composition comprising SVV and a pharmaceutically acceptable carrier. Such compositions, which can comprise an effective amount of SVV in a pharmaceutically acceptable carrier, are suitable for local or systemic administration to individuals in unit dosage forms, sterile parenteral solutions or suspensions, sterile non-parenteral solutions or oral solutions or suspensions, oil in water or water in oil emulsions, and the like. Formulations for parenteral and non-parenteral drug delivery are known in the art. Compositions also include lyophilized and/or reconstituted forms of SVV. Acceptable pharmaceutical carriers are, for example, saline solution, protamine sulfate (Elkins-Sinn, Inc., Cherry Hill, N.J.), water, aqueous buffers, such as phosphate buffers and Tris buffers, or Polybrene (Sigma Chemical, St. Louis, Mo.) and phosphate-buffered saline and sucrose. The selection of a suitable pharmaceutical carrier is deemed to be apparent to those skilled in the art from the teachings contained herein. These solutions are sterile and generally free particulate matter other than SVV. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, etc. Excipients that enhance infection of cells by SVV may be included.

SVV is administered to a host or subject in an amount that is effective to inhibit, prevent or destroy the growth of the tumor cells through replication of the virus in the tumor cells. Methods that utilize SVV for cancer therapy include systemic, regional or local delivery of the virus at safe, developable, and tolerable doses to elicit therapeutically useful destruction of tumor cells. Even following systemic administration, the therapeutic index for SVV is at least 10, preferably at least 100 or more preferably at least 1000. In general, SVV is administered in an amount of between $1 \times 10^8$ and $1 \times 10^{14}$ vp/kg. The exact dosage to be administered is dependent upon a variety of factors including the age, weight, and sex of the patient, and the size and severity of the tumor being treated. The viruses may be administered one or more times, which may be dependent upon the immune response potential of the host. Single or multiple administrations of the compositions can be carried out with dose levels and pattern being selected by the treating physician. If necessary, the immune response may be diminished by employing a variety of immunosuppressants, so as to permit repetitive administration and/or enhance replication by reducing the immune response to the viruses. Anti-neoplastic viral therapy of the present invention may be combined with other anti-neoplastic protocols. Delivery can be achieved in a variety of ways, employing liposomes, direct injection, catheters, topical application, inhalation, etc. Further, a DNA copy of the SVV genomic RNA, or portions thereof, can also be a method of delivery, where the DNA is subsequently transcribed by cells to produce SVV virus particles or particular SVV polypeptides.

A therapeutically effective dose refers to that amount of the virus that results in amelioration of symptoms or a prolongation of survival in a patient. Toxicity and therapeutic efficacy of viruses can be determined by standard procedures in cell cultures or experimental animals, e.g., for determining the $LD_{50}$ (the dose lethal to 50% of the population of animals or cells; for viruses, the dose is in units of vp/kg) and the $ED_{50}$ (the dose—vp/kg—therapeutically effective in 50% of the population of animals or cells) or the $EC_{50}$ (the effective concentration—vp/cell (see Table 1 for example)—in 50% of the population of animals or cells). The dose ratio between toxic and therapeutic effects is the therapeutic index and it can be expressed as the ratio between $LD_{50}$ and $ED_{50}$ or $EC_{50}$. Viruses which exhibit high therapeutic indices are preferred. The data obtained from these cell culture assays and animal studies can be used in formulating a range of dosage for use in human. The dosage of viruses lies preferably within a range of circulating concentrations that include the $ED_{50}$ or $EC_{50}$ with little or no toxicity. The dosage may vary within this range depending upon the dosage form employed and the route of administration utilized.

In yet another aspect, a method for treating a host organism having a neoplastic condition is provided, comprising administering a therapeutically effective amount of a viral composition of the invention to said host organism. In one embodiment, the neoplastic tissue is abnormally proliferating, and the neoplastic tissue can be malignant tumor tissue. Preferably, the virus is distributed throughout the tissue or tumor mass due to its capacity for selective replication in the tumor tissue. Neoplastic conditions potentially amenable to treatment with the methods of the invention include those with neurotropic properties.

Methods for Producing the Viruses of the Present Invention:

Methods for producing the present viruses to very high titers and yields are additional aspects of the invention. As stated, SVV can be purified to high titer and can be produced at more than 200,000 particles per cell in permissive cell lines. Cells that are capable of producing high quantities of viruses include, but are not limited to, PER.C6 (Fallaux et al., *Human Gene Therapy*, 9:1909-1917, 1998), H446 (ATCC# HTB-171) and the other cell lines listed in Table 1 where the $EC_{50}$ value is less than 10.

For example, the cultivation of picornaviruses can be conducted as follows. The virus of interest is plaque purified and a well-isolated plaque is picked and amplified in a permissive cell line, such as PER.C6. A crude virus lysate (CVL) from the infected cells can be made by multiple cycles of freeze and thaw, and used to infect large numbers of permissive cells. The permissive cells can be grown in various tissue culture flasks, for example, 50×150 cm² flasks using various media, such as Dulbecco's modified Eagle medium (DMEM, Invitrogen, Carlsbad, Calif.)) containing 10% fetal bovine serum (Biowhitaker, Walkersville, Md.) and 10 mM magnesium chloride (Sigma, St Louis, Mo.). The infected cells can be harvested between 12 and 48 hours after infection or when complete cytopathic effects (CPE) are noticed, and are collected by centrifugation at 1500 rpm for 10 minutes at 4° C. The cell pellet is resuspended in the cell culture supernatant and is subjected to multiple cycles of freeze and thaw. The resulting CVL is clarified by centrifugation at 1500 rpm for 10 minutes at 4° C. Virus can be purified by gradient centrifugation. For example, two rounds of CsCl gradients can suffice for SVV purification: a one-step gradient (density of CsCl 1.24 g/ml and 1.4 g/ml) followed by one continuous gradient centrifugation (density of CsCl 1.33 g/ml). The purified virus concentration is determined spectrophotometrically, assuming $1A260=9.5\times10^{12}$ particles (Scraba D. G., and Palmenberg, A. C. 1999. Cardioviruses (Picornaviridae). In: *Encyclopedia of Virology*, Second edition, R. G. Webster and A Granoff Eds). Infectivity titers of purified virus are also determined by a standard plaque and/or tissue culture infective dose 50 ($TCID_{50}$) assay using PER.C6 or any other suitable cell type. The yield of SVV from PER.C6 cells are greater than 200,000 particles per cell with particles to PFU ratio of about 100. The yields of SVV from other permissive cells (H446-ATCC# HTB-171) may be at least this high or higher. SVV can also be purified by column chromatography.

In addition, several steps in a commercially attractive large scale Good Manufacturing Processes (GMP) are applicable to the purification of SVV. The invention also contemplates methods for purifying SVV that are based on methods for purifying adenoviruses. These methods include isolating SVV based on its density, since SVV has a very similar density to adenovirus and can be co-purified with adenovirus.

Methods for Detecting and Studying Tumors:

The present invention provides methods for detecting tumor or neoplastic cells in a patient using the viruses of the present invention. Cellular samples can be obtained from a patient and screened by incubating the sample with an epitope-tagged SVV (or other tumor-specific viruses provided by the invention, i.e., tumor-specific mutant cardioviruses), and then screening the sample for bound SVV by detecting the epitope tag. Alternatively, the sample can be screened by detecting whether the SVV causes any cellular lysis. If SVV does cause cellular lysis, or if SVV can bind specifically to cells in the sample, this would indicate the possibility that the sample contains neoplastic or tumor cells known to be capable of being bound and/or infected by SVV.

Additionally, SVV can be used in a method for detecting a tumor cell in vivo. In such a method, epitope-tagged SVV can first be inactivated in a manner where SVV can still bind to tumor cells specifically but cannot replicate. Tumor cells that have bound SVV can be detected by assaying for the epitope tag. Detection of the epitope tag can be accomplished by antibodies that specifically bind the epitope, where the antibodies are either labeled (for example, fluorescently) or where the antibodies can then be detected by labeled secondary antibodies.

The present methods of detection encompass detecting any type of tumor or neoplastic cell that is specifically targeted by any virus of the present invention. Specific tumor types include, for example, neuroendocrine-type tumors, such as retinoblastomas, SCLC, neuroblastomas glioblastomas and medulloblastomas.

The present invention also provides the use of SVV as a tool to study tumor cells. SVV selectively destroys some tumor cell types, and has very little, if any, toxic effects on non-tumor cells. Because of these characteristics, SVV can be used to study tumors and possibly discover a new tumor specific gene and/or pathway. In other words, there is some characteristic of the tumor cells that allows replication of SVV, wherein normal cells do not exhibit said characteristic. Upon identification of a new tumor specific gene and/or pathway, therapeutic antibodies or small molecules can then be designed or screened to determine whether these reagents are anti-tumor agents.

The present invention also provides a method for identifying all types of cancers that respond to SVV. In one embodiment, the method for identifying SVV-responsive cells comprises obtaining cells, contacting said cells with SVV and detecting cell killing or detecting viral replication. Cell killing can be detected using various methods known to one skilled in the art (e.g., MTS assay, see High-Throughput section herein). Methods of detecting virus replication are also known to one skilled in the art (e.g., observance of CPE, plaque assay, DNA quantification methods, FACS to detect quantity of virus in the tumor cells, RT-PCR assays to detect viral RNA, etc.). In one embodiment, the cells are cancer cells. Examples of cancer cells include, but are not limited to, established tumor cell lines and tumor cells obtained from a mammal. In one embodiment, the mammal is a human. In a further embodiment, the cells are cancer cells obtained from a human cancer patient.

The method for identifying SVV-responsive cancer cells may be used to discover tumor cell lines or tumor tissues that are permissive for SVV replication. Also, by determining the characteristics of permissive tumor cells, one may be able to identify characteristics of tumor cells that cause the cells to be selectively killed by SVV. The discovery of these characteristics could lead to new targets for cancer drugs. Also, the methods for identifying SVV responsive cancer cells could be used as a screen for human cancer patients who would benefit from treatment with SVV.

For example, antibodies against SVV or an SVV-like picornavirus (polyclonal, monoclonal, etc.) can be used in a viral binding assay to pre-screen patients prior to SVV or SVV-like picornavirus therapy. The pre-screening can be conducted generally as follows: (1) cells from a patient are isolated, the cells can be from a tumor biopsy for example, (2) the cells are stained with anti-SVV or anti-SVV-like picornavirus antibodies, (3) a secondary antibody conjugated with a marker (such as fluorescein or some other detectable dye or fluorophore) that is specific to the anti-SVV or anti-SVV-like picornavirus antibodies is added (for example, if the antibodies were raised in a rabbit, then the secondary antibody would be specific for rabbit immunoglobulins), and (4) detection for the marker is conducted—for example, fluorescence microscopy can be conducted where the marker is fluorescein. (Step 3 is optional if the anti-SVV or anti-SVV-like picornavirus antibodies are directly conjugated, i.e, where the antibodies are monoclonal. If the antibodies are polyclonal, indirect immunofluorescence—use of a secondary antibody—is suggested.) If the patient's tumor cells are permissive for SVV or SVV-like picornavirus infection, then the patient is a candidate for SVV or SVV-like picornavirus therapy. In a virus binding assay, the patient's tumor cells can be determined to be permissive for SVV if the cells are positive for antibody staining. For example, FIGS. 92B-92C shows immunofluorescent images of cells permissive for SVV and have been infected with SVV.

In pre-screening patients with a viral binding assay, the cell sample from the patient can also be a tissue section of a tissue suspected to contain tumor cells. The tissue section can then be prepared into sections and incubated with SVV prior to histochemistry with anti-SVV or anti-SVV-like picornavirus antibodies.

The invention also provides methods of detecting SVV. In one embodiment, the detection assay is based on antibodies specific to SVV polypeptide epitopes. In another embodiment, the detection assay is based on the hybridization of nucleic acids. In one embodiment, RNA is isolated from SVV, labeled (e.g., radioactive, chemiluminsecence; fluorescence, etc.) to make a probe. RNA is then isolated from test material, bound to nitrocellulose (or a similar or functionally equivalent substrate), probed with the labeled SVV RNA, and the amount of bound probe detected. Also, the RNA of the virus may be directly or indirectly sequenced and a PCR assay developed based on the sequences. In one embodiment, the PCR assay is a real time PCR assay.

Methods for Making Viruses with Altered Tropism:

The present invention provides methods for constructing SVV mutants (or variants or derivatives) where these mutants have an altered cell-type tropism. SVV-like picornaviruses may also be mutated in order to provide a particular cell-type tropism. Specifically, SVV and SVV-like picornavirus mutants are selected for their ability to specifically bind and/or kill tumor or neoplastic cells that are known to be resistant to wild-type SVV or wild-type SVV-like picornavirus binding.

The native or wild-type SVV has a simple genome and structure that allow the modification of the native virus to target other cancer indications. These new derivatives have an expanded tropism toward non-neural cancers and still maintain the high therapeutic index found in the native SVV. One possible means of targeting is the inclusion of tissue-specific peptides or ligands onto the virus.

To select cancer-targeting viral candidates, the present invention provides methods to construct and screen an oncolytic virus library with a genetic insertion that encodes a random peptide sequence in the capsid region of the native SVV. A random peptide library with a diversity of $10^8$ is believed to be sufficient and should yield peptides that specifically direct the virus to tumor tissue.

Various studies have shown that tumor cells exhibit different characteristics from normal cells such as: (1) tumor cells have more permeable cell membranes; (2) tumors have specific stromal cell types such as angiogenic endothelial cells which have previously been shown to express cell type specific receptors; and (3) tumor cells differentially express certain receptors, antigens and extracellular matrix proteins (Arap, W. et al., *Nat. Med.*, 2002, 8(2): 121-127; Kolonin, M. et al., *Curr. Opin. Chem. Biol.*, 2001, 5(3): 308-313; St. Croix, B. et al., *Science*, 2000, 289(5482): 1997-1202). These studies demonstrated that tumor and normal tissues are distinct at the molecular level and targeted drug delivery and treatment of cancer is feasible. Specifically, several peptides selected by homing to blood vessels in mouse models have been used for targeted delivery of cytotoxic drugs (Arap, W. et al., *Science*, 1998, 279(5349): 377-380), pro-apoptotic peptides (Ellerby, H. M. et al., *Nat. Med.*, 1999, 17(8): 768-774), metalloprotease inhibitor (Koivunen, E. et al., *Nat. Biotechnol*, 1999, 17(8): 768-774), cytokine (Curnis, F. et al., *Nat. Biotechnol.*, 2000, 18(11): 1185-1190), fluorophores (Hong. F. D. and Clayman, G. L., *Cancer Res.*, 2000, 60(23): 6551-6556) and genes (Trepel, M. et al., *Hum. Gene Ther.*, 2000, 11(14): 1971-1981). The tumor-targeting peptides have proven to increase the efficacy and lower the toxicity of the parental drugs.

A library of SVV derivatives can be generated by the insertion of a random peptide sequence into the capsid region of the virus. As shown in FIG. 57, a vector is first generated that contains the SVV capsid region, i.e., "pSVV capsid." This capsid vector can then be mutagenized, for example, by cutting the vector with a restriction enzyme that cuts DNA at random positions, i.e., CviJI (a blunt cutter). The vector is cut at numerous positions, and DNA that has been cut only once by CviJI can be isolated by gel-purification (see FIG. 57). This isolated population of DNA contains a plurality of species that have been cut in the capsid region at different locations. This population is then incubated with oligonucleotides and ligase, such that a percentage of the oligonucleotides will be ligated into the capsid region of the vector at a number of different positions. In this manner, a library of mutant SVV capsids can be generated.

The oligonucleotides that are inserted into the capsid encoding region can be either random oligonucleotides, non-random oligonucleotides (i.e., the sequence of the oligonucleotide is pre-determined), or semi-random (i.e., a portion of the oligonucleotide is pre-determined and a portion has a random sequence). The non-random aspect of the contemplated oligonucleotides can comprise an epitope-encoding region. Contemplated epitopes include, but are not limited to, c-myc—a 10 amino acid segment of the human protooncogene myc (EQKLISEEDL (SEQ ID NO: 35); HA—haemoglutinin protein from human influenza hemagglutinin protein (YPYDVPDYA (SEQ ID NO: 36)); and $His_6$ (SEQ ID NO:116)—a sequence encoding for six consecutive histidines.

The library of mutant capsid polynucleotides (for example, "pSVV capsid library" in FIG. 57) can then be digested with restriction enzymes such that only the mutant capsid encoding region is excised. This mutant capsid encoding region is then ligated into a vector containing the full-length genomic sequence minus the capsid encoding region (see FIG. 58, for example). This ligation generates a vector having a full-length genomic sequence, where the population (or library) of vectors comprise a plurality of mutant capsids. In FIG. 58, this library of SVV mutants comprising different capsids is denoted as "pSVVFL capsid." The pSVVFL capsid vector library is then linearized and in vitro transcribed in order to generate mutant SVV RNA (see FIG. 59). The mutant SVV RNA is then transfected into a permissive cell line such that those SVV sequences that do not possess a dehabilitating mutation in its capsid are translated by the host cells to produce a plurality of mutant SVV particles. In FIG. 59, the plurality of mutant SVV particles are denoted as a "SVV capsid library."

The peptide encoded by the oligonucleotide inserted into the capsid encoding region can serve as a targeting moiety for specific viral infection. The viruses that target a specific type of cancer would selectively infect only those cancer cells that have a receptor to the peptide, replicate in those cells, kill those cells, and spread to only those same types of cells. This methodology enables the identification of novel tumor-targeting peptides and ligands, tumor-selective receptors, therapeutic SVV derivatives and other virus derivatives, including picornavirus derivatives.

In vitro and in vivo screening of SVV mutant libraries have several advantages over other technologies such as peptide bead libraries and phage display. Unlike these other technologies, the desirable candidate here, i.e. an SVV derivative that selectively binds to a cancer cell, will replicate in situ. This replication-based library approach has numerous advantages over prior methods of discovering new cell binding moieties, such as phage display. First, the screening of a SVV library is based on replication. Only the desired viral derivatives can replicate in the target tissue, in this case certain cancer cells. The screening/selection process will yield very specific viral candidates that have both the targeting peptide moiety and may be a cancer therapeutic itself. On the contrary, phage display screens will only result in binding events and yields only the targeting peptide candidates. Thus, SVV library screening offers a much faster and selective approach. Second, during in vitro or in vivo phage display screening, phages recovered from the target cells have to be amplified in bacteria, while SVV derivatives can be directly recovered and purified from infected cells (or from the culture supernatant of lytically infected cells). Third, SVV has a smaller genome that renders easier manipulability; thus it is possible to randomly insert the genetic information into the capsid region to ensure an optimized insertion. Therefore, construction and screening of the SVV library has a high possibility to produce highly effective viral derivatives. These derivatives are designed and screened to specifically infect cancers with non-neural properties.

The insertion of oligonucleotides into the capsid encoding region will result in the generation of some defective mutants. Mutants may be defective in the sense that the insertion of an oligonucleotide sequence can result in a stop codon, such that the viral polyprotein will not be produced. Also, mutants may be defective in the sense that the insertion of an oligonucleotide sequence may result in the alteration of the capsid structure such that capsid can no longer be assembled. To decrease the probability that the insertion of oligonucleotide sequences may result in stop codon or untenable capsid structure, random oligonucleotides can be designed such that they do not encode for stop codons or for certain amino acids using methods such as TRIM.

To determine whether there is an optimal insertion point in the capsid region for oligonucleotides, one can generate an RGD-SVV library (see Example 16). The polynucleotide encoding the SVV capsid is randomly cut, for example, with CviJI. The randomly linearized capsid polynucleotides are then ligated to oligonucleotides encoding at least the RGD amino acid sequence (arginine-glycine-aspartic acid). These RGD-capsid sequences are then ligated into SVV full-length sequence vectors that are missing the capsid sequence. RGD-SVV derivatives viruses are produced and tested for their ability to infect and replicate in certain integrin-expressing cell lines (as the RGD peptide has been shown to target entities to integrin receptors). The RGD-SVV derivatives that are successful in infecting the integrin-expressing cell lines are then analyzed to determine whether there is a predominant insertion site for the RGD oligonucleotide. This site can then be used for site-directed insertion of random, non-random or semi-random oligonucleotides.

Further, in comparing portions of the capsid encoding region between SVV and other picornaviruses (see FIG. 28), there are various non-boxed regions between the viruses where the sequence similarity is at its lowest. These regions may be important in contributing to the different tropisms between the viruses. Thus, these regions may be candidate locations for oligonucleotide insertion mutagenesis of the SVV capsid (and for other viral capsids).

Inactivated SVV as a Tumor-Specific Therapeutic:

Since SVV and SVV-capsid derivatives can target specific tumor cell-types and/or tissues, the SVV particle itself can be used as a delivery vehicle for therapeutics. In such a method, the need for the oncolytic abilities of SVV becomes optional, as the delivered therapeutic can kill the targeted tumor cell.

For example, the wild-type SVV can be inactivated such that the virus no longer lyses infected cells, but where the virus can still specifically bind and enter targeted tumor cell-types. There are many standard methods known in the art to inactivate the replicative functions of viruses. For example, whole virus vaccines are inactivated by formalin or β-propiolactone such that the viruses cannot replicate. The wild-type SVV may itself contain peptides that cause the apoptosis of cells. Alternatively, SVV can be irradiated. However, irradiated viruses should first be tested to ensure that they are still capable of specifically targeting tumor cells, as certain irradiation conditions may cause protein, and thus capsid, alterations. Further, mutant SVVs can be generated where the packaging signal sequence is deleted. These SVV mutants are able to specifically bind and enter target cells, but replicated SVV genomic RNA will not be packaged and assembled into capsids. However, this method may prove to be useful as initial entry of these mutant SVVs will cause host-protein synthesis shut-off such that tumor-cell death is still achieved.

Derivative SVVs having mutant capsids can also be inactivated and used to kill cancer cells. Derivative SVVs with oligonucleotides encoding epitope tags inserted into the capsid region can be used as vehicles to deliver toxins to tumor cells. As described herein, derivative SVVs can be randomly mutagenized and screened for tumor-specific tropisms. Toxins can be attached to the epitope tags, such that the virus delivers the toxin to tumor cells. Alternatively, therapeutic antibodies that specifically bind to the epitope tag can be used, such that the virus delivers the therapeutic antibody to the tumor cell.

High-Throughput Screening:

The present invention encompasses high-throughput methods for screening viruses that have the ability to specifically infect different cell-lines. The specificity of infection can be detected by assaying for cytopathic effects. For example, a number of different tumor cell-lines can be grown in different wells of a multi-well plate that is amenable for high-throughput screening, for example a 384 well-plate. To each well, a sample of virus is added to test whether the cells are killed by virus-mediated lysis. From those wells that show cytopathic effects, the media is collected such that any viruses in the media can be amplified by infecting permissive cell lines in flasks or large tissue culture plates. The viruses are grown such that the RNA can be isolated and the sequence analyzed to determine sequence mutations that may be responsible for providing a tumor cell-type specific tropism for a virus.

Various colorimetric and fluorometric methods can quickly assay cytopathic effects, including fluorescent-dye based assays, ATP-based assays, MTS assays and LDH assays. Fluorescent-dye based assays can include nucleic acid stains to detect dead-cell populations, as cell-impermeant nucleic acid stains can specifically detect dead-cell populations. If it is desired to simultaneously detect both live-cell and dead-cell populations, nucleic acid stains can be used in combination with intracellular esterase substrates, membrane-permeant nucleic acid stains, membrane potential-sensitive probes, organelle probes or other cell-permeant indicators to detect the live-cell population. For example, Invitrogen (Carlsbad, Calif.) offers various SYTOX™ nucleic acid stains that only penetrate cells with compromised plasma membranes. Ethidium bromide and propidium iodide can also be used to detect dead or dying cells. These stains are high-affinity nucleic acid stains that can be detected by any light-absorbance reader For example, lysis can be based on the measurement of lactate dehydrogenase (LDH) activity released from the cytosol of damaged cells into the supernatant. To detect the presence of LDH in cell culture supernatants, a substrate mixture can be added such that LDH will reduce the tetrazolium salt INT to formazan by a coupled enzymatic reaction. The formazan dye can then be detected by a light-absorbance reader. Alternatively, an MTS assay [3-(4,5-dimethylthiazol-2-yl)-5 (3-carboxymethoxyphenyl)-2-(4-sulfophenyl)-2H-tetrazolium, inner salt] using phenzine methosulfate (PMS) as the electron coupling reagent can also be used to detect cytotoxicity. Promega (Madison, Wis.) offers a CellTiter 96® $AQ_{ueous}$ One Solution Cell Proliferation Assay kit where the solution reagent is added directly to culture wells, incubated for 1-4 hours and then absorbance is recorded at 490 nm. The quantity of formazan product as measured by the amount of 490 nm absorbance is directly proportional to the number of living cells in culture.

There are numerous high-throughput devices for reading light-absorbance. For example, SpectraMax Plus 384 Absorbance Platereader (Molecular Devices) can detect wavelengths from 190-1000 nm in 1 nm increments. The device can read 96-well microplates in 5 seconds and 384-well microplates in 16 seconds for ultra fast sample throughput.

Virus replication can also be assayed as an indication of successful infection, and such detection methods can be used in a high-throughput manner. For example, real-time RT-PCR methods can be used to detect the presence of virus transcripts in cell-culture supernatants. Upon reverse-transcription of viral RNA into cDNA, the cDNA can be amplified and detected by PCR with the use of double-stranded DNA-binding dyes (for example, SYBR® Green, Qiagen GmbH, Germany). The amount of PCR product can then be directly measured using a fluorimeter.

Viruses from the wells showing cytopathic effects are grown up and tested in further in vitro (re-testing of tumor and normal cell lines) and in vivo models (testing whether the virus can kill explanted tumors in mice).

Antibodies:

The present invention is also directed to antibodies that specifically bind to the viruses of the present invention, including the proteins of the viruses. Antibodies of the present invention include naturally occurring as well as non-naturally occurring antibodies, including, for example, single chain antibodies, chimeric antibodies, bifunctional antibodies and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (Huse et al., *Science* 246:1275-1281, 1989). These and other methods of making, for example, chimeric, humanized, CDR-grafted, single chain, and bifunctional antibodies are well known to those skilled in the art (Winter and Harris, *Immunol. Today* 14:243-246, 1993; Ward et al., Nature 341:544-546, 1989; Harlow and Lane, *Antibodies: A laboratory manual*, Cold Spring Harbor Laboratory Press, 1988); Hilyard et al., *Protein Engineering: A practical approach*, IRL Press 1992; Borrabeck, *Antibody Engineering,* 2d ed., Oxford University Press 1995). Antibodies of the invention include intact molecules as well as fragments thereof, such as Fab, $F(ab')_2$, and Fv which are capable of binding to an epitopic determinant present in a polypeptide of the present invention.

Where a peptide portion of a SVV polypeptide of the invention (i.e., any peptide fragment from SEQ ID NO:2 or SEQ ID NO:169) or peptide portion of another viral polypeptide of the invention used as an immunogen for antibody generation is non-immunogenic, it can be made immunogenic by coupling the hapten to a carrier molecule such as bovine serum albumin (BSA) or keyhole limpet hemocyanin (KLH), or by expressing the peptide portion as a fusion protein. Various other carrier molecules and methods for coupling a hapten to a carrier molecule are well known in the art (for example, by Harlow and Lane, supra, 1988). Methods for raising polyclonal antibodies, for example, in a rabbit, goat, mouse or other mammal, are well known in the art (see, for example, Green et al., "Production of Polyclonal Antisera," in *Immunochemical Protocols*, Manson, ed., Humana Press 1992, pages 1-5; Coligan et al., "Production of Polyclonal Antisera in Rabbits, Rats, Mice and Hamsters," in *Curr. Protocols Immunol*. (1992), section 2.4.1).

Monoclonal antibodies also can be obtained using methods that are well known and routine in the art (Kohler and Milstein, *Nature* 256:495, 1975; Coligan et al., supra, 1992, sections 2.5.1-2.6.7; Harlow and Lane, supra, 1988). For example, spleen cells from a mouse immunized with a virus, viral polypeptide or fragment thereof, can be fused to an appropriate myeloma cell line to produce hybridoma cells. Cloned hybridoma cell lines can be screened using, for example, labeled SVV polypeptide to identify clones that secrete monoclonal antibodies having the appropriate specificity, and hybridomas expressing antibodies having a desirable specificity and affinity can be isolated and utilized as a continuous source of the antibodies. Polyclonal antibodies similarly can be isolated, for example, from serum of an immunized animal. Such antibodies, in addition to being useful for performing a method of the invention, also are useful, for example, for preparing standardized kits. A recombinant phage that expresses, for example, a single chain antibody also provides an antibody that can used for preparing standardized kits. Monoclonal antibodies, for example, can be isolated and purified from hybridoma cultures by a variety of well established techniques, including, for example, affinity chromatography with Protein-A SEPHAROSE gel, size exclusion chromatography, and ion exchange chromatography (Barnes et al., in *Meth. Mol. Biol.* 10:79-104, Humana Press 1992); Coligan et al., supra, 1992, see sections 2.7.1-2.7.12 and sections 2.9.1-2.9.3).

An antigen-binding fragment of an antibody can be prepared by proteolytic hydrolysis of a particular antibody, or by expression of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol-reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see, for example, Goldenberg, U.S. Pat. Nos. 4,036,945 and 4,331,647; Nisonhoff et al., *Arch. Biochem. Biophys.* 89:230. 1960; Porter, *Biochem. J.* 73:119, 1959; Edelman et al., Meth. Enzymol., 1:422 (Academic Press 1967); Coligan et al., supra, 1992, see sections 2.8.1-2.8.10 and 2.10.1-2.10.4).

Another example of an antigen binding fragment of an antibody is a peptide coding for a single complementarity determining region (CDR). CDR peptides can be obtained by constructing polynucleotides encoding the CDR of an antibody of interest. Such polynucleotides can be prepared, for example, using the polymerase chain reaction to synthesize a variable region encoded by RNA obtained from antibody-producing cells (for example, Larrick et al., *Methods: A Companion to Methods in Enzymology* 2:106, 1991).

The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

There are many different labels and methods of labeling antibodies known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or alternatively to the antigen, or will be able to ascertain such, using routine experimentation.

As various changes can be made in the above methods and compositions without departing from the scope and spirit of the invention as described, it is intended that all subject matter contained in the above description, shown in the accompanying drawings, or defined in the appended claims be interpreted as illustrative, and not in a limiting sense.

EXAMPLES

The examples described below are provided to illustrate the present invention and are not included for the purpose of limiting the invention.

Example 1

Amplification and Purification of Virus

Cultivation of SVV in PER.C6 cells: SVV is plaque purified once and a well isolated plaque is picked and amplified in PER.C6 cells (Fallaux et al., 1998). A crude virus lysate (CVL) from SVV infected PER.C6 cells is made by three cycles of freeze and thaw and used to infect PER.C6 cells. PER.C6 cells are grown in 50×150 $cm^2$ T.C. flasks using Dulbecco's modified Eagle medium (DMEM, Invitrogen, Carlsbad, Calif., USA)) containing 10% fetal bovine serum (Biowhitaker, Walkersvile, Md., USA) and 10 mM magnesium chloride (Sigma, St Louis, Mo., USA). The infected cells harvested 30 hr after infection when complete CPE is noticed and are collected by centrifugation at 1500 rpm for 10 minutes at 4° C. The cell pellet is resuspended in the cell culture supernatant (30 ml) and is subjected to three cycles of freeze and thaw. The resulting CVL is clarified by centrifugation at 1500 rpm for 10 minutes at 4° C. Virus is purified by two rounds of CsCl gradients: a one-step gradient (density of CsCl 1.24 g/ml and 1.4 g/ml) followed by one continuous gradient centrifugation (density of CsCl 1.33 g/ml). The purified virus concentration is determined spectrophotometrically, assuming $1A_{260}=9.5\times10^{12}$ particles (Scraba D. G., and Palmenberg, A. C. 1999. Cardioviruses (Picornaviridae). In: *Encyclopedia of Virology*, Second edition, R. G. Webster and A Granoff Eds). Titers of purified virus are also determined by a standard plaque assay using PER.C6 cells. The yield of SVV from PER.C6 cells are greater than 200,000 particles per cell with particles to PFU ratio of about 100. The yields of SVV from other permissive cells (H446-ATCC# HTB-171) may be at least this high or higher.

Example 2

Electron Microscopy

SVV is mounted onto formvar carbon-coated grids using the direct application method, stained with uranyl acetate, and examined in a transmission electron microscope. Representative micrographs of the virus are taken at high magnification. For the transmission electron microscope, ultra-thin sections of SVV-infected PER.C6 cells are cut from the embedded blocks, and the resulting sections are examined in the transmission electron microscope.

Figure 1:
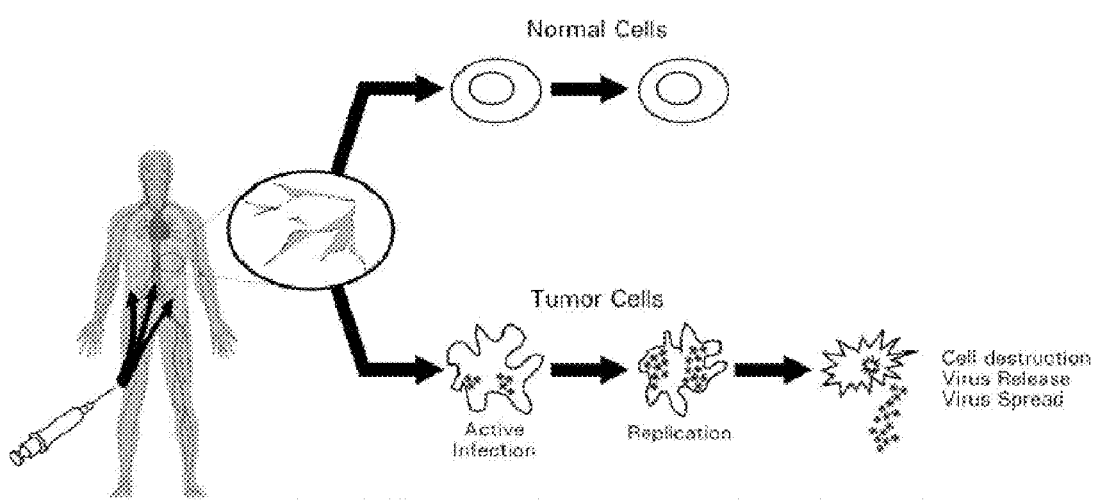
FIG. 1 shows a schematic of virotherapy using oncolytic viruses. Oncolytic viruses have the properties to replicate, spread and kill tumor cells selectively through a tumor mass by locally injecting the virus or by systemically delivering the virus.
Figure 2:
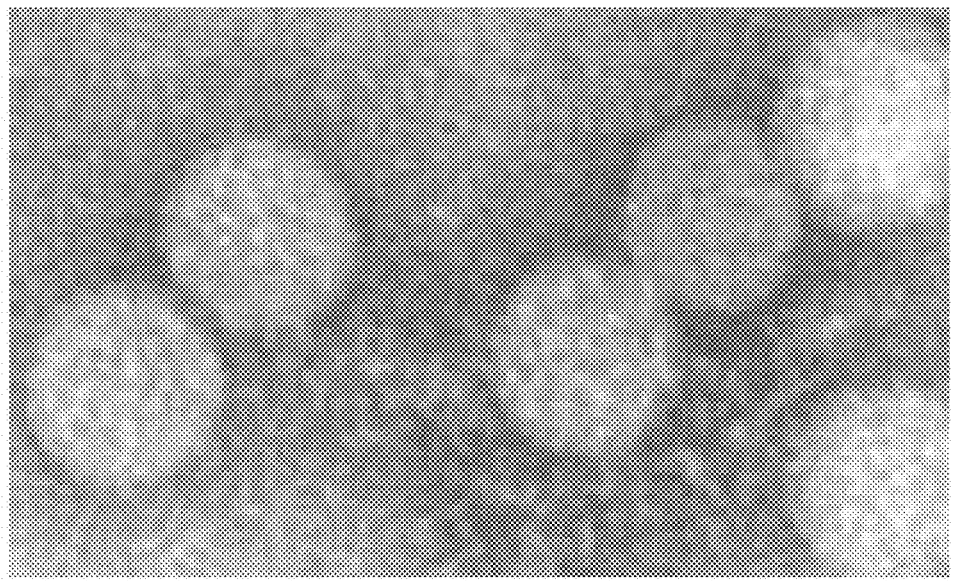
FIG. 2 shows purified SVV stained with uranyl acetate and examined by transmission electron microscopy. Spherical virus particles are about 27 nm in diameter.
Figure 3:
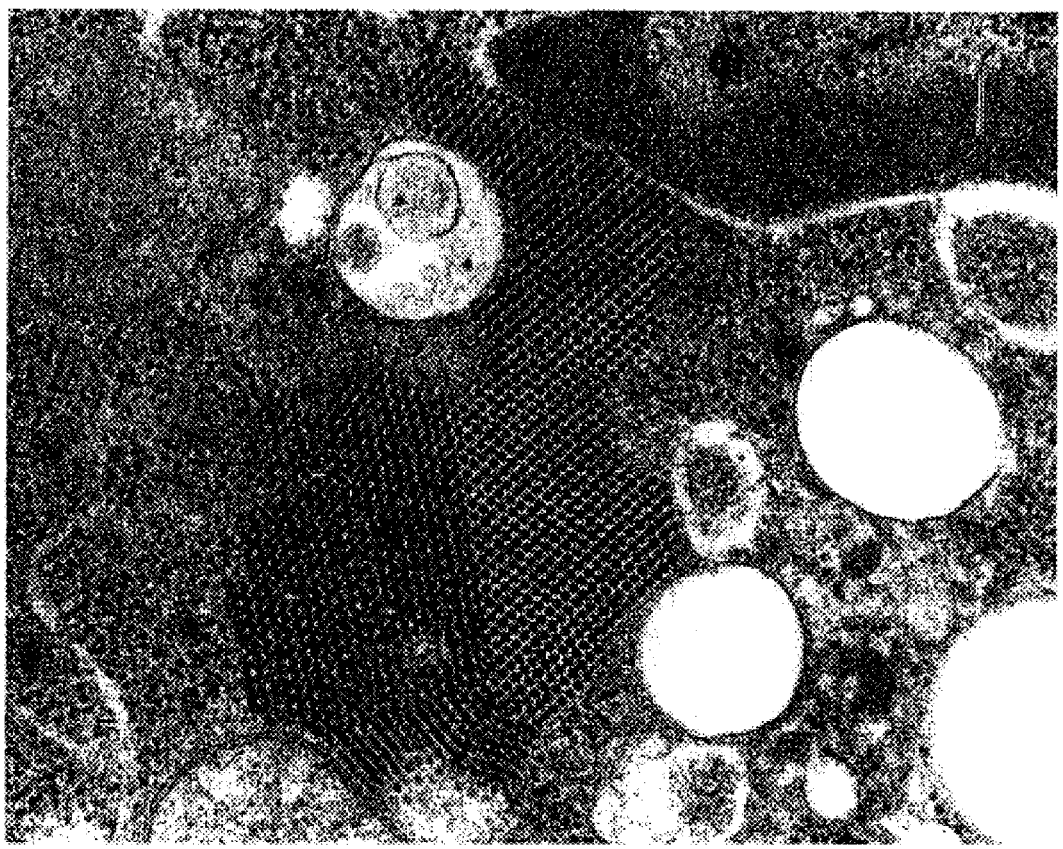
FIG. 3 is an electron micrograph of an SVV-infected PER.C6 cell that has a large crystalline inclusion and large vesicular bodies.

The purified SVV particles are spherical and about 27 nm in diameter, appearing singly or in small aggregates on the grid. A representative picture of SVV is shown in FIG. 2. In some places, broken viral particles and empty capsids with stain penetration are also seen. Ultrastructural studies of infected PER.C6 cells revealed crystalline inclusions in the cytoplasm. A representative picture of PER.C6 cells infected with SVV is shown in FIG. 3. The virus infected cells revealed a few large vesicular bodies (empty vesicles).

Example 3

Nucleic Acid Isolation of SVV

Figure 4A:
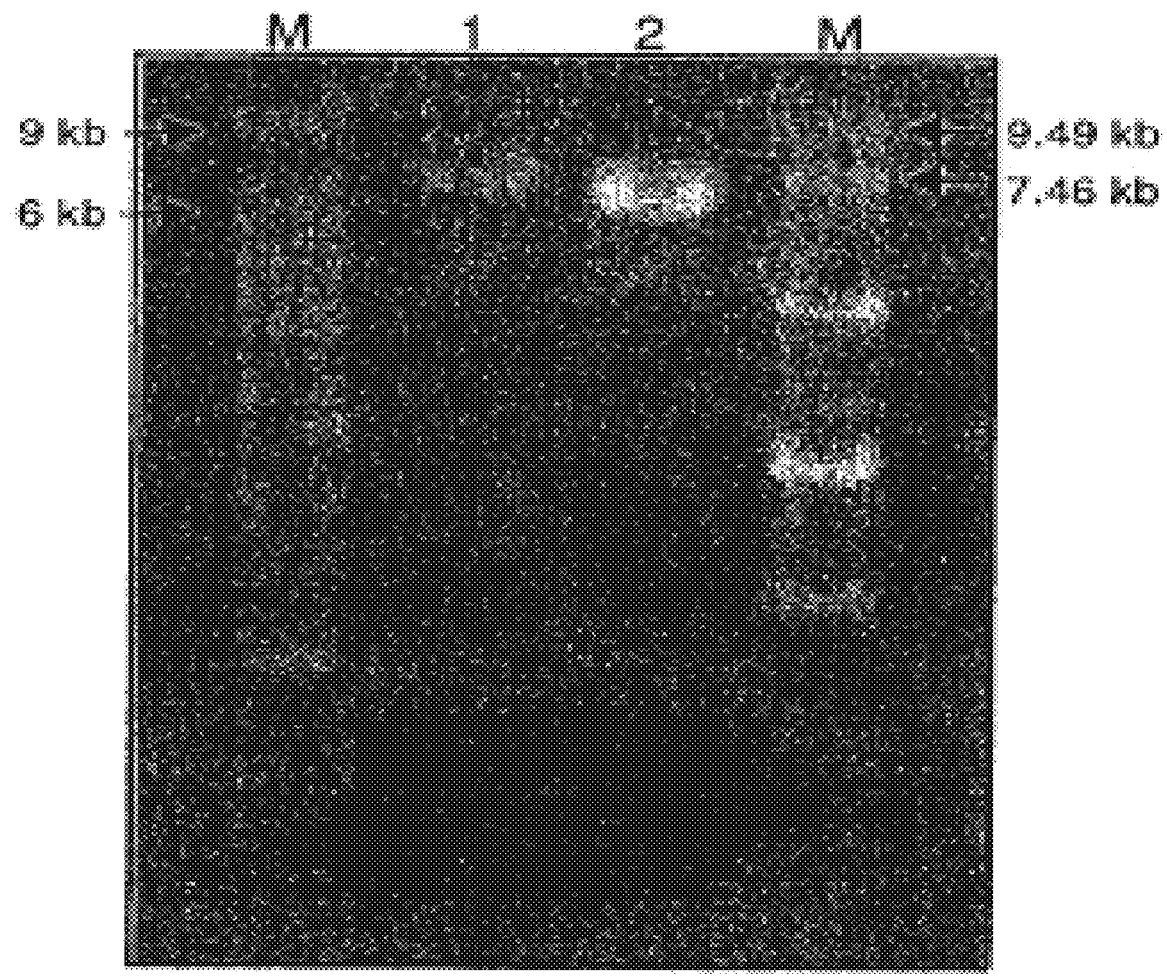
FIG. 4A shows an analysis of SVV RNA. SVV genomic RNA is extracted using guanidium thiocyanate and a phenol extraction method using Trizol (Invitrogen Corp., Carlsbad, Calif.). RNA is resolved through a 1.25% denaturing agarose gel. The band is visualized by ethidium bromide (EtBr) staining and photographed. In lane 2, a predominant band of SVV genomic RNA is observed, indicating that the size of the full-length SVV genome is about 7.5 kilobases.
Figure 4B:
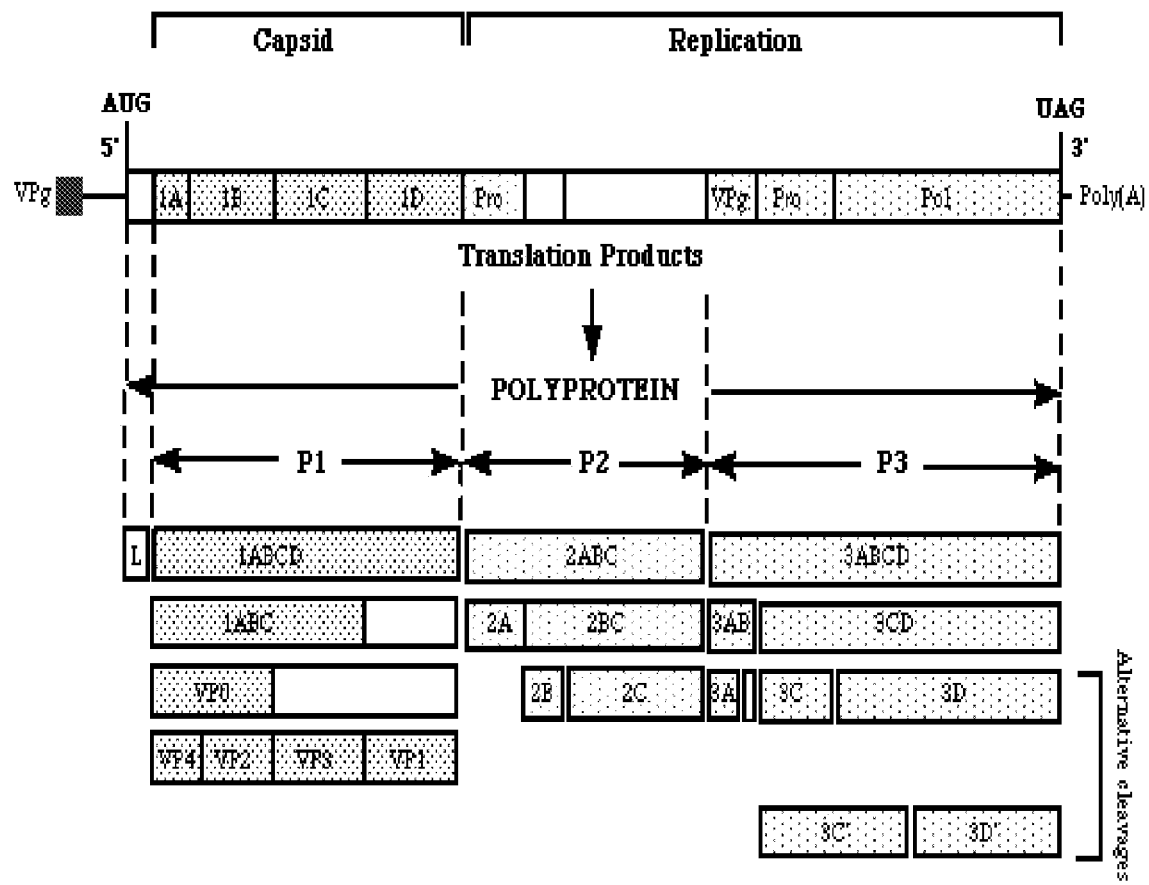
FIG. 4B is a schematic showing the genome structure and protein products generated from polyprotein processing for picornaviruses, including SVV.

RNA Isolation: SVV genomic RNA was extracted using guanidium thiocyanate and a phenol extraction method using Trizol (Invitrogen). Isolation was performed according to the supplier's recommendations. Briefly, 250 µl of the purified SVV was mixed with 3 volumes TRIZOL and 240 µl of chloroform. The aqueous phase containing RNA was precipitated with 600 µl isopropanol. The RNA pellet was washed twice with 70% ethanol, dried and dissolved in DEPC-treated water. The quantity of RNA extracted was estimated by optical density measurements at 260 nm. An aliquot of RNA was resolved through a 1.25% denaturing agarose gel (Cambrex Bio Sciences Rockland Inc., Rockland, Me. USA) and the band was visualized by ethidium bromide staining and photographed (FIG. 4).

cDNA synthesis: cDNA of the SVV genome was synthesized by RT-PCR. Synthesis of cDNA was performed under standard conditions using 1 µg of RNA, AMV reverse transcriptase, and random 14-mer oligonucleotide or oligo-dT. Fragments of the cDNA were amplified, cloned into plasmids and the clones are sequenced Example 4

SVV Sequence Analysis and Epidemiology

Part I: SVV SEQ ID NO:1

The nucleotide sequence of SVV SEQ ID NO:1 was analyzed to determine its evolutionary relationship to other viruses. The translated product (SEQ ID NO:2) for this ORF was picornavirus-like and reached from the middle of VP2 to the termination codon at the end of the 3D polymerase and was 1890 amino acids in length (FIGS. 5A-5E and 7A-7B).

The 3' untranslated region (UTR), nucleotides 5671-5734, which follows the ORF is 64 nucleotides (nt) in length, including the termination codon and excluding the poly(A) tail of which 18 residues are provided (FIG. 5E).

Preliminary comparisons (not shown) of three partial genome segments of SVV had revealed that SVV was most closely related members of the genus Cardiovirus (family Picornaviridae). Therefore an alignment of the polyprotein sequences of SVV, encephalomyocarditis virus (EMCV; species Encephalomyocarditis virus, Theiler's murine encephalomyelitis virus (TMEV; species Theilovirus), Vilyuisk human encephalomyelitis virus (VHEV; species Theilovirus) and a rat TMEV-like agent (TLV; species Theilovirus) was constructed (FIG. 28). From this alignment, the SVV polyprotein processing was compared to the polyprotein processing of the most closely related members of the Cardiovirus genus. Cleavage sites between the individual polypeptides is demarcated by the "/" character in FIG. 28.

In picornaviruses, most polyprotein cleavages are carried out by one or more virus-encoded proteases, although in cardio-, aphtho-, erbo- and teschoviruses the cleavage between P1-2A and 2B is carried out by a poorly understood cis-acting mechanism related to the 2A sequence itself and critically involving the sequence "NPG/P", where "/" represents the break between the 2A and 2B polypeptides (Donnelly et al., 1997, *J. Gen. Virol.* 78: 13-21). One of the parechoviruses, Ljungan virus, has this sequence (NPGP) present upstream of a typical parechovirus 2A and is either an additional 2A or is the C-terminal end of the P1 capsid region. In all nine currently recognised picornavirus genera, $3C^{pro}$ carries out all but the cis-acting self-cleaving reactions (i.e. 2A cleaves at its N-terminus in entero- and rhinoviruses and L cleaves at its C-terminus in aphthoviruses and erboviruses). The post-assembly cleavage of the capsid polypeptide VP0 to VP4 and VP2 is not carried out by $3C^{pro}$, but by an unknown mechanism which may involve the virus RNA. The VP0 cleavage does not occur in parechoviruses and kobuviruses. The normal cardiovirus $3C^{pro}$ cleavage site has either a glutamine (Q) or glutamate (E) at the −1 position and glycine (G), serine (S), adenine (A) or asparagine (N) at the +1 position (Table 2). The cleavages of the SVV polyprotein conform to this pattern except for the VP3/VP1 site which is histidine (H)/serine (S) (Table 2); however, H/S is probably present as the cleavage site between 3A and $3B^{VPg}$ in at least one strain of equine rhinitis A virus (ERAV; genus Aphthovirus) (Wutz et al., 1996, *J. Gen. Virol.* 77:1719-1730).

TABLE 2

Cleavage sites of SVV and cardioviruses

| Between | | SVV | EMCV | TMEV | Rat TLV | VHEV |
|---|---|---|---|---|---|---|
| L | VP4 | Not known | LQ/GN (SEQ ID NO: 125) | PQ/GN (SEQ ID NO: 138) | PQ/GN (SEQ ID NO: 152) | PQ/GN (SEQ ID NO: 163) |
| VP4 | VP2 | Not known | LA/DQ (SEQ ID NO: 126) | LL/DQ (SEQ ID NO: 139) LM/DQ (SEQ ID NO: 140) | LL/DQ (SEQ ID NO: 153) | LL/DE (SEQ ID NO: 164) |
| VP2 | VP3 | EQ/GP (SEQ ID NO: 117) | RQ/SP (SEQ ID NO: 127) | AQ/SP (SEQ ID NO: 141) | PQ/SP (SEQ ID NO: 154) | PQ/SP (SEQ ID NO: 165) |
| VP3 | VP1 | FH/ST (SEQ ID NO: 118) | PQ/GV (SEQ ID NO: 128) | PQ/GV (SEQ ID NO: 142) PQ/GI (SEQ ID NO: | PQ/GV (SEQ ID NO: 155) | PQ/GV (SEQ ID NO: 166) |

TABLE 2-continued

Cleavage sites of SVV and cardioviruses

| Between | | SVV | EMCV | TMEV | Rat TLV | VHEV |
|---|---|---|---|---|---|---|
| | | | | 143)<br>PQ/GS<br>(SEQ ID NO:<br>144) | | |
| VP1 | 2A | KQ/KM<br>(SEQ ID NO:<br>119) | LE/SP<br>(SEQ ID NO:<br>129) | LE/NP<br>(SEQ ID NO:<br>145) | LQ/NP<br>(SEQ ID NO:<br>156) | LE/NP<br>(SEQ ID NO:<br>167) |
| 2A | 2B | NPG/P*<br>(SEQ ID NO:<br>111) | NPG/P*<br>(SEQ ID NO:<br>130) | NPG/P*<br>(SEQ ID NO:<br>146) | NPG/P*<br>(SEQ ID NO:<br>157) | Nk |
| 2B | 2C | MQ/GP<br>(SEQ ID NO:<br>120) | QQ/SP<br>(SEQ ID NO:<br>131) | PQ/GP<br>(SEQ ID NO:<br>147) | AQ/SP<br>(SEQ ID NO:<br>158) | Nk |
| 2C | 3A | LQ/SP<br>(SEQ ID NO:<br>121) | AQ/GP<br>(SEQ ID NO:<br>132)<br>AQ/AP<br>(SEQ ID NO:<br>133) | AQ/SP<br>(SEQ ID NO:<br>148) | AQ/SP<br>(SEQ ID NO:<br>159) | Nk |
| 3A | 3B | SE/NA<br>(SEQ ID NO:<br>122) | EQ/GP<br>(SEQ ID NO:<br>134) | EQ/AA<br>(SEQ ID NO:<br>149) | EQ/AA<br>(SEQ ID NO:<br>160) | Nk |
| 3B | 3C | MQ/QP<br>(SEQ ID NO:<br>123) | IQ/GP<br>(SEQ ID NO:<br>135)<br>VQ/GP<br>(SEQ ID NO:<br>136) | IQ/GG<br>(SEQ ID NO:<br>150) | IQ/GG<br>(SEQ ID NO:<br>161) | Nk |
| 3C | 3D | MQ/GL<br>(SEQ ID NO:<br>124) | PQ/GA<br>(SEQ ID NO:<br>137) | PQ/GA<br>(SEQ ID NO:<br>151) | PQ/GA<br>(SEQ ID NO:<br>162) | Nk |

*the break between 2A and 2B is not a cleavage event.

Primary cleavages (P1/P2 and P2/P3) of SVV: These primary cleavage events are predicted to occur in a similar fashion to cardio-, aphtho-, erbo- and teschoviruses, involving separation of P1-2A from 2B by a novel mechanism involving the sequence NPG/P (SEQ ID NO:111) and a traditional cleavage event by 3C$^{pro}$ between 2BC and P3 (Table 2).

P1 cleavages: Cleavages within the SVV P1 capsid coding region were relatively easy to predict by alignment with sequence with EMCV and TMEV (Table 2).

P2 cleavages: The 2C protein is involved in RNA synthesis. The 2C polypeptide of SVV contains NTP-binding motifs GxxGxGKS/T (SEQ ID NO:112) (domain A) and hyhyhyxxD (in which by is any hydrophobic residue; domain B) present in putative helicases and all picornavirus 2Cs (FIG. 29).

P3 cleavages: Prediction of the P3 cleavage sites was also relatively straightforward. Little is known about the function of the 3A polypeptide. However, all picornavirus 3A proteins contain a putative transmembrane alpha-helix. Primary sequence identity is low in this protein between SVV and cardioviruses (See FIG. 28 between positions 1612 to 1701).

The genome-linked polypeptide, VPg, which is encoded by the 3B region, shares few amino acids in common with the other cardioviruses, however, the third residue is a tyrosine, consistent with its linkage to the 5' end of the virus genome (Rothberg et al., 1978). See FIG. 28 between positions 1703 and 1724.

The three-dimensional structure of four picornavirus 3C cysteine proteases have been solved and the active-site residues identified (HAV, Allaire et al., 1994, Nature, 369: 72-76; Bergmann et al., 1997, J. Virol., 71: 2436-2448; PV-1, Mosimann et al., 1997, J. Mol. Biol., 273: 1032-1047; HRV-14, Matthews et al., 1994, Cell, 77: 761-771; and HRV-2, Matthews et al., 1999, Proc. Natl. Acad. Sci. USA, 96: 11000-11007). The cysteine bolded in FIG. 29 is the nucleophile, while the first bolded histidine is the general base and the specificity for glutamine residues is defined mainly by the second bolded histidine; all three residues are conserved in the SVV sequence (FIG. 29) and all other known picornaviruses (FIG. 28; for 3C sequence comparison see between positions 1726 and 1946).

The 3D polypeptide is the major component of the RNA-dependent RNA polymerase and SVV contains motifs conserved in picorna-like virus RNA-dependent RNA polymerases, i.e. KDEL/IR (SEQ ID NO:113), PSG, YGDD (SEQ ID NO:114) and FLKR (SEQ ID NO:115) (FIG. 3; FIG. 28 between positions 1948 and 2410).

Myristoylation of the N-terminus of P1: In most picornaviruses the P1 precursor polypeptide is covalently bound by its N-terminal glycine residue (when present the N-terminal methionine is removed) to a molecule of myristic acid via an amide linkage (Chow et al., 1987, Nature, 327: 482-486). Consequently the cleavage products VP0 and VP4 which contain the P1 N-terminus are also myristoylated. This myristoylation is carried out by myristoyl transferase which recognises an eight amino acid signal beginning with glycine. In picornaviruses, a five residue consensus sequence motif, G-x-x-x-T/S, has been identified (Palmenberg, 1989, In Molecular Aspects of Picornavirus Infection and Detection, pp. 211-241, Ed. Semler & Ehrenfeld, Washington D.C., Amer. Soc. for Micro.). Parechoviruses (Human parechovirus and Ljungan virus) as well as not having a maturation cleavage of VP0 are apparently not myristoylated, however, there appears to be some type of molecule blocking the N-terminus of VP0 for these viruses.

Figure 70:
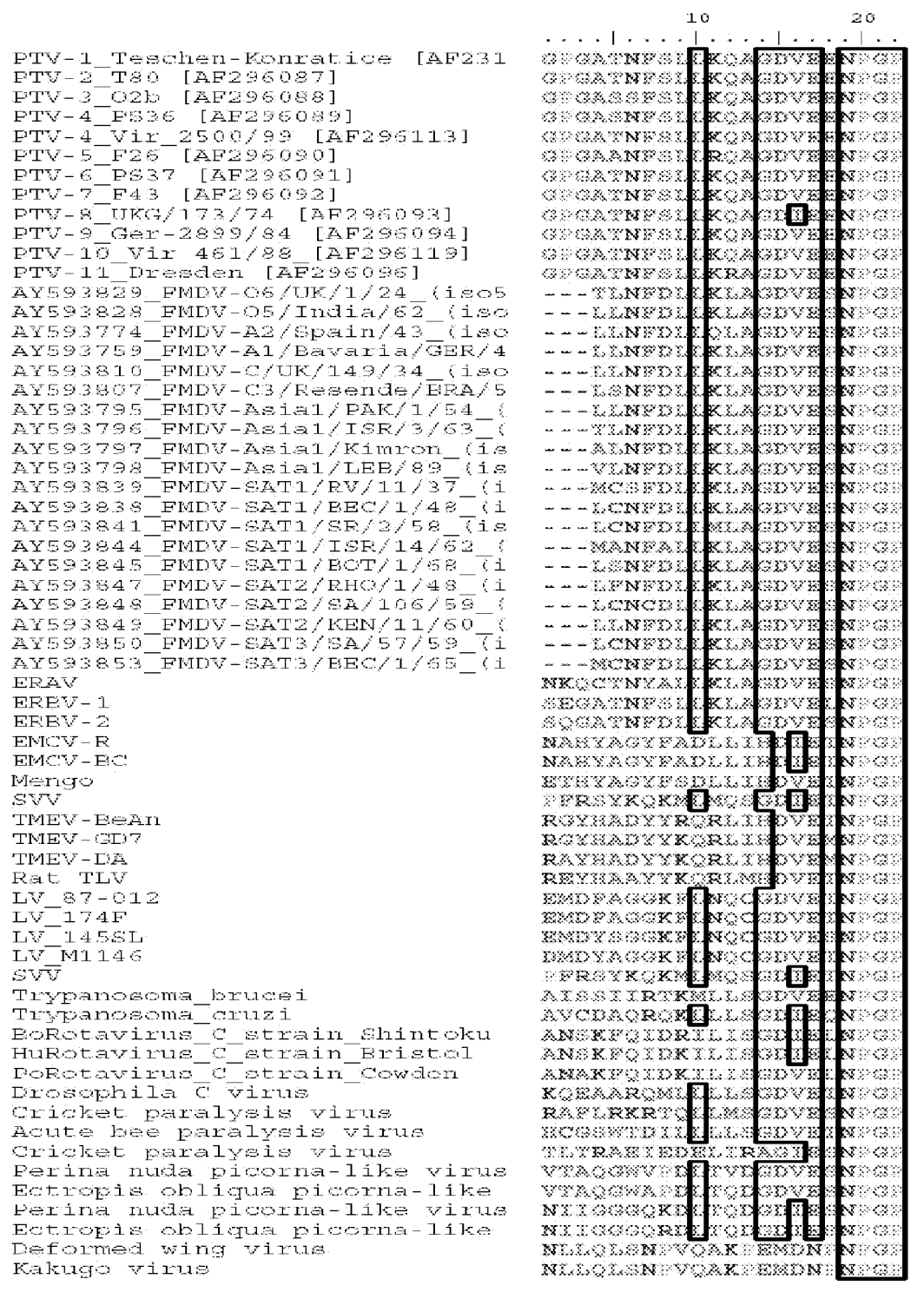

Comparisons of the Individual SVV Polypeptides with the Public Sequence Databases Each of the SVV polypeptides (SEQ ID NOS: 4, 6, 8, 10, 12, 14, 16, 18, 20 and 22) were compared to the public protein sequence databases using the FASTA online program at the European Bioinformatics Institute (EBI). The results (best matches) of these comparisons are shown in Table 3. The capsid polypeptides (VP2, VP3 and VP1) taken as a whole, along with 2C, 3C$^{Pro}$ and 3D$^{pol}$ are most closely related to members of the cardiovirus genus, however, the short predicted 2A sequence is closer to that of Ljungan virus (genus Parechovirus). A more detailed comparison of the SVV 2A nucleotide sequence with similar sequences is shown in FIG. 28 (see also FIG. 70 for 2A-like NPG/P protein comparison).

pared with the same proteins of representative members of each of the picornavirus species (Table 4). The programs BioEdit v5.0.9 (Hall, 1999, *Nucl. Acids. Symp. Ser.*, 41: 95-98) and Clustal X v1.83 (Thompson et al., 1997, *Nucl. Acids Res.*, 25:4876-4882) were used to make the alignments and to construct distance matrices and unrooted Neighbor-joining trees according to the algorithm of Saitou and Nei

TABLE 3

Database matches of individual predicted polypeptides of Seneca Valley virus

| SVV polypeptide | Length (aa) | % identity | % identity ungapped | aa overlap | Organism | Matched protein |
|---|---|---|---|---|---|---|
| L (Leader) | No data | — | — | — | — | — |
| VP4 (1A) | No data | — | — | — | — | — |
| VP2 (1B) | >142 | 42.857 | 44.037 | 112 | TMEV WW | VP2 |
|  |  | ~51 | — | ~80 | EMCV BEL-2887A/91 | VP2 |
| VP3 (1C) | 239 | 44.068 | 46.637 | 236 | EMCV ATCC VR-129B | VP3 |
| VP1 (1D) | 259 | 31.086 | 36.404 | 267 | EMCV M100/1/02 | VP1 |
| 2A | 14 | 71.429 | 71.429 | 14 | Ljungan virus 174F | 2A1 |
| 2B | 128 | 39.286 | 41.509 | 56 | *Ureaplasma urealyticum* | Multiple banded antigen |
| 2C | 322 | 38.602 | 40.190 | 329 | EMCV PV21 | 2C |
| 3A | 90 | 37.838 | 41.791 | 74 | *Chlorobium tepidum* TLS* | Enolase 2† |
| 3B$^{VPg}$ | 22 | No matches | — | — | — | — |
| 3C$^{pro}$ | 211 | 37.089 | 38.537 | 213 | EMCV-R | 3C protease |
| 3D$^{pol}$ | 462 | 58.009 | 58.515 | 462 | EMCV-PV21 | 3D polymerase |

*a photosynthetic, anaerobic, green-sulfur bacterium
†2-phosphoglycerate dehydratase 2) (2-phospho-D-glycerate hydro-lyase 2

The significance of the matches of SVV 2B with *Ureaplasma urealyticum* multiple banded antigen or 3A with *Chlorobium tepidum* endolase 2 is not clear, however, these relationships maybe worthy of further investigation.

Phylogenetic Comparison of SVV Polypeptides with Other Picornaviruses

Those SVV polypeptides which could be aligned with the cardioviruses (VP2, VP3, VP1, 2C, 3C and 3D) were compared with the same proteins of representative members of each of the picornavirus species (Table 4).

(Satiou and Nei, 1987, *Mol. Biol. Evol.*, 4: 406-425). Confidence limits on branches were accessed by bootstrap resampling (1000 pseudo-replicates). The trees were drawn using TreeView 1.6.6 (Page, 1996) (FIGS. 31 to 37). The distance matrices used to construct the trees used values corrected for multiple substitutions, while FIGS. 38-44 show the actual percentage amino acid identities. Table 4 shows the current classification of the family Picornaviridae and the representative virus sequences used in these comparisons.

TABLE 4

The taxonomic classification of the picornaviruses used in the comparisons with SVV.

| Genus | Species | Representative virus | Abbrev. | Acc. No. |
|---|---|---|---|---|
| Enterovirus | Poliovirus | Poliovirus 1 | PV-1 | V01149 |
|  | Human enterovirus A | Coxsackievirus A16 | CV-A16 | U05876 |
|  | Human enterovirus B | Coxsackievirus B5 | CV-B5 | X67706 |
|  | Human enterovirus C | Coxsackievirus A21 | CV-A21 | D00538 |
|  | Human enterovirus D | Enterovirus 70 | EV-70 | D00820 |
|  | Simian enterovirus A | Simian enterovirus A1 | SEV-A | AF201894 |
|  | Bovine enterovirus | Bovine enterovirus 1 | BEV-1 | D00214 |
|  | Porcine enterovirus B | Porcine enterovirus 9 | PEV-9 | AF363453 |
| New genus? | Not yet designated | Simian virus 2* | SV2 | AY064708 |
|  | Porcine enterovirus A | Porcine enterovirus 8* | PEV-8 | AF406813 |
| Rhinovirus | Human rhinovirus A | Human rhinovirus 2 | HRV-2 | X02316 |
|  | Human rhinovirus B | Human rhinovirus 14 | HRV-14 | K02121 |
| Cardiovirus | Encephalomyocarditis virus | Encephalomyocarditis virus | EMCV | M81861 |
|  | Theilovirus | Theiler's murine encephalomyelitis virus | TMEV | M20562 |
| Aphthovirus | Foot-and-mouth disease virus | Foot-and-mouth disease virus O | FMDV-O | X00871 |
|  | Equine rhinitis A virus | Equine rhinitis A virus | ERAV | X96870 |
| Hepatovirus | Hepatitis A virus | Hepatitis A virus | HAV | M14707 |
|  | Avian encephalomyelitis-like viruses | Avian encephalomyelitis virus | AEV | AJ225173 |
| Parechovirus | Human parechovirus | Human parechovirus 1 | HPeV-1 | L02971 |
|  | Ljungan virus | Ljungan virus | LV | AF327920 |
| Kobuvirus | Aichi virus | Aichi virus | AiV | AB040749 |
|  | Bovine kobuvirus | Bovine kobuvirus | BKV | AB084788 |

TABLE 4-continued

The taxonomic classification of the picornaviruses used in the comparisons with SVV.

| Genus | Species | Representative virus | Abbrev. | Acc. No. |
|---|---|---|---|---|
| Erbovirus | Equine rhinitis B virus | Equine rhinitis B virus 1 | ERBV-1 | X96871 |
| Teschovirus | Porcine teschovirus | Porcine teschovirus 1 | PTV-1 | AJ011380 |

*the current taxonomic status of SV2 and PEV-8 places them in the enterovirus genus, however, it has been suggested that they may be reclassified in a new genus (Krumbholz et al., 2002; Oberste et al., 2003).

The trees of the individual capsid proteins (FIGS. 31 to 33) are not all representative of the tree produced when the data from all tree polypeptides is combined (FIG. 34). This is probably the result of difficulties in aligning the capsid polypeptides, particularly when they are not full length as is the case for VP2 (FIG. 31). However, the P1, 2C, 3C$^{pro}$ and 3D$^{pol}$ trees are all in agreement and show that SVV clusters with EMCV and TMEV.

Seneca Valley Virus as a Member of the Cardiovirus Genus

Clearly the 3D$^{pol}$ of SVV is related to the cardioviruses, almost as closely as EMCV and TMEV are to each other (FIG. 37; FIG. 44). In the other polypeptides which are generally considered as being relatively conserved in picornaviruses, 2C and 3C, SVV is also most closely related to the cardioviruses although it is not as closely related to EMCV and TMEV as they are to each other (FIG. 42 and FIG. 43, respectively). In the outer capsid proteins (taken as a whole), SVV is also most closely related to the cardioviruses and has approximately the same relationship as the two aphthovirus species, Foot-and-mouth disease virus and Equine rhinitis A virus (~33%). SVV diverges greatly from the cardioviruses in the 2B and 3A polypeptides and has no detectable relationship with any known picornavirus. However, this is not without precedent; avian encephalomyelitis virus differs considerably from hepatitis A virus (HAV) in 2A, 2B and 3A (Marvil et al., 1999, *J. Gen. Virol.*, 80:653-662) but is tentatively classified within the genus Hepatovirus along with HAV.

Seneca Valley virus is clearly not a typical cardiovirus if EMCV and TMEV are taken as the standard. However, even these two viruses have their differences, notably in the 5' UTR (Pevear et al., 1987, *J. Gen. Virol.*, 61: 1507-1516). However, phylogenetically SVV clusters with EMCV and TMEV in much of its polyprotein (P1, 2C, 3C$^{pro}$ and 3D$^{pol}$ regions). Ultimately, the taxonomic position of SVV within the Picornaviridae will be decided by the Executive Committee (EC) of the International Committee for the Taxonomy of Viruses (ICTV) following recommendations by the Picornaviridae Study Group and supporting published material. There are two options: i) include SVV as a new species in the cardiovirus genus; or ii) assign SVV to a new genus.

Part II: SVV SEQ ID NO:168

The full-length genome of SVV (FIGS. 83A-83H; SEQ ID NO:168; Example 15) allowed further epidemiological studies. The results of the further epidemiological studies are shown in FIG. 86, where SVV is shown to be genetically related to cardioviruses such as EMCV and TMEV, but in a separate tree.

The features of the SVV full-length genome with respect to its untranslated and coding regions are listed at Table A supra. The features of the full-length SVV in comparison to EMCV and TMEV-GDVII are listed in the table below.

| Feature | SVV nt length | SVV aa length | EMCV [M81861] nt length | EMCV [M81861] aa length | TMEV-GDVII [M20562] nt length | TMEV-GDVII [M20562] aa length |
|---|---|---|---|---|---|---|
| 5'UTR | 666 | — | 833 | — | 1068 | — |
| Leader | 237 | 79 | 201 | 67 | 228 | 76 |
| VP4 | 213 | 71 | 210 | 70 | 213 | 71 |
| VP2 | 852 | 284 | 768 | 256 | 801 | 267 |
| VP3 | 717 | 239 | 693 | 231 | 696 | 232 |
| VP1 | 792 | 264 | 831 | 277 | 828 | 276 |
| 2A | 27 | 9 | 429 | 143 | 426 | 142 |
| 2B | 384 | 128 | 450 | 150 | 381 | 127 |
| 2C | 966 | 322 | 975 | 325 | 978 | 326 |
| 3A | 270 | 90 | 264 | 88 | 264 | 88 |
| 3B | 66 | 22 | 60 | 20 | 60 | 20 |
| 3D | 1386 | 462 | 1380 | 460 | 1383 | 461 |
| 3' UTR | 71 | — | 126 | — | 128 | — |

The cleavage sites of SVV (based on full-length sequence, see also bolded amino acids between at protein boundaries in FIGS. 83A-83H) are compared to the cleavage sites of other cardioviruses in the table below.

| Between | | SVV | EMCV | TMEV | Rat TLV | VHEV |
|---|---|---|---|---|---|---|
| L | VP4 | LQ/GN (SEQ ID NO: 192) | LQ/GN (SEQ ID NO: 192) | PQ/GN (SEQ ID NO: 193) | PQ/GN (SEQ ID NO: 193) | PQ/GN (SEQ ID NO: 193) |
| VP4 | VP2 | LK/DH (SEQ | LA/DQ (SEQ | LL/DQ (SEQ ID | LL/DQ (SEQ | LL/DE (SEQ ID |

| Between | | SVV | EMCV | TMEV | Rat TLV | VHEV |
|---|---|---|---|---|---|---|
| | | ID NO: 194) | ID NO: 195) | NO: 196)<br>LM/DQ (SEQ ID<br>NO: 197) | ID NO: 196) | NO: 198) |
| VP2 | VP3 | EQ/GP (SEQ ID<br>NO: 117) | RQ/SP (SEQ<br>ID NO: 199) | AQ/SP (SEQ ID<br>NO: 200) | PQ/SP (SEQ<br>ID NO: 201) | PQ/SP (SEQ ID<br>NO: 201) |
| VP3 | VP1 | FH/ST (SEQ ID<br>NO: 118) | PQ/GV (SEQ<br>ID NO: 202) | PQ/GV (SEQ ID<br>NO: 202)<br>PQ/GI (SEQ ID<br>NO: 203)<br>PQ/GS (SEQ ID<br>NO: 204) | PQ/GV (SEQ<br>ID NO: 202) | PQ/GV (SEQ ID<br>NO: 202) |
| VP1 | 2A | MQ/SG (SEQ<br>ID NO: 205) | LE/SP (SEQ<br>ID NO: 206) | LE/NP (SEQ ID<br>NO: 207) | LQ/NP (SEQ<br>ID NO: 208) | LE/NP (SEQ ID<br>NO: 207) |
| 2A | 2B | NPG/P* (SEQ<br>ID NO: 111) | NPG/P* (SEQ<br>ID NO: 111) | NPG/P* (SEQ<br>ID NO: 111) | NPG/P* (SEQ<br>ID NO: 111) | unknown |
| 2B | 2C | MQ/GP (SEQ<br>ID NO: 120) | QQ/SP (SEQ<br>ID NO: 209) | PQ/GP (SEQ ID<br>NO: 210) | AQ/SP (SEQ<br>ID NO: 200) | unknown |
| 2C | 3A | LQ/SP (SEQ ID<br>NO: 121) | AQ/GP (SEQ<br>ID NO: 211)<br>AQ/AP (SEQ<br>ID NO: 212) | AQ/SP (SEQ ID<br>NO: 200) | AQ/SP (SEQ<br>ID NO: 200) | unknown |
| 3A | 3B | SE/NA (SEQ ID<br>NO: 122) | EQ/GP (SEQ<br>ID NO: 213) | EQ/AA (SEQ ID<br>NO: 214) | EQ/AA (SEQ<br>ID NO: 214) | unknown |
| 3B | 3C | MQ/QP (SEQ<br>ID NO: 123) | IQ/GP (SEQ<br>ID NO: 215)<br>VQ/GP (SEQ<br>ID NO: 216) | IQ/GG (SEQ ID<br>NO: 217) | IQ/GG (SEQ<br>ID NO: 217) | unknown |
| 3C | 3D | MQ/GL (SEQ<br>ID NO: 124) | PQ/GA (SEQ<br>ID NO: 218) | PQ/GA (SEQ ID<br>NO: 218) | PQ/GA (SEQ<br>ID NO: 218) | unknown |

*ribosome skipping sequence

Multiple unique viruses were discovered at the USDA that are more similar to SVV than SVV is to other cardioviruses. These USDA virus isolates, herein considered to be members of the group called "SVV-like picornaviruses," are: MN 88-36695, NC 88-23626, IA 89-47552, NJ 90-10324, IL 92-48963, CA 131395; LA 1278; IL 66289; IL 94-9356; MN/GA 99-29256; MN 99197; and SC 363649. These SVV-like picornaviruses and SVV are considered to comprise a new picornavirus genus.

Each of these SVV-like picornaviruses are unique, and are about 95%-98% identical to SVV at the nucleotide level (see FIGS. 87-89 for nucleotide sequence comparisons between SVV and these USDA isolates).

Part III: Serum Studies

Pigs are a permissive host for the USDA virus isolates identified above. The isolate MN 88-36695 was inoculated into a gnobiotic pig and antisera generated (GP102). The antisera binds to all of the other USDA isolates listed above and to SVV. The antisera does not react with 24 common porcine virus pathogens indicating its specificity. Porcine sera was also tested for neutralizing antibodies to 1278 (Plum Island virus). Sera were collected in the US and 8/29 sera were positive with titers ranging from 1:57 to 1:36,500.

To test whether the pig is the natural source for SVV, serum samples from various animals were obtained and tested for their ability to act as neutralizing antibodies against SVV infection of permissive cells. The Serum Neutralization Assay is conducted as follows: (1) Dilute various serums 1:2 and 1:4; (2) Mix with 100 $TCID_{50}$ of virus (SVV; but any virus can be tested to determine whether a serum can neutralize its infection); (3) Incubate at 37° C. for 1 hour; (4) Add to 1×10$^4$ PER.C6 cells (or other permissive cell type); (5) Incubate at 37° C. for 3 days; and (6) Measure CPE using MTS assay. The neutralization titer is defined as the highest dilution of sera that neutralizes SVV (or other virus in question) at 100%.

The serum neutralization results showed that there is a minimal or no presence of neutralizing antibodies in human and primate populations. In one experiment, 0/22 human sera contained neutralizing antibodies to SVV. In another experiment, only 1/28 human sera contained neutralizing antibodies. In a third experiment, 0/50 human sera from Amish farmers were neutralizing. In another experiment, 0/52 primate sera from four species were neutralizing.

The serum neutralization results showed that there is a prevalence of neutralizing antibodies in farm animal populations. In one experiment, 27/71 porcine sera from farms were neutralizing. In another experiment, 4/30 porcine sera from a disease-free farm were neutralizing. In another experiment, 10/50 bovine sera were neutralizing. In yet another experiment, 5/35 wild mouse sera were neutralizing. Because antibodies cross-reactive to SVV and/or SVV-like picornaviruses have been found in pigs, cows, and mice, these data indicate that SVV and/or SVV-like picornaviruses may be prevalent in a wide-variety of non-primate animals.

A crude viral lysate of MN 88-36695 was tested to assess its cytotoxicity ability on two cell lines permissive (NCI-H446; HEK293) for SVV and on two cell lines non-permissive (NCI-H460 and S8) for SVV. The cytotoxicity profile for MN 88-36695 was identical to SVV: the TCID50 for NCI-H446 was $1.6 \times 10^{-6}$; the TCID50 for HEK293 was $1.3 \times 10^{-2}$; and NCI-H460 and S8 were non-permissive for MN 88-36695. This data indicates that SVV-like picornaviruses have the potential to be used in the present methods directed to cancer therapy. In one embodiment, the invention provides for the use of the MN 88-36695 SVV-like picornavirus in any of the methods directed to cancer therapy, diagnosis, or screening.

Antisera to MN 88-36694 and SVV were tested in serum neutralization assays on each virus. Anti-SVV mouse serum was able to neutralize infection by both MN 88-36695 and SVV (neutralization titers on infection were 1:640 for MN 88-36695 and 1:1000 for SVV). Anti-MN 88-36695 gnobiotic pig serum was able to neutralize infection by both MN 88-36695 and SVV (neutralization titers on infection were 1:5120 for MN 88-36695 and 1:100 for SVV).

These data indicate that SVV is genetically and serologically linked to the porcine USDA virus isolates.

Example 4

SDS-PAGE and N-Terminal Sequence Analysis of SVV Capsid Proteins

Purified SVV is subjected to electrophoresis using NuPAGE pre-cast Bis-Tris polyacrylamide mini-gel electrophoresis system (Novex, San Diego, Calif., USA). One half of the gel is visualized by silver stain while the other half is used to prepare samples for amino acid sequencing of the N-termini of the capsid proteins. Prior to transfer of proteins to membrane, the gel is soaked in 10 mM CAPS buffer, pH 11, for 1 hour, and a PVDF membrane (Amersham) is wetted in methanol. Proteins are transferred to the PVDF membrane. After transfer, proteins are visualized by staining with Amido black for approximately 1 minute, and bands of interest are excised with a scalpel and air dried. The proteins can be subjected to automated N-terminal sequence determination by Edman degradation using a pulsed phase sequencer.

Three major structural proteins of the purified SVV are shown in FIG. 45 (approximately 36 kDa, 31 kDa, and 27 kDa).

Example 5

Assay for Neutralization Antibodies to SVV in Human Serum Samples

Preexisting antibodies to particular viral vectors may limit the use of such vectors for systemic delivery applications such as for treatment of metastatic cancer, because preexisting antibodies may bind to systemically delivered vectors and neutralize them before the vectors have a chance to transduce the targeted tissue or organ. Therefore, it is desirable to ensure that humans do not carry neutralization antibodies to viral vectors selected for systemic delivery. To determine whether human sera samples contain SVV-specific neutralizing antibodies, neutralization assays are carried out using randomly collected human sera samples.

Tissue culture infective dose 50: One day before the experiment, 180 p. 1 of PER.C6 cell suspension containing $1 \times 10^4$ cells are plated in 96-well tissue culture dish. The crude virus lysate (CVL) of SVV is diluted in log steps from $10^{-0}$ to $10^{-11}$ in DMEM medium (Dulbecco's Modified Eagle's Medium) and 20 µl of each dilution is transferred to three wells of a Falcon 96-well tissue culture plate containing PER.C6 cells. The plates are incubated at 37° C. in 5% $CO_2$ and read at 3 days for microscopic evidence of cytopathic effect (CPE), and the tissue culture infective dose 50 ($TCID_{50}$) is calculated.

Neutralization assay: First, 40 µl of medium is placed in all the wells and then 40 µl of heat-inactivated serum is added to the first well and mixed by pipeting, making a 1:4 dilution used for screening purposes. 40 µl is then transferred to the next well to perform a two-fold dilution of the serum samples. 40 µl of SVV virus, containing 100 $TCID_{50}$, is added to wells containing diluted serum samples. Plates are incubated at 37° C. for 1 hour. 40 µl of the mix is taken and transferred to a plate containing PER.C6 cells ($1 \times 10^4$ cells/160 µl/well). The plates are incubated at 37° C. for 3 days. After this time, the cultures are read microscopically for CPE.

In a representative neutralization assay performed as described above, twenty-two human sera samples randomly collected from USA, Europe and Japan were examined for SVV specific neutralizing antibodies. The serum samples were serially diluted and mixed with a fixed amount of SVV containing 100 $TCID_{50}$. Serum-virus mixtures were then used to infect PER.C6 cells and incubated for 24 hours. Neutralizing antibody titer was determined as the reciprocal of the highest dilution of serum able to block CPE formation. In this experiment, no dilution of serum blocked CPE formation indicating that the human serum samples did not contain SVV neutralizing antibodies.

Further SVV infection of PER.C6 was not inhibited by incubation with human blood (see Example 6), indicating that SVV infection was not inhibited by complement or by hemagglutination. As a result, SVV exhibits a longer circulation time in vivo than other oncolytic viruses, which is a significant problem with the use of oncolytic adenoviruses.

Example 6

Binding of SVV to Human Erythrocytes and Hemagglutination

Various viral serotypes have been shown to cause in vitro hemagglutination of erythrocytes isolated from blood of various animal species. Hemagglutination or binding to erythrocytes may cause toxicity in vivo and may also affect in vivo biodistribution and the efficacy of a viral vector. Therefore, it is desirable to analyze the erythrocyte agglutination properties of a viral vector selected for systemic administration to treat metastatic cancers.

Hemagglutination assay: To determine whether SVV causes agglutination of human erythrocytes, hemagglutination assays are carried out in U-bottom 96-well plates. Purified SVV is serially diluted in 25 µl PBS (Phosphate Buffered Saline) in duplicates, and an equal volume of 1% erythrocyte suspension is added to each well. Blood samples used for isolation of erythrocytes are obtained from healthy individuals with heparin as an anticoagulant. Erythrocytes are prepared by washing the blood three times in cold PBS to remove the plasma and the white blood cells. After the last wash, erythrocytes are suspended in PBS to make a 1% (V/V) cell suspension. The virus and erythrocytes are gently mixed and the plates are incubated at room temperature for 1 hour and monitored for a hemagglutination pattern.

Whole blood inactivation assay: To rule out direct inactivation of SVV by blood components, aliquots of virus are incubated with heparinized human blood belonging to A, B, AB and O blood groups or PBS for 30 minutes or 1 hour at room temperature prior to separation of plasma, after which PER.C6 cells are infected and titers are calculated.

In representative assays performed as described above, no hemagglutination of human erythrocytes of different blood groups (A, B, AB and O) was seen at any tested dilutions of SVV. A slight increase in the virus titer is noticed when SVV is mixed with blood human samples and incubated for 30 minutes and 1 hour, indicating that the virus is not inactivated by blood components but becomes more infectious under tested conditions.

Example 7

In Vivo Clearance

Blood circulation time: To determine the blood circulation time and the amount of the virus in the tumor, H446 tumor bearing nude mice were treated with SVV at a dose of $1\times10^{12}$ vp/kg by tail vein injection. The mice were bled at 0, 1, 3, 6, 24, 48, 72 hours and 7 days (189 hours) post-injection and the plasma was separated from the blood immediately after collection, diluted in infection medium, and used to infect PER.C6 cells. The injected mice were sacrificed at 6, 24, 48, 72 hours and 7 days post-injection and the tumors were collected. The tumors were cut into small sections and suspended in one ml of medium and subjected to three cycles of freeze and thaw to release the virus from the infected cells. Serial log dilutions of supernatants were made and assayed for titer on PER.C6 cells. SVV titers were expressed as pfu/ml. The tumor sections were also subjected to H&E staining and immunohistochemistry to detect the virus capsid proteins in the tumor.

The circulating levels of virus particles in the blood were determined based on the assumption that 7.3% of mouse body weight is blood. In representative assays performed as essentially as described above, within 6 hours of virus administration, the circulating levels of SVV reduced to zero particles and SVV was not detectable at later time points (FIG. 46A). In the tumor, SVV was detectable at 6 hours post-injection, after which the amount of the virus increased steadily by two logs (FIG. 46B). The virus was detectable in the tumor as late as 7 days postinjection (FIG. 46B). The tumor sections when subjected to immunohistochemistry, revealed SVV proteins in the tumor cells (FIG. 47, top panels). When stained by H&E, the tumor sections revealed several rounded tumor cells (FIG. 47, bottom panels).

SVV also exhibits a substantially longer resident time in the blood compared to similar doses of i.v. adenovirus. Following a single i.v. dose, SVV remains present in the blood for up to 6 hours (FIG. 46C; FIG. 46C is a duplication of FIG. 46A for comparison purposes to FIG. 46D), whereas adenovirus is cleared from the blood in about an hour (FIG. 46D).

Example 8

Tumor Cell Selectivity

In vitro cell killing activity of SVV: To determine the susceptibility of human, bovine, porcine, and mouse cells, normal and tumor cells were obtained from various sources and infected with SVV. All cell types were cultured in media and under the conditions recommended by the supplier. Primary human hepatocytes may be purchased from In Vitro Technologies (Baltimore, Md.) and cultured in Hepatocyte Culture Media (HCM™, BioWhittaker/Clonetics Inc., San Diego, Calif.).

In vitro cytopathic assay: To determine which types of cells are susceptible to SVV infection, monolayers of proliferating normal cells and tumor cells were infected with serial dilutions of purified SVV. The cells were monitored for CPE and compared with uninfected cells. Three days following infection, a MTS cytotoxic assay is performed and effective concentration 50 ($Ec_{50}$) values in particles per cell are calculated. See Tables 5 and 6 below and Table 1A supra.

TABLE 5

Cell lines with $EC_{50}$ values less than 100

| | EC50 number |
|---|---|
| Cell lines with EC50 < 1 | |
| H446 (human sclc) | 0.001197 |
| PERC6 | 0.01996 |
| H69AR (sclc-multidrug resisitant) | 0.03477 |
| 293 (human kidney transformed with ad5E1) | 0.03615 |
| Y79 (human retinoblastoma) | 0.0003505 |

TABLE 5-continued

Cell lines with $EC_{50}$ values less than 100

| | EC50 number |
|---|---|
| IMR32 (human brain; neuroblastoma) | 0.03509 |
| D283med (human brain; cerebellum; medulloblastoma) | 0.2503 |
| SK-N-AS (human brain; neuroblastoma) | 0.474 |
| N1E-115 (mouse neuroblastoma) | 0.002846 |
| SK-NEP-1 (kidney, wilms' tumor, pleural effusion, human) | 0.03434 |
| BEKPCB3E1 (bovine embryonic kidney cells transformed with ad5E1) | 0.99 |
| Cell Lines with EC50 < 10 (1-10) | |
| H1299 (human-non sclc) | 7.656 |
| ST (pig testes) | 5.929 |
| DMS 153 (human sclc) | 9.233 |
| Cell lines with EC50 <100 (10-100) | |
| BEK (bovine embryonic kidney) | 17.55 |

TABLE 6

Cell lines with $EC_{50}$ values more than 1000

| | | |
|---|---|---|
| M059K (human brain; malignant glioblastoma) | HUVEC (human vein endothelial cells) | CMT-64 (mouse-sclc) |
| KK (human glioblastoma) | HAEC (human aortic endothelial cells) | LLC-1 (mouse-LCLC)) |
| U-118MG (human glioblatoma) | WI38 (human lung fibroblast) | RM-1 (mouse-prostate) |
| DMS 79 (human sclc) | MRC-5 (human lung fibroblast) | RM-2 (mouse-prostate) |
| H69 (human sclc) | IMR90 (human lung fibroblast) | RM-9 (mouse-prostate) |
| DMS 114 (human sclc) | HMVEC (human microvascular endothelial cells-adult) | MLTC-1 (mouse-testes) |
| DMS 53 (human sclc) | HMVEC (human microvascular endothelial cells-neonatal) | KLN-205 (mouse-sqcc) |
| H460 (human-LCLC) | HCN-1A (human brain) | CMT-93 (mouse-rectal) |
| A375-S2 (human melanoma) | HRCE (human renal cortical epithelial cells) | B16F0 (mouse melanoma) |
| SK-MEL-28 (human melanoma) | | Neuro-2A (mouse neuroblastoma) |
| PC3 (human prostate) | | C8D30 (mouse brain) |
| PC3M2AC6 (human prostate) | | PK15 (pig-kidney) |
| LNCaP (human prostate) | | FBRC (fetal bovine retina) |
| DU145 (human prostate) | | MDBK (bovine kidney) |
| Hep3B (human liver carcinoma) | | CSL 503 (sheep lung cells transformed with ad5E1) |
| Hep2G (human liver carcinoma) | | OFRC (ovine fetal retina cells) |
| SW620 (human-colon) | | |
| SW839 (human kidney) | | |
| 5637 (human bladder) | | |
| HeLa S3 | | |
| S8 | | |

The MTS assay was performed according to the manufacturer's instructions (CellTiter 96® AQ$_{ueous}$ Assay by Promega, Madison, Wis.). The CellTiter 96® AQ$_{ueous}$ Assay preferably uses the tetrazolium compound (3-(4,5-dimethylthiazol-2-yl)-5-(3-carboxymethoxyphenyl)-2-(4-sulfophenyl)-2H-tetrazolium, inner salt; MTS) and an electron coupling reagent, phenazine methosulfate (PMS). Contact-inhibited normal human cells evaluated in the study include: HUVEC (human umbilical vein endothelial cells), HAEC (human aortic endothelial cells, Clonetics/BioWhittaker # CC-2535), Wi38 (normal human embryo lung fibroblasts, ATCC # CCL-75), IMR90 (human normal lung fibroblasts, ATCC CCL-186), MRC-5 (human normal lung fibroblasts, ATCC, # CCL-171) and HRCE (human renal cortical epithelial cells, Clonetics/BioWhittaker # CC-2554).

SVV does not produce CPE in any of the above contact-inhibited normal cells. No virus-induced CPE was seen in the following human tumor cell lines: Hep3B (ATCC # HB-8064), HepG2 (human hepatocellular carcinoma, ATCC # HB-8065), LNCaP (human prostate carcinoma, ATCC # CRL-10995), PC3M-2AC6, SVV620 (human colorectal adenocarcinoma, ATCC # CCL-227), SVV 839 (human kidney adenocarcinoma, ATCC # HTB-49), 5637 (human urinary bladder carcinoma, ATCC # HTB-9), DMS-114 (small cell lung cancer, ATCC # CRL-2066), DMS 153 (human small cell lung cancer, ATCC # CRL-2064), A549 (human lung carcinoma, ATCC # CCL-185), HeLa S3 (human cervical adenocarcinoma, ATCC # CCL-2.2), NCI-H460 (human large cell lung cancer, ATCC # HTB-177), KK (glioblastoma), and U-118 MG (human glioblastoma, ATCC # HTB-15). Note—the cell lines in Table 6 with $EC_{50}$ values greater than 1000 are most likely not permissive for SVV replication and/or virion production; although the possibility remains that SVV can bind and enter into these cells but CPE is not observed because SVV replication cannot occur inside the cell or that replication does occur but CPE is not observed because there is some other post-entry block (i.e., no packaging of replicated SVV genomes into virions). However, considering the absence of CPE in these cell lines, these cell-lines, and potentially tumor-types thereof, are good candidates to test which cell and tumor-types are permissive or non-permissive for SVV replication. Although wild-type SVV is tumor-specific, and has been shown to target neuroendocrine tumors, including small cell lung cancer and neuroblastomas, there may be individual patients that have types of etiologies such that SVV is not permissive in their form of neuroendocrine tumor. Therefore, the invention does contemplate the generation of SVV derivatives that can kill tumor cell-types isolated from individual patients where the tumors are non-permissive to the wild-type SVV, and the tumor-types isolated from these individuals can include, for example, glioblastoma, lymphoma, small cell lung cancer, large cell lung cancer, melanoma, prostate cancer, liver carcinoma, colon cancer, kidney cancer, colon cancer, bladder cancer, rectal cancer and squamous cell lung cancer.

SVV-mediated cytotoxicity on primary human hepatocytes (In Vitro Technologies) was determined by LDH release assay (CytoTox® 96 Non-Radioactive Cytotoxicity Assay, Promega, # G1780). Primary human hepatocytes plated in collagen coated 12-well plates were infected with SVV at 1, 10 and 100 and 1000 particles per cell (ppc). After 3 hours of infection, the infection medium was replaced with 2 ml of growth medium and incubated for 3 days in a $CO_2$ incubator. The cell associated lactate dehydrogenase (LDH) and LDH in the culture supernatant was measured separately. Percent cytotoxicity is determined as a ratio of LDH units in supernatant over maximal cellular LDH plus supernatant LDH.

$$\text{Percent cytotoxicity} = \frac{LDH \text{ units in culture supernatant} \times 100}{\text{Sum of } LDH \text{ units in supernatant and cell lysate}}$$

The data shown in FIG. 48 illustrates the absence of SVV mediated hepatoxicity at all tested multiplicity of infections.

Example 10

Virus Production Assay

To assess the replicative abilities of SVV, several selected contact-inhibited normal cells and actively dividing tumor cells were infected with SVV at one virus particle per cell (ppc). After 72 hours, cells and the medium were subjected to three freeze-thaw cycles and centrifuged to collect the supernatant. Serial log dilutions of supernatants were made and assayed for titer on PER.C6 cells. For each cell line, the efficiency of SVV replication was expressed as pfu/ml (FIG. 49).

Example 10

Toxicity

The maximum tolerated dose (MTD) is defined as the dosage immediately preceding the dose at which animals (e.g. mice) demonstrate a dose limiting toxicity (DLT) after the treatment with SVV. DLT is defined as the dose at which the animals exhibit a loss in body weight, symptoms, and mortality attributed to SVV administration during the entire duration of the study. Neutralizing antibodies to SVV were assessed at baseline, day 15, and day 21. Neutralization assays were carried as described earlier.

Escalating doses ($1 \times 10^8$-$1 \times 10^{14}$ vp/kg) of SVV were administered intravenously into both immune deficient nude and caesarean derived-1 (CD-1) out-bred immune competent mice purchased from Harlan Sprague Dawley (Indianapolis, Ind., USA) to determine the MTD with 10 mice per dose level. The virus was well-tolerated at all tested dose levels without exhibiting any clinical symptoms and without loss in body weight (FIG. 50). Mice were bled at day 15 and 21 and the sera was monitored for the presence of SVV-specific neutralizing antibodies in neutralization assays. SVV injected CD1 mice develop neutralizing antibodies and the titers range from 1/1024 to greater than 1/4096.

Another toxicity study was conducted on the immunocompetent mouse strain (A/J). It has been demonstrated that SVV exhibits cell killing activity and replication in N1E-115 cells (see Table 1). The murine cell line N1E-115 (a neuroblastoma cell line, i.e., neuroendocrine cancer) is derived from the A/J mouse strain. Thus, a syngeneic mouse model was established where N1E-115 cells were implanted subcutaneously in A/J mice to form tumors, and the mice were then treated with SVV to investigate its efficacy and toxicity.

In the A/J study, mice were i.v. injected with SVV to determine whether A/J mice can tolerate systemic administration of SVV. Blood hematology results were obtained to look for signs of toxicity, and serum chemistry results can also be obtained. The study design is shown in Table 7 below:

TABLE 7

A/J Study Design

| Group # | Animals (Female) | Test Article | Dosage Level (particles/kg) | Dosage Volume (mL/kg) | Dosing regimen | Necropsy Day |
|---|---|---|---|---|---|---|
| 1 | 5 | Vehicle | 0 | 10 | IV on Day 1 | Day 15 |
| 2 | 5 | SVV | $10^8$ | 10 | IV on Day 1 | Day 15 |

TABLE 7-continued

A/J Study Design

| Group # | Animals (Female) | Test Article | Dosage Level (particles/kg) | Dosage Volume (mL/kg) | Dosing regimen | Necropsy Day |
|---|---|---|---|---|---|---|
| 3 | 5 | SVV | $10^{11}$ | 10 | IV on Day 1 | Day 15 |
| 4 | 5 | SVV | $10^{14}$ | 10 | IV on Day 1 | Day 15 |

The A/J mice were 8-10 week old females obtained from The Jackson Laboratory (Bar Harbor, Me.). SVV was prepared by storing isolated virions at −80° C. until use. SVV was prepared fresh by thawing on ice and diluting with HBSS (Hank's balanced salt solution). SVV was diluted to concentrations of $10^7$ particles/mL for group 2, $10^{10}$ particles/mL for group 3, and $10^{13}$ particle/mL for group 4. HBSS was used as the vehicle control for group 1. All dosing solutions were kept on wet ice until dosing.

SVV was administered to animals intravenous injection via the tail vein at a dose volume of 10 mL/kg body weight. Animals were weighed on the day of dosing and dose volumes were adjusted based on body weight (i.e., a 0.0200 kg mouse gets 0.200 mL of dosing solution). Mice were monitored twice daily for morbidity and mortality. Mice were weighed twice weekly. Information relating to moribund animals and animals exhibiting any unusual symptoms (physically or behaviorally) are recorded immediately.

Post-mortem observations and measurements entail the collection of blood from all surviving animals at terminal sacrifice for standard hematology and serum chemistry (AST, ALT, BUN, CK, LDH). The following organs are to be collected at sacrifice: brain, heart, lung, kidney, liver, and gonads. Half of each organ sample is snap frozen on dry ice and the other half will be placed in formalin.

Initial blood hematology results (CBC, differential) were obtained two weeks after SVV injection and the results are summarized below in Table 8 below. Five mice were tested from each test group (see Table 7):

TABLE 8

A/J Toxicity Results - Blood Hematology

| | Test Group 1 | Test Group 2 | Test Group 3 | Test Group 4 |
|---|---|---|---|---|
| Body Weight Result ± SD (g): | | | | |
| Day 0 | 21.48 ± 0.88 | 21.98 ± 1.93 | 22.58 ± 0.87 | 21.04 ± 1.67 |
| Day 14 | 20.26 ± 0.93 | 20.92 ± 1.71 | 21.44 ± 0.84 | 21.26 ± 1.45 |
| CBC Wet (Result ± SD (ref range)): | | | | |
| White blood count (THSN/UL) | 3.63 ± 1.57 (2.60-10.69) | 4.5 ± 1.57 (2.60-10.69) | 4.26 ± 0.94 (2.60-10.69) | 4.72 ± 0.62 (2.60-10.69) |
| Red blood count (MILL/UL) | 9.87 ± 0.03 (6.4-9.4) | 9.49 ± 0.07 (6.4-9.4) | 9.76 ± 0.37 (6.4-9.4) | 9.71 ± 0.32 (6.4-9.4) |
| Hemoglobin (GM/DL) | 15.37 ± 0.06 (11.5-16.1) | 14.78 ± 0.29 (11.5-16.1) | 15.12 ± 0.66 (11.5-16.1) | 15.02 ± 0.63 (11.5-16.1) |
| Hematocrit (%) | 46.03 ± 0.40 (36.1-49.5) | 44.52 ± 0.49 (36.1-49.5) | 45.7 ± 1.82 (36.1-49.5) | 45.28 ± 1.69 (36.1-49.5) |
| MCV (FL) | 46.67 ± 0.58 (45.4-60.3) | 47.00 ± 0.0 (45.4-60.3) | 47.0 ± 0.0 (45.4-60.3) | 46.6 ± 0.55 (45.4-60.3) |
| MHC (PICO GM) | 15.57 ± 0.06 (14.1-19.3) | 15.70 ± 0.17 (14.1-19.3) | 15.37 ± 0.06 (14.1-19.3) | 15.43 ± 0.15 (14.1-19.3) |
| MCHC (%) | 33.37 ± 0.12 (25.4-34.1) | 33.14 ± 0.48 (25.4-34.1) | 33.08 ± 0.22 (25.4-34.1) | 33.14 ± 0.25 (25.4-34.1) |
| Platelet (THSN/UL) | 885.33 ± 28.6 (592-2972) | 758.2 ± 146.2 (592-2972) | 874.8 ± 56.7 (592-2972) | 897.2 ± 105.4 (592-2972) |
| Differential (Result ± SD (ref range)): | | | | |
| Bands (THSN/UL) | 0.0 (0.0-0.1) | 0.0 (0.0-0.1) | 0.0 (0.0-0.1) | 0.0 (0.0-0.1) |
| Seg. Neutrophils (THSN/UL) | 0.92 ± 0.27 (0.13-2.57) | 1.16 ± 0.37 (0.13-2.57) | 1.09 ± 0.38 (0.13-2.57) | 0.96 ± 0.20 (0.13-2.57) |
| Lymphocytes (THSN/UL) | 2.64 ± 1.26 (1.43-9.94) | 2.98 ± 1.41 (1.43-9.94) | 3.10 ± 0.56 (1.43-9.94) | 3.70 ± 0.41 (1.43-9.94) |
| Monocytes (THSN/UL) | 0.06 ± 0.04 (0.0-0.39) | 0.15 ± 0.05 (0.0-0.39) | 0.06 ± 0.03 (0.0-0.39) | 0.05 ± 0.02 (0.0-0.39) |
| Eosinophils (THSN/UL) | 0.01 ± 0.01 (0.0-0.24) | 0.01 ± 0.01 (0.0-0.24) | 0.01 ± 0.01 (0.0-0.24) | 0.003 ± 0.01 (0.0-0.24) |
| Basophils (THSN/UL) | 0.0 (0.0-0.0) | 0.004 ± 0.005 (0.0-0.0) | 0.0 (0.0-0.0) | 0.0 (0.0-0.0) |
| Atypical Lympho. (THSN/UL) | 0.0 (0.0-0.0) | 0.0 (0.0-0.0) | 0.0 (0.0-0.0) | 0.0 (0.0-0.0) |
| Metamyelocytes (THSN/UL) | 0.0 (0.0-0.0) | 0.0 (0.0-0.0) | 0.0 (0.0-0.0) | 0.0 (0.0-0.0) |
| Myelocytes (THSN/UL) | 0.0 (0.0-0.0) | 0.0 (0.0-0.0) | 0.0 (0.0-0.0) | 0.0 (0.0-0.0) |
| NRBC (/100WBC) | 0.0 (0.0-0.0) | 0.0 (0.0-0.0) | 0.0 (0.0-0.0) | 0.0 (0.0-0.0) |

TABLE 8-continued

A/J Toxicity Results - Blood Hematology

| | Test Group 1 | Test Group 2 | Test Group 3 | Test Group 4 |
|---|---|---|---|---|
| Other (Result ± SD (ref range)): | | | | |
| AST (SGOT) (U/L) | 1762.8 ± 1129.8 (72-288) | 899.0 ± 234.6 (72-288) | 779.8 ± 312.2 (72-288) | 843.2 ± 653.4 (72-288) |
| ALT (SGPT) (U/L) | 2171.8 ± 2792.9 (24-140) | 535.2 ± 272.8 (24-140) | 555 ± 350.8 (24-140) | 380.2 ± 385.7 (24-140) |
| BUN (MG/DL) | 27.2 ± 0.8 (9-28) | 24.8 ± 1.9 (9-28) | 24.6 ± 5.5 (9-28) | 28.2 ± 12.8 (9-28) |
| Creatine phosphokinase (U/L) | 28312.8 ± 20534.4 (0-800) | 12194.4 ± 4049.2 (0-800) | 10157 ± 5420.5 (0-800) | 11829 ± 10363.9 (0-800) |
| LDH (U/L) | 6650.2 ± 4788.6 (260-680) | 3661.6 ± 933.6 (260-680) | 3450.8 ± 972.6 (260-680) | 2808.4 ± 1709.1 (260-680) |
| Hemolytic Index (MG/DL HGB) | 706.6 ± 423.4 (0-70) | 477.6 ± 195.7 (0-70) | 589.6 ± 198.6 (0-70) | 496.4 ± 321.1 (0-70) |

These results show that there are no abnormalities in blood hematology profiles obtained from mice treated with low, medium and high doses of SVV compared to blood hematology profiles obtained from untreated mice. From this study, it can be concluded that there are no measureable signs of toxicity following systemic administration of SVV, indicating that SVV is tolerated by A/J mice following i.v. injection.

Example 11

Efficacy

Athymic female nude mice (nu/nu) aged 6-7 weeks purchased from Harlan Sprague Dawley (Indianapolis, Ind.) were used in efficacy studies. Mice were injected subcutaneously with $5 \times 10^6$ H446 cells into the right flank using manual restraint. Tumor sizes were measured regularly, and the volumes were calculated using the formula $\pi/6 \times W \times L^2$, where L=length and W=width of the tumor. When the tumors reach approximately 100-150 mm³, mice (n=10) were randomly divided into groups. Mice were injected with escalating doses of SVV by tail vein injections at a dose volume of 10 ml/kg. A control group of mice was injected with an equivalent volume of HBSS. Dose escalation proceeds from $1 \times 10^7$ to $1 \times 10^{13}$ particles per kilogram body weight. Antitumoral efficacy was determined by measuring tumor volumes twice weekly following SVV administration. Complete response was defined as complete disappearance of xenograft; partial response as regression of the tumor volume by equal to or more than 50%; and no response as continuous growth of tumor as in the control group.

Tumors from mice treated with HBSS grew rapidly and the tumor volumes reached more than 2000 mm³ by study day 20 (FIG. 51; see line with open diamond). In contrast, mice given one systemic injection of SVV at all tested doses (with the exception of the lowest dose) became tumor free by study day 20. In the lowest dose group, 8 mice became tumor free, one mouse had a very large tumor and the other had a small palpable tumor (25 mm³) by study day 31. To evaluate the antitumor activity of SVV on large sized tumors, five mice from HBSS group bearing tumors >2000 mm³ were systemically injected with a single dose of $1 \times 10^{11}$ vp/kg on study day 20. For the duration of the follow-up period (11 days of after SVV injection), a dramatic regression of the tumor volumes were noted (FIG. 51).

Additional experiments to test the efficacy of a single intravenous dose of SVV was conducted in murine tumor models that express neuroendocrine markers. The tumor models tested included H446 (human SCLC) (see FIG. 90A), Y79 (human retinoblastoma) (see FIG. 90B), H69AR (human multi-drug resistant SCLC) (see FIG. 90C), H1299 (human NSCLC) (see FIG. 90D), and N1E-115 (murine neuroblastoma) (see FIG. 90E).

The results show that a single intravenous dose of SVV has efficacy in all of the murine neuroendocrine tumor models. The results also show that SVV is efficacious in the N1E-115 immunocompetent murine neuroblastoma model.

FIG. 52 shows a picture of mice that were "untreated" with SVV (i.e., treated with HBSS) or "treated" with SVV. As can be seen, the untreated mice had very large tumors and the treated mice showed no visible signs of tumor. Further, for unsacrificed mice treated with SVV, no tumor regrowth was observed for the duration of the study, 200 days.

In vitro efficacy data for SVV for specific tumor cell lines is shown in Tables 1, 1A, and 5. The data shows that SVV specifically infects particular tumor cell types and does not infect normal adult cells (except for porcine normal cells), a significant advantage over any other known oncolytic virus. SVV has been shown to have 1,000 times better cell killing specificity than chemotherapy treatments (cell killing specifity values for SVV have been shown to be greater than 10,000, whereas cell killing specificity values for chemotherapy are around 10).

Specific cytotoxic activity of SVV was demonstrated in H446 human SCLC cells. Following a two-day incubation with increasing concentrations of SVV, cell viability was determined. The results are shown in FIG. 53. FIG. 53 shows cell survival following incubation of SVV with either H446 SCLC tumor cells (top graph) or normal human H460 cells (bottom graph). SVV specifically killed the tumor cells with an $EC_{50}$ of approximately $10^{-3}$ particles per cell. In contrast, normal human cells were not killed at any concentration of SVV. Further, as summarized in Tables 1, 1A-3, SVV was also cytotoxic toward a number of other tumor cell lines, including SCLC-multidrug resistant tumor cells, and some fetal cells and cell lines. The $EC_{50}$ values for SVV cytotoxicity for the other tumor cell lines ranged from $10^{-3}$ to greater than 20,000 particles per cell. SVV was non-cytotoxic against a variety other non-neural tumors and normal human tissues. Additionally, SVV was not cytotoxic to primary human hepatocytes, as measured by LDH release at up to 1000 particles per cell (see FIG. 48).

Example 12

Biodistribution and Pharmacokinetic Study in Rodents

Pharmacokinetic and biodistribution study of SVV is performed in normal mice and immunocompromised athymic nude mice bearing H446 SCLC tumors. This study evaluates the biodistribution, elimination and persistence of SVV following a single intravenous administration to both normal and immunocompromised tumor-bearing mice. Groups of mice each receive a single i.v. dose of control buffer or one of three doses of SVV ($10^8$, $10^{1o}$, or $10^{12}$ vp/kg) and are monitored for clinical signs. Blood samples are obtained from groups of 5 mice at 1, 6, 24 and 48 hours post dose, and at 1, 2, 4, and 12 weeks post dose. Dose levels include a known low efficacious dose and two higher dose levels to determine linearity of virus elimination. Groups of mice are sacrificed at 24 hours, and 2, 4 and 12 weeks post dose. Selected tissues, including liver, heart, lung, spleen, kidney, lymph nodes, bone marrow, brain and spinal cord tissues are aseptically collected and tested for the presence of SVV RNA using a validated RT-PCR assay.

Samples of urine and feces are obtained at sacrifice, at 24 hours, and at 2, 4 and 12 weeks post dose and are examined for the presence of infectious virus. The design of the experiments in this Example are shown in Table 9 below:

TABLE 9

Biodistribtuion of SVV in CD-1 Mice and Athymic Nude Mice Bearing SCLC Tumors

| Group | Treatment | Dose Level (vp/kg) | Route | # of Mice/Timepoint for Blood Sampling | # of Mice/Timepoint for PCR Tissue Distribution |
|---|---|---|---|---|---|
| Normal CD-1 Mice | | | | | |
| 1 | Saline | 0 | i.v. | 5 | 5 |
| 2 | SVV | $10^8$ | i.v. | 5 | 5 |
| 3 | SVV | $10^{10}$ | i.v. | 5 | 5 |
| 4 | SVV | $10^{12}$ | i.v. | 5 | 5 |
| Athymic Tumor Bearing Mice | | | | | |
| 5 | Saline | 0 | i.v. | 5 | 5 |
| 6 | SVV | $10^8$ | i.v. | 5 | 5 |
| 7 | SVV | $10^{10}$ | i.v. | 5 | 5 |
| 8 | SVV | $10^{12}$ | i.v. | 5 | 5 |

Acute i.v. toxicology studies were also performed in both normal and immunocompromised athymic nude mice bearing H446 SCLC tumors. Preliminary i.v. studies in normal and SCLC tumor bearing mice indicate safety of SVV at doses up to $10^{14}$ vp/kg. No adverse clinical signs were observed and there was no loss of body weight up to 2 weeks following a single i.v. dose of $10^{14}$ vp/kg.

Example 13

Viral Transmission Study in Normal Adult and Pregnant Mice

The purpose of this Example is to determine if SVV is transmissible following cohabitation of noninfected normal mice with mice injected with a high concentration of SVV. Because SVV does not replicate in normal, non-tumor bearing mice, tumor bearing mice can also be injected with high concentrations of SVV and subsequently exposed to normal, healthy animals to better simulate the clinical scenario. A secondary purpose is to assess the potential transmissibility of SVV from an infected female to an uninfected pregnant DAM, and subsequently to the developing fetus.

Three groups of five naive male and female CD-1 mice are exposed to a single mouse of the same sex infected with either $10^8$, $10^{10}$ or $10^{12}$ vp/kg, and are monitored for the presence of SVV by blood sampling.

Similarly, an SVV exposed female is co-mingled with a number of timed pregnant females, and the ability of the virus to transmit from the infected female to an uninfected pregnant female, and subsequently to the developing fetus is determined.

Example 14

Non-Human Primate Studies

The safety, toxicity and toxicokinetics of SVV are also determined in non-human primates. In a dose range-finding phase, individual monkeys receive a single i.v. dose of SVV at $10^8$ vp/kg and are closely monitored for clinical signs of infection or toxicity. If this dose is well tolerated, additional animals are treated with a higher i.v. dose until a dose of $10^{12}$ vp/kg is achieved. Subsequently, the main study consists of groups of three male and female monkeys, and each monkey is dosed once weekly for six weeks with either vehicle alone or one of three doses of SVV and monitored for signs of toxicity. An additional two monkeys per sex are dosed with the vehicle alone and with the high dose level of SVV for six weeks, and are allowed an additional four weeks recovery prior to sacrifice.

Blood samples are obtained following dosing during week 1 and week 6. Clinical pathological and hematology blood samples are obtained prior to the initial dose and prior to sacrifice. Additional blood samples are obtained following each dose for assessing the presence of neutralizing antibodies to SVV.

Surviving monkeys are euthanized and subjected to a full gross necropsy and a full tissue list is collected from the main study and recovery monkeys. Tissues from the control and high dose groups are evaluated histopathologically. Urine and fecal samples are collected following dosing on weeks 1 and 6 and are evaluated for presence of infectious SVV. The overall design of this Example is shown in Table 10 below.

TABLE 10

Multiple Dose Toxicology Study of SVV in Primates

Dose Range-finding Phase

| Group | Treatment | Dose (vp/kg) | Route | Males | Females |
|---|---|---|---|---|---|
| 1 | SVV | $10^8$ | IV | 1 | 1 |
| 2 | SVV | $10^{10}$* | IV | 1 | 1 |
| 3 | SVV | $10^{12}$* | IV | 1 | 1 |

| Main Phase Group | Treatment | Dose (vp/kg) | Route | Main Phase Male | Main Phase Female | Recovery Male | Recovery Female |
|---|---|---|---|---|---|---|---|
| 1 | Control | — | IV | 3 | 3 | 2 | 2 |
| 2 | SVV | $10^8$* | IV | 3 | 3 | — | — |
| 3 | SVV | $10^{10}$* | IV | 3 | 3 | — | — |
| 4 | SVV | $10^{12}$* | IV | 3 | 3 | 2 | 2 |

*Doses can vary based on results of Dose Rage-finding phase

Example 15

Construction of an Infectious Full-Length and Functional Genomic SVV Plasmid With SEQ ID NO:1, only about 1.5-2 Kb of the 5' genomic sequence of SVV remains to be sequenced, representing the nucleotide region covering the 5' UTR, 1A (VP4) and part of 1B (VP2). To clone the 5' end missing in SEQ ID NO:1, polymerases that function at high temperatures and reagents that can enable a polymerase to read through secondary structures were used. Additional SVV cDNAs were prepared from isolated SVV of ATCC deposit number PTA-5343. SVV particles were infected into a permissive cell line, such as PER.C6, and viruses are isolated. Viral RNA was then recovered from the virus particles such that cDNA copies are made therefrom. Individual cDNA clones were sequenced, such that selected cDNA clones are combined into one full-length clone in a plasmid having a T7 promoter upstream of the 5' end of the SVV sequence. The full-length genomic sequence of SVV is listed in FIGS. 83A-83H and SEQ ID NO:168. The full-length SVV from this plasmid is reverse-transcribed, by utilizing T7 polymerase and an in vitro transcription system, in order to generate full-length RNA (see FIG. 55). The full-length RNA is then transfected into permissive cell lines to test the infectivity of the full-length clone (see FIG. 55).

The methodology was as follows. RNA Isolation: SVV genomic RNA was extracted using guanidium thiocyanate and a phenol extraction method using Trizol (Invitrogen). Briefly, 250 μl of the purified SVV (~3×10$^{12}$ virus particles) was mixed with 3 volumes of Trizol and 240 μl of chloroform. The aqueous phase containing RNA was precipitated with 600 μl isopropanol. The RNA pellet was washed twice with 70% ethanol, dried and dissolved in sterile DEPC-treated water. The quantity of RNA extracted can be estimated by optical density measurements at 260 nm. An aliquot of RNA can be resolved through a 1.25% denaturing agarose gel (Cambrex Bio Sciences Rockland Inc., Rockland, Me. USA) and the band visualized by ethidium bromide staining and photographed.

cDNA synthesis: cDNA of the SVV genome was synthesized by RT-PCR. Synthesis of cDNA was performed under standard conditions using 1 μg of RNA, AMV reverse transcriptase, and oligo-dT primers. Random 14-mer oligonucleotide can also be used. Fragments of the cDNA were amplified and cloned into the plasmid pGEM-3Z (Promega) and the clones were sequenced. The sequence at the 5' end of the viral genome was cloned by RACE and the sequence determined. Sequence data was compiled to generate the complete genome sequence of SVV.

Cloning of full length genome: Three cDNA fragments representing the full-length SVV genome were amplified by three PCR reactions employing six sets of SVV-specific primers. Turbo pfu polymerase (Stratagene) was used in PCR reactions. First, a fragment representing the 5' end of SVV genome was amplified with primers 5'SVV-A (SEQ ID NO:219) and SVV1029RT-RI (SEQ ID NO:220) and the resulting fragment was cut with ApaI and EcoRI and gel purified. The gel purified fragment was ligated to Nde-ApaT7SVV (SEQ ID NO:221), an annealed oligo duplex containing engineered NdeI site at 5' end, T7 core promoter sequence in the middle and first 17 nucleotides of SVV with ready to use ApaI site at 3' end and cloned into Nde I and Eco RI sites of pGEM-3Z (Promega) by three-way ligation to generate pNTX-03. Second, a fragment representing 3' end of viral genome was amplified by PCR with primers SVV6056 (SEQ ID NO:222) and SVV7309NsiB (SEQ ID NO:223).

The antisense primer, SVV7309NsiB was used to introduced poly(A) tail of 30 nucleotides in length and Nsi I recognition sequence at 3' end to clone into PstI site of pGEM-3Z plasmid. The resulting PCR product was digested with BamHI and gel purified. A fragment covering the internal part of the viral genome was amplified with primers SVV911L (SEQ ID NO:224) and SVV6157R (SEQ ID NO:225). The resulting PCR product was cut with EcoRI and BamHI and gel purified. The two gel purified fragments representing the middle and 3' end of SVV genome were cloned into EcoRI and SmaI sites of pGEM-4Z by three-way ligation to generate pNTX-02. To generate full-length SVV cDNA, pNTX-02 was digested with EcoRI and NsiI and the resulting 6.3 kb fragment was gel purified cloned into EcoRI and PstI sites of pNTX-03. The resulting full-length plasmid was called pNTX-04.

The full-length plasmid pNTX-04 was further modified at both 5' and 3' ends to facilitate in vitro transcription and rescuing of the virus following RNA transfection into PER.C6 cells. First, a SwaI restriction enzyme site was inserted immediately downstream of the poly(A) tail to liberate the 3' end of SVV-cDNA from the plasmid backbone prior to in vitro transcription. A PCR approach was used to insert the site utilizing a primer pair of SVV6056 (SEQ ID NO:222) and SVVSwaRev (SEQ ID NO:226) and pNTX-04 as template. The antisense primer SVV3SwaRev contained 58 nucleotides representing the 3' end of the SVV sequence and recognition sequences for SwaI and SphI restriction enzyme sites. The resulting PCR fragment was digested with BamHI and SphI and used to replace the corresponding fragment from pNTX-04 to generate pNTX-06. Second, an extra four nucleotides present between the T7 promoter transcription start site and 5' end of SVV cDNA in pNTX-06 were removed using annealed oligo duplex approach. The duplex nucleotides were engineered to contain KpnI recognition site, T7 core promoter sequence and the first 17 nucleotides of SVV with a ready to use ApaI site at the 3' end (SEQ ID NO:227). The annealed oligos were used to replace the corresponding portion of pNTX-06 using KpnI and ApaI sites to generate pNTX-07. Finally, a two base pair deletion noticed in the polymerase encoding region of pNTX-07 was restored by replacing BamHI and SphI fragment with a corresponding fragment amplified from SVV cDNA by PCR to generate pNTX-09.

In vitro transcription: Infectivity of in vitro transcribed RNA was tested by first digesting pNTX-09 with SwaI to liberate 3' end of SVV sequence from plasmid backbone. The linearized plasmid was subjected to in vitro transcription using T7 polymerase (Promega).

Transfection of in vitro transcribed RNA into PER. C6 cells: One day prior to transfection, PER.C6 cells were plated in 6-well tissue-culture dishes. On the next day, Lipofetamine reagent (Invitrogen) was used to transfect in vitro transcribed RNA (1.5 μg) into the cells following the recommendations of the supplier. Cytopathic effect (CPE) due to virus production was noticed within 36 hour post-transfection. The transfected cells were subjected to three cycles of freeze-thaw and the viruses in lysate were further confirmed by infecting PER.C6 cells. Thus, the full-length SVV cDNA clone proved to be infectious.

As described above, the plasmid with the full-length genome of SVV can be reverse-transcribed following standard protocols. The viral RNA (100 ng) can be used to transfect any cell line known to be permissive for the native SVV, but the most efficient cell line for viral RNA transfection can be empirically determined among a variety of cell lines.

Example 16

Construction of an RGD-Displaying SVV Library

To find the optimal insertion position for the construction of SVV capsid mutants generated with random with oligonucleotides encoding random peptide sequences, a simple model system (RGD) is employed. RGD (arginine, glycine, aspartic acid) is a short peptide ligand that binds to integrins. A successful RGD-SVV derivative should contain the following characteristics: (1) the genetic insertion should not alter any of SVV's unique and desirable properties; and (2) a successful RGD derivative virus should have tropism toward $\alpha_v\beta_5$ integrin containing cells.

A SVV plasmid containing just the contiguous capsid region will be singly cleaved at random positions and a short model peptide sequence, referred to as RGD, will be inserted at each position. The virus SVV-RGD library will be constructed from this plasmid library utilizing the general technology described in FIGS. 56 and 57.

Random insertion of the cRGD oligonucleotide into the capsid region is conducted. In brief, a plasmid is constructed that just encodes the contiguous 2.1 Kb capsid region of SVV (see FIG. 56, "pSVVcapsid"). A single random cleavage is made in pSVVcapsid by partially digesting the plasmid utilizing either CviJI or an endonuclease V method as described below (see FIG. 57). After isolating the single cleaved plasmid the RGD oligonucleotide will be inserted to create a pSVVcapsid-RGD library.

The restriction enzyme CviJI has several advantages over other random cleavage methods such as sonication or shearing. First, as CviJI is a blunt ended cutter no repair is necessary. Second, CviJI has been demonstrated to cleave at random locations such that no hot spots will occur. The procedure is also simple and rapid. Briefly, the concentration of CviJI and/or time of digestion are increasingly lowered until the majority of cleaved DNA is a linearized plasmid, i.e. a single cleavage. This can be observed by standard agarose gel electrophoresis as depicted in FIG. 57. The band is then isolated, purified and ligated with the RGD oligo.

Another method that may be utilized to randomly cleave DNA is the endonuclease V method (Kiyazaki, K., *Nucleic Acids Res.*, 2002, 30(24): e139). Endonuclease V nicks uracil-containing DNA at the second or third phosphodiester bond 3' to uracil sites. This method is also expected to randomly cleave DNA, the frequency is simply determined by adjusting the concentration of dUTP in the polymerase chain reaction. Although the cleavage sites are always two or three bases downstream of a thymidine (substituted by uracil) site, this method is expected to produce much fewer hot and cold spots than other methodologies.

The randomly linearized plasmids are ligated with the cRGD oligonucleotides. The resultant pSVV capsid library is then amplified, such that a population of polynucleotides encoding the capsid region with randomly inserted cRGD regions can be purified (see FIGS. 57 and 58). The population of capsid polynucleotides is then subcloned into a vector containing the full-length SVV sequence minus the capsid region, such that a library of full-length SVV sequences are generated (where the library manifests sequence diversity in the capsid region as the cRGD sequence is randomly inserted). This library is then reverse transcribed into RNA, and the RNA is transfected into a permissive cell line to generate a population of SVV particles having different capsids (see FIG. 59). Once this RGD-SVV population of virus particles is recovered ("RGD-SVV library"), a number of viruses (i.e., 10 or more) will be randomly picked for sequencing to confirm the insertion of the RGD sequence and diversity of insertion site.

In vitro selection of the RGD-displaying SVV library. The SVV-RGD library is screened to determine which insertion site enabled an expanded tropism of SVV. The RGD-SVV library is allowed to infect $\alpha_v\beta_5$ integrin-expressing NSCLC lines (non-small cell lung cancer cell lines, i.e., A549 expressing $\alpha_v\beta_5$). Only those SVV derivatives that contain a functional and properly displayed RGD motif can infect these cells and replicate.

Figure 63:
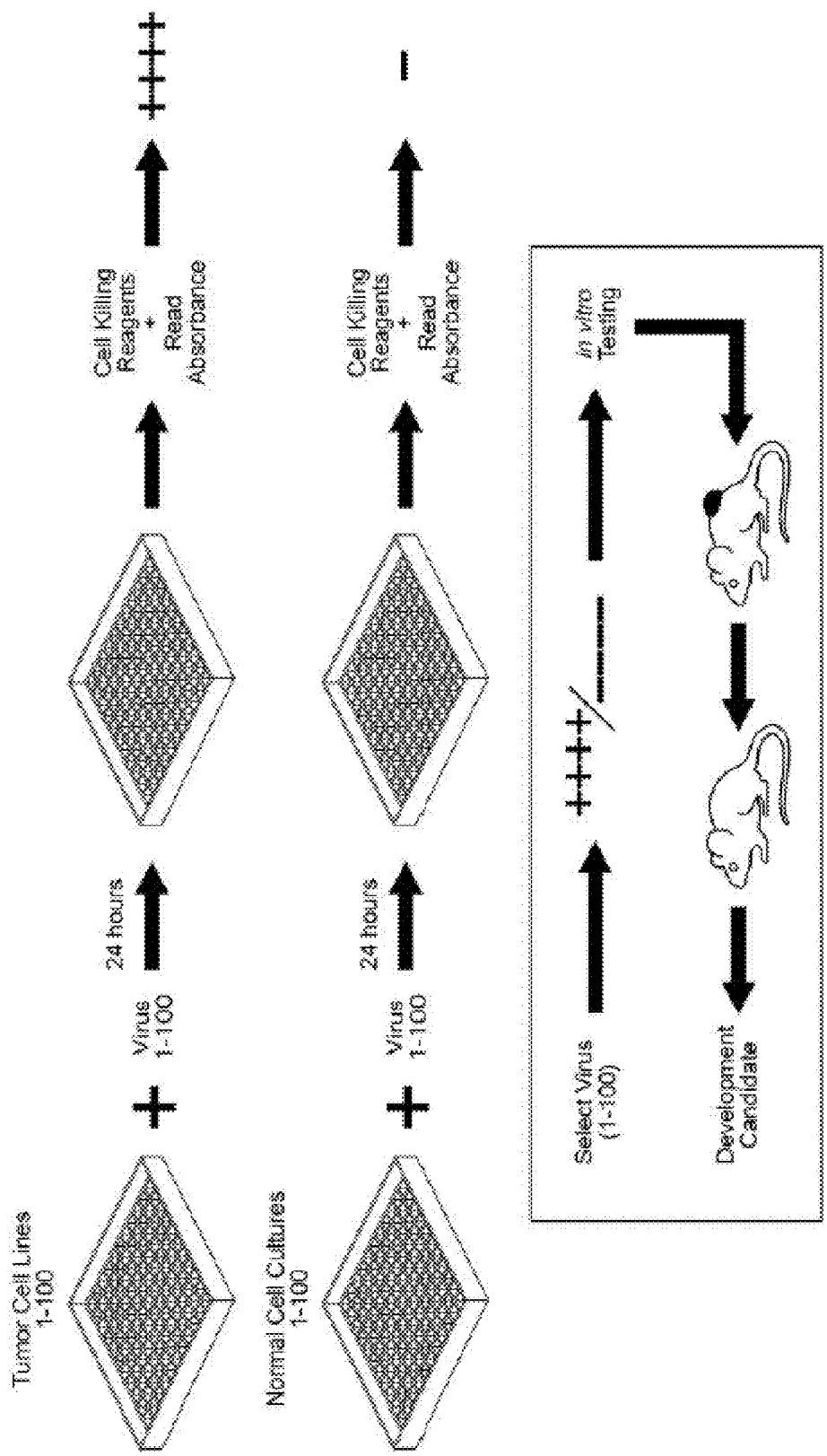
Figure 64:
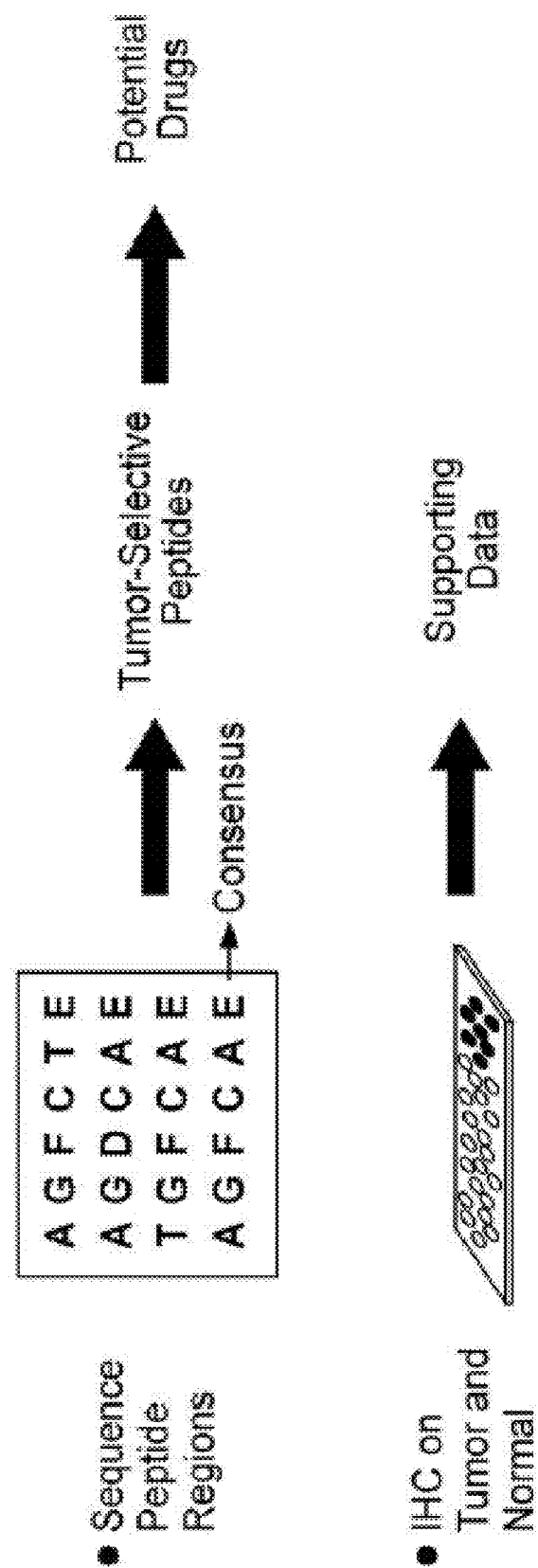
Figure 65:
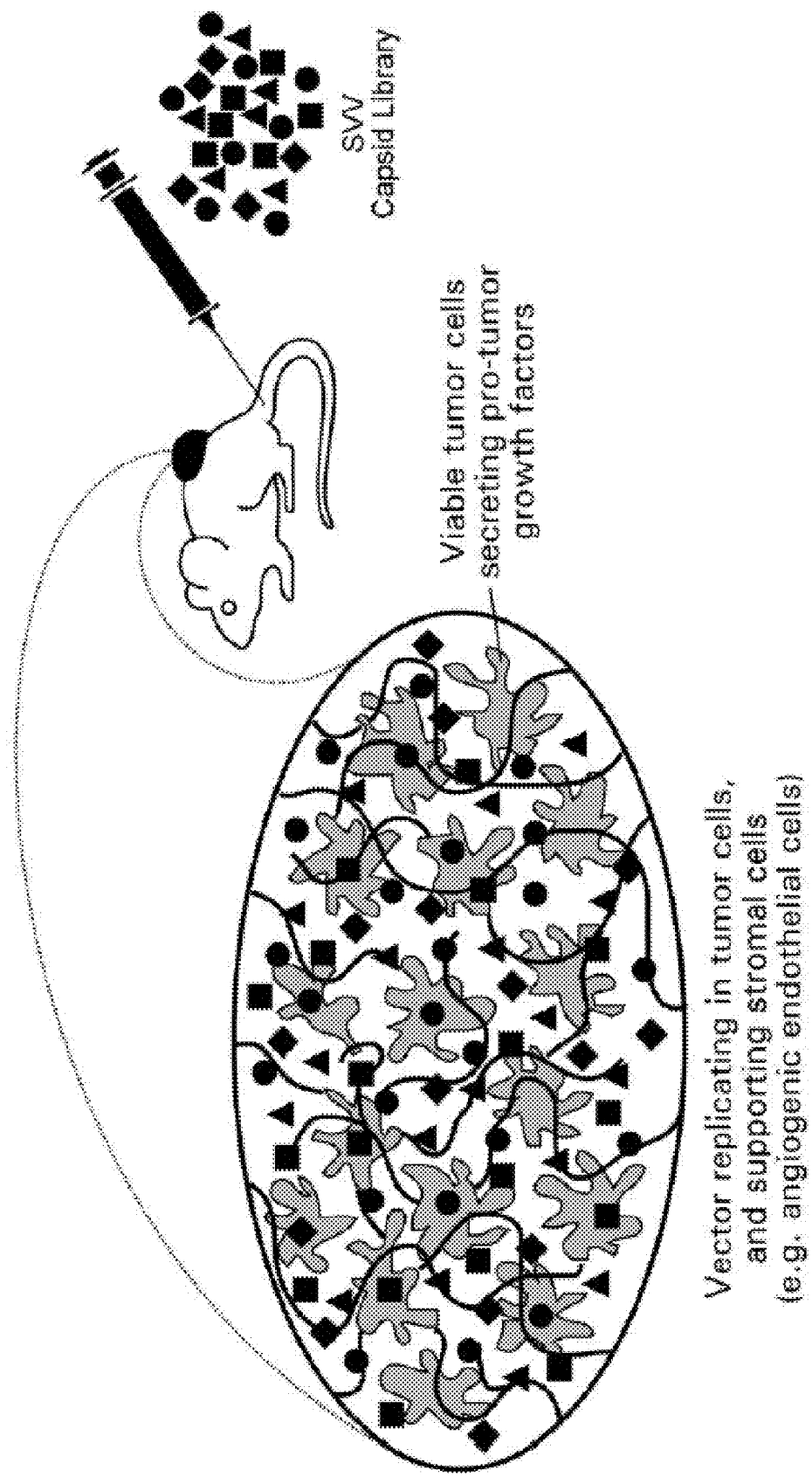
Figure 66:
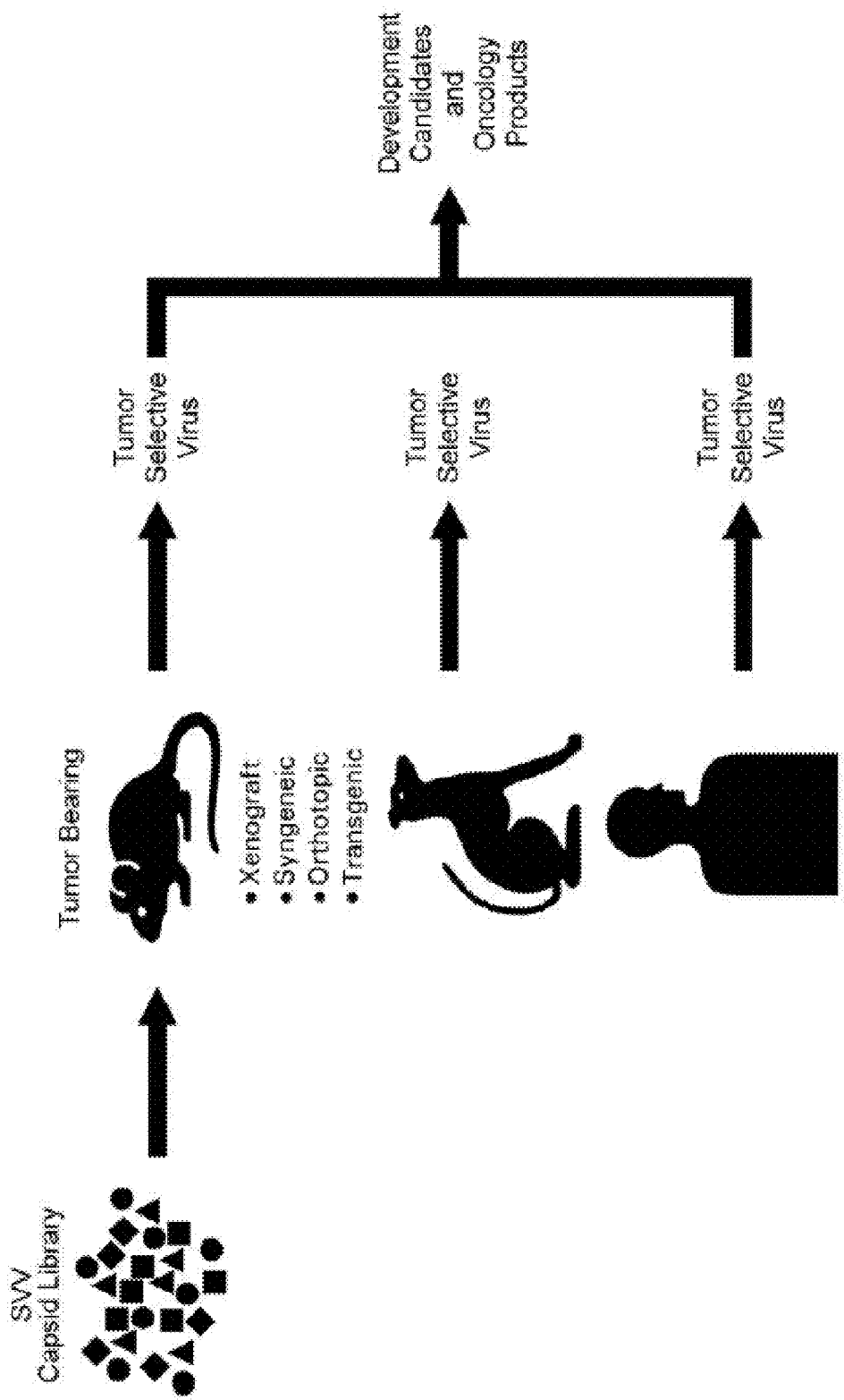
Figure 67:
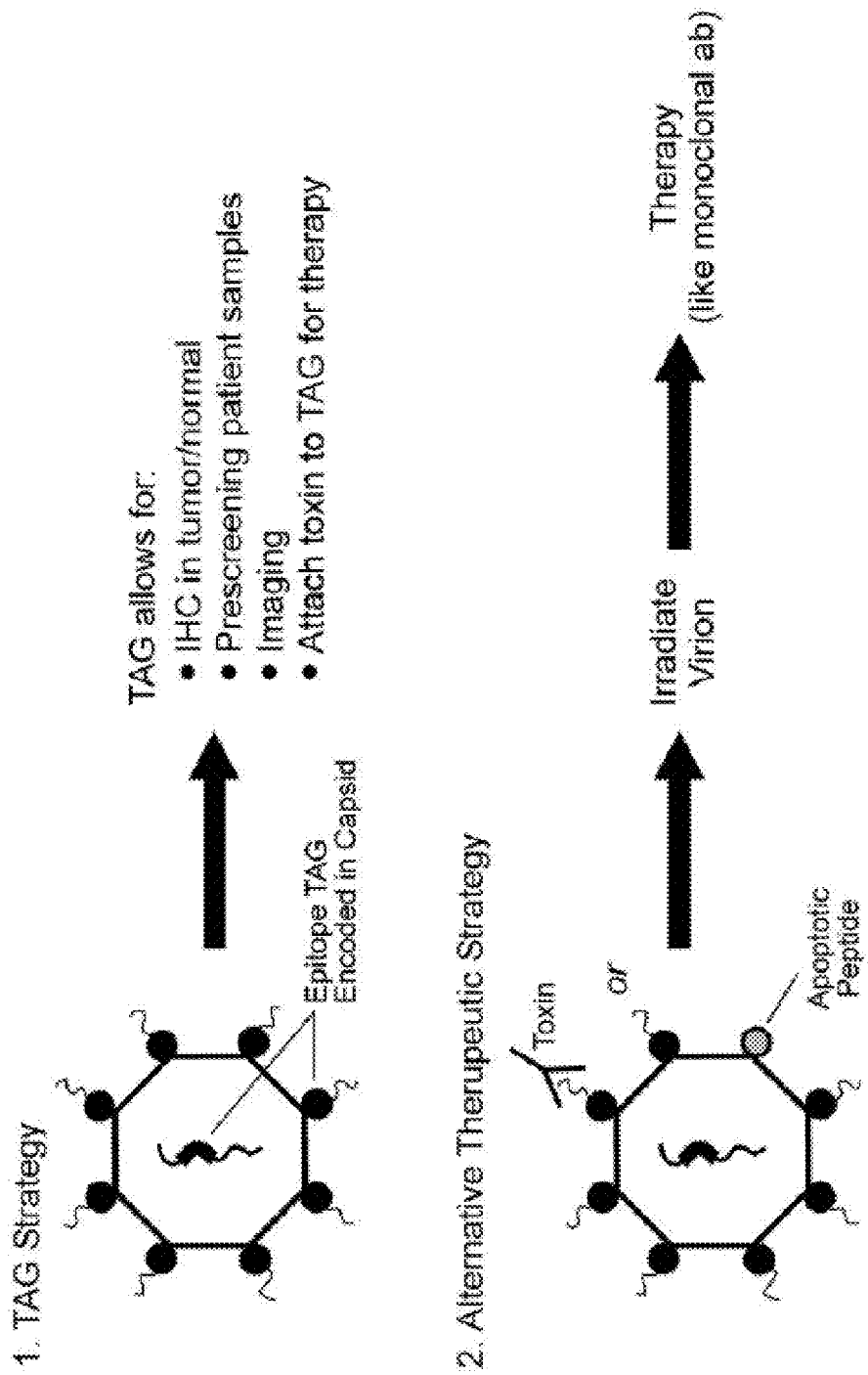

In vitro screening is carried out by a high throughput automation system (TECAN) that is capable of liquid handling, concurrent incubation of 20 cell lines and measurement in 384-well plates (see FIG. 62 and FIG. 63). The cells are harvested 30 hr after infection when complete CPE is noticed and then cells are collected by centrifugation at 1500 rpm for 10 minutes at 4° C. The cell pellets are then resuspended in the cell culture supernatant and subjected to three cycles of freeze and thaw. The resulting suspension is clarified by centrifugation at 1500 rpm for 10 minutes at 4° C. Virus is purified by two rounds of CsCl gradients: a one-step gradient (density of CsCl 1.24 g/ml and 1.4 g/ml) followed by one continuous gradient centrifugation (density of CsCl 1.33 g/ml). The purified virus concentration is determined spectrophotometrically, assuming $1A_{260}=9.5\times10^{12}$ particles (Scraba, D. G. and Palmenberg, A. C., 1999). The process may be repeated multiple times until a sufficient amount of virus is recovered from $\alpha_v\beta_5$ cells.

Analysis of recovered RGD-SVV derivatives. A small pool of individual RGD-displaying SVV derivatives (about 10-50 different derivatives) are analyzed. The viral mixture is diluted and single viral particles are expanded for analysis. Each derivative is tested to determine whether they have gained the ability to infect $\alpha_v\beta_5$-expressing cells efficiently and specifically. The capsid region of each derivative with this property is then be sequenced to determine the site of RGD insertion. The recovered cRGD-displaying SVV derivatives should possess the following properties: (1) the original properties of the virus are still intact; and (2) the derivatives have gained the ability to infect cells that express high levels of integrins that bind to RGD. This approach aims to identify one or more sites that enable an expanded tropism with RGD insertion, such that random oligonucleotides can be inserted into these sites to generate SVV derivatives with altered tropism.

The sequenced cRGD-SVV derivatives are numbered and ranked by their binding abilities to integrin. To test the binding activity, recombinant $\beta_2$ integrin is immobilized on a 96-well microtiter plate in PBS, washed twice with PBS, blocked with 3% BSA in PBS, and then incubated with a unique RGD-displaying virus. The native virus without peptide insertions is used as a negative control. After 1-5 hr of incubation, the wells are washed at least three times with PBS. Then, the viruses that are bound to the plate will be detected by anti-SVV antibodies. RGD peptide or antibodies against integrin should be able to compete with the binding of the RGD-SVV derivatives to the integrin-bound plate.

The cRGD-SVV derivatives (20) that have the strongest binding to integrin are analyzed to determine the 'successful' location(s) of cRGD oligonucleotide insertion. The insertion sites provide insights into the tropism of SVV. Based on the analysis of the insertion sites and other known structures, an ideal location to place a random peptide library can be determined (this method is an alternative method for generating SVV derivatives, where oligonucleotides (known sequence or random sequence) are inserted into random locations in the capsid). SVV derivatives generated with random sequence oligonucleotides are constructed in essentially the same manner as described above for the RGD-SVV library, except for two additional and novel methodologies. To avoid unwanted stop codons and deleterious amino acid insertions (e.g. cysteines or prolines) within a desired coding region, TRIM (trinucleotide-mutagenesis) technology developed by Morphosys (Munich, Germany) can be used to generate random oligonucleotides for capsid insertion. TRIM utilizes trinucleotides which only code for amino acids at the desired position (Virnekas, B. et al., *Nucleic Acids Res*, 1994, 22(25): 5600-5607). The random-peptide displaying SVV with a diversity of $10^8$ is believed to be sufficient and expected to yield peptides that specifically direct the virus to targeted tumor tissues. Random-peptide displaying SVV is tested in vitro as described above, or in vivo using tumor-bearing mice.

Example 17

Serum Studies

Pigs are a permissive host for the USDA virus isolates identified above. The isolate MN 88-36695 was inoculated into a gnotobiotic pig and antisera generated (GP102). The antisera binds to all of the other USDA isolates listed above and to SVV. The antisera does not react with 24 common porcine virus pathogens indicating its specificity. Porcine sera was also tested for neutralizing antibodies to 1278 (Plum Island virus). Sera were collected in the US and 8/29 sera were positive with titers ranging from 1:57 to 1:36,500.

To test whether the pig is the natural source for SVV, serum samples from various animals were obtained and tested for their ability to act as neutralizing antibodies against SVV infection of permissive cells. The Serum Neutralization Assay is conducted as follows: (1) Dilute various serums 1:2 and 1:4 and serially in increasing dilutions if necessary; (2) Mix with 100 $TCID_{50}$ of virus (SVV; but any virus can be tested to determine whether a serum can neutralize its infection); (3) Incubate at 37° C. for 1 hour; (4) Add the mixture to $1 \times 10^4$ PER.C6® cells (or other permissive cell type); (5) Incubate at 37° C. for 3 days; and (6) Measure CPE using a tetrazolium based dye cytotoxicity (such as MTS) assay. The neutralization titer is defined as the highest dilution of sera that neutralizes SVV (or other virus in question) at 100%.

The serum neutralization results showed that there is a minimal or no presence of neutralizing antibodies in human and primate populations. In one experiment, 0/22 human sera contained neutralizing antibodies to SVV. In another experiment, only 1/28 human sera contained neutralizing antibodies. In a third experiment, 0/50 human sera from Amish farmers were neutralizing. In another experiment, 0/52 primate sera from four species were neutralizing.

The serum neutralization results showed that there is a prevalence of SVV neutralizing antibodies in farm animal populations. In one experiment, 27/71 porcine sera from farms were neutralizing. In another experiment, 4/30 porcine sera from a disease-free farm were neutralizing. In another experiment, 10/50 bovine sera were neutralizing. In yet another experiment, 5/35 wild mouse sera were neutralizing.

Antisera to MN 88-36694 were tested in serum neutralization assays on SVV (see Example 2). Anti-MN 88-36695 gnotobiotic pig serum was able to neutralize infection by SVV (neutralization titer on infection was 1:100 for SVV). As stated above, the antisera binds to all of the other USDA isolates and to SVV, indicating that the herein disclosed USDA isolates are SVV-like picornaviruses due to their serological cross-reactivity with the gnotobiotic pig serum as measured in an indirect immunofluorescence assay.

These data indicate that SVV is genetically and serologically linked to the porcine USDA virus isolates.

Example 18

SVV and SVV-Like Picornaviruses

The grouping of the following isolates: MN 88-36695, NC 88-23626, IA 89-47552, NJ 90-10324, IL 92-48963, CA 131395; LA 1278; IL 66289; IL 94-9356; MN/GA 99-29256; MN 99197; and SC 363649, was deduced in part from indirect immunofluorescence experiments. Antisera GP102 was raised against isolate MN 88-36695 by inoculation of the virus into a gnotobiotic pig. The antisera binds to all twelve isolates demonstrating that they are serologically related to one another.

The GP102 antisera was tested in a neutralization assay with SVV. In this assay, serial dilutions of antisera are mixed with a known quantity of SVV (100 $TCID_{50}$). The mixtures are placed at 37° C. for 1 hour. An aliquot of the mixture is then added to $1 \times 10^4$ PER.C6® cells, or another cell line that is also permissive for SVV, and the mixtures are placed at 37° C. for 3 days. The wells are then checked for a cytopathic effect of the virus (CPE). If the serum contains neutralizing antibodies, it would neutralize the virus and inhibit the infection of the PER.C6® cells by the virus. CPE is measured quantitatively by using a tetrazolium based dye reagent that changes absorbance based on the number of live cells present. The results are expressed as the percent of viable cells of an uninfected control vs. the log dilution of serum, and are shown in FIG. 93. This data indicates that SVV is serologically linked to the porcine USDA virus isolates.

Additionally, the viral lysate of MN 88-36695 was tested in cytotoxicity assays with four different cell lines and the results are shown in Table 4. The permissivity profile is identical to that of SVV in that NCI-H446 and HEK293 are permissive for SVV, and NCI-H460 and S8 are not. Additionally, MN 88-36695, like SVV, was cytotoxic to PER.C6® cells. Further, polyclonal antisera to SVV raised in mice was used in a neutralization assay along with MN 88-36695 virus. The results are shown in FIG. 94. The anti-SVV antisera neutralized MN 88-36695, further linking SVV to the USDA viruses serologically.

TABLE 11

MN 88-36695 Cytotoxicity Results

| Cell Line | TCID50 (pfu/ml) | Result |
|---|---|---|
| NCI-H446 | $1.6 \times 10{-6}$ | Permissive |
| HEK293 | $1.3 \times 10{-2}$ | Permissive |
| NCI-H460 | 0 | Nonpermissive |
| S8 | 0 | Nonpermissive |

Partial genomic sequence analysis of several of the USDA isolates revealed that they are all very closely related to SVV (see FIGS. 87-89 for sequence alignments). Table 12 shows the percent sequence identity between SVV and six of the isolates. It was found that about 95-98% identity exists at the nucleotide (nt) level over 460 nt of the 3' end of the genome encoding $3D^{pol}$ and the 3'UTR (FIG. 89). Each of the USDA viruses is unique and is about 95-98% identical to SVV at the nucleotide level.

TABLE 12

Percent Sequence Identity Between SVV and Six USDA Isolates

| 1 | 2 | 3 | 4 | 5 | 6 | 7 | | Virus Name |
|---|---|---|---|---|---|---|---|---|
| 96.5 | 99.1 | 97.2 | 97.0 | 97.4 | 97.0 | | 1 | NJ 90-10324 |
| | 97.0 | 95.7 | 94.8 | 95.0 | 98.3* | | 2 | CA 13195 |
| | | 97.6 | 97.2 | 97.6 | 97.2 | | 3 | IA 89-47752 |
| | | | 95.4 | 96.1 | 96.3 | | 4 | IL 92-48963 |
| | | | | 98.9 | 95.2 | | 5 | MN 88-36695 |
| | | | | | 95.4 | | 6 | NC 88-23626 |
| | | | | | | | 7 | SVV-001 (SVV) |

Further sequencing of parts of the P1 (FIG. 87) and 2C (FIG. 88) genes of two of the isolates has confirmed this close relationship with SVV. The USDA isolates are more highly related to SVV than any other known viruses, including members of the genus Cardiovirus. Sequences from several regions of seven of the USDA viruses were compared with SVV and neighbor-joining trees were constructed (FIGS. 95A and 95B). These trees further confirm the high degree of relation between the viruses, and identifying CA 131395 as SVV's current closest relative.

What is claimed:

1. An isolated nucleic acid comprising a nucleic acid sequence having at least 95% sequence identity to: (i) SEQ ID NO:168 or (ii) a contiguous portion of SEQ ID NO:168 that is at least 200 nucleotides in length.

2. An isolated Seneca Valley virus or derivative or relative thereof, having a genome comprising a sequence that is at least 95% identical to SEQ ID NO:168.

3. A method of killing an abnormally proliferative cell comprising contacting the cell with the virus of claim 2.

* * * * *

SEQUENCE LISTING

<160> NUMBER OF SEQ ID NOS: 227

<210> SEQ ID NO 1
<211> LENGTH: 5752
<212> TYPE: DNA
<213> ORGANISM: Seneca Valley Virus
<220> FEATURE:
<221> NAME/KEY: modified_base
<222> LOCATION: (1)..(2)
<223> OTHER INFORMATION: a, t, c or g

<400> SEQUENCE: 1

```
nntctagccc accatggcaa caagaagagc ttacaggagc tgaatgaaga acagtgggtg      60
gaaatgtctg acgattaccg gaccgggaaa aacatgcctt ttcagtctct tggcacatac     120
tatcggcccc ctaactggac ttggggtccc aatttcatca acccctatca agtaacggtt     180
ttcccacacc aaattctgaa cgcgagaacc tctacctcgg tagacataaa cgtcccatac     240
atcggggaga cccccacgca atcctcagag acacagaact cctggaccct cctcgttatg     300
gtgctcgttc ccctagacta taaggaagga gccacaactg acccagaaat tacattttct     360
gtaaggccta caagtcccta cttcaatggg cttcgcaacc gctacacggc cgggacggac     420
gaagaacagg ggcccattcc tacggcaccc agagaaaatt cgcttatgtt tctctcaacc     480
ctccctgacg acactgtccc tgcttacggg aatgtgcgta cccctcctgt caattacctc     540
cctggtgaaa taaccgacct tttgcaactg gcccgcatac ccactctcat ggcatttgag     600
cgggtgcctg aacccgtgcc tgcctcagac acatatgtgc cctacgttgc cgttcccacc     660
cagttcgatg acaggcctct catctccttc ccgatcaccc tttcagatcc cgtctatcag     720
aacaccctgg ttggcgccat cagttcaaat ttcgccaatt accgtgggtg tatccaaatc     780
actctgacat tttgtggacc catgatggcg agagggaaat tcctgctctc gtattctccc     840
ccaaatggaa cgcaaccaca gactctttcc gaagctatgc agtgcacata ctctatttgg     900
gacataggct tgaactctag ttggaccttc gtcgtcccct acatctcgcc cagtgactac     960
cgtgaaactc gagccattac caactcggtt tactccgctg atggttggtt tagcctgcac    1020
aagttgacca aaattactct accacctgac tgtccgcaaa gtccctgcat tctcttttc    1080 gcttctgctg gtgaggatta cactctccgt ctccccgttg attgtaatcc ttcctatgtg    1140
ttccactcca ccgacaacgc cgagaccggg gttattgagg cgggtaacac tgacaccgat    1200
ttctctggtg aactggcggc tcctggccct aaccacacta atgtcaagtt cctgtttgat    1260
cgatctcgat tattgaatgt aatcaaggta ctggagaagg acgccgtttt ccccccgcct    1320
ttccctacac aagaaggtgc gcagcaggat gatggttact tttgtcttct gacccccgc    1380 ccaacagtcg cttcccgacc cgccactcgt ttcggcctgt acgccaatcc gtccggcagt    1440
```

```
ggtgttcttg ctaacacttc actggacttc aattttata gcttggcctg tttcacttac      1500
tttagatcgg accttgaggt tacggtggtc tcactagagc cggatctgga atttgctgta      1560
gggtggtttc cttctggcag tgaataccag gcttccagct ttgtctacga ccagctgcat      1620
gtgcccttcc actttactgg gcgcactccc cgcgctttcg ctagcaaggg tgggaaggta      1680
tctttcgtgc tcccttggaa ctctgtctcg tctgtgctcc ccgtgcgctg gggggggggct     1740
tccaagctct cttctgctac gcggggtcta ccggcgcatg ctgattgggg gactatttac      1800
gcctttgtcc cccgtcctaa tgagaagaaa agcaccgctg taaaacacgt ggccgtgtac      1860
attcggtaca agaacgcacg tgcctggtgc cccagcatgc ttccctttcg cagctacaag      1920
cagaagatgc tgatgcaatc tggcgatatc gagaccaatc ctggtcctgc ttctgacaac      1980
ccaattttgg agtttcttga agcagaaaat gatctagtca ctctggcctc tctctggaag      2040
atggtgcact ctgttcaaca gacctggaga agtatgtga agaacgatga ttttggccc       2100
aatttactca gcgagctagt gggggaaggc tctgtcgcct tggccgccac gctatccaac      2160
caagcttcag taaaggctct tttgggcctg cactttctct ctcgggggct caattacact      2220
gacttttact ctttactgat agagaaatgc tctagtttct ttaccgtaga accacctcct      2280
ccaccagctg aaaacctgat gaccaagccc tcagtgaagt cgaaattccg aaaactgttt      2340
aagatgcaag gacccatgga caaagtcaaa gactggaacc aaatagctgc cggcttgaag      2400
aattttcaat tgttcgtga cctagtcaaa gaggtggtcg attggctgca ggcctggatc       2460
aacaaagaga aagccagccc tgtcctccag taccagttgg agatgaagaa gctcgggcct      2520
gtggccttgg ctcatgacgc tttcatggct ggttccgggc ccctcttag cgacgaccag       2580
attgaatacc tccagaacct caaatctctt gccctaacac tggggaagac taatttggcc      2640
caaagtctca ccactatgat caatgccaaa caaagttcag cccaacgagt tgaacccgtt      2700
gtggtggtcc ttagaggcaa gccgggatgc ggcaagggct tggcctctac gttgattgcc      2760
caggctgtgt ccaagcgcct ctatggctcc caaagtgtat attctcttcc cccagatcca      2820
gatttcttcg atggatacaa aggacagttc gtgaccttga tggatgattt gggacaaaac      2880
ccggatggac aagatttccc cacctttgt cagatggtgt cgaccgccca atttctcccc       2940
aacatggcgg accttgcaga gaagggcgt ccctttacct ccaatctcat cattgcaact       3000
acaaatctcc cccacttcag tcctgtcacc attgctgatc cttctgcagt ctctcgccgt      3060
atcaactacg atctgactct agaagtatct gaggcctaca agaaacacac acggctgaat      3120
tttgacttgg ctttcaggcg cacagacgcc cccccatt atccttttgc tgcccatgtg        3180
ccctttgtgg acgtagctgt gcgcttcaaa aatggtcacc agaattttaa tctcctagag      3240
ttggtcgatt ccatttgtac agacattcga gccaagcaac aaggtgcccg aaacatgcag      3300
actctggttc tacagagccc caacgagaat gatgacaccc ccgtcgacga ggcgttgggt      3360
agagttctct ccccgctgc ggtcgatgag gcgcttgtcg acctcactcc agaggccgac       3420
ccggttggcc gtttggctat tcttgccaag ctaggtcttg ccctagctgc ggtcaccct       3480
ggtctgataa tcttggcagt gggactctac aggtacttct ctggctctga tgcagaccaa      3540
gaagaaacag aaagtgaggg atctgtcaag gcacccagga gcgaaaatgc ttatgacggc      3600
ccgaagaaaa actctaagcc ccctggagca ctctctctca tggaaatgca acagcccaac      3660
gtggacatgg gctttgaggc tgcggtcgct aagaaagtgg tcgtccccat taccttcatg      3720
gttcccaaca gaccttctgg gcttacacag tccgctcttc tggtgaccgg ccggaccttc      3780
ctaatcaatg aacatacatg gtccaatccc tcctggacca gcttcacaat ccgcggtgag      3840
```

```
gtacacactc gtgatgagcc cttccaaacg gttcatttca ctcaccacgg tattcccaca    3900
gatctgatga tggtacgtct cggaccgggc aattctttcc ctaacaatct agacaagttt    3960
ggacttgacc agatgccggc acgcaactcc cgtgtggttg cgtttcgtc cagttacgga    4020 aacttcttct tctctggaaa tttcctcgga tttgttgatt ccgtcacctc tgaacaagga    4080
acttacgcaa gactctttag gtacaggggtg acgacctaca aaggatggtg cggctcggcc    4140
ctggtctgtg aggccggtgg cgtccgacgc atcattggcc tgcattctgc tggcgccgcc    4200
ggtatcggcg ccgggaccta tatctcaaaa ttaggactaa tcaaagccct gaaacacctc    4260
ggtgaacctt tggccacaat gcaaggactg atgactgaat agagcctgg aatcaccgta    4320 catgtacccc ggaaatccaa attgagaaag acgaccgcac acgcggtgta caaaccggag    4380
tttgagcctg ctgtgttgtc aaaatttgat cccagactga acaaggatgt tgacttggat    4440
gaagtaattt ggtctaaaca cactgccaat gtcccttacc aacctccttt gttctacaca    4500
tacatgtcag agtacgctca tcgagtcttc tccttcttgg ggaaagacaa tgacattctg    4560
accgtcaaag aagcaattct gggcatcccc ggactagacc ccatggatcc ccacacagct    4620
ccgggtctgc cttacgccat caacggcctt cgacgtactg atctcgtcga ttttgtgaac    4680
ggtacagtag atgcggcgct ggctgtacaa atccagaaat tcttagacgg tgactactct    4740
gaccatgtct tccaaacttt tctgaaagat gagatcagac cctcagagaa agtccgagcg    4800
ggaaaaaccc gcattgttga tgtgccctcc ctggcgcatt gcattgtggg cagaatgttg    4860
cttgggcgct ttgctgccaa gtttcaatcc catcctggct ttctcctcgg ctctgctatc    4920
gggtctgacc ctgatgtttt ctggaccgtc ataggggctc aactcgaggg gagaaagaac    4980
acgtatgacg tggactacag tgcctttgac tcttcacacg gcactggctc cttcgaggct    5040
ctcatctctc acttttcac cgtggacaat ggttttagcc ctgcgctggg accgtatctc    5100
agatccctgg ctgtctcggt gcacgcttac ggcgagcgtc gcatcaagat taccggtggc    5160
ctcccctccg gttgtgccgc gaccagcctg ctgaacacag tgctcaacaa tgtgatcatc    5220
aggactgctc tggcattgac ttacaaggaa tttgagtatg acacggttga tatcatcgcc    5280
tacggtgacg accttctggt tggcacggat tacgatctgg acttcaatga ggtggcacga    5340
cgcgctgcca gtggggta taagatgact cctgccaaca agggttctgt cttccctccg    5400
acttcctctc tttccgatgc tgttttttcta aagcgcaaat tcgtccaaaa caacgacggc    5460
ttatacaaac cagttatgga tttaaagaat ttggaagcca tgctctccta cttcaaacca    5520
ggaacactac tcgagaagct gcaatctgtt tctatgttgg ctcaacattc tggaaaagaa    5580
gaatatgata gattgatgca ccccttcgct gactacggtg ccgtaccgag tcacgagtac    5640
ctgcaggcaa gatggagggc cttgttcgac tgacccagat agcccaaggc gcttcggtgc    5700
tgccggcgat tctgggagaa ctcagtcgga acagaaaaaa aaaaaaaaaa aa    5752
```

<210> SEQ ID NO 2
<211> LENGTH: 1890
<212> TYPE: PRT
<213> ORGANISM: Seneca Valley Virus
<220> FEATURE:
<221> NAME/KEY: MOD_RES
<222> LOCATION: (1)
<223> OTHER INFORMATION: variable amino acid

<400> SEQUENCE: 2

Xaa Leu Ala His His Gly Asn Lys Lys Ser Leu Gln Glu Leu Asn Glu
1               5                   10                  15

-continued

```
Glu Gln Trp Val Glu Met Ser Asp Asp Tyr Arg Thr Gly Lys Asn Met
             20                  25                  30

Pro Phe Gln Ser Leu Gly Thr Tyr Arg Pro Pro Asn Trp Thr Trp
         35                  40                  45

Gly Pro Asn Phe Ile Asn Pro Tyr Gln Val Thr Val Phe Pro His Gln
 50                  55                  60

Ile Leu Asn Ala Arg Thr Ser Thr Ser Val Asp Ile Asn Val Pro Tyr
 65                  70                  75                  80

Ile Gly Glu Thr Pro Thr Gln Ser Ser Glu Thr Gln Asn Ser Trp Thr
                 85                  90                  95

Leu Leu Val Met Val Leu Val Pro Leu Asp Tyr Lys Glu Gly Ala Thr
                100                 105                 110

Thr Asp Pro Glu Ile Thr Phe Ser Val Arg Pro Thr Ser Pro Tyr Phe
            115                 120                 125

Asn Gly Leu Arg Asn Arg Tyr Thr Ala Gly Thr Asp Glu Glu Gln Gly
        130                 135                 140

Pro Ile Pro Thr Ala Pro Arg Glu Asn Ser Leu Met Phe Leu Ser Thr
145                 150                 155                 160

Leu Pro Asp Asp Thr Val Pro Ala Tyr Gly Asn Val Arg Thr Pro Pro
                165                 170                 175

Val Asn Tyr Leu Pro Gly Glu Ile Thr Asp Leu Leu Gln Leu Ala Arg
            180                 185                 190

Ile Pro Thr Leu Met Ala Phe Glu Arg Val Pro Glu Pro Val Pro Ala
        195                 200                 205

Ser Asp Thr Tyr Val Pro Tyr Val Ala Val Pro Thr Gln Phe Asp Asp
210                 215                 220

Arg Pro Leu Ile Ser Phe Pro Ile Thr Leu Ser Asp Pro Val Tyr Gln
225                 230                 235                 240

Asn Thr Leu Val Gly Ala Ile Ser Ser Asn Phe Ala Asn Tyr Arg Gly
                245                 250                 255

Cys Ile Gln Ile Thr Leu Thr Phe Cys Gly Pro Met Met Ala Arg Gly
            260                 265                 270

Lys Phe Leu Leu Ser Tyr Ser Pro Pro Asn Gly Thr Gln Pro Gln Thr
        275                 280                 285

Leu Ser Glu Ala Met Gln Cys Thr Tyr Ser Ile Trp Asp Ile Gly Leu
290                 295                 300

Asn Ser Ser Trp Thr Phe Val Val Pro Tyr Ile Ser Pro Ser Asp Tyr
305                 310                 315                 320

Arg Glu Thr Arg Ala Ile Thr Asn Ser Val Tyr Ser Ala Asp Gly Trp
                325                 330                 335

Phe Ser Leu His Lys Leu Thr Lys Ile Thr Leu Pro Pro Asp Cys Pro
            340                 345                 350

Gln Ser Pro Cys Ile Leu Phe Phe Ala Ser Ala Gly Glu Asp Tyr Thr
        355                 360                 365

Leu Arg Leu Pro Val Asp Cys Asn Pro Ser Tyr Val Phe His Ser Thr
370                 375                 380

Asp Asn Ala Glu Thr Gly Val Ile Glu Ala Gly Asn Thr Asp Thr Asp
385                 390                 395                 400

Phe Ser Gly Glu Leu Ala Ala Pro Gly Pro Asn His Thr Asn Val Lys
                405                 410                 415

Phe Leu Phe Asp Arg Ser Arg Leu Leu Asn Val Ile Lys Val Leu Glu
            420                 425                 430

Lys Asp Ala Val Phe Pro Arg Pro Phe Pro Thr Gln Glu Gly Ala Gln
        435                 440                 445
```

```
Gln Asp Asp Gly Tyr Phe Cys Leu Leu Thr Pro Arg Pro Thr Val Ala
    450                 455                 460

Ser Arg Pro Ala Thr Arg Phe Gly Leu Tyr Ala Asn Pro Ser Gly Ser
465                 470                 475                 480

Gly Val Leu Ala Asn Thr Ser Leu Asp Phe Asn Phe Tyr Ser Leu Ala
                485                 490                 495

Cys Phe Thr Tyr Phe Arg Ser Asp Leu Glu Val Thr Val Val Ser Leu
            500                 505                 510

Glu Pro Asp Leu Glu Phe Ala Val Gly Trp Phe Pro Ser Gly Ser Glu
        515                 520                 525

Tyr Gln Ala Ser Ser Phe Val Tyr Asp Gln Leu His Val Pro Phe His
    530                 535                 540

Phe Thr Gly Arg Thr Pro Arg Ala Phe Ala Ser Lys Gly Gly Lys Val
545                 550                 555                 560

Ser Phe Val Leu Pro Trp Asn Ser Val Ser Ser Val Leu Pro Val Arg
                565                 570                 575

Trp Gly Gly Ala Ser Lys Leu Ser Ser Ala Thr Arg Gly Leu Pro Ala
            580                 585                 590

His Ala Asp Trp Gly Thr Ile Tyr Ala Phe Val Pro Arg Pro Asn Glu
        595                 600                 605

Lys Lys Ser Thr Ala Val Lys His Val Ala Val Tyr Ile Arg Tyr Lys
    610                 615                 620

Asn Ala Arg Ala Trp Cys Pro Ser Met Leu Pro Phe Arg Ser Tyr Lys
625                 630                 635                 640

Gln Lys Met Leu Met Gln Ser Gly Asp Ile Glu Thr Asn Pro Gly Pro
                645                 650                 655

Ala Ser Asp Asn Pro Ile Leu Glu Phe Leu Glu Ala Glu Asn Asp Leu
            660                 665                 670

Val Thr Leu Ala Ser Leu Trp Lys Met Val His Ser Val Gln Gln Thr
        675                 680                 685

Trp Arg Lys Tyr Val Lys Asn Asp Asp Phe Trp Pro Asn Leu Leu Ser
    690                 695                 700

Glu Leu Val Gly Glu Gly Ser Val Ala Leu Ala Ala Thr Leu Ser Asn
705                 710                 715                 720

Gln Ala Ser Val Lys Ala Leu Leu Gly Leu His Phe Leu Ser Arg Gly
                725                 730                 735

Leu Asn Tyr Thr Asp Phe Tyr Ser Leu Leu Ile Glu Lys Cys Ser Ser
            740                 745                 750

Phe Phe Thr Val Glu Pro Pro Pro Ala Glu Asn Leu Met Thr
        755                 760                 765

Lys Pro Ser Val Lys Ser Lys Phe Arg Lys Leu Phe Lys Met Gln Gly
    770                 775                 780

Pro Met Asp Lys Val Lys Asp Trp Asn Gln Ile Ala Ala Gly Leu Lys
785                 790                 795                 800

Asn Phe Gln Phe Val Arg Asp Leu Val Lys Glu Val Val Asp Trp Leu
                805                 810                 815

Gln Ala Trp Ile Asn Lys Glu Lys Ala Ser Pro Val Leu Gln Tyr Gln
            820                 825                 830

Leu Glu Met Lys Lys Leu Gly Pro Val Ala Leu Ala His Asp Ala Phe
        835                 840                 845

Met Ala Gly Ser Gly Pro Pro Leu Ser Asp Asp Gln Ile Glu Tyr Leu
850                 855                 860

Gln Asn Leu Lys Ser Leu Ala Leu Thr Leu Gly Lys Thr Asn Leu Ala
```

-continued

```
            865                 870                 875                 880
Gln Ser Leu Thr Thr Met Ile Asn Ala Lys Gln Ser Ser Ala Gln Arg
                    885                 890                 895

Val Glu Pro Val Val Val Leu Arg Gly Lys Pro Gly Cys Gly Lys
            900                 905                 910

Gly Leu Ala Ser Thr Leu Ile Ala Gln Ala Val Ser Lys Arg Leu Tyr
            915                 920                 925

Gly Ser Gln Ser Val Tyr Ser Leu Pro Pro Asp Pro Asp Phe Phe Asp
            930                 935                 940

Gly Tyr Lys Gly Gln Phe Val Thr Leu Met Asp Asp Leu Gly Gln Asn
945                 950                 955                 960

Pro Asp Gly Gln Asp Phe Ser Thr Phe Cys Gln Met Val Ser Thr Ala
                    965                 970                 975

Gln Phe Leu Pro Asn Met Ala Asp Leu Ala Glu Lys Gly Arg Pro Phe
            980                 985                 990

Thr Ser Asn Leu Ile Ile Ala Thr Thr Asn Leu Pro His Phe Ser Pro
            995                 1000                1005

Val Thr Ile Ala Asp Pro Ser Ala Val Ser Arg Arg Ile Asn Tyr Asp
            1010                1015                1020

Leu Thr Leu Glu Val Ser Glu Ala Tyr Lys Lys His Thr Arg Leu Asn
1025                1030                1035                1040

Phe Asp Leu Ala Phe Arg Arg Thr Asp Ala Pro Pro Ile Tyr Pro Phe
                    1045                1050                1055

Ala Ala His Val Pro Phe Val Asp Val Ala Val Arg Phe Lys Asn Gly
            1060                1065                1070

His Gln Asn Phe Asn Leu Leu Glu Leu Val Asp Ser Ile Cys Thr Asp
            1075                1080                1085

Ile Arg Ala Lys Gln Gln Gly Ala Arg Asn Met Gln Thr Leu Val Leu
            1090                1095                1100

Gln Ser Pro Asn Glu Asn Asp Asp Thr Pro Val Asp Glu Ala Leu Gly
1105                1110                1115                1120

Arg Val Leu Ser Pro Ala Ala Val Asp Glu Ala Leu Val Asp Leu Thr
                    1125                1130                1135

Pro Glu Ala Asp Pro Val Gly Arg Leu Ala Ile Leu Ala Lys Leu Gly
            1140                1145                1150

Leu Ala Leu Ala Ala Val Thr Pro Gly Leu Ile Ile Leu Ala Val Gly
            1155                1160                1165

Leu Tyr Arg Tyr Phe Ser Gly Ser Asp Ala Asp Gln Glu Glu Thr Glu
            1170                1175                1180

Ser Glu Gly Ser Val Lys Ala Pro Arg Ser Glu Asn Ala Tyr Asp Gly
1185                1190                1195                1200

Pro Lys Lys Asn Ser Lys Pro Pro Gly Ala Leu Ser Leu Met Glu Met
                    1205                1210                1215

Gln Gln Pro Asn Val Asp Met Gly Phe Glu Ala Ala Val Ala Lys Lys
            1220                1225                1230

Val Val Val Pro Ile Thr Phe Met Val Pro Asn Arg Pro Ser Gly Leu
            1235                1240                1245

Thr Gln Ser Ala Leu Leu Val Thr Gly Arg Thr Phe Leu Ile Asn Glu
            1250                1255                1260

His Thr Trp Ser Asn Pro Ser Trp Thr Ser Phe Thr Ile Arg Gly Glu
1265                1270                1275                1280

Val His Thr Arg Asp Glu Pro Phe Gln Thr Val His Phe Thr His His
                    1285                1290                1295
```

-continued

```
Gly Ile Pro Thr Asp Leu Met Met Val Arg Leu Gly Pro Gly Asn Ser
            1300                1305                1310

Phe Pro Asn Asn Leu Asp Lys Phe Gly Leu Asp Gln Met Pro Ala Arg
            1315                1320                1325

Asn Ser Arg Val Val Gly Val Ser Ser Tyr Gly Asn Phe Phe Phe
            1330                1335                1340

Ser Gly Asn Phe Leu Gly Phe Val Asp Ser Val Thr Ser Glu Gln Gly
1345                1350                1355                1360

Thr Tyr Ala Arg Leu Phe Arg Tyr Arg Val Thr Thr Tyr Lys Gly Trp
            1365                1370                1375

Cys Gly Ser Ala Leu Val Cys Glu Ala Gly Gly Val Arg Ile Ile
            1380                1385                1390

Gly Leu His Ser Ala Gly Ala Ala Gly Ile Gly Ala Gly Thr Tyr Ile
            1395                1400                1405

Ser Lys Leu Gly Leu Ile Lys Ala Leu Lys His Leu Gly Glu Pro Leu
            1410                1415                1420

Ala Thr Met Gln Gly Leu Met Thr Glu Leu Glu Pro Gly Ile Thr Val
1425                1430                1435                1440

His Val Pro Arg Lys Ser Lys Leu Arg Lys Thr Thr Ala His Ala Val
            1445                1450                1455

Tyr Lys Pro Glu Phe Glu Pro Ala Val Leu Ser Lys Phe Asp Pro Arg
            1460                1465                1470

Leu Asn Lys Asp Val Asp Leu Asp Glu Val Ile Trp Ser Lys His Thr
            1475                1480                1485

Ala Asn Val Pro Tyr Gln Pro Pro Leu Phe Tyr Thr Tyr Met Ser Glu
            1490                1495                1500

Tyr Ala His Arg Val Phe Ser Phe Leu Gly Lys Asp Asn Asp Ile Leu
1505                1510                1515                1520

Thr Val Lys Glu Ala Ile Leu Gly Ile Pro Gly Leu Asp Pro Met Asp
            1525                1530                1535

Pro His Thr Ala Pro Gly Leu Pro Tyr Ala Ile Asn Gly Leu Arg Arg
            1540                1545                1550

Thr Asp Leu Val Asp Phe Val Asn Gly Thr Val Asp Ala Ala Leu Ala
            1555                1560                1565

Val Gln Ile Gln Lys Phe Leu Asp Gly Asp Tyr Ser Asp His Val Phe
            1570                1575                1580

Gln Thr Phe Leu Lys Asp Glu Ile Arg Pro Ser Glu Lys Val Arg Ala
1585                1590                1595                1600

Gly Lys Thr Arg Ile Val Asp Val Pro Ser Leu Ala His Cys Ile Val
            1605                1610                1615

Gly Arg Met Leu Leu Gly Arg Phe Ala Ala Lys Phe Gln Ser His Pro
            1620                1625                1630

Gly Phe Leu Leu Gly Ser Ala Ile Gly Ser Asp Pro Asp Val Phe Trp
            1635                1640                1645

Thr Val Ile Gly Ala Gln Leu Glu Gly Arg Lys Asn Thr Tyr Asp Val
            1650                1655                1660

Asp Tyr Ser Ala Phe Asp Ser Ser His Gly Thr Gly Ser Phe Glu Ala
1665                1670                1675                1680

Leu Ile Ser His Phe Phe Thr Val Asp Asn Gly Phe Ser Pro Ala Leu
            1685                1690                1695

Gly Pro Tyr Leu Arg Ser Leu Ala Val Ser Val His Ala Tyr Gly Glu
            1700                1705                1710

Arg Arg Ile Lys Ile Thr Gly Gly Leu Pro Ser Gly Cys Ala Ala Thr
            1715                1720                1725
```

```
Ser Leu Leu Asn Thr Val Leu Asn Asn Val Ile Ile Arg Thr Ala Leu
        1730                1735                1740

Ala Leu Thr Tyr Lys Glu Phe Glu Tyr Asp Thr Val Asp Ile Ile Ala
1745                1750                1755                1760

Tyr Gly Asp Asp Leu Leu Val Gly Thr Asp Tyr Asp Leu Asp Phe Asn
                1765                1770                1775

Glu Val Ala Arg Arg Ala Ala Lys Leu Gly Tyr Lys Met Thr Pro Ala
            1780                1785                1790

Asn Lys Gly Ser Val Phe Pro Pro Thr Ser Ser Leu Ser Asp Ala Val
        1795                1800                1805

Phe Leu Lys Arg Lys Phe Val Gln Asn Asn Asp Gly Leu Tyr Lys Pro
    1810                1815                1820

Val Met Asp Leu Lys Asn Leu Glu Ala Met Leu Ser Tyr Phe Lys Pro
1825                1830                1835                1840

Gly Thr Leu Leu Glu Lys Leu Gln Ser Val Ser Met Leu Ala Gln His
                1845                1850                1855

Ser Gly Lys Glu Glu Tyr Asp Arg Leu Met His Pro Phe Ala Asp Tyr
            1860                1865                1870

Gly Ala Val Pro Ser His Glu Tyr Leu Gln Ala Arg Trp Arg Ala Leu
        1875                1880                1885

Phe Asp
    1890

<210> SEQ ID NO 3
<211> LENGTH: 426
<212> TYPE: DNA
<213> ORGANISM: Seneca Valley Virus

<400> SEQUENCE: 3
ctagcccacc atggcaacaa gaagagctta caggagctga atgaagaaca gtgggtggaa      60
atgtctgacg attaccggac cgggaaaaac atgccttttc agtctcttgg cacatactat     120
cggcccccta actggacttg gggtcccaat ttcatcaacc cctatcaagt aacggttttc     180
ccacaccaaa ttctgaacgc gagaacctct acctcgtgta cataaaacgt ccatacatc      240 ggggagaccc ccacgcaatc ctcagagaca cagaactcct ggaccctcct cgttatggtg     300
ctcgttcccc tagactataa ggaaggagcc acaactgacc cagaaattac attttctgta     360
aggcctacaa gtccctactt caatgggctt cgcaaccgct acacggccgg gacggacgaa     420
gaacag                                                                426

<210> SEQ ID NO 4
<211> LENGTH: 142
<212> TYPE: PRT
<213> ORGANISM: Seneca Valley Virus

<400> SEQUENCE: 4

Leu Ala His His Gly Asn Lys Lys Ser Leu Gln Glu Leu Asn Glu Glu
1               5                   10                  15

Gln Trp Val Glu Met Ser Asp Asp Tyr Arg Thr Gly Lys Asn Met Pro
            20                  25                  30

Phe Gln Ser Leu Gly Thr Tyr Tyr Arg Pro Pro Asn Trp Thr Trp Gly
        35                  40                  45

Pro Asn Phe Ile Asn Pro Tyr Gln Val Thr Val Phe Pro His Gln Ile
    50                  55                  60

Leu Asn Ala Arg Thr Ser Thr Ser Val Asp Ile Asn Val Pro Tyr Ile
65                  70                  75                  80
```

Gly Glu Thr Pro Thr Gln Ser Ser Gly Thr Gln Asn Ser Trp Thr Leu
                 85                  90                  95

Leu Val Met Val Leu Val Pro Leu Asp Tyr Lys Glu Gly Ala Thr Thr
            100                 105                 110

Asp Pro Glu Ile Thr Phe Ser Val Arg Pro Thr Ser Pro Tyr Phe Asn
            115                 120                 125

Gly Leu Arg Asn Arg Tyr Thr Ala Gly Thr Asp Glu Glu Gln
130                 135                 140

<210> SEQ ID NO 5
<211> LENGTH: 717
<212> TYPE: DNA
<213> ORGANISM: Seneca Valley Virus

<400> SEQUENCE: 5
gggcccattc ctacggcacc cagagaaaat tcgcttatgt ttctctcaac cctccctgac      60
gacactgtcc ctgcttacgg gaatgtgcgt accccctcctg tcaattacct ccctggtgaa    120
ataaccgacc ttttgcaact ggcccgcata cccactctca tggcatttga gcgggtgcct    180
gaacccgtgc ctgcctcaga cacatatgtg ccctacgttg ccgttcccac ccagttcgat    240
gacaggcctc tcatctcctt cccgatcacc ctttcagatc ccgtctatca gaacaccctg    300
gttggcgcca tcagttcaaa tttcgccaat taccgtgggt gtatccaaat cactctgaca    360
ttttgtggac ccatgatggc gagagggaaa ttcctgctct cgtattctcc cccaaatgga    420
acgcaaccac agactctttc gaagctatg cagtgcacat actctatttg gacataggc     480 ttgaactcta gttggacctt cgtcgtcccc tacatctcgc ccagtgacta ccgtgaaact    540
cgagccatta ccaactcggt ttactccgct gatggttggt ttagcctgca caagttgacc    600
aaaattactc taccacctga ctgtccgcaa agtccctgca ttctcttttt cgcttctgct    660
ggtgaggatt acactctccg tctccccgtt gattgtaatc cttcctatgt gttccac      717

<210> SEQ ID NO 6
<211> LENGTH: 239
<212> TYPE: PRT
<213> ORGANISM: Seneca Valley Virus

<400> SEQUENCE: 6

Gly Pro Ile Pro Thr Ala Pro Arg Glu Asn Ser Leu Met Phe Leu Ser
1               5                   10                  15

Thr Leu Pro Asp Asp Thr Val Pro Ala Tyr Gly Asn Val Arg Thr Pro
            20                  25                  30

Pro Val Asn Tyr Leu Pro Gly Glu Ile Thr Asp Leu Leu Gln Leu Ala
        35                  40                  45

Arg Ile Pro Thr Leu Met Ala Phe Glu Arg Val Pro Glu Pro Val Pro
    50                  55                  60

Ala Ser Asp Thr Tyr Val Pro Tyr Val Ala Val Pro Thr Gln Phe Asp
65                  70                  75                  80

Asp Arg Pro Leu Ile Ser Phe Pro Ile Thr Leu Ser Asp Pro Val Tyr
                85                  90                  95

Gln Asn Thr Leu Val Gly Ala Ile Ser Ser Asn Phe Ala Asn Tyr Arg
            100                 105                 110

Gly Cys Ile Gln Ile Thr Leu Thr Phe Cys Gly Pro Met Met Ala Arg
        115                 120                 125

Gly Lys Phe Leu Leu Ser Tyr Ser Pro Pro Asn Gly Thr Gln Pro Gln
    130                 135                 140

```
Thr Leu Ser Glu Ala Met Gln Cys Thr Tyr Ser Ile Trp Asp Ile Gly
145                 150                 155                 160

Leu Asn Ser Ser Trp Thr Phe Val Val Pro Tyr Ile Ser Pro Ser Asp
                165                 170                 175

Tyr Arg Glu Thr Arg Ala Ile Thr Asn Ser Val Tyr Ser Ala Asp Gly
            180                 185                 190

Trp Phe Ser Leu His Lys Leu Thr Lys Ile Thr Leu Pro Pro Asp Cys
        195                 200                 205

Pro Gln Ser Pro Cys Ile Leu Phe Phe Ala Ser Ala Gly Glu Asp Tyr
    210                 215                 220

Thr Leu Arg Leu Pro Val Asp Cys Asn Pro Ser Tyr Val Phe His
225                 230                 235

<210> SEQ ID NO 7
<211> LENGTH: 777
<212> TYPE: DNA
<213> ORGANISM: Seneca Valley Virus

<400> SEQUENCE: 7
tccaccgaca acgccgagac cggggttatt gaggcgggta acactgacac cgatttctct      60
ggtgaactgg cggctcctgg ccctaaccac actaatgtca agttcctgtt tgatcgatct     120
cgattattga atgtaatcaa ggtactggag aaggacgccg ttttcccccg ccctttccct     180
acacaagaag gtgcgcagca ggatgatggt tacttttgtc ttctgacccc ccgcccaaca     240
gtcgcttccc gacccgccac tcgtttcggc ctgtacgcca atccgtccgg cagtggtgtt     300
cttgctaaca cttcactgga cttcaatttt tatagcttgg cctgtttcac ttactttaga     360
tcggaccttg aggttacggt ggtctcacta gagccggatc tggaatttgc tgtagggtgg     420
tttccttctg gcagtgaata ccaggcttcc agctttgtct acgaccagct gcatgtgccc     480
ttccacttta ctgggcgcac tccccgcgct ttcgctagca agggtgggaa ggtatctttc     540
gtgctccctt ggaactctgt ctcgtctgtg ctccccgtgc gctggggggg ggcttccaag     600
ctctcttctg ctacgcgggg tctaccggcg catgctgatt gggggactat ttacgccttt     660
gtcccccgtc ctaatgagaa gaaaagcacc gctgtaaaac acgtggccgt gtacattcgg     720
tacaagaacg cacgtgcctg gtgccccagc atgcttccct ttcgcagcta caagcag        777

<210> SEQ ID NO 8
<211> LENGTH: 259
<212> TYPE: PRT
<213> ORGANISM: Seneca Valley Virus

<400> SEQUENCE: 8

Ser Thr Asp Asn Ala Glu Thr Gly Val Ile Glu Ala Gly Asn Thr Asp
1               5                   10                  15

Thr Asp Phe Ser Gly Glu Leu Ala Ala Pro Gly Pro Asn His Thr Asn
            20                  25                  30

Val Lys Phe Leu Phe Asp Arg Ser Arg Leu Leu Asn Val Ile Lys Val
        35                  40                  45

Leu Glu Lys Asp Ala Val Phe Pro Arg Pro Phe Pro Thr Gln Glu Gly
    50                  55                  60

Ala Gln Gln Asp Asp Gly Tyr Phe Cys Leu Leu Thr Pro Arg Pro Thr
65                  70                  75                  80

Val Ala Ser Arg Pro Ala Thr Arg Phe Gly Leu Tyr Ala Asn Pro Ser
                85                  90                  95

Gly Ser Gly Val Leu Ala Asn Thr Ser Leu Asp Phe Asn Phe Tyr Ser
            100                 105                 110
```

Leu Ala Cys Phe Thr Tyr Phe Arg Ser Asp Leu Glu Val Thr Val Val
            115                 120                 125

Ser Leu Glu Pro Asp Leu Glu Phe Ala Val Gly Trp Phe Pro Ser Gly
            130                 135                 140

Ser Glu Tyr Gln Ala Ser Ser Phe Val Tyr Asp Gln Leu His Val Pro
145                 150                 155                 160

Phe His Phe Thr Gly Arg Thr Pro Arg Ala Phe Ala Ser Lys Gly Gly
                165                 170                 175

Lys Val Ser Phe Val Leu Pro Trp Asn Ser Val Ser Ser Val Leu Pro
                180                 185                 190

Val Arg Trp Gly Gly Ala Ser Lys Leu Ser Ser Ala Thr Arg Gly Leu
            195                 200                 205

Pro Ala His Ala Asp Trp Gly Thr Ile Tyr Ala Phe Val Pro Arg Pro
            210                 215                 220

Asn Glu Lys Lys Ser Thr Ala Val Lys His Val Ala Val Tyr Ile Arg
225                 230                 235                 240

Tyr Lys Asn Ala Arg Ala Trp Cys Pro Ser Met Leu Pro Phe Arg Ser
                245                 250                 255

Tyr Lys Gln

<210> SEQ ID NO 9
<211> LENGTH: 42
<212> TYPE: DNA
<213> ORGANISM: Seneca Valley Virus

<400> SEQUENCE: 9
aagatgctga tgcaatctgg cgatatcgag accaatcctg gt                          42

<210> SEQ ID NO 10
<211> LENGTH: 14
<212> TYPE: PRT
<213> ORGANISM: Seneca Valley Virus

<400> SEQUENCE: 10

Lys Met Leu Met Gln Ser Gly Asp Ile Glu Thr Asn Pro Gly
1               5                   10

<210> SEQ ID NO 11
<211> LENGTH: 384
<212> TYPE: DNA
<213> ORGANISM: Seneca Valley Virus

<400> SEQUENCE: 11
cctgcttctg acaacccaat tttggagttt cttgaagcag aaaatgatct agtcactctg        60
gcctctctct ggaagatggt gcactctgtt caacagacct ggagaaagta tgtgaagaac       120
gatgattttt ggcccaattt actcagcgag ctagtggggg aaggctctgt cgccttggcc       180
gccacgctat ccaaccaagc ttcagtaaag gctcttttgg gcctgcactt tctctctcgg       240
gggctcaatt acactgactt ttactcttta ctgatagaga aatgctctag tttctttacc       300
gtagaaccac ctcctccacc agctgaaaac ctgatgacca gccctcagt gaagtcgaaa        360 ttccgaaaac tgtttaagat gcaa                                              384

<210> SEQ ID NO 12
<211> LENGTH: 128
<212> TYPE: PRT
<213> ORGANISM: Seneca Valley Virus

<400> SEQUENCE: 12

```
Pro Ala Ser Asp Asn Pro Ile Leu Glu Phe Leu Glu Ala Glu Asn Asp
1               5                   10                  15

Leu Val Thr Leu Ala Ser Leu Trp Lys Met Val His Ser Val Gln Gln
            20                  25                  30

Thr Trp Arg Lys Tyr Val Lys Asn Asp Asp Phe Trp Pro Asn Leu Leu
        35                  40                  45

Ser Glu Leu Val Gly Glu Gly Ser Val Ala Leu Ala Ala Thr Leu Ser
    50                  55                      60

Asn Gln Ala Ser Val Lys Ala Leu Leu Gly Leu His Phe Leu Ser Arg
65                  70                  75                  80

Gly Leu Asn Tyr Thr Asp Phe Tyr Ser Leu Leu Ile Glu Lys Cys Ser
                85                  90                  95

Ser Phe Phe Thr Val Glu Pro Pro Pro Pro Ala Glu Asn Leu Met
            100                 105                 110

Thr Lys Pro Ser Val Lys Ser Lys Phe Arg Lys Leu Phe Lys Met Gln
        115                 120                 125

<210> SEQ ID NO 13
<211> LENGTH: 966
<212> TYPE: DNA
<213> ORGANISM: Seneca Valley Virus

<400> SEQUENCE: 13
ggacccatgg acaaagtcaa agactggaac caaatagctg ccggcttgaa gaattttcaa      60
tttgttcgtg acctagtcaa agaggtggtc gattggctgc aggcctggat caacaaagag     120
aaagccagcc ctgtcctcca gtaccagttg agatgaaga agctcgggcc tgtggccttg      180
gctcatgacg ctttcatggc tggttccggg ccccctctta cgacgacca gattgaatac      240 ctccagaacc tcaaatctct tgccctaaca ctggggaaga ctaatttggc ccaaagtctc     300
accactatga tcaatgccaa acaaagttca gcccaacgag ttgaacccgt tgtggtggtc     360
cttagaggca agccgggatg cggcaagggc ttggcctcta cgttgattgc ccaggctgtg     420
tccaagcgcc tctatggctc ccaaagtgta tattctcttc ccccagatcc agatttcttc     480
gatggataca aggacagtt cgtgaccttg atggatgatt tgggacaaaa cccggatgga      540
caagatttcc ccacctttg tcagatggtg tcgaccgccc aatttctccc caacatggcg      600
gaccttgcag agaaagggcg tcccttttacc tccaatctca tcattgcaac tacaaatctc    660
ccccacttca gtcctgtcac cattgctgat ccttctgcag tctctcgccg tatcaactac     720
gatctgactc tagaagtatc tgaggcctac aagaaacaca cacggctgaa ttttgacttg     780
gctttcaggc gcacagacgc cccccccatt tatcctttg ctgcccatgt gcccttgtg      840 gacgtagctg tgcgcttcaa aaatggtcac cagaattttaa atctcctaga gttggtcgat   900
tccatttgta cagacattcg agccaagcaa caaggtgccc gaaacatgca gactctggtt     960
ctacag                                                                966

<210> SEQ ID NO 14
<211> LENGTH: 322
<212> TYPE: PRT
<213> ORGANISM: Seneca Valley Virus

<400> SEQUENCE: 14

Gly Pro Met Asp Lys Val Lys Asp Trp Asn Gln Ile Ala Ala Gly Leu
1               5                   10                  15

Lys Asn Phe Gln Phe Val Arg Asp Leu Val Lys Glu Val Val Asp Trp
            20                  25                  30
```

Leu Gln Ala Trp Ile Asn Lys Glu Lys Ala Ser Pro Val Leu Gln Tyr
                35                  40                  45

Gln Leu Glu Met Lys Lys Leu Gly Pro Val Ala Leu Ala His Asp Ala
 50                  55                  60

Phe Met Ala Gly Ser Gly Pro Pro Leu Ser Asp Asp Gln Ile Glu Tyr
 65                  70                  75                  80

Leu Gln Asn Leu Lys Ser Leu Ala Leu Thr Leu Gly Lys Thr Asn Leu
                85                  90                  95

Ala Gln Ser Leu Thr Thr Met Ile Asn Ala Lys Gln Ser Ser Ala Gln
                100                 105                 110

Arg Val Glu Pro Val Val Val Leu Arg Gly Lys Pro Gly Cys Gly
                115                 120                 125

Lys Gly Leu Ala Ser Thr Leu Ile Ala Gln Ala Val Ser Lys Arg Leu
            130                 135                 140

Tyr Gly Ser Gln Ser Val Tyr Ser Leu Pro Pro Asp Pro Asp Phe Phe
145                 150                 155                 160

Asp Gly Tyr Lys Gly Gln Phe Val Thr Leu Met Asp Asp Leu Gly Gln
                165                 170                 175

Asn Pro Asp Gly Gln Asp Phe Ser Thr Phe Cys Gln Met Val Ser Thr
            180                 185                 190

Ala Gln Phe Leu Pro Asn Met Ala Asp Leu Ala Glu Lys Gly Arg Pro
            195                 200                 205

Phe Thr Ser Asn Leu Ile Ile Ala Thr Thr Asn Leu Pro His Phe Ser
210                 215                 220

Pro Val Thr Ile Ala Asp Pro Ser Ala Val Ser Arg Arg Ile Asn Tyr
225                 230                 235                 240

Asp Leu Thr Leu Glu Val Ser Glu Ala Tyr Lys Lys His Thr Arg Leu
                245                 250                 255

Asn Phe Asp Leu Ala Phe Arg Arg Thr Asp Ala Pro Pro Ile Tyr Pro
            260                 265                 270

Phe Ala Ala His Val Pro Phe Val Asp Val Ala Val Arg Phe Lys Asn
            275                 280                 285

Gly His Gln Asn Phe Asn Leu Leu Glu Leu Val Asp Ser Ile Cys Thr
            290                 295                 300

Asp Ile Arg Ala Lys Gln Gln Gly Ala Arg Asn Met Gln Thr Leu Val
305                 310                 315                 320

Leu Gln

<210> SEQ ID NO 15
<211> LENGTH: 270
<212> TYPE: DNA
<213> ORGANISM: Seneca Valley Virus

<400> SEQUENCE: 15
agccccaacg agaatgatga caccccgtc gacgaggcgt tgggtagagt tctctccccc      60
gctgcggtcg atgaggcgct tgtcgacctc actccagagg ccgacccggt tggccgtttg     120
gctattcttg ccaagctagg tcttgcccta gctgcggtca ccctggtct gataatcttg      180 gcagtgggac tctacaggta cttctctggc tctgatgcag accaagaaga aacagaaagt     240
gagggatctg tcaaggcacc caggagcgaa                                      270

<210> SEQ ID NO 16
<211> LENGTH: 90
<212> TYPE: PRT
<213> ORGANISM: Seneca Valley Virus

<400> SEQUENCE: 16

Ser Pro Asn Glu Asn Asp Asp Thr Pro Val Asp Glu Ala Leu Gly Arg
1               5                   10                  15

Val Leu Ser Pro Ala Ala Val Asp Glu Ala Leu Val Asp Leu Thr Pro
            20                  25                  30

Glu Ala Asp Pro Val Gly Arg Leu Ala Ile Leu Ala Lys Leu Gly Leu
        35                  40                  45

Ala Leu Ala Ala Val Thr Pro Gly Leu Ile Ile Leu Ala Val Gly Leu
    50                  55                  60

Tyr Arg Tyr Phe Ser Gly Ser Asp Ala Asp Gln Glu Glu Thr Glu Ser
65              70                  75                  80

Glu Gly Ser Val Lys Ala Pro Arg Ser Glu
                85                  90

<210> SEQ ID NO 17
<211> LENGTH: 66
<212> TYPE: DNA
<213> ORGANISM: Seneca Valley Virus

<400> SEQUENCE: 17
aatgcttatg acggcccgaa gaaaaactct aagcccctg gagcactctc tctcatggaa      60
atgcaa                                                                66

<210> SEQ ID NO 18
<211> LENGTH: 22
<212> TYPE: PRT
<213> ORGANISM: Seneca Valley Virus

<400> SEQUENCE: 18

Asn Ala Tyr Asp Gly Pro Lys Lys Asn Ser Lys Pro Pro Gly Ala Leu
1               5                   10                  15

Ser Leu Met Glu Met Gln
            20

<210> SEQ ID NO 19
<211> LENGTH: 633
<212> TYPE: DNA
<213> ORGANISM: Seneca Valley Virus

<400> SEQUENCE: 19
cagcccaacg tggacatggg cttgaggct gcggtcgcta agaaagtggt cgtccccatt      60
accttcatgg ttcccaacag accttctggg cttacacagt ccgctcttct ggtgaccggc     120
cggaccttcc taatcaatga acatacatgg tccaatccct cctggaccag cttcacaatc     180
cgcggtgagg tacacactcg tgatgagccc ttccaaacgg ttcatttcac tcaccacggt    240
attcccacag atctgatgat ggtacgtctc ggaccgggca attctttccc taacaatcta    300
gacaagtttg acttgacca gatgccggca cgcaactccc gtgtggttgg cgtttcgtcc    360
agttacggaa acttcttctt ctctggaaat ttcctcggat tgttgattc cgtcacctct    420 gaacaaggaa cttacgcaag actctttagg tacagggtga cgacctacaa aggatggtgc    480
ggctcggccc tggtctgtga ggccggtggc gtccgacgca tcattggcct gcattctgct    540
ggcgccgccg gtatcggcgc cgggacctat atctcaaaat taggactaat caaagccctg    600
aaacacctcg gtgaaccttt ggccacaatg caa                                  633

<210> SEQ ID NO 20
<211> LENGTH: 211

<212> TYPE: PRT
<213> ORGANISM: Seneca Valley Virus

<400> SEQUENCE: 20

```
Gln Pro Asn Val Asp Met Gly Phe Glu Ala Ala Val Ala Lys Lys Val
1               5                   10                  15

Val Val Pro Ile Thr Phe Met Val Pro Asn Arg Pro Ser Gly Leu Thr
            20                  25                  30

Gln Ser Ala Leu Leu Val Thr Gly Arg Thr Phe Leu Ile Asn Glu His
        35                  40                  45

Thr Trp Ser Asn Pro Ser Trp Thr Ser Phe Thr Ile Arg Gly Glu Val
    50                  55                  60

His Thr Arg Asp Glu Pro Phe Gln Thr Val His Phe Thr His His Gly
65                  70                  75                  80

Ile Pro Thr Asp Leu Met Met Val Arg Leu Gly Pro Gly Asn Ser Phe
                85                  90                  95

Pro Asn Asn Leu Asp Lys Phe Gly Leu Asp Gln Met Pro Ala Arg Asn
            100                 105                 110

Ser Arg Val Val Gly Val Ser Ser Tyr Gly Asn Phe Phe Phe Ser
        115                 120                 125

Gly Asn Phe Leu Gly Phe Val Asp Ser Val Thr Ser Glu Gln Gly Thr
    130                 135                 140

Tyr Ala Arg Leu Phe Arg Tyr Arg Val Thr Thr Tyr Lys Gly Trp Cys
145                 150                 155                 160

Gly Ser Ala Leu Val Cys Glu Ala Gly Gly Val Arg Arg Ile Ile Gly
                165                 170                 175

Leu His Ser Ala Gly Ala Ala Gly Ile Gly Ala Gly Thr Tyr Ile Ser
            180                 185                 190

Lys Leu Gly Leu Ile Lys Ala Leu Lys His Leu Gly Glu Pro Leu Ala
        195                 200                 205

Thr Met Gln
    210
```

<210> SEQ ID NO 21
<211> LENGTH: 1389
<212> TYPE: DNA
<213> ORGANISM: Seneca Valley Virus

<400> SEQUENCE: 21

```
ggactgatga ctgaattaga gcctggaatc accgtacatg taccccggaa atccaaattg      60
agaaagacga ccgcacacgc ggtgtacaaa ccggagtttg agcctgctgt gttgtcaaaa     120
tttgatccca gactgaacaa ggatgttgac ttggatgaag taatttggtc taaacacact     180
gccaatgtcc cttaccaacc tccttttgttc tacacataca tgtcagagta cgctcatcga     240
gtcttctcct tcttggggaa agacaatgac attctgaccg tcaaagaagc aattctgggc     300
atccccggac tagaccccat ggatccccac acagctccgg gtctgcctta cgccatcaac     360
ggccttcgac gtactgatct cgtcgatttt gtgaacggta cagtagatgc ggcgctggct     420
gtacaaatcc agaaattctt agacggtgac tactctgacc atgtcttcca aacttttctg     480
aaagatgaga tcagaccctc agagaaagtc cgagcgggaa aaaccccgcat tgttgatgtg     540
ccctccctgg cgcattgcat tgtgggcaga atgttgcttg gcgctttgc tgccaagttt     600
caatcccatc ctggctttct cctcggctct gctatcgggt ctgaccctga tgttttctgg     660
accgtcatag ggctcaact cgaggggaga agaacacgt atgacgtgga ctacagtgcc     720
tttgactctt cacacggcac tggctccttc gaggctctca tctctcactt tttccaccgtg     780
```

```
gacaatggtt ttagccctgc gctgggaccg tatctcagat ccctggctgt ctcggtgcac    840
gcttacggcg agcgtcgcat caagattacc ggtggcctcc cctccggttg tgccgcgacc    900
agcctgctga acacagtgct caacaatgtg atcatcagga ctgctctggc attgacttac    960
aaggaatttg agtatgacac ggttgatatc atcgcctacg gtgacgacct tctggttggc   1020
acggattacg atctggactt caatgaggtg gcacgacgcg ctgccaagtt ggggtataag   1080
atgactcctg ccaacaaggg ttctgtcttc cctccgactt cctctctttc cgatgctgtt   1140
tttctaaagc gcaaattcgt ccaaaacaac gacggcttat acaaaccagt tatggattta   1200
aagaatttgg aagccatgct ctcctacttc aaaccaggaa cactactcga gaagctgcaa   1260
tctgtttcta tgttggctca acattctgga aaagaagaat atgatagatt gatgcacccc   1320
ttcgctgact acggtgccgt accgagtcac gagtacctgc aggcaagatg gagggccttg   1380
ttcgactga                                                            1389
```

<210> SEQ ID NO 22
<211> LENGTH: 462
<212> TYPE: PRT
<213> ORGANISM: Seneca Valley Virus

<400> SEQUENCE: 22

```
Gly Leu Met Thr Glu Leu Glu Pro Gly Ile Thr Val His Val Pro Arg
1               5                   10                  15

Lys Ser Lys Leu Arg Lys Thr Thr Ala His Ala Val Tyr Lys Pro Glu
            20                  25                  30

Phe Glu Pro Ala Val Leu Ser Lys Phe Asp Pro Arg Leu Asn Lys Asp
        35                  40                  45

Val Asp Leu Asp Glu Val Ile Trp Ser Lys His Thr Ala Asn Val Pro
    50                  55                  60

Tyr Gln Pro Pro Leu Phe Tyr Thr Tyr Met Ser Glu Tyr Ala His Arg
65                  70                  75                  80

Val Phe Ser Phe Leu Gly Lys Asp Asn Asp Ile Leu Thr Val Lys Glu
                85                  90                  95

Ala Ile Leu Gly Ile Pro Gly Leu Asp Pro Met Asp Pro His Thr Ala
            100                 105                 110

Pro Gly Leu Pro Tyr Ala Ile Asn Gly Leu Arg Arg Thr Asp Leu Val
        115                 120                 125

Asp Phe Val Asn Gly Thr Val Asp Ala Ala Leu Ala Val Gln Ile Gln
    130                 135                 140

Lys Phe Leu Asp Gly Asp Tyr Ser Asp His Val Phe Gln Thr Phe Leu
145                 150                 155                 160

Lys Asp Glu Ile Arg Pro Ser Glu Lys Val Arg Ala Gly Lys Thr Arg
                165                 170                 175

Ile Val Asp Val Pro Ser Leu Ala His Cys Ile Val Gly Arg Met Leu
            180                 185                 190

Leu Gly Arg Phe Ala Ala Lys Phe Gln Ser His Pro Gly Phe Leu Leu
        195                 200                 205

Gly Ser Ala Ile Gly Ser Asp Pro Asp Val Phe Trp Thr Val Ile Gly
    210                 215                 220

Ala Gln Leu Glu Gly Arg Lys Asn Thr Tyr Asp Val Asp Tyr Ser Ala
225                 230                 235                 240

Phe Asp Ser Ser His Gly Thr Gly Ser Phe Glu Ala Leu Ile Ser His
                245                 250                 255

Phe Phe Thr Val Asp Asn Gly Phe Ser Pro Ala Leu Gly Pro Tyr Leu
```

-continued

```
            260                 265                 270

Arg Ser Leu Ala Val Ser Val His Ala Tyr Gly Glu Arg Arg Ile Lys
        275                 280                 285

Ile Thr Gly Gly Leu Pro Ser Gly Cys Ala Ala Thr Ser Leu Leu Asn
    290                 295                 300

Thr Val Leu Asn Asn Val Ile Ile Arg Thr Ala Leu Ala Leu Thr Tyr
305                 310                 315                 320

Lys Glu Phe Glu Tyr Asp Thr Val Asp Ile Ile Ala Tyr Gly Asp Asp
                325                 330                 335

Leu Leu Val Gly Thr Asp Tyr Asp Leu Asp Phe Asn Glu Val Ala Arg
            340                 345                 350

Arg Ala Ala Lys Leu Gly Tyr Lys Met Thr Pro Ala Asn Lys Gly Ser
        355                 360                 365

Val Phe Pro Pro Thr Ser Ser Leu Ser Asp Ala Val Phe Leu Lys Arg
    370                 375                 380

Lys Phe Val Gln Asn Asn Asp Gly Leu Tyr Lys Pro Val Met Asp Leu
385                 390                 395                 400

Lys Asn Leu Glu Ala Met Leu Ser Tyr Phe Lys Pro Gly Thr Leu Leu
                405                 410                 415

Glu Lys Leu Gln Ser Val Ser Met Leu Ala Gln His Ser Gly Lys Glu
            420                 425                 430

Glu Tyr Asp Arg Leu Met His Pro Phe Ala Asp Tyr Gly Ala Val Pro
        435                 440                 445

Ser His Glu Tyr Leu Gln Ala Arg Trp Arg Ala Leu Phe Asp
    450                 455                 460

<210> SEQ ID NO 23
<211> LENGTH: 2292
<212> TYPE: PRT
<213> ORGANISM: Encephalomyocarditis virus

<400> SEQUENCE: 23

Met Ala Thr Thr Met Glu Gln Glu Thr Cys Ala His Ser Leu Thr Phe
1               5                   10                  15

Glu Glu Cys Pro Lys Cys Ser Ala Leu Gln Tyr Arg Asn Gly Phe Tyr
            20                  25                  30

Leu Leu Lys Tyr Asp Glu Glu Trp Tyr Pro Glu Glu Leu Leu Thr Asp
        35                  40                  45

Gly Glu Asp Asp Val Phe Asp Pro Glu Leu Asp Met Glu Val Val Phe
    50                  55                  60

Glu Leu Gln Gly Asn Ser Thr Ser Ser Asp Lys Asn Asn Ser Ser Ser
65                  70                  75                  80

Glu Gly Asn Glu Gly Val Ile Ile Asn Asn Phe Tyr Ser Asn Gln Tyr
                85                  90                  95

Gln Asn Ser Ile Asp Leu Ser Ala Asn Ala Ala Gly Ser Asp Pro Pro
            100                 105                 110

Arg Thr Tyr Gly Gln Phe Ser Asn Leu Phe Ser Gly Ala Val Asn Ala
        115                 120                 125

Phe Ser Asn Met Leu Pro Leu Leu Ala Asp Gln Asn Thr Glu Glu Met
    130                 135                 140

Glu Asn Leu Ser Asp Arg Val Ser Gln Asp Thr Ala Gly Asn Thr Val
145                 150                 155                 160

Thr Asn Thr Gln Ser Thr Val Gly Arg Leu Val Gly Tyr Gly Thr Val
                165                 170                 175

His Asp Gly Glu His Pro Ala Ser Cys Ala Asp Thr Ala Ser Glu Lys
```

-continued

```
                180                 185                 190
Ile Leu Ala Val Glu Arg Tyr Tyr Thr Phe Lys Val Asn Asp Trp Thr
                    195                 200                 205
Ser Thr Gln Lys Pro Phe Glu Tyr Ile Arg Ile Pro Leu Pro His Val
    210                 215                 220
Leu Ser Gly Glu Asp Gly Val Phe Gly Ala Ala Leu Arg Arg His
225                 230                 235                 240
Tyr Leu Val Lys Thr Gly Trp Arg Val Gln Val Gln Cys Asn Ala Ser
                245                 250                 255
Gln Phe His Ala Gly Ser Leu Leu Val Phe Met Ala Pro Glu Tyr Pro
            260                 265                 270
Thr Leu Asp Ala Phe Ala Met Asp Asn Arg Trp Ser Lys Asp Asn Leu
        275                 280                 285
Pro Asn Gly Thr Arg Thr Gln Thr Asn Lys Lys Gly Pro Phe Ala Met
    290                 295                 300
Asp His Gln Asn Phe Trp Gln Trp Thr Leu Tyr Pro His Gln Phe Leu
305                 310                 315                 320
Asn Leu Arg Thr Asn Thr Thr Val Asp Leu Glu Val Pro Tyr Val Asn
                325                 330                 335
Ile Ala Pro Thr Ser Trp Thr Gln His Ala Ser Trp Thr Leu Val
                340                 345                 350
Ile Ala Val Val Ala Pro Leu Thr Tyr Ser Thr Gly Ala Ser Thr Ser
                355                 360                 365
Leu Asp Ile Thr Ala Ser Ile Gln Pro Val Arg Pro Val Phe Asn Gly
370                 375                 380
Leu Arg His Glu Thr Leu Ser Arg Gln Ser Pro Ile Pro Val Thr Ile
385                 390                 395                 400
Arg Glu His Ala Gly Thr Trp Tyr Ser Thr Leu Pro Asp Ser Thr Val
                405                 410                 415
Pro Ile Tyr Gly Lys Thr Pro Val Ala Pro Ser Asn Tyr Met Val Gly
                420                 425                 430
Glu Tyr Lys Asp Phe Leu Glu Ile Ala Gln Ile Pro Thr Phe Ile Gly
            435                 440                 445
Asn Lys Ile Pro Asn Ala Val Pro Tyr Ile Glu Ala Ser Asn Thr Ala
    450                 455                 460
Val Lys Thr Gln Pro Leu Ala Thr Tyr Gln Val Thr Leu Ser Cys Ser
465                 470                 475                 480
Cys Leu Ala Asn Thr Phe Leu Ala Ala Leu Ser Arg Asn Phe Ala Gln
                485                 490                 495
Tyr Arg Gly Ser Leu Val Tyr Thr Phe Val Phe Thr Gly Thr Ala Met
                500                 505                 510
Met Lys Gly Lys Phe Leu Ile Ala Tyr Thr Pro Pro Gly Ala Gly Lys
            515                 520                 525
Pro Thr Ser Arg Asp Gln Ala Met Gln Ala Thr Tyr Ala Ile Trp Asp
        530                 535                 540
Leu Gly Leu Asn Ser Ser Tyr Ser Phe Thr Val Pro Phe Ile Ser Pro
545                 550                 555                 560
Thr His Phe Arg Met Val Gly Thr Asp Gln Val Asn Ile Thr Asn Ala
                565                 570                 575
Asp Gly Trp Val Thr Val Trp Gln Leu Thr Pro Leu Thr Tyr Pro Pro
                580                 585                 590
Gly Cys Pro Thr Ser Ala Lys Ile Leu Thr Met Val Ser Ala Gly Lys
                595                 600                 605
```

-continued

Asp Phe Ser Leu Lys Met Pro Ile Ser Pro Ala Pro Trp Ser Pro Gln
610                 615                 620

Gly Val Glu Asn Ala Glu Lys Gly Val Thr Glu Asn Thr Asn Ala Thr
625                 630                 635                 640

Ala Asp Phe Val Ala Gln Pro Val Tyr Leu Pro Glu Asn Gln Thr Lys
                645                 650                 655

Val Ala Phe Phe Tyr Asn Arg Ser Ser Pro Ile Gly Ala Phe Thr Val
                660                 665                 670

Lys Ser Gly Ser Leu Glu Ser Gly Phe Ala Pro Phe Ser Asn Gly Thr
                675                 680                 685

Cys Pro Asn Ser Val Ile Leu Thr Pro Gly Pro Gln Phe Asp Pro Ala
690                 695                 700

Tyr Asp Gln Leu Arg Pro Gln Arg Leu Thr Glu Ile Trp Gly Asn Gly
705                 710                 715                 720

Asn Glu Glu Thr Ser Lys Val Phe Pro Leu Lys Ser Lys Gln Asp Tyr
                725                 730                 735

Ser Phe Cys Leu Phe Ser Pro Phe Val Tyr Tyr Lys Cys Asp Leu Glu
                740                 745                 750

Val Thr Leu Ser Pro His Thr Ser Gly Asn His Gly Leu Leu Val Arg
                755                 760                 765

Trp Cys Pro Thr Gly Thr Pro Thr Lys Pro Thr Thr Gln Val Leu His
770                 775                 780

Glu Val Ser Ser Leu Ser Glu Gly Arg Thr Pro Gln Val Tyr Ser Ala
785                 790                 795                 800

Gly Pro Gly Ile Ser Asn Gln Ile Ser Phe Val Val Pro Tyr Asn Ser
                805                 810                 815

Pro Leu Ser Val Leu Ser Ala Val Trp Tyr Asn Gly His Lys Arg Phe
                820                 825                 830

Asp Asn Thr Gly Ser Leu Gly Ile Ala Pro Asn Ser Asp Phe Gly Thr
                835                 840                 845

Leu Phe Phe Ala Gly Thr Lys Pro Asp Ile Lys Phe Thr Val Tyr Leu
850                 855                 860

Arg Tyr Lys Asn Lys Arg Val Phe Cys Pro Arg Pro Thr Val Phe Phe
865                 870                 875                 880

Pro Trp Pro Thr Ser Gly Asp Lys Ile Asp Met Thr Pro Arg Ala Gly
                885                 890                 895

Val Leu Met Leu Glu Ser Pro Asn Ala Leu Asp Ile Ser Arg Thr Tyr
                900                 905                 910

Pro Thr Leu His Val Leu Ile Gln Phe Asn His Arg Gly Leu Glu Val
                915                 920                 925

Arg Leu Phe Arg His Gly His Phe Trp Ala Glu Thr Arg Ala Asp Val
930                 935                 940

Ile Leu Arg Ser Lys Thr Lys Gln Val Ser Phe Leu Ser Asn Gly Asn
945                 950                 955                 960

Tyr Pro Ser Met Asp Ser Arg Ala Pro Trp Asn Pro Trp Lys Asn Thr
                965                 970                 975

Tyr Gln Ala Val Leu Arg Ala Glu Pro Cys Arg Val Thr Met Asp Ile
                980                 985                 990

Tyr Tyr Lys Arg Val Arg Pro Phe Arg Leu Pro Leu Val Gln Lys Glu
                995                 1000                1005

Trp Pro Val Arg Glu Glu Asn Val Phe Gly Leu Tyr Arg Ile Phe Asn
        1010                1015                1020

Ala His Tyr Ala Gly Tyr Phe Ala Asp Leu Leu Ile His Asp Ile Glu
1025                1030                1035                1040

```
Thr Asn Pro Gly Pro Phe Met Phe Arg Pro Arg Lys Gln Val Phe Gln
            1045                1050                1055

Thr Gln Gly Ala Ala Val Ser Ser Met Ala Gln Thr Leu Leu Pro Asn
            1060                1065                1070

Asp Leu Ala Ser Lys Ala Met Gly Ser Ala Phe Thr Ala Leu Leu Asp
            1075                1080                1085

Ala Asn Glu Asp Ala Gln Lys Ala Met Lys Ile Ile Lys Thr Leu Ser
            1090                1095                1100

Ser Leu Ser Asp Ala Trp Glu Asn Val Lys Glu Thr Leu Asn Asn Pro
1105                1110                1115                1120

Glu Phe Trp Lys Gln Leu Leu Ser Arg Cys Val Gln Leu Ile Ala Gly
            1125                1130                1135

Met Thr Ile Ala Val Met His Pro Asp Pro Leu Thr Leu Leu Cys Leu
            1140                1145                1150

Gly Thr Leu Thr Ala Ala Glu Ile Thr Ser Gln Thr Ser Leu Cys Glu
            1155                1160                1165

Glu Ile Ala Ala Lys Phe Lys Thr Ile Phe Ile Thr Pro Pro Pro Arg
            1170                1175                1180

Phe Pro Thr Ile Ser Leu Phe Gln Gln Gln Ser Pro Leu Lys Gln Val
1185                1190                1195                1200

Asn Asp Ile Phe Ser Leu Ala Lys Asn Leu Asp Trp Ala Val Lys Thr
            1205                1210                1215

Val Glu Lys Val Val Asp Trp Phe Gly Thr Trp Ile Val Gln Glu Glu
            1220                1225                1230

Lys Glu Gln Thr Leu Asp Gln Leu Leu Gln Arg Phe Pro Glu His Ala
            1235                1240                1245

Lys Arg Ile Ser Asp Leu Arg Asn Gly Met Ala Ala Tyr Val Glu Cys
            1250                1255                1260

Lys Glu Ser Phe Asp Phe Phe Glu Lys Leu Tyr Asn Gln Ala Val Lys
1265                1270                1275                1280

Glu Lys Arg Thr Gly Ile Ala Ala Val Cys Glu Lys Phe Arg Gln Lys
            1285                1290                1295

His Asp His Ala Thr Ala Arg Cys Glu Pro Val Val Ile Val Leu Arg
            1300                1305                1310

Gly Asp Ala Gly Gln Gly Lys Ser Leu Ser Ser Gln Val Ile Ala Gln
            1315                1320                1325

Ala Val Ser Lys Thr Ile Phe Gly Arg Gln Ser Val Tyr Ser Leu Pro
            1330                1335                1340

Pro Asp Ser Asp Phe Phe Asp Gly Tyr Glu Asn Gln Phe Ala Ala Ile
1345                1350                1355                1360

Met Asp Asp Leu Gly Gln Asn Pro Asp Gly Ser Asp Phe Thr Thr Phe
            1365                1370                1375

Cys Gln Met Val Ser Thr Thr Asn Phe Leu Pro Asn Met Ala Ser Leu
            1380                1385                1390

Glu Arg Lys Gly Thr Pro Phe Thr Ser Gln Leu Val Val Ala Thr Thr
            1395                1400                1405

Asn Leu Pro Glu Phe Arg Pro Val Thr Ile Ala His Tyr Pro Ala Val
            1410                1415                1420

Glu Arg Arg Ile Thr Phe Asp Tyr Ser Val Ser Ala Gly Pro Val Cys
1425                1430                1435                1440

Ser Lys Thr Glu Ala Gly Tyr Lys Val Leu Asp Val Glu Arg Ala Phe
            1445                1450                1455

Arg Pro Thr Gly Glu Ala Pro Leu Pro Cys Phe Gln Asn Asn Cys Leu
```

-continued

```
                1460            1465            1470
Phe Leu Glu Lys Ala Gly Leu Gln Phe Arg Asp Asn Arg Thr Lys Glu
            1475            1480            1485
Ile Ile Ser Leu Val Asp Val Ile Glu Arg Ala Val Ala Arg Ile Glu
            1490            1495            1500
Arg Lys Lys Lys Val Leu Thr Thr Val Gln Thr Leu Val Ala Gln Gly
1505            1510            1515            1520
Pro Val Asp Glu Val Ser Phe His Ser Val Val Gln Gln Leu Lys Ala
            1525            1530            1535
Arg Gln Gln Ala Thr Asp Glu Gln Leu Glu Glu Leu Gln Glu Ala Phe
            1540            1545            1550
Ala Lys Val Gln Glu Arg Asn Ser Val Phe Ser Asp Trp Leu Lys Ile
            1555            1560            1565
Ser Ala Met Leu Cys Ala Ala Thr Leu Ala Leu Ser Gln Val Val Lys
            1570            1575            1580
Met Ala Lys Ala Val Lys Gln Met Val Lys Pro Asp Leu Val Arg Val
1585            1590            1595            1600
Gln Leu Asp Glu Gln Glu Gln Gly Pro Tyr Asn Glu Thr Ala Arg Val
            1605            1610            1615
Lys Pro Lys Thr Leu Gln Leu Leu Asp Ile Gln Gly Pro Asn Pro Val
            1620            1625            1630
Met Asp Phe Glu Lys Tyr Val Ala Lys His Val Thr Ala Pro Ile Gly
            1635            1640            1645
Phe Val Tyr Pro Thr Gly Val Ser Thr Gln Thr Cys Leu Leu Val Arg
            1650            1655            1660
Gly Arg Thr Leu Val Val Asn Arg His Met Ala Glu Ser Asp Trp Thr
1665            1670            1675            1680
Ser Ile Val Val Arg Gly Val Thr His Ala Arg Ser Thr Val Lys Ile
            1685            1690            1695
Leu Ala Ile Ala Lys Ala Gly Lys Glu Thr Asp Val Ser Phe Ile Arg
            1700            1705            1710
Leu Ser Ser Gly Pro Leu Phe Arg Asp Asn Thr Ser Lys Phe Val Lys
            1715            1720            1725
Ala Gly Asp Val Leu Pro Thr Gly Ala Ala Pro Val Thr Gly Ile Met
            1730            1735            1740
Asn Thr Asp Ile Pro Met Met Tyr Thr Gly Thr Phe Leu Lys Ala Gly
1745            1750            1755            1760
Val Ser Val Pro Val Glu Thr Gly Gln Thr Phe Asn His Cys Ile His
            1765            1770            1775
Tyr Lys Ala Asn Thr Arg Lys Gly Trp Cys Gly Ser Ala Leu Leu Ala
            1780            1785            1790
Asp Leu Gly Gly Ser Lys Lys Ile Leu Gly Ile His Ser Ala Gly Ser
            1795            1800            1805
Met Gly Ile Ala Ala Ala Ser Ile Val Ser Gln Glu Met Ile Arg Ala
            1810            1815            1820
Val Val Asn Ala Phe Glu Pro Gln Gly Ala Leu Glu Arg Leu Pro Asp
1825            1830            1835            1840
Gly Pro Arg Ile His Val Pro Arg Lys Thr Ala Leu Arg Pro Thr Val
            1845            1850            1855
Ala Arg Gln Val Phe Gln Pro Ala Tyr Ala Pro Ala Val Leu Ser Lys
            1860            1865            1870
Phe Asp Pro Arg Thr Glu Ala Asp Val Asp Glu Val Ala Phe Ser Lys
            1875            1880            1885
```

```
His Thr Ser Asn Gln Glu Ser Leu Pro Pro Val Phe Arg Met Val Ala
    1890                1895                1900

Lys Glu Tyr Ala Asn Arg Val Phe Thr Leu Leu Gly Lys Asp Asn Gly
1905            1910                1915                1920

Arg Leu Thr Val Lys Gln Ala Leu Glu Gly Leu Glu Gly Met Asp Pro
                1925                1930                1935

Met Asp Arg Asn Thr Ser Pro Gly Leu Pro Tyr Thr Ala Leu Gly Met
            1940                1945                1950

Arg Arg Thr Asp Val Val Asp Trp Glu Ser Ala Thr Leu Ile Pro Phe
                1955                1960                1965

Ala Ala Glu Arg Leu Arg Lys Met Asn Glu Gly Asp Phe Ser Glu Val
    1970                1975                1980

Val Tyr Gln Thr Phe Leu Lys Asp Glu Leu Arg Pro Ile Glu Lys Val
1985            1990                1995                2000

Gln Ala Ala Lys Thr Arg Ile Val Asp Val Pro Pro Phe Glu His Cys
                2005                2010                2015

Ile Leu Gly Arg Gln Leu Leu Gly Lys Phe Ala Ser Lys Phe Gln Thr
            2020                2025                2030

Gln Pro Gly Leu Glu Leu Gly Ser Ala Ile Gly Cys Asp Pro Asp Val
    2035                2040                2045

His Trp Thr Ala Phe Gly Val Ala Met Gln Gly Phe Glu Arg Val Tyr
    2050                2055                2060

Asp Val Asp Tyr Ser Asn Phe Asp Ser Thr His Ser Val Ala Met Phe
2065            2070                2075                2080

Arg Leu Leu Ala Glu Glu Phe Phe Thr Pro Glu Asn Gly Phe Asp Pro
            2085                2090                2095

Leu Thr Arg Glu Tyr Leu Glu Ser Leu Ala Ile Ser Thr His Ala Phe
            2100                2105                2110

Glu Glu Lys Arg Phe Leu Ile Thr Gly Gly Leu Pro Ser Gly Cys Ala
            2115                2120                2125

Ala Thr Ser Met Leu Asn Thr Ile Met Asn Asn Ile Ile Ile Arg Ala
    2130                2135                2140

Gly Leu Tyr Leu Thr Tyr Lys Asn Phe Glu Phe Asp Asp Val Lys Val
2145            2150                2155                2160

Leu Ser Tyr Gly Asp Asp Leu Leu Val Ala Thr Asn Tyr Gln Leu Asp
            2165                2170                2175

Phe Asp Lys Val Arg Ala Ser Leu Ala Lys Thr Gly Tyr Lys Ile Thr
            2180                2185                2190

Pro Ala Asn Lys Thr Ser Thr Phe Pro Leu Asn Ser Thr Leu Glu Asp
            2195                2200                2205

Val Val Phe Leu Lys Arg Lys Phe Lys Lys Glu Gly Pro Leu Tyr Arg
    2210                2215                2220

Pro Val Met Asn Arg Glu Ala Leu Glu Ala Met Leu Ser Tyr Tyr Arg
2225            2230                2235                2240

Pro Gly Thr Leu Ser Glu Lys Leu Thr Ser Ile Thr Met Leu Ala Val
                2245                2250                2255

His Ser Gly Lys Gln Glu Tyr Asp Arg Leu Phe Ala Pro Phe Arg Glu
            2260                2265                2270

Val Gly Val Val Val Pro Ser Phe Glu Ser Val Glu Tyr Arg Trp Arg
            2275                2280                2285

Ser Leu Phe Trp
    2290

<210> SEQ ID NO 24
```

<211> LENGTH: 2292
<212> TYPE: PRT
<213> ORGANISM: Encephalomyocarditis virus

<400> SEQUENCE: 24

Met Ala Thr Thr Met Glu Gln Glu Thr Cys Ala His Ser Leu Thr Phe
1 5 10 15

Glu Glu Cys Pro Lys Cys Ser Ala Leu Gln Tyr Arg Asn Gly Phe Tyr
20 25 30

Leu Leu Lys Tyr Asp Glu Glu Trp Tyr Pro Glu Glu Leu Leu Thr Asp
35 40 45

Gly Glu Asp Asp Val Phe Asp Pro Glu Leu Asp Met Glu Val Val Phe
50 55 60

Glu Leu Gln Gly Asn Ser Thr Ser Ser Asp Lys Asn Asn Ser Ser Ser
65 70 75 80

Glu Gly Asn Glu Gly Val Ile Ile Asn Asn Phe Tyr Ser Asn Gln Tyr
85 90 95

Gln Asn Ser Ile Asp Leu Ser Ala Asn Ala Ala Gly Ser Asp Pro Pro
100 105 110

Arg Thr Tyr Gly Gln Phe Ser Asn Leu Phe Ser Gly Ala Val Asn Ala
115 120 125

Phe Ser Asn Met Leu Pro Leu Leu Ala Asp Gln Asn Thr Glu Glu Met
130 135 140

Glu Asn Leu Ser Asp Arg Val Ser Gln Asp Thr Ala Gly Asn Thr Val
145 150 155 160

Thr Asn Thr Gln Ser Thr Val Gly Arg Leu Val Gly Tyr Gly Thr Val
165 170 175

His Asp Gly Glu His Pro Ala Ser Cys Ala Asp Thr Ala Ser Glu Lys
180 185 190

Ile Leu Ala Val Glu Arg Tyr Tyr Thr Phe Lys Val Asn Asp Trp Thr
195 200 205

Ser Thr Gln Lys Pro Phe Glu Tyr Ile Arg Ile Pro Leu Pro His Val
210 215 220

Leu Ser Gly Glu Asp Gly Gly Val Phe Gly Ala Ala Leu Arg Arg His
225 230 235 240

Tyr Leu Val Lys Thr Gly Trp Arg Val Gln Val Gln Cys Asn Ala Ser
245 250 255

Gln Phe His Ala Gly Ser Leu Leu Val Phe Met Ala Pro Glu Tyr Pro
260 265 270

Thr Leu Asp Thr Phe Val Met Asp Asn Arg Trp Ser Lys Asp Asn Leu
275 280 285

Pro Asn Gly Ala Arg Thr Gln Thr Asn Lys Lys Gly Pro Phe Ala Met
290 295 300

Asp His Gln Asn Phe Trp Gln Trp Thr Leu Tyr Pro His Gln Phe Leu
305 310 315 320

Asn Leu Arg Thr Asn Thr Thr Val Asp Leu Glu Val Pro Tyr Val Asn
325 330 335

Ile Ala Pro Thr Ser Ser Trp Thr Gln His Ala Ser Trp Thr Leu Val
340 345 350

Ile Ala Val Val Ala Pro Leu Thr Tyr Ser Thr Gly Ala Ser Thr Ser
355 360 365

Leu Asp Ile Thr Ala Ser Ile Gln Pro Val Arg Pro Val Phe Asn Gly
370 375 380

Leu Arg His Glu Thr Leu Ser Arg Gln Ser Pro Ile Pro Val Thr Ile
385 390 395 400

```
Arg Glu His Ala Gly Thr Trp Tyr Ser Thr Leu Pro Asp Ser Thr Val
                405             410                 415
Pro Ile Tyr Gly Lys Thr Pro Val Ala Pro Ser Asn Tyr Met Val Gly
            420             425             430
Glu Tyr Lys Asp Phe Leu Glu Ile Ala Gln Ile Pro Thr Phe Ile Gly
        435                 440                 445
Asn Lys Ile Pro Asn Ala Val Pro Tyr Ile Glu Ala Ser Asn Thr Ala
    450                 455                 460
Val Lys Thr Gln Pro Leu Ala Thr Tyr Gln Val Thr Leu Ser Cys Ser
465             470                 475                 480
Cys Leu Ala Asn Thr Phe Leu Ala Ala Leu Ser Arg Asn Phe Ala Gln
                485                 490                 495
Tyr Arg Gly Ser Leu Val Tyr Thr Phe Val Phe Thr Gly Thr Ala Met
            500                 505                 510
Met Lys Gly Lys Phe Leu Ile Ala Tyr Thr Pro Pro Gly Ala Gly Lys
            515                 520                 525
Pro Thr Ser Arg Asp Gln Ala Met Gln Ala Thr Tyr Ala Ile Trp Asp
            530                 535                 540
Leu Gly Leu Asn Ser Ser Tyr Ser Phe Thr Val Pro Phe Ile Ser Pro
545                 550                 555                 560
Thr His Phe Arg Met Val Gly Thr Asp Gln Val Asn Ile Thr Asn Ala
                565                 570                 575
Asp Gly Trp Val Thr Val Trp Gln Leu Thr Pro Leu Thr Tyr Pro Pro
            580                 585                 590
Gly Cys Pro Thr Ser Ala Lys Ile Leu Thr Met Val Ser Ala Gly Lys
            595                 600                 605
Asp Phe Ser Leu Lys Met Pro Ile Ser Pro Ala Pro Trp Ser Pro Gln
            610                 615                 620
Gly Val Glu Asn Ala Glu Lys Gly Val Thr Glu Asn Ala Asp Ala Thr
625                 630                 635                 640
Ala Asp Phe Val Ala Gln Pro Val Tyr Leu Pro Glu Asn Gln Thr Lys
                645                 650                 655
Val Ala Phe Phe Tyr Asp Arg Ser Ser Pro Ile Gly Ala Phe Thr Val
                660                 665                 670
Gln Ser Gly Ser Leu Glu Ser Gly Phe Ala Pro Phe Ser Asn Lys Thr
            675                 680                 685
Cys Pro Asn Ser Val Ile Leu Thr Pro Gly Pro Gln Phe Asp Pro Ala
            690                 695                 700
Tyr Asp Gln Leu Arg Pro Gln Arg Leu Thr Glu Ile Trp Gly Asn Gly
705             710                 715                 720
Asn Glu Glu Thr Ser Lys Val Phe Pro Leu Lys Ser Lys Gln Asp Tyr
                725                 730                 735
Ser Phe Cys Leu Phe Ser Pro Val Tyr Tyr Lys Cys Asp Leu Glu
            740                 745                 750
Val Thr Leu Ser Pro His Thr Ser Gly Asn His Gly Leu Leu Val Arg
            755                 760                 765
Trp Cys Pro Thr Gly Thr Pro Thr Lys Pro Thr Thr Gln Val Leu His
        770                 775                 780
Glu Val Ser Ser Leu Ser Glu Gly Arg Thr Pro Gln Val Tyr Ser Ala
785                 790                 795                 800
Gly Pro Gly Ile Ser Asn Gln Ile Ser Phe Val Val Pro Tyr Asn Ser
                805                 810                 815
Pro Leu Ser Val Leu Pro Ala Val Trp Tyr Asn Gly His Lys Arg Phe
```

```
                    820             825             830
Asp Asn Thr Gly Ser Leu Gly Ile Ala Pro Asn Ser Asp Phe Gly Thr
            835                 840                 845
Leu Phe Phe Ala Gly Thr Lys Pro Asp Ile Lys Phe Thr Val Tyr Leu
    850                 855                 860
Arg Tyr Lys Asn Met Arg Val Phe Cys Pro Arg Pro Thr Val Phe Phe
865                 870                 875                 880
Pro Trp Pro Thr Ser Gly Asp Lys Ile Asp Met Thr Pro Arg Ala Gly
                885                 890                 895
Val Leu Met Leu Glu Ser Pro Asn Ala Leu Asp Ile Ser Arg Thr Tyr
            900                 905                 910
Pro Thr Leu His Val Leu Ile Gln Phe Asn His Arg Gly Leu Glu Val
            915                 920                 925
Arg Leu Phe Arg His Gly Gln Phe Trp Ala Glu Thr Arg Ala Asp Val
        930                 935                 940
Ile Leu Arg Ser Lys Thr Lys Gln Val Ser Phe Leu Ser Asn Gly Asn
945                 950                 955                 960
Tyr Pro Ser Met Asp Ser Arg Ala Pro Trp Asn Pro Trp Lys Asn Thr
                965                 970                 975
Tyr Gln Ala Val Leu Arg Ala Glu Pro Cys Arg Val Thr Met Asp Ile
            980                 985                 990
Tyr Tyr Lys Arg Val Arg Pro Phe Arg Leu Pro Leu Val Gln Lys Glu
            995                 1000                1005
Trp Arg Val Arg Glu Glu Asn Val Phe Gly Leu Tyr Arg Ile Phe Asn
        1010                1015                1020
Ala His Tyr Ala Gly Tyr Phe Ala Asp Leu Leu Ile His Asp Ile Glu
1025                1030                1035                1040
Thr Asn Pro Gly Pro Phe Met Phe Arg Pro Arg Lys Gln Val Phe Gln
                1045                1050                1055
Thr Gln Gly Ala Ala Val Ser Ser Met Ala Gln Thr Leu Leu Pro Asn
            1060                1065                1070
Asp Leu Ala Ser Lys Ala Met Gly Ser Ala Phe Thr Ala Leu Leu Asp
        1075                1080                1085
Ala Asn Glu Asp Ala Arg Lys Ala Met Lys Ile Ile Lys Thr Leu Ser
    1090                1095                1100
Ser Leu Ser Asp Ala Trp Glu Asn Val Lys Glu Thr Leu Asn Asn Pro
1105                1110                1115                1120
Glu Phe Trp Lys Gln Leu Leu Ser Arg Cys Val Gln Leu Ile Ala Gly
                1125                1130                1135
Met Thr Ile Ala Val Met His Pro Asp Pro Leu Thr Leu Leu Cys Leu
            1140                1145                1150
Gly Thr Leu Thr Ala Ala Glu Ile Thr Ser Gln Thr Ser Leu Cys Glu
        1155                1160                1165
Glu Ile Ala Ala Lys Phe Lys Thr Ile Phe Ile Thr Pro Pro Arg
    1170                1175                1180
Phe Pro Thr Ile Ser Leu Phe Gln Gln Gln Ser Pro Leu Lys Gln Val
1185                1190                1195                1200
Asn Asp Phe Phe Ser Leu Ala Lys Asn Leu Asp Trp Ala Val Lys Thr
                1205                1210                1215
Val Glu Lys Val Val Asp Trp Phe Gly Thr Trp Ile Val Gln Glu Glu
            1220                1225                1230
Lys Glu Gln Thr Leu Asp Gln Leu Leu Gln Arg Phe Pro Glu His Ala
        1235                1240                1245
```

-continued

Lys Arg Ile Ser Asp Leu Arg Asn Gly Met Ala Ala Tyr Val Glu Cys
1250                1255                1260

Lys Glu Ser Phe Asp Phe Glu Lys Leu Tyr Asn Gln Ala Val Lys
1265                1270                1275                1280

Glu Lys Arg Thr Gly Ile Ala Ala Val Cys Glu Lys Phe Arg Gln Lys
                1285                1290                1295

His Asp His Ala Thr Ala Arg Cys Glu Pro Val Val Ile Val Leu Arg
            1300                1305                1310

Gly Asp Ala Gly Gln Gly Lys Ser Leu Ser Ser Gln Val Ile Ala Gln
            1315                1320                1325

Ala Val Ser Lys Thr Ile Phe Gly Arg Gln Ser Val Tyr Ser Leu Pro
            1330                1335                1340

Pro Asp Ser Asp Phe Phe Asp Gly Tyr Glu Asn Gln Phe Ala Ala Ile
1345                1350                1355                1360

Met Asp Asp Leu Gly Gln Asn Pro Asp Gly Ser Asp Phe Thr Thr Phe
                1365                1370                1375

Cys Gln Met Val Ser Thr Thr Asn Phe Leu Pro Asn Met Ala Ser Leu
            1380                1385                1390

Glu Arg Lys Gly Thr Pro Phe Thr Ser Gln Leu Val Val Ala Thr Thr
            1395                1400                1405

Asn Leu Pro Glu Phe Arg Pro Val Thr Ile Ala His Tyr Pro Ala Val
1410                1415                1420

Glu Arg Arg Ile Thr Phe Asp Tyr Ser Val Ser Ala Gly Pro Val Cys
1425                1430                1435                1440

Ser Lys Thr Glu Ala Gly Tyr Lys Val Leu Asp Val Glu Arg Ala Phe
                1445                1450                1455

Arg Pro Thr Gly Glu Ala Pro Leu Pro Cys Phe Gln Asn Asn Cys Leu
            1460                1465                1470

Phe Leu Glu Lys Ala Gly Leu Gln Phe Arg Asp Asn Arg Thr Lys Glu
            1475                1480                1485

Ile Ile Ser Leu Val Asp Val Ile Glu Arg Ala Val Ala Arg Ile Glu
1490                1495                1500

Arg Lys Lys Lys Val Leu Thr Thr Val Gln Thr Leu Val Ala Gln Ala
1505                1510                1515                1520

Pro Val Asp Glu Val Ser Phe His Ser Val Val Gln Gln Leu Lys Ala
                1525                1530                1535

Arg Gln Glu Ala Thr Asp Glu Gln Leu Glu Glu Leu Gln Glu Ala Phe
            1540                1545                1550

Ala Lys Val Gln Glu Arg Asn Ser Val Phe Ser Asp Trp Leu Lys Ile
            1555                1560                1565

Ser Ala Met Leu Cys Ala Ala Thr Leu Ala Leu Ser Gln Val Val Lys
1570                1575                1580

Met Ala Lys Ala Val Lys Gln Met Val Lys Pro Asp Leu Val Arg Val
1585                1590                1595                1600

Gln Leu Asp Glu Gln Glu Gln Gly Pro Tyr Asn Glu Thr Ala Arg Ala
                1605                1610                1615

Lys Pro Lys Thr Leu Gln Leu Leu Asp Ile Gln Gly Pro Asn Pro Val
            1620                1625                1630

Met Asp Phe Glu Lys Tyr Val Ala Lys His Val Thr Ala Pro Ile Asp
            1635                1640                1645

Phe Val Tyr Pro Thr Gly Val Ser Thr Gln Thr Cys Leu Leu Val Arg
1650                1655                1660

Gly Arg Thr Leu Ala Val Asn Arg His Met Ala Glu Ser Asp Trp Thr
1665                1670                1675                1680

```
Ser Ile Val Val Arg Gly Val Thr His Ala Arg Ser Thr Val Lys Ile
            1685                1690                1695

Leu Ala Ile Ala Lys Ala Gly Lys Glu Thr Asp Val Ser Phe Ile Arg
            1700                1705                1710

Leu Ser Ser Gly Pro Leu Phe Arg Asp Asn Thr Ser Lys Phe Val Lys
            1715                1720                1725

Ala Gly Asp Val Leu Pro Thr Gly Ala Ala Pro Val Thr Gly Ile Met
            1730                1735                1740

Asn Thr Asp Ile Pro Met Met Tyr Thr Gly Thr Phe Leu Lys Ala Gly
1745                1750                1755                1760

Val Ser Val Pro Val Glu Thr Gly Gln Thr Phe Asn His Cys Ile His
            1765                1770                1775

Tyr Lys Ala Asn Thr Arg Lys Gly Trp Cys Gly Ser Ala Leu Leu Ala
            1780                1785                1790

Asp Leu Gly Gly Ser Lys Lys Ile Leu Gly Ile His Ser Ala Gly Ser
            1795                1800                1805

Met Gly Ile Ala Ala Ala Ser Ile Val Ser Gln Glu Met Ile Arg Ala
            1810                1815                1820

Val Val Asn Ala Phe Glu Pro Gln Gly Ala Leu Glu Arg Leu Pro Asp
1825                1830                1835                1840

Gly Pro Arg Ile His Val Pro Arg Lys Thr Ala Leu Arg Pro Thr Val
            1845                1850                1855

Ala Arg Gln Val Phe Gln Pro Ala Tyr Ala Pro Ala Val Leu Ser Lys
            1860                1865                1870

Phe Asp Pro Arg Thr Glu Ala Asp Val Asp Glu Val Ala Phe Ser Lys
            1875                1880                1885

His Thr Ser Asn Gln Glu Ser Leu Pro Pro Val Phe Arg Met Val Ala
            1890                1895                1900

Lys Glu Tyr Ala Asn Arg Val Phe Thr Leu Leu Gly Lys Asp Asn Gly
1905                1910                1915                1920

Arg Leu Thr Val Lys Gln Ala Leu Glu Gly Leu Glu Gly Met Asp Pro
            1925                1930                1935

Met Asp Arg Asn Thr Ser Pro Gly Leu Pro Tyr Thr Ala Leu Gly Met
            1940                1945                1950

Arg Arg Thr Asp Val Val Asp Trp Glu Ser Ala Thr Leu Ile Pro Phe
            1955                1960                1965

Ala Ala Glu Arg Leu Arg Lys Met Asn Glu Gly Asp Phe Ser Glu Val
            1970                1975                1980

Val Tyr Gln Thr Phe Leu Lys Asp Glu Leu Arg Pro Ile Glu Lys Val
1985                1990                1995                2000

Gln Ala Ala Lys Thr Arg Ile Val Asp Val Pro Pro Phe Glu His Cys
            2005                2010                2015

Ile Leu Gly Arg Gln Leu Leu Gly Lys Phe Ala Ser Lys Phe Gln Thr
            2020                2025                2030

Gln Pro Gly Leu Glu Leu Gly Ser Ala Ile Gly Cys Asp Pro Asp Val
            2035                2040                2045

His Trp Thr Ala Phe Gly Val Ala Met Gln Gly Phe Glu Arg Val Tyr
            2050                2055                2060

Asp Val Asp Tyr Ser Asn Phe Asp Ser Thr His Ser Val Ala Met Phe
2065                2070                2075                2080

Arg Leu Leu Ala Glu Glu Phe Phe Thr Pro Glu Asn Gly Phe Asp Pro
            2085                2090                2095

Leu Thr Arg Glu Tyr Leu Glu Ser Leu Ala Ile Ser Thr His Ala Phe
```

-continued 2100 2105 2110

Glu Glu Lys Arg Phe Leu Ile Thr Gly Gly Leu Pro Ser Gly Cys Ala
2115 2120 2125

Ala Thr Ser Met Leu Asn Thr Ile Met Asn Asn Ile Ile Ile Arg Ala
2130 2135 2140

Gly Leu Tyr Leu Thr Tyr Lys Asn Phe Glu Phe Asp Asp Val Lys Val
2145 2150 2155 2160

Leu Ser Tyr Gly Asp Asp Leu Leu Val Ala Thr Asn Tyr Gln Leu Asp
2165 2170 2175

Phe Asp Lys Val Arg Ala Ser Leu Ala Lys Thr Gly Tyr Lys Ile Thr
2180 2185 2190

Pro Ala Asn Lys Thr Ser Thr Phe Pro Leu Asn Ser Thr Leu Glu Asp
2195 2200 2205

Val Val Phe Leu Lys Arg Lys Phe Lys Lys Glu Gly Pro Leu Tyr Arg
2210 2215 2220

Pro Val Met Asn Arg Glu Ala Leu Glu Ala Met Leu Ser Tyr Tyr Arg
2225 2230 2235 2240

Pro Gly Thr Leu Ser Glu Lys Leu Thr Ser Ile Thr Met Leu Ala Val
2245 2250 2255

His Ser Gly Lys Gln Glu Tyr Asp Arg Leu Phe Ala Pro Phe Arg Glu
2260 2265 2270

Val Gly Val Val Val Pro Ser Phe Glu Ser Val Glu Tyr Arg Trp Arg
2275 2280 2285

Ser Leu Phe Trp
2290

<210> SEQ ID NO 25
<211> LENGTH: 2292
<212> TYPE: PRT
<213> ORGANISM: Encephalomyocarditis virus

<400> SEQUENCE: 25

Met Ala Thr Thr Met Glu Gln Glu Ile Cys Ala His Ser Leu Thr Leu
1 5 10 15

Lys Gly Cys Pro Lys Cys Ser Ala Leu Gln Tyr Arg Asn Gly Phe Tyr
20 25 30

Leu Leu Lys Tyr Asp Glu Glu Trp Tyr Pro Glu Glu Leu Leu Thr Asp
35 40 45

Gly Glu Asp Asp Val Phe Asp Pro Glu Leu Asp Met Glu Val Val Phe
50 55 60

Glu Leu Gln Gly Asn Ser Thr Ser Ser Asp Lys Asn Asn Ser Ser Ser
65 70 75 80

Asp Gly Asn Glu Gly Val Ile Ile Asn Asn Phe Tyr Ser Asn Gln Tyr
85 90 95

Gln Asn Ser Ile Asp Leu Ser Ala Asn Ala Thr Gly Ser Asp Pro Pro
100 105 110

Arg Thr Tyr Gly Gln Phe Ser Asn Leu Leu Ser Gly Ala Val Asn Ala
115 120 125

Phe Ser Asn Met Ile Pro Leu Leu Ala Asp Gln Asn Thr Glu Glu Met
130 135 140

Glu Asn Leu Ser Asp Arg Val Leu Gln Asp Thr Ala Gly Asn Thr Val
145 150 155 160

Thr Asn Thr Gln Ser Thr Val Gly Arg Leu Val Gly Tyr Gly Ala Val
165 170 175

His Asp Gly Glu His Pro Ala Ser Cys Ala Asp Thr Ala Ser Glu Lys

```
                180             185             190
Ile Leu Ala Val Glu Arg Tyr Tyr Thr Phe Lys Val Asn Asp Trp Thr
                195                 200                 205

Ser Thr Gln Lys Pro Phe Glu Tyr Ile Arg Ile Pro Leu Pro His Val
        210                 215                 220

Leu Ser Gly Glu Asp Gly Val Phe Gly Ala Ala Leu Arg Arg His
225                 230                 235                 240

Tyr Leu Val Lys Thr Gly Trp Arg Val Gln Val Gln Cys Asn Ala Ser
                245                 250                 255

Gln Phe His Ala Gly Ser Leu Leu Val Phe Met Ala Pro Glu Tyr Pro
        260                 265                 270

Thr Leu Asp Ala Phe Ala Met Asp Asn Arg Trp Ser Lys Asp Asn Leu
        275                 280                 285

Pro Asn Gly Thr Lys Thr Gln Thr Asn Arg Lys Gly Pro Phe Ala Met
        290                 295                 300

Asp His Gln Asn Phe Trp Gln Trp Thr Leu Tyr Pro His Gln Phe Leu
305                 310                 315                 320

Asn Leu Arg Thr Asn Thr Thr Val Asp Leu Glu Val Pro Tyr Val Asn
                325                 330                 335

Ile Ala Pro Thr Ser Trp Thr Gln His Ala Ser Trp Thr Leu Val
                340                 345                 350

Ile Ala Val Val Ala Pro Leu Thr Tyr Ser Thr Gly Ala Ser Thr Ser
                355                 360                 365

Leu Asp Ile Thr Ala Ser Ile Gln Pro Val Arg Pro Val Phe Asn Gly
        370                 375                 380

Leu Arg His Glu Thr Leu Ser Arg Gln Ser Pro Ile Pro Val Thr Ile
385                 390                 395                 400

Arg Glu His Ala Gly Thr Trp Tyr Ser Thr Leu Pro Asp Ser Thr Val
                405                 410                 415

Pro Ile Tyr Gly Lys Thr Pro Val Ala Pro Ala Asn Tyr Met Val Gly
                420                 425                 430

Glu Tyr Lys Asp Phe Leu Glu Ile Ala Gln Ile Pro Thr Phe Ile Gly
                435                 440                 445

Asn Lys Ile Pro Asn Ala Val Pro Tyr Ile Glu Ala Ser Asn Thr Ala
        450                 455                 460

Val Lys Thr Gln Pro Leu Ala Thr Tyr Gln Val Thr Leu Ser Cys Ser
465                 470                 475                 480

Cys Leu Ala Asn Thr Phe Leu Ala Ala Leu Ser Arg Asn Phe Ala Gln
                485                 490                 495

Tyr Arg Gly Ser Leu Val Tyr Thr Phe Val Phe Thr Gly Thr Ala Met
            500                 505                 510

Met Lys Gly Lys Phe Leu Ile Ala Tyr Thr Pro Pro Gly Ala Gly Lys
        515                 520                 525

Pro Thr Ser Arg Asp Gln Ala Met Gln Ala Thr Tyr Ala Ile Trp Asp
        530                 535                 540

Leu Gly Leu Asn Ser Ser Tyr Ser Phe Thr Val Pro Phe Ile Ser Pro
545                 550                 555                 560

Thr His Phe Arg Met Val Gly Thr Asp Gln Val Asn Ile Thr Asn Val
                565                 570                 575

Asp Gly Trp Val Thr Val Trp Gln Leu Thr Pro Leu Thr Tyr Pro Pro
            580                 585                 590

Gly Cys Pro Thr Ser Ala Lys Ile Leu Thr Met Val Ser Ala Gly Lys
            595                 600                 605
```

```
Asp Phe Ser Leu Lys Met Pro Ile Ser Pro Ala Pro Trp Ser Pro Gln
            610                 615                 620

Gly Val Glu Asn Ala Glu Arg Gly Val Thr Glu Thr Asp Ala Thr
625                 630                 635                 640

Ala Asp Phe Val Ala Gln Pro Val Tyr Leu Pro Glu Asn Gln Thr Lys
                645                 650                 655

Val Ala Phe Phe Tyr Asp Arg Ser Ser Pro Ile Gly Ala Phe Thr Val
            660                 665                 670

Lys Ser Gly Ser Leu Glu Ser Gly Phe Thr Pro Phe Ser Asn Gln Thr
                675                 680                 685

Cys Pro Asn Ser Val Ile Leu Thr Pro Gly Pro Gln Phe Asp Pro Ala
690                 695                 700

Tyr Asp Gln Leu Arg Pro Gln Arg Leu Thr Glu Ile Trp Gly Asn Gly
705                 710                 715                 720

Asn Glu Glu Thr Ser Lys Val Phe Pro Leu Lys Ser Lys Gln Asp Tyr
                725                 730                 735

Ser Phe Cys Leu Phe Ser Pro Phe Val Tyr Tyr Lys Cys Asp Leu Glu
            740                 745                 750

Val Thr Leu Ser Pro His Thr Ser Gly Asn His Gly Leu Leu Val Arg
                755                 760                 765

Trp Cys Pro Thr Gly Thr Pro Thr Lys Pro Thr Thr Gln Val Leu His
770                 775                 780

Glu Val Ser Ser Leu Ser Glu Gly Arg Thr Pro Gln Val Tyr Ser Ala
785                 790                 795                 800

Gly Pro Gly Ile Thr Asn Gln Ile Ser Phe Val Val Pro Tyr Asn Ser
                805                 810                 815

Pro Leu Ser Val Leu Pro Ala Val Trp Tyr Asn Gly His Lys Arg Phe
            820                 825                 830

Asp Asn Thr Gly Ser Leu Gly Ile Ala Pro Asn Ser Asp Phe Gly Thr
                835                 840                 845

Leu Phe Phe Ala Gly Thr Lys Pro Asp Ile Lys Phe Thr Val Tyr Leu
850                 855                 860

Arg Tyr Lys Asn Met Arg Val Phe Cys Pro Arg Pro Thr Val Phe Phe
865                 870                 875                 880

Pro Trp Pro Ser Ser Gly Asp Lys Ile Asp Met Thr Pro Arg Ala Gly
                885                 890                 895

Val Leu Met Leu Glu Ser Pro Asn Ala Leu Asp Ile Ser Arg Thr Tyr
            900                 905                 910

Pro Thr Leu His Ile Leu Ile Gln Phe Asn His Gly Gly Leu Glu Ile
                915                 920                 925

Arg Leu Phe Arg His Gly Met Phe Trp Ala Glu Ala His Ala Asp Val
930                 935                 940

Ile Leu Arg Ser Arg Thr Lys Gln Ile Ser Phe Leu Asn Asn Gly Ser
945                 950                 955                 960

Phe Pro Ser Met Asp Ala Arg Ala Pro Trp Asn Pro Trp Lys Asn Thr
                965                 970                 975

Tyr His Ala Val Leu Arg Ala Glu Pro Tyr Arg Val Thr Met Asp Val
            980                 985                 990

Tyr His Lys Arg Ile Arg Pro Phe Arg Leu Pro Leu Val Gln Lys Glu
                995                 1000                1005

Trp Asn Val Arg Glu Glu Asn Val Phe Gly Leu Tyr Gly Ile Phe Asn
            1010                1015                1020

Ala His Tyr Ala Gly Tyr Phe Ala Asp Leu Leu Ile His Asp Ile Glu
1025                1030                1035                1040
```

Thr Asn Pro Gly Pro Phe Met Ala Lys Pro Lys Gln Val Phe Gln
                1045                1050                1055

Thr Gln Gly Ala Ala Val Ser Ser Met Ala Gln Thr Leu Leu Pro Asn
                1060                1065                1070

Asp Leu Ala Ser Lys Val Met Gly Ser Ala Phe Thr Ala Leu Leu Asp
                1075                1080                1085

Ala Asn Glu Asp Ala Gln Lys Ala Met Arg Ile Ile Lys Thr Leu Ser
                1090                1095                1100

Ser Leu Ser Asp Ala Trp Glu Asn Val Lys Glu Thr Leu Asn Asn Pro
1105                1110                1115                1120

Glu Phe Trp Lys Gln Leu Leu Ser Arg Cys Val Gln Leu Ile Ala Gly
                1125                1130                1135

Met Thr Ile Ala Val Met His Pro Asp Pro Leu Thr Leu Leu Cys Leu
                1140                1145                1150

Gly Thr Leu Thr Ala Ala Glu Ile Thr Ser Gln Thr Ser Leu Cys Glu
                1155                1160                1165

Glu Ile Val Ala Lys Phe Lys Lys Ile Phe Thr Thr Pro Pro Pro Arg
                1170                1175                1180

Phe Pro Thr Ile Ser Leu Phe Gln Gln Gln Ser Pro Leu Lys Gln Val
1185                1190                1195                1200

Asn Asp Val Phe Ser Leu Ala Lys Asn Leu Asp Trp Ala Val Lys Thr
                1205                1210                1215

Val Glu Lys Val Val Asp Trp Phe Gly Thr Trp Val Gln Glu Glu
                1220                1225                1230

Lys Glu Gln Thr Leu Asp Gln Leu Leu Gln Arg Phe Pro Glu His Ala
                1235                1240                1245

Lys Arg Ile Ser Asp Leu Arg Asn Gly Met Ser Ala Tyr Val Glu Cys
                1250                1255                1260

Lys Glu Ser Phe Asp Phe Phe Glu Lys Leu Tyr Asn Gln Ala Val Lys
1265                1270                1275                1280

Glu Lys Arg Thr Gly Ile Ala Ala Val Cys Glu Lys Phe Arg Gln Lys
                1285                1290                1295

His Asp His Ala Thr Ala Arg Cys Glu Pro Val Val Ile Val Leu Arg
                1300                1305                1310

Gly Asp Ala Gly Gln Gly Lys Ser Leu Ser Ser Gln Val Ile Ala Gln
                1315                1320                1325

Ala Val Ser Lys Thr Ile Phe Gly Arg Gln Ser Val Tyr Ser Leu Pro
                1330                1335                1340

Pro Asp Ser Asp Phe Phe Asp Gly Tyr Glu Asn Gln Phe Ala Ala Ile
1345                1350                1355                1360

Met Asp Asp Leu Gly Gln Asn Pro Asp Gly Ser Asp Phe Thr Thr Phe
                1365                1370                1375

Cys Gln Met Val Ser Thr Thr Asn Phe Leu Pro Asn Met Ala Ser Leu
                1380                1385                1390

Glu Arg Asn Gly Thr Pro Phe Thr Ser Gln Ile Val Val Ala Thr Thr
                1395                1400                1405

Asn Leu Pro Glu Phe Arg Pro Val Thr Ile Ala His Tyr Pro Ala Val
                1410                1415                1420

Glu Arg Arg Ile Thr Phe Asp Tyr Ser Val Ser Ala Gly Pro Val Cys
1425                1430                1435                1440

Ser Lys Thr Glu Ala Gly Tyr Lys Val Leu Asp Val Glu Arg Ala Phe
                1445                1450                1455

Arg Pro Thr Gly Asp Ala Pro Leu Pro Cys Phe Gln Asn Asn Cys Leu

-continued

```
                    1460            1465             1470
Phe Leu Glu Lys Ala Gly Leu Gln Phe Arg Asp Asn Arg Thr Lys Glu
            1475            1480            1485
Ile Leu Ser Leu Val Asp Val Ile Glu Arg Ala Val Ala Arg Ile Glu
            1490            1495            1500
Arg Lys Lys Lys Val Leu Thr Thr Val Gln Thr Leu Val Ala Gln Ala
1505            1510            1515            1520
Pro Val Asp Glu Val Ser Phe His Ser Val Val Gln Gln Leu Lys Ala
                    1525            1530            1535
Arg Gln Glu Ala Thr Asp Glu Gln Leu Glu Glu Leu Gln Glu Ala Phe
                1540            1545            1550
Ala Lys Thr Gln Glu Arg Ser Ser Val Phe Ser Asp Trp Met Lys Ile
            1555            1560            1565
Ser Ala Met Leu Cys Ala Ala Thr Leu Ala Leu Ser Gln Val Val Lys
            1570            1575            1580
Met Ala Lys Thr Val Lys Gln Met Val Arg Pro Asp Leu Val Arg Val
1585            1590            1595            1600
Gln Leu Asp Glu Gln Glu Gln Gly Pro Tyr Asn Glu Ala Val Arg Ala
                    1605            1610            1615
Lys Pro Lys Thr Leu Gln Leu Leu Asp Ile Gln Gly Pro Asn Pro Val
                1620            1625            1630
Met Asp Phe Glu Lys Tyr Val Ala Lys Phe Val Thr Ala Pro Ile Asp
            1635            1640            1645
Phe Val Tyr Pro Thr Gly Val Ser Thr Gln Thr Cys Leu Leu Val Lys
            1650            1655            1660
Gly Arg Thr Leu Ala Val Asn Arg His Met Ala Glu Ser Asp Trp Ser
1665            1670            1675            1680
Ser Ile Val Val Arg Gly Val Thr His Ala Arg Ser Thr Val Arg Ile
                    1685            1690            1695
Leu Ala Ile Ala Lys Ala Gly Lys Glu Thr Asp Val Ser Phe Ile Arg
                1700            1705            1710
Leu Ser Ser Gly Pro Leu Phe Arg Asp Asn Thr Ser Lys Phe Val Lys
            1715            1720            1725
Ala Asp Asp Val Leu Pro Ala Thr Ser Ala Pro Val Ile Gly Ile Met
            1730            1735            1740
Asn Thr Asp Ile Pro Met Met Phe Thr Gly Thr Phe Leu Lys Ala Gly
1745            1750            1755            1760
Val Ser Val Pro Val Glu Thr Gly Gln Thr Phe Asn His Cys Ile His
                    1765            1770            1775
Tyr Lys Ala Asn Thr Arg Lys Gly Trp Cys Gly Ser Ala Leu Leu Ala
                1780            1785            1790
Asp Leu Gly Gly Lys Lys Lys Ile Leu Gly Met His Ser Ala Gly Ser
            1795            1800            1805
Met Gly Arg Thr Ala Ala Ser Ile Val Ser Gln Glu Met Ile Cys Ala
            1810            1815            1820
Val Val Ser Ala Phe Glu Pro Gln Gly Ala Leu Glu Arg Leu Pro Asp
1825            1830            1835            1840
Gly Pro Arg Ile His Val Pro Arg Lys Thr Ala Leu Arg Pro Thr Val
                    1845            1850            1855
Ala Arg Arg Val Phe Gln Pro Ala Tyr Ala Pro Ala Val Leu Ser Lys
                1860            1865            1870
Phe Asp Pro Arg Thr Glu Ala Asp Val Asp Glu Val Ala Phe Ser Lys
            1875            1880            1885
```

```
His Thr Ser Asn Gln Glu Ser Leu Pro Pro Val Phe Arg Met Val Ala
    1890                1895                1900

Lys Glu Tyr Ala Asn Arg Val Phe Thr Leu Leu Gly Arg Asp Asn Gly
1905            1910                1915                1920

Arg Leu Thr Val Lys Gln Ala Leu Glu Gly Leu Glu Gly Met Asp Pro
                1925                1930                1935

Met Asp Lys Asn Thr Ser Pro Gly Leu Pro Tyr Thr Ala Leu Gly Met
            1940                1945                1950

Arg Arg Thr Asp Val Val Asp Trp Glu Ser Ala Thr Leu Ile Pro Tyr
                1955                1960            1965

Ala Ala Asp Arg Leu Lys Lys Met Asn Glu Gly Asp Phe Ser Asp Ile
    1970                1975                1980

Val Tyr Gln Thr Phe Leu Lys Asp Glu Leu Arg Pro Val Glu Lys Val
1985            1990                1995                2000

Gln Ala Ala Lys Thr Arg Ile Val Asp Val Pro Pro Phe Glu His Cys
                2005                2010                2015

Ile Leu Gly Arg Gln Leu Leu Gly Arg Phe Ala Ser Lys Phe Gln Thr
            2020                2025                2030

Gln Pro Gly Leu Glu Leu Gly Ser Ala Ile Gly Cys Asp Pro Asp Val
        2035                2040                2045

His Trp Thr Ala Phe Gly Val Ala Met Gln Gly Phe Glu Arg Val Tyr
        2050                2055                2060

Asp Val Asp Tyr Ser Asn Phe Asp Ser Thr His Ser Val Ala Met Phe
2065            2070                2075                2080

Arg Leu Leu Ala Glu Glu Phe Phe Thr Pro Glu Asn Gly Phe Asp Pro
                2085                2090                2095

Leu Val Lys Glu Tyr Leu Glu Ser Leu Ala Ile Ser Thr His Ala Phe
                2100                2105                2110

Glu Glu Lys Arg Tyr Leu Ile Thr Gly Gly Leu Pro Ser Gly Cys Ala
            2115                2120            2125

Ala Thr Ser Met Leu Asn Thr Ile Met Asn Asn Ile Ile Ile Arg Ala
        2130                2135                2140

Gly Leu Tyr Leu Thr Tyr Lys Asn Phe Glu Phe Asp Asp Val Lys Val
2145            2150                2155                2160

Leu Ser Tyr Gly Asp Asp Leu Leu Val Ala Thr Asn Tyr Gln Leu Asn
                2165                2170                2175

Phe Asp Lys Val Arg Ala Ser Leu Ala Lys Thr Gly Tyr Lys Ile Thr
            2180                2185                2190

Pro Ala Asn Lys Thr Ser Thr Phe Pro Leu Asp Ser Thr Leu Glu Asp
            2195                2200                2205

Val Val Phe Leu Lys Arg Lys Phe Lys Lys Glu Gly Pro Leu Tyr Arg
    2210                2215                2220

Pro Val Met Asn Arg Glu Ala Leu Glu Ala Met Leu Ser Tyr Tyr Arg
2225            2230                2235                2240

Pro Gly Thr Leu Ser Glu Lys Leu Thr Ser Ile Thr Met Leu Ala Val
                2245                2250                2255

His Ser Gly Lys Pro Glu Tyr Asp Arg Leu Phe Ala Pro Phe Arg Glu
            2260                2265                2270

Val Gly Val Val Val Pro Ser Phe Glu Ser Val Glu Tyr Arg Trp Arg
                2275                2280                2285

Ser Leu Phe Trp
    2290

<210> SEQ ID NO 26
```

```
<211> LENGTH: 2292
<212> TYPE: PRT
<213> ORGANISM: Encephalomyocarditis virus

<400> SEQUENCE: 26

Met Ala Thr Thr Met Glu Gln Glu Ile Cys Ala His Ser Leu Thr Phe
1               5                   10                  15

Lys Gly Cys Pro Lys Cys Ser Ala Leu Gln Tyr Arg Asn Gly Phe Tyr
            20                  25                  30

Leu Leu Lys Tyr Asp Glu Glu Trp Tyr Pro Glu Glu Leu Leu Thr Asp
        35                  40                  45

Gly Glu Asp Asp Val Phe Asp Pro Glu Leu Asp Met Glu Val Val Phe
50                  55                  60

Glu Leu Gln Gly Asn Ser Thr Ser Ser Asp Lys Asn Asn Ser Ser Ser
65                  70                  75                  80

Asp Gly Asn Glu Gly Val Ile Ile Asn Asn Phe Tyr Ser Asn Gln Tyr
                85                  90                  95

Gln Asn Ser Ile Asp Leu Ser Ala Asn Ala Thr Gly Ser Asp Pro Pro
            100                 105                 110

Arg Thr Tyr Gly Gln Phe Ser Asn Leu Leu Ser Gly Ala Val Asn Ala
        115                 120                 125

Phe Ser Asn Met Ile Pro Leu Leu Ala Asp Gln Asn Thr Glu Glu Met
130                 135                 140

Glu Asn Leu Ser Asp Arg Val Leu Gln Asp Thr Ala Gly Asn Thr Val
145                 150                 155                 160

Thr Asn Thr Gln Ser Thr Val Gly Arg Leu Val Gly Tyr Gly Ala Val
                165                 170                 175

His Asp Gly Glu His Pro Ala Ser Cys Ala Asp Thr Ala Ser Glu Lys
            180                 185                 190

Ile Leu Ala Val Glu Arg Tyr Tyr Thr Phe Lys Val Asn Asp Trp Thr
        195                 200                 205

Ser Thr Gln Lys Pro Phe Glu Tyr Ile Arg Ile Pro Leu Pro His Val
210                 215                 220

Leu Ser Gly Glu Asp Gly Gly Val Phe Gly Ala Ala Leu Arg Arg His
225                 230                 235                 240

Tyr Leu Val Lys Thr Gly Trp Arg Val Gln Val Gln Cys Asn Ala Ser
                245                 250                 255

Gln Phe His Ala Gly Ser Leu Leu Val Phe Met Ala Pro Glu Tyr Pro
            260                 265                 270

Thr Leu Asp Ala Phe Ala Met Asp Asn Arg Trp Ser Lys Asp Asn Leu
        275                 280                 285

Pro Asn Gly Thr Lys Thr Gln Thr Asn Arg Lys Gly Pro Phe Ala Met
290                 295                 300

Asp His Gln Asn Phe Trp Gln Trp Thr Leu Tyr Pro His Gln Phe Leu
305                 310                 315                 320

Asn Leu Arg Thr Asn Thr Thr Val Asp Leu Glu Val Pro Tyr Val Asn
                325                 330                 335

Ile Ala Pro Thr Ser Ser Trp Thr Gln His Ala Ser Trp Thr Leu Val
            340                 345                 350

Ile Ala Val Val Ala Pro Leu Thr Tyr Ser Thr Gly Ala Ser Thr Ser
        355                 360                 365

Leu Asp Ile Thr Ala Ser Ile Gln Pro Val Arg Pro Val Phe Asn Gly
370                 375                 380

Leu Arg His Glu Thr Leu Ser Arg Gln Ser Pro Ile Pro Val Thr Ile
385                 390                 395                 400
```

```
Arg Glu His Ala Gly Thr Trp Tyr Ser Thr Leu Pro Asp Ser Thr Val
                405                 410                 415

Pro Ile Tyr Gly Lys Thr Pro Val Ala Pro Ala Asn Tyr Met Val Gly
            420                 425                 430

Glu Tyr Lys Asp Phe Leu Glu Ile Ala Gln Ile Pro Thr Phe Ile Gly
        435                 440                 445

Asn Lys Ile Pro Asn Ala Val Pro Tyr Ile Glu Ala Ser Asn Thr Ala
    450                 455                 460

Val Lys Thr Gln Pro Leu Ala Thr Tyr Gln Val Thr Leu Ser Cys Ser
465                 470                 475                 480

Cys Leu Ala Asn Thr Phe Leu Ala Ala Leu Ser Arg Asn Phe Ala Gln
                485                 490                 495

Tyr Arg Gly Ser Leu Val Tyr Thr Phe Val Phe Thr Gly Thr Ala Met
            500                 505                 510

Met Lys Gly Lys Phe Leu Ile Ala Tyr Thr Pro Pro Gly Ala Gly Lys
        515                 520                 525

Pro Thr Ser Arg Asp Gln Ala Met Gln Ala Thr Tyr Ala Ile Trp Asp
    530                 535                 540

Leu Gly Leu Asn Ser Ser Tyr Ser Phe Thr Val Pro Phe Ile Ser Pro
545                 550                 555                 560

Thr His Phe Arg Met Val Gly Thr Asp Gln Val Asn Ile Thr Asn Val
                565                 570                 575

Asp Gly Trp Val Thr Val Trp Gln Leu Thr Pro Leu Thr Tyr Pro Pro
            580                 585                 590

Gly Cys Pro Thr Ser Ala Lys Ile Leu Thr Met Val Ser Ala Gly Lys
        595                 600                 605

Asp Phe Ser Leu Lys Met Pro Ile Ser Pro Ala Pro Trp Ser Pro Gln
    610                 615                 620

Gly Val Glu Asn Ala Glu Arg Gly Val Thr Glu Asp Thr Asp Ala Thr
625                 630                 635                 640

Ala Asp Phe Val Ala Gln Pro Val Tyr Leu Pro Glu Asn Gln Thr Lys
                645                 650                 655

Val Ala Phe Phe Tyr Asp Arg Ser Ser Pro Ile Gly Ala Phe Ala Val
            660                 665                 670

Lys Ser Gly Ser Leu Glu Ser Gly Phe Ala Pro Phe Ser Asn Glu Thr
        675                 680                 685

Cys Pro Asn Ser Val Ile Leu Thr Pro Gly Pro Gln Phe Asp Pro Ala
    690                 695                 700

Tyr Asp Gln Leu Arg Pro Gln Arg Leu Thr Glu Ile Trp Gly Asn Gly
705                 710                 715                 720

Asn Glu Glu Thr Ser Lys Val Phe Pro Leu Lys Ser Lys Gln Asp Tyr
                725                 730                 735

Ser Phe Cys Leu Phe Ser Pro Val Tyr Tyr Lys Cys Asp Leu Glu
            740                 745                 750

Val Thr Leu Ser Pro His Thr Ser Gly Asn His Gly Leu Leu Val Arg
        755                 760                 765

Trp Cys Pro Thr Gly Thr Pro Ala Lys Pro Thr Thr Gln Val Leu His
    770                 775                 780

Glu Val Ser Ser Leu Ser Glu Gly Arg Thr Pro Gln Val Tyr Ser Ala
785                 790                 795                 800

Gly Pro Gly Ile Ser Asn Gln Ile Ser Phe Val Val Pro Tyr Asn Ser
                805                 810                 815

Pro Leu Ser Val Leu Pro Ala Val Trp Tyr Asn Gly His Lys Arg Phe
```

```
                    820             825             830
Asp Asn Thr Gly Ser Leu Gly Ile Ala Pro Asn Ser Asp Phe Gly Thr
            835             840             845

Leu Phe Phe Ala Gly Thr Lys Pro Asp Ile Lys Phe Thr Val Tyr Leu
    850             855             860

Arg Tyr Lys Asn Met Arg Val Phe Cys Pro Arg Pro Thr Val Phe Phe
865             870             875             880

Pro Trp Pro Ser Ser Gly Asp Lys Ile Asp Met Thr Pro Arg Ala Gly
            885             890             895

Val Leu Met Leu Glu Ser Pro Asn Ala Leu Asp Ile Ser Arg Thr Tyr
                900             905             910

Pro Thr Leu His Ile Leu Ile Gln Phe Asn His Gly Gly Leu Glu Ile
            915             920             925

Arg Leu Phe Arg His Gly Met Phe Trp Ala Glu Ala His Ala Asp Val
        930             935             940

Ile Leu Arg Ser Arg Thr Lys Gln Ile Ser Phe Leu Asn Asn Gly Ser
945             950             955             960

Phe Pro Ser Met Asp Ala Arg Ala Pro Trp Asn Pro Trp Lys Asn Thr
            965             970             975

Tyr His Ala Val Leu Arg Ala Glu Pro Tyr Arg Val Thr Met Asp Val
            980             985             990

Tyr His Lys Arg Ile Arg Pro Phe Arg Leu Pro Leu Val Gln Lys Glu
            995             1000            1005

Trp Asn Val Arg Glu Glu Asn Val Phe Gly Leu Tyr Gly Ile Phe Asn
            1010            1015            1020

Ala His Tyr Ala Gly Tyr Phe Ala Asp Leu Leu Ile His Asp Ile Glu
1025            1030            1035            1040

Thr Asn Pro Gly Pro Phe Met Ala Lys Pro Lys Lys Gln Val Phe Gln
            1045            1050            1055

Thr Gln Gly Ala Ala Val Ser Ser Met Ala Gln Thr Leu Leu Pro Asn
            1060            1065            1070

Asp Leu Ala Ser Lys Val Met Gly Ser Ala Phe Thr Ala Leu Leu Asp
            1075            1080            1085

Ala Asn Glu Asp Ala Gln Lys Ala Met Arg Ile Ile Lys Thr Leu Ser
            1090            1095            1100

Ser Leu Ser Asp Ala Trp Glu Asn Val Lys Glu Thr Leu Asn Asn Pro
1105            1110            1115            1120

Glu Phe Trp Lys Gln Leu Leu Ser Arg Cys Val Gln Leu Ile Ala Gly
            1125            1130            1135

Met Thr Ile Ala Val Met His Pro Asp Pro Leu Thr Leu Leu Cys Leu
            1140            1145            1150

Gly Thr Leu Thr Ala Ala Glu Ile Thr Ser Gln Thr Ser Leu Cys Glu
            1155            1160            1165

Glu Ile Val Ala Lys Phe Lys Lys Ile Phe Thr Thr Pro Pro Pro Arg
            1170            1175            1180

Phe Pro Thr Ile Ser Leu Phe Gln Gln Gln Ser Pro Leu Lys Gln Val
1185            1190            1195            1200

Asn Asp Val Phe Ser Leu Ala Lys Asn Leu Asp Trp Ala Val Lys Thr
            1205            1210            1215

Val Glu Lys Val Val Asp Trp Phe Gly Thr Trp Val Val Gln Glu Glu
            1220            1225            1230

Lys Glu Gln Thr Leu Asp Gln Leu Leu Gln Arg Phe Pro Glu His Ala
            1235            1240            1245
```

-continued

```
Lys Arg Ile Ser Asp Leu Arg Asn Gly Met Ser Ala Tyr Val Glu Cys
1250                1255                1260

Lys Glu Ser Phe Asp Phe Glu Lys Leu Tyr Asn Gln Ala Val Lys
1265            1270                1275                1280

Glu Lys Arg Thr Gly Ile Ala Ala Val Cys Glu Lys Phe Arg Gln Lys
                1285                1290                1295

His Asp His Ala Thr Ala Arg Cys Glu Pro Val Val Ile Val Leu Arg
                1300                1305                1310

Gly Asp Ala Gly Gln Gly Lys Ser Leu Ser Ser Gln Val Ile Ala Gln
                1315                1320                1325

Ala Val Ser Lys Thr Ile Phe Gly Arg Gln Ser Val Tyr Ser Leu Pro
                1330                1335                1340

Pro Asp Ser Asp Phe Phe Asp Gly Tyr Glu Asn Gln Phe Ala Ala Ile
1345                1350                1355                1360

Met Asp Asp Leu Gly Gln Asn Pro Asp Gly Ser Asp Phe Thr Thr Phe
                1365                1370                1375

Cys Gln Met Val Ser Thr Thr Asn Phe Leu Pro Asn Met Ala Ser Leu
                1380                1385                1390

Glu Arg Asn Gly Thr Pro Phe Thr Ser Gln Ile Val Val Ala Thr Thr
                1395                1400                1405

Asn Leu Pro Glu Phe Arg Pro Val Thr Ile Ala His Tyr Pro Ala Val
1410                1415                1420

Glu Arg Arg Ile Thr Phe Asp Tyr Ser Val Ser Ala Gly Pro Val Cys
1425                1430                1435                1440

Ser Lys Thr Glu Ala Gly Tyr Lys Val Leu Asp Val Glu Arg Ala Phe
                1445                1450                1455

Arg Pro Thr Gly Asp Ala Pro Leu Pro Cys Phe Gln Asn Asn Cys Leu
                1460                1465                1470

Phe Leu Glu Lys Ala Gly Leu Gln Phe Arg Asp Asn Arg Thr Lys Glu
                1475                1480                1485

Ile Leu Ser Leu Val Asp Val Ile Glu Arg Ala Val Ala Arg Ile Glu
                1490                1495                1500

Arg Lys Lys Lys Val Leu Thr Thr Val Gln Thr Leu Val Ala Gln Ala
1505                1510                1515                1520

Pro Val Ala Glu Val Ser Phe His Ser Val Val Gln Gln Leu Lys Ala
                1525                1530                1535

Arg Gln Glu Ala Thr Asp Glu Gln Leu Glu Glu Leu Gln Glu Ala Phe
                1540                1545                1550

Ala Lys Thr Gln Glu Arg Ser Ser Val Phe Ser Asp Trp Met Lys Ile
                1555                1560                1565

Ser Ala Met Leu Cys Ala Ala Thr Leu Ala Leu Ser Gln Val Val Lys
1570                1575                1580

Met Ala Lys Thr Val Lys Gln Met Val Arg Pro Asp Leu Val Arg Val
1585                1590                1595                1600

Gln Leu Asp Glu Gln Glu Gln Gly Pro Tyr Asn Glu Ala Val Arg Ala
                1605                1610                1615

Lys Pro Lys Thr Leu Gln Leu Leu Asp Ile Gln Gly Pro Asn Pro Val
                1620                1625                1630

Met Asp Phe Glu Lys Tyr Val Ala Lys Phe Val Thr Ala Pro Ile Asp
                1635                1640                1645

Phe Val Tyr Pro Thr Gly Val Ser Thr Gln Thr Cys Leu Leu Val Lys
                1650                1655                1660

Gly Arg Thr Leu Ala Val Asn Arg His Met Ala Glu Ser Asp Trp Ser
1665                1670                1675                1680
```

```
Ser Ile Val Val Arg Gly Val Thr His Ala Arg Ser Thr Val Arg Ile
            1685                1690                1695

Leu Ala Ile Ala Lys Ala Gly Lys Glu Thr Asp Val Ser Phe Ile Arg
            1700                1705                1710

Leu Ser Ser Gly Pro Leu Phe Arg Asp Asn Thr Ser Lys Phe Val Lys
            1715                1720                1725

Ala Asp Asp Val Leu Pro Ala Thr Ser Ala Pro Val Ile Gly Ile Met
            1730                1735                1740

Asn Thr Asp Ile Pro Met Met Phe Thr Gly Thr Phe Leu Lys Ala Gly
1745                1750                1755                1760

Val Ser Val Pro Val Glu Thr Gly Gln Thr Phe Asn His Cys Ile His
            1765                1770                1775

Tyr Lys Ala Asn Thr Arg Lys Gly Trp Cys Gly Ser Ala Leu Leu Ala
            1780                1785                1790

Asp Leu Gly Gly Lys Lys Lys Ile Leu Gly Met His Ser Ala Gly Ser
            1795                1800                1805

Met Gly Arg Thr Ala Ala Ser Ile Val Ser Gln Glu Met Ile Cys Ala
            1810                1815                1820

Val Val Ser Ala Phe Glu Pro Gln Gly Ala Leu Glu Arg Leu Pro Asp
1825                1830                1835                1840

Gly Pro Arg Ile His Val Pro Arg Lys Thr Ala Leu Arg Pro Thr Val
            1845                1850                1855

Ala Arg Arg Val Phe Gln Pro Ala Tyr Ala Pro Ala Val Leu Ser Lys
            1860                1865                1870

Phe Asp Pro Arg Thr Glu Ala Asp Val Asp Glu Val Ala Phe Ser Lys
            1875                1880                1885

His Thr Ser Asn Gln Glu Ser Leu Pro Pro Val Phe Arg Met Val Ala
            1890                1895                1900

Lys Glu Tyr Ala Asn Arg Val Phe Thr Leu Leu Gly Arg Asp Asn Gly
1905                1910                1915                1920

Arg Leu Thr Val Lys Gln Ala Leu Glu Gly Leu Glu Gly Met Asp Pro
            1925                1930                1935

Met Asp Lys Asn Thr Ser Pro Gly Leu Pro Tyr Thr Ala Leu Gly Met
            1940                1945                1950

Arg Arg Thr Asp Val Val Asp Trp Glu Ser Ala Thr Leu Ile Pro Tyr
            1955                1960                1965

Ala Ala Asp Arg Leu Lys Lys Met Asn Glu Gly Asp Phe Ser Asp Ile
            1970                1975                1980

Val Tyr Gln Thr Phe Leu Lys Asp Glu Leu Arg Pro Val Glu Lys Val
1985                1990                1995                2000

Gln Ala Ala Lys Thr Arg Ile Val Asp Val Pro Pro Phe Glu His Cys
            2005                2010                2015

Ile Leu Gly Arg Gln Leu Leu Gly Arg Phe Ala Ser Lys Phe Gln Thr
            2020                2025                2030

Gln Pro Gly Leu Glu Leu Gly Ser Ala Ile Gly Cys Asp Pro Asp Val
            2035                2040                2045

His Trp Thr Ala Phe Gly Val Ala Met Gln Gly Phe Glu Arg Val Tyr
            2050                2055                2060

Asp Val Asp Tyr Ser Asn Phe Asp Ser Thr His Ser Val Ala Met Phe
2065                2070                2075                2080

Arg Leu Leu Ala Glu Glu Phe Phe Thr Pro Glu Asn Gly Phe Asp Pro
            2085                2090                2095

Leu Val Lys Glu Tyr Leu Glu Ser Leu Ala Ile Ser Thr His Ala Phe
```

2100 2105 2110

Glu Glu Lys Arg Tyr Leu Ile Thr Gly Gly Leu Pro Ser Gly Cys Ala
2115 2120 2125

Ala Thr Ser Met Leu Asn Thr Ile Met Asn Asn Ile Ile Ile Arg Ala
2130 2135 2140

Gly Leu Tyr Leu Thr Tyr Lys Asn Phe Glu Phe Asp Asp Val Lys Val
2145 2150 2155 2160

Leu Ser Tyr Gly Asp Asp Leu Leu Val Ala Thr Asn Tyr Gln Leu Asn
2165 2170 2175

Phe Asp Lys Val Arg Ala Ser Leu Ala Lys Thr Gly Tyr Lys Ile Thr
2180 2185 2190

Pro Ala Asn Lys Thr Ser Thr Phe Pro Leu Asp Ser Thr Leu Glu Asp
2195 2200 2205

Val Val Phe Leu Lys Arg Lys Phe Lys Lys Glu Gly Pro Leu Tyr Arg
2210 2215 2220

Pro Val Met Asn Arg Glu Ala Leu Glu Ala Met Leu Ser Tyr Tyr Arg
2225 2230 2235 2240

Pro Gly Thr Leu Ser Glu Lys Leu Thr Ser Ile Thr Met Leu Ala Val
2245 2250 2255

His Ser Gly Lys Pro Glu Tyr Asp Arg Leu Phe Ala Pro Phe Arg Glu
2260 2265 2270

Val Gly Val Val Val Pro Ser Phe Glu Ser Val Glu Tyr Arg Trp Arg
2275 2280 2285

Ser Leu Phe Trp
2290

<210> SEQ ID NO 27
<211> LENGTH: 2292
<212> TYPE: PRT
<213> ORGANISM: Encephalomyocarditis virus

<400> SEQUENCE: 27

Met Ala Thr Thr Met Glu Gln Glu Ile Cys Ala His Ser Leu Thr Phe
1 5 10 15

Lys Gly Cys Pro Lys Cys Ser Ala Leu Gln Tyr Arg Asn Gly Phe Tyr
20 25 30

Leu Leu Lys Tyr Asp Glu Glu Trp Tyr Pro Glu Glu Leu Leu Thr Asp
35 40 45

Gly Glu Asp Asp Val Phe Asp Pro Glu Leu Asp Met Glu Val Val Phe
50 55 60

Glu Leu Gln Gly Asn Ser Thr Ser Ser Asp Lys Asn Asn Ser Ser Ser
65 70 75 80

Asp Gly Asn Glu Gly Val Ile Ile Asn Asn Phe Tyr Ser Asn Gln Tyr
85 90 95

Gln Asn Ser Ile Asp Leu Ser Ala Asn Ala Thr Gly Ser Asp Pro Pro
100 105 110

Arg Thr Tyr Gly Gln Phe Ser Asn Leu Leu Ser Gly Ala Val Asn Ala
115 120 125

Phe Ser Asn Met Ile Pro Leu Leu Ala Asp Gln Asn Thr Glu Glu Met
130 135 140

Glu Asn Leu Ser Asp Arg Val Leu Gln Asp Thr Ala Gly Asn Thr Val
145 150 155 160

Thr Asn Thr Gln Ser Thr Val Gly Arg Leu Val Gly Tyr Gly Ala Val
165 170 175

His Asp Gly Glu His Pro Ala Ser Cys Ala Asp Thr Ala Ser Glu Lys

```
                        180             185             190
Ile Leu Ala Val Glu Arg Tyr Tyr Thr Phe Lys Val Asn Asp Trp Thr
                195                 200                 205
Ser Thr Gln Lys Pro Phe Glu Tyr Ile Arg Ile Pro Leu Pro His Val
            210                 215                 220
Leu Ser Gly Glu Asp Gly Val Phe Gly Ala Ala Leu Arg Arg His
225                 230                 235                 240
Tyr Leu Val Lys Thr Gly Trp Pro Val Gln Val Gln Cys Asn Ala Ser
                245                 250                 255
Gln Phe His Ala Gly Ser Leu Leu Val Phe Met Ala Pro Glu Tyr Pro
            260                 265                 270
Thr Leu Asp Ala Phe Ala Met Asp Asn Arg Trp Ser Lys Asp Asn Leu
        275                 280                 285
Pro Asn Gly Thr Lys Thr Gln Thr Asn Arg Lys Gly Pro Phe Ala Met
        290                 295                 300
Asp His Gln Asn Phe Trp Gln Trp Thr Leu Tyr Pro His Gln Phe Leu
305                 310                 315                 320
Asn Leu Arg Thr Asn Thr Thr Val Asp Leu Glu Val Pro Tyr Val Asn
                325                 330                 335
Ile Ala Pro Thr Ser Ser Trp Thr Gln His Ala Ser Trp Thr Leu Val
                340                 345                 350
Ile Ala Val Val Ala Pro Leu Thr Tyr Ser Thr Gly Ala Ser Thr Ser
                355                 360                 365
Leu Asp Ile Thr Ala Ser Ile Gln Pro Val Arg Pro Val Phe Asn Gly
        370                 375                 380
Leu Arg His Glu Thr Leu Ser Arg Gln Ser Pro Ile Pro Val Thr Ile
385                 390                 395                 400
Arg Glu His Ala Gly Thr Trp Tyr Ser Thr Leu Pro Asp Ser Thr Val
                405                 410                 415
Pro Ile Tyr Gly Lys Thr Pro Val Ala Pro Ala Asn Tyr Met Val Gly
                420                 425                 430
Glu Tyr Lys Asp Phe Leu Glu Ile Ala Gln Ile Pro Thr Phe Ile Gly
                435                 440                 445
Asn Lys Ile Pro Asn Ala Val Pro Tyr Ile Glu Ala Ser Asn Thr Ala
        450                 455                 460
Val Lys Thr Gln Pro Leu Ala Thr Tyr Gln Val Thr Leu Ser Cys Ser
465                 470                 475                 480
Cys Leu Ala Asn Thr Phe Leu Ala Ala Leu Ser Arg Asn Phe Ala Gln
                485                 490                 495
Tyr Arg Gly Ser Leu Val Tyr Thr Phe Val Phe Thr Gly Thr Ala Met
                500                 505                 510
Met Lys Gly Lys Phe Leu Ile Ala Tyr Thr Pro Pro Gly Ala Gly Lys
            515                 520                 525
Pro Thr Ser Arg Asp Gln Ala Met Gln Ala Thr Tyr Ala Ile Trp Asp
        530                 535                 540
Leu Gly Leu Asn Ser Ser Tyr Ser Phe Thr Val Pro Phe Ile Ser Pro
545                 550                 555                 560
Thr His Phe Arg Met Val Gly Thr Asp Gln Val Asn Ile Thr Asn Val
                565                 570                 575
Asp Gly Trp Val Thr Val Trp Gln Leu Thr Pro Leu Thr Tyr Pro Pro
                580                 585                 590
Gly Cys Pro Thr Ser Ala Lys Ile Leu Thr Met Val Ser Ala Gly Lys
                595                 600                 605
```

```
Asp Phe Ser Leu Lys Met Pro Ile Ser Pro Ala Pro Trp Ser Pro Gln
        610                 615                 620

Gly Val Glu Asn Ala Glu Arg Gly Val Thr Glu Thr Asp Ala Thr
625                 630                 635                 640

Ala Asp Phe Val Ala Gln Pro Val Tyr Leu Pro Glu Asn Gln Thr Lys
                    645                 650                 655

Val Ala Phe Phe Tyr Asp Arg Ser Ser Pro Ile Gly Ala Phe Thr Val
                660                 665                 670

Lys Ser Gly Ser Leu Glu Ser Gly Phe Ala Pro Phe Ser Asn Glu Thr
            675                 680                 685

Cys Pro Asn Ser Val Ile Leu Thr Pro Gly Pro Gln Phe Asp Pro Ala
        690                 695                 700

Tyr Asp Gln Leu Arg Pro Gln Arg Leu Thr Glu Ile Trp Gly Asn Gly
705                 710                 715                 720

Asn Glu Glu Thr Ser Lys Val Phe Pro Leu Lys Ser Lys Gln Asp Tyr
                    725                 730                 735

Ser Phe Cys Leu Phe Ser Pro Phe Val Tyr Tyr Lys Cys Asp Leu Glu
                740                 745                 750

Val Thr Leu Ser Pro His Thr Ser Gly Asn His Gly Leu Leu Val Arg
            755                 760                 765

Trp Cys Pro Thr Gly Thr Pro Ala Lys Pro Thr Thr Gln Val Leu His
        770                 775                 780

Glu Val Ser Ser Leu Ser Glu Gly Arg Thr Pro Gln Val Tyr Ser Ala
785                 790                 795                 800

Gly Pro Gly Val Ser Asn Gln Ile Ser Phe Val Val Pro Tyr Asn Ser
                    805                 810                 815

Pro Leu Ser Val Leu Pro Ala Val Trp Tyr Asn Gly His Lys Arg Phe
                820                 825                 830

Asp Asn Thr Gly Ser Leu Gly Ile Ala Pro Asn Ser Asp Phe Gly Thr
            835                 840                 845

Leu Phe Phe Ala Gly Thr Lys Pro Asp Ile Lys Phe Thr Val Tyr Leu
        850                 855                 860

Arg Tyr Lys Asn Met Arg Val Phe Cys Pro Arg Pro Thr Val Phe Phe
865                 870                 875                 880

Pro Trp Pro Ser Ser Gly Asp Lys Ile Asp Met Thr Pro Arg Ala Gly
                    885                 890                 895

Val Leu Met Leu Glu Ser Pro Asn Ala Leu Asp Ile Ser Arg Thr Tyr
                900                 905                 910

Pro Thr Leu His Ile Leu Ile Gln Phe Asn His Gly Gly Leu Glu Ile
            915                 920                 925

Arg Leu Phe Arg His Val Gln Phe Trp Ala Glu Ala His Ala Asp Val
        930                 935                 940

Ile Leu Arg Ser Arg Thr Lys Gln Ile Ser Phe Leu Asn Asn Gly Ser
945                 950                 955                 960

Phe Pro Ser Met Asp Ala Arg Ala Pro Trp Asn Pro Trp Lys Asn Thr
                    965                 970                 975

Tyr His Ala Val Leu Arg Ala Glu Pro Tyr Arg Val Thr Met Asp Val
                980                 985                 990

Tyr His Lys Arg Ile Arg Pro Phe Arg Leu Pro Leu Val Gln Lys Glu
            995                 1000                1005

Trp Asn Val Arg Glu Glu Asn Val Phe Gly Leu Tyr Gly Ile Phe Asn
        1010                1015                1020

Ala His Tyr Ala Gly Tyr Phe Ala Asp Leu Leu Ile His Asp Ile Glu
1025                1030                1035                1040
```

```
Thr Asn Pro Gly Pro Phe Met Ala Lys Pro Lys Gln Val Phe Gln
            1045                1050                1055

Thr Gln Gly Ala Ala Val Ser Ser Met Ala Gln Thr Leu Leu Pro Asn
        1060                1065                1070

Asp Leu Ala Ser Lys Val Met Gly Ser Ala Phe Thr Ala Leu Leu Asp
        1075                1080                1085

Ala Asn Glu Asp Ala Gln Lys Ala Met Arg Ile Ile Lys Thr Leu Ser
        1090                1095                1100

Ser Leu Ser Asp Ala Trp Glu Asn Val Lys Glu Thr Leu Asn Asn Pro
1105                1110                1115                1120

Glu Phe Trp Lys Gln Leu Leu Ser Arg Cys Val Gln Leu Ile Ala Gly
            1125                1130                1135

Met Thr Ile Ala Val Met His Pro Asp Pro Leu Thr Leu Leu Cys Leu
            1140                1145                1150

Gly Thr Leu Thr Ala Ala Glu Ile Thr Ser Gln Thr Ser Leu Cys Glu
            1155                1160                1165

Glu Ile Val Ala Lys Phe Lys Lys Ile Phe Thr Thr Pro Pro Pro Arg
            1170                1175                1180

Phe Pro Thr Ile Ser Leu Phe Gln Gln Gln Ser Pro Leu Lys Gln Val
1185                1190                1195                1200

Asn Asp Val Phe Ser Leu Ala Lys Asn Leu Asp Trp Ala Val Lys Thr
            1205                1210                1215

Val Glu Lys Val Val Asp Trp Phe Gly Thr Trp Val Gln Glu Glu
            1220                1225                1230

Lys Glu Gln Thr Leu Asp Gln Leu Leu Gln Arg Phe Pro Glu His Ala
            1235                1240                1245

Lys Arg Ile Ser Asp Leu Arg Asn Gly Met Ser Ala Tyr Val Glu Cys
            1250                1255                1260

Lys Glu Ser Phe Asp Phe Phe Glu Lys Leu Tyr Asn Gln Ala Val Lys
1265                1270                1275                1280

Glu Lys Arg Thr Gly Ile Ala Ala Val Cys Glu Lys Phe Arg Gln Lys
            1285                1290                1295

His Asp His Ala Thr Ala Arg Cys Glu Pro Val Val Ile Val Leu Arg
            1300                1305                1310

Gly Asp Ala Gly Gln Gly Lys Ser Leu Ser Ser Gln Val Ile Ala Gln
            1315                1320                1325

Ala Val Ser Lys Thr Ile Phe Gly Arg Gln Ser Val Tyr Ser Leu Pro
            1330                1335                1340

Pro Asp Ser Asp Phe Phe Asp Gly Tyr Glu Asn Gln Phe Ala Ala Ile
1345                1350                1355                1360

Met Asp Asp Leu Gly Gln Asn Pro Asp Gly Ser Asp Phe Thr Thr Phe
            1365                1370                1375

Cys Gln Met Val Ser Thr Thr Asn Phe Leu Pro Asn Met Ala Ser Leu
            1380                1385                1390

Glu Arg Asn Gly Thr Pro Phe Thr Ser Gln Leu Val Val Ala Thr Thr
            1395                1400                1405

Asn Leu Pro Glu Phe Arg Pro Val Thr Ile Ala His Tyr Pro Ala Val
            1410                1415                1420

Glu Arg Arg Ile Thr Phe Asp Tyr Ser Val Ser Ala Gly Pro Val Cys
1425                1430                1435                1440

Ser Lys Thr Glu Ala Gly Tyr Lys Val Leu Asp Val Glu Arg Ala Phe
            1445                1450                1455

Arg Pro Thr Gly Asp Ala Pro Leu Pro Cys Phe Gln Asn Asn Cys Leu
```

-continued

```
                1460                1465                1470
Phe Leu Glu Lys Ala Gly Leu Gln Phe Arg Asp Asn Arg Thr Lys Glu
        1475                1480                1485
Ile Leu Ser Leu Val Asp Val Ile Glu Arg Ala Val Ala Arg Ile Glu
        1490                1495                1500
Arg Lys Lys Lys Val Leu Thr Thr Val Gln Thr Leu Val Ala Gln Ala
1505                1510                1515                1520
Pro Val Ala Glu Val Ser Phe His Ser Val Val Gln Gln Leu Lys Ala
                1525                1530                1535
Arg Gln Glu Ala Thr Asp Glu Gln Leu Glu Glu Leu Gln Glu Ala Phe
                1540                1545                1550
Ala Lys Thr Gln Glu Arg Ser Ser Val Phe Ser Asp Trp Met Lys Ile
                1555                1560                1565
Ser Ala Met Leu Cys Ala Ala Thr Leu Ala Leu Thr Gln Val Val Lys
        1570                1575                1580
Met Ala Lys Thr Val Lys Gln Met Val Arg Pro Asp Leu Val Arg Val
1585                1590                1595                1600
Gln Leu Asp Glu Gln Glu Gln Gly Pro Tyr Asn Glu Ala Val Arg Ala
                1605                1610                1615
Lys Pro Lys Thr Leu Gln Leu Leu Asp Ile Gln Gly Pro Asn Pro Val
                1620                1625                1630
Met Asp Phe Glu Lys Tyr Val Ala Lys Phe Val Thr Ala Pro Ile Asp
        1635                1640                1645
Phe Val Tyr Pro Thr Gly Val Ser Thr Gln Thr Cys Leu Leu Val Lys
        1650                1655                1660
Gly Arg Thr Leu Ala Val Asn Arg His Met Ala Glu Ser Asp Trp Ser
1665                1670                1675                1680
Ser Ile Val Val Arg Gly Val Thr His Ala Arg Ser Thr Val Arg Ile
                1685                1690                1695
Leu Ala Ile Ala Lys Ala Gly Lys Glu Thr Asp Val Ser Phe Ile Arg
                1700                1705                1710
Leu Ser Ser Gly Pro Leu Phe Arg Asp Asn Thr Ser Lys Phe Val Lys
                1715                1720                1725
Ala Asp Asp Val Leu Pro Ala Thr Ser Ala Pro Val Ile Gly Ile Met
        1730                1735                1740
Asn Thr Asp Ile Pro Met Met Phe Thr Gly Thr Phe Leu Lys Ala Gly
1745                1750                1755                1760
Val Ser Val Pro Val Glu Thr Gly Gln Thr Phe Asn His Cys Ile His
                1765                1770                1775
Tyr Lys Ala Asn Thr Arg Lys Gly Trp Cys Gly Ser Ala Leu Leu Ala
                1780                1785                1790
Asp Leu Gly Gly Lys Lys Lys Ile Leu Gly Met His Ser Ala Gly Ser
        1795                1800                1805
Met Gly Val Ala Ala Ala Ser Ile Val Ser Gln Glu Met Ile Cys Ala
        1810                1815                1820
Val Val Ser Ala Phe Glu Pro Gln Gly Ala Leu Glu Arg Leu Pro Asp
1825                1830                1835                1840
Gly Pro Arg Ile His Val Pro Arg Lys Thr Ala Leu Arg Pro Thr Val
                1845                1850                1855
Ala Arg Gln Val Phe Gln Pro Ala Tyr Ala Pro Ala Val Leu Ser Lys
                1860                1865                1870
Phe Asp Pro Arg Thr Glu Ala Asp Val Asp Glu Val Ala Phe Ser Lys
        1875                1880                1885
```

His Thr Ser Asn Gln Glu Ser Leu Pro Pro Val Phe Arg Met Val Ala
1890                1895                1900

Lys Glu Tyr Ala Asn Arg Val Phe Thr Leu Leu Gly Arg Asp Asn Gly
1905                1910                1915                1920

Arg Leu Thr Val Lys Gln Ala Leu Glu Gly Leu Glu Gly Met Asp Pro
                1925                1930                1935

Met Asp Lys Asn Thr Ser Pro Gly Leu Pro Tyr Thr Ala Leu Gly Met
            1940                1945                1950

Arg Arg Thr Asp Val Val Asp Trp Glu Ser Ala Thr Leu Ile Pro Tyr
            1955                1960                1965

Ala Ala Asp Arg Leu Lys Lys Met Asn Glu Gly Asp Phe Ser Asp Ile
            1970                1975                1980

Val Tyr Gln Thr Phe Leu Lys Asp Glu Leu Arg Pro Val Glu Lys Val
1985                1990                1995                2000

Gln Ala Ala Lys Thr Arg Ile Val Asp Val Pro Pro Phe Glu His Cys
                2005                2010                2015

Ile Leu Gly Arg Gln Leu Leu Gly Arg Phe Ala Ser Lys Phe Gln Thr
                2020                2025                2030

Gln Pro Gly Leu Glu Leu Gly Ser Ala Ile Gly Cys Asp Pro Asp Val
                2035                2040                2045

His Trp Thr Ala Phe Gly Val Ala Met Gln Gly Phe Glu Arg Val Tyr
            2050                2055                2060

Asp Val Asp Tyr Ser Asn Phe Asp Ser Thr His Ser Val Ala Met Phe
2065                2070                2075                2080

Arg Leu Leu Ala Glu Glu Phe Phe Thr Pro Glu Asn Gly Phe Asp Pro
                2085                2090                2095

Leu Val Lys Glu Tyr Leu Glu Ser Leu Ala Ile Ser Thr His Ala Phe
                2100                2105                2110

Glu Glu Lys Arg Tyr Leu Ile Thr Gly Gly Leu Pro Ser Gly Cys Ala
                2115                2120                2125

Ala Thr Ser Met Leu Asn Thr Ile Met Asn Asn Ile Ile Ile Arg Ala
            2130                2135                2140

Gly Leu Tyr Leu Thr Tyr Lys Asn Phe Glu Phe Asp Asp Val Lys Val
2145                2150                2155                2160

Leu Ser Tyr Gly Asp Asp Leu Leu Val Ala Thr Asn Tyr Gln Leu Asn
                2165                2170                2175

Phe Asp Lys Val Arg Ala Ser Leu Ala Lys Thr Gly Tyr Lys Ile Thr
                2180                2185                2190

Pro Ala Asn Lys Thr Ser Thr Phe Pro Leu Asp Ser Thr Leu Glu Asp
            2195                2200                2205

Val Val Phe Leu Lys Arg Lys Phe Lys Lys Glu Gly Pro Leu Tyr Arg
            2210                2215                2220

Pro Val Met Asn Arg Glu Ala Leu Glu Ala Met Leu Ser Tyr Tyr Arg
2225                2230                2235                2240

Pro Gly Thr Leu Ser Glu Lys Leu Thr Ser Ile Thr Met Leu Ala Val
                2245                2250                2255

His Ser Gly Lys Pro Glu Tyr Asp Arg Leu Phe Ala Pro Phe Arg Glu
            2260                2265                2270

Val Gly Val Val Val Pro Ser Phe Glu Ser Val Glu Tyr Arg Trp Arg
            2275                2280                2285

Ser Leu Phe Trp
2290

<210> SEQ ID NO 28

<211> LENGTH: 2292
<212> TYPE: PRT
<213> ORGANISM: Encephalomyocarditis virus

<400> SEQUENCE: 28

```
Met Ala Thr Thr Met Glu Gln Glu Ile Cys Ala His Ser Leu Thr Phe
1               5                   10                  15

Lys Gly Cys Pro Lys Cys Ser Ala Leu Gln Tyr Arg Asn Gly Phe Tyr
            20                  25                  30

Leu Leu Lys Tyr Asp Glu Glu Trp Tyr Pro Glu Glu Leu Leu Thr Asp
        35                  40                  45

Gly Glu Asp Asp Val Phe Asp Pro Glu Leu Asp Met Glu Val Val Phe
50                  55                  60

Glu Leu Gln Gly Asn Ser Thr Ser Ser Asp Lys Asn Asn Ser Ser Ser
65                  70                  75                  80

Asp Gly Asn Glu Gly Val Ile Ile Asn Asn Phe Tyr Ser Asn Gln Tyr
                85                  90                  95

Gln Asn Ser Ile Asp Leu Ser Ala Asn Ala Thr Gly Ser Asp Pro Pro
            100                 105                 110

Arg Thr Tyr Gly Gln Phe Ser Asn Leu Leu Ser Gly Ala Val Asn Ala
        115                 120                 125

Phe Ser Asn Met Ile Pro Leu Leu Ala Asp Gln Asn Thr Glu Glu Met
130                 135                 140

Glu Asn Leu Ser Asp Arg Val Leu Gln Asp Thr Ala Gly Asn Thr Val
145                 150                 155                 160

Thr Asn Thr Gln Ser Thr Val Gly Arg Leu Val Gly Tyr Gly Ala Val
                165                 170                 175

His Asp Gly Glu His Pro Ala Ser Cys Ala Asp Thr Ala Ser Glu Lys
            180                 185                 190

Ile Leu Ala Val Glu Arg Tyr Tyr Thr Phe Lys Val Asn Asp Trp Thr
        195                 200                 205

Ser Thr Gln Lys Pro Phe Glu Tyr Ile Arg Ile Pro Leu Pro His Val
210                 215                 220

Leu Ser Gly Glu Asp Gly Gly Val Phe Gly Ala Ala Leu Arg Arg His
225                 230                 235                 240

Tyr Leu Val Lys Thr Gly Trp Arg Val Gln Val Gln Cys Asn Ala Ser
                245                 250                 255

Gln Phe His Ala Gly Ser Leu Leu Val Phe Met Ala Pro Glu Tyr Pro
            260                 265                 270

Thr Leu Asp Ala Phe Ala Met Asp Asn Arg Trp Ser Lys Asp Asn Leu
        275                 280                 285

Pro Asn Gly Thr Lys Thr Gln Thr Asn Arg Lys Gly Pro Phe Ala Met
290                 295                 300

Asp His Gln Asn Phe Trp Gln Trp Thr Leu Tyr Pro His Gln Phe Leu
305                 310                 315                 320

Asn Leu Arg Thr Asn Thr Thr Val Asp Leu Glu Val Pro Tyr Val Asn
                325                 330                 335

Ile Ala Pro Thr Ser Ser Trp Thr Gln His Ala Ser Trp Thr Leu Val
            340                 345                 350

Ile Ala Val Val Ala Pro Leu Thr Tyr Ser Thr Gly Ala Ser Thr Ser
        355                 360                 365

Leu Asp Ile Thr Ala Ser Ile Gln Pro Val Arg Pro Val Phe Asn Gly
370                 375                 380

Leu Arg His Glu Thr Leu Ser Arg Gln Ser Pro Ile Pro Val Thr Ile
385                 390                 395                 400
```

```
Arg Glu His Ala Gly Thr Trp Tyr Ser Thr Leu Pro Asp Ser Thr Val
                405                 410                 415
Pro Ile Tyr Gly Lys Thr Pro Val Ala Pro Ala Asn Tyr Met Val Gly
            420                 425                 430
Glu Tyr Lys Asp Phe Leu Glu Ile Ala Gln Ile Pro Thr Phe Ile Gly
        435                 440                 445
Asn Lys Ile Pro Asn Ala Val Pro Tyr Ile Glu Ala Ser Asn Thr Ala
    450                 455                 460
Val Lys Thr Gln Pro Leu Ala Thr Tyr Gln Val Thr Leu Ser Cys Ser
465                 470                 475                 480
Cys Leu Ala Asn Thr Phe Leu Ala Ala Leu Ser Arg Asn Phe Ala Gln
                485                 490                 495
Tyr Arg Gly Ser Leu Val Tyr Thr Phe Val Phe Thr Gly Thr Ala Met
            500                 505                 510
Met Lys Gly Lys Phe Leu Ile Ala Tyr Thr Pro Pro Gly Ala Gly Lys
        515                 520                 525
Pro Thr Ser Arg Asp Gln Ala Met Gln Ala Thr Tyr Ala Ile Trp Asp
    530                 535                 540
Leu Gly Leu Asn Ser Ser Tyr Ser Phe Thr Val Pro Phe Ile Ser Pro
545                 550                 555                 560
Thr His Phe Arg Met Val Gly Thr Asp Gln Val Asn Ile Thr Asn Val
                565                 570                 575
Asp Gly Trp Val Thr Val Trp Gln Leu Thr Pro Leu Thr Tyr Pro Pro
            580                 585                 590
Gly Cys Pro Thr Ser Ala Lys Ile Leu Thr Met Val Ser Ala Gly Lys
        595                 600                 605
Asp Phe Ser Leu Lys Met Pro Ile Ser Pro Ala Pro Trp Ser Pro Gln
    610                 615                 620
Gly Val Glu Asn Ala Glu Arg Gly Val Thr Glu Asp Thr Asp Ala Thr
625                 630                 635                 640
Ala Asp Phe Val Ala Gln Pro Val Tyr Leu Pro Glu Asn Gln Thr Lys
                645                 650                 655
Val Ala Phe Phe Tyr Asp Arg Ser Ser Pro Ile Gly Ala Phe Thr Val
            660                 665                 670
Lys Ser Gly Ser Leu Glu Ser Gly Phe Ala Pro Phe Ser Asn Lys Thr
        675                 680                 685
Cys Pro Asn Ser Val Ile Leu Thr Pro Gly Pro Gln Phe Asp Pro Ala
    690                 695                 700
Tyr Asp Gln Leu Arg Pro Gln Arg Leu Thr Glu Ile Trp Gly Asn Arg
705                 710                 715                 720
Asn Glu Glu Thr Ser Lys Val Phe Pro Leu Lys Ser Lys Gln Asp Tyr
                725                 730                 735
Ser Phe Cys Leu Phe Ser Pro Val Tyr Tyr Lys Cys Asp Leu Glu
            740                 745                 750
Val Thr Leu Ser Pro His Thr Ser Gly Asn His Gly Leu Leu Val Arg
        755                 760                 765
Trp Cys Pro Thr Gly Thr Pro Ala Lys Pro Thr Thr Gln Val Leu His
    770                 775                 780
Glu Val Ser Ser Leu Ser Glu Gly Arg Thr Pro Gln Val Tyr Ser Ala
785                 790                 795                 800
Gly Pro Gly Ile Ser Asn Gln Ile Ser Phe Val Val Pro Tyr Asn Ser
                805                 810                 815
Pro Leu Ser Val Leu Pro Ala Val Trp Tyr Asn Gly His Lys Arg Phe
```

-continued

```
                820             825             830
Asp Asn Thr Gly Ser Leu Gly Ile Ala Pro Asn Ser Asp Phe Gly Thr
        835             840             845
Leu Phe Phe Ala Gly Thr Lys Pro Asp Ile Lys Phe Thr Val Tyr Leu
    850             855             860
Arg Tyr Lys Asn Met Arg Val Phe Cys Pro Arg Pro Thr Val Phe Phe
865             870             875             880
Pro Trp Pro Ser Ser Gly Asp Lys Ile Asp Met Thr Pro Arg Ala Gly
            885             890             895
Val Leu Met Leu Glu Ser Pro Asn Ala Leu Asp Ile Ser Arg Thr Tyr
        900             905             910
Pro Thr Leu His Ile Leu Ile Gln Phe Asn His Gly Gly Leu Glu Ile
        915             920             925
Arg Leu Phe Arg His Gly Gln Phe Trp Ala Glu Ala His Ala Asp Val
        930             935             940
Ile Leu Arg Ser Arg Thr Lys Gln Ile Ser Phe Leu Asn Asn Gly Ser
945             950             955             960
Phe Pro Ser Met Asp Ala Arg Ala Pro Trp Asn Pro Trp Lys Asn Thr
            965             970             975
Tyr His Ala Val Leu Arg Ala Glu Pro Tyr Arg Val Thr Met Asp Val
        980             985             990
Tyr His Lys Arg Ile Arg Pro Phe Arg Leu Pro Leu Val Gln Lys Glu
        995             1000            1005
Trp Asn Val Arg Glu Glu Asn Val Phe Gly Leu Tyr Ser Ile Phe Asn
    1010            1015            1020
Ala His Tyr Ala Gly Tyr Phe Ala Asp Leu Leu Ile His Asp Ile Glu
1025            1030            1035            1040
Thr Asn Pro Gly Pro Phe Met Ala Lys Pro Lys Lys Gln Val Phe Gln
            1045            1050            1055
Thr Gln Gly Ala Ala Val Ser Ser Met Ala Gln Thr Leu Leu Pro Asn
        1060            1065            1070
Asp Leu Ala Ser Lys Val Met Gly Ser Ala Phe Thr Ala Leu Leu Asp
        1075            1080            1085
Ala Asn Glu Asp Ala Gln Lys Ala Met Arg Ile Ile Lys Thr Leu Ser
        1090            1095            1100
Ser Leu Ser Asp Ala Trp Glu Asn Val Lys Glu Thr Leu Asn Asn Pro
1105            1110            1115            1120
Glu Phe Trp Lys Gln Leu Leu Ser Arg Cys Val Gln Leu Ile Ala Gly
            1125            1130            1135
Met Thr Ile Ala Val Met His Pro Asp Pro Leu Thr Leu Leu Cys Leu
        1140            1145            1150
Gly Thr Leu Thr Ala Ala Glu Ile Thr Ser Gln Thr Ser Leu Cys Glu
        1155            1160            1165
Glu Ile Val Ala Lys Phe Lys Lys Ile Phe Thr Thr Pro Pro Pro Arg
        1170            1175            1180
Phe Pro Thr Ile Ser Leu Phe Gln Gln Gln Ser Pro Leu Lys Gln Val
1185            1190            1195            1200
Asn Asp Val Phe Ser Leu Ala Lys Asn Leu Asp Trp Ala Val Lys Thr
            1205            1210            1215
Val Glu Lys Val Val Asp Trp Phe Gly Thr Trp Val Val Gln Glu Glu
        1220            1225            1230
Lys Glu Gln Thr Leu Asp Gln Leu Leu Gln Arg Phe Pro Glu His Ala
        1235            1240            1245
```

```
Lys Arg Ile Ser Asp Leu Arg Asn Gly Met Ser Ala Tyr Val Glu Cys
1250                1255                1260

Lys Glu Ser Phe Asp Phe Glu Lys Leu Tyr Asn Gln Ala Val Lys
1265            1270            1275            1280

Glu Lys Arg Thr Gly Ile Ala Ala Val Cys Glu Lys Phe Arg Gln Lys
                1285            1290            1295

His Asp His Ala Thr Ala Arg Cys Glu Pro Val Val Ile Val Leu Arg
                1300            1305            1310

Gly Asp Ala Gly Gln Gly Lys Ser Leu Ser Ser Gln Val Ile Ala Gln
                1315            1320            1325

Ala Val Ser Lys Thr Ile Phe Gly Arg Gln Ser Val Tyr Ser Leu Pro
                1330            1335            1340

Pro Asp Ser Asp Phe Phe Asp Gly Tyr Glu Asn Gln Phe Ala Ala Ile
1345            1350            1355            1360

Met Asp Asp Leu Gly Gln Asn Pro Asp Gly Ser Asp Phe Thr Thr Phe
                1365            1370            1375

Cys Gln Met Val Ser Thr Thr Asn Phe Leu Pro Asn Met Ala Ser Leu
                1380            1385            1390

Glu Arg Lys Gly Thr Pro Phe Thr Ser Gln Leu Val Val Ala Thr Thr
                1395            1400            1405

Asn Leu Pro Glu Phe Arg Pro Val Thr Ile Ala His Tyr Pro Ala Val
1410            1415            1420

Glu Arg Arg Ile Thr Phe Asp Tyr Ser Val Ser Ala Gly Pro Val Cys
1425            1430            1435            1440

Ser Lys Thr Glu Ala Gly Tyr Lys Val Leu Asp Val Glu Arg Ala Phe
                1445            1450            1455

Arg Pro Thr Gly Asp Ala Pro Leu Pro Cys Phe Gln Asn Asn Cys Leu
                1460            1465            1470

Phe Leu Glu Lys Ala Gly Leu Gln Phe Arg Asp Asn Arg Thr Lys Glu
                1475            1480            1485

Ile Leu Ser Leu Val Asp Val Ile Glu Arg Ala Val Ala Arg Ile Glu
                1490            1495            1500

Arg Lys Lys Lys Val Leu Thr Thr Val Gln Thr Leu Val Ala Gln Ala
1505            1510            1515            1520

Pro Val Asp Glu Val Ser Phe His Ser Val Val Gln Gln Leu Lys Ala
                1525            1530            1535

Arg Gln Glu Ala Thr Asp Glu Gln Leu Glu Glu Leu Gln Glu Ala Phe
                1540            1545            1550

Ala Lys Thr Gln Glu Arg Ser Ser Val Phe Ser Asp Trp Met Lys Ile
                1555            1560            1565

Ser Ala Met Leu Cys Ala Ala Thr Leu Ala Leu Thr Gln Val Val Lys
1570            1575            1580

Met Ala Lys Thr Val Lys Gln Met Val Arg Pro Asp Leu Val Arg Val
1585            1590            1595            1600

Gln Leu Asp Glu Gln Glu Gln Gly Pro Tyr Asn Glu Ala Val Arg Ala
                1605            1610            1615

Lys Pro Lys Thr Leu Gln Leu Leu Asp Ile Gln Gly Pro Asn Pro Val
                1620            1625            1630

Met Asp Phe Glu Lys Tyr Val Ala Lys Phe Val Thr Ala Pro Ile Asp
                1635            1640            1645

Phe Val Tyr Pro Thr Gly Val Ser Thr Gln Thr Cys Leu Leu Val Lys
                1650            1655            1660

Gly Arg Thr Leu Ala Val Asn Arg His Met Ala Glu Ser Asp Trp Ser
1665            1670            1675            1680
```

Ser Ile Val Val Arg Gly Val Thr His Ala Arg Ser Thr Val Arg Ile
        1685                1690                1695

Leu Ala Ile Ala Lys Ala Gly Lys Glu Thr Asp Val Ser Phe Ile Arg
        1700                1705                1710

Leu Ser Ser Gly Pro Leu Phe Arg Asp Asn Thr Ser Lys Phe Val Lys
        1715                1720                1725

Ala Asp Asp Val Leu Pro Ala Thr Ser Ala Pro Val Ile Gly Ile Met
        1730                1735                1740

Asn Thr Asp Ile Pro Met Met Phe Thr Gly Thr Phe Leu Lys Ala Gly
1745                1750                1755                1760

Val Ser Val Pro Val Glu Thr Gly Gln Thr Phe Asn His Cys Ile His
        1765                1770                1775

Tyr Lys Ala Asn Thr Arg Lys Gly Trp Cys Gly Ser Ala Leu Leu Ala
        1780                1785                1790

Asp Leu Gly Gly Lys Lys Lys Ile Leu Gly Met His Ser Ala Gly Ser
        1795                1800                1805

Met Gly Arg Thr Ala Ala Ser Ile Val Ser Gln Glu Met Ile Cys Ala
        1810                1815                1820

Val Val Ser Ala Phe Glu Pro Gln Gly Ala Leu Glu Arg Leu Pro Asp
1825                1830                1835                1840

Gly Pro Arg Ile His Val Pro Arg Lys Thr Ala Leu Arg Pro Thr Val
        1845                1850                1855

Ala Arg Gln Val Phe Gln Pro Ala Tyr Ala Pro Ala Val Leu Ser Lys
        1860                1865                1870

Phe Asp Pro Arg Thr Glu Ala Asp Val Asp Glu Val Ala Phe Ser Lys
        1875                1880                1885

His Thr Ser Asn Gln Glu Ser Leu Pro Pro Val Phe Arg Met Val Ala
        1890                1895                1900

Lys Glu Tyr Ala Asn Arg Val Phe Thr Leu Leu Gly Arg Asp Asn Gly
1905                1910                1915                1920

Arg Leu Thr Val Lys Gln Ala Leu Glu Gly Leu Glu Gly Met Asp Pro
        1925                1930                1935

Met Asp Lys Asn Thr Ser Pro Gly Leu Pro Tyr Thr Ala Leu Gly Met
        1940                1945                1950

Arg Arg Thr Asp Val Val Asp Trp Glu Ser Ala Thr Leu Ile Pro Tyr
        1955                1960                1965

Ala Ala Asp Arg Leu Lys Lys Met Asn Glu Gly Asp Phe Ser Asp Ile
        1970                1975                1980

Val Tyr Gln Thr Phe Leu Lys Asp Glu Leu Arg Pro Val Glu Lys Val
1985                1990                1995                2000

Gln Ala Ala Lys Thr Arg Ile Val Asp Val Pro Pro Phe Glu His Cys
        2005                2010                2015

Ile Leu Gly Arg Gln Leu Leu Gly Arg Phe Ala Ser Lys Phe Gln Thr
        2020                2025                2030

Gln Pro Gly Leu Glu Leu Gly Ser Ala Ile Gly Cys Asp Pro Asp Val
        2035                2040                2045

His Trp Thr Ala Phe Gly Val Ala Met Gln Gly Phe Glu Arg Val Tyr
        2050                2055                2060

Asp Val Asp Tyr Ser Asn Phe Asp Ser Thr His Ser Val Ala Met Phe
2065                2070                2075                2080

Arg Leu Leu Ala Glu Glu Phe Phe Thr Pro Glu Asn Gly Phe Asp Pro
        2085                2090                2095

Leu Val Lys Glu Tyr Leu Glu Ser Leu Ala Ile Ser Thr His Ala Phe

-continued

```
                2100                2105                2110
Glu Glu Lys Arg Tyr Leu Ile Thr Gly Gly Leu Pro Ser Gly Cys Ala
            2115                2120                2125

Ala Thr Ser Met Leu Asn Thr Ile Met Asn Asn Ile Ile Ile Arg Ala
        2130                2135                2140

Gly Leu Tyr Leu Thr Tyr Lys Asn Phe Glu Phe Asp Asp Val Lys Val
2145                2150                2155                2160

Leu Ser Tyr Gly Asp Asp Leu Leu Val Ala Thr Asn Tyr Gln Leu Asn
            2165                2170                2175

Phe Asp Lys Val Arg Ala Ser Leu Ala Lys Thr Gly Tyr Lys Ile Thr
        2180                2185                2190

Pro Ala Asn Lys Thr Ser Thr Phe Pro Leu Asp Ser Thr Leu Glu Asp
            2195                2200                2205

Val Val Phe Leu Lys Arg Lys Phe Lys Lys Glu Gly Pro Leu Tyr Arg
        2210                2215                2220

Pro Val Met Asn Arg Glu Ala Leu Glu Ala Met Leu Ser Tyr Tyr Arg
2225                2230                2235                2240

Pro Gly Thr Leu Ser Glu Lys Leu Thr Ser Ile Thr Met Leu Ala Val
            2245                2250                2255

His Ser Gly Lys Pro Glu Tyr Asp Arg Leu Phe Ala Pro Phe Arg Glu
            2260                2265                2270

Val Gly Val Val Val Pro Ser Phe Glu Ser Val Glu Tyr Arg Trp Arg
        2275                2280                2285

Ser Leu Phe Trp
    2290

<210> SEQ ID NO 29
<211> LENGTH: 2293
<212> TYPE: PRT
<213> ORGANISM: Encephalomyocarditis virus

<400> SEQUENCE: 29

Met Ala Thr Thr Met Glu Gln Glu Ile Cys Ala His Ser Met Thr Phe
1               5                   10                  15

Glu Glu Cys Pro Lys Cys Ser Ala Leu Gln Tyr Arg Asn Gly Phe Tyr
            20                  25                  30

Leu Leu Lys Tyr Asp Glu Glu Trp Tyr Pro Glu Glu Ser Leu Thr Asp
        35                  40                  45

Gly Glu Asp Asp Val Phe Asp Pro Asp Leu Asp Met Glu Val Val Phe
    50                  55                  60

Glu Thr Gln Gly Asn Ser Thr Ser Ser Asp Lys Asn Asn Ser Ser Ser
65                  70                  75                  80

Glu Gly Asn Glu Gly Val Ile Ile Asn Asn Phe Tyr Ser Asn Gln Tyr
                85                  90                  95

Gln Asn Ser Ile Asp Leu Ser Ala Asn Ala Thr Gly Ser Asp Pro Pro
            100                 105                 110

Lys Thr Tyr Gly Gln Phe Ser Asn Leu Leu Ser Gly Ala Val Asn Ala
        115                 120                 125

Phe Ser Asn Met Leu Pro Leu Leu Ala Asp Gln Asn Thr Glu Glu Met
    130                 135                 140

Glu Asn Leu Ser Asp Arg Val Ser Gln Asp Thr Ala Gly Asn Thr Val
145                 150                 155                 160

Thr Asn Thr Gln Ser Thr Val Gly Arg Leu Val Gly Tyr Gly Thr Val
                165                 170                 175

His Asp Gly Glu His Pro Ala Ser Cys Ala Asp Thr Ala Ser Glu Lys
```

-continued

```
                180                 185                 190
Ile Leu Ala Val Glu Arg Tyr Tyr Thr Phe Lys Val Asn Asp Trp Thr
            195                 200                 205

Ser Thr Gln Lys Pro Phe Glu Tyr Ile Arg Ile Pro Leu Pro His Val
        210                 215                 220

Leu Ser Gly Glu Asp Gly Val Phe Gly Ala Thr Leu Arg Arg His
225                 230                 235                 240

Tyr Leu Val Lys Thr Gly Trp Arg Val Gln Val Gln Cys Asn Ala Ser
                245                 250                 255

Gln Phe His Ala Gly Ser Leu Leu Val Phe Met Ala Pro Glu Tyr Pro
            260                 265                 270

Thr Leu Asp Val Phe Ala Met Asp Asn Arg Trp Ser Lys Asp Asn Leu
        275                 280                 285

Pro Asn Gly Thr Arg Thr Gln Thr Asn Arg Lys Gly Pro Phe Ala Met
    290                 295                 300

Asp His Gln Asn Phe Trp Gln Trp Thr Leu Tyr Pro His Gln Phe Leu
305                 310                 315                 320

Asn Leu Arg Thr Asn Thr Thr Val Asp Leu Glu Val Pro Tyr Val Asn
                325                 330                 335

Ile Ala Pro Thr Ser Trp Thr Gln His Ala Ser Trp Thr Leu Val
            340                 345                 350

Ile Ala Val Val Ala Pro Leu Thr Tyr Ser Thr Gly Ala Ser Thr Ser
                355                 360                 365

Leu Asp Ile Thr Ala Ser Ile Gln Pro Val Arg Pro Val Phe Asn Gly
        370                 375                 380

Leu Arg His Glu Val Leu Ser Arg Gln Ser Pro Ile Pro Val Thr Ile
385                 390                 395                 400

Arg Glu His Ala Gly Thr Trp Tyr Ser Thr Leu Pro Asp Ser Thr Val
                405                 410                 415

Pro Ile Tyr Gly Lys Thr Pro Val Ala Pro Ala Asn Tyr Met Val Gly
            420                 425                 430

Glu Tyr Lys Asp Phe Leu Glu Ile Ala Gln Ile Pro Thr Phe Ile Gly
        435                 440                 445

Asn Lys Val Pro Asn Ala Val Pro Tyr Ile Glu Ala Ser Asn Thr Ala
    450                 455                 460

Val Lys Thr Gln Pro Leu Ala Val Tyr Gln Val Thr Leu Ser Cys Ser
465                 470                 475                 480

Cys Leu Ala Asn Thr Phe Leu Ala Ala Leu Ser Arg Asn Phe Ala Gln
                485                 490                 495

Tyr Arg Gly Ser Leu Val Tyr Thr Phe Val Phe Thr Gly Thr Ala Met
            500                 505                 510

Met Lys Gly Lys Phe Leu Ile Ala Tyr Thr Pro Pro Gly Ala Gly Lys
        515                 520                 525

Pro Thr Ser Arg Asp Gln Ala Met Gln Ala Thr Tyr Ala Ile Trp Asp
    530                 535                 540

Leu Gly Leu Asn Ser Ser Tyr Ser Phe Thr Val Pro Phe Ile Ser Pro
545                 550                 555                 560

Thr His Phe Arg Met Val Gly Thr Asp Gln Ala Asn Ile Thr Asn Val
                565                 570                 575

Asp Gly Trp Val Thr Val Trp Gln Leu Thr Pro Leu Thr Tyr Pro Pro
            580                 585                 590

Gly Cys Pro Thr Ser Ala Lys Ile Leu Thr Met Val Ser Ala Gly Lys
        595                 600                 605
```

-continued

```
Asp Phe Ser Leu Lys Met Pro Ile Ser Pro Ala Pro Trp Ser Pro Gln
610                 615                 620
Gly Val Glu Asn Ala Glu Lys Gly Val Thr Glu Asn Thr Asp Ala Thr
625                 630                 635                 640
Ala Asp Phe Val Ala Gln Pro Val Tyr Leu Pro Glu Asn Gln Thr Lys
                645                 650                 655
Val Ala Phe Phe Tyr Asp Arg Ser Ser Pro Ile Gly Ala Phe Ala Val
                660                 665                 670
Lys Ser Gly Ser Leu Glu Ser Gly Phe Ala Pro Phe Ser Asn Lys Ala
                675                 680                 685
Cys Pro Asn Ser Val Ile Leu Thr Pro Gly Pro Gln Phe Asp Pro Ala
690                 695                 700
Tyr Asp Gln Leu Arg Pro Gln Arg Leu Thr Glu Ile Trp Gly Asn Gly
705                 710                 715                 720
Asn Glu Glu Thr Ser Glu Val Phe Pro Leu Lys Thr Lys Gln Asp Tyr
                725                 730                 735
Ser Phe Cys Leu Phe Ser Pro Phe Val Tyr Lys Cys Asp Leu Glu
                740                 745                 750
Val Thr Leu Ser Pro His Thr Ser Gly Ala His Gly Leu Leu Val Arg
                755                 760                 765
Trp Cys Pro Thr Gly Thr Pro Thr Lys Pro Thr Thr Gln Val Leu His
770                 775                 780
Glu Val Ser Ser Leu Ser Glu Gly Arg Thr Pro Gln Val Tyr Ser Ala
785                 790                 795                 800
Gly Pro Gly Thr Ser Asn Gln Ile Ser Phe Val Val Pro Tyr Asn Ser
                805                 810                 815
Pro Leu Ser Val Leu Pro Ala Val Trp Tyr Asn Gly His Lys Arg Phe
                820                 825                 830
Asp Asn Thr Gly Asp Leu Gly Ile Ala Pro Asn Ser Asp Phe Gly Thr
                835                 840                 845
Leu Phe Phe Ala Gly Thr Lys Pro Asp Ile Lys Phe Thr Val Tyr Leu
850                 855                 860
Arg Tyr Lys Asn Met Arg Val Phe Cys Pro Arg Pro Thr Val Phe Phe
865                 870                 875                 880
Pro Trp Pro Thr Ser Gly Asp Lys Ile Asp Met Thr Pro Arg Ala Gly
                885                 890                 895
Val Leu Met Leu Glu Ser Pro Asn Pro Leu Asp Val Ser Lys Thr Tyr
                900                 905                 910
Pro Thr Leu His Ile Leu Leu Gln Phe Asn His Arg Gly Leu Glu Ala
                915                 920                 925
Arg Ile Phe Arg His Gly Gln Leu Trp Ala Glu Thr His Ala Glu Val
930                 935                 940
Val Leu Arg Ser Lys Thr Lys Gln Ile Ser Phe Leu Ser Asn Gly Ser
945                 950                 955                 960
Tyr Pro Ser Met Asp Ala Thr Thr Pro Leu Asn Pro Trp Lys Ser Thr
                965                 970                 975
Tyr Gln Ala Val Leu Arg Ala Glu Pro His Arg Val Thr Met Asp Val
                980                 985                 990
Tyr His Lys Arg Ile Arg Pro Phe Arg Leu Pro Leu Val Gln Lys Glu
                995                 1000                1005
Trp Arg Thr Cys Glu Glu Asn Val Phe Gly Leu Tyr His Val Phe Glu
        1010                1015                1020
Thr His Tyr Ala Gly Tyr Phe Ser Asp Leu Leu Ile His Asp Val Glu
1025                1030                1035                1040
```

Thr Asn Pro Gly Pro Phe Thr Phe Lys Pro Arg Gln Arg Pro Val Phe
                1045                1050                1055

Gln Thr Gln Gly Ala Ala Val Ser Ser Met Ala Gln Thr Leu Leu Pro
                1060                1065                1070

Asn Asp Leu Ala Ser Lys Ala Met Gly Ser Ala Phe Thr Ala Leu Leu
                1075                1080                1085

Asp Ala Asn Glu Asp Ala Gln Lys Ala Met Lys Ile Ile Lys Thr Leu
                1090                1095                1100

Ser Ser Leu Ser Asp Ala Trp Glu Asn Val Lys Gly Thr Leu Asn Asn
1105                1110                1115                1120

Pro Glu Phe Trp Lys Gln Leu Leu Ser Arg Cys Val Gln Leu Ile Ala
                1125                1130                1135

Gly Met Thr Ile Ala Val Met His Pro Asp Pro Leu Thr Leu Leu Cys
                1140                1145                1150

Leu Gly Val Leu Thr Ala Ala Glu Ile Thr Ser Gln Thr Ser Leu Cys
                1155                1160                1165

Glu Glu Ile Ala Ala Lys Phe Lys Thr Ile Phe Thr Thr Pro Pro Pro
                1170                1175                1180

Arg Phe Pro Val Ile Ser Leu Phe Gln Gln Gln Ser Pro Leu Lys Gln
1185                1190                1195                1200

Val Asn Asp Val Phe Ser Leu Ala Lys Asn Leu Asp Trp Ala Val Lys
                1205                1210                1215

Thr Val Glu Lys Val Val Asp Trp Phe Gly Thr Trp Val Ala Gln Glu
                1220                1225                1230

Glu Arg Glu Gln Thr Leu Asp Gln Leu Leu Gln Arg Phe Pro Glu His
                1235                1240                1245

Ala Lys Arg Ile Ser Asp Leu Arg Asn Gly Met Ala Ala Tyr Val Glu
                1250                1255                1260

Cys Lys Glu Ser Phe Asp Phe Phe Glu Lys Leu Tyr Asn Gln Ala Val
1265                1270                1275                1280

Lys Glu Lys Arg Thr Gly Ile Ala Ala Val Cys Glu Lys Phe Arg Gln
                1285                1290                1295

Lys His Asp His Ala Thr Ala Arg Cys Glu Pro Val Val Ile Val Leu
                1300                1305                1310

Arg Gly Asp Ala Gly Gln Gly Lys Ser Leu Ser Ser Gln Ile Ile Ala
                1315                1320                1325

Gln Ala Val Ser Lys Thr Ile Phe Gly Arg Gln Ser Val Tyr Ser Leu
                1330                1335                1340

Pro Pro Asp Ser Asp Phe Phe Asp Gly Tyr Glu Asn Gln Phe Ala Ala
1345                1350                1355                1360

Ile Met Asp Asp Leu Gly Gln Asn Pro Asp Gly Ser Asp Phe Thr Thr
                1365                1370                1375

Phe Cys Gln Met Val Ser Thr Thr Asn Leu Leu Pro Asn Met Ala Ser
                1380                1385                1390

Leu Glu Arg Lys Gly Thr Pro Phe Thr Ser Gln Leu Val Val Ala Thr
                1395                1400                1405

Thr Asn Leu Pro Glu Phe Arg Pro Val Thr Ile Ala His Tyr Pro Ala
                1410                1415                1420

Val Glu Arg Arg Ile Thr Phe Asp Tyr Ser Val Ser Ala Gly Pro Val
1425                1430                1435                1440

Cys Ser Lys Thr Glu Ala Gly Cys Lys Val Leu Asp Val Glu Arg Ala
                1445                1450                1455

Phe Arg Pro Thr Gly Asp Ala Pro Leu Pro Cys Phe Gln Asn Asn Cys

```
                1460            1465            1470
Leu Phe Leu Glu Lys Ala Gly Leu Gln Phe Arg Asp Asn Arg Ser Lys
            1475            1480            1485
Glu Ile Leu Ser Leu Val Asp Val Ile Glu Arg Ala Val Thr Arg Ile
            1490            1495        1500
Glu Arg Lys Lys Val Leu Thr Ala Val Gln Thr Leu Val Ala Gln
1505            1510            1515            1520
Gly Pro Val Asp Glu Val Ser Phe Tyr Ser Val Gln Gln Leu Lys
                1525            1530            1535
Ala Arg Gln Glu Ala Thr Asp Glu Gln Leu Glu Glu Leu Gln Glu Ala
            1540            1545            1550
Phe Ala Arg Val Gln Glu Arg Ser Ser Val Phe Ser Asp Trp Met Lys
            1555            1560            1565
Ile Ser Ala Met Leu Cys Ala Ala Thr Leu Ala Leu Thr Gln Val Val
            1570            1575            1580
Lys Met Ala Lys Ala Val Lys Gln Met Val Arg Pro Asp Leu Val Arg
1585            1590            1595            1600
Val Gln Leu Asp Glu Gln Glu Gln Gly Pro Tyr Asn Glu Thr Thr Arg
                1605            1610            1615
Ile Lys Pro Lys Thr Leu Gln Leu Leu Asp Val Gln Gly Pro Asn Pro
            1620            1625            1630
Thr Met Asp Phe Glu Lys Phe Val Ala Lys Phe Val Thr Ala Pro Ile
            1635            1640            1645
Gly Phe Val Tyr Pro Thr Gly Val Ser Thr Gln Thr Cys Leu Leu Val
            1650            1655            1660
Lys Gly Arg Thr Leu Ala Val Asn Arg His Met Ala Glu Ser Asp Trp
1665            1670            1675            1680
Thr Ser Ile Val Val Arg Gly Val Ser His Thr Arg Ser Ser Val Lys
                1685            1690            1695
Ile Ile Ala Ile Ala Lys Ala Gly Lys Glu Thr Asp Val Ser Phe Ile
            1700            1705            1710
Arg Leu Ser Ser Gly Pro Leu Phe Arg Asp Asn Thr Ser Lys Phe Val
            1715            1720            1725
Lys Ala Ser Asp Val Leu Pro His Ser Ser Pro Leu Ile Gly Ile
            1730            1735            1740
Met Asn Val Asp Ile Pro Met Met Tyr Thr Gly Thr Phe Leu Lys Ala
1745            1750            1755            1760
Gly Val Ser Val Pro Val Glu Thr Gly Gln Thr Phe Asn His Cys Ile
                1765            1770            1775
His Tyr Lys Ala Asn Thr Arg Lys Gly Trp Cys Gly Ser Ala Ile Leu
            1780            1785            1790
Ala Asp Leu Gly Gly Ser Lys Lys Ile Leu Gly Phe His Ser Ala Gly
            1795            1800            1805
Ser Met Gly Val Ala Ala Ala Ser Ile Ile Ser Gln Glu Met Ile Asp
            1810            1815            1820
Ala Val Val Gln Ala Phe Glu Pro Gln Gly Ala Leu Glu Arg Leu Pro
1825            1830            1835            1840
Asp Gly Pro Arg Ile His Val Pro Arg Lys Thr Ala Leu Arg Pro Thr
                1845            1850            1855
Val Ala Arg Gln Val Phe Gln Pro Ala Phe Ala Pro Ala Val Leu Ser
            1860            1865            1870
Lys Phe Asp Pro Arg Thr Asp Ala Asp Val Asp Glu Val Ala Phe Ser
            1875            1880            1885
```

```
Lys His Thr Ser Asn Gln Glu Thr Leu Pro Pro Val Phe Arg Met Val
    1890                1895                1900

Ala Arg Glu Tyr Ala Asn Arg Val Phe Ala Leu Leu Gly Arg Asp Asn
1905                1910                1915                1920

Gly Arg Leu Ser Val Lys Gln Ala Leu Asp Gly Leu Glu Gly Met Asp
                1925                1930                1935

Pro Met Asp Lys Asn Thr Ser Pro Gly Leu Pro Tyr Thr Thr Leu Gly
            1940                1945                1950

Met Arg Arg Thr Asp Val Val Asp Trp Glu Thr Ala Thr Leu Ile Pro
        1955                1960                1965

Phe Ala Ala Glu Arg Leu Glu Lys Met Asn Asn Lys Asp Phe Ser Asp
    1970                1975                1980

Ile Val Tyr Gln Thr Phe Leu Lys Asp Glu Leu Arg Pro Ile Glu Lys
1985                1990                1995                2000

Val Gln Ala Ala Lys Thr Arg Ile Val Asp Val Pro Pro Phe Glu His
                2005                2010                2015

Cys Ile Leu Gly Arg Gln Leu Leu Gly Lys Phe Ala Ser Lys Phe Gln
            2020                2025                2030

Thr Gln Pro Gly Leu Glu Leu Gly Ser Ala Ile Gly Cys Asp Pro Asp
        2035                2040                2045

Val His Trp Thr Ala Phe Gly Val Ala Met Gln Gly Phe Glu Arg Val
    2050                2055                2060

Tyr Asp Val Asp Tyr Ser Asn Phe Asp Ser Thr His Ser Val Ala Ile
2065                2070                2075                2080

Phe Arg Leu Leu Ala Glu Phe Phe Ser Glu Asn Gly Phe Asp
                2085                2090                2095

Pro Leu Val Lys Asp Tyr Leu Glu Ser Leu Ala Ile Ser Lys His Ala
            2100                2105                2110

Tyr Glu Glu Lys Arg Tyr Leu Ile Thr Gly Gly Leu Pro Ser Gly Cys
        2115                2120                2125

Ala Ala Thr Ser Met Leu Asn Thr Ile Met Asn Asn Ile Ile Ile Arg
    2130                2135                2140

Ala Gly Leu Tyr Leu Thr Tyr Lys Asn Phe Glu Phe Asp Asp Val Lys
2145                2150                2155                2160

Val Leu Ser Tyr Gly Asp Asp Leu Leu Val Ala Thr Asn Tyr Gln Leu
                2165                2170                2175

Asn Phe Asp Arg Val Arg Thr Ser Leu Ala Lys Thr Gly Tyr Lys Ile
            2180                2185                2190

Thr Pro Ala Asn Lys Thr Ser Thr Phe Pro Leu Glu Ser Thr Leu Glu
        2195                2200                2205

Asp Val Val Phe Leu Lys Arg Lys Phe Lys Glu Gly Pro Leu Tyr
    2210                2215                2220

Arg Pro Val Met Asn Arg Glu Ala Leu Glu Ala Met Leu Ser Tyr Tyr
2225                2230                2235                2240

Arg Pro Gly Thr Leu Ser Glu Lys Leu Thr Ser Ile Thr Met Leu Ala
                2245                2250                2255

Val His Ser Gly Lys Gln Glu Tyr Asp Arg Leu Phe Ala Pro Phe Arg
            2260                2265                2270

Glu Val Gly Val Ile Val Pro Thr Phe Glu Ser Val Glu Tyr Arg Trp
        2275                2280                2285

Arg Ser Leu Phe Trp
    2290

<210> SEQ ID NO 30
```

<211> LENGTH: 2301
<212> TYPE: PRT
<213> ORGANISM: Theiler's murine encephalomyelitis virus

<400> SEQUENCE: 30

```
Met Ala Cys Lys His Gly Tyr Pro Asp Val Cys Pro Ile Cys Thr Ala
1               5                   10                  15

Val Asp Val Thr Pro Gly Phe Glu Tyr Leu Leu Leu Ala Asp Gly Glu
            20                  25                  30

Trp Phe Pro Thr Asp Leu Leu Cys Val Asp Leu Asp Asp Asp Val Phe
        35                  40                  45

Trp Pro Ser Asn Ser Ser Asn Gln Ser Glu Thr Met Glu Trp Thr Asp
    50                  55                  60

Leu Pro Leu Val Arg Asp Ile Val Met Glu Pro Gln Gly Asn Ala Ser
65                  70                  75                  80

Ser Ser Asp Lys Ser Asn Ser Gln Ser Ser Gly Asn Glu Gly Val Ile
                85                  90                  95

Ile Asn Asn Phe Tyr Ser Asn Gln Tyr Gln Asn Ser Ile Asp Leu Ser
            100                 105                 110

Ala Ser Gly Gly Asn Ala Gly Asp Ala Pro Gln Asn Asn Gly Gln Leu
        115                 120                 125

Ser Asn Ile Leu Gly Gly Ala Ala Asn Ala Phe Ala Thr Met Ala Pro
    130                 135                 140

Leu Leu Leu Asp Gln Asn Thr Glu Glu Met Glu Asn Leu Ser Asp Arg
145                 150                 155                 160

Val Ala Ser Asp Lys Ala Gly Asn Ser Ala Thr Asn Thr Gln Ser Thr
                165                 170                 175

Val Gly Arg Leu Cys Gly Tyr Gly Glu Ala His His Gly Glu His Pro
            180                 185                 190

Ala Ser Cys Ala Asp Thr Ala Thr Asp Lys Val Leu Ala Ala Glu Arg
        195                 200                 205

Tyr Tyr Thr Ile Asp Leu Ala Ser Trp Thr Thr Thr Gln Glu Ala Phe
    210                 215                 220

Ser His Ile Arg Ile Pro Leu Pro His Val Leu Ala Gly Glu Asp Gly
225                 230                 235                 240

Gly Val Phe Gly Ala Thr Leu Arg Arg His Tyr Leu Cys Lys Thr Gly
                245                 250                 255

Trp Arg Val Gln Val Gln Cys Asn Ala Ser Gln Phe His Ala Gly Ser
            260                 265                 270

Leu Leu Val Phe Met Ala Pro Glu Phe Tyr Thr Gly Lys Gly Thr Lys
        275                 280                 285

Thr Gly Asp Met Glu Pro Thr Asp Pro Phe Thr Met Asp Thr Thr Trp
    290                 295                 300

Arg Ala Pro Gln Gly Ala Pro Thr Gly Tyr Arg Tyr Asp Ser Arg Thr
305                 310                 315                 320

Gly Phe Phe Ala Met Asn His Gln Asn Gln Trp Gln Trp Thr Val Tyr
                325                 330                 335

Pro His Gln Ile Leu Asn Leu Arg Thr Asn Thr Thr Val Asp Leu Glu
            340                 345                 350

Val Pro Tyr Val Asn Ile Ala Pro Thr Ser Ser Trp Thr Gln His Ala
        355                 360                 365

Asn Trp Thr Leu Val Val Ala Val Phe Ser Pro Leu Gln Tyr Ala Ser
    370                 375                 380

Gly Ser Ser Ser Asp Val Gln Ile Thr Ala Ser Ile Gln Pro Val Asn
385                 390                 395                 400
```

```
Pro Val Phe Asn Gly Leu Arg His Glu Thr Val Ile Ala Gln Ser Pro
                405                 410                 415
Ile Ala Val Thr Val Arg Glu His Lys Gly Cys Phe Tyr Ser Thr Asn
                420                 425                 430
Pro Asp Thr Thr Val Pro Ile Tyr Gly Lys Thr Ile Ser Thr Pro Asn
                435                 440                 445
Asp Tyr Met Cys Gly Glu Phe Ser Asp Leu Glu Leu Cys Lys Leu
    450                 455                 460
Pro Thr Phe Leu Gly Asn Pro Asn Ser Asn Asn Lys Arg Tyr Pro Tyr
465                 470                 475                 480
Phe Ser Ala Thr Asn Ser Val Pro Thr Thr Ser Leu Val Asp Tyr Gln
                485                 490                 495
Val Ala Leu Ser Cys Ser Cys Met Cys Asn Ser Met Leu Ala Ala Val
                500                 505                 510
Ala Arg Asn Phe Asn Gln Tyr Arg Gly Ser Leu Asn Phe Leu Phe Val
                515                 520                 525
Phe Thr Gly Ala Ala Met Val Lys Gly Lys Phe Leu Ile Ala Tyr Thr
                530                 535                 540
Pro Pro Gly Ala Gly Lys Pro Thr Thr Arg Asp Gln Ala Met Gln Ala
545                 550                 555                 560
Thr Tyr Ala Ile Trp Asp Leu Gly Leu Asn Ser Ser Phe Val Phe Thr
                565                 570                 575
Ala Pro Phe Ile Ser Pro Thr His Tyr Arg Gln Thr Ser Tyr Thr Ser
                580                 585                 590
Ala Thr Ile Ala Ser Val Asp Gly Trp Val Thr Val Trp Gln Leu Thr
                595                 600                 605
Pro Leu Thr Tyr Pro Ser Gly Ala Pro Val Asn Ser Asp Ile Leu Thr
                610                 615                 620
Leu Val Ser Ala Gly Asp Asp Phe Thr Leu Arg Met Pro Ile Ser Pro
625                 630                 635                 640
Thr Lys Trp Ala Pro Gln Gly Ser Asp Asn Ala Glu Lys Gly Lys Val
                645                 650                 655
Ser Asn Asp Asp Ala Ser Val Asp Phe Val Ala Glu Pro Val Lys Leu
                660                 665                 670
Pro Glu Asn Gln Thr Arg Val Ala Phe Phe Tyr Asp Arg Ala Val Pro
                675                 680                 685
Ile Gly Met Leu Arg Pro Gly Gln Asn Ile Glu Ser Thr Phe Val Tyr
                690                 695                 700
Gln Glu Asn Asp Leu Arg Leu Asn Cys Leu Leu Leu Thr Pro Leu Pro
705                 710                 715                 720
Ser Phe Cys Pro Asp Ser Thr Ser Gly Pro Val Lys Thr Lys Ala Pro
                725                 730                 735
Val Gln Trp Arg Trp Val Arg Ser Gly Gly Thr Thr Asn Phe Pro Leu
                740                 745                 750
Met Thr Lys Gln Asp Tyr Ala Phe Leu Cys Phe Ser Pro Phe Thr Tyr
                755                 760                 765
Tyr Lys Cys Asp Leu Glu Val Thr Val Ser Ala Leu Gly Thr Asp Thr
                770                 775                 780
Val Ala Ser Val Leu Arg Trp Ala Pro Thr Gly Ala Pro Ala Asp Val
785                 790                 795                 800
Thr Asp Gln Leu Ile Gly Tyr Thr Pro Ser Leu Gly Glu Thr Arg Asn
                805                 810                 815
Pro His Met Trp Leu Val Gly Ala Gly Asn Thr Gln Ile Ser Phe Val
```

```
                820             825             830
Val Pro Tyr Asn Ser Pro Leu Ser Val Leu Pro Ala Ala Trp Phe Asn
            835             840             845
Gly Trp Ser Asp Phe Gly Asn Thr Lys Asp Phe Gly Val Ala Pro Asn
        850             855             860
Ala Asp Phe Gly Arg Leu Trp Ile Gln Gly Asn Thr Ser Ala Ser Val
865             870             875             880
Arg Ile Arg Tyr Lys Lys Met Lys Val Phe Cys Pro Arg Pro Thr Leu
            885             890             895
Phe Phe Pro Trp Pro Val Ser Thr Arg Ser Lys Ile Asn Ala Asp Asn
        900             905             910
Pro Val Pro Ile Leu Glu Leu Glu Asn Pro Ala Ala Phe Tyr Arg Ile
        915             920             925
Asp Leu Phe Ile Thr Phe Ile Asp Glu Phe Ile Thr Phe Asp Tyr Lys
        930             935             940
Val His Gly Arg Pro Val Leu Thr Phe Arg Ile Pro Gly Phe Gly Leu
945             950             955             960
Thr Pro Ala Gly Arg Met Leu Val Cys Met Gly Glu Lys Pro Ala His
            965             970             975
Gly Pro Phe Thr Ser Ser Arg Ser Leu Tyr His Val Ile Phe Thr Ala
            980             985             990
Thr Cys Ser Ser Phe Ser Phe Ser Ile Tyr Lys Gly Arg Tyr Arg Ser
            995             1000            1005
Trp Lys Lys Pro Ile His Asp Glu Leu Val Asp Arg Gly Tyr Thr Thr
        1010            1015            1020
Phe Gly Glu Phe Phe Arg Ala Val Arg Ala Tyr His Ala Asp Tyr Tyr
1025            1030            1035            1040
Lys Gln Arg Leu Ile His Asp Val Glu Met Asn Pro Gly Pro Val Gln
            1045            1050            1055
Ser Val Phe Gln Pro Gln Gly Ala Val Leu Thr Lys Ser Leu Ala Pro
            1060            1065            1070
Gln Ala Gly Ile Gln Asn Leu Leu Leu Arg Leu Leu Gly Ile Asp Gly
            1075            1080            1085
Asp Cys Ser Glu Val Ser Lys Ala Ile Thr Val Val Thr Asp Leu Phe
        1090            1095            1100
Ala Ala Trp Glu Arg Ala Lys Thr Thr Leu Val Ser Pro Glu Phe Trp
1105            1110            1115            1120
Ser Lys Leu Ile Leu Lys Thr Thr Lys Phe Ile Ala Ala Ser Val Leu
            1125            1130            1135
Tyr Leu His Asn Pro Asp Phe Thr Thr Thr Val Cys Leu Ser Leu Met
            1140            1145            1150
Thr Gly Val Asp Leu Leu Thr Asn Asp Ser Val Phe Asp Trp Leu Lys
            1155            1160            1165
Asn Lys Leu Ser Ser Phe Arg Thr Pro Pro Val Cys Pro Asn
            1170            1175            1180
Val Leu Gln Pro Gln Gly Pro Leu Arg Glu Ala Asn Glu Gly Phe Thr
1185            1190            1195            1200
Phe Ala Lys Asn Ile Glu Trp Ala Met Lys Thr Ile Gln Ser Ile Val
            1205            1210            1215
Asn Trp Leu Thr Ser Trp Phe Lys Gln Glu Asp His Pro Gln Ser
            1220            1225            1230
Lys Leu Asp Lys Phe Leu Met Glu Phe Pro Asp His Cys Arg Asn Ile
            1235            1240            1245
```

-continued

```
Met Asp Met Arg Asn Gly Arg Lys Ala Tyr Cys Glu Cys Thr Ala Ser
    1250                1255                1260
Phe Lys Tyr Phe Asp Glu Leu Tyr Asn Leu Ala Val Thr Cys Lys Arg
1265            1270                1275                1280
Ile Pro Leu Ala Ser Leu Cys Glu Lys Phe Lys Asn Arg His Asp His
                1285                1290                1295
Ser Val Thr Arg Pro Glu Pro Val Val Val Leu Arg Gly Ala Ala
            1300                1305                1310
Gly Gln Gly Lys Ser Val Thr Ser Gln Ile Ile Ala Gln Ser Val Ser
        1315                1320                1325
Lys Met Ala Phe Gly Arg Gln Ser Val Tyr Ser Met Pro Pro Asp Ser
    1330                1335                1340
Glu Tyr Phe Asp Gly Tyr Glu Asn Gln Phe Ser Val Ile Met Asp Asp
1345            1350                1355                1360
Leu Gly Gln Asn Pro Asp Gly Glu Asp Phe Thr Val Phe Cys Gln Met
                1365                1370                1375
Val Ser Ser Thr Asn Phe Leu Pro Asn Met Ala His Leu Glu Arg Lys
            1380                1385                1390
Gly Thr Pro Phe Thr Ser Ser Phe Ile Val Ala Thr Thr Asn Leu Pro
        1395                1400                1405
Lys Phe Arg Pro Val Thr Val Ala His Tyr Pro Ala Val Asp Arg Arg
    1410                1415                1420
Ile Thr Phe Asp Phe Thr Val Thr Ala Gly Pro His Cys Thr Thr Ser
1425            1430                1435                1440
Asn Gly Met Leu Asp Ile Glu Lys Ala Phe Asp Glu Ile Pro Gly Ser
                1445                1450                1455
Lys Pro Gln Leu Ala Cys Phe Ser Ala Asp Cys Pro Leu Leu His Lys
            1460                1465                1470
Arg Gly Val Met Phe Thr Cys Asn Arg Thr Lys Ala Val Tyr Asn Leu
        1475                1480                1485
Gln Gln Val Val Lys Met Val Asn Asp Thr Ile Thr Arg Lys Thr Glu
    1490                1495                1500
Asn Val Lys Lys Met Asn Ser Leu Val Ala Gln Ser Pro Pro Asp Trp
1505            1510                1515                1520
Glu His Phe Glu Asn Ile Leu Thr Cys Leu Arg Gln Asn Asn Ala Ala
                1525                1530                1535
Leu Gln Asp Gln Leu Asp Glu Leu Gln Glu Ala Phe Ala Gln Ala Arg
            1540                1545                1550
Glu Arg Ser Asp Phe Leu Ser Asp Trp Leu Lys Val Ser Ala Ile Ile
        1555                1560                1565
Phe Ala Gly Ile Ala Ser Leu Ser Ala Val Ile Lys Leu Ala Ser Lys
    1570                1575                1580
Phe Lys Glu Ser Ile Trp Pro Ser Pro Val Arg Val Glu Leu Ser Glu
1585            1590                1595                1600
Gly Glu Gln Ala Ala Tyr Ala Gly Arg Ala Arg Ala Gln Lys Gln Ala
                1605                1610                1615
Leu Gln Val Leu Asp Ile Gln Gly Gly Gly Lys Val Leu Ala Gln Ala
            1620                1625                1630
Gly Asn Pro Val Met Asp Phe Glu Leu Phe Cys Ala Lys Asn Met Val
        1635                1640                1645
Ala Pro Ile Thr Phe Tyr Tyr Pro Asp Lys Ala Glu Val Thr Gln Ser
    1650                1655                1660
Cys Leu Leu Leu Arg Ala His Leu Phe Val Val Asn Arg His Val Ala
1665            1670                1675                1680
```

```
Glu Thr Glu Trp Thr Ala Phe Lys Leu Lys Asp Val Arg His Glu Arg
            1685                1690                1695

Asp Thr Val Val Thr Arg Ser Val Asn Arg Ser Gly Ala Glu Thr Asp
            1700                1705                1710

Leu Thr Phe Ile Lys Val Thr Lys Gly Pro Leu Phe Lys Asp Asn Val
        1715                1720                1725

Asn Lys Phe Cys Ser Asn Lys Asp Asp Phe Pro Ala Arg Asn Asp Ala
        1730                1735                1740

Val Thr Gly Ile Met Asn Thr Gly Leu Ala Phe Val Tyr Ser Gly Asn
1745                1750                1755                1760

Phe Leu Ile Gly Asn Gln Pro Val Asn Thr Thr Gly Ala Cys Phe
            1765                1770                1775

Asn His Cys Leu His Tyr Arg Ala Gln Thr Arg Arg Gly Trp Cys Gly
            1780                1785                1790

Ser Ala Val Ile Cys Asn Val Asn Gly Lys Lys Ala Val Tyr Gly Met
        1795                1800                1805

His Ser Ala Gly Gly Gly Leu Ala Ala Ala Thr Ile Ile Thr Arg
        1810                1815                1820

Glu Leu Ile Glu Ala Ala Glu Lys Ser Met Leu Ala Leu Glu Pro Gln
1825                1830                1835                1840

Gly Ala Ile Val Asp Ile Ser Thr Gly Ser Val Val His Val Pro Arg
            1845                1850                1855

Lys Thr Lys Leu Arg Arg Thr Val Ala His Asp Val Phe Gln Pro Lys
            1860                1865                1870

Phe Glu Pro Ala Val Leu Ser Arg Tyr Asp Pro Arg Thr Asp Lys Asp
        1875                1880                1885

Val Asp Val Val Ala Phe Ser Lys His Thr Thr Asn Met Glu Ser Leu
        1890                1895                1900

Pro Pro Val Phe Asp Ile Val Cys Asp Glu Tyr Ala Asn Arg Val Phe
1905                1910                1915                1920

Thr Ile Leu Gly Lys Asp Asn Gly Leu Leu Thr Val Glu Gln Ala Val
            1925                1930                1935

Leu Gly Leu Pro Gly Met Asp Pro Met Glu Lys Asp Thr Ser Pro Gly
            1940                1945                1950

Leu Pro Tyr Thr Gln Gln Gly Leu Arg Arg Thr Asp Leu Leu Asn Phe
        1955                1960                1965

Asn Thr Ala Lys Met Thr Pro Gln Leu Asp Tyr Ala His Ser Lys Leu
        1970                1975                1980

Val Leu Gly Val Tyr Asp Asp Val Val Tyr Gln Ser Phe Leu Lys Asp
1985                1990                1995                2000

Glu Ile Arg Pro Leu Glu Lys Ile His Glu Ala Lys Thr Arg Ile Val
            2005                2010                2015

Asp Val Pro Pro Phe Ala His Cys Ile Trp Gly Arg Gln Leu Leu Gly
            2020                2025                2030

Arg Phe Ala Ser Lys Phe Gln Thr Lys Pro Gly Leu Glu Leu Gly Ser
        2035                2040                2045

Ala Ile Gly Thr Asp Pro Asp Val Asp Trp Thr Pro Tyr Ala Ala Glu
        2050                2055                2060

Leu Ser Gly Phe Asn Tyr Val Tyr Asp Val Asp Tyr Ser Asn Phe Asp
2065                2070                2075                2080

Ala Ser His Ser Thr Ala Met Phe Glu Cys Leu Ile Lys Asn Phe Phe
            2085                2090                2095

Thr Glu Gln Asn Gly Phe Asp Arg Arg Ile Ala Glu Tyr Leu Arg Ser
```

-continued

```
                2100                2105                2110
Leu Ala Val Ser Arg His Ala Tyr Glu Asp Arg Arg Val Leu Ile Arg
            2115                2120                2125

Gly Gly Leu Leu Ser Gly Cys Ala Ala Thr Ser Met Leu Asn Thr Ile
            2130                2135            2140

Met Asn Asn Val Ile Ile Arg Ala Ala Leu Tyr Leu Thr Tyr Ser Asn
2145                2150                2155                2160

Phe Glu Phe Asp Asp Ile Lys Val Leu Ser Tyr Gly Asp Leu Leu
            2165                2170                2175

Ile Gly Thr Asn Tyr Gln Ile Asp Phe Asn Leu Val Lys Glu Arg Leu
            2180                2185                2190

Ala Pro Phe Gly Tyr Lys Ile Thr Pro Ala Asn Lys Thr Thr Thr Phe
            2195                2200                2205

Pro Leu Thr Ser His Leu Gln Asp Val Thr Phe Leu Lys Arg Arg Phe
            2210                2215                2220

Val Arg Phe Asn Ser Tyr Leu Phe Arg Pro Gln Met Asp Ala Val Asn
2225                2230                2235                2240

Leu Lys Ala Met Val Ser Tyr Cys Lys Pro Gly Thr Leu Lys Glu Lys
            2245                2250                2255

Leu Met Ser Ile Ala Leu Leu Ala Val His Ser Gly Pro Asp Ile Tyr
            2260                2265                2270

Asp Glu Ile Phe Leu Pro Phe Arg Asn Val Gly Ile Val Pro Thr
            2275                2280                2285

Tyr Ser Ser Met Leu Tyr Arg Trp Leu Ser Leu Phe Arg
            2290                2295                2300

<210> SEQ ID NO 31
<211> LENGTH: 2303
<212> TYPE: PRT
<213> ORGANISM: Theiler's murine encephalomyelitis virus

<400> SEQUENCE: 31

Met Ala Cys Lys His Gly Tyr Pro Asp Val Cys Pro Ile Cys Thr Ala
1               5                   10                  15

Val Asp Ala Thr Pro Asp Phe Glu Tyr Leu Leu Met Ala Asp Gly Glu
            20                  25                  30

Trp Phe Pro Thr Asp Leu Leu Cys Val Asp Leu Asp Asp Asp Val Phe
        35                  40                  45

Trp Pro Ser Asp Thr Ser Thr Gln Pro Gln Thr Met Glu Trp Thr Asp
    50                  55                  60

Val Pro Leu Val Cys Asp Thr Val Met Glu Pro Gln Gly Asn Ala Ser
65                  70                  75                  80

Ser Ser Asp Lys Ser Asn Ser Gln Ser Ser Gly Asn Glu Gly Val Ile
                85                  90                  95

Ile Asn Asn Phe Tyr Ser Asn Gln Tyr Gln Asn Ser Ile Asp Leu Ser
            100                 105                 110

Ala Ser Gly Gly Asn Ala Gly Asp Ala Pro Gln Asn Asn Gly Gln Leu
        115                 120                 125

Ser Ser Ile Leu Gly Gly Ala Ala Asn Ala Phe Ala Thr Met Ala Pro
    130                 135                 140

Leu Leu Met Asp Gln Asn Thr Glu Glu Met Glu Asn Leu Ser Asp Arg
145                 150                 155                 160

Val Ala Ser Asp Lys Ala Gly Asn Ser Ala Thr Asn Thr Gln Ser Thr
                165                 170                 175

Val Gly Arg Leu Cys Gly Tyr Gly Lys Ser His His Gly Glu His Pro
```

```
                    180                 185                 190
Thr Ser Cys Ala Asp Ala Ala Thr Asp Lys Val Leu Ala Ala Glu Arg
        195                 200                 205

Tyr Tyr Thr Ile Asp Leu Ala Ser Trp Thr Ser Gln Glu Ala Phe
    210                 215                 220

Ser His Ile Arg Ile Pro Leu Pro His Val Leu Ala Gly Glu Asp Gly
225                 230                 235                 240

Gly Val Phe Gly Ala Thr Leu Arg Arg His Tyr Leu Cys Lys Thr Gly
                245                 250                 255

Trp Arg Val Gln Val Gln Cys Asn Ala Ser Gln Phe His Ala Gly Ser
            260                 265                 270

Leu Leu Val Phe Met Ala Pro Glu Phe Tyr Thr Gly Lys Gly Thr Lys
        275                 280                 285

Ser Gly Thr Met Glu Pro Ser Asp Pro Phe Thr Met Asp Thr Thr Trp
    290                 295                 300

Arg Ser Pro Gln Ser Ala Pro Thr Gly Tyr Arg Tyr Asp Arg Gln Ala
305                 310                 315                 320

Gly Phe Phe Ala Met Asn His Gln Asn Gln Trp Gln Trp Thr Val Tyr
                325                 330                 335

Pro His Gln Ile Leu Asn Leu Arg Thr Asn Thr Thr Val Asp Leu Glu
            340                 345                 350

Val Pro Tyr Val Asn Val Ala Pro Ser Ser Trp Thr Gln His Ala
        355                 360                 365

Asn Trp Thr Leu Val Val Ala Val Leu Ser Pro Leu Gln Tyr Ala Thr
    370                 375                 380

Gly Ser Ser Pro Asp Val Gln Ile Thr Ala Ser Leu Gln Pro Val Asn
385                 390                 395                 400

Pro Val Phe Asn Gly Leu Arg His Glu Thr Val Leu Ala Gln Ser Pro
                405                 410                 415

Ile Pro Val Thr Val Arg Glu His Gln Gly Cys Phe Tyr Ser Thr Asn
            420                 425                 430

Pro Asp Thr Thr Val Pro Ile Tyr Gly Lys Thr Ile Ser Thr Pro Ser
        435                 440                 445

Asp Tyr Met Cys Gly Glu Phe Ser Asp Leu Leu Glu Leu Cys Lys Leu
    450                 455                 460

Pro Thr Phe Leu Gly Asn Pro Ser Thr Asp Asn Lys Arg Tyr Pro Tyr
465                 470                 475                 480

Phe Ser Ala Thr Asn Ser Val Pro Ala Thr Ser Leu Val Asp Tyr Gln
                485                 490                 495

Val Ala Leu Ser Cys Ser Cys Thr Ala Asn Ser Met Leu Ala Ala Val
            500                 505                 510

Ala Arg Asn Phe Asn Gln Tyr Arg Gly Ser Leu Asn Phe Leu Phe Val
        515                 520                 525

Phe Thr Gly Ala Ala Met Val Lys Gly Lys Phe Arg Ile Ala Tyr Thr
    530                 535                 540

Pro Pro Gly Ala Gly Lys Pro Thr Thr Arg Asp Gln Ala Met Gln Ala
545                 550                 555                 560

Thr Tyr Ala Ile Trp Asp Leu Gly Leu Asn Ser Ser Phe Asn Phe Thr
                565                 570                 575

Ala Pro Phe Ile Ser Pro Thr His Tyr Arg Gln Thr Ser Tyr Thr Ser
            580                 585                 590

Pro Thr Ile Thr Ser Val Asp Gly Trp Val Thr Val Trp Gln Leu Thr
        595                 600                 605
```

-continued

Pro Leu Thr Tyr Pro Ser Gly Thr Pro Thr His Ser Asp Ile Leu Thr
610                 615                 620

Leu Val Ser Ala Gly Asp Phe Thr Leu Arg Met Pro Ile Ser Pro
625                 630                 635                 640

Thr Lys Trp Val Pro Gln Gly Ile Asp Asn Ala Glu Lys Gly Lys Val
                    645                 650                 655

Ser Asn Asp Asp Ala Ser Val Asp Phe Val Ala Glu Pro Val Lys Leu
                660                 665                 670

Pro Glu Asn Gln Thr Arg Val Ala Phe Phe Tyr Asp Arg Ala Val Pro
                675                 680                 685

Ile Gly Met Leu Arg Pro Gly Gln Asn Met Glu Thr Thr Phe Ser Tyr
690                 695                 700

Gln Glu Asn Asp Phe Arg Leu Asn Cys Leu Leu Leu Thr Pro Leu Pro
705                 710                 715                 720

Ser Tyr Cys Pro Asp Ser Ser Ser Gly Pro Val Arg Thr Lys Ala Pro
                725                 730                 735

Val Gln Trp Arg Trp Val Arg Ser Gly Gly Ala Asn Gly Ala Asn Phe
                740                 745                 750

Pro Leu Met Thr Lys Gln Asp Tyr Ala Phe Leu Cys Phe Ser Pro Phe
                755                 760                 765

Thr Tyr Tyr Lys Cys Asp Leu Glu Val Thr Val Ser Ala Met Gly Ala
770                 775                 780

Gly Thr Val Ser Ser Val Leu Arg Trp Ala Pro Thr Gly Ala Pro Ala
785                 790                 795                 800

Asp Val Thr Asp Gln Leu Ile Gly Tyr Thr Pro Ser Leu Gly Glu Thr
                805                 810                 815

Arg Asn Pro His Met Trp Ile Val Gly Ser Gly Asn Ser Gln Ile Ser
                820                 825                 830

Phe Val Val Pro Tyr Asn Ser Pro Leu Ser Val Leu Pro Ala Ala Trp
                835                 840                 845

Phe Asn Gly Trp Ser Asp Phe Gly Asn Thr Lys Asp Phe Gly Val Ala
850                 855                 860

Pro Thr Ser Asp Phe Gly Arg Ile Trp Ile Gln Gly Asn Ser Ser Ala
865                 870                 875                 880

Ser Val Arg Ile Arg Tyr Lys Lys Met Lys Val Phe Cys Pro Arg Pro
                885                 890                 895

Thr Leu Phe Phe Pro Trp Pro Thr Pro Thr Thr Lys Ile Asn Ala
                900                 905                 910

Asp Asn Pro Val Pro Ile Leu Glu Leu Glu Asn Pro Ala Ser Leu Tyr
                915                 920                 925

Arg Ile Asp Leu Phe Ile Thr Phe Thr Asp Glu Leu Ile Thr Phe Asp
930                 935                 940

Tyr Lys Val His Gly Arg Pro Val Leu Thr Phe Arg Ile Pro Gly Phe
945                 950                 955                 960

Gly Leu Thr Pro Ala Gly Arg Met Leu Val Cys Met Gly Ala Lys Pro
                965                 970                 975

Ala His Ser Pro Phe Thr Ser Ser Lys Ser Leu Tyr His Val Ile Phe
                980                 985                 990

Thr Ser Thr Cys Asn Ser Phe Ser Phe Thr Ile Tyr Lys Gly Arg Tyr
                995                 1000                1005

Arg Ser Trp Lys Lys Pro Ile His Asp Glu Leu Val Asp Arg Gly Tyr
                1010                1015                1020

Thr Thr Phe Arg Glu Phe Phe Lys Ala Val Arg Gly Tyr His Ala Asp
1025                1030                1035                1040

-continued

```
Tyr Tyr Lys Gln Arg Leu Ile His Asp Val Glu Met Asn Pro Gly Pro
            1045                1050                1055
Val Gln Ser Val Phe Gln Pro Gln Gly Ala Val Leu Thr Lys Ser Leu
        1060                1065                1070
Ala Pro Gln Ala Gly Ile Gln Asn Ile Leu Leu Arg Leu Leu Gly Ile
    1075                1080                1085
Glu Gly Asp Cys Ser Glu Val Ser Lys Ala Ile Thr Val Val Thr Asp
1090                1095                1100
Leu Val Ala Ala Trp Glu Lys Ala Lys Thr Thr Leu Val Ser Pro Glu
1105                1110                1115                1120
Phe Trp Ser Glu Leu Ile Leu Lys Thr Thr Lys Phe Ile Ala Ala Ser
            1125                1130                1135
Val Leu Tyr Leu His Asn Pro Asp Phe Thr Thr Thr Val Cys Leu Ser
        1140                1145                1150
Leu Met Thr Gly Val Asp Leu Leu Thr Asn Asp Ser Val Phe Asp Trp
    1155                1160                1165
Leu Lys Ser Lys Leu Ser Ser Phe Arg Thr Pro Pro Pro Ala Cys
1170                1175                1180
Pro Asn Val Met Gln Pro Gln Gly Pro Leu Arg Glu Ala Asn Glu Gly
1185                1190                1195                1200
Phe Thr Phe Ala Lys Asn Ile Glu Trp Ala Thr Lys Thr Ile Gln Ser
            1205                1210                1215
Ile Val Asn Trp Leu Thr Ser Trp Phe Lys Gln Glu Glu Asp His Pro
        1220                1225                1230
Gln Ser Lys Leu Asp Lys Leu Leu Met Glu Phe Pro Asp His Cys Arg
    1235                1240                1245
Asn Ile Met Asp Met Arg Asn Gly Arg Lys Ala Tyr Cys Glu Cys Thr
1250                1255                1260
Ala Ser Phe Lys Tyr Phe Asp Asp Leu Tyr Asn Leu Ala Val Thr Cys
1265                1270                1275                1280
Lys Arg Ile Pro Leu Ala Ser Leu Cys Glu Lys Phe Lys Asn Arg His
            1285                1290                1295
Asp His Ser Val Thr Arg Pro Glu Pro Val Val Ala Val Leu Arg Gly
        1300                1305                1310
Ala Ala Gly Gln Gly Lys Ser Val Thr Ser Gln Ile Ile Ala Gln Ser
    1315                1320                1325
Val Ser Lys Met Ala Phe Gly Arg Gln Ser Val Tyr Ser Met Pro Pro
1330                1335                1340
Asp Ser Glu Tyr Phe Asp Gly Tyr Glu Asn Gln Phe Ser Val Ile Met
1345                1350                1355                1360
Asp Asp Leu Gly Gln Asn Pro Asp Gly Glu Asp Phe Thr Val Phe Cys
            1365                1370                1375
Gln Met Val Ser Ser Thr Asn Phe Leu Pro Asn Met Ala His Leu Glu
        1380                1385                1390
Arg Lys Gly Thr Pro Phe Thr Ser Ser Phe Ile Val Ala Thr Thr Asn
    1395                1400                1405
Leu Pro Lys Phe Arg Pro Val Thr Val Ala His Tyr Pro Ala Val Asp
    1410                1415                1420
Arg Arg Ile Thr Phe Asp Phe Val Thr Ala Gly Pro His Cys Lys
1425                1430                1435                1440
Thr Pro Ala Gly Met Leu Asp Ile Glu Lys Ala Phe Asp Glu Ile Pro
            1445                1450                1455
Gly Ser Lys Pro Gln Leu Ala Cys Phe Ser Ala Asp Cys Pro Leu Leu
```

```
                        1460              1465              1470
His Lys Arg Gly Val Met Phe Thr Cys Asn Arg Thr Lys Thr Val Tyr
            1475              1480              1485
Asn Leu Gln Gln Val Val Lys Met Val Asn Asp Thr Ile Thr Arg Lys
            1490              1495              1500
Thr Glu Asn Val Lys Lys Met Asn Ser Leu Val Ala Gln Ser Pro Pro
1505              1510              1515              1520
Asp Trp Gln His Phe Glu Asn Ile Leu Thr Cys Leu Arg Gln Asn Asn
            1525              1530              1535
Ala Ala Leu Gln Asp Gln Val Asp Glu Leu Gln Glu Ala Phe Thr Gln
            1540              1545              1550
Ala Arg Glu Arg Ser Asp Phe Leu Ser Asp Trp Leu Lys Val Ser Ala
            1555              1560              1565
Ile Ile Phe Ala Gly Ile Val Ser Leu Ser Ala Val Ile Lys Leu Ala
            1570              1575              1580
Ser Lys Phe Lys Glu Ser Ile Trp Pro Thr Pro Val Arg Val Glu Leu
1585              1590              1595              1600
Ser Glu Gly Glu Gln Ala Ala Tyr Ala Gly Arg Ala Arg Ala Gln Lys
                  1605              1610              1615
Gln Ala Leu Gln Val Leu Asp Ile Gln Gly Gly Lys Val Leu Ala
            1620              1625              1630
Gln Ala Gly Asn Pro Val Met Asp Phe Glu Leu Phe Cys Ala Lys Asn
            1635              1640              1645
Met Val Ser Pro Ile Thr Phe Tyr Tyr Pro Asp Lys Ala Glu Val Thr
            1650              1655              1660
Gln Ser Cys Leu Leu Leu Arg Ala His Leu Phe Val Val Asn Arg His
1665              1670              1675              1680
Val Ala Glu Thr Glu Trp Thr Ala Phe Lys Leu Arg Asp Val Arg His
            1685              1690              1695
Glu Arg Asp Thr Val Val Met Arg Ser Val Asn Arg Ser Gly Ala Glu
            1700              1705              1710
Thr Asp Leu Thr Phe Val Lys Val Thr Lys Gly Pro Leu Phe Lys Asp
            1715              1720              1725
Asn Val Asn Lys Phe Cys Ser Asn Lys Asp Asp Phe Pro Ala Arg Asn
            1730              1735              1740
Asp Thr Val Thr Gly Ile Met Asn Thr Gly Leu Ala Phe Val Tyr Ser
1745              1750              1755              1760
Gly Asn Phe Leu Ile Gly Asn Gln Pro Val Asn Thr Thr Thr Gly Ala
                  1765              1770              1775
Cys Phe Asn His Cys Leu His Tyr Arg Ala Gln Thr Arg Arg Gly Trp
            1780              1785              1790
Cys Gly Ser Ala Ile Ile Cys Asn Val Asn Gly Lys Lys Ala Val Tyr
            1795              1800              1805
Gly Met His Ser Ala Gly Gly Gly Leu Ala Ala Thr Ile Ile
            1810              1815              1820
Thr Arg Glu Leu Ile Glu Ala Ala Glu Lys Ser Met Leu Ala Leu Glu
1825              1830              1835              1840
Pro Gln Gly Ala Ile Val Asp Ile Ser Thr Gly Ser Val Val His Val
            1845              1850              1855
Pro Arg Lys Thr Lys Leu Arg Arg Thr Val Ala His Asp Val Phe Gln
            1860              1865              1870
Pro Lys Phe Glu Pro Ala Val Leu Ser Arg Tyr Asp Pro Arg Thr Asp
            1875              1880              1885
```

-continued

Lys Asp Val Asp Val Val Ala Phe Ser Lys His Thr Thr Asn Met Glu
            1890                1895                1900

Ser Leu Pro Pro Ile Phe Asp Ile Val Cys Gly Glu Tyr Ala Asn Arg
1905                1910                1915                1920

Val Phe Thr Ile Leu Gly Lys Asp Asn Gly Leu Leu Thr Val Glu Gln
                1925                1930                1935

Ala Val Leu Gly Leu Ser Gly Met Asp Pro Met Glu Lys Asp Thr Ser
            1940                1945                1950

Pro Gly Leu Pro Tyr Thr Gln Gln Gly Leu Arg Arg Thr Asp Leu Leu
                1955                1960                1965

Asp Phe Asn Thr Ala Lys Met Thr Pro Gln Leu Asp Tyr Ala His Ser
            1970                1975                1980

Lys Leu Val Leu Gly Val Tyr Asp Asp Val Val Tyr Gln Ser Phe Leu
1985                1990                1995                2000

Lys Asp Glu Ile Arg Pro Leu Glu Lys Ile His Glu Ala Lys Thr Arg
                2005                2010                2015

Ile Val Asp Val Pro Pro Phe Ala His Cys Ile Trp Gly Arg Gln Leu
            2020                2025                2030

Leu Gly Arg Phe Ala Ser Lys Phe Gln Thr Lys Pro Gly Phe Glu Leu
            2035                2040                2045

Gly Ser Ala Ile Gly Thr Asp Pro Asp Val Asp Trp Thr Arg Tyr Ala
            2050                2055                2060

Ala Glu Leu Ser Gly Phe Asn Tyr Val Tyr Asp Val Asp Tyr Ser Asn
2065                2070                2075                2080

Phe Asp Ala Ser His Ser Thr Ala Met Phe Glu Cys Leu Ile Asn Asn
            2085                2090                2095

Phe Phe Thr Glu Gln Asn Gly Phe Asp Arg Arg Ile Ala Glu Tyr Leu
            2100                2105                2110

Arg Ser Leu Ala Val Ser Arg His Ala Tyr Glu Asp Arg Arg Val Leu
            2115                2120                2125

Ile Arg Gly Gly Leu Pro Ser Gly Cys Ala Ala Thr Ser Met Leu Asn
            2130                2135                2140

Thr Ile Met Asn Asn Val Ile Ile Arg Ala Ala Leu Tyr Leu Thr Tyr
2145                2150                2155                2160

Ser Asn Phe Glu Phe Asp Asp Ile Lys Val Leu Ser Tyr Gly Asp Asp
            2165                2170                2175

Leu Leu Ile Gly Thr Asn Tyr Gln Ile Asp Phe Asn Leu Val Lys Glu
            2180                2185                2190

Arg Leu Ala Pro Phe Gly Tyr Lys Ile Thr Pro Ala Asn Lys Thr Thr
            2195                2200                2205

Thr Phe Pro Leu Thr Ser His Leu Gln Asp Val Thr Phe Leu Lys Arg
            2210                2215                2220

Arg Phe Val Arg Phe Asn Ser Tyr Leu Phe Arg Pro Gln Met Asp Ala
2225                2230                2235                2240

Val Asn Leu Lys Ala Met Val Ser Tyr Cys Lys Pro Gly Thr Leu Lys
            2245                2250                2255

Glu Lys Leu Met Ser Ile Ala Leu Leu Ala Val His Ser Gly Pro Asp
            2260                2265                2270

Ile Tyr Asp Glu Ile Phe Leu Pro Phe Arg Asn Val Gly Ile Val Val
            2275                2280                2285

Pro Thr Tyr Asp Ser Met Leu Tyr Arg Trp Leu Ser Leu Phe Arg
            2290                2295                2300

<210> SEQ ID NO 32

<211> LENGTH: 2303
<212> TYPE: PRT
<213> ORGANISM: Theiler's murine encephalomyelitis virus

<400> SEQUENCE: 32

```
Met Ala Cys Lys His Gly Tyr Pro Asp Val Cys Pro Ile Cys Thr Ala
1               5                   10                  15

Val Asp Ala Thr Pro Gly Phe Glu Tyr Leu Leu Met Ala Asp Gly Glu
            20                  25                  30

Trp Tyr Pro Thr Asp Leu Leu Cys Val Asp Leu Asp Asp Asp Val Phe
        35                  40                  45

Trp Pro Ser Asp Thr Ser Asn Gln Ser Gln Thr Met Asp Trp Thr Asp
    50                  55                  60

Val Pro Leu Ile Arg Asp Ile Val Met Glu Pro Gln Gly Asn Ser Ser
65                  70                  75                  80

Ser Ser Asp Lys Ser Asn Ser Gln Ser Ser Gly Asn Glu Gly Val Ile
                85                  90                  95

Ile Asn Asn Phe Tyr Ser Asn Gln Tyr Gln Asn Ser Ile Asp Leu Ser
            100                 105                 110

Ala Ser Gly Gly Asn Ala Gly Asp Ala Pro Gln Thr Asn Gly Gln Leu
        115                 120                 125

Ser Asn Ile Leu Gly Gly Ala Ala Asn Ala Phe Ala Thr Met Ala Pro
    130                 135                 140

Leu Leu Leu Asp Gln Asn Thr Glu Glu Met Glu Asn Leu Ser Asp Arg
145                 150                 155                 160

Val Ala Ser Asp Lys Ala Gly Asn Ser Ala Thr Asn Thr Gln Ser Thr
                165                 170                 175

Val Gly Arg Leu Cys Gly Tyr Gly Lys Ser His His Gly Glu His Pro
            180                 185                 190

Ala Ser Cys Ala Asp Thr Ala Thr Asp Lys Val Leu Ala Ala Glu Arg
        195                 200                 205

Tyr Tyr Thr Ile Asp Leu Ala Ser Trp Thr Thr Ser Gln Glu Ala Phe
    210                 215                 220

Ser His Ile Arg Ile Pro Leu Pro His Val Leu Ala Gly Glu Asp Gly
225                 230                 235                 240

Gly Val Phe Gly Ala Thr Leu Arg Arg His Tyr Leu Cys Lys Thr Gly
                245                 250                 255

Trp Arg Val Gln Val Gln Cys Asn Ala Ser Gln Phe His Ala Gly Ser
            260                 265                 270

Leu Leu Val Phe Met Ala Pro Glu Phe Tyr Thr Gly Lys Gly Thr Lys
        275                 280                 285

Thr Gly Thr Met Glu Pro Ser Asp Pro Phe Thr Met Asp Thr Glu Trp
    290                 295                 300

Arg Ser Pro Gln Gly Ala Pro Thr Gly Tyr Arg Tyr Asp Ser Arg Thr
305                 310                 315                 320

Gly Phe Phe Ala Thr Asn His Gln Asn Gln Trp Gln Trp Thr Val Tyr
                325                 330                 335

Pro His Gln Ile Leu Asn Leu Arg Thr Asn Thr Thr Val Asp Leu Glu
            340                 345                 350

Val Pro Tyr Val Asn Val Ala Pro Ser Ser Ser Trp Thr Gln His Ala
        355                 360                 365

Asn Trp Thr Leu Val Val Ala Val Leu Ser Pro Leu Gln Tyr Ala Thr
    370                 375                 380

Gly Ser Ser Pro Asp Val Gln Ile Thr Ala Ser Leu Gln Pro Val Asn
385                 390                 395                 400
```

```
Pro Val Phe Asn Gly Leu Arg His Glu Thr Val Ile Ala Gln Ser Pro
            405                 410                 415
Ile Pro Val Thr Val Arg Glu His Lys Gly Cys Phe Tyr Ser Thr Asn
            420                 425                 430
Pro Asp Thr Thr Val Pro Ile Tyr Gly Lys Thr Ile Ser Thr Pro Ser
            435                 440                 445
Asp Tyr Met Cys Gly Glu Phe Ser Asp Leu Glu Leu Cys Lys Leu
            450                 455                 460
Pro Thr Phe Leu Gly Asn Pro Asn Thr Asn Lys Arg Tyr Pro Tyr
465             470                 475                 480
Phe Ser Ala Thr Asn Ser Val Pro Ala Thr Ser Met Val Asp Tyr Gln
                485                 490                 495
Val Ala Leu Ser Cys Ser Cys Met Ala Asn Ser Met Leu Ala Ala Val
                500                 505                 510
Ala Arg Asn Phe Asn Gln Tyr Arg Gly Ser Leu Asn Phe Leu Phe Val
                515                 520                 525
Phe Thr Gly Ala Ala Met Val Lys Gly Lys Phe Leu Ile Ala Tyr Thr
            530                 535                 540
Pro Pro Gly Ala Gly Lys Pro Thr Thr Arg Asp Gln Ala Met Gln Ser
545             550                 555                 560
Thr Tyr Ala Ile Trp Asp Leu Gly Leu Asn Ser Ser Phe Asn Phe Thr
                565                 570                 575
Ala Pro Phe Ile Ser Pro Thr His Tyr Arg Gln Thr Ser Tyr Thr Ser
                580                 585                 590
Pro Thr Ile Thr Ser Val Asp Gly Trp Val Thr Val Trp Lys Leu Thr
            595                 600                 605
Pro Leu Thr Tyr Pro Ser Gly Thr Pro Thr Asn Ser Asp Ile Leu Thr
            610                 615                 620
Leu Val Ser Ala Gly Asp Asp Phe Thr Leu Arg Met Pro Ile Ser Pro
625             630                 635                 640
Thr Lys Trp Val Pro Gln Gly Val Asp Asn Ala Glu Lys Gly Lys Val
                645                 650                 655
Ser Asn Asp Asp Ala Ser Val Asp Phe Val Ala Glu Pro Val Lys Leu
                660                 665                 670
Pro Glu Asn Gln Thr Arg Val Ala Phe Phe Tyr Asp Arg Ala Val Pro
                675                 680                 685
Ile Gly Met Leu Arg Pro Gly Gln Asn Met Glu Thr Thr Phe Asn Tyr
            690                 695                 700
Gln Glu Asn Asp Tyr Arg Leu Asn Cys Leu Leu Leu Thr Pro Leu Pro
705             710                 715                 720
Ser Phe Cys Pro Asp Ser Ser Ser Gly Pro Gln Lys Thr Lys Ala Pro
                725                 730                 735
Val Gln Trp Arg Trp Val Arg Ser Gly Gly Val Asn Gly Ala Asn Phe
            740                 745                 750
Pro Leu Met Thr Lys Gln Asp Tyr Ala Phe Leu Cys Phe Ser Pro Phe
            755                 760                 765
Thr Phe Tyr Lys Cys Asp Leu Glu Val Thr Val Ser Ala Leu Gly Met
            770                 775                 780
Thr Arg Val Ala Ser Val Leu Arg Trp Ala Pro Thr Gly Ala Pro Ala
785             790                 795                 800
Asp Val Thr Asp Gln Leu Ile Gly Tyr Thr Pro Ser Leu Gly Glu Thr
                805                 810                 815
Arg Asn Pro His Met Trp Leu Val Gly Ala Gly Asn Ser Gln Val Ser
```

```
                820             825             830
Phe Val Val Pro Tyr Asn Ser Pro Leu Ser Val Leu Pro Ala Ala Trp
        835                 840             845

Phe Asn Gly Trp Ser Asp Phe Gly Asn Thr Lys Asp Phe Gly Val Ala
    850              855             860

Pro Asn Ala Asp Phe Gly Arg Leu Trp Ile Gln Gly Asn Thr Ser Ala
865              870              875             880

Ser Val Arg Ile Arg Tyr Lys Lys Met Lys Val Phe Cys Pro Arg Pro
                885             890             895

Thr Leu Phe Phe Pro Trp Pro Thr Pro Thr Thr Lys Ile Asn Ala
        900             905             910

Asp Asn Pro Val Pro Ile Leu Glu Leu Glu Asn Pro Ala Ala Leu Tyr
        915             920             925

Arg Ile Asp Leu Phe Ile Thr Phe Thr Asp Glu Phe Ile Thr Phe Asp
        930             935             940

Tyr Lys Val His Gly Arg Pro Val Leu Thr Phe Arg Ile Pro Gly Phe
945             950             955             960

Gly Leu Thr Pro Ala Gly Arg Met Leu Val Cys Met Gly Glu Gln Pro
                965             970             975

Ala His Gly Pro Phe Thr Ser Ser Arg Ser Leu Tyr His Val Ile Phe
            980             985             990

Thr Ala Thr Cys Ser Ser Phe Ser Phe Ser Ile Tyr Lys Gly Arg Tyr
        995             1000            1005

Arg Ser Trp Lys Lys Pro Ile His Asp Glu Leu Val Asp Arg Gly Tyr
        1010            1015            1020

Thr Thr Phe Gly Glu Phe Phe Lys Ala Val Arg Gly Tyr His Ala Asp
1025            1030            1035            1040

Tyr Tyr Arg Gln Arg Leu Ile His Asp Val Glu Thr Asn Pro Gly Pro
            1045            1050            1055

Val Gln Ser Val Phe Gln Pro Gly Ala Val Leu Thr Lys Ser Leu
        1060            1065            1070

Ala Pro Gln Ala Gly Ile Gln Asn Leu Leu Leu Arg Leu Leu Gly Ile
        1075            1080            1085

Asp Gly Asp Cys Ser Glu Val Ser Lys Ala Ile Thr Val Val Thr Asp
        1090            1095            1100

Leu Val Ala Ala Trp Glu Lys Ala Lys Thr Thr Leu Val Ser Pro Glu
1105            1110            1115            1120

Phe Trp Ser Lys Leu Ile Leu Lys Thr Thr Lys Phe Ile Ala Ala Ser
            1125            1130            1135

Val Leu Tyr Leu His Asn Pro Asp Phe Thr Thr Val Cys Leu Ser
        1140            1145            1150

Leu Met Thr Gly Val Asp Leu Leu Thr Asn Asp Ser Val Phe Asp Trp
        1155            1160            1165

Leu Lys Gln Lys Leu Ser Ser Phe Phe Arg Thr Pro Pro Pro Ala Cys
        1170            1175            1180

Pro Asn Val Met Gln Pro Gln Gly Pro Leu Arg Glu Ala Asn Glu Gly
1185            1190            1195            1200

Phe Thr Phe Ala Lys Asn Ile Glu Trp Ala Met Lys Thr Ile Gln Ser
            1205            1210            1215

Val Val Asn Trp Leu Thr Ser Trp Phe Lys Gln Glu Asp His Pro
        1220            1225            1230

Gln Ser Lys Leu Asp Lys Leu Leu Met Glu Phe Pro Asp His Cys Arg
        1235            1240            1245
```

```
Asn Ile Met Asp Met Arg Asn Gly Arg Lys Ala Tyr Cys Glu Cys Thr
            1250                1255                1260
Ala Ser Phe Lys Tyr Phe Asp Glu Leu Tyr Asn Leu Ala Val Thr Cys
1265                1270                1275                1280
Lys Arg Ile Pro Leu Ala Ser Leu Cys Glu Lys Phe Lys Asn Arg His
                1285                1290                1295
Asp His Ser Val Thr Arg Pro Glu Pro Val Val Val Leu Arg Gly
            1300                1305                1310
Ala Ala Gly Gln Gly Lys Ser Val Thr Ser Gln Ile Ile Ala Gln Ser
            1315                1320                1325
Val Ser Lys Met Ala Phe Gly Arg Gln Ser Val Tyr Ser Met Pro Pro
    1330                1335                1340
Asp Ser Glu Tyr Phe Asp Gly Tyr Glu Asn Gln Phe Ser Val Ile Met
1345                1350                1355                1360
Asp Asp Leu Gly Gln Asn Pro Asp Gly Glu Asp Phe Thr Val Phe Cys
                1365                1370                1375
Gln Met Val Ser Ser Thr Asn Phe Leu Pro Asn Met Ala His Leu Glu
                1380                1385                1390
Arg Lys Gly Thr Pro Phe Thr Ser Ser Phe Ile Val Ala Thr Thr Asn
            1395                1400                1405
Leu Pro Lys Phe Arg Pro Val Thr Val Ala His Tyr Pro Ala Val Asp
    1410                1415                1420
Arg Arg Ile Thr Phe Asp Phe Thr Val Thr Ala Gly Pro His Cys Lys
1425                1430                1435                1440
Thr Pro Ala Gly Met Leu Asp Val Glu Lys Ala Phe Asp Glu Ile Pro
                1445                1450                1455
Gly Ser Lys Pro Gln Leu Ala Cys Phe Ser Ala Asp Cys Pro Leu Leu
            1460                1465                1470
His Lys Arg Gly Val Met Phe Thr Cys Asn Arg Thr Gln Thr Val Tyr
            1475                1480                1485
Asn Leu Gln Gln Val Val Lys Met Val Asn Asp Thr Ile Thr Arg Lys
            1490                1495                1500
Thr Glu Asn Val Lys Lys Met Asn Ser Leu Val Ala Gln Ser Pro Pro
1505                1510                1515                1520
Asp Trp Glu His Phe Glu Asn Ile Leu Thr Cys Leu Arg Gln Asn Asn
                1525                1530                1535
Ala Ala Leu Gln Asp Gln Leu Asp Glu Leu Gln Glu Ala Phe Ala Gln
            1540                1545                1550
Ala Arg Glu Arg Ser Asp Phe Leu Ser Asp Trp Leu Lys Val Ser Ala
            1555                1560                1565
Ile Ile Phe Ala Gly Ile Ala Ser Leu Ser Ala Val Ile Lys Leu Ala
    1570                1575                1580
Ser Lys Phe Lys Glu Ser Ile Trp Pro Thr Pro Val Arg Val Glu Leu
1585                1590                1595                1600
Ser Glu Gly Glu Gln Ala Ala Tyr Ala Gly Arg Ala Arg Ala Gln Lys
                1605                1610                1615
Gln Ala Leu Gln Val Leu Asp Ile Gln Gly Gly Gly Lys Val Leu Ala
            1620                1625                1630
Gln Ala Gly Asn Pro Val Met Asp Phe Glu Leu Phe Cys Ala Lys Asn
            1635                1640                1645
Ile Val Ala Pro Ile Thr Phe Tyr Tyr Pro Asp Lys Ala Glu Val Thr
    1650                1655                1660
Gln Ser Cys Leu Leu Leu Arg Ala His Leu Phe Val Val Asn Arg His
1665                1670                1675                1680
```

```
Val Ala Glu Thr Asp Trp Thr Ala Phe Lys Leu Lys Asp Val Arg His
            1685                1690                1695

Glu Arg His Thr Val Ala Leu Arg Ser Val Asn Arg Ser Gly Ala Lys
            1700                1705                1710

Thr Asp Leu Thr Phe Ile Lys Val Thr Lys Gly Pro Leu Phe Lys Asp
            1715                1720                1725

Asn Val Asn Lys Phe Cys Ser Asn Lys Asp Asp Phe Pro Ala Arg Asn
            1730                1735                1740

Asp Thr Val Thr Gly Ile Met Asn Thr Gly Leu Ala Phe Val Tyr Ser
1745                1750                1755                1760

Gly Asn Phe Leu Ile Gly Asn Gln Pro Val Asn Thr Thr Gly Ala
            1765                1770                1775

Cys Phe Asn His Cys Leu His Tyr Arg Ala Gln Thr Arg Arg Gly Trp
            1780                1785                1790

Cys Gly Ser Ala Ile Ile Cys Asn Val Asn Gly Lys Lys Ala Val Tyr
            1795                1800                1805

Gly Met His Ser Ala Gly Gly Gly Leu Ala Ala Ala Thr Ile Ile
            1810                1815                1820

Thr Lys Glu Leu Ile Glu Ala Ala Glu Lys Ser Met Leu Ala Leu Glu
1825                1830                1835                1840

Pro Gln Gly Ala Ile Val Asp Ile Ala Thr Gly Ser Val Val His Val
            1845                1850                1855

Pro Arg Lys Thr Lys Leu Arg Arg Thr Val Ala His Asp Val Phe Gln
            1860                1865                1870

Pro Lys Phe Glu Pro Ala Val Leu Ser Arg Tyr Asp Pro Arg Thr Asp
            1875                1880                1885

Lys Asp Val Asp Val Val Ala Phe Ser Lys His Thr Thr Asn Met Glu
            1890                1895                1900

Ser Leu Pro Pro Ile Phe Asp Val Val Cys Gly Glu Tyr Ala Asn Arg
1905                1910                1915                1920

Val Phe Thr Ile Leu Gly Lys Glu Asn Gly Leu Leu Thr Val Glu Gln
            1925                1930                1935

Ala Val Leu Gly Leu Pro Gly Met Asp Pro Met Glu Lys Asp Thr Ser
            1940                1945                1950

Pro Gly Leu Pro Tyr Thr Gln Gln Gly Leu Arg Arg Thr Asp Leu Leu
            1955                1960                1965

Asn Phe Ile Thr Ala Lys Met Thr Pro Gln Leu Asp Tyr Ala His Ser
            1970                1975                1980

Lys Leu Val Ile Gly Val Tyr Asp Asp Val Val Tyr Gln Ser Phe Leu
1985                1990                1995                2000

Lys Asp Glu Ile Arg Pro Ile Glu Lys Ile His Glu Ala Lys Thr Arg
            2005                2010                2015

Ile Val Asp Val Pro Pro Phe Ala His Cys Ile Trp Gly Arg Gln Leu
            2020                2025                2030

Leu Gly Arg Phe Ala Ser Lys Phe Gln Thr Lys Pro Gly Leu Glu Leu
            2035                2040                2045

Gly Ser Ala Ile Gly Thr Asp Pro Asp Val Asp Trp Thr Arg Tyr Ala
            2050                2055                2060

Val Glu Leu Ser Gly Phe Asn Tyr Val Tyr Asp Val Asp Tyr Ser Asn
2065                2070                2075                2080

Phe Asp Ala Ser His Ser Thr Ala Met Phe Glu Cys Leu Ile Asn Asn
            2085                2090                2095

Phe Phe Thr Glu Gln Asn Gly Phe Asp Arg Arg Ile Ala Glu Tyr Leu
```

-continued

```
                        2100                2105                2110
Arg Ser Leu Ala Val Ser Arg His Ala Tyr Glu Asp Arg Arg Val Leu
                2115                2120                2125

Ile Arg Gly Gly Leu Pro Ser Gly Cys Ala Ala Thr Ser Met Leu Asn
            2130                2135                2140

Thr Ile Met Asn Asn Val Ile Ile Arg Ala Ala Leu Tyr Leu Thr Tyr
2145                2150                2155                2160

Ser Asn Phe Asp Phe Asp Asp Ile Lys Val Leu Ser Tyr Gly Asp Asp
                2165                2170                2175

Leu Leu Ile Gly Thr Asn Tyr Gln Ile Asp Phe Asn Leu Val Lys Glu
            2180                2185                2190

Arg Leu Ala Pro Phe Gly Tyr Lys Ile Thr Pro Ala Asn Lys Thr Thr
            2195                2200                2205

Thr Phe Pro Leu Thr Ser His Leu Gln Asp Val Thr Phe Leu Lys Arg
        2210                2215                2220

Arg Phe Val Arg Phe Asn Ser Tyr Leu Phe Arg Pro Gln Met Asp Ala
2225                2230                2235                2240

Val Asn Leu Lys Ala Met Val Ser Tyr Cys Lys Pro Gly Thr Leu Lys
                2245                2250                2255

Glu Lys Leu Met Ser Ile Ala Leu Leu Ala Val His Ser Gly Pro Asp
            2260                2265                2270

Ile Tyr Asp Glu Ile Phe Leu Pro Phe Arg Asn Val Gly Ile Val Val
            2275                2280                2285

Pro Thr Tyr Ser Ser Met Leu Tyr Arg Trp Leu Ser Leu Phe Arg
        2290                2295                2300

<210> SEQ ID NO 33
<211> LENGTH: 2307
<212> TYPE: PRT
<213> ORGANISM: Theiler's murine encephalomyelitis virus

<400> SEQUENCE: 33

Met Met Ala Cys Ile His Gly Tyr Pro Ser Val Cys Pro Ile Cys Thr
1               5                   10                  15

Ala Ile Asp Lys Ser Ser Asp Gly Met Tyr Leu Leu Leu Ala Asp Asn
                20                  25                  30

Glu Trp Phe Pro Ala Asp Leu Leu Thr Met Asp Leu Asp Asp Asp Val
            35                  40                  45

Phe Trp Pro Asn Asp Glu Ser Asp Val Ser Glu Thr Met Asp Trp Thr
        50                  55                  60

Asp Leu Pro Phe Ile Leu Asp Thr Ile Met Glu Pro Gln Gly Asn Ser
65                  70                  75                  80

Thr Ser Ser Asp Lys Ser Asn Ser Gln Ser Ser Gly Asn Glu Gly Val
                85                  90                  95

Ile Ile Asn Asn Phe Tyr Ser Asn Gln Tyr Gln Asn Ser Ile Asp Leu
            100                 105                 110

Ser Ala Asn Gly Gly Asn Ala Gly Gly Ala Pro Lys Thr Glu Gly Gln
        115                 120                 125

Leu Gly Asn Ile Leu Gly Asn Ala Ala Asn Ala Phe Ser Thr Met Ala
    130                 135                 140

Pro Leu Leu Leu Asp Gln Asn Thr Glu Glu Met Glu Asn Leu Ser Asp
145                 150                 155                 160

Arg Val Asp Ser Asp Lys Ala Gly Asn Ser Ala Val Asn Thr Gln Ser
                165                 170                 175

Ser Val Gly Arg Leu Cys Gly Tyr Gly Met His His Lys Gly Lys His
```

-continued

```
                180                 185                 190
Pro Ala Ser Cys Ala Asp Thr Ala Thr Asp Lys Val Leu Ser Ala Glu
            195                 200                 205
Arg Tyr Tyr Thr Ile Asp Leu Ala Thr Trp Thr Thr Leu Gly Thr
        210                 215                 220
Phe Ser His Ile Arg Ile Pro Leu Pro His Val Leu Ala Gly Glu Asp
225                 230                 235                 240
Gly Gly Val Phe Gly Ser Thr Leu Arg Arg His Tyr Leu Cys Lys Cys
            245                 250                 255
Gly Trp Arg Ile Gln Val Gln Cys Asn Ala Ser Gln Phe His Ala Gly
            260                 265                 270
Ser Leu Leu Val Phe Met Ala Pro Glu Phe Tyr Thr Gly His Thr Pro
            275                 280                 285
Val Thr Gly Thr Thr Glu Pro Ala Thr Pro Phe Thr Met Asp Ser Ser
            290                 295                 300
Trp Gln Thr Pro Gln Gln Asn Pro Val Gly Phe Arg Tyr Asp Gly Arg
305                 310                 315                 320
Thr Gly Tyr Phe Ala Leu Asn His Gln Asn Tyr Trp Gln Trp Met Val
            325                 330                 335
Tyr Pro His Gln Ile Leu Asn Leu Arg Thr Asn Thr Ser Val Asp Leu
            340                 345                 350
Glu Val Pro Phe Thr Asn Ile Ala Pro Thr Ser Ser Trp Thr Gln His
            355                 360                 365
Ala Asn Trp Thr Leu Val Val Ala Val Leu Thr Pro Leu Gln Tyr Ala
            370                 375                 380
Ala Gly Ser Ala Thr Asp Val Gln Ile Thr Ala Ser Ile Gln Pro Val
385                 390                 395                 400
Lys Pro Val Phe Asn Gly Leu Arg His Glu Ala Val Val Pro Gln Ser
            405                 410                 415
Pro Ile Pro Val Thr Val Arg Glu His Gln Gly Thr Phe Tyr Ser Thr
            420                 425                 430
Asn Pro Asp Thr Thr Val Pro Ile Tyr Gly Lys Thr Ile Ala Thr Pro
            435                 440                 445
Ser Asp Tyr Met Cys Gly Glu Phe Ser Asp Leu Val Glu Leu Cys Lys
            450                 455                 460
Leu Pro Thr Phe Leu Gly Asn Pro Ala Asn Thr Ser Pro Ala Gly Gly
465                 470                 475                 480
Arg Tyr Pro Tyr Phe Ser Ala Thr Asn Ser Val Pro Ala Thr Ala Leu
            485                 490                 495
Ala Ser Tyr Gln Val Ala Leu Ser Cys Ser Cys Met Ser Asn Ser Met
            500                 505                 510
Leu Ala Ala Val Ala Arg Asn Phe Asn Gln Tyr Arg Gly Ser Leu Asn
            515                 520                 525
Phe Leu Phe Val Phe Thr Gly Thr Ala Met Thr Lys Gly Lys Phe Leu
            530                 535                 540
Ile Ala Tyr Thr Pro Pro Gly Ala Gly Lys Pro Thr Thr Arg Glu Gln
545                 550                 555                 560
Ala Met Gln Ala Thr Tyr Ala Ile Trp Asp Leu Gly Leu Asn Ser Ser
            565                 570                 575
Tyr Asn Phe Thr Val Pro Phe Ile Ser Pro Thr His Tyr Arg Gln Thr
            580                 585                 590
Ser Tyr Thr Ser Thr Ser Ile Thr Ser Val Asp Gly Trp Leu Thr Val
            595                 600                 605
```

-continued

Trp Gln Leu Thr Pro Leu Thr Tyr Pro Ala Asn Thr Pro Asn Ala
610                 615                 620

Asp Ile Leu Thr Leu Val Ser Ala Gly Asp Phe Thr Leu Arg Met
625                 630                 635                 640

Pro Ile Ser Pro Thr Lys Trp Ile Pro Gln Gly Val Asp Asn Ala Glu
            645                 650                 655

Lys Gly Lys Val Ser Asn Asp Asp Ala Thr Val Asp Phe Val Ala Glu
            660                 665                 670

Pro Val Lys Phe Pro Asp Asn Gln Thr Lys Val Ser Phe Phe Tyr Asp
            675                 680                 685

Arg Ser Val Pro Leu Gly Leu Leu Arg Pro Ala Gln Gly Met Glu Gln
690                 695                 700

Asp Phe Ala Tyr Ala Ala Asn Asp Ser Arg Ala Asn Ser Ile Leu Leu
705                 710                 715                 720

Thr Pro Leu Pro Ser Tyr Ala Pro Asp Ser Thr Thr Gly Pro Thr Glu
            725                 730                 735

Thr Gln Ala Pro Ile Gln Trp Arg Trp Leu Arg Gly Thr Ser Asp Gly
            740                 745                 750

Ser Thr Thr Phe Pro Leu Met Thr Lys Gln Asp Tyr Ala Phe Leu Leu
            755                 760                 765

Phe Ser Pro Phe Thr Tyr Tyr Lys Ala Asp Leu Glu Val Thr Leu Ser
770                 775                 780

Ala Ile Ser Asn Ser Asn Asn Val Thr Val Val Arg Trp Ala Pro Thr
785                 790                 795                 800

Gly Ala Pro Ala Asp Ile Ser Arg Gln Leu Ser Gly Tyr Thr Pro Ser
            805                 810                 815

Ile Gly Asp Thr Arg Asp Pro His Leu Trp Phe Val Gly Ala Gly Asn
            820                 825                 830

Ser Gln Thr Ser Phe Val Val Pro Tyr Asn Ser Pro Leu Ser Val Leu
            835                 840                 845

Pro Ala Ala Trp Phe Asn Gly Trp Ser Asp Phe Gly Asn Thr Lys Asp
850                 855                 860

Phe Gly Val Ala Pro Asn Ala Asp Phe Gly Arg Leu Trp Ile Gln Gly
865                 870                 875                 880

Asn Thr Ser Val Ala Val Arg Val Arg Tyr Lys Lys Met Lys Val Phe
            885                 890                 895

Cys Pro Arg Pro Thr Leu Phe Leu Pro Trp Pro Ser Thr Thr Thr Thr
            900                 905                 910

Arg Ile His Ala Asp Asn Pro Val Ser Val Met Glu Leu Gln Asn Pro
            915                 920                 925

Phe Ser Phe Tyr Arg Val Asp Leu Phe Ile Thr Phe Thr Asp Glu Leu
930                 935                 940

Ile Thr Phe Asp Tyr Lys Val His Gly Arg Pro Val Leu Gln Tyr Gln
945                 950                 955                 960

Val Pro Gly Leu Gly Leu Thr Cys Ala Gly Arg Met Leu Val Cys Met
            965                 970                 975

Gly Gln Met Pro Asn His Ala Pro Phe Ser Thr Val Arg His Leu Tyr
            980                 985                 990

His Val Val Phe Thr Gly Ser Arg Asn Ser Phe Gly Val Val Ile Tyr
            995                 1000                1005

Tyr Lys Arg His Arg Pro Trp Lys Pro Leu His Glu Glu Leu His
    1010                1015                1020

Asp Tyr Gly Phe Glu Cys Phe Ser Asp Phe Phe Lys His Val Arg Glu
1025                1030                1035                1040

```
Tyr His Ala Ala Tyr Tyr Lys Gln Arg Leu Met His Asp Val Glu Thr
            1045                1050                1055
Asn Pro Gly Pro Pro Val Gln Ser Val Phe Arg Pro Gln Gly Gly Val
        1060                1065                1070
Leu Thr Lys Ser Gln Ala Pro Met Ser Gly Ile Gln Asn Leu Phe Leu
        1075                1080                1085
Arg Ala Leu Gly Ile Asp Ala Asp His Gly Glu Phe Thr Arg Ala Val
        1090                1095                1100
Thr Met Ile Thr Asp Leu Cys Asn Thr Trp Glu Lys Ala Lys Asn Thr
1105                1110                1115                1120
Leu Val Ser Pro Glu Phe Trp Thr Val Leu Ile Met Lys Thr Val Lys
            1125                1130                1135
Phe Ile Ala Ala Ser Val Leu Tyr Leu His Asn Pro Asp Leu Thr Ala
            1140                1145                1150
Thr Ile Cys Leu Ser Leu Met Thr Gly Val Asp Val Leu Thr Asn Glu
            1155                1160                1165
Ser Ile Phe Asn Trp Leu Ser Asn Lys Leu Ser Lys Leu Phe His Thr
        1170                1175                1180
Pro Pro Pro Thr Ser Pro Leu Leu Gln Ala Gln Ser Pro Leu Arg
1185                1190                1195                1200
Glu Ala Asn Asp Gly Phe Asn Leu Ala Lys Asn Ile Glu Trp Ala Ile
            1205                1210                1215
Lys Thr Val Gln Lys Ile Val Asp Trp Leu Met Ser Trp Phe Lys Gln
            1220                1225                1230
Glu Glu Ala His Pro Gln Ala Lys Leu Asp Lys Met Leu Ala Asp Phe
        1235                1240                1245
Pro Glu His Cys Ala Ser Ile Leu Ala Met Arg Asn Gly Arg Lys Ala
        1250                1255                1260
Tyr Thr Asp Cys Ala Gly Ala Phe Lys Tyr Phe Glu Asp Leu Tyr Asn
1265                1270                1275                1280
Leu Ala Val Gln Cys Lys Arg Ile Pro Leu Ala Thr Leu Cys Glu Lys
            1285                1290                1295
Phe Lys Asn Lys His Asp His Ala Val Ala Arg Pro Glu Pro Val Val
        1300                1305                1310
Val Val Leu Arg Gly Asn Ala Gly Gln Gly Lys Ser Val Thr Ser Gln
        1315                1320                1325
Ile Ile Ala Gln Ala Val Ser Lys Leu Ala Phe Gly Arg Gln Ser Val
        1330                1335                1340
Tyr Ser Ile Pro Pro Asp Ser Asp Tyr Leu Asp Gly Tyr Glu Asn Gln
1345                1350                1355                1360
Phe Ser Val Ile Met Asp Asp Leu Gly Gln Asn Pro Asp Gly Glu Asp
            1365                1370                1375
Phe Lys Val Phe Cys Gln Met Val Ser Ser Thr Asn Phe Leu Pro Asn
        1380                1385                1390
Met Ala His Leu Glu Lys Lys Gly Thr Pro Phe Thr Ser Asn Phe Ile
        1395                1400                1405
Val Ala Thr Thr Asn Leu Pro Lys Phe Arg Pro Val Thr Val Ala His
        1410                1415                1420
Tyr Pro Ala Val Asp Arg Arg Ile Thr Phe Asp Leu Thr Val Glu Ala
1425                1430                1435                1440
Gly Pro Ala Cys Lys Thr Pro Thr Gly Met Leu Asp Val Glu Lys Ala
            1445                1450                1455
Phe Gln Glu Ile Pro Gly Glu Pro Gln Leu Asp Cys Phe Ser Ser Asp
```

```
              1460           1465           1470
Cys Ala Leu Leu His Lys Arg Gly Val Gln Phe Ile Cys Asn Arg Thr
        1475           1480           1485
Lys Lys Ile Tyr Asn Leu Gln Gln Ile Val Lys Met Val Lys Asp Thr
        1490           1495           1500
Ile Asp Asn Lys Val Ala Asn Leu Lys Lys Met Asn Thr Leu Val Ala
1505           1510           1515           1520
Gln Ser Pro Asn Asn Gly Asn Asp Met Glu His Ile Ile Thr Cys Leu
                1525           1530           1535
Arg Gln Asn Asn Ala Ala Leu Gln Asp Gln Ile Asp Glu Leu Gln Glu
        1540           1545           1550
Ala Phe Ala Gln Ala Gln Glu Arg Gln Asn Phe Leu Ser Asp Trp Met
        1555           1560           1565
Lys Val Ser Ala Ile Ile Phe Ala Gly Ile Ala Ser Leu Ser Ala Val
        1570           1575           1580
Cys Lys Leu Val Gly Arg Leu Lys Asn Leu Ile Trp Pro Ser Pro Val
1585           1590           1595           1600
His Val Glu Leu Ser Glu Gly Glu Gln Ala Ala Tyr Ala Gly Ala Lys
                1605           1610           1615
Arg Gly Ala Lys Gln Ala Leu Gln Val Leu Asp Leu Gln Gly Gly Gly
        1620           1625           1630
Arg Ile Ile Ala Gln Ala Gly Asn Pro Val Met Asp Tyr Glu Val Cys
        1635           1640           1645
Val Ala Lys Asn Met Val Ala Pro Ile Thr Phe Tyr Tyr Ala Asp Lys
        1650           1655           1660
Ala Gln Val Thr Gln Ser Cys Leu Leu Val Lys Gly Arg Leu Phe Val
1665           1670           1675           1680
Val Asn Arg His Val Ala Glu Thr Asp Trp Val Ser Phe Glu Leu Arg
                1685           1690           1695
Asp Val Arg His Glu Arg Asp Thr Val Thr Met Arg Ser Val Asn Arg
        1700           1705           1710
Ser Gly Met Glu Val Asp Leu Thr Phe Ile Lys Val Thr Lys Gly Pro
        1715           1720           1725
Leu Phe Lys Asp Asn Thr Lys Lys Phe Cys Ser Asn Lys Asp Asp Phe
        1730           1735           1740
Pro Gln Lys Asn Glu Thr Val Thr Gly Ile Met Asn Thr Gly Leu Pro
1745           1750           1755           1760
Phe Val Phe Asn Gly Lys Phe Ile Ile Gly Asn His Pro Val Asn Thr
                1765           1770           1775
Thr Thr Gly Ala Thr Phe Asn His Cys Leu His Tyr Arg Ala Asn Thr
        1780           1785           1790
Arg Arg Gly Trp Cys Gly Ser Ala Val Ile Cys Gln Val Asn Gly Lys
        1795           1800           1805
Lys Ala Val Tyr Gly Met His Ser Ala Gly Gly Gly Gly Leu Ala Ala
        1810           1815           1820
Ala Thr Ile Ile Thr Gln Glu Leu Val Glu Ala Ala Glu Gln Asn Met
1825           1830           1835           1840
Asp Arg Leu Val Pro Gln Gly Ala Ile Met Glu Ile Gly Thr Gly Ser
                1845           1850           1855
Val Val His Val Pro Arg Lys Thr Lys Leu Arg Arg Thr Val Ala His
        1860           1865           1870
Glu Ile Phe Leu Pro Lys Phe Glu Pro Ala Val Leu Ser Arg Tyr Asp
        1875           1880           1885
```

```
Pro Arg Thr Glu Lys Asp Val Asp Gln Val Ala Phe Ser Lys His Thr
    1890                1895                1900

Thr Asn Met Glu Glu Leu Pro Ala Val Phe Ser Met Val Ala Lys Glu
1905                1910                1915                1920

Tyr Ala Asn Arg Val Phe Thr Lys Leu Gly Lys Glu Asn Gln Leu Leu
                1925                1930                1935

Thr Thr Gln Gln Ala Ile Leu Gly Leu Pro Gly Met Asp Pro Met Glu
            1940                1945                1950

Lys Asp Thr Ser Pro Gly Leu Pro Tyr Thr Gln Gln Gly Leu Arg Arg
        1955                1960                1965

Thr Asp Leu Val Asn Phe Glu Thr Gly Lys Met Asp His Asn Leu Asp
    1970                1975                1980

Tyr Ala His Ser Lys Leu Met Leu Gly His Tyr Glu Asp Val Val Tyr
1985                1990                1995                2000

Gln Ser Phe Leu Lys Asp Glu Ile Arg Pro Ile Glu Lys Ile His Glu
                2005                2010                2015

Ala Lys Thr Arg Ile Val Asp Val Pro Pro Phe His His Cys Ile Trp
            2020                2025                2030

Gly Arg Gln Leu Leu Gly Arg Phe Ala Ser Arg Phe Gln Thr Asn Pro
        2035                2040                2045

Gly Leu Asp Leu Gly Ser Ala Ile Gly Thr Asp Pro Asp Val Asp Trp
    2050                2055                2060

Thr Val Phe Ala His Gln Leu Ala Glu Phe Lys Tyr Ile Tyr Asp Val
2065                2070                2075                2080

Asp Tyr Ser Asn Phe Asp Ala Ser His Ser Thr Ala Ile Phe Glu Ile
                2085                2090                2095

Leu Ile Gln Glu Phe Phe Thr Pro Gln Asn Gly Phe Asp Pro Arg Ile
            2100                2105                2110

Gly Glu Tyr Leu Arg Ser Leu Ala Val Ser Arg His Ala Tyr Glu Asp
        2115                2120                2125

Arg Arg Val Leu Ile Arg Gly Gly Leu Pro Ser Gly Cys Ala Ala Thr
    2130                2135                2140

Ser Met Ile Asn Thr Ile Ile Asn Asn Ile Val Ile Arg Ala Ala Leu
2145                2150                2155                2160

Tyr Met Thr Tyr Ala Asn Phe Glu Phe Asp Asp Ile Lys Val Leu Ser
                2165                2170                2175

Tyr Gly Asp Asp Leu Leu Ile Ala Thr Asn Tyr Glu Ile Asn Phe Asn
            2180                2185                2190

Leu Val Lys Glu Arg Leu Ala Pro Phe Asn Tyr Lys Ile Thr Pro Ala
        2195                2200                2205

Asn Lys Thr Ser Thr Phe Pro Gln Thr Ser His Leu Gln Asp Val Val
    2210                2215                2220

Phe Leu Lys Arg Arg Phe Val Gln Phe Asn Ser Phe Leu Phe Arg Pro
2225                2230                2235                2240

Gln Met Glu Thr Glu Asn Leu Lys Ala Met Val Ser Tyr Cys Arg Pro
                2245                2250                2255

Gly Val Leu Lys Glu Lys Leu Met Ser Ile Ala Leu Leu Ala Val His
            2260                2265                2270

Ser Gly Pro Asp Val Tyr Asp Glu Ile Phe Met Pro Phe Arg Arg Ile
        2275                2280                2285

Gly Val Val Val Pro Glu Tyr Ser Thr Met Leu Tyr Arg Trp Leu Asn
    2290                2295                2300

Leu Phe Arg
2305
```

<210> SEQ ID NO 34
<211> LENGTH: 930
<212> TYPE: PRT
<213> ORGANISM: Theiler's murine encephalomyelitis virus
<220> FEATURE:
<221> NAME/KEY: MOD_RES
<222> LOCATION: (557)
<223> OTHER INFORMATION: variable amino acid

<400> SEQUENCE: 34

```
Met Ala Cys Lys His Gly Tyr Pro Asp Val Cys Pro Ile Cys Thr Ala
1               5                   10                  15

Ile Asp Val Thr Pro Gly Phe Glu Tyr Leu Leu Leu Ala Asp Gly Glu
            20                  25                  30

Trp Phe Pro Thr Asp Leu Leu Cys Val Asp Leu Asp Asp Asp Val Phe
        35                  40                  45

Trp Pro Ser Asp Ser Ser Asn Gln Ser Gln Thr Met Glu Trp Thr Asp
    50                  55                  60

Ile Pro Leu Ile Cys Asp Thr Val Met Glu Pro Gln Gly Asn Ser Thr
65                  70                  75                  80

Ser Ser Asp Lys Ser Asn Ser Gln Ser Ser Gly Asn Glu Gly Val Ile
                85                  90                  95

Ile Asn Asn Phe Tyr Ser Asn Gln Tyr Gln Asn Ser Ile Asp Leu Ser
            100                 105                 110

Ala Asn Gly Gly Asn Ala Gly Asp Gly Pro Lys Thr Glu Gly Gln Leu
        115                 120                 125

Ser Asn Ile Leu Gly Gly Ala Ala Asn Ala Phe Ala Thr Met Ala Pro
    130                 135                 140

Leu Leu Leu Asp Glu Asn Thr Glu Glu Met Glu Asn Leu Ser Asp Arg
145                 150                 155                 160

Val Asp Ser Asp Lys Ala Gly Asn Ser Ala Thr Asn Thr Gln Ser Ser
                165                 170                 175

Val Gly Arg Leu His Gly Tyr Gly Ala Thr His Arg Gly Asp His Pro
            180                 185                 190

Ala Ser Cys Ala Asp Thr Ala Thr Asp Lys Val Leu Ala Ala Glu Arg
        195                 200                 205

Tyr Tyr Thr Ile Asp Leu Ala Thr Trp Thr Thr Ala Gln Thr Thr Phe
    210                 215                 220

Ser His Ile Arg Val Pro Leu Pro His Ala Leu Ala Gly Glu His Gly
225                 230                 235                 240

Gly Val Phe Gly Ala Thr Leu Arg Arg His Tyr Leu Ala Lys Cys Gly
                245                 250                 255

Trp Arg Val Gln Val Gln Cys Asn Ala Ser Gln Phe His Ala Gly Ser
            260                 265                 270

Leu Leu Val Phe Leu Ala Pro Glu Phe Tyr Thr Gly Thr Gly Val Ala
        275                 280                 285

Thr Ser Gly Gln Glu Pro Asn Lys Val Phe Leu Met Asp Thr Thr Trp
    290                 295                 300

Gln Glu Pro Gln Ala Ala Pro Thr Gly Phe Arg Tyr Asp Gly Lys Asn
305                 310                 315                 320

Gly Phe Phe Thr Leu Asn His Gln Asn Tyr Trp Gln Trp Thr Val Tyr
                325                 330                 335

Pro His Gln Ile Leu Asn Leu Arg Thr Asn Thr Ser Val Asp Leu Glu
            340                 345                 350

Val Pro Tyr Val Asn Val Ala Pro Thr Ser Ser Trp Thr Gln His Ala
```

```
                355                 360                 365
Asn Trp Ala Leu Val Val Ala Val Leu Thr Pro Leu Gln Tyr Ser Thr
370                 375                 380
Gly Ala Ala Thr Asp Val Ala Ile Thr Val Ser Leu Gln Pro Val Asn
385                 390                 395                 400
Pro Val Phe Asn Gly Leu Arg His Glu Ala Gln Val Pro Gln Ser Pro
                405                 410                 415
Val Ala Val Thr Val Arg Glu His Gln Gly Ser Phe Tyr Ser Thr Asn
                420                 425                 430
Pro Asp Thr Thr Val Pro Ile Tyr Gly Lys Thr Ile Val Thr Pro Ser
                435                 440                 445
Asp Tyr Met Cys Gly Glu Phe Thr Asp Leu Leu Glu Leu Cys Lys Leu
                450                 455                 460
Pro Thr Phe Leu Gly Asn Leu Ser Asn Asp Thr Arg Val Pro Phe Phe
465                 470                 475                 480
Thr Ala Thr Asn Ser Val Pro Thr Glu Ser Leu Val Glu Tyr Gln Val
                485                 490                 495
Thr Leu Ser Cys Ser Cys Met Ser Asn Ser Met Leu Ala Ser Val Ala
                500                 505                 510
Arg Asn Phe Asn Gln Tyr Arg Gly Ser Leu Asn Phe Leu Phe Val Phe
                515                 520                 525
Thr Gly Ser Ala Met Thr Lys Gly Lys Phe Leu Ile Ala Tyr Thr Pro
                530                 535                 540
Pro Gly Ala Gly Lys Pro Thr Thr Arg Asp Gln Ala Xaa Gln Ser Thr
545                 550                 555                 560
Tyr Ala Ile Trp Asp Leu Gly Leu Asn Ser Ser Tyr Asn Phe Thr Val
                565                 570                 575
Pro Phe Ile Ser Pro Ser His Tyr Arg Gln Thr Ser Tyr Thr Ser Pro
                580                 585                 590
Ser Ile Ala Ala Val Asp Gly Trp Leu Thr Val Trp Gln Leu Thr Pro
                595                 600                 605
Leu Thr Phe Pro Ala Asn Val Pro Pro Ser Ser Asp Ile Leu Thr Leu
                610                 615                 620
Val Ser Ala Gly Asn Asp Phe Thr Leu Arg Met Pro Ile Ser Pro Thr
625                 630                 635                 640
Lys Trp Ile Pro Gln Gly Val Asp Asn Ala Glu Lys Gly Lys Val Ser
                645                 650                 655
Asp Asp Asn Ala Ser Val Asp Phe Val Ala Glu Pro Ile Lys Leu Pro
                660                 665                 670
Glu Asn Gln Thr Arg Val Asn Phe Phe Tyr Asp Arg Ser Ser Pro Ile
                675                 680                 685
Gly Leu Leu Arg Pro Asn Gln Ala Ile Glu Ser Asn Phe Ser Tyr Ser
                690                 695                 700
Ala Asp Ser Asn Gly Ala Thr Asn Cys Ala Leu Leu Thr Pro Leu Pro
705                 710                 715                 720
Ser Tyr Ser Pro Asp Arg Pro Gly Gln Ser Pro Asp Thr Ser Lys Ala
                725                 730                 735
Pro Ile Gln Trp Arg Trp Ile Ser Ala Val Thr Glu Ser Gly Thr Val
                740                 745                 750
Ser Asn Thr Phe Pro Thr Arg Thr Arg Gln Asp Tyr Ala Phe Leu Leu
                755                 760                 765
Phe Ser Pro Phe Thr Tyr Tyr Lys Cys Asp Leu Glu Val Thr Leu Ser
770                 775                 780
```

```
Ser Val Gly Asn Gly Val Val Ala Ser Leu Val Arg Trp Ala Pro Thr
785                 790                 795                 800

Gly Ala Pro Ala Asp Ile Thr Thr Gln Leu Thr Thr Ser Thr Pro Ser
            805                 810                 815

Ile Gly Asp Thr Arg Asp Pro His Met Trp Leu Val Gly Ala Gly Asn
        820                 825                 830

Ser Gln Thr Ser Phe Val Ile Pro Tyr Asn Ser Pro Leu Ser Val Leu
    835                 840                 845

Pro Ala Ala Trp Phe Asn Gly Trp Ser Asn Phe Ser Asn Thr Tyr Asp
850                 855                 860

Phe Gly Ile Ala Pro Cys Ser Asp Phe Gly Arg Leu Trp Ile Gln Gly
865                 870                 875                 880

Asn Ala Pro Leu Ala Ile Arg Val Arg Tyr Lys Lys Met Arg Val Phe
            885                 890                 895

Cys Pro Arg Pro Thr Leu Phe Phe Pro Trp Pro Thr Pro Thr Thr Thr
        900                 905                 910

Lys Val Asn Ala Asp Asn Pro Val Pro Ile Leu Asp Leu Glu Asn Pro
    915                 920                 925

Ala Ala
    930

<210> SEQ ID NO 35
<211> LENGTH: 142
<212> TYPE: PRT
<213> ORGANISM: Seneca Valley Virus

<400> SEQUENCE: 35

Leu Ala His His Gly Asn Lys Lys Ser Leu Gln Glu Leu Asn Glu Glu
1               5                   10                  15

Gln Trp Val Glu Met Ser Asp Asp Tyr Arg Thr Gly Lys Asn Met Pro
            20                  25                  30

Phe Gln Ser Leu Gly Thr Tyr Tyr Arg Pro Pro Asn Trp Thr Trp Gly
        35                  40                  45

Pro Asn Phe Ile Asn Pro Tyr Gln Val Thr Val Phe Pro His Gln Ile
    50                  55                  60

Leu Asn Ala Arg Thr Ser Thr Ser Val Asp Ile Asn Val Pro Tyr Ile
65                  70                  75                  80

Gly Glu Thr Pro Thr Gln Ser Ser Glu Thr Gln Asn Ser Trp Thr Leu
                85                  90                  95

Leu Val Met Val Leu Val Pro Leu Asp Tyr Lys Glu Gly Ala Thr Thr
            100                 105                 110

Asp Pro Glu Ile Thr Phe Ser Val Arg Pro Thr Ser Pro Tyr Phe Asn
        115                 120                 125

Gly Leu Arg Asn Arg Tyr Thr Ala Gly Thr Asp Glu Glu Gln
    130                 135                 140

<210> SEQ ID NO 36
<211> LENGTH: 239
<212> TYPE: PRT
<213> ORGANISM: Seneca Valley Virus

<400> SEQUENCE: 36

Gly Pro Ile Pro Thr Ala Pro Arg Glu Asn Ser Leu Met Phe Leu Ser
1               5                   10                  15

Thr Leu Pro Asp Asp Thr Val Pro Ala Tyr Gly Asn Val Arg Thr Pro
            20                  25                  30

Pro Val Asn Tyr Leu Pro Gly Glu Ile Thr Asp Leu Leu Gln Leu Ala
```

```
                    35                  40                  45
Arg Ile Pro Thr Leu Met Ala Phe Glu Arg Val Pro Glu Pro Val Pro
 50                  55                  60
Ala Ser Asp Thr Tyr Val Pro Tyr Val Ala Val Pro Thr Gln Phe Asp
 65                  70                  75                  80
Asp Arg Pro Leu Ile Ser Phe Pro Ile Thr Leu Ser Asp Pro Val Tyr
                 85                  90                  95
Gln Asn Thr Leu Val Gly Ala Ile Ser Ser Asn Phe Ala Asn Tyr Arg
                100                 105                 110
Gly Cys Ile Gln Ile Thr Leu Thr Phe Cys Gly Pro Met Met Ala Arg
                115                 120                 125
Gly Lys Phe Leu Leu Ser Tyr Ser Pro Pro Asn Gly Thr Gln Pro Gln
130                 135                 140
Thr Leu Ser Glu Ala Met Gln Cys Thr Tyr Ser Ile Trp Asp Ile Gly
145                 150                 155                 160
Leu Asn Ser Ser Trp Thr Phe Val Val Pro Tyr Ile Ser Pro Ser Asp
                165                 170                 175
Tyr Arg Glu Thr Arg Ala Ile Thr Asn Ser Val Tyr Ser Ala Asp Gly
                180                 185                 190
Trp Phe Ser Leu His Lys Leu Thr Lys Ile Thr Leu Pro Pro Asp Cys
                195                 200                 205
Pro Gln Ser Pro Cys Ile Leu Phe Phe Ala Ser Ala Gly Glu Asp Tyr
                210                 215                 220
Thr Leu Arg Leu Pro Val Asp Cys Asn Pro Ser Tyr Val Phe His
225                 230                 235

<210> SEQ ID NO 37
<211> LENGTH: 259
<212> TYPE: PRT
<213> ORGANISM: Seneca Valley Virus

<400> SEQUENCE: 37

Ser Thr Asp Asn Ala Glu Thr Gly Val Ile Glu Ala Gly Asn Thr Asp
  1               5                  10                  15
Thr Asp Phe Ser Gly Glu Leu Ala Ala Pro Gly Pro Asn His Thr Asn
                 20                  25                  30
Val Lys Phe Leu Phe Asp Arg Ser Arg Leu Leu Asn Val Ile Lys Val
                 35                  40                  45
Leu Glu Lys Asp Ala Val Phe Pro Arg Pro Phe Pro Thr Gln Glu Gly
 50                  55                  60
Ala Gln Gln Asp Asp Gly Tyr Phe Cys Leu Leu Thr Pro Arg Pro Thr
 65                  70                  75                  80
Val Ala Ser Arg Pro Ala Thr Arg Phe Gly Leu Tyr Ala Asn Pro Ser
                 85                  90                  95
Gly Ser Gly Val Leu Ala Asn Thr Ser Leu Asp Phe Asn Phe Tyr Ser
                100                 105                 110
Leu Ala Cys Phe Thr Tyr Phe Arg Ser Asp Leu Glu Val Thr Val Val
                115                 120                 125
Ser Leu Glu Pro Asp Leu Glu Phe Ala Val Gly Trp Phe Pro Ser Gly
130                 135                 140
Ser Glu Tyr Gln Ala Ser Ser Phe Val Tyr Asp Gln Leu His Val Pro
145                 150                 155                 160
Phe His Phe Thr Gly Arg Thr Pro Arg Ala Phe Ala Ser Lys Gly Gly
                165                 170                 175
Lys Val Ser Phe Val Leu Pro Trp Asn Ser Val Ser Ser Val Leu Pro
```

-continued

```
                180                 185                 190
Val Arg Trp Gly Gly Ala Ser Lys Leu Ser Ser Ala Thr Arg Gly Leu
            195                 200                 205

Pro Ala His Ala Asp Trp Gly Thr Ile Tyr Ala Phe Val Pro Arg Pro
        210                 215                 220

Asn Glu Lys Lys Ser Thr Ala Val Lys His Val Ala Val Tyr Ile Arg
225                 230                 235                 240

Tyr Lys Asn Ala Arg Ala Trp Cys Pro Ser Met Leu Pro Phe Arg Ser
                245                 250                 255

Tyr Lys Gln

<210> SEQ ID NO 38
<211> LENGTH: 14
<212> TYPE: PRT
<213> ORGANISM: Seneca Valley Virus

<400> SEQUENCE: 38

Lys Met Leu Met Gln Ser Gly Asp Ile Glu Thr Asn Pro Gly
1               5                   10

<210> SEQ ID NO 39
<211> LENGTH: 128
<212> TYPE: PRT
<213> ORGANISM: Seneca Valley Virus

<400> SEQUENCE: 39

Pro Ala Ser Asp Asn Pro Ile Leu Glu Phe Leu Glu Ala Glu Asn Asp
1               5                   10                  15

Leu Val Thr Leu Ala Ser Leu Trp Lys Met Val His Ser Val Gln Gln
            20                  25                  30

Thr Trp Arg Lys Tyr Val Lys Asn Asp Asp Phe Trp Pro Asn Leu Leu
        35                  40                  45

Ser Glu Leu Val Gly Glu Gly Ser Val Ala Leu Ala Ala Thr Leu Ser
    50                  55                  60

Asn Gln Ala Ser Val Lys Ala Leu Leu Gly Leu His Phe Leu Ser Arg
65                  70                  75                  80

Gly Leu Asn Tyr Thr Asp Phe Tyr Ser Leu Leu Ile Glu Lys Cys Ser
                85                  90                  95

Ser Phe Phe Thr Val Glu Pro Pro Pro Pro Ala Glu Asn Leu Met
            100                 105                 110

Thr Lys Pro Ser Val Lys Ser Lys Phe Arg Lys Leu Phe Lys Met Gln
        115                 120                 125

<210> SEQ ID NO 40
<211> LENGTH: 322
<212> TYPE: PRT
<213> ORGANISM: Seneca Valley Virus

<400> SEQUENCE: 40

Gly Pro Met Asp Lys Val Lys Asp Trp Asn Gln Ile Ala Ala Gly Leu
1               5                   10                  15

Lys Asn Phe Gln Phe Val Arg Asp Leu Val Lys Glu Val Val Asp Trp
            20                  25                  30

Leu Gln Ala Trp Ile Asn Lys Glu Lys Ala Ser Pro Val Leu Gln Tyr
        35                  40                  45

Gln Leu Glu Met Lys Lys Leu Gly Pro Val Ala Leu Ala His Asp Ala
    50                  55                  60

Phe Met Ala Gly Ser Gly Pro Pro Leu Ser Asp Asp Gln Ile Glu Tyr
```

```
                    65                  70                  75                  80
Leu Gln Asn Leu Lys Ser Leu Ala Leu Thr Leu Gly Lys Thr Asn Leu
                85                  90                  95
Ala Gln Ser Leu Thr Thr Met Ile Asn Ala Lys Gln Ser Ser Ala Gln
               100                 105                 110
Arg Val Glu Pro Val Val Val Leu Arg Gly Lys Pro Gly Cys Gly
               115                 120                 125
Lys Gly Leu Ala Ser Thr Leu Ile Ala Gln Ala Val Ser Lys Arg Leu
               130                 135                 140
Tyr Gly Ser Gln Ser Val Tyr Ser Leu Pro Pro Asp Pro Asp Phe Phe
145                 150                 155                 160
Asp Gly Tyr Lys Gly Gln Phe Val Thr Leu Met Asp Asp Leu Gly Gln
                165                 170                 175
Asn Pro Asp Gly Gln Asp Phe Ser Thr Phe Cys Gln Met Val Ser Thr
                180                 185                 190
Ala Gln Phe Leu Pro Asn Met Ala Asp Leu Ala Glu Lys Gly Arg Pro
                195                 200                 205
Phe Thr Ser Asn Leu Ile Ile Ala Thr Thr Asn Leu Pro His Phe Ser
                210                 215                 220
Pro Val Thr Ile Ala Asp Pro Ser Ala Val Ser Arg Arg Ile Asn Tyr
225                 230                 235                 240
Asp Leu Thr Leu Glu Val Ser Glu Ala Tyr Lys Lys His Thr Arg Leu
                245                 250                 255
Asn Phe Asp Leu Ala Phe Arg Arg Thr Asp Ala Pro Pro Ile Tyr Pro
                260                 265                 270
Phe Ala Ala His Val Pro Phe Val Asp Val Ala Val Arg Phe Lys Asn
                275                 280                 285
Gly His Gln Asn Phe Asn Leu Leu Glu Leu Val Asp Ser Ile Cys Thr
                290                 295                 300
Asp Ile Arg Ala Lys Gln Gln Gly Ala Arg Asn Met Gln Thr Leu Val
305                 310                 315                 320
Leu Gln

<210> SEQ ID NO 41
<211> LENGTH: 90
<212> TYPE: PRT
<213> ORGANISM: Seneca Valley Virus

<400> SEQUENCE: 41

Ser Pro Asn Glu Asn Asp Thr Pro Val Asp Glu Ala Leu Gly Arg
1               5                  10                  15
Val Leu Ser Pro Ala Ala Val Asp Glu Ala Leu Val Asp Leu Thr Pro
                20                  25                  30
Glu Ala Asp Pro Val Gly Arg Leu Ala Ile Leu Ala Lys Leu Gly Leu
                35                  40                  45
Ala Leu Ala Ala Val Thr Pro Gly Leu Ile Ile Leu Ala Val Gly Leu
                50                  55                  60
Tyr Arg Tyr Phe Ser Gly Ser Asp Ala Asp Gln Glu Glu Thr Glu Ser
65                  70                  75                  80
Glu Gly Ser Val Lys Ala Pro Arg Ser Glu
                85                  90

<210> SEQ ID NO 42
<211> LENGTH: 22
<212> TYPE: PRT
<213> ORGANISM: Seneca Valley Virus
```

```
<400> SEQUENCE: 42

Asn Ala Tyr Asp Gly Pro Lys Lys Asn Ser Lys Pro Pro Gly Ala Leu
1               5                   10                  15

Ser Leu Met Glu Met Gln
            20

<210> SEQ ID NO 43
<211> LENGTH: 211
<212> TYPE: PRT
<213> ORGANISM: Seneca Valley Virus

<400> SEQUENCE: 43

Gln Pro Asn Val Asp Met Gly Phe Glu Ala Ala Val Ala Lys Lys Val
1               5                   10                  15

Val Val Pro Ile Thr Phe Met Val Pro Asn Arg Pro Ser Gly Leu Thr
                20                  25                  30

Gln Ser Ala Leu Leu Val Thr Gly Arg Thr Phe Leu Ile Asn Glu His
            35                  40                  45

Thr Trp Ser Asn Pro Ser Trp Thr Ser Phe Thr Ile Arg Gly Glu Val
    50                  55                  60

His Thr Arg Asp Glu Pro Phe Gln Thr Val His Phe Thr His His Gly
65                  70                  75                  80

Ile Pro Thr Asp Leu Met Met Val Arg Leu Gly Pro Gly Asn Ser Phe
                85                  90                  95

Pro Asn Asn Leu Asp Lys Phe Gly Leu Asp Gln Met Pro Ala Arg Asn
                100                 105                 110

Ser Arg Val Val Gly Val Ser Ser Tyr Gly Asn Phe Phe Phe Ser
            115                 120                 125

Gly Asn Phe Leu Gly Phe Val Asp Ser Val Thr Ser Glu Gln Gly Thr
    130                 135                 140

Tyr Ala Arg Leu Phe Arg Tyr Arg Val Thr Thr Tyr Lys Gly Trp Cys
145                 150                 155                 160

Gly Ser Ala Leu Val Cys Glu Ala Gly Gly Val Arg Arg Ile Ile Gly
                165                 170                 175

Leu His Ser Ala Gly Ala Ala Gly Ile Gly Ala Gly Thr Tyr Ile Ser
                180                 185                 190

Lys Leu Gly Leu Ile Lys Ala Leu Lys His Leu Gly Glu Pro Leu Ala
            195                 200                 205

Thr Met Gln
    210

<210> SEQ ID NO 44
<211> LENGTH: 462
<212> TYPE: PRT
<213> ORGANISM: Seneca Valley Virus

<400> SEQUENCE: 44

Gly Leu Met Thr Glu Leu Glu Pro Gly Ile Thr Val His Val Pro Arg
1               5                   10                  15

Lys Ser Lys Leu Arg Lys Thr Thr Ala His Ala Val Tyr Lys Pro Glu
                20                  25                  30

Phe Glu Pro Ala Val Leu Ser Lys Phe Asp Pro Arg Leu Asn Lys Asp
            35                  40                  45

Val Asp Leu Asp Glu Val Ile Trp Ser Lys His Thr Ala Asn Val Pro
    50                  55                  60

Tyr Gln Pro Pro Leu Phe Tyr Thr Tyr Met Ser Glu Tyr Ala His Arg
```

```
            65                  70                  75                  80
Val Phe Ser Phe Leu Gly Lys Asp Asn Asp Ile Leu Thr Val Lys Glu
                    85                  90                  95

Ala Ile Leu Gly Ile Pro Gly Leu Asp Pro Met Asp Pro His Thr Ala
                100                 105                 110

Pro Gly Leu Pro Tyr Ala Ile Asn Gly Leu Arg Arg Thr Asp Leu Val
            115                 120                 125

Asp Phe Val Asn Gly Thr Val Asp Ala Ala Leu Ala Val Gln Ile Gln
        130                 135                 140

Lys Phe Leu Asp Gly Asp Tyr Ser Asp His Val Phe Gln Thr Phe Leu
145                 150                 155                 160

Lys Asp Glu Ile Arg Pro Ser Glu Lys Val Arg Ala Gly Lys Thr Arg
                165                 170                 175

Ile Val Asp Val Pro Ser Leu Ala His Cys Ile Val Gly Arg Met Leu
                180                 185                 190

Leu Gly Arg Phe Ala Ala Lys Phe Gln Ser His Pro Gly Phe Leu Leu
            195                 200                 205

Gly Ser Ala Ile Gly Ser Asp Pro Asp Val Phe Trp Thr Val Ile Gly
        210                 215                 220

Ala Gln Leu Glu Gly Arg Lys Asn Thr Tyr Asp Val Asp Tyr Ser Ala
225                 230                 235                 240

Phe Asp Ser Ser His Gly Thr Gly Ser Phe Glu Ala Leu Ile Ser His
                245                 250                 255

Phe Phe Thr Val Asp Asn Gly Phe Ser Pro Ala Leu Gly Pro Tyr Leu
                260                 265                 270

Arg Ser Leu Ala Val Ser Val His Ala Tyr Gly Glu Arg Arg Ile Lys
            275                 280                 285

Ile Thr Gly Gly Leu Pro Ser Gly Cys Ala Ala Thr Ser Leu Leu Asn
        290                 295                 300

Thr Val Leu Asn Asn Val Ile Ile Arg Thr Ala Leu Ala Leu Thr Tyr
305                 310                 315                 320

Lys Glu Phe Glu Tyr Asp Thr Val Asp Ile Ile Ala Tyr Gly Asp Asp
                325                 330                 335

Leu Leu Val Gly Thr Asp Tyr Asp Leu Asp Phe Asn Glu Val Ala Arg
                340                 345                 350

Arg Ala Ala Lys Leu Gly Tyr Lys Met Thr Pro Ala Asn Lys Gly Ser
            355                 360                 365

Val Phe Pro Pro Thr Ser Ser Leu Ser Asp Ala Val Phe Leu Lys Arg
        370                 375                 380

Lys Phe Val Gln Asn Asn Asp Gly Leu Tyr Lys Pro Val Met Asp Leu
385                 390                 395                 400

Lys Asn Leu Glu Ala Met Leu Ser Tyr Phe Lys Pro Gly Thr Leu Leu
                405                 410                 415

Glu Lys Leu Gln Ser Val Ser Met Leu Ala Gln His Ser Gly Lys Glu
                420                 425                 430

Glu Tyr Asp Arg Leu Met His Pro Phe Ala Asp Tyr Gly Ala Val Pro
            435                 440                 445

Ser His Glu Tyr Leu Gln Ala Arg Trp Arg Ala Leu Phe Asp
        450                 455                 460

<210> SEQ ID NO 45
<211> LENGTH: 6
<212> TYPE: PRT
<213> ORGANISM: Seneca Valley Virus
```

```
<400> SEQUENCE: 45

Ala Gly Phe Cys Thr Glu
1               5

<210> SEQ ID NO 46
<211> LENGTH: 6
<212> TYPE: PRT
<213> ORGANISM: Seneca Valley Virus

<400> SEQUENCE: 46

Ala Gly Asp Cys Ala Glu
1               5

<210> SEQ ID NO 47
<211> LENGTH: 6
<212> TYPE: PRT
<213> ORGANISM: Seneca Valley Virus

<400> SEQUENCE: 47

Thr Gly Phe Cys Ala Glu
1               5

<210> SEQ ID NO 48
<211> LENGTH: 6
<212> TYPE: PRT
<213> ORGANISM: Seneca Valley Virus

<400> SEQUENCE: 48

Ala Gly Phe Cys Ala Glu
1               5

<210> SEQ ID NO 49
<211> LENGTH: 22
<212> TYPE: PRT
<213> ORGANISM: Porcine teschovirus

<400> SEQUENCE: 49

Gly Pro Gly Ala Thr Asn Phe Ser Leu Leu Lys Gln Ala Gly Asp Val
1               5                   10                  15

Glu Glu Asn Pro Gly Pro
            20

<210> SEQ ID NO 50
<211> LENGTH: 22
<212> TYPE: PRT
<213> ORGANISM: Porcine teschovirus

<400> SEQUENCE: 50

Gly Pro Gly Ala Thr Asn Phe Ser Leu Leu Lys Gln Ala Gly Asp Val
1               5                   10                  15

Glu Glu Asn Pro Gly Pro
            20

<210> SEQ ID NO 51
<211> LENGTH: 22
<212> TYPE: PRT
<213> ORGANISM: Porcine teschovirus

<400> SEQUENCE: 51

Gly Pro Gly Ala Ser Ser Phe Ser Leu Leu Lys Gln Ala Gly Asp Val
1               5                   10                  15

Glu Glu Asn Pro Gly Pro
            20
```

<210> SEQ ID NO 52
<211> LENGTH: 22
<212> TYPE: PRT
<213> ORGANISM: Porcine teschovirus

<400> SEQUENCE: 52

Gly Pro Gly Ala Ser Asn Phe Ser Leu Leu Lys Gln Ala Gly Asp Val
1               5                   10                  15

Glu Glu Asn Pro Gly Pro
            20

<210> SEQ ID NO 53
<211> LENGTH: 22
<212> TYPE: PRT
<213> ORGANISM: Porcine teschovirus

<400> SEQUENCE: 53

Gly Pro Gly Ala Thr Asn Phe Ser Leu Leu Lys Gln Ala Gly Asp Val
1               5                   10                  15

Glu Glu Asn Pro Gly Pro
            20

<210> SEQ ID NO 54
<211> LENGTH: 22
<212> TYPE: PRT
<213> ORGANISM: Porcine teschovirus

<400> SEQUENCE: 54

Gly Pro Gly Ala Ala Asn Phe Ser Leu Leu Arg Gln Ala Gly Asp Val
1               5                   10                  15

Glu Glu Asn Pro Gly Pro
            20

<210> SEQ ID NO 55
<211> LENGTH: 22
<212> TYPE: PRT
<213> ORGANISM: Porcine teschovirus

<400> SEQUENCE: 55

Gly Pro Gly Ala Thr Asn Phe Ser Leu Leu Lys Gln Ala Gly Asp Val
1               5                   10                  15

Glu Glu Asn Pro Gly Pro
            20

<210> SEQ ID NO 56
<211> LENGTH: 22
<212> TYPE: PRT
<213> ORGANISM: Porcine teschovirus

<400> SEQUENCE: 56

Gly Pro Gly Ala Thr Asn Phe Ser Leu Leu Lys Gln Ala Gly Asp Val
1               5                   10                  15

Glu Glu Asn Pro Gly Pro
            20

<210> SEQ ID NO 57
<211> LENGTH: 22
<212> TYPE: PRT
<213> ORGANISM: Porcine teschovirus

<400> SEQUENCE: 57

Gly Pro Gly Ala Thr Asn Phe Ser Leu Leu Lys Gln Ala Gly Asp Ile
1               5                   10                  15

Glu Glu Asn Pro Gly Pro
            20

<210> SEQ ID NO 58
<211> LENGTH: 22
<212> TYPE: PRT
<213> ORGANISM: Porcine teschovirus

<400> SEQUENCE: 58

Gly Pro Gly Ala Thr Asn Phe Ser Leu Leu Lys Gln Ala Gly Asp Val
1               5                   10                  15

Glu Glu Asn Pro Gly Pro
            20

<210> SEQ ID NO 59
<211> LENGTH: 22
<212> TYPE: PRT
<213> ORGANISM: Porcine teschovirus

<400> SEQUENCE: 59

Gly Pro Gly Ala Thr Asn Phe Ser Leu Leu Lys Gln Ala Gly Asp Val
1               5                   10                  15

Glu Glu Asn Pro Gly Pro
            20

<210> SEQ ID NO 60
<211> LENGTH: 22
<212> TYPE: PRT
<213> ORGANISM: Porcine teschovirus

<400> SEQUENCE: 60

Gly Pro Gly Ala Thr Asn Phe Ser Leu Leu Lys Arg Ala Gly Asp Val
1               5                   10                  15

Glu Glu Asn Pro Gly Pro
            20

<210> SEQ ID NO 61
<211> LENGTH: 19
<212> TYPE: PRT
<213> ORGANISM: Foot and mouth disease virus

<400> SEQUENCE: 61

Thr Leu Asn Phe Asp Leu Leu Lys Leu Ala Gly Asp Val Glu Ser Asn
1               5                   10                  15

Pro Gly Pro

<210> SEQ ID NO 62
<211> LENGTH: 19
<212> TYPE: PRT
<213> ORGANISM: Foot and mouth disease virus

<400> SEQUENCE: 62

Leu Leu Asn Phe Asp Leu Leu Lys Leu Ala Gly Asp Val Glu Ser Asn
1               5                   10                  15

Pro Gly Pro

<210> SEQ ID NO 63
<211> LENGTH: 19
<212> TYPE: PRT
<213> ORGANISM: Foot and mouth disease virus

<400> SEQUENCE: 63

-continued

Leu Leu Asn Phe Asp Leu Leu Gln Leu Ala Gly Asp Val Glu Ser Asn
1               5                   10                  15

Pro Gly Pro

<210> SEQ ID NO 64
<211> LENGTH: 19
<212> TYPE: PRT
<213> ORGANISM: Foot and mouth disease virus

<400> SEQUENCE: 64

Leu Leu Asn Phe Asp Leu Leu Lys Leu Ala Gly Asp Val Glu Pro Asn
1               5                   10                  15

Pro Gly Pro

<210> SEQ ID NO 65
<211> LENGTH: 19
<212> TYPE: PRT
<213> ORGANISM: Foot and mouth disease virus

<400> SEQUENCE: 65

Leu Leu Asn Phe Asp Leu Leu Lys Leu Ala Gly Asp Val Glu Ser Asn
1               5                   10                  15

Pro Gly Pro

<210> SEQ ID NO 66
<211> LENGTH: 19
<212> TYPE: PRT
<213> ORGANISM: Foot and mouth disease virus

<400> SEQUENCE: 66

Leu Ser Asn Phe Asp Leu Leu Lys Leu Ala Gly Asp Val Glu Ser Asn
1               5                   10                  15

Pro Gly Pro

<210> SEQ ID NO 67
<211> LENGTH: 19
<212> TYPE: PRT
<213> ORGANISM: Foot and mouth disease virus

<400> SEQUENCE: 67

Leu Leu Asn Phe Asp Leu Leu Lys Leu Ala Gly Asp Val Glu Ser Asn
1               5                   10                  15

Pro Gly Pro

<210> SEQ ID NO 68
<211> LENGTH: 19
<212> TYPE: PRT
<213> ORGANISM: Foot and mouth disease virus

<400> SEQUENCE: 68

Thr Leu Asn Phe Asp Leu Leu Lys Leu Ala Gly Asp Val Glu Ser Asn
1               5                   10                  15

Pro Gly Pro

<210> SEQ ID NO 69
<211> LENGTH: 19
<212> TYPE: PRT
<213> ORGANISM: Foot and mouth disease virus

<400> SEQUENCE: 69

Ala Leu Asn Phe Asp Leu Leu Lys Leu Ala Gly Asp Val Glu Ser Asn
1               5                   10                  15

Pro Gly Pro

<210> SEQ ID NO 70
<211> LENGTH: 19
<212> TYPE: PRT
<213> ORGANISM: Foot and mouth disease virus

<400> SEQUENCE: 70

Val Leu Asn Phe Asp Leu Leu Lys Leu Ala Gly Asp Val Glu Ser Asn
1               5                   10                  15

Pro Gly Pro

<210> SEQ ID NO 71
<211> LENGTH: 19
<212> TYPE: PRT
<213> ORGANISM: Foot and mouth disease virus

<400> SEQUENCE: 71

Met Cys Ser Phe Asp Leu Leu Lys Leu Ala Gly Asp Val Glu Ser Asn
1               5                   10                  15

Pro Gly Pro

<210> SEQ ID NO 72
<211> LENGTH: 19
<212> TYPE: PRT
<213> ORGANISM: Foot and mouth disease virus

<400> SEQUENCE: 72

Leu Cys Asn Phe Asp Leu Leu Lys Leu Ala Gly Asp Val Glu Ser Asn
1               5                   10                  15

Pro Gly Pro

<210> SEQ ID NO 73
<211> LENGTH: 19
<212> TYPE: PRT
<213> ORGANISM: Foot and mouth disease virus

<400> SEQUENCE: 73

Leu Cys Asn Phe Asp Leu Leu Met Leu Ala Gly Asp Val Glu Ser Asn
1               5                   10                  15

Pro Gly Pro

<210> SEQ ID NO 74
<211> LENGTH: 19
<212> TYPE: PRT
<213> ORGANISM: Foot and mouth disease virus

<400> SEQUENCE: 74

Met Ala Asn Phe Ala Leu Leu Lys Leu Ala Gly Asp Val Glu Ser Asn
1               5                   10                  15

Pro Gly Pro

<210> SEQ ID NO 75
<211> LENGTH: 19
<212> TYPE: PRT
<213> ORGANISM: Foot and mouth disease virus

<400> SEQUENCE: 75

Leu Ser Asn Phe Asp Leu Leu Lys Leu Ala Gly Asp Val Glu Ser Asn
1               5                   10                  15

Pro Gly Pro

<210> SEQ ID NO 76
<211> LENGTH: 19
<212> TYPE: PRT
<213> ORGANISM: Foot and mouth disease virus

<400> SEQUENCE: 76

Leu Phe Asn Phe Asp Leu Leu Lys Leu Ala Gly Asp Val Glu Ser Asn
1               5                   10                  15

Pro Gly Pro

<210> SEQ ID NO 77
<211> LENGTH: 19
<212> TYPE: PRT
<213> ORGANISM: Foot and mouth disease virus

<400> SEQUENCE: 77

Leu Cys Asn Cys Asp Leu Leu Lys Leu Ala Gly Asp Val Glu Ser Asn
1               5                   10                  15

Pro Gly Pro

<210> SEQ ID NO 78
<211> LENGTH: 19
<212> TYPE: PRT
<213> ORGANISM: Foot and mouth disease virus

<400> SEQUENCE: 78

Leu Leu Asn Phe Asp Leu Leu Lys Leu Ala Gly Asp Val Glu Ser Asn
1               5                   10                  15

Pro Gly Pro

<210> SEQ ID NO 79
<211> LENGTH: 19
<212> TYPE: PRT
<213> ORGANISM: Foot and mouth disease virus

<400> SEQUENCE: 79

Leu Cys Asn Phe Asp Leu Leu Lys Leu Ala Gly Asp Val Glu Ser Asn
1               5                   10                  15

Pro Gly Pro

<210> SEQ ID NO 80
<211> LENGTH: 19
<212> TYPE: PRT
<213> ORGANISM: Foot and mouth disease virus

<400> SEQUENCE: 80

Met Cys Asn Phe Asp Leu Leu Lys Leu Ala Gly Asp Val Glu Ser Asn
1               5                   10                  15

Pro Gly Pro

<210> SEQ ID NO 81
<211> LENGTH: 22
<212> TYPE: PRT
<213> ORGANISM: Equine rhinitis virus

<400> SEQUENCE: 81

Asn Lys Gln Cys Thr Asn Tyr Ala Leu Leu Lys Leu Ala Gly Asp Val
1               5                   10                  15

Glu Ser Asn Pro Gly Pro
            20

<210> SEQ ID NO 82
<211> LENGTH: 22
<212> TYPE: PRT
<213> ORGANISM: Equine rhinitis virus

<400> SEQUENCE: 82

Ser Glu Gly Ala Thr Asn Phe Ser Leu Leu Lys Leu Ala Gly Asp Val
1               5                   10                  15

Glu Leu Asn Pro Gly Pro
            20

<210> SEQ ID NO 83
<211> LENGTH: 22
<212> TYPE: PRT
<213> ORGANISM: Equine rhinitis virus

<400> SEQUENCE: 83

Ser Gln Gly Ala Thr Asn Phe Asp Leu Leu Lys Leu Ala Gly Asp Val
1               5                   10                  15

Glu Ser Asn Pro Gly Pro
            20

<210> SEQ ID NO 84
<211> LENGTH: 22
<212> TYPE: PRT
<213> ORGANISM: Encephalomyocarditis virus

<400> SEQUENCE: 84

Asn Ala His Tyr Ala Gly Tyr Phe Ala Asp Leu Leu Ile His Asp Ile
1               5                   10                  15

Glu Thr Asn Pro Gly Pro
            20

<210> SEQ ID NO 85
<211> LENGTH: 22
<212> TYPE: PRT
<213> ORGANISM: Encephalomyocarditis virus

<400> SEQUENCE: 85

Asn Ala His Tyr Ala Gly Tyr Phe Ala Asp Leu Leu Ile His Asp Ile
1               5                   10                  15

Glu Thr Asn Pro Gly Pro
            20

<210> SEQ ID NO 86
<211> LENGTH: 22
<212> TYPE: PRT
<213> ORGANISM: Mengo virus

<400> SEQUENCE: 86

Glu Thr His Tyr Ala Gly Tyr Phe Ser Asp Leu Leu Ile His Asp Val
1               5                   10                  15

Glu Thr Asn Pro Gly Pro
            20

<210> SEQ ID NO 87
<211> LENGTH: 22
<212> TYPE: PRT
<213> ORGANISM: Seneca Valley Virus

<400> SEQUENCE: 87

Pro Phe Arg Ser Tyr Lys Gln Lys Met Leu Met Gln Ser Gly Asp Ile
1               5                   10                  15

Glu Thr Asn Pro Gly Pro
            20

<210> SEQ ID NO 88
<211> LENGTH: 22
<212> TYPE: PRT
<213> ORGANISM: Theiler's murine encephalomyelitis virus

<400> SEQUENCE: 88

Arg Gly Tyr His Ala Asp Tyr Tyr Arg Gln Arg Leu Ile His Asp Val
1               5                   10                  15

Glu Thr Asn Pro Gly Pro
            20

<210> SEQ ID NO 89
<211> LENGTH: 22
<212> TYPE: PRT
<213> ORGANISM: Theiler's murine encephalomyelitis virus

<400> SEQUENCE: 89

Arg Gly Tyr His Ala Asp Tyr Tyr Lys Gln Arg Leu Ile His Asp Val
1               5                   10                  15

Glu Met Asn Pro Gly Pro
            20

<210> SEQ ID NO 90
<211> LENGTH: 22
<212> TYPE: PRT
<213> ORGANISM: Theiler's murine encephalomyelitis virus

<400> SEQUENCE: 90

Arg Ala Tyr His Ala Asp Tyr Tyr Lys Gln Arg Leu Ile His Asp Val
1               5                   10                  15

Glu Met Asn Pro Gly Pro
            20

<210> SEQ ID NO 91
<211> LENGTH: 22
<212> TYPE: PRT
<213> ORGANISM: Rat theiler's like virus

<400> SEQUENCE: 91

Arg Glu Tyr His Ala Ala Tyr Tyr Lys Gln Arg Leu Met His Asp Val
1               5                   10                  15

Glu Thr Asn Pro Gly Pro
            20

<210> SEQ ID NO 92
<211> LENGTH: 22
<212> TYPE: PRT
<213> ORGANISM: Ljungan virus

<400> SEQUENCE: 92

Glu Met Asp Phe Ala Gly Gly Lys Phe Leu Asn Gln Cys Gly Asp Val
1               5                   10                  15

Glu Thr Asn Pro Gly Pro
            20

<210> SEQ ID NO 93
<211> LENGTH: 22
<212> TYPE: PRT
<213> ORGANISM: Ljungan virus -continued

```
<400> SEQUENCE: 93

Glu Met Asp Phe Ala Gly Gly Lys Leu Phe Asn Gln Cys Gly Asp Val
1               5                   10                  15

Glu Thr Asn Pro Gly Pro
            20

<210> SEQ ID NO 94
<211> LENGTH: 22
<212> TYPE: PRT
<213> ORGANISM: Ljungan virus

<400> SEQUENCE: 94

Glu Met Asp Tyr Ser Gly Gly Lys Phe Leu Asn Gln Cys Gly Asp Val
1               5                   10                  15

Glu Ser Asn Pro Gly Pro
            20

<210> SEQ ID NO 95
<211> LENGTH: 22
<212> TYPE: PRT
<213> ORGANISM: Ljungan virus

<400> SEQUENCE: 95

Asp Met Asp Tyr Ala Gly Gly Lys Leu Phe Asn Gln Cys Gly Asp Val
1               5                   10                  15

Glu Thr Asn Pro Gly Pro
            20

<210> SEQ ID NO 96
<211> LENGTH: 22
<212> TYPE: PRT
<213> ORGANISM: Trypanosoma brucei

<400> SEQUENCE: 96

Ala Ile Ser Ser Ile Ile Arg Thr Lys Met Leu Leu Ser Gly Asp Val
1               5                   10                  15

Glu Glu Asn Pro Gly Pro
            20

<210> SEQ ID NO 97
<211> LENGTH: 22
<212> TYPE: PRT
<213> ORGANISM: Trypanosoma cruzi

<400> SEQUENCE: 97

Ala Val Cys Asp Ala Gln Arg Gln Lys Leu Leu Ser Gly Asp Ile
1               5                   10                  15

Glu Gln Asn Pro Gly Pro
            20

<210> SEQ ID NO 98
<211> LENGTH: 22
<212> TYPE: PRT
<213> ORGANISM: Bovine rotavirus

<400> SEQUENCE: 98

Ala Asn Ser Lys Phe Gln Ile Asp Arg Ile Leu Ile Ser Gly Asp Ile
1               5                   10                  15

Glu Leu Asn Pro Gly Pro
            20

<210> SEQ ID NO 99
```

```
<211> LENGTH: 22
<212> TYPE: PRT
<213> ORGANISM: Human rotavirus

<400> SEQUENCE: 99

Ala Asn Ser Lys Phe Gln Ile Asp Lys Ile Leu Ile Ser Gly Asp Ile
1               5                   10                  15

Glu Leu Asn Pro Gly Pro
            20

<210> SEQ ID NO 100
<211> LENGTH: 23
<212> TYPE: PRT
<213> ORGANISM: Porcine rotavirus

<400> SEQUENCE: 100

Ala Asn Ala Lys Phe Gly Gln Ile Asp Lys Ile Leu Ile Ser Gly Asp
1               5                   10                  15

Val Glu Leu Asn Pro Gly Pro
            20

<210> SEQ ID NO 101
<211> LENGTH: 22
<212> TYPE: PRT
<213> ORGANISM: Drosophila C virus

<400> SEQUENCE: 101

Lys Gln Glu Ala Ala Arg Gln Met Leu Leu Leu Ser Gly Asp Val
1               5                   10                  15

Glu Thr Asn Pro Gly Pro
            20

<210> SEQ ID NO 102
<211> LENGTH: 22
<212> TYPE: PRT
<213> ORGANISM: Cricket paralysis virus

<400> SEQUENCE: 102

Arg Ala Phe Leu Arg Lys Arg Thr Gln Leu Leu Met Ser Gly Asp Val
1               5                   10                  15

Glu Ser Asn Pro Gly Pro
            20

<210> SEQ ID NO 103
<211> LENGTH: 22
<212> TYPE: PRT
<213> ORGANISM: Acute bee paralysis virus

<400> SEQUENCE: 103

His Cys Gly Ser Trp Thr Asp Ile Leu Leu Leu Ser Gly Asp Val
1               5                   10                  15

Glu Thr Asn Pro Gly Pro
            20

<210> SEQ ID NO 104
<211> LENGTH: 22
<212> TYPE: PRT
<213> ORGANISM: Cricket paralysis virus

<400> SEQUENCE: 104

Thr Leu Thr Arg Ala Glu Ile Glu Asp Glu Leu Ile Arg Ala Gly Ile
1               5                   10                  15

Glu Ser Asn Pro Gly Pro
```

<210> SEQ ID NO 105
<211> LENGTH: 22
<212> TYPE: PRT
<213> ORGANISM: Perina nuda picorna like virus

<400> SEQUENCE: 105

Val Thr Ala Gln Gly Trp Val Pro Asp Leu Thr Val Asp Gly Asp Val
1               5                   10                  15

Glu Ser Asn Pro Gly Pro
            20

<210> SEQ ID NO 106
<211> LENGTH: 22
<212> TYPE: PRT
<213> ORGANISM: Ectropis obliqua picorna like virus

<400> SEQUENCE: 106

Val Thr Ala Gln Gly Trp Ala Pro Asp Leu Thr Gln Asp Gly Asp Val
1               5                   10                  15

Glu Ser Asn Pro Gly Pro
            20

<210> SEQ ID NO 107
<211> LENGTH: 22
<212> TYPE: PRT
<213> ORGANISM: Perina nuda picorna like virus

<400> SEQUENCE: 107

Asn Ile Ile Gly Gly Gly Gln Lys Asp Leu Thr Gln Asp Gly Asp Ile
1               5                   10                  15

Glu Ser Asn Pro Gly Pro
            20

<210> SEQ ID NO 108
<211> LENGTH: 22
<212> TYPE: PRT
<213> ORGANISM: Ectropis obliqua picorna like virus

<400> SEQUENCE: 108

Asn Ile Ile Gly Gly Gly Gln Arg Asp Leu Thr Gln Asp Gly Asp Ile
1               5                   10                  15

Glu Ser Asn Pro Gly

Asn Leu Leu Gln Leu Ser Asn Pro Val Gln Ala Lys Pro Glu Met Asp
1               5                   10                  15

Asn Pro Asn Pro Gly Pro
            20

<210> SEQ ID NO 111
<211> LENGTH: 4
<212> TYPE: PRT
<213> ORGANISM: Seneca Valley Virus

<400> SEQUENCE: 111

Asn Pro Gly Pro
1

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence:
      Illustrative conserved motif
<220> FEATURE:
<221> NAME/KEY: MOD_RES
<222> LOCATION: (2)..(3)
<223> OTHER INFORMATION: variable residue
<220> FEATURE:
<221> NAME/KEY: MOD_RES
<222> LOCATION: (5)
<223> OTHER INFORMATION: variable residue

<400> SEQUENCE: 112

Gly Xaa Xaa Gly Xaa Gly Lys Ser Thr
1               5

<210> SEQ ID NO 113
<211> LENGTH: 6
<212> TYPE: PRT
<213> ORGANISM: Seneca Valley Virus

<400> SEQUENCE: 113

Lys Asp Glu Leu Ile Arg
1               5

<210> SEQ ID NO 114
<211> LENGTH: 4
<212> TYPE: PRT
<213> ORGANISM: Seneca Valley Virus

<400> SEQUENCE: 114

Tyr Gly Asp Asp
1

<210> SEQ ID NO 115
<211> LENGTH: 4
<212> TYPE: PRT
<213> ORGANISM: Seneca Valley Virus

<400> SEQUENCE: 115

Phe Leu Lys Arg
1

<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence: synthetic
      6-His tag peptide

<400> SEQUENCE: 116

His His His His His His
1               5

<210> SEQ ID NO 117
<211> LENGTH: 4
<212> TYPE: PRT
<213> ORGANISM: Seneca Valley Virus

<400> SEQUENCE: 117

Glu Gln Gly Pro
1

<210> SEQ ID NO 118
<211> LENGTH: 4
<212> TYPE: PRT
<213> ORGANISM: Seneca Valley Virus

<400> SEQUENCE: 118

Phe His Ser Thr
1

<210> SEQ ID NO 119
<211> LENGTH: 4
<212> TYPE: PRT
<213> ORGANISM: Seneca Valley Virus

<400> SEQUENCE: 119

Lys Gln Lys Met
1

<210> SEQ ID NO 120
<211> LENGTH: 4
<212> TYPE: PRT
<213> ORGANISM: Seneca Valley Virus

<400> SEQUENCE: 120

Met Gln Gly Pro
1

<210> SEQ ID NO 121
<211> LENGTH: 4
<212> TYPE: PRT
<213> ORGANISM: Seneca Valley Virus

<400> SEQUENCE: 121

Leu Gln Ser Pro
1

<210> SEQ ID NO 122
<211> LENGTH: 4
<212> TYPE: PRT
<213> ORGANISM: Seneca Valley Virus

<400> SEQUENCE: 122

Ser Glu Asn Ala
1

<210> SEQ ID NO 123
<211> LENGTH: 4
<212> TYPE: PRT
<213> ORGANISM: Seneca Valley Virus

<400> SEQUENCE: 123

```
Met Gln Gln Pro
1

<210> SEQ ID NO 124
<211> LENGTH: 4
<212> TYPE: PRT
<213> ORGANISM: Seneca Valley Virus

<400> SEQUENCE: 124

Met Gln Gly Leu
1

<210> SEQ ID NO 125
<211> LENGTH: 4
<212> TYPE: PRT
<213> ORGANISM: Encephalomyocarditis virus

<400> SEQUENCE: 125

Leu Gln Gly Asn
1

<210> SEQ ID NO 126
<211> LENGTH: 4
<212> TYPE: PRT
<213> ORGANISM: Encephalomyocarditis virus

<400> SEQUENCE: 126

Leu Ala Asp Gln
1

<210> SEQ ID NO 127
<211> LENGTH: 4
<212> TYPE: PRT
<213> ORGANISM: Encephalomyocarditis virus

<400> SEQUENCE: 127

Arg Gln Ser Pro
1

<210> SEQ ID NO 128
<211> LENGTH: 4
<212> TYPE: PRT
<213> ORGANISM: Encephalomyocarditis virus

<400> SEQUENCE: 128

Pro Gln Gly Val
1

<210> SEQ ID NO 129
<211> LENGTH: 4
<212> TYPE: PRT
<213> ORGANISM: Encephalomyocarditis virus

<400> SEQUENCE: 129

Leu Glu Ser Pro
1

<210> SEQ ID NO 130
<211> LENGTH: 4
<212> TYPE: PRT
<213> ORGANISM: Encephalomyocarditis virus

<400> SEQUENCE: 130

Asn Pro Gly Pro
1
```

```
<210> SEQ ID NO 131
<211> LENGTH: 4
<212> TYPE: PRT
<213> ORGANISM: Encephalomyocarditis virus

<400> SEQUENCE: 131

Gln Gln Ser Pro
1

<210> SEQ ID NO 132
<211> LENGTH: 4
<212> TYPE: PRT
<213> ORGANISM: Encephalomyocarditis virus

<400> SEQUENCE: 132

Ala Gln Gly Pro
1

<210> SEQ ID NO 133
<211> LENGTH: 4
<212> TYPE: PRT
<213> ORGANISM: Encephalomyocarditis virus

<400> SEQUENCE: 133

Ala Gln Ala Pro
1

<210> SEQ ID NO 134
<211> LENGTH: 4
<212> TYPE: PRT
<213> ORGANISM: Encephalomyocarditis virus

<400> SEQUENCE: 134

Glu Gln Gly Pro
1

<210> SEQ ID NO 135
<211> LENGTH: 4
<212> TYPE: PRT
<213> ORGANISM: Encephalomyocarditis virus

<400> SEQUENCE: 135

Ile Gln Gly Pro
1

<210> SEQ ID NO 136
<211> LENGTH: 4
<212> TYPE: PRT
<213> ORGANISM: Encephalomyocarditis virus

<400> SEQUENCE: 136

Val Gln Gly Pro
1

<210> SEQ ID NO 137
<211> LENGTH: 4
<212> TYPE: PRT
<213> ORGANISM: Encephalomyocarditis virus

<400> SEQUENCE: 137

Pro Gln Gly Ala
1

<210> SEQ ID NO 138
<211> LENGTH: 4
```

```
<212> TYPE: PRT
<213> ORGANISM: Theiler's murine encephalomyelitis virus

<400> SEQUENCE: 138

Pro Gln Gly Asn
1

<210> SEQ ID NO 139
<211> LENGTH: 4
<212> TYPE: PRT
<213> ORGANISM: Theiler's murine encephalomyelitis virus

<400> SEQUENCE: 139

Leu Leu Asp Gln
1

<210> SEQ ID NO 140
<211> LENGTH: 4
<212> TYPE: PRT
<213> ORGANISM: Theiler's murine encephalomyelitis virus

<400> SEQUENCE: 140

Leu Met Asp Gln
1

<210> SEQ ID NO 141
<211> LENGTH: 4
<212> TYPE: PRT
<213> ORGANISM: Theiler's murine encephalomyelitis virus

<400> SEQUENCE: 141

Ala Gln Ser Pro
1

<210> SEQ ID NO 142
<211> LENGTH: 4
<212> TYPE: PRT
<213> ORGANISM: Theiler's murine encephalomyelitis virus

<400> SEQUENCE: 142

Pro Gln Gly Val
1

<210> SEQ ID NO 143
<211> LENGTH: 4
<212> TYPE: PRT
<213> ORGANISM: Theiler's murine encephalomyelitis virus

<400> SEQUENCE: 143

Pro Gln Gly Ile
1

<210> SEQ ID NO 144
<211> LENGTH: 4
<212> TYPE: PRT
<213> ORGANISM: Theiler's murine encephalomyelitis virus

<400> SEQUENCE: 144

Pro Gln Gly Ser
1

<210> SEQ ID NO 145
<211> LENGTH: 4
<212> TYPE: PRT
<213> ORGANISM: Theiler's murine encephalomyelitis virus
```

```
<400> SEQUENCE: 145

Leu Glu Asn Pro
1

<210> SEQ ID NO 146
<211> LENGTH: 4
<212> TYPE: PRT
<213> ORGANISM: Theiler's murine encephalomyelitis virus

<400> SEQUENCE: 146

Asn Pro Gly Pro
1

<210> SEQ ID NO 147
<211> LENGTH: 4
<212> TYPE: PRT
<213> ORGANISM: Theiler's murine encephalomyelitis virus

<400> SEQUENCE: 147

Pro Gln Gly Pro
1

<210> SEQ ID NO 148
<211> LENGTH: 4
<212> TYPE: PRT
<213> ORGANISM: Theiler's murine encephalomyelitis virus

<400> SEQUENCE: 148

Ala Gln Ser Pro
1

<210> SEQ ID NO 149
<211> LENGTH: 4
<212> TYPE: PRT
<213> ORGANISM: Theiler's murine encephalomyelitis virus

<400> SEQUENCE: 149

Glu Gln Ala Ala
1

<210> SEQ ID NO 150
<211> LENGTH: 4
<212> TYPE: PRT
<213> ORGANISM: Theiler's murine encephalomyelitis virus

<400> SEQUENCE: 150

Ile Gln Gly Gly
1

<210> SEQ ID NO 151
<211> LENGTH: 4
<212> TYPE: PRT
<213> ORGANISM: Theiler's murine encephalomyelitis virus

<400> SEQUENCE: 151

Pro Gln Gly Ala
1

<210> SEQ ID NO 152
<211> LENGTH: 4
<212> TYPE: PRT
<213> ORGANISM: Rat Theilovirus

<400> SEQUENCE: 152

Pro Gln Gly Asn
```

```
<210> SEQ ID NO 153
<211> LENGTH: 4
<212> TYPE: PRT
<213> ORGANISM: Rat Theilovirus

<400> SEQUENCE: 153

Leu Leu Asp Gln
1

<210> SEQ ID NO 154
<211> LENGTH: 4
<212> TYPE: PRT
<213> ORGANISM: Rat Theilovirus

<400> SEQUENCE: 154

Pro Gln Ser Pro
1

<210> SEQ ID NO 155
<211> LENGTH: 4
<212> TYPE: PRT
<213> ORGANISM: Rat Theilovirus

<400> SEQUENCE: 155

Pro Gln Gly Val
1

<210> SEQ ID NO 156
<211> LENGTH: 4
<212> TYPE: PRT
<213> ORGANISM: Rat Theilovirus

<400> SEQUENCE: 156

Leu Gln Asn Pro
1

<210> SEQ ID NO 157
<211> LENGTH: 4
<212> TYPE: PRT
<213> ORGANISM: Rat Theilovirus

<400> SEQUENCE: 157

Asn Pro Gly Pro
1

<210> SEQ ID NO 158
<211> LENGTH: 4
<212> TYPE: PRT
<213> ORGANISM: Rat Theilovirus

<400> SEQUENCE: 158

Ala Gln Ser Pro
1

<210> SEQ ID NO 159
<211> LENGTH: 4
<212> TYPE: PRT
<213> ORGANISM: Rat Theilovirus

<400> SEQUENCE: 159

Ala Gln Ser Pro
1
```

```
<210> SEQ ID NO 160
<211> LENGTH: 4
<212> TYPE: PRT
<213> ORGANISM: Rat Theilovirus

<400> SEQUENCE: 160

Glu Gln Ala Ala
1

<210> SEQ ID NO 161
<211> LENGTH: 4
<212> TYPE: PRT
<213> ORGANISM: Rat Theilovirus

<400> SEQUENCE: 161

Ile Gln Gly Gly
1

<210> SEQ ID NO 162
<211> LENGTH: 4
<212> TYPE: PRT
<213> ORGANISM: Rat Theilovirus

<400> SEQUENCE: 162

Pro Gln Gly Ala
1

<210> SEQ ID NO 163
<211> LENGTH: 4
<212> TYPE: PRT
<213> ORGANISM: Vilyuisk human encephalomyelitis virus

<400> SEQUENCE: 163

Pro Gln Gly Asn
1

<210> SEQ ID NO 164
<211> LENGTH: 4
<212> TYPE: PRT
<213> ORGANISM: Vilyuisk human encephalomyelitis virus

<400> SEQUENCE: 164

Leu Leu Asp Glu
1

<210> SEQ ID NO 165
<211> LENGTH: 4
<212> TYPE: PRT
<213> ORGANISM: Vilyuisk human encephalomyelitis virus

<400> SEQUENCE: 165

Pro Gln Ser Pro
1

<210> SEQ ID NO 166
<211> LENGTH: 4
<212> TYPE: PRT
<213> ORGANISM: Vilyuisk human encephalomyelitis virus

<400> SEQUENCE: 166

Pro Gln Gly Val
1

<210> SEQ ID NO 167
<211> LENGTH: 4
<212> TYPE: PRT
```

<213> ORGANISM: Vilyuisk human encephalomyelitis virus

<400> SEQUENCE: 167

Leu Glu Asn Pro
1

<210> SEQ ID NO 168
<211> LENGTH: 7310
<212> TYPE: DNA
<213> ORGANISM: Seneca Valley Virus

<400> SEQUENCE: 168

```
tttgaaatgg ggggctgggc cctgatgccc agtccttcct ttcccttcc gggggttaa        60
ccggctgtgt tgctagagg cacagagggg caacatccaa cctgcttttg cggggaacgg      120
tgcggctccg attcctgcgt cgccaaaggt gttagcgcac ccaaacggcg cacctaccaa      180
tgttattggt gtggtctgcg agttctagcc tactcgtttc tccccgacc attcactcac      240
ccacgaaaag tgtgttgtaa ccataagatt taaccccgc acgggatgtg cgataaccgt      300
aagactggct caagcgcgga aagcgctgta accacatgct gttagtccct ttatggctgc      360
aagatggcta cccacctcgg atcactgaac tggagctcga ccctccttag taagggaacc      420
gagaggcctt cgtgcaacaa gctccgacac agagtccacg tgactgctac caccatgagt      480
acatggttct cccctctcga cccaggactt ctttttgaat atccacggct cgatccagag      540
ggtgggggcat gacccctagc atagcgagct acagcgggaa ctgtagctag gccttagcgt      600
gccttggata ctgcctgata gggcgacggc ctagtcgtgt cggttctata ggtagcacat      660
acaaatatgc agaactctca tttttctttc gatacagcct ctggcacctt tgaagatgta      720
accggaacaa aagtcaagat cgttgaatac cccagatcgg tgaacaatgg tgtttacgat      780
tcgtctactc atttggagat actgaaccta cagggtgaaa ttgaaatttt aaggtctttc      840
aatgaatacc aaattcgcgc cgccaaacaa caactcggac tggacatcgt gtacgaacta      900
cagggtaatg ttcagacaac gtcaaagaat gattttgatt cccgtggcaa taatggtaac      960
atgaccttca attactacgc aaacacttat cagaattcag tagacttctc gacctcctcg     1020
tcggcgtcag gcgccggacc cgggaactcc cggggcggat tagcgggtct cctcacaaat     1080
ttcagtggaa tcttgaaccc tcttggctac ctcaaagatc acaacaccga agaaatggaa     1140
aactctgctg atcgagtcac aacgcaaacg gcgggcaaca ctgccataaa cacgcaatca     1200
tcattgggtg tgttgtgtgc ctacgttgaa gacccgacca atctgatcc tccgtccagc     1260
agcacagatc aacccaccac cactttcact gccatcgaca ggtggtacac tggacgtctc     1320
aattcttgga caaagctgt aaaaaccttc tcttttcagg ccgtcccgct tcccggggcc     1380
tttctgtcta ggcagggagg cctcaacgga ggggccttca cagctaccct acatagacac     1440
ttttttgatga agtgcgggtg gcaggtgcag gtccaatgta atttgacaca attccaccaa     1500
ggcgctcttc ttgttgccat ggttcctgaa accacccttg atgtcaagcc cgacggtaag     1560
gcaaagagct acaggagct gaatgaagaa cagtgggtgg aaatgtctga cgattaccgg     1620
accgggaaaa acatgccttt tcagtctctt ggcacatact atcggccccc taactggact     1680
tggggtccca atttcatcaa cccctatcaa gtaacggttt tcccacacca aattctgaac     1740
gcgagaacct ctacctcgt agacataaac gtcccataca tcggggagac ccccacgcaa     1800
tcctcagaga cacagaactc ctggaccctc tcgttatgg tgctcgttcc cctagactat     1860
aaggaaggag ccacaactga cccagaaatt acattttctg taaggcctac aagtcccta     1920
ttcaatgggc ttcgcaaccg ctacacggcc gggacggacg aagaacaggg gcccattcct     1980
```

```
acggcaccca gagaaaattc gcttatgttt ctctcaaccc tccctgacga cactgtccct    2040
gcttacggga atgtgcgtac ccctcctgtc aattacctcc ctggtgaaat aaccgacctt    2100
ttgcaactgg cccgcatacc cactctcatg gcatttgagc gggtgcctga cccgtgcct    2160 gcctcagaca catatgtgcc ctacgttgcc gttcccaccc agttcgatga caggcctctc    2220
atctccttcc cgatcaccct ttcagatccc gtctatcaga acaccctggt tggcgccatc    2280
agttcaaatt tcgccaatta ccgtgggtgt atccaaatca ctctgacatt ttgtggaccc    2340
atgatggcga gagggaaatt cctgctctcg tattctcccc caaatggaac gcaaccacag    2400
actctttccg aagctatgca gtgcacatac tctatttggg acataggctt gaactctagt    2460
tggaccttcg tcgtcccta catctcgccc agtgactacc gtgaaactcg agccattacc    2520
aactcggttt actccgctga tggttggttt agcctgcaca agttgaccaa aattactcta    2580
ccacctgact gtccgcaaag tccctgcatt ctctttttcg cttctgctgg tgaggattac    2640
actctccgtc tccccgttga ttgtaatcct tcctatgtgt tccactccac cgacaacgcc    2700
gagaccgggg ttattgaggc gggtaacact gacaccgatt tctctggtga actggcggct    2760
cctggctcta accacactaa tgtcaagttc ctgtttgatc gatctcgatt attgaatgta    2820
atcaaggtac tggagaagga cgccgttttc ccccgccctt ccctacaca agaaggtgcg    2880 cagcaggatg atgcttactt tgtcttctg accccccgcc caacagtcgc ttcccgaccc    2940
gccactcgtt tcggcctgta cgccaatccg tccggcagtg gtgttcttgc taacacttca    3000
ctggacttca atttttatag cttggcctgt ttcacttact ttagatcgga ccttgaggtt    3060
acggtggtct cactagagcc ggatctggaa tttgctgtag ggtggtttcc ttctggcagt    3120
gaataccagg cttccagctt tgtctacgac cagctgcatg tgcccttcca ctttactggg    3180
cgcactcccc gcgctttcgc tagcaagggt gggaaggtat ctttcgtgct cccttggaac    3240
tctgtctcgt ctgtgctccc cgtgcgctgg ggggggcttt ccaagctctc ttctgctacg    3300
cggggtctac cggcgcatgc tgattggggg actatttacg cctttgtccc ccgtcctaat    3360
gagaagaaaa gcaccgctgt aaaacacgtg gccgtgtaca ttcggtacaa gaacgcacgt    3420
gcctggtgcc ccagcatgct tcccttccgc agctacaagc agaagatgct gatgcaatct    3480
ggcgatatcg agaccaatcc tggtcctgct tctgacaacc caattttgga gtttcttgaa    3540
gcagaaaatg atctagtcac tctggcctct ctctggaaga tggtgcactc tgttcaacag    3600
acctggagaa agtatgtgaa gaacgatgat ttttggccca atttactcag cgagctagtg    3660
ggggaaggct ctgtcgcctt ggccgccacg ctatccaacc aagcttcagt aaaggctctt    3720
ttgggcctgc actttctctc tcgggggctc aattacactg acttttactc tttactgata    3780
gagaaatgct ctagtttctt taccgtagaa ccacctcctc caccagctga aaacctgatg    3840
accaagccct cagtgaagtc gaaattccga aaactgttta agatgcaagg acccatggac    3900
aaagtcaaag actggaacca aatagctgcc ggcttgaaga ttttcaatt tgttcgtgac    3960 ctagtcaaag aggtggtcga ttggctgcag gcctggatca caaagagaa agccagccct    4020 gtcctccagt accagttgga gatgaagaag ctcgggcctg tggccttggc tcatgacgct    4080
ttcatggctg gttccgggcc ccctcttagc gacgaccaga ttgaatacct ccagaacctc    4140
aaatctcttg ccctaacact ggggaagact aatttggccc aaagtctcac cactatgatc    4200
aatgccaaac aaagttcagc ccaacgagtt gaacccgttg tggtggtcct tagaggcaag    4260
ccgggatgcg gcaagagctt ggcctctacg ttgattgccc aggctgtgtc caagcgcctc    4320
tatggctccc aaagtgtata ttctcttccc ccagatccag atttcttcga tggatacaaa    4380
```

```
ggacagttcg tgaccttgat ggatgatttg ggacaaaacc cggatggaca agatttctcc    4440 acctttgtc agatggtgtc gaccgcccaa tttctcccca acatggcgga ccttgcagag     4500
aaagggcgtc cctttacctc aatctcatc attgcaacta caaatctccc ccacttcagt     4560
cctgtcacca ttgctgatcc ttctgcagtc tctcgccgta tcaactacga tctgactcta    4620
gaagtatctg aggcctacaa gaaacacaca cggctgaatt ttgacttggc tttcaggcgc    4680
acagacgccc cccccattta tccttttgct gcccatgtgc cctttgtgga cgtagctgtg    4740
cgcttcaaaa atggtcacca gaattttaat ctcctagagt tggtcgattc catttgtaca    4800
gacattcgag ccaagcaaca aggtgcccga aacatgcaga ctctggttct acagagcccc    4860
aacgagaatg atgacacccc cgtcgacgag gcgttgggta gagttctctc ccccgctgcg    4920
gtcgatgagg cgcttgtcga cctcactcca gaggccgacc cggttggccg tttgctatt    4980 cttgccaagc taggtcttgc cctagctgcg gtcaccctg gtctgataat cttggcagtg     5040
ggactctaca ggtacttctc tggctctgat gcagaccaag aagaaacaga aagtgaggga    5100
tctgtcaagg cacccaggag cgaaaatgct tatgacggcc cgaagaaaaa ctctaagccc    5160
cctggagcac tctctctcat ggaaatgcaa cagcccaacg tggacatggg ctttgaggct    5220
gcggtcgcta agaaagtggt cgtccccatt accttcatgg ttcccaacag accttctggg    5280
cttacacagt ccgctcttct ggtgaccggc cggaccttcc taatcaatga acatacatgg    5340
tccaatccct cctggaccag cttcacaatc cgcggtgagg tacacactcg tgatgagccc    5400
ttccaaacgg ttcatttcac tcaccacggt attcccacag atctgatgat ggtacgtctc    5460
ggaccgggca attcttccc taacaatcta gacaagtttg gacttgacca gatgccggca    5520
cgcaactccc gtgtggttgg cgtttcgtcc agttacggaa acttcttctt ctctggaaat    5580
ttcctcggat tgttgattc catcacctct gaacaaggaa cttacgcaag actctttagg    5640
tacagggtga cgacctacaa aggatggtgc ggctcggccc tggtctgtga ggccggtggc    5700
gtccgacgca tcattggcct gcattctgct ggcgccgccg gtatcggcgc cgggacctat    5760
atctcaaaat taggactaat caaagccctg aaacacctcg gtgaacctt ggccacaatg     5820 caaggactga tgactgaatt agagcctgga atcaccgtac atgtaccccg gaaatccaaa    5880
ttgagaaaga cgaccgcaca cgcggtgtac aaaccggagt ttgagcctgc tgtgttgtca    5940
aaatttgatc ccagactgaa caaggatgtt gacttggatg aagtaatttg gtctaaacac    6000
actgccaatg tccccttacca acctcctttg ttctacacat acatgtcaga gtacgctcat    6060
cgagtcttct ccttcttggg gaaagacaat gacattctga ccgtcaaaga agcaattctg    6120
ggcatccccg gactagaccc catggatccc cacacagctc cgggtctgcc ttacgccatc    6180
aacggccttc gacgtactga tctcgtcgat tttgtgaacg gtacagtaga tgcggcgctg    6240
gctgtacaaa tccagaaaat cttagacggt gactactctg accatgtctt ccaaactttt    6300
ctgaaagatg agatcagacc ctcagagaaa gtccgagcgg gaaaaacccg cattgttgat    6360
gtgccctccc tggcgcattg cattgtgggc agaatgttgc ttgggcgctt tgctgccaag    6420
tttcaatccc atcctggctt tctcctcggc tctgctatcg ggtctgaccc tgatgttttc    6480
tggaccgtca tagggctca actcgagggg agaaagaaca cgtatgacgt ggactacagt    6540
gcctttgact cttcacacgg cactggctcc ttcgaggctc tcatctctca cttttcacc    6600 gtggacaatg gttttagccc tgcgctggga ccgtatctca gatccctggc tgtctcggtg    6660
cacgcttacg gcgagcgtcg catcaagatt accggtggcc tccctccgg ttgtgccgcg     6720 accagcctgc tgaacacagt gctcaacaat gtgatcatca ggactgctct ggcattgact    6780
```

```
tacaaggaat tgaatatga catggttgat atcatcgcct acggtgacga ccttctggtt      6840
ggcacggatt acgatctgga cttcaatgag gtggcacgac gcgctgccaa gttggggtat      6900
aagatgactc ctgccaacaa gggttctgtc ttccctccga cttcctctct ttccgatgct      6960 gttttctaa agcgcaaatt cgtccaaaac aacgacggct tatacaaacc agttatggat       7020
ttaaagaatt tggaagccat gctctcctac ttcaaaccag gaacactact cgagaagctg      7080
caatctgttt ctatgttggc tcaacattct ggaaagaag aatatgatag attgatgcac       7140
cccttcgctg actacggtgc cgtaccgagt cacgagtacc tgcaggcaag atggagggcc      7200
ttgttcgact gacccagata gcccaaggcg cttcggtgct gccggcgatt ctgggagaac      7260
tcagtcggaa cagaaagggg aaaaaaaaaa aaaaaaaaa aaaaaaaaa                   7310
```

<210> SEQ ID NO 169
<211> LENGTH: 2181
<212> TYPE: PRT
<213> ORGANISM: Seneca Valley Virus

<400> SEQUENCE: 169

```
Met Gln Asn Ser His Phe Ser Phe Asp Thr Ala Ser Gly Thr Phe Glu
1               5                   10                  15

Asp Val Thr Gly Thr Lys Val Lys Ile Val Glu Tyr Pro Arg Ser Val
            20                  25                  30

Asn Asn Gly Val Tyr Asp Ser Thr His Leu Glu Ile Leu Asn Leu
        35                  40                  45

Gln Gly Glu Ile Glu Ile Leu Arg Ser Phe Asn Glu Tyr Gln Ile Arg
    50                  55                  60

Ala Ala Lys Gln Gln Leu Gly Leu Asp Ile Val Tyr Glu Leu Gln Gly
65                  70                  75                  80

Asn Val Gln Thr Thr Ser Lys Asn Asp Phe Asp Ser Arg Gly Asn Asn
                85                  90                  95

Gly Asn Met Thr Phe Asn Tyr Tyr Ala Asn Thr Tyr Gln Asn Ser Val
            100                 105                 110

Asp Phe Ser Thr Ser Ser Ala Ser Gly Ala Gly Pro Gly Asn Ser
        115                 120                 125

Arg Gly Gly Leu Ala Gly Leu Leu Thr Asn Phe Ser Gly Ile Leu Asn
    130                 135                 140

Pro Leu Gly Tyr Leu Lys Asp His Asn Thr Glu Glu Met Glu Asn Ser
145                 150                 155                 160

Ala Asp Arg Val Thr Thr Gln Thr Ala Gly Asn Thr Ala Ile Asn Thr
                165                 170                 175

Gln Ser Ser Leu Gly Val Leu Cys Ala Tyr Val Glu Asp Pro Thr Lys
            180                 185                 190

Ser Asp Pro Pro Ser Ser Thr Asp Gln Pro Thr Thr Thr Phe Thr
        195                 200                 205

Ala Ile Asp Arg Trp Tyr Thr Gly Arg Leu Asn Ser Trp Thr Lys Ala
    210                 215                 220

Val Lys Thr Phe Ser Phe Gln Ala Val Pro Leu Pro Gly Ala Phe Leu
225                 230                 235                 240

Ser Arg Gln Gly Gly Leu Asn Gly Gly Ala Phe Thr Ala Thr Leu His
                245                 250                 255

Arg His Phe Leu Met Lys Cys Gly Trp Gln Val Gln Val Gln Cys Asn
            260                 265                 270

Leu Thr Gln Phe His Gln Gly Ala Leu Leu Val Ala Met Val Pro Glu
        275                 280                 285
```

```
Thr Thr Leu Asp Val Lys Pro Asp Gly Lys Ala Lys Ser Leu Gln Glu
    290                 295                 300

Leu Asn Glu Glu Gln Trp Val Glu Met Ser Asp Asp Tyr Arg Thr Gly
305                 310                 315                 320

Lys Asn Met Pro Phe Gln Ser Leu Gly Thr Tyr Tyr Arg Pro Pro Asn
                325                 330                 335

Trp Thr Trp Gly Pro Asn Phe Ile Asn Pro Tyr Gln Val Thr Val Phe
            340                 345                 350

Pro His Gln Ile Leu Asn Ala Arg Thr Ser Thr Ser Val Asp Ile Asn
        355                 360                 365

Val Pro Tyr Ile Gly Glu Thr Pro Thr Gln Ser Ser Glu Thr Gln Asn
    370                 375                 380

Ser Trp Thr Leu Leu Val Met Val Leu Val Pro Leu Asp Tyr Lys Glu
385                 390                 395                 400

Gly Ala Thr Thr Asp Pro Glu Ile Thr Phe Ser Val Arg Pro Thr Ser
                405                 410                 415

Pro Tyr Phe Asn Gly Leu Arg Asn Arg Tyr Thr Ala Gly Thr Asp Glu
            420                 425                 430

Glu Gln Gly Pro Ile Pro Thr Ala Pro Arg Glu Asn Ser Leu Met Phe
        435                 440                 445

Leu Ser Thr Leu Pro Asp Asp Thr Val Pro Ala Tyr Gly Asn Val Arg
    450                 455                 460

Thr Pro Pro Val Asn Tyr Leu Pro Gly Glu Ile Thr Asp Leu Leu Gln
465                 470                 475                 480

Leu Ala Arg Ile Pro Thr Leu Met Ala Phe Glu Arg Val Pro Glu Pro
                485                 490                 495

Val Pro Ala Ser Asp Thr Tyr Val Pro Tyr Val Ala Val Pro Thr Gln
            500                 505                 510

Phe Asp Asp Arg Pro Leu Ile Ser Phe Pro Ile Thr Leu Ser Asp Pro
        515                 520                 525

Val Tyr Gln Asn Thr Leu Val Gly Ala Ile Ser Ser Asn Phe Ala Asn
    530                 535                 540

Tyr Arg Gly Cys Ile Gln Ile Thr Leu Thr Phe Cys Gly Pro Met Met
545                 550                 555                 560

Ala Arg Gly Lys Phe Leu Leu Ser Tyr Ser Pro Pro Asn Gly Thr Gln
                565                 570                 575

Pro Gln Thr Leu Ser Glu Ala Met Gln Cys Thr Tyr Ser Ile Trp Asp
            580                 585                 590

Ile Gly Leu Asn Ser Ser Trp Thr Phe Val Val Pro Tyr Ile Ser Pro
        595                 600                 605

Ser Asp Tyr Arg Glu Thr Arg Ala Ile Thr Asn Ser Val Tyr Ser Ala
    610                 615                 620

Asp Gly Trp Phe Ser Leu His Lys Leu Thr Lys Ile Thr Leu Pro Pro
625                 630                 635                 640

Asp Cys Pro Gln Ser Pro Cys Ile Leu Phe Phe Ala Ser Ala Gly Glu
                645                 650                 655

Asp Tyr Thr Leu Arg Leu Pro Val Asp Cys Asn Pro Ser Tyr Val Phe
            660                 665                 670

His Ser Thr Asp Asn Ala Glu Thr Gly Val Ile Glu Ala Gly Asn Thr
        675                 680                 685

Asp Thr Asp Phe Ser Gly Glu Leu Ala Ala Pro Gly Ser Asn His Thr
    690                 695                 700

Asn Val Lys Phe Leu Phe Asp Arg Ser Arg Leu Leu Asn Val Ile Lys
```

```
                    705                 710                 715                 720
Val Leu Glu Lys Asp Ala Val Phe Pro Arg Pro Phe Pro Thr Gln Glu
                    725                 730                 735

Gly Ala Gln Gln Asp Asp Gly Tyr Phe Cys Leu Leu Thr Pro Arg Pro
                    740                 745                 750

Thr Val Ala Ser Arg Pro Ala Thr Arg Phe Gly Leu Tyr Ala Asn Pro
                    755                 760                 765

Ser Gly Ser Gly Val Leu Ala Asn Thr Ser Leu Asp Phe Asn Phe Tyr
                    770                 775                 780

Ser Leu Ala Cys Phe Thr Tyr Phe Arg Ser Asp Leu Glu Val Thr Val
785                 790                 795                 800

Val Ser Leu Glu Pro Asp Leu Glu Phe Ala Val Gly Trp Phe Pro Ser
                    805                 810                 815

Gly Ser Glu Tyr Gln Ala Ser Ser Phe Val Tyr Asp Gln Leu His Val
                    820                 825                 830

Pro Phe His Phe Thr Gly Arg Thr Pro Arg Ala Phe Ala Ser Lys Gly
                    835                 840                 845

Gly Lys Val Ser Phe Val Leu Pro Trp Asn Ser Val Ser Ser Val Leu
                    850                 855                 860

Pro Val Arg Trp Gly Gly Ala Ser Lys Leu Ser Ser Ala Thr Arg Gly
865                 870                 875                 880

Leu Pro Ala His Ala Asp Trp Gly Thr Ile Tyr Ala Phe Val Pro Arg
                    885                 890                 895

Pro Asn Glu Lys Lys Ser Thr Ala Val Lys His Val Ala Val Tyr Ile
                    900                 905                 910

Arg Tyr Lys Asn Ala Arg Ala Trp Cys Pro Ser Met Leu Pro Phe Arg
                    915                 920                 925

Ser Tyr Lys Gln Lys Met Leu Met Gln Ser Gly Asp Ile Glu Thr Asn
                    930                 935                 940

Pro Gly Pro Ala Ser Asp Asn Pro Ile Leu Glu Phe Leu Glu Ala Glu
945                 950                 955                 960

Asn Asp Leu Val Thr Leu Ala Ser Leu Trp Lys Met Val His Ser Val
                    965                 970                 975

Gln Gln Thr Trp Arg Lys Tyr Val Lys Asn Asp Asp Phe Trp Pro Asn
                    980                 985                 990

Leu Leu Ser Glu Leu Val Gly Glu  Gly Ser Val Ala Leu  Ala Ala Thr
                    995                 1000                1005

Leu Ser Asn Gln Ala Ser Val  Lys Ala Leu Leu Gly  Leu His Phe
         1010                1015                1020

Leu Ser Arg Gly Leu Asn Tyr  Thr Asp Phe Tyr Ser  Leu Leu Ile
1025                1030                1035

Glu Lys Cys Ser Ser Phe Phe  Thr Val Glu Pro Pro  Pro Pro Pro
                    1040                1045                1050

Ala Glu Asn Leu Met Thr Lys  Pro Ser Val Lys Ser  Lys Phe Arg
                    1055                1060                1065

Lys Leu Phe Lys Met Gln Gly  Pro Met Asp Lys Val  Lys Asp Trp
         1070                1075                1080

Asn Gln Ile Ala Ala Gly Leu  Lys Asn Phe Gln Phe  Val Arg Asp
         1085                1090                1095

Leu Val Lys Glu Val Val Asp  Trp Leu Gln Ala Trp  Ile Asn Lys
1100                1105                1110

Glu Lys Ala Ser Pro Val Leu  Gln Tyr Gln Leu Glu  Met Lys Lys
                    1115                1120                1125
```

-continued

```
Leu Gly Pro Val Ala Leu Ala His Asp Ala Phe Met Ala Gly Ser
        1130                1135                1140
Gly Pro Pro Leu Ser Asp Asp Gln Ile Glu Tyr Leu Gln Asn Leu
        1145                1150                1155
Lys Ser Leu Ala Leu Thr Leu Gly Lys Thr Asn Leu Ala Gln Ser
        1160                1165                1170
Leu Thr Thr Met Ile Asn Ala Lys Gln Ser Ser Ala Gln Arg Val
1175                1180                1185
Glu Pro Val Val Val Leu Arg Gly Lys Pro Gly Cys Gly Lys
        1190                1195                1200
Ser Leu Ala Ser Thr Leu Ile Ala Gln Ala Val Ser Lys Arg Leu
        1205                1210                1215
Tyr Gly Ser Gln Ser Val Tyr Ser Leu Pro Pro Asp Pro Asp Phe
        1220                1225                1230
Phe Asp Gly Tyr Lys Gly Gln Phe Val Thr Leu Met Asp Asp Leu
1235                1240                1245
Gly Gln Asn Pro Asp Gly Gln Asp Phe Ser Thr Phe Cys Gln Met
1250                1255                1260
Val Ser Thr Ala Gln Phe Leu Pro Asn Met Ala Asp Leu Ala Glu
        1265                1270                1275
Lys Gly Arg Pro Phe Thr Ser Asn Leu Ile Ile Ala Thr Thr Asn
        1280                1285                1290
Leu Pro His Phe Ser Pro Val Thr Ile Ala Asp Pro Ser Ala Val
        1295                1300                1305
Ser Arg Arg Ile Asn Tyr Asp Leu Thr Leu Glu Val Ser Glu Ala
        1310                1315                1320
Tyr Lys Lys His Thr Arg Leu Asn Phe Asp Leu Ala Phe Arg Arg
1325                1330                1335
Thr Asp Ala Pro Pro Ile Tyr Pro Phe Ala Ala His Val Pro Phe
                1340                1345                1350
Val Asp Val Ala Val Arg Phe Lys Asn Gly His Gln Asn Phe Asn
        1355                1360                1365
Leu Leu Glu Leu Val Asp Ser Ile Cys Thr Asp Ile Arg Ala Lys
        1370                1375                1380
Gln Gln Gly Ala Arg Asn Met Gln Thr Leu Val Leu Gln Ser Pro
        1385                1390                1395
Asn Glu Asn Asp Asp Thr Pro Val Asp Glu Ala Leu Gly Arg Val
1400                1405                1410
Leu Ser Pro Ala Ala Val Asp Glu Ala Leu Val Asp Leu Thr Pro
                1415                1420                1425
Glu Ala Asp Pro Val Gly Arg Leu Ala Ile Leu Ala Lys Leu Gly
                1430                1435                1440
Leu Ala Leu Ala Ala Val Thr Pro Gly Leu Ile Ile Leu Ala Val
                1445                1450                1455
Gly Leu Tyr Arg Tyr Phe Ser Gly Ser Asp Ala Asp Gln Glu Glu
        1460                1465                1470
Thr Glu Ser Glu Gly Ser Val Lys Ala Pro Arg Ser Glu Asn Ala
1475                1480                1485
Tyr Asp Gly Pro Lys Lys Asn Ser Lys Pro Pro Gly Ala Leu Ser
                1490                1495                1500
Leu Met Glu Met Gln Gln Pro Asn Val Asp Met Gly Phe Glu Ala
                1505                1510                1515
Ala Val Ala Lys Lys Val Val Val Pro Ile Thr Phe Met Val Pro
        1520                1525                1530
```

-continued

```
Asn Arg Pro Ser Gly Leu Thr  Gln Ser Ala Leu Leu  Val Thr Gly
    1535                1540                 1545

Arg Thr Phe Leu Ile Asn Glu  His Thr Trp Ser Asn  Pro Ser Trp
1550                1555                 1560

Thr Ser Phe Thr Ile Arg Gly  Glu Val His Thr Arg  Asp Glu Pro
            1565                 1570                 1575

Phe Gln Thr Val His Phe Thr  His His Gly Ile Pro  Thr Asp Leu
            1580                 1585                 1590

Met Met Val Arg Leu Gly Pro  Gly Asn Ser Phe Pro  Asn Asn Leu
            1595                 1600                 1605

Asp Lys Phe Gly Leu Asp Gln  Met Pro Ala Arg Asn  Ser Arg Val
    1610                1615                 1620

Val Gly Val Ser Ser Ser Tyr  Gly Asn Phe Phe Phe  Ser Gly Asn
1625                1630                 1635

Phe Leu Gly Phe Val Asp Ser  Ile Thr Ser Glu Gln  Gly Thr Tyr
            1640                 1645                 1650

Ala Arg Leu Phe Arg Tyr Arg  Val Thr Thr Tyr Lys  Gly Trp Cys
            1655                 1660                 1665

Gly Ser Ala Leu Val Cys Glu  Ala Gly Gly Val Arg  Arg Ile Ile
        1670                 1675                 1680

Gly Leu His Ser Ala Gly Ala  Ala Gly Ile Gly Ala  Gly Thr Tyr
    1685                 1690                 1695

Ile Ser Lys Leu Gly Leu Ile  Lys Ala Leu Lys His  Leu Gly Glu
1700                1705                 1710

Pro Leu Ala Thr Met Gln Gly  Leu Met Thr Glu Leu  Glu Pro Gly
            1715                 1720                 1725

Ile Thr Val His Val Pro Arg  Lys Ser Lys Leu Arg  Lys Thr Thr
            1730                 1735                 1740

Ala His Ala Val Tyr Lys Pro  Glu Phe Glu Pro Ala  Val Leu Ser
        1745                 1750                 1755

Lys Phe Asp Pro Arg Leu Asn  Lys Asp Val Asp Leu  Asp Glu Val
    1760                 1765                 1770

Ile Trp Ser Lys His Thr Ala  Asn Val Pro Tyr Gln  Pro Pro Leu
1775                1780                 1785

Phe Tyr Thr Tyr Met Ser Glu  Tyr Ala His Arg Val  Phe Ser Phe
            1790                 1795                 1800

Leu Gly Lys Asp Asn Asp Ile  Leu Thr Val Lys Glu  Ala Ile Leu
            1805                 1810                 1815

Gly Ile Pro Gly Leu Asp Pro  Met Asp Pro His Thr  Ala Pro Gly
        1820                 1825                 1830

Leu Pro Tyr Ala Ile Asn Gly  Leu Arg Arg Thr Asp  Leu Val Asp
    1835                 1840                 1845

Phe Val Asn Gly Thr Val Asp  Ala Ala Leu Ala Val  Gln Ile Gln
1850                1855                 1860

Lys Phe Leu Asp Gly Asp Tyr  Ser Asp His Val Phe  Gln Thr Phe
            1865                 1870                 1875

Leu Lys Asp Glu Ile Arg Pro  Ser Glu Lys Val Arg  Ala Gly Lys
            1880                 1885                 1890

Thr Arg Ile Val Asp Val Pro  Ser Leu Ala His Cys  Ile Val Gly
        1895                 1900                 1905

Arg Met Leu Leu Gly Arg Phe  Ala Ala Lys Phe Gln  Ser His Pro
    1910                 1915                 1920

Gly Phe Leu Leu Gly Ser Ala  Ile Gly Ser Asp Pro  Asp Val Phe
```

Trp Thr Val Ile Gly Ala Gln Leu Glu Gly Arg Lys Asn Thr Tyr
1925            1930            1935

Asp Val Asp Tyr Ser Ala Phe Asp Ser Ser His Gly Thr Gly Ser
        1940            1945            1950

Phe Glu Ala Leu Ile Ser His Phe Phe Thr Val Asp Asn Gly Phe
    1955            1960            1965

Ser Pro Ala Leu Gly Pro Tyr Leu Arg Ser Leu Ala Val Ser Val
    1970            1975            1980

His Ala Tyr Gly Glu Arg Arg Ile Lys Ile Thr Gly Gly Leu Pro
1985            1990            1995

Ser Gly Cys Ala Ala Thr Ser Leu Leu Asn Thr Val Leu Asn Asn
2000            2005            2010

Val Ile Ile Arg Thr Ala Leu Ala Leu Thr Tyr Lys Glu Phe Glu
2015            2020            2025

Tyr Asp Met Val Asp Ile Ile Ala Tyr Gly Asp Asp Leu Leu Val
2030            2035            2040

Gly Thr Asp Tyr Asp Leu Asp Phe Asn Glu Val Ala Arg Arg Ala
2045            2050            2055

Ala Lys Leu Gly Tyr Lys Met Thr Pro Ala Asn Lys Gly Ser Val
2060            2065            2070

Phe Pro Pro Thr Ser Ser Leu Ser Asp Ala Val Phe Leu Lys Arg
2075            2080            2085

Lys Phe Val Gln Asn Asn Asp Gly Leu Tyr Lys Pro Val Met Asp
2090            2095            2100

Leu Lys Asn Leu Glu Ala Met Leu Ser Tyr Phe Lys Pro Gly Thr
2105            2110            2115

Leu Leu Glu Lys Leu Gln Ser Val Ser Met Leu Ala Gln His Ser
2120            2125            2130

Gly Lys Glu Glu Tyr Asp Arg Leu Met His Pro Phe Ala Asp Tyr
2135            2140            2145

Gly Ala Val Pro Ser His Glu Tyr Leu Gln Ala Arg Trp Arg Ala
2150            2155            2160

Leu Phe Asp
2165            2170            2175

<210> SEQ ID NO 170
<211> LENGTH: 1560
<212> TYPE: DNA
<213> ORGANISM: Seneca Valley Virus

<400> SEQUENCE: 170
aatgggcttc gcaaccgcta cacggccggg acggacgaag aacaggggcc cattcctacg      60
gcacccagag aaaattcgct tatgtttctc tcaaccctcc ctgacgacac tgtccctgct     120
tacgggaatg tgcgtacccc tcctgtcaat tacctccctg gtgaaataac cgaccttttg     180
caactggccc gcatacccac tctcatggca tttgagcggg tgcctgaacc cgtgcctgcc     240
tcagacacat atgtgcccta cgttgccgtt cccacccagt cgatgacag gcctctcatc     300 tccttcccga tcacccttc agatcccgtc tatcagaaca ccctggttgg cgccatcagt     360
tcaaatttcg ccaattaccg tgggtgtatc caaatcactc tgacattttg tggacccatg     420
atggcgagag ggaaattcct gctctcgtat tctcccccaa atggaacgca accacagact     480
cttcccgaag ctatgcagtg cacatactct atttgggaca taggcttgaa ctctagttgg     540
accttcgtcg tccctactacat ctcgcccagt gactaccgtg aaactcgagc cattaccaac     600

```
tcggtttact ccgctgatgg ttggtttagc ctgcacaagt tgaccaaaat tactctacca      660
cctgactgtc cgcaaagtcc ctgcattctc tttttcgctt ctgctggtga ggattacact      720
ctccgtctcc ccgttgattg taatccttcc tatgtgttcc actccaccga caacgccgag      780
accggggtta ttgaggcggg taacactgac accgatttct ctggtgaact ggcggctcct      840
ggctctaacc acactaatgt caagttcctg tttgatcgat ctcgattatt gaatgtaatc      900
aaggtactgg agaaggacgc cgttttcccc cgccctttcc ctacacaaga aggtgcgcag      960
caggatgatg gttacttttg tcttctgacc ccccgcccaa cagtcgcttc ccgacccgcc     1020
actcgtttcg gcctgtacgc caatccgtcc ggcagtggtg ttcttgctaa cacttcactg     1080
gacttcaatt tttatagctt ggcctgtttc acttacttta gatcggacct tgaggttacg     1140
gtggtctcac tagagccgga tctggaattt gctgtagggt ggtttccttc tggcagtgaa     1200
taccaggctt ccagctttgt ctacgaccag ctgcatgtgc ccttccactt tactgggcgc     1260
actccccgcg ctttcgctag caaggtgtgg aaggtatctt tcgtgctccc ttggaactct     1320
gtctcgtctg tgctccccgt gcgctggggg ggggcttcca agctctcttc tgctacgcgg     1380
ggtctaccgg cgcatgctga ttgggggact atttacgcct ttgtcccccg tcctaatgag     1440
aagaaaagca ccgctgtaaa acacgtggcc gtgtacattc ggtacaagaa cgcacgtgcc     1500
tggtgcccca gcatgcttcc ctttcgcagc tacaagcaga agatgctgat gcaatctggc     1560
```

<210> SEQ ID NO 171
<211> LENGTH: 1560
<212> TYPE: DNA
<213> ORGANISM: Picornavirus
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 171
aatgggcntc gcaaccgcta catggccggg acggacgaag aacaggggcc nattcccacg 60
gcacccagag agaattcgct tatgtttctt tcaactctgc ctgacgacac agttcctgct 120
tacgggaatg tgcgcacccc tcctgtcaat tacctccctg gtgaaataac cgacctcttg 180
caactggccc gcatacccac tctcatggca tttgagcggg tgcccgaacc cgtgcctgcc 240
tcagatacgt atgtgcccta cgttgccgtt cccacccaat tcgctgacag gcctctcatc 300
tccttcccga tcaccctttc agaccctgtc tatcaaaaca ccctggttgg cgccatcagt 360
tcttactttg ccaattaccg tgggtgtatc cagatcactc tgacgttttg tggacccatg 420
atggcgagag ggaaattcct actgttatat tctcccccaa atggaacgca accacagact 480
ctttccgaag ctatgcagtg cacatactct atttgggaca taggcttgaa ctcgagttgg 540
accttcgtcg tcccctacat ctcgcccagt gactaccgtg aaacccgggc cattaccaac 600
tcggtttact ccgctgatgg ttggtttagc ctgcacaagt tgaccaaaat tactctccca 660
cctgactgtc cgcaaagtcc ctgcgttctc tttttcgctt ctgctggtga ggattacact 720
ctccgtctcc ccattgattg taatccttcc tacgtgttcc actccaccga caacgccgaa 780
actggggttg ttgaggcggg taacactgac accgatttct ctggtgaact agcggctcct 840
ggctccaacc acactaatgt caagttcctg tttgatcgat ctcgattatt gaatgtaatt 900
aaggtactgg agaaagacgc cgttttcccc caccctttcc ctacgctaga aggtgcgcaa 960

```
caggatgatg gttacttttg tcttctgacc ccccgcccaa cagtcgcttc ccgacccgcc   1020
actcgtttcg gcctgtacgc caatccgtcc ggcagcggtg ttcttgctaa tacttcattg   1080
gactttaact tttatagctt ggcctgtttc acttacttta gatcggacct cgaggttacg   1140
gtggtctcac tggagccaga tctggaattt gctgtagggt ggtttccttc cggcagtgaa   1200
tatcaggctt ccagctttgt ctacgaccag ctgcacgtgc ccttccactt cactggacgc   1260
accccccgcg cttttgctag caagggtggg aaggtatcct ttgtgctccc ttggaactct   1320
gtctcatctg tgctcccccgt gcgctggggg ggggcttcca agctctcttc tgccacgcgg   1380
ggtctaccgg cgcatgctga ctgggggact atctacgcct ttgtccccccg tcccaatgaa   1440 aagaaaagca ccgctgcaaa acacgtggcc gtgtacattc ggtacaagaa cgcacgcgcc   1500
tggtgcccca gcatgcttcc ctttcgcagc tataagcaga agatgctgat gcaatctggc   1560

<210> SEQ ID NO 172
<211> LENGTH: 1560
<212> TYPE: DNA
<213> ORGANISM: Picornavirus

<400> SEQUENCE: 172
aatgggcttc gcaaccgcta cacgaccggg acggacgagg aacaggggcc cattcccacg     60
gcacccagag aacattcgct tatgtttctc tcaaccctcc ctgacgacac tgtccctgct    120
tacgggaatg tgcgtaccccc tcctgtcaat tacctccctg gtgaaataac cgacctttttg    180 caactggccc gcatacccac tctcatggcg tttgagcggg tgcctgaacc cgtgcctgcc    240
tcagacacat atgtgcccta cgttgccgtt cccacccagt ttgatgacaa gcctctcatc    300
tccttcccga tcacccttttc agatcctgtc tatcagaaca ccctggtagg cgccatcagt    360
tcaaatttcg ccaactaccg tgggtgtatc caaatcactc tgacattttg tggacccatg    420
atggcaagag ggaaattcct actctcgtat tctcccccaa atggaacgca accacagact    480 cttttccgaag ctatgcagtg cacatactct atttgggaca taggcttgaa ctctagttgg    540
accttcgtcg tcccctacat ctcgcccagt gactaccgtg aaactcgggc cattaccaac    600
tcggtttact ccgctgatgg ttggtttagt ctgcacaagt tgaccaaaat tactctacca    660
cctgactgcc cgcaaaagtcc ctgtattctc tttttcgctt ctgctggtga ggattacacc    720
ctccgtctcc ccgttgattg taatccttcc tatgtgttcc actccaccga caacgccgag    780
actggggtta ttgaggcggg taacactgac accgatttct ctggtgaact ggcggctcct    840
ggctctaacc acactaatgt caagttcctg tttgatcgat ctcgattact gaatgtaatt    900
aaggtactgg agaaggacgc cgttttccccc cgtcccttcc ctacaaaaga aggtgcgcag    960
caggacgatg gttacttttg tcttctgaca ccccgcccaa cagtcgcctc ccgacccgcc   1020
actcgtttcg gcctgtacgt caatccgtcc ggcagtggtg ttctcgccaa cacttcactg   1080
gacttcaatt tttatagctt ggcctgtttc acttacttta gatcggacct tgaagttacg   1140
gtggtctcac tggagccaga tctggaattt gctgtagggt ggtttccttc tggcagtgaa   1200
taccaggctt ccagctttgt ctacggcccag ctgcatgtac ccttccactt tactgggcgc   1260
actccccgcg ctttcgccag caagggtggg aaggtatctt tcgtgctccc ttggaactct   1320
gtctcatctg tgctcccccgt gcgctggggg ggcgcttcca agctctcttc tgccacgcgg   1380
ggtctaccgg cgcatgctga ctgggggact atttacgcct ttgtccccccg tcctaatgag   1440 aagaaaagca ccgctgtaaa gcacgtggcc gtgtacgttc ggtacaagaa cgcacgtgcc   1500
tggtgcccca gcatgcttcc ttttcgcagc tacaagcaga agatgctgat gcaatctggc   1560
```

<210> SEQ ID NO 173
<211> LENGTH: 936
<212> TYPE: DNA
<213> ORGANISM: Picornavirus

<400> SEQUENCE: 173

```
tttagcctgc acaagttgac caaaattact ctaccacctg actgcccgca aaatccctgc     60
attctctttt tcgcttctgc tggtgaggat tacactctcc gtctccccat tgattgcaat    120
ccttcctacg tgttccactc caccgacaac gccgaaactg gggttgtcga ggcgggtaac    180
actgacaccg atttctctgg tgaactagcg gctcctggct ccaaccacac taatgtcaag    240
ttcctgtttg atcgatctcg gttattgaat gtaattaagg tactggagaa agacgctgtt    300
ttccctcacc ctttccctac gctagaaggt gtgcaacagg atgatggcta cttttgtctt    360
ctgacccccc gcccaacagt cgcttcccgg cctgccactc gtttcggcct gtacgccaat    420
ccgtccggca gcggtgttct tgctaatact tcattggact ttaactttta tagcttggcc    480
tgtttcactt actttagatc ggacctcgag gttacggtgg tctcactaga gccggatctg    540
gaatttgctg tggggtggtt tccttccggc agtgaatatc aggcttccag ctttgtctac    600
gaccagctgc acgtgccctt ccacttcact ggacgcaccc cccgcgcttt tgctagcaag    660
ggtgggaagg tatcctttgt gctcccttgg aactctgtct catctgtgct ccccgtgcgc    720
tgggggggag cttccaagct ctcttctgcc acgcggggtc taccggtgca cgctgactgg    780
gggactatct acgcctttgt cccccgtccc aatgaaaaga aaagcaccgc tgcaaaacat    840
gtggccgtgt acattcggta caagaacgca cgcgcctggt gtcccaacat gctccccttt    900
cgcagctata agcagaagat gctgatgcaa tctggc                              936
```

<210> SEQ ID NO 174
<211> LENGTH: 936
<212> TYPE: DNA
<213> ORGANISM: Picornavirus

<400> SEQUENCE: 174

```
tttagcctgc acaagttgac caaaataact ctaccacctg actgcccgca aaatccctgc     60
attctctttt tcgcttctgc tggtgaggat tacactctcc gtctccccat tgattgcaat    120
ccttcctacg tgttccactc caccgacaac gccgaaactg gggttgtcga ggcgggtaac    180
actgacaccg atttctctgg tgaactagcg gctcctggct ccaaccacac taatgtcaag    240
ttcctgtttg atcgatctcg gttattgaat gtaattaagg tactggagaa agacgctgtt    300
ttccctcacc ctttccctac gctagaaggt gtgcaacagg atgatggcta cttttgtctt    360
ctgacccccc gcccaacagt cgcttcccgg cctgccactc gtttcggcct gtacgccaat    420
ccgtccggca gcggtgttct tgctaatact tcattggact ttaactttta tagcttggcc    480
tgtttcactt actttagatc ggacctcgag gttacggtgg tctcactaga gccggatctg    540
gaatttgctg tggggtggtt tccttccggc agtgaatatc aggcttccag ctttgtctac    600
gaccagctgc acgtgccctt ccacttcact ggacgcaccc cccgcgcttt tgctagcaag    660
ggtgggaagg tatcctttgt gctcccttgg aactctgtct catctgtgct ccccgtgcgc    720
tgggggggag cttccaagct ctcttctgcc acgcggggtc taccggtgca cgctgactgg    780
gggactatct acgcctttgt cccccgtccc aatgaaaaga aaagcaccgc tgcaaaacat    840
gtggccgtgt acattcggta caagaacgca cgcgcctggt gtcccaacat gctccccttt    900
cgcagctata agcagaagat gctgatgcaa tctggc                              936
```

<210> SEQ ID NO 175
<211> LENGTH: 936
<212> TYPE: DNA
<213> ORGANISM: Picornavirus

<400> SEQUENCE: 175

```
tttagcctgc acaagttgac caaaattact ytaccacctg actgtccgca aagtccctgc      60
attctctttt tcgcttctgc tggtgaggat tacactctcc gtctccccat tgattgtaat     120
ccttcctacg tgttccactc caccgacaac gccgaaactg gggttgttga ggcgggtaac     180
actgacaccg atttctctgg tgaactagcg gctcctggct ccaaccacac taatgtcaag     240
ttcctgtttg atcgatctcg attattgaat gtaattaagg tactggagaa agacgccgtt     300
ttcccccacc ctttccctac gctagaaggt gcgcaacagg atgatggtta cttttgtctt     360
ctgaccccc gcccaacagt cgcttcccga cccgccactc gtttcggcct gtacgccaat     420
ccgtccggca gcggtgttct tgctaatact tcattggact ttaactttta tagcttggcc     480
tgcttcactt actttagatc ggacctcgag gttacggtgg tctcactgga gccagatctg     540
gaatttgctg tagggtggtt tccttccggc agtgaatatc aggcttccag ctttgtctac     600
gaccagctgc acgtgccctt ccacttcact ggacgcaccc ccgcgctttt gctagcaag     660
ggtgggaagg tatcctttgt gctcccttgg aactctgtct catctgtgct ccccgtgcgc     720
tgggggggg cttccaagct ctcttctgcc acgcggggtc taccggcgca tgctgactgg     780
gggactatct acgcctttgt cccccgtccc aatgaaaaga aaagcaccgc tgcaaaacac     840
gtggccgtgt acattcggta caagaacgca cgcgcctggt gccccagcat gcttcccttt     900
cgcagctata agcagaagat gctgatgcaa tctggc                              936
```

<210> SEQ ID NO 176
<211> LENGTH: 936
<212> TYPE: DNA
<213> ORGANISM: Picornavirus

<400> SEQUENCE: 176

```
tttagcctgc acaagttgac aaaaattact ctaccacctg actgtccgca aagtccctgc      60
attctctttt tcgcttctgc tggtgaggat tacactctcc gtctccccgt tgattgtaat     120
ccttcttacg tgttccactc caccgacaac gccgaaactg gggttgttga ggcgggtaac     180
actgacaccg atttctctgg tgaactagcg gctcctggtt ccaaccacac taacgtcaag     240
ttcctgtttg atcgatctcg attattgaat gtaattaagg tactggagaa agacgccgtt     300
ttccctcacc ctttccctac gctagaaggt gcgcaacagg atgatggtta cttttgtctt     360
ctgaccccc gcccaacagt cgcttcccga cccgccactc gtttcggcct gtacgccaat     420
ccgtccggca gtggtgttct tgctaatact tcattggact ttaactttta tagcttggcc     480
tgtttcactt actttagatc ggacctcgag gttacggtgg tctcactgga gccagatctg     540
gaatttgctg taggatggtt tccttccggc agtgaatacc aggcttccag ctttgtctac     600
gaccagctgc acgtgccttt ccacttcact gggcgcactc ccgcgctttt gctagcaag     660
ggtgggaagg tatccttcgt gctcccttgg aactctgttt cgtctgtgct ccccgtgcgc     720
tgggggggg cttccaagct ctcttctgcc acgcggggtc taccggcgca tgctgactgg     780
gggactatct acgcctttgt cccccgtccc aatgaaaaga aaagcaccgc tgcaaaacac     840
gtggccgtgt acattcggta caagaacgca cgcgcctggt gccccagcat gcttcccttt     900
cgcagctata agcagaagat gctgatgcaa tctggc                              936
```

<210> SEQ ID NO 177
<211> LENGTH: 936
<212> TYPE: DNA
<213> ORGANISM: Picornavirus

<400> SEQUENCE: 177

```
tttagcctgc acaagttgac caaaattact ctaccacctg actgtccgca aagtccctgc      60
attctctttt tcgcttctgc tggtgaggat tacactctcc gtctcccgt tgattgtaat     120
ccttcctatg tgttccactc caccgacaac gccgagactg gggttattga ggcgggtaac    180
actgacaccg atttctctgg tgaactggcg gctcctggct ctaaccacac taatgtcaag    240
ttcctgtttg atcgatctcg attattgaat gtaattaagg tactggagaa ggacgccgtt    300
ttcccccgcc ctttccctac acaagaaggt gcgcagcagg acgatggtta cttttgtctt    360
ctgaccccc gcccaacagt cgcttcccga cccgccactc gtttcggcct gtacgccaat    420
ccgtccggca gtggtgttct cgccaacact tcactggact tcaattttta tagcttggcc    480
tgtttcactt actttagatc ggaccttgag gttacggtgg tctcactgga gccaaatctc    540
gaatttgctg tagggtggtt tccttccggt agtgaatacc aggcttccag ttttgtctac    600
gaccagctgc acgtgccctt ccacttcact gggcgcactc cccgcgcttt cgctagcaag    660
ggtgggaagg tgtccttcgt gctcccttgg aactctgtct cgtctgtgct ccccgtgcgc    720
tggggggggg cttccaagct ctcttctgcc acacggggtc taccagtgca tgctgactgg    780
gggactattt acgcctttgt cccccgtccc aatgaaaaga aaagcactgc tgtaaaacac    840
gtggccgtgt acattcggta caagaacgca cgcgcctggt gccccagcat gcttcctttt    900
cgcagctaca agcagaagat gctgatgcaa tctggc                              936
```

<210> SEQ ID NO 178
<211> LENGTH: 1421
<212> TYPE: DNA
<213> ORGANISM: Artificial Sequence
<220> FEATURE:
<223> OTHER INFORMATION: Consensus Sequence from SVV and SVV-like
      Picornaviruses in a coding region sequence for VP2(partial), VP3,
      VP1, and 2A (partial)

<400> SEQUENCE: 178

```
aatgggctcg caaccgctac agccgggacg gacgagaaca ggggccattc cacggcaccc     60
agagaattcg cttatgtttc ttcaacctcc tgacgacacg tcctgcttac gggaatgtgc    120
gacccctcct gtcaattacc tccctggtga ataaccgac ctttgcaact ggcccgcata     180
cccactctca tggctttgag cgggtgccga accgtgcct gctcagaac tatgtgccct      240
acgttgccgt tcccacccat tgtgacagcc tctcatctcc ttcccgatca ccctttcaga    300
ccgtctatca aacaccctgg tggcgccatc agttcattgc caataccgtg ggtgtatcca    360
atcactctga cttttgtgga cccatgatgg cagagggaaa ttcctcttta ttctccccca    420
aatggaacgc aaccacagac tcttttccgaa gctatgcagt gcacatactc tatttgggac    480
ataggcttga actcagttgg accttcgtcg tcccctacat ctcgcccagt gactaccgtg    540
aaaccggcca ttaccaactc ggtttactcc gctgatggtt ggtttagctg cacaagttga    600
caaaatactt ccacctgact gccgcaaatc cctgttctct ttttcgcttc tgctggtgag    660
gattacacct ccgtctcccc ttgattgaat ccttctagtg ttccactcca ccgacaacgc    720
cgaacggggt ttgaggcggg taacactgac accgatttct ctggtgaact gcggctcctg    780
gtcaaccaca ctaagtcaag ttcctgtttg atcgatctcg ttatgaatgt aataaggtac    840
```

```
tggagaagac gcgttttccc cccttttccct acagaaggtg gcacaggaga tggtactttt    900
gtcttctgac ccccgcccaa cagtcgctcc cgccgccact cgtttcggcc tgtacgcaat    960
ccgtccggca gggtgttctg caaacttcat ggacttaatt ttatagcttg gcctgttcac   1020
ttactttaga tcggacctga gttacggtgg tctcactgag ccatctgaat ttgctgtggt   1080
ggtttccttc ggagtgaata caggcttcca gtttgtctac gccagctgca gtccttccac   1140
ttactggcgc accccgcgc tttgcagcaa gggtgggaag gttcttgtgc tcccttggaa    1200
ctctgttctc tgtgctcccc gtgcgctggg ggggcttcc aagctctctt ctgcaccggg    1260
gtctaccggc agctgatggg ggactattac gcctttgtcc cccgtccaat gaaagaaaag   1320
cacgctgaaa cagtggccgt gtacttcggt acaagaacgc acggcctggt gcccacatgc   1380
tcctttcgca gctaaagcag aagatgctga tgcaatctgg c                       1421
```

<210> SEQ ID NO 179
<211> LENGTH: 551
<212> TYPE: DNA
<213> ORGANISM: Seneca Valley Virus

<400> SEQUENCE: 179

```
aaactgttta agatgcaagg acccatggac aaagtcaaag actggaacca aatagctgcc     60
ggcttgaaga atttttcaatt tgttcgtgac ctagtcaaag aggtggtcga ttggctgcag    120
gcctggatca acaaagagaa agccagccct gtcctccagt accagttgga gatgaagaag    180
ctcgggcctg tggccttggc tcatgacgct ttcatggctg gttccgggcc cctcttagc     240 gacgaccaga ttgaatacct ccagaacctc aaatctcttg ccctaacact ggggaagact    300
aatttggccc aaagtctcac cactatgatc aatgccaaac aaagttcagc ccaacgagtt    360
gaacccgttg tggtggtcct tagaggcaag ccgggatgcg gcaagagctt ggcctctacg    420
ttgattgccc aggctgtgtc caagcgcctc tatggctccc aaagtgtata ttctcttccc    480
ccagatccag atttcttcga tggatacaaa ggacagttcg tgaccttgat ggatgatttg    540 ggacaaaaacc c                                                        551
```

<210> SEQ ID NO 180
<211> LENGTH: 551
<212> TYPE: DNA
<213> ORGANISM: Picornavirus

<400> SEQUENCE: 180

```
aaactgttta agatgcaagt acccatggac aaagtcaaag actggaacca aatagccgcc     60
ggcttgaaga actttcaatt tgttcgtgac ctagtcaaag aggtggtcga ctggctgcag    120
gcctggatca acaaggagaa agccagccct gtcctccaat accagttgga gatgaagaag    180
ctcgggcctg tggctttggc tcatgacgct tttatggctg gttccgggcc cctcttagc     240 gacgaccaga ttgagtatct ccagaacctc aaatctcttg ccctaacact agggaagact    300
aatttggccc aaagtctcac cactatgatc aatgccaaac aaagttccgc ccaacgagtt    360
gaacccgttg tggtggtcct tagaggtaag cctggatgtg gcaagagctt ggcctctacg    420
ctgattgctc aggctgtgtc caagcgcctc tatggctccc aaagtgtata ttccctcccc    480
ccagacccag atttctttga tggatacaaa ggacaattcg tgaccttgat ggatgatttg    540 ggacaaaaacc c                                                        551
```

<210> SEQ ID NO 181
<211> LENGTH: 551

```
<212> TYPE: DNA
<213> ORGANISM: Picornavirus

<400> SEQUENCE: 181
aaactgttta agatgcaagt acccatggac aaagtcaaag actggaacca aatagccgcc      60
ggcttgaaga attttcaatt tgttcgtgac ctagtcaaag aggtggtcga ctggctgcag     120
gcctggatca acaaagagaa agccagcccc gtcctccagt accagttgga gatgaagaag     180
ctcgggcccg tggctttggc tcatgacgct ttcatggctg gttccgggcc ccctcttagc     240
gacgaccaga ttgaatacct ccagaacctc aaatctcttg ccctaacact ggggaagact     300
aatttggccc aaagtctcac cactatgatc aatgccaaac aaagttccgc caacgagtt      360
gaacccgttg tggtggtcct tagaggcaag ccgggatgcg gcaagagctt ggcctccacg     420
ttgattgccc aggctgtgtc caagcgtctc tatggctccc aaagtgtgta ttctcttccc     480
ccggatccag atttcttcga tggatacaaa ggacagtttg tgaccttgat ggatgatttg     540
ggacaaaacc c                                                         551

<210> SEQ ID NO 182
<211> LENGTH: 523
<212> TYPE: DNA
<213> ORGANISM: Artificial Sequence
<220> FEATURE:
<223> OTHER INFORMATION: Consensus Sequence from SVV and SVV-like
      Picornaviruses in a partial coding region sequence for 2C

<400> SEQUENCE: 182
aaactgttta agatgcaaga cccatggaca aagtcaaaga ctggaaccaa atagcgccgg      60
cttgaagaat tcaatttgt tcgtgaccta gtcaaagagg tggtcgatgg ctgcaggcct     120
ggatcaacaa gagaaagcca gccctgtcct ccataccagt tggagatgaa gaagctcggg     180
ccgtggcttg gctcatgacg ctttatggct ggttccgggc ccctcttag cgacgaccag     240
attgatactc cagaacctca aatctcttgc cctaacactg gaagactaa tttggcccaa     300
agtctcacca ctatgatcaa tgccaaacaa agttcgccca acgagttaa cccgttgtgg     360
tggtccttag aggaagccgg atgggcaaga gcttggcctc acgtgattgc aggctgtgt     420
ccaagcgctc tatggctccc aaagtgttat tcctcccccg accagatttc ttgatggata     480
caaaggacat tgtgaccttg atggatgatt tgggacaaaa ccc                       523

<210> SEQ ID NO 183
<211> LENGTH: 460
<212> TYPE: DNA
<213> ORGANISM: Seneca Valley Virus

<400> SEQUENCE: 183
cttctggttg gcacggatta cgatctggac ttcaatgagg tggcacgacg cgctgccaag      60
ttggggtata agatgactcc tgccaacaag ggttctgtct ccctccgac ttcctctctt     120
tccgatgctg ttttctaaa gcgcaaattc gtccaaaaca acgacggctt atacaaacca     180
gttatggatt taagaatttt ggaagccatg ctctcctact tcaaaccagg aacactactc     240
gagaagctgc aatctgtttc tatgttggct caacattctg gaaagaaga atatgataga     300
ttgatgcacc ccttcgctga ctacggtgcc gtaccgagtc acgagtacct gcaggcaaga     360
tggaggggcct tgttcgactg acccagatag cccaaggcgc ttcggtgctg ccggcgattc     420
tgggagaact cagtcggaac agaaaaggga aaaaaaaaa                            460

<210> SEQ ID NO 184
```

```
<211> LENGTH: 460
<212> TYPE: DNA
<213> ORGANISM: Picornavirus
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 184
cttctggttg gcacggatna cnatctggac ttcaatgagg tggcgcggcg cgctgccaaa      60
ttggggtata agatgacgcc tgccaacaag ggttccgtct tccctccgac ttcctctctt     120
tccaatgctg tttttctaaa acgtaaattc gtccaaaaca atgacggctt gtacaagcca     180
gttatggatt caaagaattt ggaagccatg ctctcctact tcaaaccagg aacactactc     240
gagaagctgc aatctgtttc tatgttggct caacattctg gaaaagaaga atacgataga     300
ttgatgcatc ccttcgctga ctacggtgcc gtaccgagtc acgagtacct gcaggcaaga     360
tggagggcct tgttcgattg acccagatag cccaaggcgc ttcggtgctg acggtgattc     420
tgggagaact cagtcggaac aaaaagggga aaaaaaaaa                            460

<210> SEQ ID NO 185
<211> LENGTH: 460
<212> TYPE: DNA
<213> ORGANISM: Picornavirus
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (403)..(403)
<223> OTHER INFORMATION: n is a, c, g, or t

<400> SEQUENCE: 185
cttctggttg gcacggatta cgatctggac ttcaatgagn tggcgcggcg cgctgccaaa      60
ttggggtata agatgacgcc tgccaacaag ggttccgtct tccctccgac ttcctctctt     120
tccaatgctg tttttctaaa acgtaaattc gtccaaaaca atgacggctt gtacaagcca     180
gttatggatt caaagaattt ggaagccatg ctctcctact tcaaaccagg aacactactc     240
gagaagctgc aatctgtttc tatgttggct caacattctg gaaaagaaga atacgataga     300
ttgatgcatc ccttcgctga ctacggtgcc gtaccgagtc acgagtacct gcaggcaaga     360
tggagggcct tgttcgattg acccaganag cccaaggcgc ttnggtgctg acggtgattc     420
tgggagaact cagtcggaac aaaaagggga aaaaaaaaa                            460

<210> SEQ ID NO 186
<211> LENGTH: 460
<212> TYPE: DNA
<213> ORGANISM: Picornavirus

<400> SEQUENCE: 186
cttctggttg gcacggatga cgatctggac ttcaatgagg tggcgcggcg cgctgccaaa      60
ttggggtata agatgacgcc tgccaacaag ggttccgtct tccctccgac ttcctctctt     120
tccgatgctg tttttctaaa acgcaaattc gtccaaaaca acgacggctt gtacaaacca     180
```

```
gttatggatt caaagaattt ggaagccatg ctctcctact tcaaaccagg aacactactc    240
gagaagctgc aatctgtttc tatgttggct caacattctg gaaaagaaga atatgataga    300
ttgatgcatc ccttcgctga ctacggtgcc gtaccgagtc acgagtacct gcaggcaaga    360
tggagggcct tgttcgactg acccagatag cccaaggcgc ttcggtgctg acggtgattc    420
tgggagaact cagtcggaac agaaaagggg aaaaaaaaaa    460
```

<210> SEQ ID NO 187
<211> LENGTH: 460
<212> TYPE: DNA
<213> ORGANISM: Picornavirus
<220> FEATURE:
<221> NAME/KEY: misc_feature
<222> LOCATION: (5)..(5)
<223> OTHER INFORMATION: n is a, c, g, or t

<400> SEQUENCE: 187

```
cttcnggttg gcacggatga cgatctggac ttcaatgagg tggcgcggcg cgctgccaaa     60
ttggggtata agatgacgcc tgccaacaag ggttccgtct ccctccgac ttcctctctt    120 tccgatgctg ttttttctaaa acgcaaattc gtccaaaaca acgacggctt gtacaaacca    180
gttatggatt caaagaattt ggaagccatg ctctcctact tcaaaccagg aacactactc    240
gagaagctgc aatctgtctc tatgttggct caacattctg gaaaagaaga atatgataga    300
ttgatgcatc ccttcgctga ctacggtgcc gtaccgagtc acgagtacct gcaggcaaga    360
tggagggcct tgttcgactg acccagatag cccaaggcgc ttcggtgctg acggtgattc    420
tgggagaact cagtcggaac agaaaagggga aaaaaaaaaa    460
```

<210> SEQ ID NO 188
<211> LENGTH: 460
<212> TYPE: DNA
<213> ORGANISM: Picornavirus
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (422)..(422)
<223> OTHER INFORMATION: n is a, c, g, or t

<400> SEQUENCE: 188

```
cttctggttg ncacggatna cgatctgnac ttcaatgagg tggcgcggcg cgctgccaaa     60
ttggggtata agatgacgcc tgccaacaag ggttccgtct ccctccgac ttcctctctt    120 tccgatgctg ttttttctaaa acgcaaattc gtccaaaaca acgacggctt gtacaaacca    180
gttatggatt caaagaattt ggaagccatg ctctcctact tcaaaccagg aacactactc    240
gagaagctgc aatctgtttc tatgttggct caacattctg gaaaagaaga atatgataga    300
ctgatgcacc ccttcgctga ctacggtgcc gtaccgagtc acgagtacct gcaggcaaga    360
tggagggcct tgttcgactg acccagatag cccaaggcgc ctcggtgctg ccggtgattn    420
```

```
tnggagaact cagtcggaac agaaaaggga gaaaaaaaaa              460
```

<210> SEQ ID NO 189
<211> LENGTH: 460
<212> TYPE: DNA
<213> ORGANISM: Picornavirus

<400> SEQUENCE: 189

```
cttctggttg gcacggatta cgatctggac ttcaatgagg tggcgcgacg cgctgccaaa    60
ttggggtata agatgactcc tgccaacaag ggttccgtct tcccttcgac ttcctctctt   120
tccgacgctg tttttctaaa acgcaaattc gtccaaaaca acgacggctt atacaaacca   180
gttatggatt taaagaattt ggaagccatg ctctcctact tcaaaccagg aacactactc   240
gagaagctgc aatctgtttc tatgttggct caacattctg gaaaagaaga atatgataga   300
ttgatgcacc ccttcgctga ctacggtgcc gtaccgagtc acgagtacct gcaggcaaga   360
tggagggcct tgttcgactg acccagatag cccaaggcgc ttcggtgctg ccggcgattc   420
tgggagaact cagtcggaac agaaagggga aaaaaaaaaa                          460
```

<210> SEQ ID NO 190
<211> LENGTH: 460
<212> TYPE: DNA
<213> ORGANISM: Picornavirus

<400> SEQUENCE: 190

```
cttctggttg gtacggatta cgatctggac ttcaatgagg tggcgcgacg cgctgccaag    60
ctggggtata agatgactcc tgccaacaag ggttccgtct ccctccgac ttcctctctc    120
tccgatgctg tttcctaaa acgcaaattc gtccaaaaca acgacggctt atacaaacca   180
gttatggatt taaagaattt ggaagccatg ctctcctact tcaaaccagg aacactactc   240
gagaagctgc aatctgtttc tatgttggct caacattctg gaaaagaaga atatgataga   300
ttgatgcacc ccttcgctga ctacggtgcc gtaccgagtc acgagtacct gcaggcaaga   360
tggagggcct tgttcgactg acccagatag cccaaggcgc ttcggtgctg ccggcgattc   420
tgggagaact cagtcggaac agaaaagggg aaaaaaaaaa                          460
```

<210> SEQ ID NO 191
<211> LENGTH: 420
<212> TYPE: DNA
<213> ORGANISM: Artificial Sequence
<220> FEATURE:
<223> OTHER INFORMATION: Consensus Sequence from SVV and SVV-like
      Picornaviruses in a partial coding region sequence for the 3D
      polymerase and the 3'UTR region

<400> SEQUENCE: 191

```
cttcggttga cggatacatc tgacttcaat gagtggccgc gcgctgccaa tggggtataa    60
gatgaccctg ccaacaaggg ttcgtcttcc ctcgacttcc tctcttccag ctgttttcta   120
aacgaaattc gtccaaaaca agacggcttt acaaccagtt atggattaaa gaatttggaa   180
gccatgctct cctacttcaa accaggaaca ctactcgaga gctgcaatc tgttctatgt    240
tggctcaaca ttctggaaaa gaagaataga tagatgatgc accttcgct gactacggtg    300
ccgtaccgag tcacgagtac ctgcaggcaa gatggagggc cttgttcgat gacccagaag   360
cccaaggcgc tggtgctgcg ggatttggag aactcagtcg gaacaaaagg gaaaaaaaaa   420
```

<210> SEQ ID NO 192
<211> LENGTH: 4
<212> TYPE: PRT

```
<213> ORGANISM: Picornavirus

<400> SEQUENCE: 192

Leu Gln Gly Asn
1

<210> SEQ ID NO 193
<211> LENGTH: 4
<212> TYPE: PRT
<213> ORGANISM: Picornavirus

<400> SEQUENCE: 193

Pro Gln Gly Asn
1

<210> SEQ ID NO 194
<211> LENGTH: 4
<212> TYPE: PRT
<213> ORGANISM: Picornavirus

<400> SEQUENCE: 194

Leu Lys Asp His
1

<210> SEQ ID NO 195
<211> LENGTH: 4
<212> TYPE: PRT
<213> ORGANISM: Picornavirus

<400> SEQUENCE: 195

Leu Ala Asp Gln
1

<210> SEQ ID NO 196
<211> LENGTH: 4
<212> TYPE: PRT
<213> ORGANISM: Picornavirus

<400> SEQUENCE: 196

Leu Leu Asp Gln
1

<210> SEQ ID NO 197
<211> LENGTH: 4
<212> TYPE: PRT
<213> ORGANISM: Picornavirus

<400> SEQUENCE: 197

Leu Met Asp Gln
1

<210> SEQ ID NO 198
<211> LENGTH: 4
<212> TYPE: PRT
<213> ORGANISM: Picornavirus

<400> SEQUENCE: 198

Leu Leu Asp Glu
1

<210> SEQ ID NO 199
<211> LENGTH: 4
<212> TYPE: PRT
<213> ORGANISM: Picornavirus

<400> SEQUENCE: 199
```

Arg Gln Ser Pro
1

<210> SEQ ID NO 200
<211> LENGTH: 4
<212> TYPE: PRT
<213> ORGANISM: Picornavirus

<400> SEQUENCE: 200

Ala Gln Ser Pro
1

<210> SEQ ID NO 201
<211> LENGTH: 4
<212> TYPE: PRT
<213> ORGANISM: Picornavirus

<400> SEQUENCE: 201

Pro Gln Ser Pro
1

<210> SEQ ID NO 202
<211> LENGTH: 4
<212> TYPE: PRT
<213> ORGANISM: Picornavirus

<400> SEQUENCE: 202

Pro Gln Gly Val
1

<210> SEQ ID NO 203
<211> LENGTH: 4
<212> TYPE: PRT
<213> ORGANISM: Picornavirus

<400> SEQUENCE: 203

Pro Gln Gly Ile
1

<210> SEQ ID NO 204
<211> LENGTH: 4
<212> TYPE: PRT
<213> ORGANISM: Picornavirus

<400> SEQUENCE: 204

Pro Gln Gly Ser
1

<210> SEQ ID NO 205
<211> LENGTH: 4
<212> TYPE: PRT
<213> ORGANISM: Picornavirus

<400> SEQUENCE: 205

Met Gln Ser Gly
1

<210> SEQ ID NO 206
<211> LENGTH: 4
<212> TYPE: PRT
<213> ORGANISM: Picornavirus

<400> SEQUENCE: 206

Leu Glu Ser Pro
1

<210> SEQ ID NO 207
<211> LENGTH: 4
<212> TYPE: PRT
<213> ORGANISM: Picornavirus

<400> SEQUENCE: 207

Leu Glu Asn Pro
1

<210> SEQ ID NO 208
<211> LENGTH: 4
<212> TYPE: PRT
<213> ORGANISM: Picornavirus

<400> SEQUENCE: 208

Leu Gln Asn Pro
1

<210> SEQ ID NO 209
<211> LENGTH: 4
<212> TYPE: PRT
<213> ORGANISM: Picornavirus

<400> SEQUENCE: 209

Gln Gln Ser Pro
1

<210> SEQ ID NO 210
<211> LENGTH: 4
<212> TYPE: PRT
<213> ORGANISM: Picornavirus

<400> SEQUENCE: 210

Pro Gln Gly Pro
1

<210> SEQ ID NO 211
<211> LENGTH: 4
<212> TYPE: PRT
<213> ORGANISM: Picornavirus

<400> SEQUENCE: 211

Ala Gln Gly Pro
1

<210> SEQ ID NO 212
<211> LENGTH: 4
<212> TYPE: PRT
<213> ORGANISM: Picornavirus

<400> SEQUENCE: 212

Ala Gln Ala Pro
1

<210> SEQ ID NO 213
<211> LENGTH: 4
<212> TYPE: PRT
<213> ORGANISM: Picornavirus

<400> SEQUENCE: 213

Glu Gln Gly Pro
1

<210> SEQ ID NO 214

```
<211> LENGTH: 4
<212> TYPE: PRT
<213> ORGANISM: Picornavirus

<400> SEQUENCE: 214

Glu Gln Ala Ala
1

<210> SEQ ID NO 215
<211> LENGTH: 4
<212> TYPE: PRT
<213> ORGANISM: Picornavirus

<400> SEQUENCE: 215

Ile Gln Gly Pro
1

<210> SEQ ID NO 216
<211> LENGTH: 4
<212> TYPE: PRT
<213> ORGANISM: Picornavirus

<400> SEQUENCE: 216

Val Gln Gly Pro
1

<210> SEQ ID NO 217
<211> LENGTH: 4
<212> TYPE: PRT
<213> ORGANISM: Picornavirus

<400> SEQUENCE: 217

Ile Gln Gly Gly
1

<210> SEQ ID NO 218
<211> LENGTH: 4
<212> TYPE: PRT
<213> ORGANISM: Picornavirus

<400> SEQUENCE: 218

Pro Gln Gly Ala
1

<210> SEQ ID NO 219
<211> LENGTH: 20
<212> TYPE: DNA
<213> ORGANISM: Artificial Sequence
<220> FEATURE:
<223> OTHER INFORMATION: Primer sequence for Seneca Valley Virus

<400> SEQUENCE: 219
tttgaaatgg ggggctgggc                                              20

<210> SEQ ID NO 220
<211> LENGTH: 19
<212> TYPE: DNA
<213> ORGANISM: Artificial Sequence
<220> FEATURE:
<223> OTHER INFORMATION: Primer Sequence for Seneca Valley Virus

<400> SEQUENCE: 220
gaggagaccc gctaatccg                                               19

<210> SEQ ID NO 221
<211> LENGTH: 54
```

```
<212> TYPE: DNA
<213> ORGANISM: Artificial Sequence
<220> FEATURE:
<223> OTHER INFORMATION: Primer Sequence for generating an infectious
      plasmid clone of Seneca Valley Virus

<400> SEQUENCE: 221
tatgggtacc tgtaatacga ctcactatag ggctttgaaa tgggggctg ggcc              54

<210> SEQ ID NO 222
<211> LENGTH: 24
<212> TYPE: DNA
<213> ORGANISM: Artificial Sequence
<220> FEATURE:
<223> OTHER INFORMATION: Primer sequence for generating an infectious
      plasmid clone of Seneca Valley Virus

<400> SEQUENCE: 222
ccgtcaaaga agcaattctg ggca                                              24

<210> SEQ ID NO 223
<211> LENGTH: 60
<212> TYPE: DNA
<213> ORGANISM: Artificial Sequence
<220> FEATURE:
<223> OTHER INFORMATION: Primer sequence for generating an infectious
      plasmid clone of Seneca Valley Virus

<400> SEQUENCE: 223
gcatgcattt ttttttttt ttttttttt tttttttccc ttttctgttc cgactgagtt         60

<210> SEQ ID NO 224
<211> LENGTH: 30
<212> TYPE: DNA
<213> ORGANISM: Artificial Sequence
<220> FEATURE:
<223> OTHER INFORMATION: Primer sequence for generating an infectious
      clone of Seneca Valley Virus

<400> SEQUENCE: 224
ggtaacatga ccttcaatta ctacgcaaac                                        30

<210> SEQ ID NO 225
<211> LENGTH: 23
<212> TYPE: DNA
<213> ORGANISM: Artificial Sequence
<220> FEATURE:
<223> OTHER INFORMATION: Primer sequence for generating an infectious
      plasmid clone of Seneca Valley Virus

<400> SEQUENCE: 225
gatcagtacg tcgaaggccg ttg                                               23

<210> SEQ ID NO 226
<211> LENGTH: 76
<212> TYPE: DNA
<213> ORGANISM: Artificial Sequence
<220> FEATURE:
<223> OTHER INFORMATION: Primer sequence for generating an infectious
      plasmid clone of Seneca Valley Virus

<400> SEQUENCE: 226
gcttgcatgc atttaaattt ttttttttt ttttttttt ttttttttcc cttttctgtt         60
ccgactgagt tctccc                                                       76

<210> SEQ ID NO 227
<211> LENGTH: 47
```

```
<212> TYPE: DNA
<213> ORGANISM: Artificial Sequence
<220> FEATURE:
<223> OTHER INFORMATION: Primer sequence for generating an infectious
      plasmid clone of Seneca Valley Virus

<400> SEQUENCE: 227
caattgtgta atacgactca ctatagtttg aaatgggggg ctgggcc                47
```